(12) United States Patent
Shimojo et al.

(10) Patent No.: US 7,148,234 B2
(45) Date of Patent: *Dec. 12, 2006

(54) USE OF EP4 RECEPTOR LIGANDS IN THE TREATMENT OF IL-6 INVOLVED DISEASES

(75) Inventors: Masato Shimojo, Aichi (JP); Kana Taniguchi, Aichi (JP)

(73) Assignee: Pfizer Inc., New York, NY (US)

( * ) Notice: Subject to any disclaimer, the term of this patent is extended or adjusted under 35 U.S.C. 154(b) by 538 days.

This patent is subject to a terminal disclaimer.

(21) Appl. No.: 10/411,491

(22) Filed: Apr. 10, 2003

(65) Prior Publication Data

US 2003/0236260 A1    Dec. 25, 2003

Related U.S. Application Data

(60) Provisional application No. 60/372,364, filed on Apr. 12, 2002.

(51) Int. Cl.
*A61K 31/437* (2006.01)
*C07D 471/04* (2006.01)

(52) U.S. Cl. ............. 514/303; 546/118; 546/273.4; 548/302.1; 548/304.4; 548/309.7; 548/306.1; 514/338; 514/394; 514/393

(58) Field of Classification Search ............. 514/243, 514/248, 303, 118
See application file for complete search history.

(56) References Cited

U.S. PATENT DOCUMENTS 4,536,507 A * 8/1985 Rokach et al. ............ 514/362
5,972,965 A    10/1999 Taniguchi et al.
6,710,054 B1 * 3/2004 Nakao et al. ............ 514/303

FOREIGN PATENT DOCUMENTS

| WO | WO 00/16760 A2 | 3/2000 |
|---|---|---|
| WO | WO 00/16760 A3 | 3/2000 |
| WO | WO 00/18744 A1 | 4/2000 |
| WO | WO 02/32900 A2 | 4/2002 |
| WO | WO 02/32900 A3 | 4/2002 |
| WO | WO 02/50033 A1 | 6/2002 |

OTHER PUBLICATIONS

R. W. Alexander, et al., "Inflammation and Coronary Artery Disease", The New England Journal of Medicine, Aug. 18, 1994, pp. 468-469, vol. 331, No. 7.
C. S. R. Baker, et al., "Cyclooxygenase-2 is Widely Expressed in Atherosclerotic Lesions Affecting Native and Transplanted Human Coronary Arteries and Colocalized with Inducible Nitric Oxide Synthase and Nitrotyrosine Particularly in Macrophages", Arterioscler Thromb Vascular Biology, 1999, pp. 646-655, vol. 19.
T. A. Blaine, et al., "Modulation of the Production of Cytokines in Titanium-Stimulated Human Peripheral Blood Monocytes by Pharmacological Agents", The Journal of Bone and Joint Surgery, Oct. 1997, pp. 1519-1528, vol. 79-A, No. 10.

(Continued)

*Primary Examiner*—Shengjun Wang
*Assistant Examiner*—Yong S. Chong
(74) *Attorney, Agent, or Firm*—Charles W. Ashbrook; David R. Kurlandsky

(57) ABSTRACT

Methods of treating IL-6 involved diseases with EP4 receptor ligands, including EP4 receptor antagonists. Assays to determine the effect of test compounds on PGE2-induced whole blood cells activation.

3 Claims, 8 Drawing Sheets

OTHER PUBLICATIONS

P. K. Bourassa, et al., "Estrogen Reduces Atherosclerotic Lesion Development in Apolipoprotein E-deficient Mice", Proc. Natl. Academy of Science, Sep. 1996, pp. 10022-10027, vol. 93.

F. R. Cochran, et al., "Interleukin-6 Can Prime THP-1 Macrophages for Enhanced Production of Tumor Necrosis Factor-alpha in Response to LPS", Immunopharmacology, 1992, pp. 97-103, vol. 23.

R. A. Coleman, et al., "International Union of Pharmacology Classification of Prostanoid Receptors: Properties, Distrubtion, and Structure of the Receptors and Their Subtypes", Pharmacological Reviews, 1994, pp. 205-209, vol. 46, No. 2.

U. Ikeda, et al., "Interleukin 6 Stimulates Growth of Vascular Smooth Muscle Cells in a PDGF-dependent Manner," American Journal of Physiology, May 1991, pp. H1713-H1717, vol. 260 No. 5.

K. Kauser, et al., "Effect of 17Beta-Estradiol on Atherosclerotic Lesion Formation In ApoE-Deficient Mice", Journal of Vascular Research, 1996, p. 48, vol. 33, Suppl 1.

H. Kishikawa, et al., "Localization of T Lymphocytes and Macrohpghages Expressing IL-1, IL-2 Receptor, IL-6 and TNF in Human Aortic Intima. Role of Cell-mediated Immunity in Human Atherogenesis", Virchows Archive A Pathological Anatomy and Histopathology, 1993,.

P. Libby, et al., "The Role of Macrophages in Atherogenesis", Current Opinion in Lipidology, 1993, pp. 355-363, vol. 4.

G. Liuzzo, et al., "The Prognostic Value of C-Reactive Protein and Serum Amyloid a Protein in Severe Unstable Angina", The New England Journal of Medicine, Aug. 18, 1994, pp. 417-424, vol. 331, No. 7.

S. Monkada, et al., "An enzyme Isolated from Arteries Transforms Prostaglandin Endoperoxides to an Unstable Substance that Inhibits Platelet Aggregation", Nature, Oct. 21, 1976, pp. 663-665, vol. 263.

P. Needleman, et al., "The Discovery and Function of COX-2", The Journal of Rheumatology, 1997, pp. 6-8, vol. 24, Suppl. 49.

M. Negishi, et al., "Molecular Mechanisms of Diverse Actions of Prostanoid Receptors", Biochimica et Biophysica Acta, 1995, pp. 109-120, vol. 1259.

P. M. Ridker, et al., "Inflammation, Aspirin, and the Risk of Cardiovascular Disease in Apparently Healthy Men", The New England Journal of Medicine, Apr. 3, 1997, pp. 973-979, vol. 336, No. 14.

R. Ross, et al., "The Pathogenesis of Atherosclerosis: A Perspective for the 1990s", Nature, Apr. 29, 1993, pp. 801-809, vol. 362.

Y. Seino, et al., Interleukin 6 Gene Transcripts are Expressed in Human Atherosclerotic Lesions, Cytokine, Jan. 1994, pp. 87-91, vol. 6, No. 1.

V. Stemme, et al., "Expression of Cyclo-Oxygenase-2 in Human Atherosclerotic Carotid Arteries", European Journal of Vascular and Endovascular Surgery, 2000, pp. 146-152, vol. 20.

D. A. Sukovich, et al., "Expression of Interleukin-6 Atherosclerotic Lesions of Male ApoE-Knockout Mice Inhibition by 17Beta-Estradiol", Arteriosclerosis, Thrombosis, and Vascular Biology, 1998, pp. 1498-1505, vol. 18, No. 9.

A. C. Van Der Wal, et al., "Site of Intimal Rupture or Erosion of Thrombosed Coronary Atherosclerotic Plaques Is Characterized by an Inflammatory Process Irrespective of the Dominant Plaque Morphology", Circulation, Jan. 1994, pp. 36-44, vol. 89, No. 1.

K. Yoshizaki, et al., "Therapy of Rheumatoid Arthritis by Blocking IL-6 Signal Transduction with a Humanized Anti-IL-6 Receptor Antibody", Springer Seminars in Immunopathology, 1998, pp. 247-259, vol. 20.

* cited by examiner

Compound A)

Compound B)

US 7,148,234 B2

USE OF EP4 RECEPTOR LIGANDS IN THE TREATMENT OF IL-6 INVOLVED DISEASES

PRIORITY INFORMATION

This application claims benefit of provisional application Ser. No. 60/372,364, filed Apr. 12, 2002, herein incorporated by reference in its entirety.

FIELD OF THE INVENTION

The present invention features new uses for EP4 receptor ligands. The invention also includes methods of identifying agents that affect peripheral whole blood cell activation, and specifically assays to identify compounds that affect secretion of IL-6 from these peripheral whole blood cells by modulating $PGE_2$-mediated activity. The present invention also features new uses for EP4 receptor antagonists. The assays of the invention include assays for testing peripheral whole blood cells activation by contacting with compounds and PGE2, which can be identified by cellular activity by measuring IL-6 production.

BACKGROUND

Prostaglandin $E_2$ ($PGE_2$) is a potent modulator involved in the pathogenesis of arthritis. $PGE_2$ binds to at least four subtypes of PGE receptor, designated EP1, EP2, EP3, and EP4. Molecular studies have revealed that all subtypes are 7-transmembrane spanning receptors that belong to the G-protein coupled receptor superfamily (Robert et al., Am. Soc. Pharm. Exp. Ther. 46:205–29, 1994). EP1 activation stimulates the release of intracellular calcium via a G protein-mediated mechanism; EP2 and EP4 both activate adenylate cyclase via stimulatory G proteins, but differ in their response to certain ligands; and EP3 inhibits adenylate cyclase via inhibitory G-proteins (Robert et al., supra, Negishi et al., Biochimica Biophys. Acta 1259:109–20, 1995).

Increased levels of interleukin-6 (IL-6), a pleiotropic inflammatory cytokine, have been proposed to contribute to a number of pathological disorders such as rheumatoid arthritis autoimmune diseases and atherosclerosis.

Interleukin-6 (IL-6) is a key cytokine required for plasma cell induction, antibody secretion, B cell growth, activation of acute-phase protein synthesis, T cell activation, hematopoietic stem cell growth and maintaining optical immune function. Its action ensures that the immune system is activated and the activation is sustained during infections and in response to other inflammatory stimuli. It has been well described that IL-6 plays critical role in the development and maintenance of chronic inflammatory disease such as rheumatoid arthritis in mammals. In the recent clinical study, anti-IL-6 receptor antibody improved stiffness, joint pain and swelling in patients with rheumatoid arthritis (Yoshizaki et al., Springer Semin Immunopathol. Vol. 20, 247–259, 1998). This evidence implicating the regulation of IL-6 production provides a promising strategy for the treatment of chronic inflammatory diseases.

Atherosclerosis is a complex disease that is characterized by cholesterol deposition and monocyte infiltration into the subendothelial space, resulting in foam cell formation (Ross R.(1993) Nature 362:801–809). The presence of macrophages and T lymphocytes in the atherosclerotic lesion suggests an important role for the immune system and the inflammatory process in the pathogenesis of atherosclerosis (Libby et al.(1993) Curr. Opin. Lipidol. 4:355–363).

The mRNA transcripts of IL-6 have been detected in human atherosclerotic lesions (Seino et al. Cytokine 1994, 6, 87–91). This observation has been confirmed and extended by immunohistochemical studies that have demonstrated co-localized IL-6 protein expression with macrophages as well as smooth muscle cells in human atherosclerotic plaques (Kishikawa H. et al., Virchows. Arch. A Pathol. Anat. Histopathol. 1992, 423, 433–442). Moreover, IL-6 has been shown to have important effects on the cell types that are components of atherosclerotic lesions. IL-6 can prime THP-1 macrophage cells to produce enhanced amounts of tumor necrosis factor-α in response to lipopolysaccharide (LPS)(Cochran F R et al., Immunopharmacology, 1992,23, 97–103), suggesting that IL-6 may play a role in stimulating macrophages to attain their full inflammatory potential. IL-6 has been shown to stimulate the growth of vascular smooth muscle cells in a platelet-derived growth factor-dependent manner (Ikeda U. et al., Am. J. Physiol. 1991,260, H1713–H1717). Recent data demonstrated that the apolipoprotein E-knock out (KO) mouse developed atherosclerosis which is relevant to human pathology (Bourassa P-AK et al., Proc. Natl. Acad Sci USA 1996, 93, 10022–10027; Kauser K. et al., J. Vasc. Res. 1996, 33(suppl 1)48, Abstract). The secretion of IL-6 from isolated aorta from apoE-KO mice showed positive correlation with the lesion area of the same apoE-KO aorta, and immunohistochemical staining revealed that macrophages predominantly produced IL-6 (Sukovich D. A. et al., Arterioscler Thromb Vasc Biol. 1998, 18, 1498–1505). Thus, IL-6 appears to play important role in the development of atherosclerosis.

Additional current data supports the hypothesis that atherosclerosis is an inflammatory disease (Ross, R., et al., Nature, 1993, 362, 801–809; Alexander, R. W., et al., N. Engl. J. Med., 1994, 331, 468–469), and studies examining markers of inflammation demonstrate a relation between increasing inflammation and risk of myocardial infarction (Rider, P. M. et al., N. Engl. J. Med., 1997, 336, 973–979; Liuzzo, G. et al., N. Engl. J. Med., 1994, 331, 417–424). Plaque rupture leading to thrombosis is the key event in infarction and has been shown to be related to increased inflammation within the plaque (van der Wal. A. C., et al., Circulation, 1994, 89, 36–44). Furthermore, reduction in the inflammatory response may be associated with a reduction in the risk of subsequent ischemic events (Ridker, P. M. et al., N. Engl. J. Med., 1997, 336, 973–979), and the beneficial effect of aspirin, a cyclooxygenase inhibitor, in reducing the risk of myocardial infarction has been suggested to be partly attribute to is anti-inflammatory action. This evidence implies that in addition to cytokines and growth factors, prostaglandins also seems to play pivotal role in atherosclerosis.

Prostaglandins are normally produced by the enzyme cyclooxygenase-1 (COX-1), which is constitutively expressed by the vascular endothelium, platelets, kidneys, and elsewhere (Monkada, S. et al., Nature, 1976, 263, 663–665). In addition, a cytokine-inducible cyclooxygenase, COX-2, has been detected in several different cell types. The expression of COX-2 is restricted under basal conditions and unregulated during inflammation such as in rheumatoid arthritis (Needeleman, P. et al., J. Rheumatol, 1997, 24(suppl 49), 6–8). In human atherosclerotic lesions, COX-2 was found in macrophages, in some smooth muscle cells and in endothelial cells (Christopher, S. R., et al., Arterioscler Thromb. Vasc. Biol. 1999, 19, 646–655; stemme, V. et al., Eur. J. Vasc. Endovasc, Surg., 2000, 20, 146–152). Since the COX-2 activation produces prostaglandin $E_2$ and $I_2$ which are well recognized as crucial and positive factor in inflammation, such as $PGE_2$ and/or $PGI_2$ might play important role in the atherosclelotic disorders.

Several lines of evidence suggest that prostaglandins and IL-6 production from macrophages at inflammatory site or atherosclerotic lesion relates disease development and maintenance. Indeed, it has already reported when monocytes from human peripheral blood were co-stimulated with PGE2 and titanium particles, PGE2 enhanced IL-6 production to a great extent (Blaine, T. A. et al, J. Bone Joint Surgery, 1997, 10, 1519–1528). In the present study, we also show that PGE2 enhances IL-6 production in Concanavalin A (ConA)-treated human peripheral blood mononuclear cells (PBMC). We have surprisingly found that EP4 subtype selective antagonists inhibit the IL-6 production in both PBMC and peripheral whole blood that was co-stimulated with PGE2 and ConA (See DETAILED DESCRIPTION OF THE INVENTION).

SUMMARY OF THE INVENTION

The present invention features the use of an EP4 receptor ligand in the manufacture of a medicament for the treatment of IL-6 involved diseases. Preferably, the IL-6 involved disease is selected from the group consisting of alcoholic cirrhosis, amyloidosis, atherosclerosis, cardiac disease such as angina pectoris, myocardial infarction, myocardiopathy and myocarditis, sclerosis such as multiple sclerosis, and organ transplantation reactions.

In a further aspect the invention features a method of treating IL-6 involved diseases in a mammal, including man, comprising administration of an effective amount of an EP4 receptor ligand. Preferably, IL-6 involved disease is selected from the group consisting of alcoholic cirrhosis, amyloidosis, atherosclerosis, cardiac disease such as angina pectoris, myocardial infarction, myocardiopathy and myocarditis, sclerosis such as multiple sclerosis, and organ transplantation reactions.

In a further aspect the invention features a pharmaceutical composition comprising an EP4 receptor ligand for use in the treatment of IL-6 involved diseases. Preferably, IL-6 involved disease is selected from the group consisting of alcoholic cirrhosis, amyloidosis, atherosclerosis, cardiac disease such as angina pectoris, myocardial infarction, myocardiopathy and myocarditis, sclerosis such as multiple sclerosis, and organ transplantation reactions.

In one embodiment of the invention, the EP4 receptor ligand used in this invention is a selective EP4 receptor antagonist.

In another embodiment of the invention, the EP4 receptor ligand(antagonist) is an aryl or heteroaryl fused imidazole compound of the following Formula I

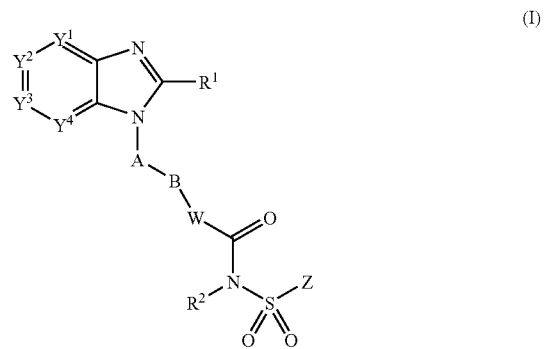

or a pharmaceutically acceptable salt thereof, wherein $Y_1$, $Y^2$, $Y^3$ and $Y^4$ are independently selected from N, CH or C(L);

$R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$-, pyrrolidinyl, piperidyl, oxopyrrolidinyl, oxopiperidyl, amino, mono- or di-($C_{1-8}$ alkyl)amino, $C_{1-4}$alkyl-C(=O)—N($R^3$)— or $C_{1-4}$alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$-, $Q^1$-C(=O)—, $Q^1$-O—, $Q^1$-S(O)m-, $Q^1$-$C_{1-4}$alkyl-O—, $Q^1$-$C_{1-4}$alkyl-S(O)m-, $Q^1$-$C_{1-4}$alkyl-C(O)—N($R^3$)—, $Q^1$-$C_{1-4}$alkyl-N($R^3$)— or $C_{1-4}$alkyl-C(O)—N($R^3$)—;

$Q^1$ is a 5–12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, HO(O=)C—, $C_{1-4}$alkyl-O(O=)C—, $R^3$N($R^4$)C(=O)—, $C_{1-4}$ alkylsulfonylamino, $C_{3-7}$ cycloalkyl, $R^3$C(=O)N($R^4$)— or $NH_2$(HN=)C—;

A is a 5–6 membered monocyclic aromatic ring optionally containing up to 3 heteroatoms selected from O, N and S, wherein said 5–6 membered monocyclic aromatic ring is optionally substituted with up to 3 substituents selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, acetyl, $R^3$N($R^4$)C(=O)—, HO(O=)C—, $C_{1-4}$alkyl-O(O=)C—, $C_{1-4}$ alkylsulfonylamino, $C_{3-7}$ cycloalkyl, $R^3$C(=O)N($R^4$)— and $NH_2$(HN=)C—;

B is halo-substituted $C_{1-6}$ alkylene, $C_{3-7}$ cycloalkylene, $C_{2-6}$ alkenylene, $C_{2-6}$ alkynylene, —O— $C_{1-5}$ alkylene, $C_{1-2}$ alkylene-O—C$_{1-2}$ alkylene or C$_{1-6}$ alkylene optionally substituted with an oxo group or C$_{1-3}$ alkyl;

W is NH, N—C$_{1-4}$ alkyl, O, S, N—OR$^5$ or a covalent bond;

R$^2$ is H, C$_{1-4}$ alkyl, OH or C$_{1-4}$ alkoxy;

Z is a 5–12 membered monocyclic or bicyclic aromatic ring optionally containing up to 3 heteroatoms selected from O, N and S, wherein said 5–12 membered monocyclic or bicyclic aromatic ring is optionally substituted with halo, C$_{1-4}$ alkyl, halo-substituted C$_{1-4}$ alkyl, C$_{1-4}$ alkenyl, C$_{1-4}$ alkynyl, hydroxy, C$_{1-4}$ alkoxy, halo-substituted C$_{1-4}$ alkoxy, C$_{1-4}$ alkylthio, nitro, amino, mono- or di-(C$_{1-4}$ alkyl)amino, cyano, HO—C$_{1-4}$ alkyl, C$_{1-4}$ alkoxy-C$_{1-4}$ alkyl, C$_{1-4}$ alkylsulfonyl, aminosulfonyl, C$_{1-4}$alkylC(=O)—, R$^3$C(=O)N(R$^4$)—, HO(O=)C—, C$_{1-4}$alkyl-O(O=) C—, C$_{1-4}$ alkylsulfonylamino, C$_{3-7}$ cycloalkyl, NH$_2$(HN=)C—, Q$^2$-S(O)m-, Q$^2$-O—, Q$^2$-N(R$^3$)— or Q$^2$-;

L is halo, C$_{1-4}$ alkyl, halo-substituted C$_{1-4}$ alkyl, hydroxy, C$_{1-4}$ alkoxy, halo-substituted C$_{1-4}$ alkoxy, C$_{1-4}$ alkylthio, nitro, amino, mono- or di-(C$_{1-4}$ alkyl)amino, cyano, HO—C$_{1-4}$ alkyl, C$_{1-4}$ alkoxy-C$_{1-4}$alkyl, C$_{1-4}$ alkylsulfonyl, aminosulfonyl, C$_{1-4}$alkylC(=O)—, HO(O=)C—, C$_{1-4}$alkyl-O(O=)C—, C$_{1-4}$ alkylsulfonylamino, C$_{3-7}$ cycloalkyl, R$^3$C(=O)N(R$^4$)—, NH$_2$(HN=)C—, R$^3$N(R$^4$)C(=O)—, R$^3$N(R$^4$)S(O)m-, Q$^2$-, Q$^2$-C(=O)—, Q$^2$-O—, Q$^2$-C$_{1-4}$alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;

R$^3$ and R$^4$ are independently selected from H and C$_{1-4}$ alkyl;

R$^5$ is H, C$_{1-4}$ alkyl, C$_{1-4}$ alkyl-(O=)C— or C$_{1-4}$ alkyl-O—(O=)C—; and Q$^2$ is a 5–12 membered monocyclic or bicyclic aromatic ring, or a 5–12 membered tricyclic ring optionally containing up to 3 heteroatoms selected from O, N and S, wherein said 5–12 membered monocyclic or bicyclic aromatic ring is optionally substituted with halo, C$_{1-4}$ alkyl, halo-substituted C$_{1-4}$ alkyl, C$_{1-4}$ alkenyl, C$_{1-4}$ alkynyl, hydroxy, C$_{1-4}$ alkoxy, halo-substituted Cl$_{1-4}$ alkoxy, C$_{1-4}$ alkylthio, nitro, amino, mono- or di-(C$_{1-4}$ alkyl)amino, cyano, HO—C$_{1-4}$ alkyl, C$_{1-4}$ alkoxy-C$_{1-4}$alkyl, C$_{1-4}$ alkylsulfonyl, aminosulfonyl, C$_{1-4}$alkyl-(O=)C—, R$^3$(R$^4$)C(=O)N—, HO(O=)C—, C$_{1-4}$ alkyl-O(O=)C—, C$_{1-4}$ alkylsulfonylamino, C$_{3-7}$ cycloalkyl, C$_{1-4}$ alkyl-C(=O)NH— or NH$_2$(HN=)C—.

In another embodiment, the EP4 receptor ligand (antagonist), which is disclosed in WO 00/16760, is an aryl or heteroaryl fused imidazole compound of the following Formula II

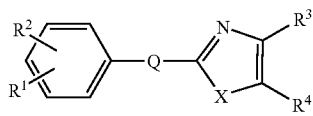

(II)

or the pharmaceutically acceptable salts thereof, wherein

R$^1$ is lower alkyl substituted with hydroxy, protected carboxy or carboxy; carboxy; protected carboxy; carbamoyl; a heterocyclic group; cyano; halo(lower)alkylsulfonyloxy; lower alkoxy substituted with hydroxy or carbamoyl; aryl substituted with carboxy, protected carboxy, carbamoyl or heterocyclic group; or amino optionally substituted with protected carboxy or lower alkylsufonyl, R$^2$ is hydrogen or lower alkyl, R$^3$ is aryl optionally substituted with halogen, R$^4$ is aryl optionally substituted with halogen, Q is

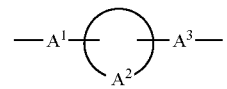

[in which -A$^1$— is a single bond or lower alkylene,

is cyclo(C$_5$–C$_9$)alkene, cyclo(C$_3$–C$_9$)alkane, bicyclo(C$_6$–C$_9$)alkene or bicyclo(C$_5$–C$_9$)alkane, and -A$^3$— is a single bond or lower alkylene], and X is O, NH or S.

In another aspect, the invention provides an assay involving culturing peripheral whole blood with a test compound; and determining the effect of the compound on PGE2-induced whole blood cells activation. Preferably, the measurable change in cellular activity is increased cytokine release. Preferably, the effect of the compound is determined by comparing the effect with a control culture in the absence of the compound.

In another aspect, the invention provides an assay involving activating peripheral whole blood cells by combination with PGE2 and other stimulants such as concanavalin A, CD3 or titanium.

Those skilled in the art will fully understand the terms used herein in the description and the appendant claims to describe the present invention. Nonetheless, unless otherwise provided herein, the following terms are as described immediately below.

"IL-6 involved disease" as used herein means a disease caused by IL-6, or a disease in which levels of IL-6 are increased, or a disease in which IL-6 activates the immune system.

Examples of such IL-6 involved diseases include, alcoholic cirrhosis, amyloidosis, atherosclerosis, cardiac disease such as angina pectoris, myocardial infarction, myocardiopathy and myocarditis, sclerosis such as multiple sclerosis, and organ transplantation reactions.

"EP4 receptor ligand" as used herein means a compound that binds to an EP4 receptor, including a stereoisomer of the compound, a pharmaceutically acceptable salt of the compound or stereoisomer, a prodrug of the compound or stereoisomer, or a pharmaceutically acceptable salt of the prodrug. It is also contemplated that any additional pharmaceutically active compound used in combination with a EP4 receptor ligand can be a stereoisomer of the additional active compound, a salt of the additional active compound or stereoisomer thereof, a prodrug of the additional compound or stereoisomer thereof, or a salt of the prodrug.

"EP4 receptor antagonist" as used herein means a chemical substance that reduces or attenuates the biological activity of an EP4 receptor. Such antagonists may include proteins such as anti-EP4 antibodies, nucleic acids, amino acids, peptides carbohydrates, small molecules (organic or inorganic), or any other compound or composition which decreases the activity of an EP4 receptor either by reducing the amount of EP4 receptors present in a cell, or by decreasing the binding or signaling activity of the EP4 receptors.

The term "alkyl", as used herein, means a straight or branched saturated monovalent hydrocarbon radical including, but not limited to, methyl, ethyl, propyl, isopropyl, n-butyl, iso-butyl, sec-butyl, tert-butyl, neopentyl and the like.

The term "alkenyl", as used herein, means a hydrocarbon radical having at least one double bond including, but not limited to, ethenyl, propenyl, 1-butenyl, 2-butenyl and the like.

The term "alkynyl", as used herein, means a hydrocarbon radical having at least one triple bond including, but not limited to, ethynyl, propynyl, 1-butynyl, 2-butynyl and the like.

The term "halo", as used herein, refers to F, Cl, Br or I, preferably F or Cl.

The term "cycloalkyl", as used herein, means a saturated carbocyclic radical including, but not limited to, cyclopropyl, cyclobutyl, cyclohexyl, cycloheptyl, cyclooctyl, cyclononyl, cyclodecyl and the like.

The term "alkoxy", as used herein, means an O-alkyl group wherein "alkyl" is defined above.

The term "monocyclic aromatic ring", as used herein, means a monocyclic aromatic carbocyclic or heterocyclic ring (and containing 0–4 heteroatoms selected from O, N and S) including, but not limited to, phenyl, pyrazolyl, furyl, thienyl, oxazolyl, tetrazolyl, thiazolyl, imidazolyl, thiadiazolyl, pyridyl, pyrimidinyl, pyrrolyl, thiophenyl, pyrazinyl, pyridazinyl, isooxazolyl, isothiazolyl, triazolyl, furazanyl and the like.

The term "bicyclic aromatic ring", as used herein, means a monocyclic or bicyclic aromatic carbocyclic or heterocyclic ring (and containing 0–4 heteroatoms selected from O, N and S) including, but not limited to, naphthyl, benzofuranyl, isobenzofuranyl, benzothiophenyl, indolyl, isoindolyl, benzoxazolyl, benzothiazolyl, indazolyl, benzimidazolyl, quinolyl, isoquinolyl, cinnolinyl, phthalazinyl, quinazolinyl quinoxalinyl and the like.

The term "alkylene", as used herein, means saturated hydrocarbon (straight chain or branched) wherein a hydrogen atom is removed from each of the terminal carbons such as methylene, ethylene, propylene, butylene, pentylene, hexylene and the like.

The term "cycloalkylene", as used herein, means divalent cycloalkyl groups including, but not limited to, cyclopropylene, cyclobutylene, cyclopentylene, cyclohexylene and cycloheptylene and the like.

The term "alkenylene", as used herein, means a straight or branched hydrocarbon chain spacer radical having at least one double bond including, but not limited to, —CH=CH—, —CH=CHCH—, —CH=CHCH(CH$_3$)—, and the like.

The term "alkynylene", as used herein, means a straight or branched hydrocarbon chain spacer radical having at least one triple bond including, but not limited to, —C≡C—, —C—C≡CCH$_2$—, —C≡CCH(CH$_3$)—, and the like.

The term "tricyclic ring", as used herein, means a saturated carbocyclic radical including, but not limited to, adamantyl, tricyclo[5.2.1.0$^{2,6}$]decane, and the like.

The term "two adjacent L groups are optionally joined together to form an alkylene chain having 3 or 4 members in which one or two (non-adjacent) carbon atoms are optionally replaced by oxygen atoms", as used herein, means, but not limited to, —O—CH$_2$—O—, —CH$_2$—O—CH$_2$—, —O—CH$_2$CH$_2$—, —CH$_2$CH$_2$—O—, —O—CH$_2$CH$_2$—O—, —CH$_2$CH$_2$CH$_2$—O—, —O—CH$_2$CH$_2$CH$_2$—, —CH$_2$—O—CH$_2$CH$_2$—, —CH$_2$CH$_2$—O—CH$_2$—, and the like.

The term "aryl", as used herein, means aromatic radicals including, but not limited to, phenyl, naphthyl, tetrahydronaphthyl, indanyl, biphenyl and the like.

The term "protecting group", as used herein, means a hydroxy or amino protecting group which is selected from typical hydroxy or amino protecting groups described in Protective Groups in Organic Synthesis edited by T. W. Greene et al. (John Wiley & Sons, 1991);

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

Other features and advantages of the invention will be apparent from the following detailed description and from the claims. While the invention is described in connection with specific embodiments, it will be understood that other changes and modifications that may be practiced are also part of this invention and are also within the scope of the appendant claims. This application is intended to cover any equivalents, variations, uses, or adaptations of the invention that follow, in general, the principles of the invention, including departures from the present disclosure that come within known or customary practice within the art. Additional guidance with respect to making and using nucleic acids and polypeptides is found in standard textbooks of molecular biology, protein science, and immunology (see, e.g., Davis et al., *Basic Methods in Molecular Biology*, Elsevir Sciences Publishing, Inc., New York, N.Y., 1986; Hames et al., *Nucleic Acid Hybridization*, IL Press, 1985; *Molecular Cloning*, Sambrook et al., *Current Protocols in Molecular Biology*, Eds. Ausubel et al., John Wiley and Sons; *Current Protocols in Human Genetics*, Eds. Dracopoli et al., John Wiley and Sons; *Current Protocols in Protein Science*, Eds. John E. Coligan et al., John Wiley and Sons; and *Current Protocols in Immunology*, Eds. John E. Coligan et al., John Wiley and Sons). All publications mentioned herein are incorporated by reference in their entireties.

DETAILED DESCRIPTION

Figure 1:
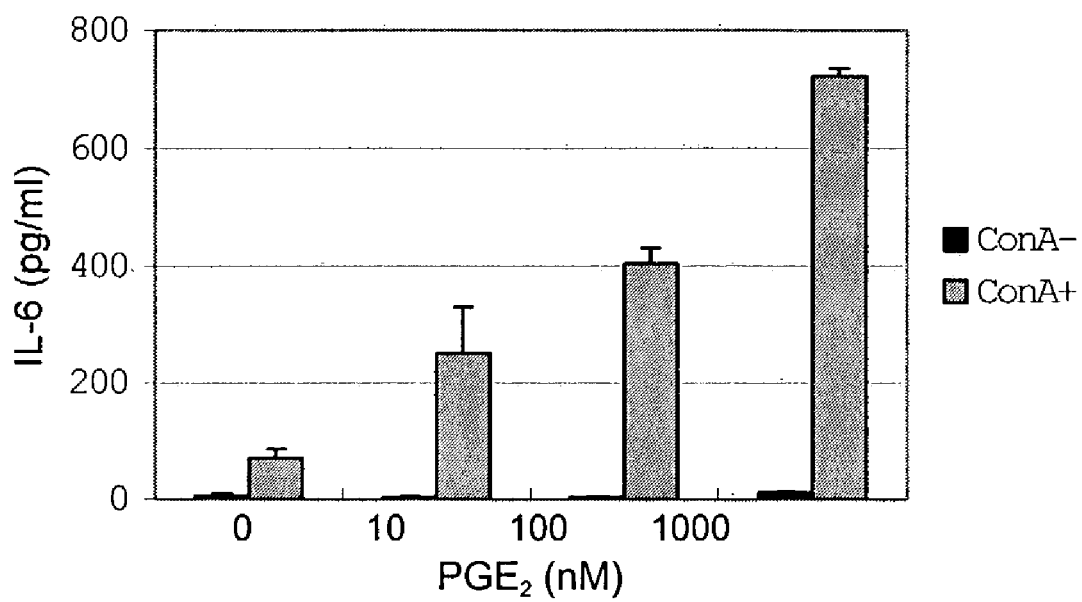
FIG. 1 is a bar graph showing IL-6 secretion stimulated by PGE2 in ConA-treated human PBMC (shaded bar) and in ConA-untreated human PBMC (filled bar).

The present invention is directed to the use of an EP4 receptor ligand in the manufacture of a medicament for the treatment of IL-6 involved diseases. This invention is based upon the discovery that EP4 knockout mice are relatively resistant to developing symptoms of arthritis subsequent to disease induction with administration of an anti-type II collagen antibody (an experimental model for rheumatoid arthritis). The invention also features screening methods to identify agents that inhibit EP4 activity in vivo for use, for example, as anti-rheumatoid arthritis therapeutics.

Therapeutic Methods

Agents identified as EP4 receptor ligands are administered in a dose effective to treat IL-6 involved diseases selected from the group consisting of alcoholic cirrhosis, amyloidosis, atherosclerosis, cardiac disease, sclerosis and organ transplantation reactions. Such therapeutically effective amounts will be determined using routine optimization techniques that are dependent on the particular condition to be treated, the condition of the patient, the route of administration, the formulation, the judgment of the practitioner, and other factors evident to those skilled in the art in light of this disclosure.

An agent that inhibits EP4 activity can be incorporated into a therapeutic composition. Such EP4 receptor ligands can include small molecules, nucleic acids, e.g., EP4 antisense nucleic acids, amino acids, peptides, carbohydrates, and anti-EP4 antibodies. Preferably, such agents are combined with a pharmaceutically acceptable delivery vehicle or carrier. Examples of EP4 antibodies include, for example, polyclonal, monoclonal, humanized, anti-idiotypic, chimeric or single chain antibodies, Fab, F(ab')$_2$, and Fab expression library fragments, scFV molecules, and epitope-binding fragments thereof. An antisense oligonucleotide directed to the EP4 gene or MRNA to inhibit its expression is made according to standard techniques (see, e.g., Agrawal et al. *Methods in Molecular Biology:Protocols for Oligonucleotides and Analogs*, Vol. 20 (1993)).

As used herein, a pharmaceutically acceptable delivery vehicle includes solvents, dispersion media, coatings, antibacterial and antifungal agents, and isotonic and absorption delaying agents that are compatible with pharmaceutical administration. The vehicle may also include other active or inert components, and/or may be targeted to joint tissue by virtue of its composition.

A therapeutic composition is formulated to be compatible with its intended route of administration. Non-limiting examples of routes of administration include parenteral, e.g., intravenous, intradermal, subcutaneous, oral (e.g., by ingestion or inhalation), transdermal (topical), transmucosal, and rectal administration. Solutions or suspensions can be made as described in *Remington's Pharmaceutical Sciences*, (18$^{th}$ ed., Gennaro, ed., Mack Publishing Co., Easton, Pa., (1990)).

Therapeutic efficacy of such EP4 inhibitors can be determined in light of this disclosure by standard therapeutic procedures in cell cultures or experimental animals, e.g., for determining the ED$_{50}$ (the dose therapeutically effective in 50% of the population).

The data obtained from the cell culture assays and animal studies can be used in formulating a range of dosage for use in humans. The dosage may vary depending upon the formulation and the route of administration. For any EP4 inhibitor used in the method of the invention, the therapeutically effective dose can be estimated initially from cell culture assays. A dose may be formulated in animal models to achieve a circulating plasma concentration range that includes the IC$_{50}$ as determined in cell culture. Such information can be used to more accurately determine useful doses in humans. Levels in plasma may be measured, for example, by high performance liquid chromatography.

The skilled artisan will appreciate that certain factors may influence the dosage and timing required to effectively treat a mammal including, but not limited to, the severity of the disease or disorder, previous treatments, the general health and/or age of the mammal, and other diseases present. Moreover, treatment of a mammal with a therapeutically effective amount of an EP4 inhibitor can include a single treatment or, preferably, can include a series of treatments.

For anti-EP4 antibodies, the preferred dosage is generally 10 mg/kg to 20 mg/kg body weight. Generally, partially humanized antibodies and fully human antibodies have a longer half-life within the human body than other antibodies. Accordingly, lower dosages and less frequent administration are possible. Modifications such as lipidation can be used to stabilize antibodies and to enhance uptake and tissue penetration. A method for lipidation of antibodies is described in Cruikshank et al. (J. Acquired Immune Deficiency Syndromes Hum. Retrovirol. 14: 193, 1997).

EP4 receptor ligands (e.g., antagonists) that can be administered include those that are included within Formula I, as further described below, and as described in U.S. provisional application No. 60/241,825, filed Oct. 19, 2000, and in Akiyoshi et al., a U.S. non-provisional application filed on approximately Oct. 10, 2001 and entitled "Aryl or Heteroaryl Fused Imidazole Compounds as Anti-Inflammatory and Analgesic Agents," herein incorporated by reference. This has been published as WO 02/32900. The whole of the teaching of WO 02/32900 is incorporated by reference in the present application. Other EP4 inhibitors that can be administered include those disclosed in EP 0985663, WO 00/15608, WO 00/03980, WO 98/55468, WO 01/62708, WO 01/42281, WO 01/02855, WO 01/10426, WO 99/47497, WO 00/16760, WO 00/18744, WO 00/16760, WO 00/21532, WO 00/18405, EP 0855389, GB 2330307, GB 2342799, and GB 2075503.

The invention includes both general and specific disclosures of the above-mentioned references.

EXAMPLE A

PGE2 Stimulation of IL-6 Secretion in ConA-treated Human PBMC

Incubation of PBMC with 5 μg/ml of ConA for 24 hr enhanced secretion of IL-6 (FIG. 1). When PBMC cells were concurrently stimulated with ConA and various concentrations of PGE2 for 24 hr, IL-6 secretion was further enhanced 3.5-, 5.7-and 10.1-fold by 10, 100 and 1000 M PGE2, respectively, when compared with IL-6 secretion by ConA stimulation without PGE2 (FIG. 1). In contrast, in the ConA unstimulated PBMC, 10–1000 nM PGE2 application did not affect the secretion of IL-6.

PBMC were stimulated with 5 μg/ml of Con A alone or with 10 nM to 1000 nM PGE2 at 37° C. for 24 hr. The secreted IL-6 in culture medium was measured by ELISA. Data are expressed as mean±s.d.(FIG. 1)

Effects of EP4 Antagonists on the Secretion of IL-6 in PBMC

The PGE2 concentration-dependence of stimulation of IL-6 secretion by human PBMC without and with ConA-stimulation, and the inhibitory effect of Compound A. PBMC were stimulated with 5 μg/ml of Concanavalin A alone or with 10 nM to 1000 nM PGE2 at 37° C. in 5% $CO_2$ for 24 hr. To see the effect of Compound A, 50 μM of Compound A was added simultaneously with ConA and PGE2, and incubated for 24 hr. Data in parenthesis are expressed % control of mitocondrial dehydrogenase activity.(FIG. 2)

Figure 2:
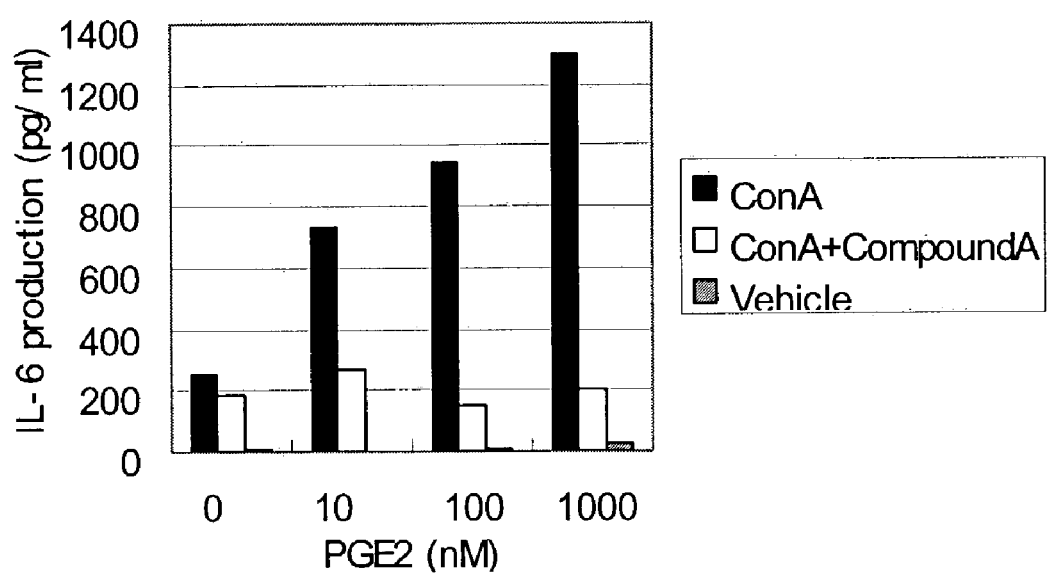
FIG. 2 is a graph showing the PGE2 concentration-dependence of stimulation of IL-6 secretion by human PBMC without and with ConA-stimulation, and the inhibitory effect of EP4 antagonist Compound A (N-[({2-[4-(2-ethyl-5,7-dimethyl-3H-imidazo[4,5-b]pyridin-3-yl)phenyl]ethyl}amino)carbonyl]-4-methylbenzenesulfonamide). In ConA-treated PBMC, Compound A significantly inhibited IL-6 secretion.
Figure 3:
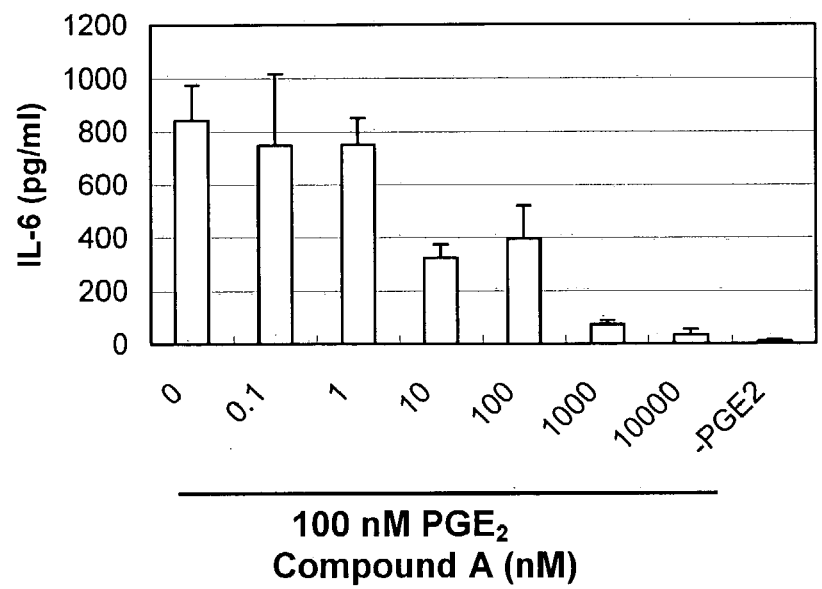
FIG. 3 is a bar graph showing the effects of EP4 antagonist Compound A and Compound B (3-{[(1S)-2-(4,5-diphenyl-1,3-oxazol-2-yl)-2-cyclohexen-1-yl]methyl}benzoic acid) in inhibiting the IL-6 secretion in ConA-treated PBMC.
Figure 3:
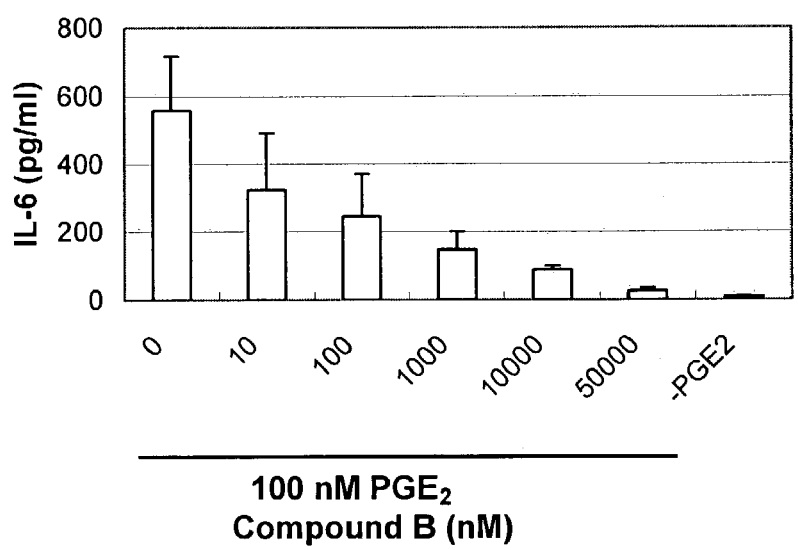

Compound A inhibited the IL-6 production enhanced by at all range of concentration of PGE2 (10–1000 nM) (FIG. 2). Simultaneously, to ensure 50 μM of Compound A is not toxic to PBMC, viable cells were checked after 24 hr incubation of PBMC by the colorimetric method with cell counting Kit. Compound A treated cells showed similar viability to that of untreated cells, suggesting that inhibitory effect of Compound A on IL-6 secretion is not due to cytotoxicity. FIG. 3 shows the dose response curve of Compound A and Compound B when PBMC were stimulated with 5 μg/ml ConA and 100 nM PGE2 for 24 hr. Both Compound A and Compound B dose dependently inhibited IL-6 production with IC50 values of 13 and 32 nM, respectively.

Compound A and Compound B inhibited the IL-6 secretion in ConA-treated PBMC. (FIG. 3.) PBMC were incubated with 5 μg/ml of Con A, 100 nM PGE2 and various doses of EP4 antagonists at 37° C. for 24 hr. The secreted IL-6 in culture medium was measured by ELISA. Data are expressed as mean±s.d.

EXAMPLE B

Preparation of Human Whole Blood (HWB) Cultures and Activation with PGE2

Figure 4:
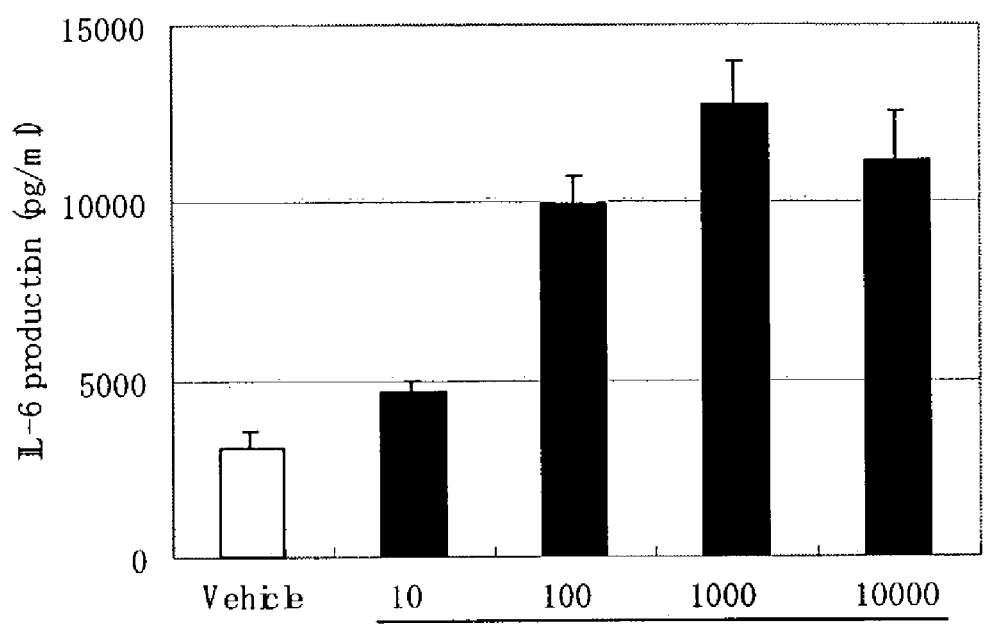
FIG. 4 is a graph showing the effect of PGE2 application to the human whole blood on the production of IL-6.

Methods:

Peripheral human whole blood (HWB) was collected from healthy volunteers into the sample tubes (nine volumes into one volume of 3.8% trisodium citrate, Becton Dickinson), and chilled at 4° C. until the experiment. HWB (50 μl) was put into the assay plate and mixed for 10 sec with plate mixer (intensity level at 4, TAITAC, Micromixer). The samples were placed for 3 min at room temperature, then 45 μl of AIM medium was added and mixed for 10 sec with plate mixer (intensity level at 4). The samples were placed for 3 min at room temperature. The mixture (100 μl) of 10–10000 nM PGE2 and 100 μM argatroban were added to the samples, and mixed for 10 seconds with plate mixer (intensity level at 4). The samples were incubated in 5% CO2 at 37° C. for 24 hrs. Then, the samples were stirred and centrifuged at 200 g for 10 minutes. The supernatants were collected, and the IL-6 concentration was measured by ELISA-Kit (Cyto screen). The results of this experiment are shown in FIG. 4.

Results:

In this experiment, we have established PGE2-induced IL-6 production assay using human whole blood (HWB). To prevent fibrin synthesis, argatroban, a thrombin inhibitor, was added to the culture samples. The addition of 100 μM argatroban inhibited the fibrin formation in the blood samples during 24 hrs incubation, and did not affect the amount of IL-6 production. In this condition, when blood samples were stimulated with 10, 100 and 1000 nM of PGE2, the IL-6 concentrations in the assay mixtures were 1.5~10 ng/ml, 3~15 ng/ml and 4.5~20 ng/ml, respectively (FIG. 4). Diluted human whole blood samples were stimulated with 10–10,000 nM of PGE2 and incubated at 37° C. for 24 hrs. The IL-6 concentration in the supernatant was determined by ELISA. The results represented the mean±s.d. from one representative experiment performed in triplicate.

EXAMPLE C

Effects of EP Agonists on the Production of IL-6 in HWB

Methods:

Peripheral human whole blood (HWB) was collected from healthy volunteers into the sample tubes (nine volumes into one volume of 3.8% trisodium citrate, Becton Dickinson), and chilled at 4° C. until the experiment. TVVB (50 μl) was put into the assay plate and mixed for 10 sec with plate mixer (intensity level at 4, TAITAC, Micromixer). The samples were placed for 3 min at room temperature, then 45 μl of AIM medium was added and mixed for 10 sec with plate mixer (intensity level at 4). The samples were placed for 3 min at room temperature. The mixture (100 μl) of 10–10000 nM each EP agonist and 100 μM argatroban were added to the samples, and mixed for 10 sec with plate mixer (intensity level at 4). The samples were incubated in 5% CO2 at 37° C. for 24 hrs. Then, the samples were stirred and centrifuged at 200 g for 10 minutes. The supernatants were collected, and the IL-6 concentration was measured by ELISA-Kit (Cyto screen).

Figure 5:
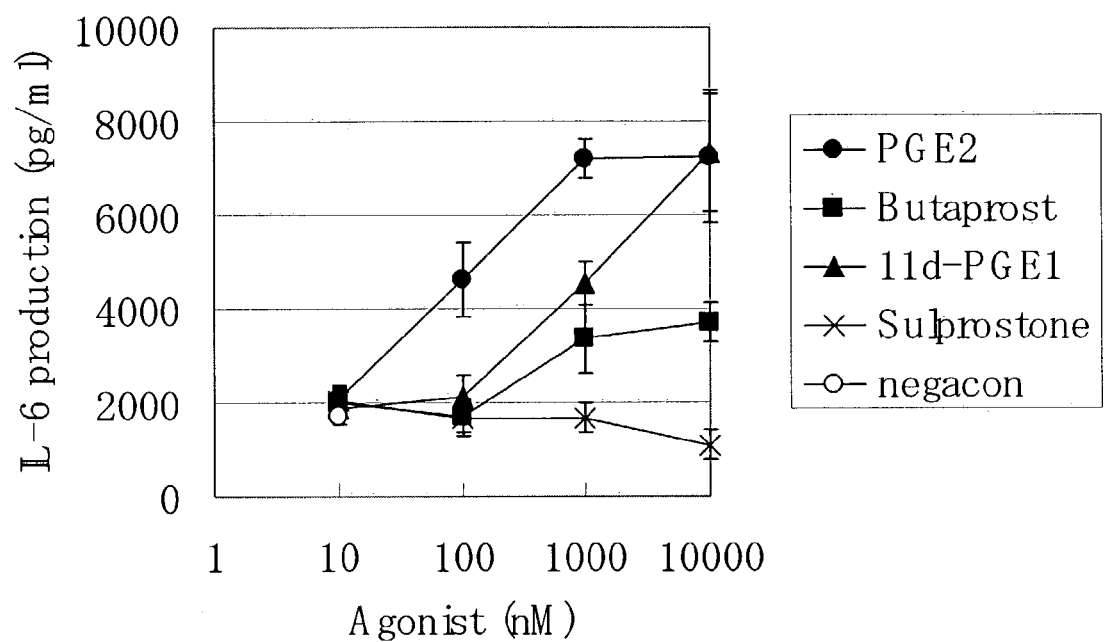
FIG. 5 is a graph showing the effects of EP2 (butaprost), EP4 (11-deoxy-PGE1) and EP1/EP3 (sulprostone) agonists on the production of IL-6 in HWB.

Results:

The application of 1–10 μM Butaprost, an EP2 agonist, enhanced IL-6 production (FIG. 5). 11-deoxy-PGE1 (1–10 μM), an EP4 agonist, enhanced IL-6 production, whereas sulprostone (EP1/EP3 agonist) did not up to a concentration of 10 μM (FIG. 5). Effects of EP2 (butaprost), EP4 (11-deoxy-PGE1) and EP1/EP3 (sulprostone) agonists on the production of IL-6 in HWB was measured respectively. Each agonist was added to the HWB, and incubated in 5% $CO_2$ at 37° C. for 24 hrs. The results represented the mean±s.d. of the results in triplicate. This experiment was performed for the samples from 3 people, and obtained similar results from 3 people.

EXAMPLE D

Effects of EP4 Antagonist on the Production of IL-6 in PGE2-stimulated HWB

Materials and methods:

Peripheral human whole blood (HWB) was collected from healthy volunteers into the sampling tubes (nine volumes into one volume of 3.8% trisodium citrate, Becton Dickinson), and chilled at 4° C. until the experiment. Compound B(5 μl) or vehicle (AIM medium containing 0.2% DMSO) was added into 96-well culture plates. HWB (50 μl) was put into the assay plate and mixed for 10 sec with plate mixer (intensity level at 4, TAITAC, Micromixer). The samples were placed for 3 min at room temperature, and then 45 μl of AIM medium was added and mixed for 10 sec with plate mixer (intensity level at 4). The samples were placed for 3 min at room temperature. The mixture (100 μl) of 100 nM PGE2 and 100 μM argatroban was added to the samples, and mixed for 10 sec with plate mixer (intensity level at 4). The samples were incubated in 5% CO2 at 37° C. for 24 hrs. Then, the samples were stirred and centrifuged at 200 g for 10 minutes. The supernatants were collected, and the IL-6 concentration was measured by ELISA-Kit (Cyto screen).

Figure 6:
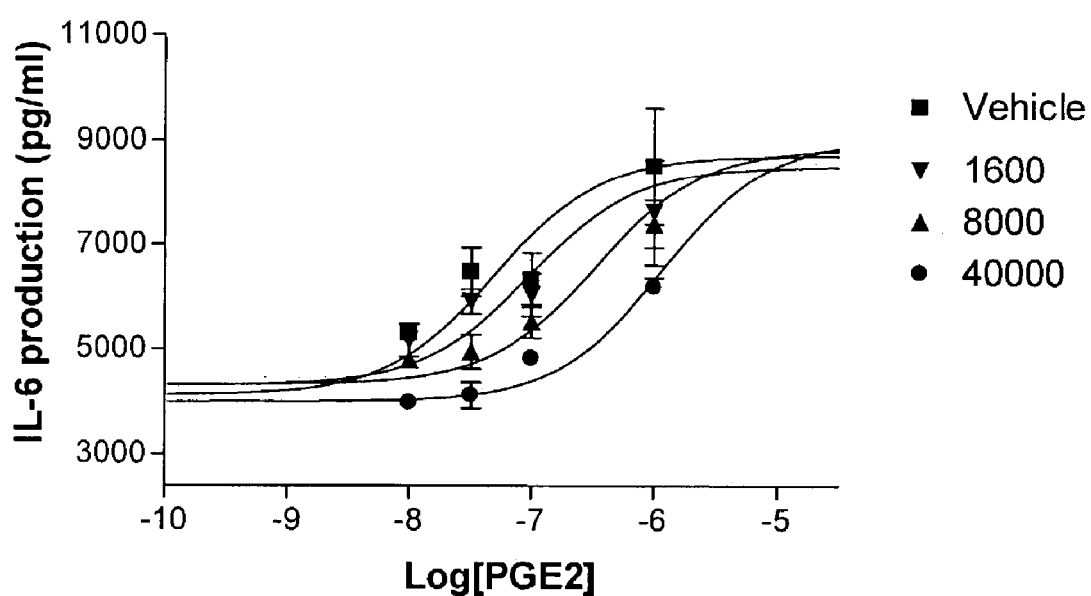
FIG. 6 is a graph showing the effect of Compound B (320–40,000 nM) on the IL-6 production in PGE2-stimulated HWB.

Results:

Compound B inhibited the PGE2-stimulated IL-6 production in a dose dependent manner (FIG. 6). Diluted human whole blood samples containing Compound B were stimulated with 10–10,000 nM of PGE2 and incubated at 37° C. for 24 hrs. The IL-6 concentration in the supernatant was determined by ELISA. The results represented the mean±s.d. from one representative experiment performed in triplicate.

EXAMPLE E

The IL-6 Production in ConA and PGE2 Co-stimulated Human Whole Blood

Methods:

Compound B (50 μl), ConA and PGE2 (50 μl, 1:1) were diluted with the AIM medium (Gibco) in the appropriate concentrations (conc.) and were placed onto 96-well culture plates (assay plates). Peripheral blood was collected from healthy volunteers (nine volumes into one volume of 3.8% trisodium citrate, Becton Dickinson). Human whole-blood samples were diluted with the same volume of AIM medium, and 100 μl of diluted-blood samples were place onto the assay plates. The final DMSO conc. of assay mixtures was 0.25%. The assay mixtures were incubated in 5% CO2 at 37° C. for 24 hrs. Then, the assay mixtures were stirred and centrifuged at 200 g for 10 minutes. The supernatants were collected, and the IL-6 concentration was measured by ELISA-Kit (Cyto screen).

Figure 7:
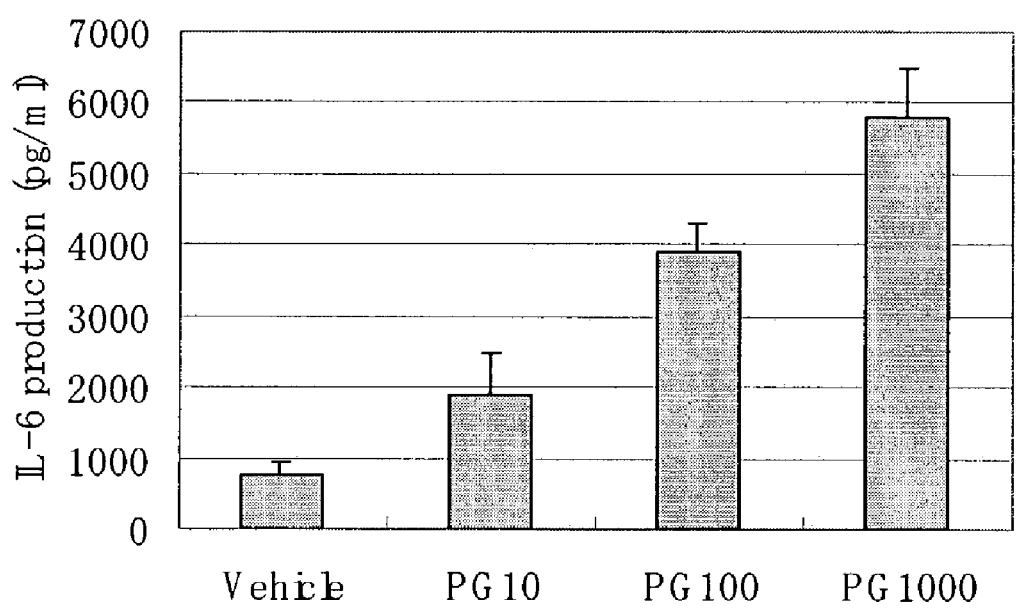
FIG. 7 is a graph showing the effect of PGE2 on the production of IL-6 in ConA-stimulated human whole blood (HWB).
Figure 8:
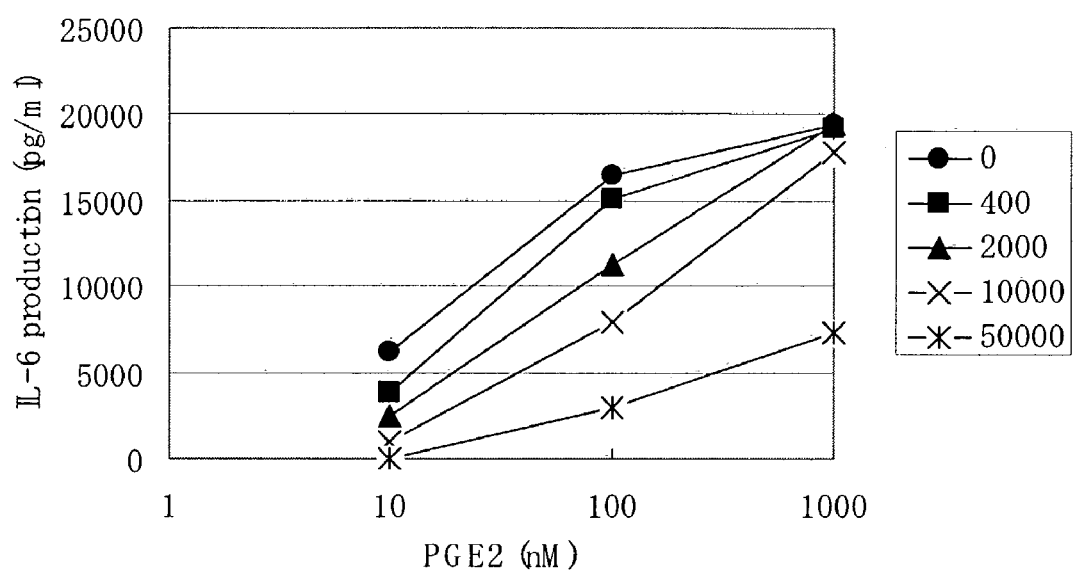
FIG. 8 is a graph showing the effect of Compound C (N-[({2-[4-(5-acetyl-2-ethyl-1H-benzimidazol-1-yl)phenyl]ethyl}amino)carbonyl]-4-methylbenzenesulfonamide) (16–50,000 nM) on IL-6 production in ConA and PGE2 co-stimulated HWB.

Results:

PGE2 enhanced IL-6 production dose dependently from 10 to 1000 nM (FIG. 7). When blood samples were stimulated with 10, 100 and 1000 nM of PGE2, the IL-6 concentrations in the assay mixtures were 1.8~10.8 ng/ml, 4~20 ng/ml and 5.8~23 ng/ml, respectively. The concentrations of PGE2 (10–1000 nM) gave sufficient IL-6 production to determine the IC50s of the EP4 antagonists. Of primary importance among these findings is the fact that Compound C showed dose-dependent inhibition (FIG. 8). Compound C inhibited IL-6 production competitively with PGE2. The pA2 values of Compound C in the three people were 6.3, 6.4 and 7.1. Diluted human whole-blood samples were stimulated with 5 μg/ml of ConA and three different concentrations of PGE2 (10–1000 nM). The IL-6 concentration in the supernatant was determined after 24 hrs of incubation at 37° C. Diluted human whole blood was co-stimulated with 5 μg/ml of ConA and 100 nM of PGE2 and incubated at 37° C. for 24 hrs. The IL-6 concentration in the supernatant was determined by ELISA.

Pharmaceutically acceptable salts of EP4 receptor ligands (e.g., antagonists) mentioned in this invention include the acid addition and base salts (including disalts) thereof.

Suitable acid addition salts are formed from acids which form non-toxic salts. Examples include the acetate, aspartate, benzoate, besylate, bicarbonate/carbonate, bisulphate, camsylate, citrate, edisylate, esylate, fumarate, gluceptate, gluconate, glucuronate, hibenzate, hydrochloride/chloride, hydrobromide/bromide, hydroiodide/iodide, hydrogen phosphate, isethionate, D-and L-lactate, malate, maleate, malonate, mesylate, methylsulphate, 2-napsylate, nicotinate, nitrate, orotate, palmoate, phosphate, saccharate, stearate, succinate sulphate, D- and L-tartrate, and tosylate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see Stahl and Wermuth, Handbook of Pharmaceutical Salts: Properties, Selection, and Use, Wiley-VCH, Weinheim, Germany (2002). A pharmaceutically acceptable salt of EP4 receptor ligands (e.g., antagonists) mentioned in this invention may be readily prepared by mixing together solutions of the EP4 receptor ligands (e.g., antagonists) mentioned in this invention and the desired acid or base, as appropriate. The salt may precipitate from solution and be collected by filtration or may be recovered by evaporation of the solvent.

Pharmaceutically acceptable solvates in accordance with the invention include hydrates and solvates wherein the solvent of crystallization may be isotopically substituted, e.g. $D_2O$, $d_6$-acetone, $d_6$-DMSO.

Also within the scope of the invention are clathrates, drug-host inclusion complexes wherein, in contrast to the aforementioned solvates, the drug and host are present in non-stoichiometric amounts. For a review of such complexes, see J Pharm Sci, 64 (8), 1269–1288 by Haleblian (August 1975).

Hereinafter all references to EP4 receptor ligands (e.g., antagonists) mentioned in this invention include references to salts thereof and to solvates and clathrates of EP4 receptor ligands (e.g., antagonists) mentioned in this invention and salts thereof.

The invention includes all polymorphs of the EP4 receptor ligands (e.g., antagonists) mentioned in this invention as hereinbefore defined.

Also within the scope of the invention are so-called "prodrugs" of the EP4 receptor ligands (e.g., antagonists) mentioned in this invention. Thus certain derivatives of EP4 receptor ligands (e.g., antagonists) mentioned in this invention which have little or no pharmacological activity themselves can, when metabolised upon administration into or onto the body, give rise to EP4 receptor ligands (e.g., antagonists) mentioned in this invention having the desired activity. Such derivatives are referred to as "prodrugs".

Prodrugs in accordance with the invention can, for example, be produced by replacing appropriate functionalities present in the EP4 receptor ligands (e.g., antagonists) mentioned in this invention with certain moieties known to those skilled in the art as "pro-moieties" as described, for example, in "Design of Prodrugs" by H Bundgaard (Elsevier, 1985).

Finally, certain EP4 receptor ligands (e.g., antagonists) mentioned in this invention may themselves act as prodrugs of other EP4 receptor ligands (e.g., antagonists) mentioned in this invention.

EP4 receptor ligands (e.g., antagonists) mentioned in this invention containing one or more asymmetric carbon atoms can exist as two or more optical isomers. Where EP4 receptor ligands (e.g., antagonists) mentioned in this invention contain an alkenyl or alkenylene group, geometric cis/trans (or Z/E) isomers are possible, and where the EP4 receptor ligands (e.g., antagonists) mentioned in this invention contain, for example, a keto or oxime group, tautomeric isomerism ('tautomerism') may occur. It follows that a single compound may exhibit more than one type of isomerism.

Included within the scope of the present invention are all optical isomers, geometric isomers and tautomeric forms of the EP4 receptor ligands (e.g., antagonists) mentioned in this invention, including compounds exhibiting more than one type of isomerism, and mixtures of one or more thereof.

Cis/trans isomers may be separated by conventional techniques well known to those skilled in the art, for example, fractional crystallisation and chromatography.

Conventional techniques for the preparation/isolation of individual stereoisomers include the conversion of a suitable optically pure precursor, resolution of the racemate (or the racemate of a salt or derivative) using, for example, chiral HPLC, or fractional crystallisation of diastereoisomeric salts formed by reaction of the racemate with a suitable optically active acid or base, for example, tartaric acid.

The present invention also includes all pharmaceutically acceptable isotopic variations of EP4 receptor ligands (e.g., antagonists) mentioned in this invention. An isotopic variation is defined as one in which at least one atom is replaced by an atom having the same atomic number, but an atomic mass different from the atomic mass usually found in nature.

Examples of isotopes suitable for inclusion in the EP4 receptor ligands (e.g., antagonists) mentioned in this invention include isotopes of hydrogen, such as $^2$H and $^3$H, carbon, such as $^{13}$C and $^{14}$C, nitrogen, such as $^{15}$N, oxygen, such as $^{17}$O and $^{18}$O, phosphorus, such as $^{32}$P, sulphur, such as $^{35}$S, fluorine, such as $^{18}$F, and chlorine, such as $^{36}$Cl.

Substitution of the EP4 receptor ligands (e.g., antagonists) mentioned in this invention with isotopes such as deuterium, i.e. $^2$H, may afford certain therapeutic advantages resulting from greater metabolic stability, for example, increased in vivo half-life or reduced dosage requirements, and hence may be preferred in some circumstances.

Certain isotopic variations of the EP4 receptor ligands (e.g., antagonists) mentioned in this invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Isotopic variations of EP4 receptor ligands (e.g., antagonists) mentioned in this invention can generally be prepared by conventional techniques known to those skilled in the art or by processes analogous to those described in the accompanying Examples and Preparations using appropriate isotopic variations of suitable reagents.

EP4 receptor ligands (e.g., antagonists) mentioned in this invention may be freeze-dried, spray-dried, or evaporatively dried to provide a solid plug, powder, or film of crystalline or amorphous material. Microwave or radio frequency drying may be used for this purpose.

EP4 receptor ligands (e.g., antagonists) mentioned in this invention may be administered alone or in combination with other drugs and will generally be administered as a formulation in association with one or more pharmaceutically acceptable excipients. Examples of such drugs are a COX-2 selective, COX-1 selective or non-selective NSAID(nonsteroidal anti-inflammatory drug), opioid, anticonvulsant, antidepressant, local anesthetic, disease-modifying anti-rheumatoid drug, or steroid. The combination with a COX-2 selective NSAID is particularly favoured for use in the prophylaxis and treatment of pain, arthritis, alcoholic cirrhosis, amyloidosis, atherosclerosis, cardiac disease such as angina pectoris, myocardial infarction, myocardiopathy and myocarditis, sclerosis such as multiple sclerosis, and organ transplantation reactions. Examples of a COX-2 selective NSAID are nimesulide, celecoxib, rofecoxib and valdecoxib. The term "excipient" is used herein to describe any ingredient other than EP4 receptor ligands (e.g., antagonists) mentioned in this invention. The choice of excipient will to a large extent depend on the particular mode of administration.

Oral Administration

EP4 receptor ligands (e.g., antagonists) mentioned in this invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, propylene glycol, methylcellulose, or a suitable oil, and one or more emulsifying agents and/or suspending agencs. Liquid formulations may also be prepared by the reconstitution of a solid, for example, from a sachet.

EP4 receptor ligands (e.g., antagonists) mentioned in this invention may also be used in fast-dissolving, fast-disintegrating dosage forms such as those described in Expert Opinion in Therapeutic Patents, 11 (6), 981–986 by Liang and Chen (2001).

The composition of a typical tablet in accordance with the invention may comprise:

| Ingredient | % w/w |
| --- | --- |
| EP4 receptor ligands (e.g., antagonists) mentioned in this invention | 10.00* |
| Microcrystalline cellulose | 64.12 |
| Lactose | 21.38 |
| Croscarmellose sodium | 3.00 |
| Magnesium stearate | 1.50 |

*Quantity adjusted in accordance with drug activity.

A typical tablet may be prepared using standard processes known to a formulation chemist, for example, by direct compression, granulation (dry, wet, or melt), melt congealing, or extrusion. The tablet formulation may comprise one or more layers and may be coated or uncoated.

Examples of excipients suitable for oral administration include carriers, for example, cellulose, calcium carbonate, dibasic calcium phosphate, mannitol and sodium citrate, granulation binders, for example, polyvinylpyrrolidine, hydroxypropylcellulose, hydroxypropylmethylcellulose and gelatin, disintegrants, for example, sodium starch glycolate and silicates, lubricating agents, for example, magnesium stearate and stearic acid, wetting agents, for example, sodium lauryl sulphate, preservatives, anti-oxidants, flavours and colourants.

Solid formulations for oral administration may be formulated to be immediate and/or modified release. Modified release formulations include delayed-, sustained-, pulsed-, controlled dual-, targeted and programmed release. Details of suitable modified release technologies such as high energy dispersions, osmotic and coated particles are to be found in Verma et al, Pharmaceutical Technology On-line, 25(2), 1–14 (2001). Other modified release formulations are described in U.S. Pat. No. 6,106,864.

Parenteral Administration

EP4 receptor ligands (e.g., antagonists) mentioned in this invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilisation, may readily be accomplished using standard pharmaceutical techniques well known to those skilled in the art.

The solubility of EP4 receptor ligands (e.g., antagonists) mentioned in this invention used in the preparation of parenteral solutions may be increased by suitable processing, for example, the use of high energy spray-dried dispersions (see WO 01/47495) and/or by the use of appropriate formulation techniques, such as the use of solubility-enhancing agents.

Formulations for parenteral administration may be formulated to be immediate and/or modified release. Modified release formulations include delayed-, sustained-, pulsed-, controlled dual-, targeted and programmed release.

Topical Administration

EP4 receptor ligands (e.g., antagonists) mentioned in this invention may also be administered topically to the skin or mucosa, either dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin and propylene glycol. Penetration enhancers may be incorporated—see, for example, J Pharm Sci, 88 (10), 955–958 by Finnin and Morgan (October 1999).

Other means of topical administration include delivery by iontophoresis, electroporation, phonophoresis, sonophoresis and needle-free or microneedle injection.

Formulations for topical administration may be formulated to be immediate and/or modified release. Modified release formulations include delayed-, sustained-, pulsed-, controlled dual-, targeted and programmed release. Thus EP4 receptor ligands (e.g., antagonists) mentioned in this invention may be formulated in a more solid form for administration as an implanted depot providing long-term release of the active compound.

Inhaled/Intranasal Administration

EP4 receptor ligands (e.g., antagonists) mentioned in this invention can also be administered intranasally or by inhalation, typically in the form of a dry powder (either alone, as a mixture, for example, in a dry blend with lactose, or as a mixed component particle, for example, mixed with phospholipids) from a dry powder inhaler or as an aerosol spray from a pressurised container, pump, spray, atomiser (preferably an atomiser using electrohydrodynamics to produce a fine mist), or nebuliser, with or without the use of a suitable propellant, such as dichlorofluoromethane.

The pressurised container, pump, spray, atomizer, or nebuliser contains a solution or suspension of the active compound comprising, for example, ethanol (optionally, aqueous ethanol) or a suitable alternative agent for dispersing, solubilising, or extending release of the active, the propellant(s) as solvent and an optional surfactant, such as sorbitan trioleate or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

A suitable solution formulation for use in an atomiser using electrohydrodynamics to produce a fine mist may contain from 1 µg to 10 mg of EP4 receptor ligands (e.g., antagonists) mentioned in this invention per actuation and the actuation volume may vary from 1 µl to 100 µl. A typical formulation may comprise EP4 receptor ligands (e.g., antagonists) mentioned in this invention, propylene glycol, sterile water, ethanol and sodium chloride. Alternative solvents which may be used instead of propylene glycol include glycerol and polyethylene glycol.

Capsules, blisters and cartridges (made, for example, from gelatin or HPMC) for use in an inhaler or insufflator may be formulated to contain a powder mix of EP4 receptor ligands (e.g., antagonists) mentioned in this invention, a suitable powder base such as lactose or starch and a performance modifier such as l-leucine, mannitol, or magnesium stearate.

In the case of dry powder inhalers and aerosols, the dosage unit is determined by means of a valve which delivers a metered amount. Units in accordance with the invention are typically arranged to administer a metered dose or "puff".

Formulations for inhaled/intranasal administration may be formulated to be immediate and/or modified release. Modified release formulations include delayed-, sustained-, pulsed-, controlled dual-, targeted and programmed release.

Rectal/Intravaginal Administration

EP4 receptor ligands (e.g., antagonists) mentioned in this invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled dual-, targeted and programmed release.

Ocular/Andial Administration

EP4 receptor ligands (e.g., antagonists) mentioned in this invention may also be administered directly to the eye or ear, typically in the form of drops of a micronised suspension or solution in isotonic, pH-adjusted, sterile saline. Other formulations suitable for ocular and andial administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/andial administration may be formulated to be immediate and/or modified release. Modified release formulations include delayed-, sustained-, pulsed-, controlled dual-, targeted, or programmed release.

Enabling Technologies

EP4 receptor ligands (e.g., antagonists) mentioned in this invention may be combined with soluble macromolecular entities such as cyclodextrin or polyethylene glycol-containing polymers to improve their solubility, dissolution rate, taste-masking, bioavailability and/or stability. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Dosage

EP4 receptor ligands (e.g., antagonists) mentioned in this invention can be administered via either the oral, parenteral or topical routes to mammals. In general, these compounds are most desirably administered to humans in doses ranging from 0.1 mg to 3000 mg, preferably from 1 mg to 500 mg, which may be administered in a single dose or in divided doses throughout the day, although variations will necessarily occur depending upon the weight and condition of the subject being treated, the disease state being treated and the particular route of administration chosen.

These dosages are based on an average human subject having a weight of about 65 to 70 kg. The physician will readily be able to determine doses for subjects whose weight falls outside this range, such as infants and the elderly.

For example, a dosage level that is in the range of from 0.01 mg to 10 mg per kg of body weight per day is most desirably employed for treatment of pain associated with inflammation.

EP4 Antagonists: Aryl and Heteroaryl Fused Imidazole Compounds of Formula I

Aryl and heteroaryl fused imidazole compounds of Formula I have the following formula:

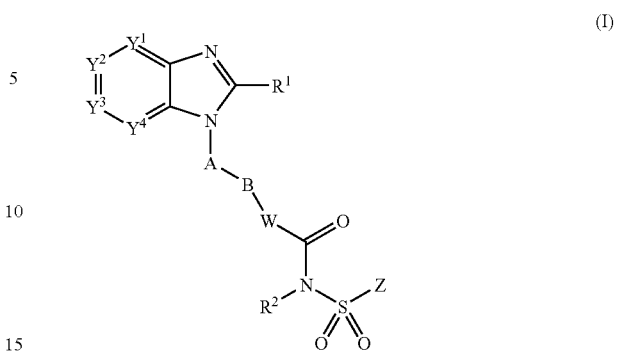

or a pharmaceutically acceptable salt thereof.

In the compounds of Formula I, $Y^1$, $Y^2$, $Y^3$, and $Y^4$ are preferably independently selected from N, CH and C(L);

L is halo, $C_{1-4}$ alkyl, halo-substituted $C_{1-4}$ alkyl, hydroxy, $C_{1-4}$ alkoxy, mono- or di-($C_{1-4}$ alkyl)amino, halo-substituted $C_{1-4}$ alkoxy, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3C(=O)N(R^4)$—, $R^3N(R^4)C(=O)$—, $R^3N(R^4)S(O)m$-, $Q^2$-, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0 or 2;

$R^3$ and $R^4$ are independently selected from H and $C_{1-4}$ alkyl; and $Q^2$ is a 5–12 membered monocyclic or bicyclic aromatic ring, or a 8–12 membered tricyclic ring optionally containing up to 3 heteroatoms selected from O, N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkyl-(O=)C—, $R^3(R^4)C(=O)N$—, HO(O=)C—, $C_{1-4}$ alkyl-O(O=)C—, $C_{1-4}$ alkylsulfonylamino, $C_{3-7}$ cycloalkyl or $C_{1-4}$ alkyl-C(=O)NH—, more preferably $Y^1$, $Y^2$, $Y^3$, and $Y^4$ are independently selected from N, CH and C(L);

L is halo, $C_{1-4}$ alkyl, halo-substituted $C_{1-4}$ alkyl, hydroxy, $C_{1-4}$ alkoxy, mono- or di-($C_{1-4}$ alkyl)amino, halo-substituted $C_{1-4}$ alkoxy, cyano, HO—$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3C(=O)N(R^4)$—, $R^3N(R^4)C(=O)$—, $R^3N(R^4)S(O)m$-, $Q^2$-, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0 or 2;

$R^3$ and $R^4$ are independently selected from H and $C_{1-4}$ alkyl; and $Q^2$ is a 5 or 6 membered monocyclic aromatic ring, or a 8–12 membered tricyclic ring containing up to 3 heteroatoms selected from N and S, wherein said 5 or 6 membered monocyclic aromatic ring is optionally substituted with halo, more preferably $Y^1$, $Y^2$, $Y^3$, and $Y^4$ are independently selected from N, CH and C(L);

m is 0 or 2;

$R^3$ and $R^4$ are independently selected from H and $C_{1-4}$ alkyl; and $Q^2$ is 5 or 6 membered monocyclic aromatic ring or a 8–12 membered tricyclic ring optionally containing 1 sulfur atom wherein said 5 or 6 membered monocyclic aromatic ring is optionally substituted with halo, more preferably $Y^1$, $Y^2$, $Y^3$, and $Y^4$ are independently selected from N, CH and C(L);

L is halo, $C_{1-4}$ alkyl, halo-substituted $C_{1-4}$ alkyl, hydroxy, $C_{1-4}$ alkoxy, halo-substituted $C_{1-4}$ alkoxy, cyano, HO—$C_{1-4}$ alkyl, acetyl, $R^3N(R^4)C(=O)$—, $R^3N(R^4)S(O)$m-, $Q^2$-, $Q^2$-C(=O)—, $Q^2$-O—, $Q^2$-$C_{1-4}$alkyl-O—, or two adjacent L groups are joined together to form a methylenedioxy group;

$R^3$ and $R^4$ are independently selected from H and $C_{1-4}$ alkyl; and $Q^2$ is 5 or 6 membered monocyclic aromatic ring system, more preferably $Y^1$, $Y^2$, $Y^3$, and $Y^4$ are independently selected from N, CH and C-L;

L is chloro, methyl, trifuluoromethyl, hydroxy, methoxy, cyano, acetyl, —C(=O)NH$_2$, trifuluoromethyloxy, methanesulfonyl, or 1-hydroxy-1-methyl-ethyl, or two adjacent L groups are joined together to form a methylenedioxy group, more preferably $Y^1$, $Y^2$, $Y^3$ and $Y^4$ are selected from the group consisting of a) $Y^1$ and $Y^3$ are C(L), $Y^2$ is CH and $Y^4$ is N;
b) $Y^1$ is CH, $Y^2$ and $Y^3$ are C(L) and $Y^4$ is N;
c) $Y^1$, $Y^2$ and $Y^3$ are C(L) and $Y^4$ is N;
d) $Y^1$ and $Y^3$ are C(L), $Y^2$ is N and $Y^4$ is CH;
e) $Y^1$ is C(L) and $Y^2$, $Y^3$ and $Y^4$ are CH;
f) $Y^1$, $Y^3$ and $Y^4$ are CH, and $Y^2$ is C(L);
g) $Y^1$, $Y^2$ and $Y^3$ are CH, and $Y^4$ is C(L);
h) $Y^1$ and $Y^2$ are C(L), and $Y^3$ and $Y^4$ are CH;
i) $Y^1$ and $Y^3$ are C(L), and $Y^2$ and $Y^4$ are CH;
j) $Y^1$ and $Y^4$ are CH, and $Y^2$ and $Y^3$ are C(L);
k) $Y^1$ and $Y^2$ are CH, $Y^3$ is C(L) and $Y^4$ is N;
l) $Y^1$ and $Y^3$ are CH, $Y^2$ is C(L) and $Y^4$ is N;
m) $Y^1$, $Y^2$, $Y^3$ and $Y^4$ are CH;
n) $Y^1$ and $Y^2$ are C(L), $Y^3$ is CH and $Y^4$ is N;
o) $Y^1$, $Y^2$ and $Y^4$ are CH, and $Y^3$ is C(L);
p) $Y^1$ and $Y^2$ are C(L), $Y^3$ is N and $Y^4$ is CH;
q) $Y^1$ and $Y^3$ are C(L), and $Y^2$ and $Y^4$ are N;
r) $Y^1$ is C(L), $Y^2$ and $Y^3$ are CH, and $Y^4$ is N;
s) $Y^2$ is C(L), $Y^1$ and $Y^3$ are CH, and $Y^4$ is N; and
t) $Y^1$, $Y^2$ and $Y^3$ are C(L), and $Y^4$ is CH L is chloro, methyl, trifuluoromethyl, hydroxy, methoxy, cyano, acetyl, —C(=O)NH$_2$, trifuluoromethyloxy, methanesulfonyl, or 1-hydroxy-1-methyl-ethyl, or two adjacent L groups are joined together to form a methylenedioxy group, most preferably $Y^1$, $Y^2$, $Y^3$ and $Y^4$ are selected from the group consisting of a) $Y^1$ and $Y^3$ are C(L), $Y^2$ is CH and $Y^4$ is N;
b) $Y^1$ is CH, $Y^2$ and $Y^3$ are C(L) and $Y^4$ is N;
c) $Y^1$, $Y^2$ and $Y^3$ are C(L) and $Y^4$ is N;
d) $Y^1$ and $Y^3$ are C(L), $Y^2$ is N and $Y^4$ is CH;
e) $Y^1$ is C(L) and $Y^2$, $Y^3$ and $Y^4$ are CH;
f) $Y^1$, $Y^3$ and $Y^4$ are CH, and $Y^2$ is C(L);
g) $Y^1$, $Y^2$ and $Y^3$ are CH, and $Y^4$ is C(L);
h) $Y^1$ and $Y^2$ are C(L), and $Y^3$ and $Y^4$ are CH;
i) $Y^1$ and $Y^3$ are C(L), and $Y^2$ and $Y^4$ are CH;
j) $Y^1$ and $Y^4$ are CH, and $Y^2$ and $Y^3$ are C(L); and
k) $Y^1$, $Y^2$ and $Y^3$ are C(L), and $Y^4$ is CH L is chloro, methyl, trifuluoromethyl, hydroxy, methoxy, cyano, acetyl, —C(=O)NH$_2$, trifuluoromethyloxy, methanesulfonyl, or 1-hydroxy-1-methyl-ethyl, or two adjacent L groups are joined together to form a methylenedioxy group.

In the compounds of Formula I, $R^1$ is preferably H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$-, pyrrolidinyl, piperidyl, oxopyrrolidinyl, oxopiperidyl, amino, mono- or di-($C_{1-8}$ alkyl)amino, $C_{1-4}$alkyl-C(=O)—N($R^3$)— or $C_{1-4}$alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$-, $Q^1$-C(=O)—, $Q^1$-O—, $Q^1$-S(O)m-, $Q^1$-$C_{1-4}$ alkyl-O—, $Q^1$-$C_{1-4}$ alkyl-S(O)m-, $Q^1$-$C_{1-4}$ alkyl-C(O)—N($R^3$)—, $Q^1$-$C_{1-4}$alkyl-N($R^3$)— or $C_{1-4}$alkyl-C(O)—N($R^3$)—;

$Q^1$ is a 5–12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$ alkylC(=O)—, HO(O=)C—, $C_{1-4}$ alkyl-O(O)C—, $R^3N(R^4)C(=O)$—, $C_{1-4}$ alkylsulfonylamino, $C_{3-7}$ cycloalkyl, $R^3C(=O)N(R^4)$— or NH$_2$(HN=)C—;

m is 0 or 2; and $R^3$ is H or $C_{1-4}$ alkyl, more preferably $R^1$ is H, $C_{1-8}$ alkyl, $C_{2-8}$ alkenyl, $C_{2-8}$ alkynyl, $C_{3-7}$ cycloalkyl, $Q^1$-, pyrrolidinyl, piperidyl, oxopyrrolidinyl, oxopiperidyl, amino, mono- or di-($C_{1-8}$ alkyl)amino, wherein said $C_{1-8}$ alkyl is optionally substituted with halo, $C^{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$-, $Q^1$-C(O)—, $Q^1$-O—, $Q^1$-S— or $Q^1$-$C_{1-4}$ alkyl-O—, or $C_{1-4}$alkyl-C(O)—N($R^3$)—;

$Q^1$ is a 5–12 membered monocyclic aromatic ring optionally containing up to 4 heteroatoms selected from N and S, and is optionally substituted with halo, $C_{1-4}$ alkyl, $C_{1-4}$ alkylsulfonyl and $C_{1-4}$ alkylC(=O)—; and m is 0 or 2, more preferably $R^1$ is H, $C_{1-8}$ alkyl, $C_{2-8}$ alkenyl, $C_{2-8}$ alkynyl, $C_{3-7}$ cycloalky, $Q^1$-, or mono- or di-($C_{1-8}$ alkyl)amino wherein said $C_{1-8}$ alkyl is optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$-, $Q^1$-C(=O)—, $Q^1$-O—, $Q^1$-S—, $Q^1$-$C_{1-4}$ alkyl-O—, or $C_{1-4}$alkyl-C(O)—N(H)—;

$Q^1$ is a 5 or 6 membered monocyclic aromatic ring optionally containing up to 4 heteroatoms selected from N and S; and m is 0 or 2, more preferably $R^1$ is $C_{1-5}$ alkyl, $C_{3-7}$ cycloalkyl, or $Q^1$-, mono- or di-($C_{1-8}$alkyl)amino wherein said $C_{1-5}$ alkyl is optionally substituted with $C_{1-3}$ alkyl, hydroxy, oxo, pyrrolidinyl, piperidyl, oxopyrrolidinyl, oxopiperidyl, $Q^1$-, or $C_{1-4}$alkyl-C(O)—N(H)—; and $Q^1$ is 5–12 membered monocyclic aromatic ring system optionally containing up to 2 heteroatoms selected from N and S, more preferably $R^1$ is $C_{1-5}$ alkyl, mono- or di-($C_{1-8}$ alkyl)amino, pyrrolidinyl, or pyridyl optionally substituted with $C_{1-3}$ alkyl, hydroxy, oxo, 5 or 6 membered monocyclic aromatic ring, wherein said 5 or 6 membered monocyclic aromatic ring is containing 1 or 2 heteroatoms selected from N and S, or $C_{1-4}$alkyl-C(O)—N(H)—, most preferably $R^1$ is methyl, ethyl, n-propyl, isopropyl, n-butyl, isobutyl, neopentyl, thiazolylethyl methylamino, dimethylamino, pyrrolidinyl, pyridyl, or 1-acetylamino-1-methylethyl.

In the compounds of Formula I, $R^2$ is preferably H or $C_{1-4}$ alkyl, most preferably H.

In the compounds of Formula I,

A is preferably a 5–6 membered monocyclic aromatic ring optionally containing up to 2 heteroatoms selected from O, N, and S, wherein said 5–6 membered monocyclic aromatic ring is optionally substituted with up to 2 substituents selected from halo, $C_{1-4}$ alkyl, halo-substituted $C_{1-4}$ alkyl, hydroxy, $C_{1-4}$ alkoxy and halo-substituted $C_{1-4}$ alkoxy, more preferably 5–6 membered mono cyclic aromatic ring optionally substituted with halo, $C_{1-4}$ alkyl or $C_{1-4}$ alkoxy, more preferably 5–6 membered monocyclic aromatic ring system optionally substituted with halo or $C_{1-4}$ alkyl, more preferably 5–6 membered monocyclic aromatic ring system, most preferably phenyl or pyridyl.

In the compounds of Formula I,

B is preferably $C_{3-7}$ cycloalkylene or $C_{1-6}$ alkylene optionally substituted with an oxo group or $C_{1-3}$ alkyl, more preferably $C_{1-3}$ alkylene optionally substituted with $C_{1-3}$ alkyl, more preferably $C_{1-2}$ alkylene optionally substituted with methyl, most preferably ethylene or propylene.

In the compounds of Formula I,

W is preferably NH, N—$C_{1-4}$ alkyl, O or N—OH, more preferably NH, N—$C_{1-2}$ alkyl or O, most preferably NH, N—$CH_3$ or O.

In the compounds of Formula I,

Z is preferably a 5–12 membered monocyclic or bicyclic aromatic ring optionally containing up to 3 heteroatoms selected from, N, O, and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, hydroxy, $C_{1-4}$ alkoxy, nitro, amino, cyano, HO—$C_{1-4}$ alkyl, $C_{1-4}$ alkylsulfonyl, aminosulfonyl, $C_{1-4}$ alkylC(=O)—, $R^3C(=O)N(R^4)$—, HO(O=)C—, $C_{1-4}$ alkyl-O(O=)C—, $C_{1-4}$ alkylsulfonylamino, $C_{1-4}$ alkyl-C(=O)NH—, $Q^2$-S(O)m-, $Q^2$-O—, $Q^2$-N($R^3$)— or $Q^2$-;

m is 0 or 2;

$R^3$ and $R^4$ are independently selected from H and $C_{1-4}$ alkyl; and $Q^2$ is a 5–12 membered monocyclic or bicyclic aromatic ring, or a 8–12 membered tricyclic ring optionally containing up to 3 heteroatoms selected from O, N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkoxy, nitro, amino, cyano, $R^3C(=O)N(R^4)$—, $C_{1-4}$ alkyl-O(O=)C—, $Q^2$-S(O)m-, $Q^2$-O—, $Q^2$-N($R^3$)— or $Q^2$-;

m is 0 or 2;

$R^3$ and $R^4$ are independently selected from H and $C_{1-4}$ alkyl; and $Q^2$ is a 5 or 6 membered monocyclic aromatic ring, or a 8–12 membered tricyclic ring containing up to 3 heteroatoms selected from N and S, wherein said 5 or 6 membered monocyclic aromatic ring is optionally substituted with halo, more preferably Z is 5–12 membered monocyclic or bicyclic aromatic ring optionally containing up to 3 heteroatoms selected from N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkoxy, nitro, amino, cyano, $R^3C(=O)N(R^4)$—, $C_{1-4}$ alkyl-O(O=)C—, $Q^2$-S(O)m-, $Q^2$-O—, $Q^2$-N($R^3$)— or $Q^2$-;

m is 0 or 2;

$R^3$ and $R^4$ are independently selected from H and $C_{1-4}$ alkyl; and $Q^2$ is 5 or 6 membered monocyclic aromatic ring or a 8–12 membered tricyclic ring optionally containing 1 sulfur atom wherein said 5 or 6 membered monocyclic aromatic ring is optionally substituted with halo, more preferably Z is 5–12 membered monocyclic or bicyclic aromatic ring optionally containing up to 3 heteroatoms selected from N and S, wherein said 5–12 membered monocyclic aromatic ring is optionally substituted with halo, $C_{1-4}$ alkyl, nitro, $R^3C(=O)N(R^4)$— or $Q^2$-;

$R^3$ and $R^4$ are independently selected from H and $C_{1-4}$ alkyl; and $Q^2$ is 5 or 6 membered monocyclic aromatic ring system, more preferably Z is 5–10 membered monocyclic or bicyclic aromatic ring optionally containing up to 3 heteroatoms selected from N and S, wherein said 5–10 membered monocyclic aromatic ring is optionally substituted with chloro, bromo, methyl, nitro, $CH_3C(=O)$NH—, tBuC(=O)NH— or phenyl, most preferably Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl.

One group of compounds of Formula I includes compounds wherein $Y^1$, $Y^2$, $Y^3$, and $Y^4$ are independently selected from N, CH and C(L);

$R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$-, pyrrolidinyl, piperidyl, oxopyrrolidinyl, oxopiperidyl, amino, mono- or di-($C_{1-8}$ alkyl)amino, $C_{1-4}$alkyl-C(=O)—N($R^3$)— or $C_{1-4}$alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$, $Q^1$-C(=O)—, $Q^1$-O—, $Q^1$-S(O)m-, $Q^1$-$C_{1-4}$ alkyl-O—, $Q^1$-$C_{1-4}$ alkyl-S(O)m-, $Q^1$-$C_{1-4}$ alkyl-C(=O)—N($R^3$)—, or $C_{1-4}$alkyl-C(=O)—N($R^3$)—;

$Q^1$ is a 5–12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$ alkylC(=O)—, HO(O=)C—, $C_{1-4}$ alkyl-O(O)C—, $R^3N(R^4)C(=O)-$, $C_{1-4}$ alkylsulfonylamino, $C_{3-7}$ cycloalkyl, $R^3C(=O)N(R^4)-$ or $NH_2(HN=)C-$;

A is a 5–6 membered monocyclic aromatic ring optionally containing up to 2 heteroatoms selected from O, N, and S, wherein said 5–6 membered monocyclic aromatic ring is optionally substituted with up to 2 substituents selected from halo, $C_{1-4}$ alkyl, halo-substituted $C_{1-4}$ alkyl, hydroxy, $C_{1-4}$ alkoxy and halo-substituted $C_{1-4}$ alkoxy;

B is $C_{3-7}$ cycloalkylene or $C_{1-6}$ alkylene optionally substituted with an oxo group or $C_{1-3}$ alkyl;

W is NH, N—$C_{1-4}$ alkyl, O or N—OH;

$R^2$ is H or $C_{1-4}$ alkyl;

Z is a 5–12 membered monocyclic or bicyclic aromatic ring optionally containing up to 3 heteroatoms selected from, N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, hydroxy, $C_{1-4}$ alkoxy, nitro, amino, cyano, HO—$C_{1-4}$ alkyl, $C_{1-4}$ alkylsulfonyl, aminosulfonyl, $C_{1-4}$ alkylC(=O)—, $R^3C(=O)N(R^4)-$, HO(O=)C—, $C_{1-4}$ alkyl-O(O=)C—, $C_{1-4}$ alkylsulfonylamino, $C_{1-4}$ alkyl-C(=O)NH—, $Q^2$-S(O)m-, $Q^2$-O—, $Q^2$-N($R^3$)— or $Q^2$-;

L is halo, $C_{1-4}$ alkyl, halo-substituted $C_{1-4}$ alkyl, hydroxy, $C_{1-4}$ alkoxy, mono- or di-($C_{1-4}$ alkyl)amino, halo-substituted $C_{1-4}$ alkoxy, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3C(=O)N(R^4)-$, $R^3N(R^4)C(=O)-$, $R^3N(R^4)S(O)m-$, $Q^2$-, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0 or 2;

$R^3$ and $R^4$ are independently selected from H and $C_{1-4}$ alkyl; and $Q^2$ is a 5–12 membered monocyclic or bicyclic aromatic ring, or a 8–12 membered tricyclic ring optionally containing up to 3 heteroatoms selected from O, N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkyl-(O=)C—, $R^3(R^4)C(=O)N-$, HO(O=)C—, $C_{1-4}$ alkyl-O(O=)C—, $C_{1-4}$ alkylsulfonylamino, $C_{3-7}$ cycloalkyl or $C_{1-4}$ alkyl-C(=O)NH—.

A further group of compounds of Formula I includes compounds wherein $Y^1$, $Y^2$, $Y^3$, and $Y^4$ are independently selected from N, CH and C(L);

$R^1$ is H, $C_{1-8}$ alkyl, $C_{2-8}$ alkenyl, $C_{2-8}$ alkynyl, $C_{3-7}$ cycloalkyl, $Q^1$-, pyrrolidinyl, oxopyrrolidinyl, oxopiperidyl, amino, mono- or di-($C_{1-8}$ alkyl)amino, wherein said $C_{1-8}$ alkyl is optionally substituted with halo, $C^{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$-, $Q^1$-C(O)—, $Q^1$-O—, $Q^1$-S—, $Q^1$-$C_{1-4}$ alkyl-O—, or $C_{1-4}$alkyl-C(O)—N($R^3$)—;

$Q^1$ is a 5–12 membered monocyclic aromatic ring optionally containing up to 4 heteroatoms selected from N and S, and is optionally substituted with halo, $C_{1-4}$ alkyl, $C_{1-4}$ alkylsulfonyl and $C_{1-4}$ alkylC(=O)—;

A is 5–6 membered monocyclic aromatic ring optionally substituted with halo, $C_{1-4}$ alkyl or $C_{1-4}$ alkoxy;

B is $C_{3-7}$ cycloalkylene or $C_{1-6}$ alkylene optionally substituted with an oxo group or $C_{1-3}$ alkyl;

W is NH, N—$C_{1-4}$ alkyl, O or N—OH;

$R^2$ is H or $C_{1-4}$ alkyl;

Z is 5–12 membered monocyclic or bicyclic aromatic ring optionally containing up to 3 heteroatoms selected from, N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkoxy, nitro, amino, cyano, $R^3C(=O)N(R^4)-$, $C_{1-4}$ alkyl-O(O=)C—, $Q^2$-S(O)m-, $Q^2$-O—, $Q^2$-N($R^3$)— or $Q^2$-;

L is halo, $C_{1-4}$ alkyl, halo-substituted $C_{1-4}$ alkyl, hydroxy, $C_{1-4}$ alkoxy, halo-substituted $C_{1-4}$ alkoxy, mono- or di-($C_{1-4}$ alkyl)amino, cyano, HO—$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3C(=O)N(R^4)-$, $R^3N(R^4)C(=O)-$, $R^3N(R^4)S(O)m-$, $Q^2$-, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0 or 2;

$R^3$ and $R^4$ are independently selected from H and $C_{1-4}$ alkyl; and $Q^2$ is a 5 or 6 membered monocyclic aromatic ring, or a 8–12 membered tricyclic ring containing up to 3 heteroatoms selected from N and S, wherein said 5 or 6 membered monocyclic aromatic ring is optionally substituted with halo.

A further group of compounds of Formula I includes compounds wherein $Y^1$, $Y^2$, $Y^3$ and $Y^4$ are independently selected from N, CH and C(L);

$R^1$ is H, $C_{1-8}$ alkyl, $C_{2-8}$ alkenyl, $C_{2-8}$ alkynyl or $C_{3-7}$ cycloalkyl, wherein said $C_{1-8}$ alkyl is optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$-, $Q^1$-C(=O)—, $Q^1$-O—, $Q^1$-S—, $Q^1$-$C_{1-4}$ alkyl-O—, or $C_{1-4}$alkyl-C(O)—N($R^3$)—;

$Q^1$ is a 5 or 6 membered monocyclic aromatic ring optionally containing up to 4 heteroatoms selected from N and S;

A is 5–6 membered monocyclic aromatic ring system optionally substituted with halo or $C_{1-4}$ alkyl;

B is or $C_{3-7}$ cycloalkylene or $C_{1-6}$ alkylene optionally substituted with an oxo group or $C_{1-3}$ alkyl;

W is NH, N—$C_{1-4}$ alkyl, O or N—OH;

$R^2$ is H or $C_{1-4}$ alkyl;

Z is 5–12 membered monocyclic or bicyclic aromatic ring optionally containing up to 3 heteroatoms selected from N and S, wherein said 5–12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkoxy, nitro, amino, cyano, $R^3C(=O)N(R^4)-$, $C_{1-4}$ alkyl-O(O=)C—, $Q^2$-S(O)m-, $Q^2$-O—, $Q^2$-N($R^3$)— or $Q^2$-;

L is halo, $C_{1-4}$ alkyl, halo-substituted $C_{1-4}$ alkyl, hydroxy, $C_{1-4}$ alkoxy, halo-substituted $C_{1-4}$ alkoxy, cyano, HO—$C_{1-4}$ alkyl, $C_{1-4}$ alkylsulfonyl, aminosulfonyl, $C_{1-4}$ alkylC(=O), HO(O=)C—, $C_{1-4}$ alkyl-O(O=)C—, $C_{1-4}$ alkylsulfonylamino, $C_{3-7}$ cycloalkyl, $R^3C(=O)NR^4-$, $R^3N(R^4)C(=O)-$, $R^3N(R^4)S(O)m-$, $Q^2$-, $Q^2$-C(=O)—, $Q^2$—O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0 or 2;

$R^3$ and $R^4$ are independently selected from H and $C_{1-4}$ alkyl; and $Q^2$ is 5 or 6 membered monocyclic aromatic ring or a 8–12 membered tricyclic ring optionally containing 1 sulfur atom wherein said 5 or 6 membered monocyclic aromatic ring is optionally substituted with halo.

A further group of compounds of Formula I includes compounds wherein $Y^1$, $Y^2$, $Y^3$ and $Y^4$ are independently selected from N, CH and C(L);

$R^1$ is $C_{1-5}$ alkyl or $C_{3-7}$ cycloalkyl, wherein said $C_{1-5}$ alkyl is optionally substituted with $C_{1-3}$ alkyl, hydroxy, oxo, pyrrolidinyl, piperidyl, oxopyrrolidinyl, oxopiperidyl, $Q^1$-, or $C_{1-4}$alkyl-C(O)—N(H)—;

$Q^1$ is 5–12 membered monocyclic aromatic ring system optionally containing up to 2 heteroatoms selected from N and S, A is 5–6 membered monocyclic aromatic ring system;

B is $C_{1-3}$ alkylene optionally substituted with $C_{1-3}$ alkyl;

W is NH, N—$C_{1-2}$ alkyl or O;

$R^2$ is H;

Z is 5–12 membered monocyclic or bicyclic aromatic ring optionally containing up to 3 heteroatoms selected from N and S, wherein said 5–12 membered monocyclic aromatic ring is optionally substituted with halo, $C_{1-4}$ alkyl, nitro, $R^3$C(=O)N($R^4$)— or $Q^2$-;

L is halo, $C_{1-4}$ alkyl, halo-substituted $C_{1-4}$ alkyl, hydroxy, $C_{1-4}$ alkoxy, halo-substituted $C_{1-4}$ alkoxy, cyano, HO—$C_{1-4}$ alkyl, acetyl, $R^3$N($R^4$)C(=O)—, $R^3$N($R^4$)S(O)m-, $Q^2$-, $Q^2$-C(=O)—, or two adjacent L groups are joined together to form a methylenedioxy group;

$R^3$ and $R^4$ are independently selected from H and $C_{1-4}$ alkyl; and $Q^2$ is 5 or 6 membered monocyclic aromatic ring system.

A further group of compounds of Formula I includes compounds wherein $Y^1$, $Y^2$, $Y^3$ and $Y^4$ are independently selected from N, CH and C-L;

$R^1$ is $C_{1-5}$ alkyl optionally substituted with $C_{1-3}$ alkyl, hydroxy, oxo, 5 or 6 membered monocyclic aromatic ring, wherein said 5 or 6 membered monocyclic aromatic ring is containing 1 or 2 heteroatoms selected from N and S, or $C_{1-4}$alkyl-C(O)—N($R^3$)—;

A is phenyl;

B is $C_{1-2}$ alkylene optionally substituted with methyl;

W is NH, N—CH$_3$ or O;

$R^2$ is H;

Z is 5–10 membered monocyclic or bicyclic aromatic ring optionally containing up to 3 heteroatoms selected from N and S, wherein said 5–10 membered monocyclic aromatic ring is optionally substituted with chloro, bromo, methyl, nitro, CH$_3$C(=O)NH—, tBuC(=O)NH— or phenyl; and L is chloro, methyl, trifuluoromethyl, hydroxy, methoxy, cyano, acetyl, —C(=O)NH$_2$, trifuluoromethyloxy, methanesulfonyl, or 1-hydroxy-1-methyl-ethyl, or two adjacent L groups are joined together to form a methylenedioxy group.

A further group of compounds of Formula I includes compounds wherein $Y^1$, $Y^2$, $Y^3$ and $Y^4$ are independently selected from N, CH and C-L;

$R^1$ is methyl, ethyl, n-propyl, isopropyl, n-butyl, isobutyl, neopentyl, thiazolylethyl methylamino, dimethylamino, pyrrolidinyl, pyridyl, or 1-acetylamino-1-methylethyl;

A is phenyl;

B is ethylene or propylene;

W is NH, N—CH$_3$ or O;

$R^2$ is H;

Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl; and L is chloro, methyl, trifuluoromethyl, hydroxy, methoxy, cyano, acetyl, —C(=O)NH$_2$, trifuluoromethyloxy, methanesulfonyl, or 1-hydroxy-1-methyl-ethyl, or two adjacent L groups are joined together to form a methylenedioxy group.

A further group of compounds of Formula I includes compounds wherein $Y^1$, $Y^2$, $Y^3$ and $Y^4$ are selected from the group consisting of
a) $Y^1$ and $Y^3$ are C(L), $Y^2$ is CH and $Y^4$ is N;
b) $Y^1$ is CH, $Y^2$ and $Y^3$ are C(L) and $Y^4$ is N;
c) $Y^1$, $Y^2$ and $Y^3$ are C(L) and $Y^4$ is N;
d) $Y^1$ and $Y^3$ are C(L), $Y^2$ is N and $Y^4$ is CH;
e) $Y^1$ is C(L) and $Y^2$, $Y^3$ and $Y^4$ are CH;
f) $Y^1$, $Y^3$ and $Y^4$ are CH, and $Y^2$ is C(L);
g) $Y^1$, $Y^2$ and $Y^3$ are CH, and $Y^4$ is C(L);
h) $Y^1$ and $Y^2$ are C(L), and $Y^3$ and $Y^4$ are CH;
i) $Y^1$ and $Y^3$ are C(L), and $Y^2$ and $Y^4$ are CH;
j) $Y^1$ and $Y^4$ are CH, and $Y^2$ and $Y^3$ are C(L);
k) $Y^1$ and $Y^2$ are CH, $Y^3$ is C(L) and $Y^4$ is N;
l) $Y^1$ and $Y^3$ are CH, $Y^2$ is C(L) and $Y^4$ is N;
m) $Y^1$, $Y^2$, $Y^3$ and $Y^4$ are CH;
n) $Y^1$ and $Y^2$ are C(L), $Y^3$ is CH and $Y^4$ is N;
o) $Y^1$, $Y^2$ and $Y^4$ are CH, and $Y^3$ is C(L);
p) $Y^1$ and $Y^2$ are C(L), $Y^3$ is N and $Y^4$ is CH;
q) $Y^1$ and $Y^3$ are C(L), and $Y^2$ and $Y^4$ are N;
r) $Y^1$ is C(L), $Y^2$ and $Y^3$ are CH, and $Y^4$ is N; and
s) $Y^2$ is C(L), $Y^1$ and $Y^3$ are CH, and $Y^4$ is N;

$R^1$ is methyl, ethyl, n-propyl, isopropyl, n-butyl, isobutyl, neopentyl, thiazolylethyl methylamino, dimethylamino, pyrrolidinyl, pyridyl, or 1-acetylamino-1-methylethyl;

A is phenyl;

B is ethylene or propylene;

W is NH, N—CH$_3$ or O;

$R^2$ is H;

Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl; and L is chloro, methyl, trifuluoromethyl, hydroxy, methoxy, cyano, acetyl, —C(=O)NH$_2$, trifuluoromethyloxy, methanesulfonyl, or 1-hydroxy-1-methyl-ethyl, or two adjacent L groups are joined together to form a methylenedioxy group.

A further group of compounds of Formula I includes compounds wherein $Y^1$, $Y^2$, $Y^3$ and $Y^4$ are selected from the group consisting of
a) $Y^1$ and $Y^3$ are C(L), $Y^2$ is CH and $Y^4$ is N;
b) $Y^1$ is CH, $Y^2$ and $Y^3$ are C(L) and $Y^4$ is N;
c) $Y^1$, $Y^2$ and $Y^3$ are C(L) and $Y^4$ is N;
d) $Y^1$ and $Y^3$ are C(L), $Y^2$ is N and $Y^4$ is CH;
e) $Y^1$ is C(L) and $Y^2$, $Y^3$ and $Y^4$ are CH;
f) $Y^1$, $Y^3$ and $Y^4$ are CH, and $Y^2$ is C(L);

g) Y$^1$, Y$^2$ and Y$^3$ are CH, and Y$^4$ is C(L);
h) Y$^1$ and Y$^2$ are C(L), and Y$^3$ and Y$^4$ are CH;
i) Y$^1$ and Y$^3$ are C(L), and Y$^2$ and Y$^4$ are CH; and
j) Y$^1$ and Y$^4$ are CH, and Y$^2$ and Y$^3$ are C(L);

R$^1$ is methyl, ethyl, n-propyl, isopropyl, n-butyl, isobutyl, neopentyl, thiazolylethyl methylamino, dimethylamino, pyrrolidinyl, pyridyl, or 1-acetylamino-1-methylethyl;

A is phenyl;

B is ethylene or propylene;

W is NH, N—CH$_3$ or O;

R$^2$ is H;

Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl; and L is chloro, methyl, trifuluoromethyl, hydroxy, methoxy, cyano, acetyl, —C(=O)NH$_2$, trifuluoromethyloxy, methanesulfonyl, or 1-hydroxy-1-methyl-ethyl, or two adjacent L groups are joined together to form a methylenedioxy group.

Individual compounds of Formula I include the following:

3-(4-{2-[({[(5-chloro-1,3-dimethyl-1h-pyrazol-4-yl)sulfonyl]amino}carbonyl)amino]ethyl}phenyl)-2-ethyl-5,7-dimethyl-3H-imidazo[4,5-b]pyridine;

3-(4-{2-[({[(2,4-dimethyl-1,3-thiazol-5-yl)sulfonyl]amino}carbonyl)amino]ethyl}phenyl)-2-ethyl-5,7-dimethyl-3H-imidazo[4,5-b]pyridine;

N-[5-({[({2-[4-(2-ethyl-5,7-dimethyl-3H-imidazo[4,5-b]pyridine-3-yl)phenyl]ethyl}amino)carbonyl]amino}sulfonyl)-1,3,4-thiadiazol-2-yl]acetamide;

6-ethyl-5-(4-{2-[({[(4-methylphenyl)sulfonyl]amino}carbonyl)amino]ethyl}phenyl)-5H-[1,3]dioxolo[4,5-f]benzimidazole;

6-chloro-5-cyano-2-ethyl-1-(4-{2-[({[(4-methylphenylsulfonyl]amino}carbonyl)amino]ethyl}phenyl)-1H-benzimidazole;

2-ethyl-5,7-dimethyl-3-(4-{2-[methyl({[(4-methylphenyl)sulfonyl]amino}carbonyl)amino]ethyl}phenyl)-3H-imidazo[4,5-b]pyridine;

2-ethyl-5,7-dimethyl-3-(4-{2-[({[(4-methylphenyl)sulfonyl]amino}carbonyl)amino]propyl}yl)-3H-imidazo[4,5-b]pyridine;

2-[4-(2-ethyl-5,7-dimethyl-3H-imidazo[4,5-b]pyridine-3-yl)phenyl]-1-methylethyl(4-methylphenyl)sulfonylcarbamate;

5,7-dimethyl-3-(4-{2-[({[(4-methylphenyl)sulfonyl]amino}carbonyl)amino]ethyl}phenyl)-2-propyl-3H-imidazo[4,5-b]pyridine;

2-isopropyl-5,7-dimethyl-3-(4-{2-[({[(4-methylphenyl)sulfonyl]amino}carbonyl)amino]ethyl}phenyl)-3H-imidazo[4,5-b]pyridine;

2-butyl-5,7-dimethyl-3-(4-{2-[({[(4-methylphenyl)sulfonyl]amino}carbonyl)amino]ethyl}phenyl)-3H-imidazo[4,5-b]pyridine;

2-isobutyl-5,7-dimethyl-3-(4-{2-[({[(4-methylphenyl)sulfonyl]amino}carbonyl)amino]ethyl}phenyl)-3H-imidazo[4,5-b]pyridine;

5,7-dimethyl-3-(4-{2-[({[(4-methylphenyl)sulfonyl]amino}carbonyl)amino]ethyl}phenyl)-2-neopentyl-3H-imidazo[4,5-b]pyridine;

5,7-dimethyl-3-(4-{2-[({[(4-methylphenyl)sulfonyl]amino}carbonyl)amino]ethyl}phenyl)-2-[2-(1,3-thiazol-2-yl)ethyl]-3H-imidazo[4,5-b]pyridine;

3-{4-[2-({[(4-biphenylsulfonyl)amino]carbonyl}amino)ethyl]phenyl}-2-ethyl-5,7-dimethyl-3H-imidazo[4,5-b]pyridine;

2-ethyl-5,7-dimethyl-3-{4-[2-({[(1-naphthyl sulfonyl)amino]carbonyl}amino)ethyl]phenyl}-3H-imidazo[4,5-b]pyridine;

2-ethyl-5,7-dimethyl-3-{4-[2-({[(2-naphthylsulfonyl)amino]carbonyl}amino)ethyl]phenyl}-3H-imidazo[4,5-b]pyridine;

2-ethyl-5,7-dimethyl-3-(4-{2-[({[(2-thienyl)sulfonyl]amino}carbonyl)amino]ethyl}phenyl)-3H-imidazo[4,5-b]pyridine;

3-(4-{2-[({[(5-chloro-2-thienyl)sulfonyl]amino}carbonyl)amino]ethyl}phenyl)-2-ethyl-5,7-dimethyl-3H-imidazo[4,5-b]pyridine;

3-(4-{2-[({[(4,5-dichloro-2-thienyl)sulfonyl]amino}carbonyl)amino]ethyl}phenyl)-2-ethyl-5,7-dimethyl-3H-imidazo[4,5-b]pyridine;

3-{4-[2-({[(1-benzothien-2-ylsulfonyl)amino]carbonyl}amino)ethyl]phenyl}-2-ethyl-5,7-dimethyl-3H-imidazo[4,5-b]pyridine;

3-(4-{2-[({[(2-chlorophenyl)sulfonyl]amino}carbonyl)amino]ethyl}phenyl)-2-ethyl-5,7-dimethy-3H-imidazo[4,5-b]pyridine;

2-ethyl-5,6-dimethyl-3-(4-{2-[({[(4-methylphenyl)sulfonyl]amino}carbonyl)amino]ethyl}phenyl)-3H-imidazo[4,5-b]pyridine;

5,6-dichloro-2-ethyl-3-(4-{2-[({[(4-methylphenyl)sulfonyl]amino}carbonyl)amino]ethyl}phenyl)-3h-imidazo[4,5-b]pyridine;

5-chloro-2-ethyl-7-methyl-3-(4-{2-[({[(4-methylphenyl)sulfonyl]amino}carbonyl)amino]ethyl}phenyl)-3H-imidazo[4,5-b]pyridine;

6-cyano-2-ethyl-5,7-dimethyl-3-(4-{2-[({[(4-methylphenyl)sulfonyl]amino}carbonyl)amino]ethyl}phenyl)-3H-imidazo[4,5-b]pyridine;

2-ethyl-4,6-dimethyl-1-(4-{2-[({[(4-methylphenyl)sulfonyl]amino}carbonyl)amino]ethyl}phenyl)-1H-imidazo[4,5-c]pyridine;

4-methyl-2-ethyl-3-(4-{2-[({[(4-methylphenyl)sulfonyl]amino}carbonyl)amino]ethyl}phenyl)benzimidazole;

7-chloro-2-ethyl-3-(4-{2-[({[(4-methylphenyl)sulfonyl]amino}carbonyl)amino]ethyl}phenyl)benzimidazole;

5-methoxy-2-ethyl-3-(4-{2-[({[(4-methylphenyl)sulfonyl]amino}carbonyl)amino]ethyl}phenyl)benzimidazole;

5-acetyl-2-ethyl-3-(4-{2-[({[(4-methylphenyl)sulfonyl]amino}carbonyl)amino]ethyl}phenyl)benzimidazole;

5-cyano-2-ethyl-1-(4-{2-[({[(4-methylphenyl)sulfonyl]amino}carbonyl)amino]ethyl}phenyl)-1H-benzimidazole;

2-ethyl-5-hydroxy-1-(4-{2-[({[(4-methylphenyl)sulfonyl]amino}carbonyl)amino]ethyl}phenyl)-1H-benzimidazole;

2-ethyl-4,5-dimethyl-1-(4-{2-[({[(4-methylphenyl)sulfonyl]amino}carbonyl)amino]ethyl}phenyl)-1H-benzimidazole;

4,6-dimethyl-2-ethyl-3-(4-{2-[({[(4-methylphenyl)sulfonyl]amino}carbonyl)amino]ethyl}phenyl)benzimidazole;

5,6-dimethyl-1-(4-{2-[({[(4-methylphenyl)sulfonyl]amino}carbonyl)amino]ethyl}phenyl)-1H-benzimidazole;

5,6-dichloro-2-ethyl-1-(4-{2-[({[(4-methylphenyl)sulfonyl]amino}carbonyl)amino]ethyl}phenyl)-1H-benzimidazole;

2-[4-(5,6-dichloro-2-ethyl-1H-benzimidazol-1-yl)phenyl]ethyl-(4-methylphenyl)sulfonylcarbamate;

6-chloro-5-trifluoromethyl-1-(4-{2-[({[(4-methylphenyl)sulfonyl]amino}carbonyl)amino]ethyl}phenyl)-1H-benzimidazole;

4-(6-chloro-2-ethyl-5-trifluoromethyl-1H-benzimidazol-1-yl)phenethyl-(4-methylphenyl)sulfonylcarbamate;

5-chloro-6-methyl-1-(4-{2-[({[(4-methylphenyl)sulfonyl]amino}carbonyl)amino]ethyl}phenyl)-1H-benzimidazole;

6-chloro-2-ethyl-1-(4-{2-[({[(4-methylphenyl)sulfonyl]amino}carbonyl)amino]ethyl}phenyl)-1H-benzimidazole-5-carboxamide;

2-ethyl-3-{4-[2-({[({3-[hydroxy(oxido)amino]phenyl}sulfonyl)amino]carbonyl}amino)ethyl]phenyl}-5,7-dimethyl-3H-imidazo[4,5-b]pyridine;

3-(4-{2-[({[(4-chlorophenyl)sulfonyl]amino}carbonyl)amino]ethyl}phenyl)-2-ethyl-5,7-dimethyl-3H-imidazo[4,5-b]pyridine;

n-[4-({[({2-[4-(2-ethyl-5,7-dimethyl-3H-imidazo[4,5-b]pyridine-3-yl)phenyl]ethyl}amino)carbonyl]amino}sulfonyl)phenyl]-2,2-dimethylpropanamide;

3-(4-{2-[({[(2-chlorophenyl)sulfonyl]amino}carbonyl)amino]ethyl}phenyl)-2-ethyl-5,7-dimethyl-3H-imidazo[4,5-b]pyridine;

3-(4-{2-[({[(3-chlorophenyl)sulfonyl]amino}carbonyl)amino]ethyl}phenyl)-2-ethyl-5,7-dimethyl-3H-imidazo[4,5-b]pyridine;

3-(4-{2-[({[(5-chloro-2-thienyl)sulfonyl]amino}carbonyl)amino]ethyl}phenyl)-2-ethyl-5,7-dimethyl-3H-imidazo[4,5-b]pyridine;

3-(4-{2-[({[(5-bromo-2-thienyl)sulfonyl]amino}carbonyl)amino]ethyl}phenyl)-2-ethyl-5,7-dimethyl-3H-imidazo[4,5-b]pyridine;

3-(4-{2-[({[(2-bromophenyl)sulfonyl]amino}carbonyl)amino]ethyl}phenyl)-2-ethyl-5,7-dimethyl-3H-imidazo[4,5-b]pyridine;

3-{4-[2-({[({4-chloro-3-nitrophenyl}sulfonyl)amino]carbonyl}amino)ethyl]phenyl}-2-ethyl-5,7-dimethyl-3H-imidazo[4,5-b]pyridine;

2-[4-(2-ethyl-4,6-dimethyl-1H-imidazo[4,5-c]pyridin-1-yl)phenyl]ethyl(4-methylphenyl)sulfonylcarbamate;

2-{4-[5,7-dimethyl-2-(methylamino)-3H-imidazo[4,5-b]pyridin-3-yl]phenyl}ethyl4-methylphenyl)sulfonylcarbamate;

N-{[(2-{4-[5,7-dimethyl-2-(methylamino)-3H-imidazo[4,5-b]pyridin-3-yl]phenyl}amino]carbonyl}-4-methylbenzenesulfonamide;

N-{[(2-{4-[2-ethyl-5-(1-hydroxy-1-methylethyl)-1H-benzimidazol-1-yl]phenyl}ethyl)amino]carbonyl}-4-methylbenzenesulfonamide;

2-ethyl-4,6-dimethyl-1-(4-{2-[({[(4-methylphenyl)sulfonyl]amino}carbonyl)amino]ethyl}phenyl)-1H-benzimidazole-5-carboxamide;

2-{4-[6-chloro-2-ethyl-5-(trifluoromethyl)-1H-benzimidazol-1-yl]phenyl}ethyl(2-chlorophenyl)sulfonylcarbamate;

2-{5-[6-chloro-2-ethyl-5-(trifluoromethyl)-1H-benzimidazol-1-yl]-2-pyridinyl}ethyl(4-methylphenyl)sulfonylcarbamate;

2-{4-[6-chloro-2-ethyl-5-(trifluoromethyl)-1H-benzimidazol-1-yl]phenyl}ethyl(5-methyl-2-pyridinyl)sulfonylcarbamate;

2-{4-[6-chloro-2-(1H-pyrazol-3-yl)-5-(trifluoromethyl)-1H-benzimidazol-1-yl]phenyl}ethyl(4-methylphenyl)sulfonylcarbamate;

2-{4-[6-chloro-2-(4-pyridinyl)-5-(trifluoromethyl)-1H-benzilmidazol-1-yl]phenyl}methylphenyl)sulfonylcarbamate;

2-{4-[5-(aminocarbonyl)-6-chloro-2-ethyl-1H-benzimidazol-1-yl]phenyl}ethyl(4-methylphenyl)sulfonylcarbamate;

N-{[(2-{4-[6-chloro-2-ethyl-5-(methylsulfonyl)-1H-benzimidazol-1-yl]phenyl}ethyl)amino]carbonyl}-4-methylbenzenesulfonamide;

2-{4-[6-chloro-2-ethyl-5-(methylsulfonyl)-1H-benzimidazol-1-yl]phenyl}ethyl(4-methylphenyl)sulfonylcarbamate;

N-[({2-[4-(2-ethyl-5,7-dimethyl-3H-imidazo[4,5-b]pyridin-3-yl)phenyl]ethyl}amino)carbonyl]-2-thiophenesulfonamide;

2-[4-(4,6-dimethyl-2-phenyl-1H-imidazo[4,5-c]pyridin-1-yl)phenyl]ethyl(4-methylphenyl)sulfonylcarbamate;

2-[4-(2-butyl-4,6-dimethyl-1H-imidazo[4,5-c]pyridin-1-yl)phenyl]ethyl(4-methylphenyl)sulfonylcarbamate;

2-{4-[6-chloro-2-ethyl-5-(trifluoromethyl)-1H-benzimidazol-1-yl]phenyl}ethyl(5-chloro-1,3-dimethyl-1H-pyrazol-4-yl)sulfonylcarbamate;

2-{4-[4,6-dimethyl-2-(3-phenylpropyl)-1H-imidazo[4,5-c]pyridin-1-yl]phenyl}ethyl(4-methylphenyl)sulfonylcarbamate;

2-{4-[6-chloro-2-(2-pyridinyl)-5-(trifluoromethyl)-1H-benzimidazol-1-yl]phenyl}ethyl(4-methylphenyl)sulfonylcarbamate;

(1S)-2-{4-[6-chloro-2-ethyl-5-(trifluoromethyl)-1H-benzimidazol-1-yl]phenyl}-1-methylethyl(4-methylphenyl)sulfonylcarbamate;

2-{6-[6-chloro-2-ethyl-5-(trifluoromethyl)-1H-benzimidazol-1-yl]-3-pyridinyl}ethyl(4-methylphenyl)sulfonylcarbamate;

N-{[(2-{4-[6-chloro-2-(1-hydroxy-1-methylethyl)-5-(trifluoromethyl)-1H-benzimidazo-1-yl]phenyl}ethyl)amino]carbonyl}-4-methylbenzenesulfonamide; and N-{[(2-{4-[5,7-dimethyl-2-(1H-pyrazol-3-yl)-3H-imidazo[4,5-b]pyridin-3-yl]phenyl}ethyl)amino]carbonyl}-4-methylbenzenesulfonamide;

2-{4-[2-(1,1-dimethylethyl)-4,6-dimethyl-1H-imidazo[4,5-c]pyridin-1-yl]phenyl}(4-methylphenyl)sulfonylcarbamate;

2-{4-[2-[1-(acetylamino)-1-methylethyl]-6-chloro-5-(trifluoromethyl)-1H-benzimidazo-1-yl]phenyl}ethyl(4-methylphenyl)sulfonylcarbamate;

6-chloro-2-ethyl-1-(4-{2-[methyl({[(4-methylphenyl)sulfonyl]amino}carbonyl)amino]ethyl}phenyl)-1H-benzimidazole-5-carboxamide; and salts thereof.

Further individual compounds of Formula I are following:

6-ethyl-5-(4-{2-[({[(4-methylphenyl)sulfonyl]amino}carbonyl)amino]ethyl}phenyl)-5H-[1,3]dioxolo[4,5-f]benzimidazole;

6-chloro-5-cyano-2-ethyl-1-(4-{2-[({[(4-methylphenylsulfonyl]amino}carbonyl)amino}phenyl)-1H-benzimidazole;

2-[4-(2-ethyl-5,7-dimethyl-3H-imidazo[4,5-b]pyridin-3-yl)phenyl]-1-methylethyl(4-methylethyl)sulfonylcarbamate;

5,7-dimethyl-3-(4-{2-[({[(4-methylphenyl)sulfonyl]amino}carbonyl)amino]ethyl}phenyl)-2-[2-(1,3-thiazol-2-yl)ethyl]-3H-imidazo[4,5-b]pyridine;

2-ethyl-5,7-dimethyl-3-(4-{2-[({[(2-thienyl)sulfonyl]amino}carbonyl)amino]ethyl}phenyl)-3H-imdazo[4,5-b]pyridine;

3-(4-{2-[({[(2-chlorophenyl)sulfonyl]amino}carbonyl)amino]ethyl}phenyl)-2-ethyl-5,7-dimethyl-3H-imidazo[4,5-b]pyridine;

2-ethyl-5,6-dimethyl-3-(4-{2-[({[(4-methylphenyl)sulfonyl]amino}carbonyl)amino]ethyl}phenyl)-3H-imidazo[4,5-b]pyridine;

5,6-dichloro-2-ethyl-3-(4-{2-[({[(4-methylphenyl)sulfonyl]amino}carbonyl)amino]ethyl}phenyl)-3h-imidazo[4,5-b]pyridine;

2-ethyl-4,6-dimethyl-1-(4-{2-[({[(4-methylphenyl)sulfonyl]amino}carbonyl)amino]ethyl}phenyl)-1H-imidazo[4,5-c]pyridine;

5-methoxy-2-ethyl-3-(4-{2-[({[(4-methylphenyl)sulfonyl]amino}carbonyl)amino]ethyl}phenyl)benzimidazole;

5-acetyl-2-ethyl-3-(4-{2-[({[(4-methylphenyl)sulfonyl]amino}carbonyl)amino]ethyl}phenyl)benzimidazole;

5-cyano-2-ethyl-1-(4-{2-[({[(4-methylphenyl)sulfonyl]amino}carbonyl)amino]ethyl}phenyl)-1H-benzimidazole;

2-ethyl-5-hydroxy-1-(4-{2-[({[(4-methylphenyl)sulfonyl]amino}carbonyl)amino]ethyl}phenyl)-1H-benzimidazole;

2-ethyl-4,5-dimethyl-1-(4-{2-[({[(4-methylphenyl)sulfonyl]amino}carbonyl)amino]ethyl}phenyl)-1H-benzimidazole;

4-(6-chloro-2-ethyl-5-trifluoromethyl-1H-benzimidazol-1-yl)phenethyl-(4-methylphenyl)sulfonylcarbamate; and 6-chloro-2-ethyl-1-(4-{2-[({[(4-methylphenyl)sulfonyl]amino}carbonyl)amino]ethyl}phenyl-1H-benzimidazole-5-carboxamide;

2-[4-(2-ethyl-4,6-dimethyl-1H-imidazo[4,5-c]pyridin-1-yl)phenyl]ethyl(4-methylphenyl)sulfonylcarbamate;

2-{4-[5,7-dimethyl-2-(methylamino)-3H-imidazo[4,5-b]pyridin-3-yl]phenyl}ethyl(4-methylphenyl)sulfonylcarbamate;

N-{[(2-{4-[5,7-dimethyl-2-(methylamino)-3H-imidazo[4,5-b]pyridin-3-yl]phenyl}ethyl)amino]carbonyl}-4-methylbenzenesulfonamide;

N-{[(2-{4-[2-ethyl-5-(1-hydroxy-1-methylethyl)-1H-benzimidazol-1-yl]phenyl}ethyl)amino]carbonyl}-4-methylbenzenesulfonamide;

2-ethyl-4,6-dimethyl-1-(4-{2-[({[(4-methylphenyl)sulfonyl]amino}carbonyl)amino]ethyl}phenyl)-1H-benzimidazole-5-carboxamide;

2-{4-[6-chloro-2-ethyl-5-(trifluoromethyl)-1H-benzimidazol-1-yl]phenyl}ethyl(2-chlorophenyl)sulfonylcarbamate;

2-{5-[6-chloro-2-ethyl-5-(trifluoromethyl)-1H-benzimidazol-1-yl]-2-pyridinyl}ethyl(4-methylphenyl)sulfonylcarbamate;

2-{4-[6-chloro-2-ethyl-5-(trifluoromethyl)-1H-benzimidazol-1-yl]phenyl}ethyl(5-methyl-2-pyridinyl)sulfonylcarbamate;

2-{4-[6-chloro-2-(1H-pyrazol-3-yl)-5-(trifluoromethyl)-1H-benzimidazol-1-yl]phenyl}ethyl(4-methylphenyl)sulfonylcarbamate;

2-{4-[6-chloro-2-(4-pyridinyl)-5-(trifluoromethyl)-1H-benzimidazol-1-yl]phenyl}ethyl(4-methylphenyl)sulfonylcarbamate;

2-{4-[5-(aminocarbonyl)-6-chloro-2-ethyl-1H-benzimidazol-1-yl]phenyl}ethyl(4-methylphenyl)sulfonylcarbamate;

N-{[(2-{4-[6-chloro-2-ethyl-5-(methylsulfonyl)-1H-benzimidazol-1-yl]phenyl}ethyl)amino]carbonyl}-4-methylbenzenesulfonamide;

2-{4-[6-chloro-2-ethyl-5-(methylsulfonyl)-1H-benzimidazol-1-yl]phenyl}ethyl(4-methylphenyl)sulfonylcarbamate;

N-[({2-[4-(2-ethyl-5,7-dimethyl-3H-imidazo[4,5-b]pyridin-3-yl)phenyl]ethyl}amino)carbonyl]-2-thiophenesulfonamide;

2-[4-(4,6-dimethyl-2-phenyl-1H-imidazo[4,5-c]pyridin-1-yl)phenyl]ethyl(4-methylphenyl)sulfonylcarbamate;

2-[4-(2-butyl-4,6-dimethyl-1H-imidazo[4,5-c]pyridin-1-yl)phenyl]ethyl(4-methylphenyl)sulfonylcarbamate;

2-{4-[6-chloro-2-ethyl-5-(trifluoromethyl)-1H-benzimidazol-1-yl]phenyl}ethyl(5-chloro-1,3-dimethyl-1H-pyrazol-4-yl)sulfonylcarbamate;

2-{4-[4,6-dimethyl-2-(3-phenylpropyl)-1H-imidazo[4,5-c]pyridin-1-yl]phenyl}ethyl(4-methylphenyl)sulfonylcarbamate;

2-{4-[6-chloro-2-(2-pyridinyl)-5-(trifluoromethyl)-1H-benzimidazol-1-yl]phenyl}ethyl(4-methylphenyl)sulfonylcarbamate;

(1S)-2-{4-[6-chloro-2-ethyl-5-(trifluoromethyl)-1H-benzimidazol-1-yl]phenyl}-1-methylethyl(4-methylphenyl)sulfonylcarbamate;

2-{6-[6-chloro-2-ethyl-5-(trifluoromethyl)-1H-benzimidazol-1-yl]-3-pyridinyl}ethyl(4-methylphenyl)sulfonylcarbamate;

N-{[(2-{4-[6-chloro-2-(1-hydroxy-1-methylethyl)-5-(trifluoromethyl)-1H-benzimidazol-1-yl]phenyl}ethyl)amino]carbonyl}-4-methylbenzenesulfonamide; and N-{[(2-{4-[5,7-dimethyl-2-(1H-pyrazol-3-yl)-3H-imidazo[4,5-b]pyridin-3-yl]phenyl}ethyl)amino]carbonyl}-4-methylbenzenesulfonamide;

2-{4-[2-(1,1-dimethylethyl)-4,6-dimethyl-1H-imidazo[4,5-c]pyridin-1-yl]phenyl}ethyl(4-methylphenyl)sulfonylcarbamate;

2-{4-[2-[1-(acetylamino)-1-methylethyl]-6-chloro-5-(trifluoromethyl)-1H-benzimidazol-1-yl]phenyl}ethyl(4-methylphenyl)sulfonylcarbamate;

6-chloro-2-ethyl-1-(4-{2-[methyl({[(4-methylphenyl)sulfonyl]amino}carbonyl)amino]ethyl}phenyl)-1H-benzimidazole-5-carboxamide; and salts thereof. Synthesis of Formula I Compounds.

Representative Formula I compounds and methods of synthesizing Formula 1 compounds are described in the following Examples 1–380. Additional general synthesis schemes are described in U.S. provisional application No. 60/241,825, filed Oct. 19, 2000, and in Akiyoshi et al., a non-provisional application filed on approximately Oct. 10, 2001 and entitled "Aryl or Heteroaryl Fused Imidazole Compounds as Anti-Inflammatory and Analgesic Agents."

Unless stated otherwise, all operations described in the Examples below were carried out at room or ambient temperature, that is, in the range of 18–25° C.; evaporation of solvent was carried out using a rotary evaporator under reduced pressure with a bath temperature of up to 60° C.; reactions were monitored by thin layer chromatography (TLC) and reaction times are given for illustration only; melting points (mp) given are uncorrected (polymorphism may result in different melting points); the structure and purity of all isolated compounds were assured by at least one of the following techniques: TLC (Merck silica gel 60 $F_{254}$ precoated TLC plates), mass spectrometry, nuclear magnetic resonance (NMR), infrared red absorption spectra (IR) or microanalysis. Yields are given for illustrative purposes only. Flash column chromatography was carried out using Merck silica gel 60 (230–400 mesh ASTM). Low-resolution mass spectral data (EI) were obtained on a Automass 120 (JEOL) mass spectrometer. Low-resolution mass spectral data (ESI) were obtained on a Quattro II (Micromass) mass spectrometer or a ZMD (Micromass). NMR data was determined at 270 MHz (JEOL JNM-LA 270 spectrometer) or 300 MHz (JEOL JNM-LA300 spectrometer) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, quint=quintet, m=multiplet, br.=broad, etc. IR spectra were measured by a Shimazu infrared spectrometer (IR-470). Chemical symbols have their usual meanings; bp (boiling point), mp (melting point), L (liter(s)), mL (milliliter(s)), g (gram(s)), mg (milligram(s)), mol (moles), mmol (millimoles), eq. (equivalent(s)), quant. (quantitative yield).

EXAMPLE 1

2-ETHYL-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE

STEP 1. 4,6-Dimethyl-3-nitro-2(1H)-pyridinone

A mixture of ethyl nitroacetate (80.0 g, 601 mmol) in ammonium hydroxide (25% $NH_3$ in water, 400 mL) was stirred at room temperature for 3 days, and then the solution was concentrated by air-drying. The residue was dissolved in water (450 mL). To the solution was added 2,4-pentanedione (73.1 g, 730 mmol), pyridine (16.2 mL, 200 mmol) and acetic acid (11.4 mL, 200 mmol), and the mixture was stirred for an additional 7 days. The resulting precipitates were collected by filtration and dried under reduced pressure to give 35.0 g (35%) of the title compound as yellow solids: $^1$H-NMR (DMSO-$d_6$) δ 12.44 (1H, br.s), 6.06 (1H, s), 2.19 (3H, s), 2.13 (3H, s).

STEP 2. 2-Chloro-4,6-dimethyl-3-nitropyridine

A mixture of 4,6-dimethyl-3-nitro-2(1H)-pyridinone (step 1, 10.0 g, 29.7 mmol) in phosphorus oxychloride (35 mL, 187.3 mmol) was stirred at 95° C. for 3 h, then cooled to 45° C. The excess amount of phosphorus oxychloride was removed by distillation under reduced pressure at 45° C. The residue was cooled to room temperature, and diluted with dichloromethane (75 mL). The resulting solution was cooled to 0° C., and 2N hydrochloric acid (50 mL) was added dropwise into the solution. The organic layer was separated, and washed with 2N hydrochloric acid (4×25 mL), 2N aqueous NaOH (2×50 mL) and brine (50 mL). The organic phase was dried ($MgSO_4$) and concentrated under reduced pressure to give 10.0 g (90%) of the title compound as white solids: $^1$H-NMR ($CDCl_3$) δ 7.07 (1H, s), 2.56 (3H, s), 2.35 (3H, s).

STEP 3. 2-{4-[(4,6-Dimethyl-3-nitro-2-pyridinyl)amino]phenyl}ethanol

A mixture of 2-chloro-4,6-dimethyl-3-nitropyridine (step 2, 1.3 g, 7.0 mmol) and 4-aminophenylethyl alcohol (1.4 g, 10.2 mmol) was placed in a sealed tube and heated at 150° C. for 3 h. The reaction mixture was cooled and purified by flash column chromatography on silica gel eluting with hexane/ethyl acetate (2:1) to afford 1.6 g (80%) of the title compound as orange solids: $^1$H-NMR ($CDCl_3$) δ 9.55 (1H, br.s), 7.57 (2H, d, J=8.4 Hz), 7.20 (2H, d, J=8.4 Hz, 6.52 (1H, s), 3.84 (2H, t, J=6.4 Hz), 2.85 (2H, t, J=6.4 Hz), 2.54 (3H, s), 2.42 (3H, s).

STEP 4. 2-{4-[(3-Amino-4,6-dimethyl-2-pyridinyl)amino]phenyl}ethanol

To a stirred solution of 2-{4-[(4,6-dimethyl-3-nitro-2-pyridinyl)amino]phenyl}ethanol (step 3, 1.6 g, 5.6 mmol) in ethyl acetate (15 mL) was added 10% Pd—C (160 mg). The mixture was stirred at room temperature for 6 h under hydrogen atmosphere. The palladium catalyst was removed by filtration and washed with ethanol (100 mL). The filtrate was concentrated under reduced pressure to afford 1.3 g (92%) of the title compound as pale yellow solids: $^1$H-NMR ($CDCl_3$) δ 7.10 (4H, s), 6.61 (1H, s), 3.81 (2H, t, J=6.4 Hz), 2.80 (2H, t, J=6.4 Hz), 2.36 (3H, s), 2.19 (3H, s).

STEP 5. 2-[4-(2-Ethyl-5,7-dimethyl-3H-imidazo[4,5-b]pyridin-3-yl)phenyl]ethyl propionate To a stirred suspension of 2-{4-[(3-amino-4,6-dimethyl-2-pyridinyl)amino]phenyl}ethanol (step 4, 1.3 g, 5.1 mmol) in toluene (30 mL) was added dropwise propionyl chloride (990 mg, 10.7 mmol) at 0° C., and the reaction mixture was heated at reflux temperature for 2 h. After cooling, the mixture was poured into water (50 mL) and extracted with ethyl acetate (100 mL). The organic layer was washed with 2N aqueous NaOH (50 mL) and brine (50 mL), then dried ($MgSO_4$). Removal of solvent gave 1.8 g (quant.) of the title compound as brown solids: $^1$H-NMR ($CDCl_3$) δ 7.41 (2H, d, J=8.4 Hz), 7.33 (2H, d, J=8.4 Hz), 6.90 (1H, s), 4.37 (2H, t, J=6.9 Hz), 3.04 (2H, t, J=6.9 Hz), 2.82 (2H, q, J=7.6 Hz), 2.65 (3H, s), 2.52 (3H, s), 2.35 (2H, q, J=7.6 Hz), 1.27 (3H, t, J=7.6 Hz), 1.14 (3H, t, J=7.6 Hz).

STEP 6. 2-[4-(2-Ethyl-5,7-dimethyl-3H-imidazo[4,5-b]pyridin-3-yl)phenyl]ethanol

To a solution of 2-[4-(2-ethyl-5,7-dimethyl-3H-imidazo[4,5-b]pyridin-3-yl)phenyl]ethyl propionate (step 5, 1.75 g, 5.1 mmol) in methanol/THF (v/v, 1:1, 28 mL) was added 4N aqueous LiOH (4.6 mL, 18.4 mmol) and the resulting mixture was stirred at room temperature. After 3 h, the mixture was concentrated. The residue was dissolved in water (30 mL) and extracted with ethyl acetate (100 mL). The organic layer was washed with brine (50 mL), dried ($MgSO_4$), and concentrated. Purification by flash column chromatography on silica gel eluting with hexane/ethyl acetate (gradient elution from 2:1 to 0:1) to afford 1.3 g (86%) of the title compound as pale brown solids: $^1$H-NMR ($CDCl_3$) δ 7.40 (2H, d, J=8.4 Hz), 7.31 (2H, d, J=8.4 Hz), 6.91 (1H, s), 3.81–3.75 (2H, m), 3.47 (1H, br.s), 2.92 (2H, t, J=6.9 Hz), 2.81 (2H, q, J=7.6 Hz), 2.66 (3H, s), 2.51 (3H, s), 1.27 (3H, t, J=7.6 Hz).

STEP 7. 3-[4-(2-Chloroethyl)phenyl]-2-ethyl-5,7-dimethyl-3H-imidazo[4,5-b]pyridine To a solution of 2-[4-(2-ethyl-5,7-dimethyl-3H-imidazo[4,5-b]pyridin-3-yl)phenyl]ethanol (step 6, 2.2 g, 7.4 mmol) in toluene (40 mL) was added thionyl chloride (2.0 mL, 23.6 mmol), and the resulting mixture was stirred at 80° C. for 3 h. The volatile components were removed under reduced pressure, and the residue was purified by flash column chromatography on silica gel eluting with hexane/ethyl acetate (gradient elution from 2:1 to 1:1) to afford 2.1 g (90%) of the title compound as white solids: $^1$H-NMR ($CDCl_3$) δ 7.41 (2H, d, J=8.4 Hz), 7.35 (2H, d, J=8.4 Hz), 6.90 (1H, s), 3.78 (2H, t, J=7.4 Hz), 3.15 (2H, t, J=7.4 Hz), 2.83 (2H, q, J=7.6 Hz), 2.71 (3H, s), 2.54 (3H, s), 1.28 (3H, t, J=7.6 Hz).

STEP 8. 2-[4-(2-Ethyl-5,7-dimethyl-3H-imidazo[4,5-b]pyridin-3-yl)phenyl]ethyl azide To a stirred solution of 3-[4-(2-chloroethyl)phenyl]-2-ethyl-5,7-dimethyl-3H-imidazo[4,5-b]pyridine (step 7, 2.8 g, 9.0 mmol) and KI (1.5 g, 9.0 mmol) in DMF (50 mL) was added sodium azide (1.2 g, 18.0 mmol), and then the resulting mixture was stirred overnight at 100° C. The reaction mixture was poured into water (100 mL), and extracted with ethyl acetate (100 mL). The organic layer was washed with water (50 mL) and brine (50 mL), then dried (Na$_2$SO$_4$). After removal of solvent, the crude product was purified by flash column chromatography on silica gel eluting with hexane/ethyl acetate (1:1) to afford 2.35 g (85%) of the title compound as white solids: $^1$H-NMR (CDCl$_3$) δ 7.41 (2H, d, J=8.4 Hz), 7.35 (2H, d, J=8.4 Hz), 6.90 (1H, s), 3.59 (2H, t, J=7.1 Hz), 2.99 (2H, t, J=7.1 Hz), 2.83 (2H, q, J=7.6 Hz), 2.65 (3H, s), 1.27 (3H, t, J=7.6 Hz).

STEP 9. 2-[4-(2-Ethyl-5,7-dimethyl-3H-imidazo[4,5-b]pyridin-3-yl)phenyl]ethylamine To a solution of 2-[4-(2-ethyl-5,7-dimethyl-3H-imidazo [4,5-b]pyridin-3-yl)phenyl]ethyl azide (step 8, 2.35 g, 7.3 mmol) in methanol (50 mL) was added 10% Pd—C (200 mg). The resulting mixture was stirred for 4 h under hydrogen atmosphere. The mixture was filtered through a pad of Celite and the filtrate was concentrated. The residue was purified by flash column chromatography on silica gel eluting with dichloromethane/methanol/triethylamine (100:5:1) to afford 2.01 g (94%) of the title compound as white solids: $^1$H-NMR (CDCl$_3$) δ 7.39 (2H, d, J=8.4 Hz), 7.32 (2H, d, J=8.4 Hz), 6.90 (1H, s), 3.05 (2H, t, J=7.3 Hz), 2.88–2.78 (4H, m), 2.65 (3H, s), 2.51 (3H, s), 1.28 (3H, t, J=7.6 Hz).

STEP 10. 2-Ethyl-5,7-dimethyl-3-(4-{2-[({[(4-methylphenyl)sulfonyl]amino}carbonyl)amino]ethyl}phenyl)-3H-imidazo[4,5-b]pyridine To a solution of 2-[4-(2-ethyl-5,7-dimethyl-3H-imidazo [4,5-b]pyridin-3-yl)phenyl]ethylamine (step 9, 1.2 g, 4.0 mmol) in dichloromethane (15 mL) was added p-toluenesulfonyl isocyanate (805 mg, 4.0 mmol). The resulting mixture was stirred at room temperature for 3 h. After removal of solvent, the residue was purified by flash column chromatography on silica gel eluting with dichloromethane/methanol (20:1) to afford 1.10 g (56%) of the title compound as white solids: $^1$H-NMR (CDCl$_3$) δ 7.85 (2H, d, J=8.2 Hz), 7.32 (2H, d, J=8.2 Hz), 7.23 (2H, d, J=8.4 Hz), 7.16 (2H, d, J=8.4 Hz), 6.91 (1H, s), 6.12 (1H, br.s), 3.55–3.46 (2H, m), 2.85 (2H, t, J=6.3 Hz), 2.74–2.64 (5H, m), 2.42 (3H, s), 2.41 (3H, s), 1.21 (3H, t, J=7.6 Hz).

EXAMPLE 2

2-ETHYL-5,7-DIMETHYL-3-(4-{2-[({[(4-METHYLPHENYL)SULFONYL]AMINO}CARBONYL) AMINO]ETHYL}PHENYL)-3H-IMIDAZO[4,5-b] PYRIDINE, SODIUM SALT

To a solution of 2-ethyl-5,7-dimethyl-3-(4-{2-[({[(4-methylphenyl)sulfonyl]amino}carbonyl)amino] ethyl}phenyl)-3H-imidazo[4,5-b]pyridine (Example 1, 5.0 g, 10.2 mmol) in methanol (20 mL) was added 2N aqueous NaOH (5.1 mL, 10.2 mmol). The resulting mixture was stirred at room temperature for 5 min and concentrated. The residual solids were collected by filtration and dried under reduced pressure at 50° C. to afford the title compound as white solids: $^1$H-NMR (DMSO-d$_6$) δ 7.60 (2H, d, J=8.2 Hz), 7.31–7.39 (4H, m), 7.14 (2H, d, J=8.2 Hz), 6.96 (1H, s), 3.15 (2H, br.s), 2.66–2.75 (4H, m), 2.53 (3H, s), 2.40 (3H, s), 2.28 (3H, s), 1.20 (3H, t, J=7.6 Hz).

EXAMPLE 3

2-[4-(2-ETHYL-5,7-DIMETHYL-3H-IMIDAZO[4,5-b]PYRIDINE-3-YL)PHENYL]ETHYL(4-METHYLPHENYL)SULFONYLCARBAMATE

To a solution of 2-[4-(2-ethyl-5,7-dimethyl-3H-imidazo [4,5-b]pyridin-3-yl)phenyl]ethanol (step 6 of Example 1, 300 mg, 1.0 mmol) in dichloromethane (10 mL) was added p-toluenesulfonyl isocyanate (237 mg, 1.2 mmol). The resulting mixture was stirred at room temperature overnight. After removal of solvent, the residual solids were recrystallized from ethyl acetate to afford 454 mg (92%) of the title compound as white solids: $^1$H-NMR (CDCl$_3$) δ 7.93 (2H, d, J=8.4 Hz), 7.33 (2H, d, J=8.4 Hz), 7.22 (4H, s), 6.92 (1H, s), 4.87 (1H, br.s), 4.35 (2H, t, J=6.6 Hz), 2.96 (2H, t, J=6.6 Hz), 2.78 (2H, q, J=7.7 Hz), 2.66 (3H, s), 2.50 (3H, s), 2.43 (3H, s), 1.24 (3H, t, J=7.7 Hz).

EXAMPLE 4

2-ETHYL-5,7-DIMETHYL-3-(4-{2-[({METHYL [(4-METHYLPHENYL)SULFONYL] AMINO}CARBONYL)AMINO] ETHYL}PHENYL)-3H-IMIDAZO[4,5-b] PYRIDINE

To a stirred solution of 2-ethyl-5,7-dimethyl-3-(4-{2-[({[(4-methylphenyl)sulfonyl]amino}carbonyl)amino] ethyl}phenyl)-3H-imidazo[4,5-b]pyridine (Example 1, 200 mg, 0.41 mmol) in THF (10 mL) was added dropwise a solution of lithium diisopropylamide (LDA) (2.0 N in heptane/hexane/ethylbenzene, 0.8 mL, 1.6 mmol) with ice-cooling over a period of 10 min. After completion of the addition, the stirring was continued for an additional 20 min at the same temperature. To the resulting mixture was added dropwise MeI (0.5 mL) at 0° C., and stirred at room temperature for 15 h. The mixture was poured into a solution of phosphate buffer (100 mL) and extracted with dichloromethane (100 mL). The organic layer was washed with brine (50 mL), dried (Na$_2$SO$_4$), and concentrated. The residue was purified by flash chromatography on silica gel eluting with dichloromethane/methanol (10:1) to give 10 mg (5%) of the title compound as a colorless oil: $^1$H-NMR (CDCl$_3$) δ 7.64 (2H, d, J=8.3 Hz), 7.53–7.25 (7H, m), 6.89 (1H, s), 3.65–3.55 (2H, m), 3.14 (3H, s), 2.96 (2H, t, J=6.7 Hz), 2.82 (2H, q, J=7.6 Hz), 2.66 (3H, s), 2.50 (3H, s), 2.40 (3H, s), 1.25 (3H, t, J=7.6 Hz).

EXAMPLE 5

2-ETHYL-5,7-DIMETHYL-3-(4-{2-[METHYL ({[(4-METHYLPHENYL)SULFONYL] AMINO}CARBONYL)AMINO] ETHYL}PHENYL)-3H-IMIDAZO[4,5-b]PYRIDINE

STEP 1. N-{2-[4-(2-Ethyl-5,7-dimethyl-3H-imidazo[4,5-b] pyridin-3-yl)phenyl]ethyl}-N-methylamine A mixture of 3-[4-(2-chloroethyl)phenyl]-2-ethyl-5,7-dimethyl-3H-imidazo[4,5-b]pyridine (step 7 of Example 1, 627 mg, 9.0 mmol), a solution of methylamine (40% in methanol, 6 mL) and water (6 mL) was placed in a sealed tube and heated overnight at 130° C. The reaction mixture was partitioned between dichloromethane (50 mL) and water (50 mL). The organic phase was separated and the aqueous phase was extracted with dichloromethane (50 mL). The combined organic extracts were washed with brine (50 mL) and dried ($Na_2SO_4$). After removal of solvent, the crude product was purified by flash column chromatography on silica gel eluting with dichloromethane/methanol (5:1) to afford 523 mg (85%) of the title compound as white solids: $^1$H-NMR (CDCl$_3$) δ 7.41 (2H, d, J=8.3 Hz), 7.31 (2H, d, J=8.3 Hz), 6.90 (1H, s), 4.73 (1H, br.s), 2.93 (4H, s), 2.82 (2H, q, J=7.5 Hz), 2.65 (3H, s), 2.51 (3H, s), 2.49 (3H, t, J=7.5 Hz).

STEP 2. 2-Ethyl-5,7-dimethyl-3-(4-{2-[methyl({[(4-methylphenyl)sulfonyl]amino}carbonyl)amino]ethyl}phenyl)-3H-imidazo[4,5-b]pyridine To a solution of N-{2-[4-(2-ethyl-5,7-dimethyl-3H-imidazo[4,5-b]pyridin-3-yl)phenyl]ethyl}-N-methylamine (step 1, 523 mg, 1.7 mmol) in dichloromethane (10 mL) and triethylamine (2 mL) was added p-toluenesulfonyl isocyanate (400 mg, 2.0 mmol). The resulting reaction mixture was stirred at room temperature for 6 h. After removal of solvent, the residue was purified by flash column chromatography on silica gel eluting with dichloromethane/methanol (10:1) to afford 358 mg (42%) of the title compound as white solids: $^1$H-NMR (CDCl$_3$) δ 7.93 (2H, d, J=8.3 Hz), 7.31 (2H, d, J=8.4 Hz), 7.24 (2H, d, J=8.3 Hz), 7.14 (2H, d, J=8.4 Hz), 6.92 (1H, s), 3.66–3.49 (2H, m), 3.51 (3H, s), 2.93–2.70 (4H, m), 2.65 (3H, s), 2.50 (3H, s), 2.38 (3H, s) 1.24 (3H, t, J=7.2 Hz).

EXAMPLE 6

2-ETHYL-5,7-DIMETHYL-3-(4-{2-[({[(4-METHYLPHENYL)SULFONYL]AMINO}CARBONYL)AMINO]PROPYL}PHENYL)-3H-IMIDAZO[4,5-b]PYRIDINE

STEP 1. 1-(4-Aminophenyl)-2-propanol

A mixture of 1-(4-nitrophenyl)-2-propanol (Schadt, F. L.; et al. *J. Am. Chem. Soc.*, 1978, 100, 228., 2.2 g, 12.3 mmol), iron powder (3.3 g, 59.1 mmol), ammonium chloride (370 mg, 6.9 mmol), ethanol (48 mL) and water (24 mL) was heated at reflux temperature for 2 h. The mixture was cooled and filtered through a pad of Celite. The filtrate was concentrated. The residue was diluted with ethyl acetate (200 mL) and washed with water (2×100 mL). The organic layer was dried (MgSO$_4$), and concentrated. Purification by flash column chromatography on silica gel eluting with hexane/ethyl acetate (1:1) to afford 1.45 g (78%) of the title compound as a yellow oil: $^1$H-NMR (CDCl$_3$) δ 7.00 (2H, d, J=8.6 Hz), 6.64 (2H, d, J=8.8 Hz), 3.99–3.89 (1H, m), 3.60 (2H, br s), 2.72–2.52 (2H, m), 1.22 (3H, d, J=6.2 Hz).

STEP 2. 1-{4-[(4,6-Dimethyl-3-nitro-2-pyridinyl)amino]phenyl}-2-propanol

The title compound was prepared according to the procedure described in step 3 of Example 1 from 1-(4-aminophenyl)-2-propanol (step 1) and 2-chloro-4,6-dimethyl-3-nitropyridine (step 2 of Example 1).

$^1$H-NMR (CDCl$_3$) δ 9.59 (1H, br.s), 7.58 (2H, d, J=8.4 Hz), 7.20 (2H, d, J=8.4 Hz), 6.53 (1H, s), 4.13–4.01 (1H, m), 2.82–2.64 (2H, m), 2.55 (3H, s), 2.44 (3H, s), 1.25 (3H, d, J=6.2 Hz).

STEP 3. 1-{4-[(3-Amino-4,6-dimethyl-2-pyridinyl)amino]phenyl}-2-propanol

A mixture of 1-{4-[(4,6-dimethyl-3-nitro-2-pyridinyl)amino]phenyl}-2-propanol (step 2, 500 mg, 1.66 mmol), iron powder (440 mg, 7.88 mmol), ammonium chloride (80 mg, 1.5 mmol) in ethanol/water (v/v, 31:8, 39 mL) was heated at reflux temperature for 2 h. The mixture was cooled and filtered through a pad of Celite. The filtrate was concentrated. The residue was diluted with dichloromethane (200 mL) and washed with water (2×100 mL). The organic layer was dried (MgSO$_4$), and concentrated. Removal of solvent gave 450 mg (quant.) of the title compound as brown solids: TLC Rf 0.10 (hexane/ethyl acetate=1:1).

STEP 4. 2-[4-(2-Ethyl-5,7-dimethyl-3H-imidazo[4,5-b]pyridin-3-yl)phenyl]-1-methylethyl propionate The title compound was prepared according to the procedure described in step 5 of Example 1 from 1-{4-[(3-amino-4,6-dimethyl-2-pyridinyl)amino]phenyl}-2-propanol (step 3) and propionyl chloride.

TLC Rf=0.30 (hexane/ethyl acetate=1:1).

STEP 5. 1-[4-(2-Ethyl-5,7-dimethyl-3H-imidazo[4,5-b]pyridin-3-yl)phenyl]-2-propanol The title compound was prepared according to the procedure described in step 6 of Example 1 from 2-[4-(2-ethyl-5,7-dimethyl-3H-imidazo[4,5-b]pyridin-3-yl)phenyl]-1-methylethyl propionate (step 4).

$^1$H-NMR (CDCl$_3$) δ 7.40 (2H, d, J=8.0 Hz), 7.33 (2H, d, J=8.0 Hz), 6.91 (1H, s), 4.16–4.07 (1H, m), 2.90–2.76 (4H, m), 2.66 (2H, s), 2.52 (3H, s), 1.32–1.22 (6H, m).

STEP 6. 3-[4-(2-Chloropropyl)phenyl]-2-ethyl-5,7-dimethyl-3H-imidazo[4,5-b]pyridine The title compound was prepared according to the procedure described in step 7 of Example 1 from 1-[4-(2-ethyl-5,7-dimethyl-3H-imidazo[4,5-b]pyridin-3-yl)phenyl]-2-propanol (step 5).

TLC Rf=0.50 (hexane/ethyl acetate=1:1).

STEP 7. 2-[4-(2-Ethyl-5,7-dimethyl-3H-imidazo[4,5-b]pyridin-3-yl)phenyl]-1-methylethyl azide The title compound was prepared according to the procedure described in step 8 of Example 1 from 3-[4-(2-chloropropyl)phenyl]-2-ethyl-5,7-dimethyl-3H-imidazo[4,5-b]pyridine (step 6).

$^1$H-NMR (CDCl$_3$) δ 7.40 (2H, d, J=8.4 Hz), 7.34 (2H, d, J=8.4 Hz), 6.91 (1H, s), 3.81–3.74 (1H, m), 2.95–2.79 (4H, m), 2.66 (3H, s), 2.52 (3H, s), 1.35 (3H, d, J=6.6 Hz), 1.27 (3H, t, J=7.5 Hz).

STEP 8. 1-[4-(2-Ethyl-5,7-dimethyl-3H-imidazo[4,5-b]pyridin-3-yl)phenyl]-2-propanamine The title compound was prepared according to the procedure described in step 9 of Example 1 from 2-[4-(2-ethyl-5,7-dimethyl-3H-imidazo[4,5-b]pyridin-3-yl)phenyl]-1-methylethyl azide (step 7).

$^1$H-NMR (CDCl$_3$) δ 7.40–7.31 (4H, m), 6.90 (1H, s), 3.31–3.20 (1H, m), 2.87–2.77 (3H, m), 2.66–2.58 (4H, m), 2.52 (3H, s), 1.28 (3H, t, J=8.3 Hz), 1.19 (3H, d, J=6.8 Hz).

STEP 9. 2-Ethyl-5,7-dimethyl-3-(4-{2-[({[(4-methylphenyl)sulfonyl]amino}carbonyl)amino]propyl}phenyl)-3H-imidazo[4,5-b]pyridine The title compound was prepared according to the procedure described in step 10 of Example 1 from 1-[4-(2-ethyl-5,7-dimethyl-3H-imidazo[4,5-b]pyridin-3-yl)phenyl]-2-propanamine (step 8).

mp 128° C.; MS (ESI) m/z 506.19 (M+H)$^+$; $^1$H-NMR (CDCl$_3$) δ 7.74 (2H, d, J=8.3 Hz), 7.30–7.19 (6H, m), 6.90 (1H, s), 4.08–4.02 (1H, m), 2.84–2.72 (4H, m), 2.65 (3H, s), 2,48 (3H, s), 2.32 (3H, s), 1.20–1.13 (6H, m).

EXAMPLE 7

2-[4-(2-ETHYL-5,7-DIMETHYL-3H-IMIDAZO[4,5-b]PYRIDIN-3-YL)PHENYL]-1-METHYL-ETHYL(4-METHYLPHENYL)SULFONYLCARBAMATE

The title compound was prepared according to the procedure described in Example 3 from 1-[4-(2-ethyl-5,7-dimethyl-3H-imidazo[4,5-b]pyridin-3-yl)phenyl]-2-propanol (step 5 of Example 6).

mp 108° C.; MS (ESI) m/z 507.18 (M+H)$^+$; $^1$H-NMR (CDCl$_3$) δ 7.91 (2H, d, J=8.4 Hz), 7.31 (2H, d, J=8.3 Hz), 7.23 (4H, s), 6.91 (1H, s), 5.10–5.04 (1H, m), 2.95–2.76 (4H, m), 2.65 (3H, s), 2.50 (3H, s), 2.41 (3H, s), 1.28–1.21 (6H, m).

EXAMPLE 8

5,7-DIMETHYL-3-(4-{2-[({[(4-METHYLPHENYL)SULFONYL]AMINO}CARBONYL)AMINO]ETHYL}PHENYL)-2-PROPYL-3H-IMIDAZO[4,5-b]PYRIDINE

STEP 1. 2-[4-(5,7-Dimethyl-2-propyl-3H-imidazo[4,5-b]pyridin-3-yl)phenyl]ethyl butyrate The title compound was prepared according to the procedure described in step 5 of Example 1 from 2-{4-[(3-amino-4,6-dimethyl-2-pyridinyl)amino]phenyl}ethanol (step 4 of Example 1) and butyryl chloride.

$^1$H-NMR (CDCl$_3$) δ 7.42 (2H, d, J=8.2 Hz), 7.32 (2H, d, J=8.2 Hz), 6.92 (1H, s), 4.39 (2H, t, J=6.4 Hz), 3.09 (2H, t, J=6.4 Hz), 2.77, (2H, t, J=7.7 Hz), 2.66 (3H, s), 2.52 (3H, s), 2.32 (2H, t, J=7.7 Hz), 1.81–1.58 (4H, m), 1.00–0.86 (6H, m).

STEP 2. 2-[4-(5,7-Dimethyl-2-propyl-3H-imidazo[4,5-b]pyridin-3-yl)phenyl]ethanol The title compound was prepared according to the procedure described in step 6 of Example 1 from 2-[4-(5,7-dimethyl-2-propyl-3H-imidazo[4,5-b]pyridin-3-yl)phenyl]ethyl butyrate (step 1).

$^1$H-NMR (CDCl$_3$) δ 7.43 (2H, d, J=8.0 Hz), 7.32 (2H, d, J=8.0 Hz), 6.90 (1H, s), 4.00–3.89 (2H, m), 2.97 (2H, t, J=6.4 Hz), 2.78 (2H, t, J=7.8 Hz), 2.65 (3H, s), 2.51 (3H, s), 1.80–1.64 (2H, m), 0.92 (3H, t, J=7.4 Hz).

STEP 3. 3-[4-(2-Chloroethyl)phenyl]-5,7-dimethyl-2-propyl-3H-imidazo[4,5-b]pyridine The title compound was prepared according to the procedure described in step 7 of Example 1 from 2-[4-(5,7-dimethyl-2-propyl-3H-imidazo[4,5-b]pyridin-3-yl)phenyl]ethanol (step 2).

MS (EI) m/z 327 (M$^+$).

STEP 4. 2-[4-(5,7-Dimethyl-2-propyl-3H-imidazo[4,5-b]pyridin-3-yl)phenyl]ethyl azide The title compound was prepared according to the procedure described in step 8 of Example 1 from 3-[4-(2-chloroethyl)phenyl]-5,7-dimethyl-2-propyl-3H-imidazo[4,5-b]pyridine (step 3).

MS (EI) m/z 334 (M$^+$); $^1$H-NMR (CDCl$_3$) δ 7.42 (2H, d, J=8.4 Hz), 7.34 (2H, d, J=8.4 Hz), 6.91 (1H, s), 3.60 (2H, t, J=7.2 Hz), 3.00 (2H, t, J=7.2 Hz), 2.77 (2H, t, J=7.8 Hz), 2.65 (3H, s) 2.52 (3H, s), 1.75–1.62 (2H, m), 0.90 (3H, t, J=7.4 Hz).

STEP 5. 2-[4-(5,7-Dimethyl-2-propyl-3H-imidazo[4,5-b]pyridin-3-yl)phenyl]ethylamine The title compound was prepared according to the procedure described in step 9 of Example 1 from 2-[4-(5,7-dimethyl-2-propyl-3H-imidazo[4,5-b]pyridin-3-yl)phenyl] ethyl azide (step 4).

$^1$H-NMR (CDCl$_3$) δ 7.42 (2H, d, J=8.3 Hz), 7.29 (2H, d, J=8.3 Hz), 6.88 (1H, s), 3.89 (2H, br.s), 3.18 (2H, t, J=6.8 Hz), 3.01 (2H, t, J=6.8 Hz), 2.75 (2H, t, J=7.5 Hz), 2.64 (3H, s), 2.48 (3H, s), 1.78–1.63 (2H, m), 0.90 (3H, t, J=7.3 Hz).

STEP 6. 5,7-Dimethyl-3-(4-{2-[({[(4-methylphenyl)sulfonyl]amino}carbonyl)amino]ethyl}phenyl)-2-propyl-3H-imidazo[4,5-b]pyridine The title compound was prepared according to the procedure described in step 10 of Example 1 from 2-[4-(5,7-dimethyl-2-propyl-3H-imidazo[4,5-b]pyridin-3-yl)phenyl] ethylamine (step 5).

$^1$H-NMR (CDCl$_3$) δ 7.86 (2H, d, J=8.3 Hz), 7.30 (2H, d, J=8.3 Hz), 7.23 (2H, d, J=8.3 Hz), 7,16 (2H, d, J=8.3 Hz), 6.90 (1H, s), 6.10 (1H, br.s), 3.58–3.46 (2H, m), 2.87 (2H, t, J=6.4 Hz), 2.71–2.59 (5H, m), 2.42 (3H, s), 2.40 (3H, s), 1.74–1.61 (2H, m), 0.89 (3H, t, J=7.0 Hz).

EXAMPLE 9

2-ISOPROPYL-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE

STEP 1. 5-Bromo-4,6-dimethyl-3-nitro-2-pyridinol

To a solution of 5-bromo-4,6-dimethyl-3-nitro-2-pyridinylamine (Heitsch, H.; et al. *Bioorg. Med. Chem.* 1997, 5, 673., 2.0 g, 8.1 mmol) in trifluoroacetic acid/water (v/v, 2:1, 30 mL) was added sodium nitrite (1.1 g, 16 mmol) in small portions at room temperature, and then the reaction mixture was stirred overnight. The resulting precipitates were collected by filtration, washed with water, and dried under reduced pressure to give 2.2 g (quant.) of the title compound: $^1$H-NMR (CDCl$_3$) δ 2.53 (3H, s), 2.38 (3H, s).

STEP 2. 3-Bromo-6-chloro-2,4-dimethyl-5-nitropyridine

The title compound was prepared according to the procedure described in step 2 of Example 1 from 5-bromo-4,6-dimethyl-3-nitro-2-pyridinol (step 1).

$^1$H-NMR (CDCl$_3$) δ 2.72 (3H, s), 2.41 (3H, s).

STEP 3. 2-{4-[(5-Bromo-4,6-dimethyl-3-nitro-2-pyridinyl)amino]phenyl}ethanol

The title compound was prepared according to the procedure described in step 3 of Example 1 from 3-bromo-6-chloro-2,4-dimethyl-5-nitropyridine (step 2) and 4-aminophenylethyl alcohol.

$^1$H-NMR (CDCl$_3$) δ 8.66 (1H, br.s), 7.51 (2H, d, J=8.4 Hz), 7.22 (2H, d, J=8.4 Hz), 3.90–3.77 (2H, m), 2.88 (2H, t, J=6.5 Hz), 2.65 (3H, s), 2.59 (3H, s).

STEP 4. 2-{4-[(3-Amino-5-bromo-4,6-dimethyl-2-pyridinyl)amino]phenyl}ethanol

The title compound was prepared according to the procedure described in step 4 of Example 1 from 2-{4-[(5-bromo-4,6-dimethyl-3-nitro-2-pyridinyl)amino]phenyl}ethanol (step 3).

$^1$H-NMR (CDCl$_3$) δ 7.12 (4H, s), 6.21 (1H, s), 3.38 (1H, br.s), 3.82 (2H, t, J=6.5 Hz), 2.80 (2H, t, J=6.5 Hz), 2.54 (3H, s), 2.38 (3H, s).

STEP 5. 2-[4-(6-Bromo-2-isopropyl-5,7-dimethyl-3H-imidazo[4,5-b]pyridin-3-yl)phenyl]ethyl 2-methylpropanoate The title compound was prepared according to the procedure described in step 5 of Example 1 from 2-{4-[(3-amino-5-bromo-4,6-dimethyl-2-pyridinyl)amino]phenyl}ethanol (step 4) and isobutyryl chloride.

MS (EI) m/z 457 (M$^+$).

STEP 6. 2-[4-(6-Bromo-2-isopropyl-5,7-dimethyl-3H-imidazo[4,5-b]pyridin-3-yl)phenyl]ethylnol The title compound was prepared according to the procedure described in step 6 of Example 1 from 2-[4-(6-bromo-2-isopropyl-5,7-dimethyl-3H-imidazo[4,5-b]pyridin-3-yl)phenyl]ethyl 2-methylpropanoate (step 5).

$^1$H-NMR (CDCl$_3$) δ 7.45 (2H, d, J=8.3 Hz), 7.30 (2H, d, J=8.3 Hz), 3.96 (2H, t, J=7.3 Hz), 3.15–3.03 (1H, m), 2.97 (2H, t, J=7.3 Hz), 2.76 (3H, s), 2.67 (3H, s), 1.34 (6H, d, J=6.8 Hz).

STEP 7. 6-Bromo-3-[4-(2-chloroethyl)phenyl]-2-isopropyl-5,7-dimethyl-3H-imidazo[4,5-b]pyridine The title compound was prepared according to the procedure described in step 7 Example 1 from 2-[4-(6-bromo-2-isopropyl-5,7-dimethyl-3H-imidazo[4,5-b]pyridin-3-yl)phenyl]ethanol (step 6).

$^1$H-NMR (CDCl$_3$) δ 7.43 (2H, d, J=8.3 Hz), 7.32 (2H, d, J=8.3 Hz), 3.81 (2H, t, J=7.3 Hz), 319 (2H, t, J=7.3 Hz), 3.15–3.02 (1H, m), 2.76 (3H, s), 2.66 (3H, s), 1.33 (6H, d, J=6.9 Hz).

STEP 8. 2-[4-(6-Bromo-2-isopropyl-5,7-dimethyl-3H-imidazo[4,5-b]pyridin-3-yl)phenyl]ethyl azide The title compound was prepared according to the procedure described in step 8 Example 1 from 6-bromo-3-[4-(2-chloroethyl)phenyl]-2-isopropyl-5,7-dimethyl-3H-imidazo[4,5-b]pyridine (step 7).

MS (EI) m/z 412 (M$^+$); $^1$H-NMR (CDCl$_3$) δ 7.42 (2H, d, J=8.4 Hz), 7.30 (2H, d, J=8.4 Hz), 3.60 (2H, t, J=6.5 Hz), 3.16–3.02 (1H, m), 3.02 (2H, t, J=6.5 Hz), 2.77 (3H, s), 2.68 (3H, s), 1.33 (6H, d, J=6.9 Hz).

STEP 9. [4-(2-Isopropyl-5,7-dimethyl-3H-imidazo[4,5-b]pyridin-3-yl)phenyl]ethylamine The title compound was prepared according to the procedure described in step 9 of Example 1 from 2-[4-(6-bromo-2-isopropyl-5,7-dimethyl-3H-imidazo[4,5-b]pyridin-3-yl)phenyl]ethyl azide (step 8).

H-NMR (CDCl$_3$) δ 7.49 (2H, d, J=8.3 Hz), 7.28 (2H, d, J=8.3 Hz), 6.93 (1H, s), 6.60 (2H, br.s), 3.32–3.00 (5H, m), 2.65 (3H, s), 2.48 (3H, s), 1.31 (6H, d, J=6.8 Hz).

STEP 10. 2-Isopropyl-5,7-dimethyl-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from [4-(2-isopropyl-5,7-dimethyl-3H-imidazo[4,5-b]pyridin-3-yl)phenyl]ethylamine (step 9).

$^1$H-NMR (CDCl$_3$) δ 7.87 (2H, d, J=8.3 Hz), 7.31 (2H, d, J=8.3 Hz), 7.23 (2H, d, J=8.4 Hz), 7.17 (2H, d, J=8.4 Hz), 6.91 (1H, s), 6.08 (1H, br.s), 3.56–3.43 (2H, m), 3.02–2.89 (1H, m), 2.85 (2H, t, J=6.3 Hz), 2.67 (3H, s), 2.41 (6H, s), 1.26 (6H, d, J=6.8 Hz).

EXAMPLE 10

2-ISOPROPYL-5,7-DIMETHYL-3-(4-{2-[({[(4-METHYLPHENYL)SULFONYL]AMINO}CARBONYL)AMINO]ETHYL}PHENYL)-3H-IMIDAZO[4,5-]PYRIDINE, SODIUM SALT

The title compound was prepared according to the procedure described in Example 2 from 2-isopropyl-5,7-dimethyl-3-(4-{2-[({[(4-methylphenyl)sulfonyl]amino}carbonyl)amino]ethyl}phenyl)-3H-imidazo[4,5-b]pyridine (Example 9).

MS (ESI) m/z 506 (M+H)$^+$.

EXAMPLE 11

2-BUTYL-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE

STEP 1. 2-[4-(6-Bromo-2-butyl-5,7-dimethyl-3H-imidazo[4,5-b]pyridin-3-yl)phenyl]ethyl pentanoate The title compound was prepared according to the procedure described in step 5 of Example 1 from 2-{4-[(3-amino-5-bromo-4,6-dimethyl-2-pyridinyl)amino]phenyl}ethanol (step 4 of Example 9) and pentanoyl chloride.

MS (EI) m/z 485 (M$^+$); $^1$H-NMR (CDCl$_3$) δ 7.42 (2H, d, J=8.3 Hz), 7.31 (2H, d, J=8.3 Hz), 4.37 (2H, t, J=6.9 Hz), 3.05 (2H, t, J=6.9 Hz), 2.79 (2H, t, J=7.7 Hz), 2.75 (3H, s), 2.67 (3H, s), 2.33 (2H, t, J=7.5 Hz), 1.75–1.54 (4H, m), 1.40–1.20 (4H, m), 0.91 (3H, t, J=7.3 Hz), 0.84 (3H, t, J=7.3 Hz).

STEP 2. 2-[4-(6-Bromo-2-butyl-5,7-dimethyl-3H-imidazo[4,5-b]pyridin-3-yl)phenyl]ethanol The title compound was prepared according to the procedure described in step 6 of Example 1 from 2-[4-(6-bromo-2-butyl-5,7-dimethyl-3H-imidazo[4,5-b]pyridin-3-yl)phenyl]ethyl pentanoate (step 1).

MS (EI) m/z 401 (M$^+$).

STEP 3. 6-Bromo-2-butyl-3-[4-(2-chloroethyl)phenyl]-5,7-dimethyl-3H-imidazo[4,5-b]pyridine The title compound was prepared according to the procedure described in step 7 Example 1 from 2-[4-(6-bromo-2-butyl-5,7-dimethyl-3H-imidazo[4,5-b]pyridin-3-yl)phenyl]ethanol (step 2).

MS (EI) m/z 419 (M$^+$).

STEP 4. 2-[4-(6-Bromo-2-butyl-5,7-dimethyl-3H-imidazo[4,5-b]pyridin-3-yl)phenyl]ethyl azide The title compound was prepared according to the procedure described in step 8 Example 1 from 6-bromo-2-butyl-3-[4-(2-chloroethyl)phenyl]-5,7-dimethyl-3H-imidazo[4,5-b]pyridine (step 3).

MS (EI) m/z 426 (M$^+$); $^1$H-NMR (CDCl$_3$) δ 7.43 (2H, d, J=8.4 Hz), 7.33 (2H, d, J=8.4 Hz), 3.61 (2H, t, J=7.2 Hz), 3.01 (2H, t, J=7.2 Hz), 2.79 (2H, t, J=7.9 Hz), 2.75 (3H, s), 1.75–1.60 (2H, m), 1.36–1.20 (2H, m), 0.84 (3H, t, J=7.3 Hz).

STEP 5. 2-[4-(2-Butyl-5,7-dimethyl-3H-imidazo[4,5-b]pyridin-3-yl)phenyl]ethylamine The title compound was prepared according to the procedure described in step 9 of Example 1 from 2-[4-(6- bromo-2-butyl-5,7-dimethyl-3H-imidazo[4,5-b]pyridin-3-yl)phenyl]ethyl azide (step 4).

¹H-NMR (CDCl₃) δ 7.59 (2H, d, J=8.3 Hz), 7.35 (2H, d, J=8.3 Hz), 6.90 (1H, s), 3.52–3.22 (4H, m), 3.01 (2H, br.s), 2.90 (2H, t, J=7.7 Hz), 2.74 (3H, s), 2.56 (3H, s), 1.79–1.62 (2H, m), 1.41–1.23 (2H, m), 0.84 (3H, t, J=7.5 Hz).

STEP 6. 2-Butyl-5,7-dimethyl-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(2-butyl-5,7-dimethyl-3H-imidazo[4,5-b]pyridin-3-yl)phenyl]ethylamine (step 5).

¹H-NMR (CDCl₃) δ 7.86 (2H, d, J=8.2 Hz), 7.31 (2H, d, J=8.2 Hz), 7.22 (2H, d, J=8.3 Hz), 7.14 (2H, d, J=8.3 Hz), 6.91 (1H, s), 6.09 (1H, br.s), 3.56–3.44 (2H, m), 2.84 (2H, t, J=6.4 Hz), 2.70–2.59 (5H, m), 2.42 (3H, s), 2.41 (3H, s), 1.69–1.43 (2H, m), 1.30–1.18 (2H, m), 0.80 (3H, t, J=7.3 Hz).

EXAMPLE 12

2-BUTYL-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, SODIUM SALT

The title compound was prepared according to the procedure described in Example 2 from 2-butyl-5,7-dimethyl-3-(4-{2-[({[(4-methylphenyl)sulfonyl]amino}carbonyl)amino]ethyl}phenyl)-3H-imidazo[4,5-b]pyridine (Example 11).

MS (ESI) m/z 520 (M+H)⁺.

EXAMPLE 13

2-ISOBUTYL-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE

STEP 1. 2-[4-(2-Isobutyl-5,7-dimethyl-3H-imidazo[4,5-b]pyridin-3-yl)phenyl]ethyl 3-methylbutanoate The title compound was prepared according to the procedure described in step 5 of Example 1 from 2-{4-[(3-amino-4,6-dimethyl-2-pyridinyl)amino]phenyl}ethanol (step 4 of Example 1) and isovaleryl chloride.

MS (EI) m/z 407 (M⁺).

STEP 2. 2-[4-(2-Isobutyl-5,7-dimethyl-3H-imidazo[4,5-b]pyridin-3-yl)phenyl]ethanol The title compound was prepared according to the procedure described in step 6 of Example 1 from 2-[4-(2-isobutyl-5,7-dimethyl-3H-imidazo[4,5-b]pyridin-3-yl)phenyl]ethyl 3-methylbutanoate (step 1).

MS (EI) m/z 323 (M⁺).

STEP 3. 3-[4-(2-Chloroethyl)phenyl]-2-isobutyl-5,7-dimethyl-3H-imidazo[4,5-b]pyridine The title compound was prepared according to the procedure described in step 7 Example 1 from 2-[4-(2-isobutyl-5,7-dimethyl-3H-imidazo[4,5-b]pyridin-3-yl)phenyl]ethanol (step 2).

MS (EI) m/z 341 (M⁺); ¹H-NMR (CDCl₃) δ 7.41 (2H, d, J=8.2 Hz), 7.33 (2H, d, J=8.2 Hz), 6.90 (1H, s), 3.80 (2H, t, J=6.5 Hz), 3.18 (2H, t, J=6.5 Hz), 2.68 (2H, d, J=7.5 Hz), 2.66 (3H, s) 2.51 (3H, s), 2.14–1.96 (1H, m), 0.86 (6H, d, J=6.6 Hz).

STEP 4. 2-[4-(2-Isobutyl-5,7-dimethyl-3H-imidazo[4,5-b]pyridin-3-yl)phenyl]ethyl azide The title compound was prepared according to the procedure described in step 8 Example 1 from 3-[4-(2-chloroethyl)phenyl]-2-isobutyl-5,7-dimethyl-3H-imidazo[4,5-b]pyridine (step 3).

MS (EI) m/z 348 (M⁺); ¹H-NMR (CDCl₃) δ 7.42 (2H, d, J=8.4 Hz), 7.31 (2H, d, J=8.4 Hz), 6.91 (1H, s), 3.60 (2H, t, J=6.5 Hz), 3.00 (2H, t, J=6.5 Hz), 2.69 (2H, d, J=7.5 Hz), 2.65 (3H, s), 2.52 (3H, s), 2.08–1.98 (1H, m), 0.87 (6H, d, J=6.7 Hz).

STEP 5. 2-[4-(2-Isobutyl-5,7-dimethyl-3H-imidazo[4,5-b]pyridin-3-yl)phenyl]ethylamine The title compound was prepared according to the procedure described in step 9 of Example 1 from 2-[4-(2-isobutyl-5,7-dimethyl-3H-imidazo[4,5-b]pyridin-3-yl)phenyl]ethyl azide (step 4).

¹H-NMR (CDCl₃) δ 7.40 (2H, d, J=8.3 Hz), 7.28 (2H, d, J=8.3 Hz), 6.91 (1H, s), 3.09 (2H, t, J=6.4 Hz), 2.93 (2H, t, J=6.4 Hz), 2.80 (2H, br.s), 2.68 (2H, d, J=7.5 Hz), 2.66 (3H, s), 2.53 (3H, s), 2.18–2.00 (1H, m), 0.88 (6H, d, J=6.8 Hz).

STEP 6. 2-Isobutyl-5,7-dimethyl-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(2-isobutyl-5,7-dimethyl-3H-imidazo[4,5-b]pyridin-3-yl)phenyl]ethylamine (step 5).

¹H-NMR (CDCl₃) δ 7.85 (2H, d, J=8.3 Hz), 7.28 (2H, d, J=8.3 Hz), 7.21 (2H, d, J=8.3 Hz), 7.12 (2H, d, J=8.3 Hz), 6.91 (1H, s), 6.14 (1H, br.s), 3.55–3.42 (2H, m), 2.82 (2H, t, J=6.3 Hz, 2.65 (3H, s), 2.53 (2H, d, J=7.3 Hz), 2.41 (3H, s), 2.39 (3H, s), 2.10–1.92 (1H, m), 0.81 (6H, d, J=6.6 Hz).

EXAMPLE 14

2-ISOBUTYL-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, SODIUM SALT

The title compound was prepared according to the procedure described in Example 2 from 2-isobutyl-5,7-dimethyl-3-(4-{2-[({[(4-methylphenyl)sulfonyl]amino}carbonyl)amino]ethyl}phenyl)-3H-imidazo[4,5-b]pyridine (Example 13).

MS (ESI) m/z 520 (M+H)⁺.

EXAMPLE 15

5,7-DIMETHYL-3-(4-{2-[({[(4-METHYLPHENYL)SULFONYL]AMINO}CARBONYL)AMINO]ETHYL}PHENYL)-2-NEOPENTYL-3H-IMIDAZO[4,5-b]PYRIDINE

STEP 1. 2-[4-(2-Neopentyl-5,7-dimethyl-3H-imidazo[4,5-b]pyridin-3-yl)phenyl]ethyl 3,3-dimethylbutanoate The title compound was prepared according to the procedure described in step 5 of Example 1 from 2-{4-[(3- amino-4,6-dimethyl-2-pyridinyl)amino]phenyl}ethanol (step 4 of Example 1) and tert-butylacetyl chloride.

MS (EI) m/z 435 (M+).

STEP 2. 2-[4-(2-Neopentyl-5,7-dimethyl-3H-imidazo[4,5-b]pyridin-3-yl)phenyl]ethanol The title compound was prepared according to the procedure described in step 6 of Example 1 from 2-[4-(2-neopentyl-5,7-dimethyl-3H-imidazo[4,5-b]pyridin-3-yl)phenyl]ethyl 3,3-dimethylbutanoate (step 1).

MS (EI) m/z 337 (M+).

STEP 3. 3-[4-(2-Chloroethyl)phenyl]-2-neopentyl-5,7-dimethyl-3H-imidazo[4,5-b]pyridine The title compound was prepared according to the procedure described in step 7 Example 1 from 2-[4-(2-neopentyl-5,7-dimethyl-3H-imidazo[4,5-b]pyridin-3-yl)phenyl]ethanol (step 2).

$^1$H-NMR (CDCl$_3$) δ 7.41 (2H, d, J=8.2 Hz), 7.30 (2H, d, J=8.2 Hz), 6.89 (1H, s), 3.81(2H, t, J=6.5 Hz), 3.18 (2H, t, J=6.5 Hz), 2.79 (2H, s), 2.66 (3H, s), 2.51 (3H, s), 0.89 (9H, s).

STEP 4. 2-[4-(2-Neopentyl-5,7-dimethyl-3H-imidazo[4,5-b]pyridin-3-yl)phenyl]ethyl azide The title compound was prepared according to the procedure described in step 8 Example 1 from 3-[4-(2-chloroethyl)phenyl]-2-neopentyl-5,7-dimethyl-3H-imidazo[4,5-b]pyridine (step 3).

MS (EI) m/z 362 (M+); $^1$H-NMR (CDCl$_3$) δ 7.42 (2H, d, J=8.3 Hz), 7.31 (2H, d, J=8.3, 6.91 (1H, s), 3.62 (2H, t, J=6.5 Hz), 3.02 (2H, t, J=6.5 Hz), 2.78 (2H, s), 2.68 (3H, s), 2.53 (3H, s), 0.88 (9H, s).

STEP 5. 2-[4-(2-Neopentyl-5,7-dimethyl-3H-imidazo[4,5-b]pyridin-3-yl)phenyl]ethylamine The title compound was prepared according to the procedure described in step 9 of Example 1 from 2-[4-(2-neopentyl-5,7-dimethyl-3H-imidazo[4,5-b]pyridin-3-yl)phenyl]ethyl azide (step 4).

MS (EI) m/z 336 (M+).

STEP 6. 2-Neopentyl-5,7-dimethyl-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(2-neopentyl-5,7-dimethyl-3H-imidazo[4,5-b]pyridin-3-yl)phenyl]ethylamine (step 5).

$^1$H-NMR (CDCl$_3$) δ 7.86 (2H, d, J=8.3 Hz), 7.31 (2H, d, J=8.3 Hz), 7.22 (2H, d, J=8.3 Hz), 7.14 (2H, d, J=8.3 Hz), 6.91 (1H, s), 6.18 (1H, br.s), 3.56–3.46 (2H, m), 2.85 (2H, t, J=6.4 Hz), 2.65 (3H, s), 2.60 (2H, s), 2.41 (3H, s), 2.40 (3H, s), 0.87 (9H, s).

EXAMPLE 16

5,7-DIMETHYL-3-(4-{2-[({[(4-METHYLPHENYL)SULFONYL]AMINO}CARBONYL)AMINO]ETHYL}PHENYL)-2-NEOPHENTYL-3H-IMIDAZO[4,5-b]PYRIDINE, SODIUM SALT

The title compound was prepared according to the procedure described in Example 2 from 5,7-dimethyl-3-(4-{2-[({[(4-methylphenyl)sulfonyl]amino}carbonyl)amino]ethyl}phenyl)-2-neopentyl-3H-imidazo[4,5-b]pyridine (Example 15).

MS (ESI) m/z 534 (M+H)+.

EXAMPLE 17

5,7-DIMETHYL-3-(4-{2-[({[(4-METHYLPHENYL)SULFONYL]AMINO}CARBONYL)AMINO]ETHYL}PHENYL)-2-[2-(1,3-THIAZOL-2-YL)ETHYL]-3H-IMIDAZO[4,5-b]PYRIDINE

STEP 1. N-[4-(2-Chloroethyl)phenyl]-N-(4,6-dimethyl-3-nitro-2-pyridinyl)amine

The title compound was prepared according to the procedure described in step 7 Example 1 from 2-{4-[(4,6-dimethyl-3-nitro-2-pyridinyl)amino]phenyl}ethanol (step 3 of Example 1).

$^1$H-NMR (CDCl$_3$) δ 9.46 (1H, br.s), 8.29 (1H, d, J=8.8 Hz), 7.42 (1H, d, J=1.7 Hz), 7.35 (2H, d, J=8.3 Hz), 7.22 (2H, d, J=8.3 Hz), 6.97 (1H, dd, J=8.8, 1.7 Hz), 3.77 (2H, t, J=7.2 Hz), 3.13 (2H, t, J=7.2 Hz).

STEP 2. N$^2$-[4-(2-Chloroethyl)phenyl]-4,6-dimethyl-2,3-pyridinediamine

The title compound was prepared according to the procedure described in step 3 of Example 6 from N-[4-(2-chloroethyl)phenyl]-N-(4,6-dimethyl-3-nitro-2-pyridinyl)amine (step 1).

MS (EI) m/z 383 (M+).

STEP 3. 3-[4-(2-Chloroethyl)phenyl]-5,7-dimethyl-2-[2-(1,3-thiazol-2-yl)ethyl]-3H-imidazo[4,5-b]pyridine To a mixture of N$^2$-[4-(2-chloroethyl)phenyl]-4,6-dimethyl-2,3-pyridinediamine (step 2, 276 mg, 1.0 mmol) and 3-(1,3-thiazol-2-yl)propanoic acid (157 mg, 1.0 mmol) in dichloromethane (10 mL) was added 1-ethyl-3-(3-dimethylaminopropyl)carbodiimide, hydrochloride (WSC) (192 mg, 1.0 mmol) in one portion. The reaction mixture was stirred overnight at room temperature. The reaction mixture was concentrated under reduced pressure. The residue was suspended in toluene (20 mL) and heated at 150° C. for 5 h. The reaction mixture was poured into water (50 mL), the organic phase was separated, and the aqueous phase was extracted with ethyl acetate (100 mL). The combined organic phases were washed with brine (50 mL) and dried (Na$_2$SO$_4$). After removal of solvent, the crude product was purified by flash column chromatography on silica gel eluting with hexane/ethyl acetate (1:1) to afford 210 mg (53%) of the title compound:

MS (EI) m/z 396 (M+); $^1$H-NMR (CDCl$_3$) δ 7.63 (1H, d, J=3.4 Hz), 7.39 (2H, d, J=8.3 Hz), 7.28 (2H, d, J=8.3 Hz), 7.15 (1H, d, J=3.4 Hz), 6.93 (1H, s), 3.78 (2H, t, J=7.4 Hz), 3.69–3.50 (2H, m), 3.39–3.20 (2H, m), 3.15 (2H, t, J=7.4 Hz), 2.66 (3H, s), 2.53 (3H, s).

STEP 4. 2-(4-{5,7-Dimethyl-2-[2-(1,3-thiazol-2-yl)ethyl]-3H-imidazo[4,5-b]pyridin-3-yl}phenyl)ethyl azide The title compound was prepares, according to the procedure described in step 8 Example 1 from 3-[4-(2-chloroethyl)phenyl]-5,7-dimethyl-2-[2-(1,3-thiazol-2-yl)ethyl]-3H-imidazo[4,5-b]pyridine (step 3).

MS (EI) m/z 403 (M+); $^1$H-NMR (CDCl$_3$) δ 7.63 (1H, d, J=3.5 Hz), 7.38 (2H, d, J=8.4 Hz), 7.28 (2H, d, J=8.4 Hz), 7.15 (1H, d, J=3.5 Hz), 6.93 (1H, s), 3.63–3.54 (4H, m), 3.34–3.26 (2H, m), 2.98 (2H, t, J=7.4 Hz), 2.68 (3H, s), 2.53 (3H, s).

STEP 5. 2-(4-{5.7-Dimethyl-2-[2-(1,3-thiazol-2-yl)ethyl]-3H-imidazo[4,5-b]pyridin-3-yl}phenyl)ethylamine The title compound was prepared according to the procedure described in step 9 of Example 1 from 2-(4-{5,7- dimethyl-2-[2-(1,3-thiazol-2-yl)ethyl]-3H-imidazo[4,5-b]pyridin-3-yl}phenyl)ethyl azide (step 4).

MS (EI) m/z 377 (M+).

STEP 6. 5,7-Dimethyl-3-(4-{2-[({[(4-methylphenyl)sulfonyl]amino}carbonyl)amino]ethyl}phenyl)-2-[2-(1,3-thiazole-2-yl)ethyl]-3H-imidazo[4,5-b]pyridine The title compound was prepared according to the procedure described in step 10 of Example 1 from 2-(4-{5,7-dimethyl-2-[2-(1,3-thiazol-2-yl)ethyl]-3H-imidazo[4,5-b]pyridin-3-yl}phenyl)ethylamine (step 5).

MS (ESI) m/z 575 (M+H)+; $^1$H-NMR (CDCl$_3$) δ 7.83 (2H, d, J=8.3 Hz), 7.61 (1H, d, J=3.5 Hz), 7.32 (2H, d, J=8.3 Hz), 7.19–7.15 (3H, m), 7.07 (2H, d, J=8.2 Hz), 6.91 (1H, br.s) 3.52–3.40 (4H, m), 3.20–3.13 (2H, m), 2.81 (2H, t, J=6.1 Hz), 2.65 (3H, s), 2.44 (3H, s), 2.41 (3H, s).

EXAMPLE 18

3-{4-[2-({[(4-BIPHENYLSULFONYL)AMINO]CARBONYL}AMINO)ETHYL]PHENYL}-2-ETHYL-5,7-DIMETHYL-3H-IMIDAZO[4,5-b]PYRIDINE

STEP 1. Phenyl 2-[4-(2-ethyl-5,7-dimethyl-3H-imidazo[4,5-b]pyridin-3-yl)phenyl]ethylcarbamate To a stirred solution of 2-[4-(2-ethyl-5,7-dimethyl-3H-imidazo[4,5-b]pyridin-3-yl)phenyl]ethylamine (step 9 of Example 1, 1.55 g, 5.3 mmol) and triethylamine (0.80 mL, 5.8 mmol) in dichloromethane (26 mL) cooled in an ice bath was added dropwise phenyl chloroformate (0.69 mL, 5.5 mmol), and the mixture was stirred at ambient temperature. After 30 min, the reaction mixture was partitioned between saturated aqueous sodium bicarbonate (30 mL) and dichloromethane (30 mL). The organic layer was separated and the aqueous phase was extracted with dichloromethane (30 mL). The combined organic phases were dried (Na$_2$SO$_4$) and concentrated under reduced pressure. The residue was recrystallized from dichloromethane/hexane to give 1.90 g (87%) of the title compound as pale brown crystals: $^1$H-NMR (CDCl$_3$) δ 7.43–7.11 (9H, m), 6.91 (1H, s), 5.50 (1H, br.s), 3.57 (2H, pseudo q, J=6.9 Hz), 2.98 (2H, t, J=6.9 Hz), 2.83 (2H, q, J=7.6 Hz), 2.66 (3H, s), 2.52 (3H, s), 1.28 (3H, t, J=7.6 Hz).

STEP 2. 3-{4-[2-({[(4-Biphenylsulfonyl)amino]carbonyl}amino)ethyl]phenyl}-2-ethyl-5,7-dimethyl-3H-imidazo[4,5-b]pyridine To a stirred solution of 4-biphenylsulfonamide (Greenlee, W. J.; Walsh, T. F.; et al. *Eur. Pat. Appl.*, EP 617001 (1994)., 56 mg, 0.24 mmol) in DMF (3 mL) was added NaH (60% oil dispersion, 20 mg, 0.5 mmol) at room temperature. After 5 min, phenyl 2-[4-(2-ethyl-5,7-dimethyl-3H-imidazo[4,5-b]pyridin-3-yl)phenyl]ethylcarbamate (step 1, 100 mg, 0.24 mmol) was added, and the mixture was stirred for an additional 1 h. The mixture was poured into water (50 mL) and extracted with diethyl ether (2×50 mL). The combined extracts were washed with water (50 mL), brine (50 mL) and dried (MgSO$_4$). Removal of solvent gave white oily solids. Purification by preparative TLC (ethyl acetate) gave 66 mg (50%) of the title compound as a colorless oil: MS (ESI) m/z 554 (M+H)+; $^1$H-NMR (CDCl$_3$) δ 8.06 (2H, d, J=8.6 Hz), 7.13 (2H, d, J=8.6 Hz), 7.60–7.53 (2H, m), 7.48–7.36 (3H, m), 7.21 (2H, d, J=8.4 Hz), 7.12 (2H, d, J=8.3 Hz), 6.92 (1H, s), 6.11 (1H, br.t, J=5.5 Hz), 3.54 (2H, dt, J=5.9, 6.0 Hz), 2.89 (2H, J=6.0 Hz), 2.64 (2H, q, J=7.5 Hz), 2.66 (3H, s), 2.40 (3H, s), 1.18 (3H, t, J=7.5 Hz).

EXAMPLE 19

2-ETHYL-5,7-DIMETHYL-3-{4-[2-({[(1-NAPHTHYLSULFONYL)AMINO]CARBONYL}AMINO)ETHYL]PHENYL}-3H-IMIDAZO[4,5-b]PYRIDINE

The title compound was prepared according to the procedure described in step 2 of Example 18 from phenyl 2-[4-(2-ethyl-5,7-dimethyl-3H-imidazo[4,5-b]pyridin-3-yl)phenyl]ethylcarbamate (step 1 of Example 18) and 1-naphtylsulfonamide (Arnswald, M.; Neumann, W. P. *Chem. Ber.*, 1991, 124, 1997; Khorgami, M. H. *Synthesis*, 1972, 574).

MS (ESI) m/z 528 (M+H)+; $^1$H-NMR (CDCl$_3$) δ 8.52–8.48 (1H, m), 8.36 (1H, dd, J=1.1, 7.3 Hz), 8.11 (1H, d, 8.3 Hz), 8.00–7.94 (1H, m), 7.63–7.50 (3H, m), 7.20 (2H, d, J=8.4 Hz), 7.13 (2H, d, J=8.4 Hz), 6.94 (1H, s), 6.32 (1H, br.t, J=5.7 Hz), 3.50 (2H, dt, J=5.9, 6.0 Hz), 2.82 (2H, t, J=6.2 Hz), 2.68 (2H, q, J=7.5 Hz), 2.65 (3H, s), 2.41 (3H, s), 1.21 (3H, t, J=7.5 Hz).

EXAMPLE 20

2-ETHYL-5,7-DIMETHYL-3-{4-[2-({[(2-NAPHTHYLSULFONYL)AMINO]CARBONYL}AMINO)ETHYL]PHENYL}-3H-IMIDAZO[4,5-b]PYRIDINE

The title compound was prepared according to the procedure described in step 2 of Example 18 from phenyl 2-[4-(2-ethyl-5,7-dimethyl-3H-imidazo[4,5-b]pyridin-3-yl)phenyl]ethylcarbamate (step 1 of Example 18) and 2-naphtylsulfonamide.

MS (ESI) m/z 528 (M+H)+; $^1$H-NMR (CDCl$_3$) δ 8.60 (1H, s), 8.01–7.84 (5H, m), 7.64–7.52 (2H, m), 7.20–7.08 (4H, m), 6.92 (1H, s), 6.20 (1H, t, J=5.6 Hz), 3.52–3.45 (2H, q, J=6.1 Hz), 2.84–2.80 (2H, t, J=6.3 Hz), 2.71–2.62 (2H, q, J=6.6 Hz), 2.66 (3H, s), 2.43 (3H, s), 1.22–1.16 (3H, t, J=6.6 Hz).

EXAMPLE 21

2-ETHYL-5,7-DIMETHYL-3-(4-{2-[({[(2-THIENYL)SULFONYL]AMINO}CARBONYL)AMINO]ETHYL}PHENYL)-3H-IMIDAZO[4,5-b]PYRIDINE

The title compound was prepared according to the procedure described in step 2 of Example 18 from phenyl 2-[4-(2-ethyl-5,7-dimethyl-3H-imidazo[4,5-b]pyridin-3-yl)phenyl]ethylcarbamate (step 1 of Example 18) and 2-thiophenesulfonamide (Huang, H. C.; Reinhard, E. J.; Reitz, D. B. *Tetrahedron Lett.*, 1994, 35, 7201.; Graham, S. L.; Scholz, T. H. *Synthesis*, 1986, 1031).

$^1$H-NMR (CDCl$_3$) δ 8.01 (1H, s), 7.78 (1H, dd, J=1.3, 4.9 Hz), 7.63 (1H, dd, J=1.3, 4.9 Hz), 7.22 (2H, d, J=8.3 Hz), 7.14 (2H, d, J=8.3 Hz), 7.09 (1H, dd, J=3.8, 5.0 Hz), 6.92 (1H, s), 6.05 (1H, t, J=5.3 Hz), 3.53 (2H, q, J=6.2 Hz), 2.96 (3H, s), 2.88 (3H, s), 2.87 (2H, t, J=6.2 Hz), 2.67 (2H, q, J=7.5 Hz), 2.65 (3H, s), 2.43 (3H, s), 1.20 (3H, t, J=7.5 Hz).

EXAMPLE 22

3-(4-{2-[({[(5-CHLORO-2-THIENYL)SULFO-NYL]AMINO}CARBONYL)AMINO]ETHYL}PHENYL)-2-ETHYL-5,7-DIMETHYL-3H-IMIDAZO[4,5-b]PYRIDINE

The title compound was prepared according to the procedure described in step 2 of Example 18 from phenyl 2-[4-(2-ethyl-5,7-dimethyl-3H-imidazo[4,5-b]pyridin-3-yl)phenyl]ethylcarbamate (step 1 of Example 18) and 5-chloro-2-thiophenesulfonamide.

MS (ESI) m/z 518 (M+H)$^+$; $^1$H-NMR (CDCl$_3$) δ 7.99 (1H, s), 7.58–7.56 (1H, m), 7.23–7.15 (4H, m), 6.94–6.92 (1H, m), 6.04 (1H, br), 3.53–3.51 (2H, m), 2.87 (2H, m), 2.73–2.65 (2H, q, J=7.6 Hz), 2.65 (3H, s), 2.44 (3H, s), 1.21 (3H, t, J=7.6 Hz).

EXAMPLE 23

3-(4-{2-[({[(4,5-DICHLORO-2-THIENYL)SULFO-NYL]AMINO}CARBONYL)AMINO]ETHYL}PHENYL)-2-ETHYL-5,7-DIMETHYL-3H-IMIDAZO[4,5-b]PYRIDINE

The title compound was prepared according to the procedure described in step 2 of Example 18 from phenyl 2-[4-(2-ethyl-5,7-dimethyl-3H-imidazo[4,5-b]pyridin-3-yl)phenyl]ethylcarbamate (step 1 of Example 18) and 5,6-dichloro-2-thiophenesulfonamide.

MS (ESI) m/z 552 (M+H)$^+$; $^1$H-NMR (CDCl$_3$) δ 7.49 (1H, s), 7.27–7.14 (4H, m), 6.84 (1H, s), 3.47 (2H, br), 2.75 (2H, br), 2.69 (2H, q, J=7.6 Hz), 2.64 (3H, s), 2.38 (3H, t, J=7.6 Hz).

EXAMPLE 24

3-{4-[2-({[(1-BENZOTHIEN-2-YLSULFONYL)AMINO]CARBONYL}AMINO)ETHYL]PHENYL}-2-ETHYL-5,7-DIMETHYL-3H-IMIDAZO[4,5-b]PYRIDINE

The title compound was prepared according to the procedure described in step 2 of Example 18 from phenyl 2-[4-(2-ethyl-5,7-dimethyl-3H-imidazo[4,5-b]pyridin-3-yl)phenyl]ethylcarbamate (step 1 of Example 18) and 1-benzothiophene-2-sulfonamide (Chem, J.; Leu, Y.; et al. *J. Med. Chem.*, 1997, 40, 2276.; Graham, S. L.; Shepard, K. L.; et al. *J. Med. Chem.*, 1989, 32, 2548).

mp 128.0–130.0° C.; MS (ESI) m/z 534 (M+H)$^+$; $^1$H-NMR (DMSO-d$_6$) δ 8.05–8.00 (3H, m), 7.50–7.42 (2H, m), 7.36 (2H, d, J=7.4 Hz), 7.32 (2H, d, J=7.4 Hz), 6.96 (1H, s), 6.61–6.56 (1H, m), 3.34–3.28 (2H, m), 2.80 (2H, t, J=6.6 Hz), 2.68 (2H, q, J=7.5 Hz), 2.54 (3H, s), 2.40 (3H, s), 1.19 (3H, t, J=7.5 Hz).

EXAMPLE 25

3-(4-{2-[({[(2-CHLOROPHENYL)SULFONYL]AMINO}CARBONYL)AMINO]ETHYL}PHENYL)-2-ETHYL-5,7-DIMETHYL-3H-IMIDAZO[4,5-b]PYRIDINE

The title compound was prepared according to the procedure described in step 10 of Example 1 from 2-[4-(2-ethyl-5,7-dimethyl-3H-imidazo[4,5-b]pyridin-3-yl)phenyl]ethylamine (step 9 of Example 1) and 2-chlorobenzenesulfonyl isocyanate.

MS (ESI) m/z 512 (M+H)$^+$; $^1$H-NMR (CDCl$_3$) δ 8.21–8.17 (1H, d, 7.7 Hz), 7.57–7.43 (3H, m), 7.32–7.22 (4H, m), 6.93 (s, 1H), 6.34 (1H, t, J=5.6 Hz), 3.56–3.49 (2H, q, J=6.3 Hz), 2.89–2.85 (2H, t, J=6.4 Hz), 2.80–2.71 (q, 2H, J=7.6 Hz), 2.67 (3H, s), 2.49 (3H, s), 1.28–1.22 (3H, t, J=7.6 Hz).

EXAMPLE 26

2-ETHYL-5-METHYL-3-(4-{2-[({[(4-METHYLPHENYL)SULFONYL]AMINO}CARBONYL)AMINO]ETHYL}PHENYL)-3H-IMIDAZO[4,5-b]PYRIDINE

STEP 1. 2-{4-[(6-Methyl-3-nitro-2-pyridinyl)amino]phenyl}ethanol

The title compound was prepared according to the procedure described in step 3 of Example 1 from 2-chloro-6-methyl-3-nitropyridine (Takayama, K.; Iwata, M.; Kono, N.; et al. *Jpn. Kokai Tokkyo Koho*, JP11292877 (1999).; Ding, C. Z.; Hunt, J. T.; Kim, S.; et al. *PCT Int. Appl.*, WO 9730992 (1997)) and 4-aminophenylethyl alcohol.

$^1$H-NMR (CDCl$_3$) δ 8.24 (1H, d, J=9.1 Hz), 7.28–7.33 (4H, m), 6.65 (1H, d, J=9.2 Hz), 3.89 (2H, d, J=6.4 Hz), 2.89 (2H, d, J=6.4 Hz), 2.81 (3H, s).

STEP 2. 2-{4-[(3-Amino-6-methyl-2-pyridinyl)amino]phenyl}ethanol

To a solution of 2-{4-[(6-methyl-3-nitro-2-pyridinyl)amino]phenyl}ethanol (step 1, 4.6 g, 16.9 mmol) in methanol (100 mL) was added 10% Pd—C (300 mg). The resulting mixture was stirred for 2 h under hydrogen atmosphere. The mixture was filtered through a pad of Celite and the filtrate was concentrated. The residue was purified by flash column chromatography eluting with hexane/ethyl acetate (gradient elution from 1:2 to 1:5) to afford 3.8 g (92%) of the title compound as yellow solids: $^1$H-NMR (CDCl$_3$) δ: 7.10–7.16 (4H, m), 6.91 (1H, d, J=8.4 Hz), 6.70 (1H, d, J=8.4 Hz), 6.19 (1H, s), 3.83 (2H, t, J=6.4 Hz), 2.81 (2H, t, J=6.4 Hz), 2.35 (3H, s).

STEP 3. 2-[4-(2-Ethyl-5-methyl-3H-imidazo[4,5-b]pyridin-3-yl)phenyl]ethyl propionate The title compound was prepared according to the procedure described in step 5 of Example 1 from 2-{4-[(3-amino-6-methyl-2-pyridinyl)amino]phenyl}ethanol (step 2) and propionyl chloride.

MS (EI) m/z 337 (M$^+$).

STEP 4. 2-[4-(2-Ethyl-5-methyl-3H-imidazo[4,5-b]pyridin-3-yl)phenyl]ethanol

The title compound was prepared according to the procedure described in step 6 of Example 1 from 2-[4-(2-ethyl-5-methyl-3H-imidazo[4,5-b]pyridin-3-yl)phenyl]ethyl propionate (step 3).

$^1$H-NMR (CDCl$_3$) δ 7.90 (1H, d, J=8.3 Hz), 7.43 (2H, d, J=8.2 Hz), 7.34 (2H, d, J=8.2 Hz), 7.07 (1H, d, J=8.3 Hz), 3.93 (2H, t, J=6.6 Hz), 2.97 (2H, t, J=6.6 Hz), 2.80 (2H, q, J=7.5 Hz), 2.56 (3H, s), 1.35 (3H, t, J=7.5 Hz).

STEP 5. 2-[4-(2-Ethyl-5-methyl-3H-imidazo[4,5-b]pyridin-3-yl)phenyl]ethyl azide

A mixture of 2-[4-(2-ethyl-5-methyl-3H-imidazo[4,5-b]pyridin-3-yl)phenyl]ethanol (step 4, 217 mg, 0.77 mmol) in THF (20 mL) was added diethyl azodicarboxylate (DEAD) (0.3 ml, 1.5 mmol), triphenylphosphine (380 mg, 1.5 mmol)

and diphenylphosphoryl azide (DPPA) (0.4 mL, 1.5 mmol). The mixture was stirred at room temperature for 4.5 h. After removal of solvent, the residue was purified by flash column chromatography on silica gel eluting with hexane/ethyl acetate (gladient elution from 1:1 to 1:2) to afford 70 mg (30%) of the title compound as a brown oil: $^1$H-NMR (CDCl$_3$) δ 7.90 (1H, d, J=8.1 Hz), 7.34–7.44 (4H, m), 7.08 (1H, d, J=8.1 Hz), 3.60 (2H, t, J=7.1 Hz), 3.00 (2H, t, J=7.1 Hz), 2.80 (2H, q, J=7.5 Hz), 2.57 (3H, s) 1.35 (3H, t, J=7.5 Hz).

STEP 6. 2-[4-(2-Ethyl-5-methyl-3H-imidazo[4,5-b]pyridin-3-yl)phenyl]ethylamine

The title compound was prepared according to the procedure described in step 9 of Example 1 from 2-[4-(2-ethyl-5-methyl-3H-imidazo[4,5-b]pyridin-3-yl)phenyl]ethyl azide (step 5).

$^1$H-NMR (CDCl$_3$) δ 7.91 (1H, d, J=8.1 Hz), 7.42 (2H, d, J=8.3 Hz), 7.32 (2H, d, J=8.3 Hz), 2.55 (1H, d, J=8.1 Hz), 3.13 (2H, t, J=6.8 Hz), 2.95 (2H, t, J=6.8 Hz), 2.81 (2H, q, J=7.6 Hz), 2.55 (3H, s), 1.34 (3H, t, J=7.6 Hz).

STEP 7. 2-Ethyl-5-methyl-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(2-ethyl-5-methyl-3H-imidazo[4,5-b]pyridin-3-yl)phenyl]ethylamine (step 6).

MS (ESI) m/z 476 (M+H)$^+$; $^1$H-NMR (CDCl$_3$) δ 7.95 (1H, d, J=8.0 Hz), 7.84 (2H, d, J=8.2 Hz), 7.32 (2H, d, J=8.2 Hz), 7.25 (2H, d, J=8.2 Hz), 7.17 (2H, d, J=8.2 Hz), 7.10 (1H, d, J=8.0 Hz), 6.17 (1H, br.s), 3.52 (2H, t, J=6.6 Hz), 2.86 (2H, t, J=6.6 Hz), 2.69 (2H, q, J=7.5 Hz), 2.49(3H, s), 2.41 (3H, s), 1.27 (3H, t, J=7.5 Hz).

EXAMPLE 27

2-ETHYL-5-METHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, SODIUM SALT

The title compound was prepared according to the procedure described in Example 2 from 2-ethyl-5-methyl-3-(4-{2-[({[(4-methylphenyl)sulfonyl]amino}carbonyl)amino]ethyl}phenyl-3-imidazo[4,5-b]pyridine (Example 26).

$^1$H-NMR (DMSO-d$_6$) δ 7.91 (1H, d, J=7.9 Hz), 7.61 (2H, d, J=6.8 Hz), 7.36 (4H, s), 7.11–7.15 (3H, m), 2.67–2.75 (4H, m), 2.50 (2H, br.s), 2.45 (3H, s), 2.28 (3H, s), 1.21–1.24 (3H, m).

EXAMPLE 28

2-ETHYL-5-METHOXY-3-(4-{2-[({[(4-METHYLPHENYL)SULFONYL]AMINO}CARBONYL)AMINO]ETHYL}PHENYL)-3H-IMIDAZO[4,5-b]PYRIDINE

STEP 1. 2-{4-[(6-Methoxy-3-nitro-2-pyridinyl)amino]phenyl}ethanol

The title compound was prepared according to the procedure described in step 3 of Example 1 from 2-chloro-6-methoxy-3-nitropyridine and 4-aminophenylethyl alcohol.

$^1$H-NMR (CDCl$_3$) δ 10.59 (1H, br.s), 8.38 (1H, d, J=9.2 Hz), 7.59 (2H, d, J=8.3 Hz), 7.23 (2H, d, J=8.3 Hz), 6.20 (1H, d, J=9.2 Hz), 3.94 (3H, s), 3.87 (2H, t, J=6.6 Hz), 2.87 (2H, t, J=6.6 Hz).

STEP 2. 2-{4-[(3-Amino-6-methoxy-2-pyridinyl)amino]phenyl}ethanol

A mixture of 2-{4-[(6-methoxy-3-nitro-2-pyridinyl)amino]phenyl}ethanol (step 1, 3.52 g, 12.17 mmol), iron powder (3.4 g, 60.84 mmol) and ammonium chloride (325 mg, 6.08 mmol) in ethanol/water (v/v, 2:1, 90 mL) was heated at reflux temperature for 1 h. After cooling, the catalyst was removed and the filtrate was concentrated. The residue was extracted with ethyl acetate (100 mL) and washed with water. The organic layer was dried (MgSO$_4$), and concentrated to give 3.41 g (quant.) of the title compound as a black oil: $^1$H-NMR (CDCl$_3$) δ 7.48 (2H, d, J=8.4 Hz), 7.14 (2H, d, J=8.4 Hz), 7.04 (1H, d, J=8.2 Hz), 6.75 (1H, br.s), 6.13 (1H, d, J=8.2 Hz), 3.87 (3H, s), 3.83 (2H, t, J=6.6 Hz), 2.81 (2H, t, J=6.6 Hz).

STEP 3. 2-[4-(2-Ethyl-5-methoxy-3H-imidazo[4,5-b]pyridin-3-yl)phenyl]ethyl propionate The title compound was prepared according to the procedure described in step 5 of Example 1 from 2-{4-[(3-amino-6-methoxy-2-pyridinyl)amino]phenyl}ethanol (step 2) and propionyl chloride.

TLC Rf=0.50 (hexane/ethyl acetate=2:1).

STEP 4. 2-[4-(2-Ethyl-5-methoxy-3H-imidazo[4,5-b]pyridin-3-yl)phenyl]ethanol

The title compound was prepared according to the procedure described in step 6 of Example 1 from 2-[4-(2-ethyl-5-methoxy-3H-imidazo[4,5-b]pyridin-3-yl)phenyl]ethyl propionate (step 3).

$^1$H-NMR (CDCl$_3$) δ 7.91 (1H, d, J=8.6 Hz), 7.43 (2H, d, J=8.4 Hz), 7.35 (2H, d, J=8.4 Hz), 6.67 (1H, d, J=8.6 Hz), 3.98–3.88 (2H, m), 3.82 (3H, s), 2.99 (2H, t, J=6.4 Hz), 2.81 (2H, q, J=7.4 Hz 1.34 (3H, t, J=7.4 Hz).

STEP 5. 2-[4-(2-Ethyl-5-methoxy-3H-imidazo[4,5-b]pyridin-3-yl)phenyl]ethyl azide The title compound was prepared according to the procedure described in step 5 of Example 26 from 2-(4-(2-ethyl-5-methoxy-3H-imidazo[4,5-b]pyridin-3-yl)phenyl)ethanol (step 4).

TLC Rf=0.78 (hexane/ethyl acetate=1/1).

STEP 6. 2-[4-(2-Ethyl-5-methoxy-3H-imidazo[4,5-b]pyridin-3-yl)phenyl]ethylamine

The title compound was prepared according to the procedure described in step 9 of Example 1 from 2-[4-(2-ethyl-5-methoxy-3H-imidazo[4,5-b]pyridin-3-yl)phenyl]ethyl azide (step 5).

$^1$H-NMR (CDCl$_3$) δ 7.92 (1H, d, J=8.6 Hz), 7.40–7.31 (4H, m), 6.67 (1H, d, J=8.6 Hz), 3.82 (3H, s), 3.13–3.10 (2H, m), 3.00–2.97 (2H, m), 2.80 (2H, q, J=7.6 Hz), 1.33 (3H, t, J=7.6 Hz.

STEP 7. 2-Ethyl-5-methoxy-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(2-ethyl-5-methoxy-3H-imidazo[4,5-b]pyridin-3-yl)phenyl]ethylamine (step 6).

$^1$H-NMR (CDCl$_3$) δ 7.95 (1H, d, J=8.7 Hz), 7.74 (2H, d, J=8.4 Hz), 7.34–7.27 (6H, m), 6.69 (1H, d, J=8.7 Hz), 6.55 (1H, m), 3.79 (3H, s), 3.60–3.53 (2H, m), 2.90 (2H, t, J=6.8 Hz), 2.77 (2H, q, J=7.4 Hz), 1.30 (3H, t, J=7.4 Hz).

EXAMPLE 29

2-ETHYL-5-METHOXY-3-(4-{2-[({[(4-METH-YLPHENYL)SULFONYL]AMINO}CARBONYL)AMINO]ETHYL}PHENYL)-3H-IMIDAZO[4,5-b]PYRIDINE, SODIUM SALT

The title compound was prepared according to the procedure described in Example 2 from 2-ethyl-5-methoxy-3-(4-{2-[({[(4-methylphenyl)sulfonyl]amino}carbonyl)amino]ethyl}phenyl)-3H-imidazo[4,5-b]pyridine (Example 28).

$^1$H-NMR (DMSO-$d_6$) δ 7.94 (1H, d, J=8.4 Hz), 7.59 (2H, d, J=8.1 Hz), 7.41–7.34 (4H, m), 7.12 (2H, d, J=8.1 Hz), 6.68 (1H, d, J=8.4 Hz), 3.71 (3H, s), 3.14 (2H, m), 2.75–2.68 (4H, m), 2.27 (3H, s), 1.20 (3H, t, J=7.5 Hz); IR (KBr) $ν_{max}$ 1597, 1518, 1489, 1425, 1389, 1261, 1130, 1086 cm$^{-1}$.

EXAMPLE 30

6-CHLORO-2-ETHYL-3-(4-{2-[({[(4-METH-YLPHENYL)SULFONYL]AMINO}CARBONYL)AMINO]ETHYL}PHENYL)-3H-IMIDAZO[4,5-b]PYRIDINE

STEP 1. 2-{4-[(5-Methyl-3-nitro-2-pyridinyl)amino]phenyl}ethanol

The title compound was prepared according to the procedure described in step 3 of Example 1 from 2-chloro-5-methyl-3-nitropyridine and 4-aminophenylethyl alcohol.

$^1$H-NMR (CDCl$_3$) δ 9.96 (1H, br.s), 8.32–8.31 (2H, m), 7.55 (2H, d, J=8.3 Hz), 7.24 (2H, d, J=8.3 Hz), 3.85 (2H, m), 2.86 (2H, t, J=6.6 Hz), 2.32 (3H, s).

STEP 2. 2-{4-[(3-Amino-5-methyl-2-pyridinyl)amino]phenyl}ethanol

The title compound was prepared according to the procedure described in step 2 of Example 28 from 2-{4-[(5-methyl-3-nitro-2-pyridinyl)amino]phenyl}ethanol (step 1).

$^1$H-NMR (CDCl$_3$) δ 7.59 (1H, m), 7.08–7.00 (4H, m), 6.80 (1H, m), 3.74 (2H, t, J=6.6 Hz) 2.74 (2H, t, J=6.6 Hz), 2.19 (3H, s).

STEP 3. 2-[4-(2-Ethyl-6-methyl-3H-imidazo[4,5-b]pyridin-3-yl)phenyl]ethyl propionate The title compound was prepared according to the procedure described in step 5 of Example 1 from 2-{4-[(3-amino-5-methyl-2-pyridinyl)amino]phenyl}ethanol (step 2) and propionyl chloride.

TLC Rf=0.74 (dichloromethane/methanol=10:1).

STEP 4. 2-[4-(2-Ethyl-6-methyl-3H-imidazo[4,5-b]pyridin-3-yl)phenyl]ethanol

The title compound was prepared according to the procedure described in step 6 of Example 1 from 2-[4-(2-ethyl-6-methyl-3H-imidazo[4,5-b]pyridin-3-yl)phenyl]ethyl propionate (step 3).

$^1$H-NMR (CDCl$_3$) δ 8.12 (1H, s), 7.84 (1H, s), 7.44 (2H, d, J=8.1 Hz), 7.33 (2H, d, J=8.1 Hz), 3.91–3.85 (2H, m), 2.96 (2H, t, J=6.7 Hz), 2.82 (2H, q, J=7.5 Hz), 2.46 (3H, s) 1.36 (3H, t, J=7.5 Hz).

STEP 5. 2-[4-(2-Ethyl-6-methyl-3H-imidazo[4,5-b]pyridin-3-yl)phenyl]ethyl azide

The title compound was prepared according to the procedure described in step 5 Example 26 from 2-[4-(2-ethyl-6-methyl-3H-imidazo[4,5-b]pyridin-3-yl)phenyl]ethanol (step 4).

$^1$H-NMR (CDCl$_3$) δ 8.13 (1H, s), 7.84 (1H, s), 7.44 (2H, d, J=8.4 Hz), 7.36 (2H, d, J=8.4 Hz), 3.59 (2H, t, J=7.3 Hz), 3.00 (2H, t, J=7.3 Hz), 2.83 (2H, q, J=7.6 Hz), 2.46 (3H, t, J=7.6 Hz).

STEP 4. 2-[4-(2-Ethyl-6-methyl-3H-imidazo[4,5-b]pyridin-3-yl)phenol]ethylamine

The title compound was prepared according to the procedure described in step 9 of Example 1 from 2-[4-(2-ethyl-6-methyl-3H-imidazo[4,5-b]pyridin-3-yl)phenyl]ethyl azide (step 5).

$^1$H-NMR (CDCl$_3$) δ 8.12 (1H, s), 7.84 (1H, s), 7.42 (2H, d, J=8.4 Hz), 7.33 (2H, d, J=8.4 Hz), 3.07 (2H, t, J=6.8 Hz), 2.91–2.78 (4H, m), 2.46 (3H, s), 1.36 (3H, t, J=7.5 Hz).

STEP 5. 2-Ethyl-6-methyl-3-(4-{2-[({[(4-methylphenyl)sulfonyl]amino}carbonyl)amino]ethyl}phenyl)-3H-imidazo[4,5-b]pyridine The reaction was carried out according to the procedure described in step 10 of Example 1 from 2-[4-(2-ethyl-6-methyl-3H-imidazo[4,5-b]pyridin-3-yl)phenyl]ethylamine (step 6).

$^1$H-NMR (CDCl$_3$) δ 8.04 (1H, d, J=1.8 Hz), 7.86–7.82 (3H, m), 7.33–7.21 (6H, m), 6.27 (1H, m), 3.52–3.49 (2H, m), 2.87 (2H, t, J=6.8 Hz), 2.76 (2H, q, J=7.6 Hz), 2.45 (3H, s), 2.41 (3H, s), 1.30 (3H, t, J=7.6 Hz).

EXAMPLE 31

6-CHLORO-2-ETHYL-3-(4-{2-[({[(4-METH-YLPHENYL)SULFONYL]AMINO}CARBONYL)AMINO]ETHYL}PHENYL)-3H-IMIDAZO[4,5-b]PYRIDINE, SODIUM SALT

The title compound was prepared according to the procedure described in Example 2 from 2-ethyl-6-methyl-3-(4-{2-[({[(4-methylphenyl)sulfonyl]amino}carbonyl)amino]ethyl}phenyl)-3H-imidazo[4,5-b]pyridine (Example 30).

$^1$H-NMR (DMSO-$d_6$) δ 8.04 (1H, m), 7.84 (1H, m), 7.60 (2H, d, J=8.1 Hz), 7.36 (4H, s), 7.12 (2H, d, J=8.1 Hz), 3.13 (2H, m), 2.78–2.71 (4H, m), 2.39 (3H, s), 2.27 (3H, s), (3H, t, J=7.5 Hz); IR (KBr) $ν_{max}$ 1601, 1518, 1423, 1375, 1283, 1250, 1128, 1084 cm$^{-1}$.

EXAMPLE 32

6-CHLORO-2-ETHYL-3-(4-{2-[({[(4-METH-YLPHENYL)SULFONYL]AMINO}CARBONYL)AMINO]ETHYL}PHENYL)-3H-IMIDAZO[4,5-b]PYRIDINE

STEP 1. 2-{4-[(5-Chloro-3-nitro-2-pyrindinyl)amino]phenyl}ethanol

The title compound was prepared according to the procedure described in step 3 of Example 1 from 2,5-dichloro-3-nitropyridine (Marfat, A.; Robinson, R. P. US pat. Appl., U.S. Pat. No. 5,811,432 (1998).; Haessig, R.; Siegrist, U. Eur. Pat. Appl., EP 483061 (1992).) and 4-aminophenylethyl alcohol.

$^1$H-NMR (CDCl$_3$) δ 10.00 (1H, br.s), 8.51–8.50 (1H, m), 8.41 (1H, d, J=2.4 Hz), 7.53 (2H, d, J=8.4 Hz), 7.27 (2H, d, J=8.4 Hz), 3.88–3.87 (2H, m), 2.88 (2H, t, J=6.6 Hz).

STEP 2. 2-{4-[(3-Amino-5-chloro-2-pyridinyl)amino]phenyl}ethanol

The title compound was prepared according to the procedure described in step 2 of Example 28 from 2-{4-[(5-chloro-3-nitro-2-pyridinyl)amino]phenyl}ethanol (step 1).

$^1$H-NMR (CDCl$_3$) δ 7.73 (1H, d, J=2.2 Hz), 7.19–7.01 (4H, m), 6.97 (1H, d, J=2.2 Hz), 6.12 (1H, br.s), 3.81 (2H, t, J=6.4 Hz), 2.80 (2H, t, J=6.4 Hz).

STEP 3. 2-[4-(6-Chloro-2-ethyl-3H-imidazo[4,5-b]pyridin-3-yl)phenyl]ethyl propionate The title compound was prepared according to the procedure described in step 5 of Example 1 from 2-{4-[(3-amino-5-chloro-2-pyridinyl)amino]phenyl}ethanol (step 2).

TLC Rf=0.43 (hexane/ethyl acetate=2:1).

STEP 4. 2-[4-(6-Chloro-2-ethyl-3H-imidazo[4,5-b]pyridin-3-yl)phenyl]ethanol

The title compound was prepared according to the procedure described in step 6 of Example 1 from 2-[4-(6-chloro-2-ethyl-3H-imidazo[4,5-b]pyridin-3-yl)phenyl]ethyl propionate (step 3).

$^1$H-NMR (CDCl$_3$) δ 8.23 (1H, d, J=2.1 Hz), 8.01 (1H, d, J=2.1 Hz), 7.45 (2H, d, J=8.4 Hz), 7.31 (2H, d, J=8.4 Hz), 7.09 (1H, s), 3.92 (2H, t, J=6.4 Hz), 2.95 (2H, t, J=6.4 Hz), 2.83 (2H, q, J=7.4 Hz), 1.36 (3H, t, J=7.4 Hz).

STEP 5. 2-[4-(6-Chloro-2-ethyl-3H-imidazo[4,5-b]pyridin-3-yl)phenyl]ethyl azide

The title compound was prepared according to the procedure described in step 5 of Example 26 from 2-[4-(6-chloro-2-ethyl-3H-imidazo[4,5-b]pyridin-3-yl)phenyl]ethanol (step 4).

$^1$H-NMR (CDCl$_3$) δ 8.25 (1H, d, J=2.2 Hz), 8.02 (1H, d, J=2.2 Hz), 7.46 (2H, d, J=8.3 Hz), 7.35 (2H, d, J=8.3 Hz), 3.60 (2H, t, J=7.2 Hz), 3.00 (2H, t, J=7.2 Hz), 2.84 (2H, q, J=7.5 Hz), 1.37 (3H, t, J=7.5 Hz).

STEP 6. 2-[4-(6-Chloro-2-ethyl-3H-imidazo[4,5-b]pyridin-3-yl)phenyl]ethylamine

The title compound was prepared according to the procedure described in step 9 of Example 1 from 2-[4-(6-chloro-2-ethyl-3H-imidazo[4,5-b]pyridin-3-yl)phenyl]ethyl azide (step 5).

$^1$H-NMR (CDCl$_3$) δ 8.22 (1H, d, J=2.1 Hz), 8.01 (1H, d, J=2.1 Hz), 7.45 (2H, d, J=8.2 Hz), 7.32 (2H, d, J=8.2 Hz), 3.13–3.08 (2H, m), 2.95–2.78 (4H, m), 1.36 (3H, t, J=7.6 Hz).

STEP 7. 6-Chloro-2-ethyl-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(6-chloro-2-ethyl-3H-imidazo[4,5-b]pyridin-3-yl)phenyl]ethylamine (step 6).

$^1$H-NMR (CDCl$_3$) δ 8.20 (1H, d, J=2.2 Hz), 8.03 (1H, d, J=2.2 Hz), 7.77 (2H, d, J=8.1 Hz), 7.38–7.27 (6H, m), 6.51–6.48 (1H, m), 3.57–3.50 (2H, m), 2.90 (2H, t, J=6.8 Hz), 2.81 (2H, t, J=7.5 Hz), 1.34 (3H, t, J=7.5 Hz).

EXAMPLE 33

6-CHLORO-2-ETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, SODIUM SALT

The title compound was prepared according to the procedure described in Example 2 from 6-chloro-2-ethyl-3-(4-{2-[({[(4-methylphenyl)sulfonyl]amino}carbonyl)amino]ethyl}phenyl)-3H-imidazo[4,5-b]pyridine (Example 32).

$^1$H-NMR (DMSO-$_6$) δ 8.24–8.21 (2H, m), 7.60 (2H, d, J=8.1 Hz), 7.42–7.34 (4H, m), 7.12 (2H, d, J=8.1 Hz), 3.13 (2H, m), 2.81–2.69 (4H, m), 2.27 (3H, s), 1.24 (3H, t, J=7.4 Hz); IR (KBr) ν$_{max}$ 1597, 1516, 1421, 1375, 1246, 1128, 1084 cm$^{-1}$.

EXAMPLE 34

2-ETHYL-5,6-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE

STEP 1. 2-{4-[(5,6-Dimethyl-3-nitro-2-pyridinyl)amino]phenyl}ethanol

A mixture of 2-chloro-5,6-dimethyl-3-nitropyridine (Godard, A.; Rocca, P.; Pomel, V.; et al. J. *Organomet. Chem.*, 1996, 517, 25.; Rocca, P.; Marsais, F.; Godard, A.; et al. *Tetrahedron Lett.*, 1993, 34, 2937., 3.3 g, 17.5 mmol), 4-aminophenylethyl alcohol (3.6 g, 26.3 mmol) and 2,6-lutidine (3.7 mL) in toluene (80 mL) was stirred under reflux temperature for 19 h. The mixture was diluted with ethyl acetate (100 mL) and washed with 1N aqueous NaOH (50 mL) and brine (50 mL). The organic layer was dried (Na$_2$SO$_4$), and concentrated. Purification by flash column chromatography on silica gel eluting with hexane/ethyl acetate (1:1) to afford 1.8 g (37%) of the title compound as orange solids: $^1$H-NMR (CDCl$_3$) δ 8.24 (1H, br.s), 7.68 (2H, d, J=8.6 Hz), 7.24 (2H, d, J=8.6 Hz), 3.88 (2H, dt, J=6.1, 7.6 Hz), 2.88 (2H, t, J=7.6 Hz), 2.49 (3H, s), 2.26 (3H, s), 1.43 (1H, t, J=6.1 Hz).

STEP 2. 2-{4-[(3-Amino-5,6-dimethyl-2-pyridinyl)amino]phenyl}ethanol

The title compound was prepared according to the procedure described in step 2 of Example 28 from 2-{4-[(5,6-dimethyl-3-nitro-2-pyridinyl)amino]phenyl}ethanol (step 1).

$^1$H-NMR (CDCl$_3$) δ 6.97 (2H, d, J=8.4 Hz), 6.92 (2H, d, J=8.4 Hz), 6.71 (1H, s), 6.22 (1H, br s), 3.67 (2H, t, J=6.8 Hz), 2.68 (2H, t, J=6.8 Hz), 2.29 (3H, s), 2.12 (3H, s).

STEP 3. 2-[4-(2-Ethyl-5,6-dimethyl-3H-imidazo[4,5-b]pyridin-3-yl)phenyl]ethyl propionate The title compound was prepared according to the procedure described in step 5 of Example 1 from 2-{4-[(3-amino-5,6-dimethyl-2-pyridinyl)amino]phenyl}ethanol (step 2) and propionyl chloride.

$^1$H-NMR (CDCl$_3$) δ 7.75 (1H, br.s), 7.42 (2H, d, J=8.6 Hz), 7.34 (2H, d, J=8.6 Hz), 4.37 (2H, t, J=6.6 Hz), 3.05 (2H, t, J=6.6 Hz), 2.80 (2H, q, J=7.6 Hz), 2.49 (3H, s), 2.38 (3H, s), 2.37–2.28 (2H, m), 1.34 (3H, t, J=7.6 Hz), 1.18 (3H, t, J=7.5 Hz).

STEP 4. 2-[4-(2-Ethyl-5,6-dimethyl-3H-imidazo[4,5-b]pyridin-3-yl)phenyl]ethanol

The title compound was prepared according to the procedure described in step 6 of Example 1 from 2-[4-(2-ethyl-5,6-dimethyl-3H-imidazo[4,5-b]pyridin-3-yl)phenyl]ethyl propionate (step 3).

MS (ESI) m/z 296 (M+H)$^+$; $^1$H-NMR (CDCl$_3$) δ: 7.75 (1H, br.s), 7.43 (2H, d, J=8.6 Hz), 7.33 (2H, d, J=8.6 Hz), 3.92 (2H, br.t, J=6.6 Hz), 2.97 (2H, t, J=6.6 Hz), 2.80 (2.49 (3H, s), 2.38 (3H, s), 1.34 (3H, t, J=7.6 Hz).

STEP 5. 3-[4-(2-Chloroethyl)phenyl]-2-ethyl-5,6-dimethyl-3H-imidazo[4,5-b]pyridine The title compound was prepared according to the procedure described in step 7 of Example 1 from 2-[4-(2-ethyl-5,6-dimethyl-3H-imidazo[4,5-b]pyridin-3-yl)phenyl]ethanol (step 4).

¹H-NMR (CDCl₃) δ 7.75 (1H, br.s), 7.43 (2H, d, J=8.6 Hz), 7.36 (2H, d, J=8.6 Hz), 3.80 (2H, t, J=7.3 Hz), 3.18 (2H, t, J=7.3 Hz), 2.81 (2H, q, J=7.6 Hz), 2.50 (3H, s), 2.38 (3H, s), 1.34 (3H, t, J=7.6 Hz).

STEP 6. 2-[4-(2-Ethyl-5,6-dimethyl-3H-imidazo[4,5-b]pyridin-3-yl)phenyl]ethyl azide The title compound was prepared according to the procedure described in step 8 of Example 1 from 3-[4-(2-chloroethyl)phenyl]-2-ethyl-5,6-dimethyl-3H-imidazo[4,5-b]pyridine (step 5).

¹H-NMR (CDCl₃) δ 7.75 (1H, br.s), 7.42 (2H, d, J=8.4 Hz), 7.36 (2H, d, J=8.4 Hz), 3.60 (2H, t, J=7.3 Hz), 3.00 (2H, t, J=7.3 Hz), 2.80 (2H, q, J=7.6 Hz), 2.49 (3H, s), 2.38 (3H, s), 1.34 (3H, t, J=7.6 Hz).

STEP 7. 2-[4-(2-Ethyl-5,6-dimethyl-3H-imidazo[4,5-b]pyridin-3-yl)phenyl]ethylamine The title compound was prepared according to the procedure described in step 9 of Example 1 from 2-[4-(2-ethyl-5,6-dimethyl-3H-imidazo[4,5-b]pyridin-3-yl)phenyl]ethyl azide (step 6).

¹H-NMR (CDCl₃) δ 7.76 (1H, br.s), 7.41 (2H, d, J=7.9 Hz), 7.33 (2H, d, J=7.9 Hz), 3.12 (2H, t, J=6.9 Hz), 2.95 (2H, t, J=6.9 Hz), 2.79 (2H, q, J=6.9 Hz), 2.47 (3H, s), 2.37 (3H, s), 1.33 (3H, t, J=6.9 Hz).

STEP 8. 2-Ethyl-5,6-dimethyl-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(2-ethyl-5,6-dimethyl-3H-imidazo[4,5-b]pyridin-3-yl)phenyl]ethylamine (step 7).

MS (ESI) m/z 492 (M+H)⁺; ¹H-NMR (CDCl₃) δ 7.87 (2H, d, J=8.2 Hz), 7.79 (1H, s), 7.31 (2H, d, J=8.2 Hz), 7.23 (2H, d, J=8.1 Hz), 7.15 (2H, d, J=8.1 Hz), 6.24 (1H, m), 3.51 (2H, m), 2.85 (2H, t, J=6.1 Hz), 2.66 (2H, q, J=7.4 Hz), 2.39 (3H, s), 2.38 (3H, s), 2.36 (3H, s), 1.25 (3H, t, J=7.4 Hz).

EXAMPLE 35

2-ETHYL-5,6-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, SODIUM SALT

The title compound was prepared according to the procedure described in Example 2 from 2-ethyl-5,6-dimethyl-3-(4-{2-[({[(4-methylphenyl)sulfonyl]amino}carbonyl)amino]ethyl}phenyl)-3H-imidazo[4,5-b]pyridine (Example 34).

mp 156.0–158.5° C.; ¹H-NMR (DMSO-d₆) δ 7.58 (1H, s), 7.48 (2H, d, J=8.1 Hz), 7.19–7.13 (4H, m), 6.98 (2H, d, J=8.1 Hz), 6.01 (1H, br.s), 3.15–2.98 (2H, m), 2.59–2.55 (2H, q, J=7.6 Hz), 2.19 (3H, s), 2.13 (3H, s), 2.09 (3H, s), 1.01 (3H, t, J=7.6 Hz).

EXAMPLE 36

2-[4-(2-ETHYL-5,6-DIMETHYL-3H-IMIDAZO[4,5-b]PYRIDIN-3-YL)PHENYL]ETHYL(4-METHYLPHENYL)SULFONYLCARBAMATE

The title compound was prepared according to the procedure described in Example 3 from 2-[4-(2-ethyl-5,6-dimethyl-3H-imidazo[4,5-b]pyridin-3-yl)phenyl]ethanol (step 4 of Example 34).

MS (ESI) m/z 493 (M+H)⁺; ¹H-NMR (DMSO-d₆) δ 7.94 (2H, d, J=8.4 Hz), 7.78 (1H, s), 7.33 (2H, d, J=8.1 Hz), 7.25–7.16 (4H, m), 4.35 (2H, t, J=6.6 Hz), 2.93 (2H, t, J=6.6 Hz), 2.73 (2H, q, J=7.4 Hz), 2.46 (3H, s), 2.43 (3H, s), 2.39 (3H, s), 1.28 (3H, t, J=7.4 Hz).

EXAMPLE 37

5,6-DICHLORO-2-ETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE

STEP 1. 2-{4-[(5,6-Dichloro-3-nitro-2-pyridinyl)amino]phenyl}ethanol

The title compound was prepared according to the procedure described in step 1 of Example 34 from 3-nitro-2,5,6-trichloropyridine (Horn, U.; Mutterer, F.; Weis, C. D. *Helv. Chim. Acta.*, 1976, 59,190.) and 4-aminophenylethyl alcohol.

MS (EI) m/z 327 (M⁺); ¹H-NMR (CDCl₃) δ 10.11 (1H, br.s), 8.58 (1H, s), 7.57 (2H, d, J=8.4 Hz), 7.28 (2H, d, J=8.4 Hz), 3.93–3.86 (2H, m), 2.89 (2H, t, J=6.6 Hz).

STEP 2. 2-{4-[(3-Amino-5,6-dichloro-2-pyridinyl)amino]phenyl}ethanol

The title compound was prepared according to the procedure described in step 2 of Example 28 from 2-{4-[(5,6-dichloro-3-nitro-2-pyridinyl)amino]phenyl}ethanol (step 1).

MS (EI) m/z 297 (M⁺).

STEP 3. 2-[4-(2-Ethyl-5,6-dichloro-3H-imidazo[4,5-b]pyridin-3-yl)phenyl]ethyl propionate The title compound was prepared according to the procedure described in step 5 of Example 1 from 2-{4-[(3-amino-5,6-dichloro-2-pyridinyl)amino]phenyl}ethanol (step 2) and propionyl chloride.

TLC Rf=0.63 (ethyl acetate/hexane=1:1).

STEP 4. 2-[4-(2-Ethyl-5,6-dichloro-3H-imidazo[4,5-b]pyridin-3-yl)phenyl]ethanol

The title compound was prepared according to the procedure described in step 6 of Example 1 from 2-[4-(2-Ethyl-5,6-dichloro-3H-imidazo[4,5-b]pyridin-3-yl)phenyl]ethyl propionate (step 3).

MS (EI) m/z 335 (M⁺); ¹H-NMR (CDCl₃) δ 8.11 (1H, s), 7.46 (2H, d, J=8.1 Hz), 7.32 (2H, d, J=8.1 Hz), 3.97 (2H, t, J=6.2 Hz), 2.99 (2H, t, J=6.2 Hz), 2.82 (2H, q, J=7.5 Hz), 1.36 (3H, t, J=7.5 Hz).

STEP 5. 3-[4-(2-Chloroethyl)phenyl]-2-ethyl-5,6-dichloro-3H-imidazo[4,5-b]pyridine The title compound was, prepared according to the procedure described in step 7 of Example 1 from 2-[4-(2-ethyl-5,6-dichloro-3H-imidazo[4,5-b]pyridin-3-yl)phenyl]ethanol (step 4).

¹H-NMR (CDCl₃) δ 8.13 (1H, s), 7.45 (2H, d, J=8.1 Hz), 7.33 (2H, d, J=8.1 Hz), 3.80 (2H, t, J=7.2 Hz), 3.19 (2H, t, J=7.2 Hz), 2.82 (2H, q, J=7.5 Hz), 1.36 (3H, t, J=7.5 Hz).

STEP 6. 2-[4-(2-Ethyl-5,6-dichloro-3H-imidazo[4,5-b]pyridin-3-yl)phenyl]ethyl azide The title compound was prepared according to the procedure described in step 8 of Example 1 from 3-[4-(2-chloroethyl)phenyl]-2-ethyl-5,6-dichloro-3H-imidazo[4,5-b]pyridine (step 5).

MS (EI) m/z 360 (M⁺); ¹H-NMR (CDCl₃) δ 8.11 (1H, s), 7.44 (2H, d, J=8.4 Hz), 7.33 (2H, d, J=8.4 Hz), 3.61 (2H, t, J=7.2 Hz), 3.00 (2H, t, J=7.2 Hz), 2.81 (2H, q, J=7.5 Hz), 1.35 (3H, t, J=7.5 Hz).

STEP 7. 2-[4-(2-Ethyl-5,6-dichloro-3H-imidazo[4,5-b]pyridin-3-yl)phenyl]ethylamine To a solution of 2-[4-(2-ethyl-5,6-dichloro-3H-imidazo[4,5-b]pyridin-3-yl)phenyl]ethyl azide (step 6, 69 mg, 0.2 mmol) in methanol (10 mL) was added Lindlar catalyst (5 mg). The resulting mixture was stirred for 6 h under hydrogen atmosphere. The mixture was filtered through a pad of Celite and the filtrate was concentrated. Purification by preparative TLC (dichloromethane/methanol=10:1) gave 60 mg (94%) of the title compound as colorless solids:

MS (EI) m/z 334 (M⁺); ¹H-NMR (CDCl₃) δ 8.11 (1H, s), 7.43 (2H, d, J=8.3 Hz, Hz), 7.30 (2H, d, J=8.3 Hz), 3.11 (2H, t, J=6.6 Hz), 2.92 (2H, t, J=6.6 Hz), 2.81 (2H, q, J=7.5 Hz), 1.35 (3H, t, J=7.5 Hz).

STEP 8. 5,6-Dichloro-2-ethyl-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(2-ethyl-5,6-dichloro-3H-imidazo[4,5-b]pyridin-3-yl)phenyl]ethylamine (step 7).

mp 188.0–189.0° C.; MS (ESI) m/z 532 (M+H)⁺; ¹H-NMR (CDCl₃) δ 8.12 (1H, s), 7.77 (2H, d, J=8.4 Hz), 7.36–7.25 (6H, m), 6.49 (1H, br.t, J=5.9 Hz), 3.54 (2H, dt, J=5.9, 7.0 Hz), 2.90 (2H, t, J=7.0 Hz), 2.78 (2H, q, J=7.5 Hz), 2.41 (3H, s), 1.33 (3H, t, J=7.5 Hz).

EXAMPLE 38

5-CHLORO-2-ETHYL-6-METHYL-3-(4-{2-[({[(4-METHYLPHENYL)SULFONYL]AMINO}CARBONYL)AMINO]ETHYL}PHENYL)-3H-IMIDAZO[4,5-b]PYRIDINE

STEP 1. 2-{4-[(6-Chloro-5-methyl-3-nitro-2-pyridinyl)amino]phenyl}ethanol

The title compound was prepared according to the procedure described in step 1 of Example 34 from 2,6-dichloro-5-methyl-3-nitropyridine (Horn, U.; Mutterer, F.; Weis, C. D. *Helv. Chim. Acta.*, 1976, 59,190.) and 4-aminophenylethyl alcohol.

¹H-NMR (CDCl₃) δ 10.05 (1H, br.s), 8.34 (1H, s), 7.57 (2H, d, J=7.7 Hz), 7.24 (2H, d, J=7.7 Hz), 3.86 (2H, t, J=5.9 Hz), 2.87 (2H, t, J=5.9 Hz), 2.33 (3H, s).

STEP 2. 2-{4-[(3-Amino-6-chloro-5-methyl-2-pyridinyl)amino]phenyl}ethanol

The title compound was prepared according to the procedure described in step 2 of Example 28 from 2-{4-[(6-chloro-5-methyl-3-nitro-2-pyridinyl)amino]phenyl}ethanol (step 1).

¹H-NMR (CDCl₃) δ 7.14–7.08 (4H, m), 6.86 (1H, s), 6.21 (1H, br.s), 3.79 (2H, t, J6.4 Hz), 2.78 (2H, t, J=6.4 Hz), 2.33 (3H, s).

STEP 3. 2-[4-(5-Chloro-2-ethyl-6-methyl-3H-imidazo[4,5-b]pyridin-3-yl)phenyl]ethyl propionate The title compound was prepared according to the procedure described in step 5 of Example 1 from 2-{4-[(3-amino-6-chloro-5-methyl-2-pyridinyl)amino]phenyl}ethanol (step 2) and propionyl chloride.

MS (EI) m/z 371 (M⁺).

STEP 4. 2-[4-(5-Chloro-2-ethyl-6-methyl-3H-imidazo[4,5-b]pyridin-3-yl)phenyl]ethanol The title compound was prepared according to the procedure described in step 6 of Example 1 from 2-[4-(5-chloro-2-ethyl-6-methyl-3H-imidazo[4,5-b]pyridin-3-yl)phenyl]ethyl propionate (step 3).

MS (EI) m/z 315 (M⁺); ¹H-NMR (CDCl₃) δ 7.87 (1H, s), 7.42 (2H, d, J=8.4 Hz), 7.29 (2H, d, J=8.4 Hz), 3.92 (2H, t, J=6.6 Hz), 2.96 (2H, t, J=6.6 Hz), 2.79 (2H, q, J=7.7 Hz), 2.47 (3H, s), 1.34 (3H, t, J=7.7 Hz).

STEP 5. 3-[4-(2-Chloroethyl)phenyl]-5-chloro-2-ethyl-5-methyl-3H-imidazo[4,5-b]pyridine The title compound was prepared according to the procedure described in step 7 of Example 1 from 2-[4-(5-chloro-2-ethyl-6-methyl-3H-imidazo[4,5-b]pyridin-3-yl)phenyl]ethanol (step 4).

MS (EI) m/z 333 (M⁺); ¹H-NMR (CDCl₃) δ 7.88 (1H, s), 7.42 (2H, d, J=8.3 Hz), 7.33 (2H, d, J=8.3 Hz), 3.79 (2H, t, J=7.3 Hz), 3.17 (2H, t, J=7.3 Hz), 2.80 (2H, q, J=7.0 Hz), 2.48 (3H, s), 1.35 (3H, t, J=7.0 Hz).

STEP 6. 2-[4-(5-Chloro-2-ethyl-6-methyl-3H-imidazo[4,5-b]pyridin-3-yl)phenyl]ethyl azide The title compound was prepared according to the procedure described in step 8 of Example 1 from 3-[4-(2-chloroethyl)phenyl]-5-chloro-2-ethyl-5-methyl-3H-imidazo[4,5-b]pyridine (step 5).

¹H-NMR (CDCl₃) δ 7.87 (1H, s), 7.42 (2H, d, J=8.4 Hz), 7.34 (2H, d, J=8.4 Hz), 3.59 (2H, t, J=7.1 Hz), 2.98 (2H, t, J=7.1 Hz), 2.81 (2H, q, J=7.6 Hz), 2.48 (3H, s), 1.35 (3H, t, J=7.6 Hz).

STEP 7. 2-[4-(5-Chloro-2-ethyl-6-methyl-3H-imidazo[4,5-b]pyridin-3-yl)phenyl]ethylamine.

The title compound was prepared according to the procedure described in step 7 of Example 37 from 2-[4-(5-chloro-2-ethyl-6-methyl-3H-imidazo[4,5-b]pyridin-3-yl)phenyl]ethyl azide (step 6).

¹H-NMR (CDCl₃) δ 7.88 (1H, s), 7.40 (2H, d, J=8.3 Hz), 7.31 (2H, d, J=8.3 Hz), 3.07 (2H, t, J=6.8 Hz), 2.87 (2H, t, J=6.8 Hz), 2.80 (2H, q, J=7.3 Hz), 2.48 (3H, s), 1.34 (3H, t, J=7.3 Hz).

STEP 8. 5-Chloro-2-ethyl-6-methyl-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(5-chloro-2-ethyl-6-methyl-3H-imidazo[4,5-b]pyridin-3-yl)phenyl]ethylamine (step 7).

mp 205–206° C.; MS (ESI) m/z 512 (M+H)⁺; ¹H-NMR (CDCl₃) δ 7.90 (1H, s), 7.79 (2H, d, J=8.3 Hz), 7.33–7.23 (6H, m), 6.46 (1H, br.s), 3.55–3.49 (2H, m), 2.88 (2H, t, J=6.8 Hz), 2.76 (2H, q, J=7.6 Hz), 2.48 (3H, s), 2.41 (3H, s), 1.31 (3H, t, J=7.6 Hz).

EXAMPLE 39

5-CHLORO-2-ETHYL-7-METHYL-3-(4-{2-[({[(4-METHYLPHENYL)SULFONYL]AMINO}CARBONYL)AMINO]ETHYL}PHENYL)-3H-IMIDAZO[4,5-b]PYRIDINE

STEP 1. 2-{4-[(6-Chloro-4-methyl-3-nitro-2-pyridinyl)amino]phenyl}ethanol

The title compound was prepared according to the procedure described in step 1 of Example 34 from 2,6-dichloro-4-methyl-3-nitropyridine (Inubushi, A.; Kawano, E.; Shimada, Ke.; et al. *PCT Int. Appl.*, WO 9802442 (1998)) and 4-aminophenylethyl alcohol.

$^1$H-NMR (CDCl$_3$) δ: 9.56 (1H, s), 7.49 (2H, d, J=8.4 Hz), 7.22 (2H, d, J=8.4 Hz), 6.64 (1H, s), 3.84 (2H, t, J=6.4 Hz), 2.84 (2H, t, J=6.4 Hz), 2.55 (3H, s).

STEP 2. 2-{4-[(3-Amino-6-chloro-4-methyl-2-pyridinyl)amino]phenyl}ethanol

The title compound was prepared according to the procedure described in step 2 of Example 28 from 2-{4-[(6-chloro-4-methyl-3-nitro-2-pyridinyl)amino]phenyl}ethanol (step 1).

MS (EI) m/z 277 (M$^+$).

STEP 3. 2-[4-(5-Chloro-2-ethyl-7-methyl-3H-imidazo[4,5-b]pyridin-3-yl)phenyl]ethyl propionate The title compound was prepared according to the procedure described in step 5 of Example 1 from 2-{4-[(3-amino-6-chloro-4-methyl-2-pyridinyl)amino]phenyl}ethanol (step 2).

TLC Rf=0.46 (ethyl acetate/hexane=1:1).

STEP 4. 2-[4-(5-Chloro-2-ethyl-7-methyl-3H-imidazo[4,5-b]pyridin-3-yl)phenyl]ethanol The title compound was prepared according to the procedure described in step 6 of Example 1 from 2-[4-(5-chloro-2-ethyl-7-methyl-3H-imidazo[4,5-b]pyridin-3-yl)phenyl]ethyl propionate (step 3).

MS (EI) m/z 315 (M$^+$); $^1$H-NMR (CDCl$_3$) δ 7.43 (2H, d, J=8.4 Hz), 7.31 (2H, d, J=8.4 Hz), 7.31 (2H, d, J=8.4 Hz), 7.07 (1H, s), 4.00–3.85 (2H, m), 2.97 (2H, t, J=6.6 Hz), 2.83 (2H, q, J=7.5 Hz), 2.68 (3H, s), 1.30 (3H, t, J=7.5 Hz).

STEP 5. 3-[4-(2-Chloroethyl)phenyl]-5-chloro-2-ethyl-7-methyl-3H-imidazo[4,5-b]pyridine The title compound was prepared according to the procedure described in step 7 of Example 1 from 2-[4-(5-chloro-2-ethyl-7-methyl-3H-imidazo[4,5-b]pyridin-3-yl)phenyl]ethanol (step 4).

$^1$H-NMR (CDCl$_3$) δ 7.42 (2H, d, J=8.1 Hz), 7.33 (2H, d, J=8.1 Hz), 7.07 (1H, s), 3.79 (2H, t, J=7.3 Hz), 3.17 (2H, t, J=7.3 Hz), 2.83 (2H, q, J=7.5 Hz), 2.68 (3H, s), 1.30 (3H, t, J=7.5 Hz).

STEP 6. 2-[4-(5-Chloro-2-ethyl-7-methyl-3H-imidazo[4,5-b]pyridin-3-yl)phenyl]ethyl azide The title compound was prepared according to the procedure described in step 8 of Example 1 from 3-[4-(2-chloroethyl)phenyl]-5-chloro-2-ethyl-7-methyl-3H-imidazo[4,5-b]pyridine (step 5).

$^1$H-NMR (CDCl$_3$) δ 7.42 (2H, d, J=8.6 Hz), 7.33 (2H, d, J=8.6 Hz), 7.07 (1H, s), 3.79 (2H, t, J=7.2 Hz), 2.99 (2H, t, J=7.2 Hz), 2.83 (2H, q, J=7.5 Hz), 2.68 (3H, s), 1.29 (3H, t, J=7.5 Hz).

STEP 7. 2-[4-(5-Chloro-2-ethyl-7-methyl-3H-imidazo[4,5-b]pyridin-3-yl)phenyl]ethylamine.

To a stirred solution of 2-[4-(5-chloro-2-ethyl-7-methyl-3H-imidazo[4,5-b]pyridin-3-yl)phenyl]ethyl azide (step 6, 57 mg, 0.2 mmol) in THF (5 mL,) was added triphenylphosphine (47 mg, 0.2 mmol) at room temperature. After completion of the addition, the stirring was continued for an additional 3 h at the same temperature. To the resulting mixture was added water (0.1 mL) at room temperature, and the reaction mixture was stirred at room temperature for 20 h. The mixture was concentrated to give colorless solids. Purification by preparative TLC (dichloromethane/methanol/triethylamine=10:1:1) gave 13 mg (25%) of the title compound as colorless solids: MS (EI) m/z 313 (M$^+$).

STEP 8. 5-Chloro-2-ethyl-7-methyl-3-(4-{2-[({[4-methylphenyl)sulfonyl]amino}carbonyl)amino]ethyl}phenyl)-3H-imidazo[4,5-b]pyridine The title compound was prepared according to the procedure described in step 10 of Example 1 from 2-[4-(5-chloro-2-ethyl-7-methyl-3H-imidazo[4,5-b]pyridin-3-yl)phenyl]ethylamine (step 7).

MS (ESI) m/z 512 (M+H)$^+$; $^1$H-NMR (CDCl$_3$) δ: 7.80 (2H, d, J=8.4 Hz), 7.34–7.23 (6H, m), 7.09 (1H, s), 6.37 (1H, br s), 3.56–3.52 (2H, m), 2.88 (2H, t, J=6.8 Hz), 2.77 (2H, q, J=7.5 Hz), 2.69 (3H, s), 2.42 (3H, s), 1.26 (3H, t, J=7.5 Hz).

EXAMPLE 40

2-ETHYL-7-METHYL-3-(4-{2-[({[(4-METHYLPHENYL)SULFONYL]AMINO}CARBONYL)AMINO]ETHYL}PHENYL)-6-[(METHYLSULFONYL)AMINO]-3H-IMIDAZO[4,5-b]PYRIDINE

STEP 1. 2-{4-[(4-Methyl-3,5-dinitro-2-pyridinyl)amino]phenyl}ethanol

The title compound was prepared according to the procedure described in step 3 of Example 1 from 2-chloro-4-methyl-3,5-dinitropyridine. (Czuba, *Rocz. Chem.*, 1967, 41, 479) and 4-aminophenylethyl alcohol.

$^1$H-NMR (CDCl$_3$) δ 8.90 (1H, s), 8.50 (1H, br.s), 7.40 (2H, d, J=8.4 Hz), 7.23 (2H, d, J=8.4 Hz), 3.82 (2H, t, J=6.6 Hz), 2.84 (2H, t, J=6.6 Hz), 2.62 (3H, s).

STEP 2. 2-{4-[(3-Amino-4-methyl-5-nitro-2-pyridinyl)amino]phenyl}ethanol

To a stirred solution of 2-{4-[(4-methyl-3,5-dinitro-2-pyridinyl)amino}phenyl]ethanol (step 1, 4.2 g, 13.1 mmol), triethylamine (9.6 mL, 68.9 mmol), 10% Pd—C (624 mg, 0.59 mmol) in acetonitrile (14 mL) was added dropwise a solution of formic acid (2.3 mL, 61.0 mmol) in acetonitrile (6.2 ml,) at 0° C. over a period of 30 min. After stirring at room temperature for 5 h, the mixture was filtered through a pad of Celite, and the filtrate was concentrated. The residue was dissolved in dichloromethane (100 mL). The solution was washed with 1N aqueous NaOH (50 mL), brine (50 mL), dried (MgSO$_4$), and concentrated. Purification by flash column chromatography on silica gel eluting with hexane/ethyl acetate (gradient elution from 1:1 to 1:2) afforded 2.2 g (60%) of the title compound as red crystals: $^1$H-NMR (CDCl$_3$) δ 8.42 (1H, s), 7.42 (2H, d, J=8.4 Hz), 7.21 (2H, d, J=8.4 Hz), 6.7 (1H, br s), 3.85 (2H, t, J=6.6 Hz), 2.47 (3H, s).

STEP 3. 2-[4-(2-Ethyl-7-methyl-6-nitro-3H-imidazo[4,5-b]pyridin-3-yl)phenyl]ethyl propionate The title compound was prepared according to the procedure described in step 5 of Example 1 from 2-{4-[(3-amino-4-methyl-5-nitro-2-pyridinyl)amino]phenyl}ethanol (step 2) and propionate chloride.

$^1$H-NMR (CDCl$_3$) δ 9.03 (1H, s), 7.48 (2H, d, J=8.6 Hz), 7.33 (2H, d, J=8.4 Hz), 4.38 (2H, t, J=6.9 Hz), 3.07 (2H, t, J=6.9 Hz), 3.03 (3H, s), 2.87 (2H, q, J=7.6 Hz), 2.35 (2H, q, J=7.6 Hz), 1.35 (3H, t, J=7.4 Hz), 1.13 (3H, t, J=7.4 Hz).

STEP 4. 2-[4-(6-Amino-2-ethyl-7-methyl-3H-imidazo[4,2-b]pyridin-3-yl)phenyl]ethyl propionate A suspension of 2-[4-(2-ethyl-7-methyl-6-nitro-3H-imidazo[4,5-b]pyridin-3-yl)phenyl]ethyl propionate (step 3, 2.5 g, 6.6 mmol), 10% Pd—C (250 mg, 0.23 mmol) in methanol (100 mL) was stirred under hydrogen atmosphere for 2 h. The suspension was filtered through a pad of Celite, and the filtrate was concentrated to afford 2.4 g (99%) of the title compound as a brown oil: $^1$H-NMR (CDCl$_3$) δ 7.82 (1H, s), 7.41 (2H, d, J=8.2 Hz), 7.32 (2H, d, J=8.4 Hz), 4.35 (2H, t, J=7.0 Hz), 3.51 (2H, br.s), 3.03 (2H, t, J=7.0 Hz), 2.82 (2H, q, J=7.5 Hz), 2.53 (3H, s), 2.35 (2H, q, J=7.5 Hz), 1.29 (3H, t, J=7.5 Hz), 1.44 (3H, t, J=7.5 Hz).

STEP 5. 2-(4-{2-Ethyl-7-methyl-6-[(methylsulfonyl)amino]-3H-imidazo[4,5-b]pyridin-3-yl}phenyl)ethyl propionate To a stirred solution of 2-[4-(6-amino-2-ethyl-7-methyl-3H-imidazo[4,5-b]pyridin-3-yl)phenyl]ethyl propionate (step 4, 1.0 g, 3.0 mmol) and pyridine (280 mg, 3.5 mmol) in dichloromethane (18 mL) was added methanesulfonyl chloride (372 mg, 3.3 mmol) at 0° C., and the mixture was stirred at room temperature for 16 h. The reaction was quenched with water (10 mL), and the mixture was extracted with dichloromethane (50 mL). The organic layer was washed with brine (50 mL), dried (MgSO$_4$), and concentrated. Purification by flash column chromatography on silica gel eluting with ethyl acetate (gradient elution from 1:1 to 1:2) afforded 890 mg (70%) of the title compound as an amber oil: $^1$H-NMR (CDCl$_3$) δ 8.26 (1H, s), 7.43 (2H, d, J=8.4 Hz), 7.32 (2H, d, J=8.2 Hz), 7.00 (1H, br.s), 4.35 (2H, t, J=7.0 Hz), 3.03–3.01 (5H, m), 2.85 (2H, q, J=7.5 Hz), 2.75 (3H, s), 2.35 (2H, q, J=7.5 Hz), 1.30 (3H, t, J=7.5 Hz), 1.14 (3H, t, J=7.5 Hz).

STEP 6. N-{2-Ethyl-3-[4-(2-hydroxyethyl)phenyl]-7-methyl-3H-imidazo[4,5-b]pyridin-6-yl}methanesulfonamide The title compound was prepared according to the procedure described in step 6 of Example 1 from 2-(4-{2-ethyl-7-methyl-6-[(methylsulfonyl)amino]-3H-imidazo[4,5-b]pyridin-3-yl}phenyl)ethyl propionate (step 5).

$^1$H-NMR (CDCl$_3$) δ 8.22 (1H, s), 7.46 (2H, d, J=8.2 Hz), 7.31 (2H, d, J=8.4 Hz), 6.52 (1H, br.s), 3.93 (2H, t, J=6.6 Hz), 3.03 (3H, s), 2.97 (2H, t, J=6.6 Hz), 2.85 (2H, q, J=7.6 Hz), 2.76 (3H, s), 1.32 (3H, t, J=7.4 Hz).

STEP 7. N-{3-[4-(2-Chloroethyl)phenyl]-2-ethyl-7-methyl-3H-imidazo[4,5-b]pyridin-6-yl}methanesulfonamide The title compound was prepared according to the procedure described in step 7 of Example 1 from N-{2-ethyl-3-[4-(2-hydroxyethyl)phenyl]-7-methyl-3H-imidazo[4,5-b]pyridin yl}methanesulfonamide (step 6).

TLC Rf=0.40 (ethyl acetate).

STEP 8. N-{3-[4-(2-Azidoethyl)phenyl]-2-ethyl-7-methyl-3H-imidazo[4.5-b]pyridin-6-yl}methanesulfonamide The title compound was prepared according to the procedure described in step 8 of Example 1 from N-{3-[4-(2-chloroethyl)phenyl]-2-ethyl-7-methyl-3H-imidazo[4,5-b]pyridin-6-yl}methanesulfonamide (step 7).

$^1$H-NMR (CDCl$_3$) δ 8.26 (1H, s), 7.44 (2H, d, J=8.1 Hz), 7.34 (2H, d, J=8.1 Hz), 6.65 (1H, br.s), 3.59 (2H, t, J=7.0 Hz), 3.03 (3H, s), 2.99 (2H, t, J=7.1 Hz), 2.86 (2H, q, J=7.4 Hz), 2.75 (3H, s), 1.31 (3H, t, J=7.5 Hz).

STEP 9. N-{3-[4-(2-Aminoethyl)phenyl]-2-ethyl-7-methyl-3H-imidazo[4,5-b]pyridin-6-yl}methanesulfonamide The title compound was prepared according to the procedure described in step 9 of Example 1 from N-{3-[4-(2-azidoethyl)phenyl]-2-ethyl-7-methyl-3H-imidazo[4,5-b]pyridin-6-yl}methanesulfonamide (step 8).

TLC Rf=0.05 (ethyl acetate).

STEP 10. 2-Ethyl-7-methyl-3-(4-{2-[({[(4-methylphenyl)sulfonyl]amino}carbonyl)amino]ethyl}phenyl)-6-[(methylsulfonyl)amino]-3H-imidazo[4,5-b]pyridine The title compound was prepared according to the procedure described in step 10 of Example 1 from N-{3-[4-(2-aminoethyl)phenyl]-2-ethyl-7-methyl-3H-imidazo[4,5-b]pyridin-6-yl}methanesulfonaimde (step 9).

mp 166° C.; MS (ESI) m/z 571.25 (M+H)$^+$; $^1$H-NMR (CDCl$_3$) δ 8.16 (1H, s), 7.81 (2H, d, J=8.1 Hz), 7.31–7.18 (6H, m), 6.39 (1H, br.s), 3.48–3.46 (2H, m), 3.00 (3H, s), 2.82–2.71 (7H, m), 2.39 (3H, s), 1.26 (3H, t, J=7.2 Hz).

EXAMPLE 41

6-CYANO-2-ETHYL-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE

STEP 1,6-Hydroxy-2,4-dimethylnicotinonitrile

To a stirred solution of 6-amino-2,4-dimethylnicotinonitrile (Sato, K.; et al. Bull. Chem. Soc. Jpn., 1969, 42, 2319., 22.4 g, 152 mmol) in 5% aqueous sulfuric acid (600 mL) was added dropwise a solution of sodium nitrite (25.2 g, 365 mmol) in water (100 mL) at 0° C., and the mixture was stirred at room temperature for 16 h. The resulting precipitate was collected by filtration to afford 10.2 g (45%) of the title compound: $^1$H-NMR (DMSO-d$_6$) δ 12.27 (1H, br.s), 6.17 (1H, s), 2.38 (3H, s), 2.20 (3H, s).

STEP 2. 6-Hydroxy-2,4-dimethyl-5-nitronicotinonitrile

To a stirring mixture of nitric acid (fuming, 36 mL) and sulfuric acid (18 mL) was added 6-hydroxy-2,4-dimethylnicotinonitrile (step 1, 9.0 g, 60.8 mmol) in one portion, and the mixture was stirred at room temperature. After 1 h, the mixture was poured in water (100 mL) and neutralized with 2N aqueous NaOH. The resulting precipitates were collected by filtration to afford 3.2 g (27%) of the title compound: $^1$H-NMR (DMSO-d$_6$) δ 2.28 (3H, s), 2.11 (3H, s).

STEP 3. 6-Chloro-2,4-dimethyl-5-nitronicotinonitrile

A mixture of 6-hydroxy-2,4-dimethyl-5-nitronicotinonitrile (step 2, 3.2 g, 16.6 mmol) and phosphorus oxychloride (20 mL) was stirred at 100° C. for 16 h. After cooling, the mixture was poured in water (100 mL). The resulting mixture was extracted with dichloromethane (3×100 mL). The organic layer was washed with brine (50 mL), dried (MgSO$_4$), and concentrated to afford 2.3 g (66%) of the title compound as brown solids: $^1$H-NMR (DMSO-d$_6$) δ 2.82 (3H, s), 2.52 (3H, s).

STEP 4. 6-[4-(2-Hydroxyethyl)anilino]-2,4-dimethyl-5-nitronicotinonitrile

The title compound was prepared according to the procedure described in step 3 of Example 1 from 6-chloro-2,4-dimethyl-5-nitronicotinonitrile (step 3) and 4-aminophenylethyl alcohol.

$^1$H-NMR (CDCl$_3$) δ 9.37 (1H, br.s), 7.51 (2H, d, J=8.4 Hz), 7.26 (2H, d, J=8.4 Hz), 3.89–3.87 (2H, m), 2.89 (2H, t, J=6.4 Hz), 2.72 (3H, s), 2.65 (3H, s), 1.46 (1H, t, J=5.8 Hz).

STEP 5. 5-Amino-6-[4-(2-hydroxyethyl)anilino]-2,4-dimethylnicotinonitrile

The title compound was prepared according to the procedure described in step 4 of Example 1 from 6-[4-(2-hydroxyethyl)anilino]-2,4-dimethyl-5-nitronicotinonitrile (step 4).

$^1$H-NMR (CDCl$_3$) δ 7.49 (2H, d, J=8.6 Hz), 7.19 (2H, d, J=8.4 Hz), 6.98 (1H, br.s), 3.89–3.82 (2H, m), 3.11 (2H, br.s), 2.85 (2H, t, J=6.6 Hz), 2.58 (3H, s), 2.38 (3H, s), 1.44 (1H, t, J=5.6 Hz).

STEP 6. 2-[4-(6-Cyano-2-ethyl-5,7-dimethyl-3H-imidazo[4,5-b]pylidin-3-yl)phenyl]ethyl propionate The title compound was prepared according to the procedure described in step 5 of Example 1 from 5-amino-6-[4-(2-hydroxyethyl)anilino]-2,4-dimethylnicotinonitrile (step 5) and propionyl chloride.

TLC Rf=0.4 (hexane/ethyl acetate=1:1).

STEP 7. 2-Ethyl-3-[4-(2-hydroxyethyl)phenyl]-5,7-dimethyl-3H-imidazo[4,5-b]pyridine-6-carbonitrile The title compound was prepared according to the procedure described in step 6 of Example 1 from 2-[4-(6-cyano-2-ethyl-5,7-dimethyl-3H-imidazo[4,5-b]pyridin-3-yl)phenyl]ethyl propionate (step 6).

$^1$H-NMR (CDCl$_3$) δ 7.46 (2H, d, J=8.2 Hz), 7.31 (2H, d, J=8.2 Hz), 4.01–3.94 (2H, 3.49–3.47 (1H, m), 3.00 (2H, t, J=6.3 Hz), 2.86 (3H, s), 2.83 (2H, q, J=7.4 Hz), 2.74 (3H, s), 1.32 (3H, t, J=7.6 Hz).

STEP 8. 3-[4-(2-Chloroethyl)phenyl]-2-ethyl-5,7-dimethyl-3H-imidazo[4,5-b]pyridine-6-carbonitrile The title compound was prepared according to the procedure described in step 7 of Example 1 from 2-ethyl-3-[4-(2-hydroxyethyl)phenyl]-5,7-dimethyl-3H-imidazo[4,5-b]pyridine-6-carbonitrile (step 7).

TLC Rf=0.8 (hexane/ethyl acetate=1:1).

STEP 9. 3-[4-(2-Azidoethyl)phenyl]-2-ethyl-5,7-dimethyl-3H-imidazo[4,5-b]pyridine-6-carbonitrile The title compound was prepared according to the procedure described in step 8 of Example 1 from 3-[4-(2-chloroethyl)phenyl]-2-ethyl-5,7-dimethyl-3H-imidazo[4,5-b]pyridine-6-carbonitrile (step 8).

$^1$H-NMR (CDCl$_3$) δ 7.46 (2H, d, J=8.1 Hz), 7.33 (2H, d, J=8.2 Hz), 3.62 (2H, t, J=7.1 Hz), 3.02 (2H, t, J=7.1 Hz), 2.86 (3H, s), 2.82 (2H, q, J=7.6 Hz), 2.73 (3H, s), 1.31 (3H, t, J=7.6 Hz).

STEP 10. 3-[4-(2-Aminoethyl)phenyl]-2-ethyl-5,7-dimethyl-3H-imidazo[4,5-b]pyridine-6-carbonitrile The title compound was prepared according to the procedure described in step 9 of Example 1 from 3-[4-(2-azidoethyl)phenyl]-2-ethyl-5,7-dimethyl-3H-imidazo[4,5-b]pyridine-6-carbon (step 9).

TLC Rf=0.05 (hexane/ethyl acetate=1:1).

STEP 11. 6-Cyano-2-ethyl-5,7-dimethyl-3-(4-{2-[({[(4-methylphenyl)sulfonyl]amino}carbonyl)amino]ethyl}phenyl)-3H-imidazo[4,5-b]pyridine The title compound was prepared according to the procedure described in step 10 of Example 1 from 3-[4-(2-aminoethyl)phenyl]-2-ethyl-5,7-dimethyl-3H-imidazo[4,5-b]pyridine-6-carbonitrile (step 10).

mp 133° C.; MS (ESI) m/z 517.12 (M+H)$^+$; $^1$H-NMR (CDCl$_3$) δ 7.78 (2H, d, J=8.1 Hz), 7.37–7.25 (6H, m), 6.46 (1H, br.s), 3.56–3.54 (2H, m), 2.92 (2H, t, J=7.0 Hz), 2.85 (3H, s), 2.76 (2H, q, J=6.0 Hz), 2.68 (3H, s), 2.41 (3H, s), 1.29 (3H, t, J=6.2 Hz).

EXAMPLE 42

2-ETHYL-4,6-DIMETHYL-1-(4-{2-[({[(4-METHYLPHENYL)SULFONYL]AMINO}CARBONYL))AMINO]ETHYL}PHENYL)-1H-IMIDAZO[4,5-c]PYRINE

STEP 1. 2-{4-[(2,6-Dimethyl-3-nitro-4-pyridinyl)amino]phenyl}ethanol

The title compound was prepared according to the procedure described in step 3 of Example 1 from 4-chloro-2,6-dimethyl-3-nitropyridine (Tanaka, A.; et al. *J. Med. Chem.*, 1999, 41, 4408.) and 4-aminophenylethyl alcohol.

$^1$H-NMR (CDCl$_3$) δ 8.74 (1H, br.s), 7.31 (2H, d, J=8.2 Hz), 7.18 (2H, d, J=8.2 Hz), 6.68 (1H, s), 3.95–3.89 (2H, m), 2.91 (2H, t, J=6.6 Hz), 2.72 (3H, s), 2.36 (3H, s).

STEP 2. 2-{4-[(3-Amino-2,6-dimethyl-4-pyridinyl)amino]phenyl}ethanol

The title compound was prepared according to the procedure described in step 4 of Example 1 from 2-{4-[(2,6-dimethyl-3-nitro-4-pyridinyl)amino]phenyl}ethanol (step 1).

1-NMR (CDCl$_3$) δ 7.19 (2H, d, J=8.4 Hz), 7.01 (2H, d, J=8.6 Hz), 6.76 (1H, br.s), 3,87 (2H, t, J=6.4 Hz), 3.18 (2H, br.s), 2.85 (2H, t, J=6.4 Hz), 2.44 (3H, s).

STEP 3. 2-[4-(2-Ethyl-[6-dimethyl-1H-imidazo[4,5-c]pyridin-1-yl)]phenyl]ethyl propionate A mixture of 2-{4-[(3-amino-2,6-dimethyl-4-pyridinyl)amino]phenyl}ethanol (step 2, 2.4 g, 9.3 mmol), propionic anhydride (13 mL, 101 mmol) and propionic acid (13 mL, 174 mmol) was stirred at 120° C. for 16 h. After cooling, the mixture was diluted with 2N aqueous NaOH (150 mL) and extracted with dichloromethane (3×150 mL). The combined organic extracts were washed with brine (50 mL), dried (MgSO$_4$), and concentrated. Purification by flash column chromatography on silica gel eluting with dichloromethane/methanol (gradient elution from 20:1 to 10:1) afforded 2.3 g (69%) of the title compound as a brown oil: $^1$H-NMR (CDCl$_3$) δ 7.44 (2H, d, J=8.1 Hz), 7.27 (2H, d, J=8.2 Hz), 6.72 (1H, s), 4.38 (2H, t, J=6.9 Hz), 3.07 (2H, t, J=7.1 Hz), 2.88 (3H, s), 2.82 (2H, q, J=7.6 Hz), 2.56 (3H, s), 2.36 (2H, q, J=7.6 Hz), 1.29 (3H, t, J=7.6 Hz), 1.15 (3H, t, J=7.7 Hz).

STEP 4. 2-[4-(2-Ethyl-4,6-dimethyl-1H-imidazo[4,5-c]pyridin-1-yl)phenyl]ethanol

The title compound was prepared according to the procedure described in step 6 of Example 1 from 2-[4-(2-ethyl-4,6-dimethyl-1H-imidazo[4,5-c]pyridin-1-yl)phenyl]ethyl propionate (step 3).

$^1$H-NMR (CDCl$_3$) δ 7.46 (2H, d, J=8.1 Hz), 7.26 (2H, d, J=8.1 Hz), 6.73 (1H, s), 4.00 (2H, t, J=6.6 Hz), 3.01 (2H, t, J=6.4 Hz), 2.88 (3H, s), 2.81 (2H, q, J=7.5 Hz), 2.54 (3H, s), 1.29 (3H, t, J=7.5 Hz).

STEP 5. 1-[4-(2-Chloroethyl)phenyl]-2-ethyl-4,6-dimethyl-1H-imidazo[4,5-c]pyridine The title compound was prepared according to the procedure described in step 7 of Example 1 from 2-[4-(2-ethyl-4,6-dimethyl-1H-imidazo[4,5-c]pyridin-1-yl)phenyl]ethanol (step 4).

TLC Rf=0.1 (ethyl acetate).

STEP 6. 1-[4-(2-Azidoethyl)phenyl]-2-ethyl-4,6-dimethyl-1H-imidazo[4,5-c]pyridine The title compound was prepared according to the procedure described in step 8 of Example 1 from 1-[4-(2-chloroethyl)phenyl]-2-ethyl-4,6-dimethyl-1H-imidazo[4,5-c]pyridine (step 5).

$^1$H-NMR (CDCl$_3$) δ 7.46 (2H, d, J=8.0 Hz), 7.29 (2H, d, J=7.7 Hz), 6.72 (1H, s), 3.62 (2H, t, J=6.9 Hz), 3.02 (2H, t, J=6.9 Hz), 2.88 (3H, s), 2.81 (2H, q, J=7.4 Hz), 2.56 (3H, s), 1.29 (3H, t, J=7.6 Hz).

STEP 7. 2-[4-(2-Ethyl-4,6-dimethyl-1H-imidazo[4,5-c]pyridin-1-yl)phenyl]ethylamine The title compound was prepared according to the procedure described in step 9 of Example 1 from 1-[4-(2-azidoethyl)phenyl]-2-ethyl-4,6-dimethyl-1H-imidazo[4,5-c]pyridine (step 6).

$^1$H-NMR (CDCl$_3$) δ 7.42 (2H, d, J=8.2 Hz), 7.26 (2H, d, J=8.4 Hz), 6.73 (1H, s), 3.08 (2H, t, J=6.9 Hz), 2.90–2.78 (4H, m), 2.88 (3H, s), 2.56 (3H, s), 1.30 (3H, t, J=7.3 Hz).

STEP 8. 2-Ethyl-4,6-dimethyl-1-(4-{2-[({[(4-methylphenyl)sulfonyl]amino}carbonyl)amino]ethyl}phenyl)-1H-imidazo[4,5-c]pyridine The title compound was prepared according to the procedure described in step 10 of Example 1 from 2-[4-(2-ethyl-4,6-dimethyl-1H-imidazo[4,5-c]pyridin-1-yl)phenyl]ethylamine (step 7).

mp 143° C.; MS (ESI) m/z 492.12 (M+H)$^+$; $^1$H-NMR (CDCl$_3$) δ 7.77 (2H, d, J=8.3 Hz), 7.38 (2H, d, J=8.4 Hz), 7.25 (2H, d, J=8.4 Hz), 7.20 (2H, d, J=8.4 Hz), 6.77 (1H, s), 3.58–3.51 (2H, m), 2.92 (2H, t, J=7.0 Hz), 2.89 (3H, s), 2.79 (2H, q, J=7.5 Hz), 2.53 (3H, s), 2.38 (3H, s), 1.28 (3H, t, J=7.5 Hz).

EXAMPLE 43

2-ETHYL-1-(4-{2-[({[(4-METHYLPHENYL)SULFONYL]AMINO}CARBONYL)AMINO]ETHYL}PHENYL)-1H-BENZIMIDAZOLE

STEP 1. 2-[4-(2-Nitroanilino)phenyl]ethanol

The title compound was prepared according to the procedure described in step 3 of Example 1 from 2-chloronitrobenzene and 4-aminophenylethyl alcohol.

$^1$H-NMR (CDCl$_3$) δ 9.47 (1H, s), 8.21 (1H, dd, J=1.5, 8.8 Hz), 7.40–7.16 (6H, m), 6.81–6.70 (1H, m), 3.91 (2H, t, J=6.5 Hz), 2.90 (2H, t, J=6.5 Hz).

STEP 2. 2-[4-(2-Aminoanilino)phenyl]ethanol

The title compound was prepared according to the procedure described in step 4 of Example 1 from 2-[4-(2-nitroanilino)phenyl]ethanol (step 1).

$^1$H-NMR (CDCl$_3$) δ 7.15–6.96 (4H, m), 6.82–6.66 (4H, m), 5.14 (1H, s), 3.80 (2H, t, J=6.6 Hz), 3.75 (2H, br.s), 2.79 (2H, t, J=6.6 Hz).

STEP 3. 2-[4-(2-Ethyl-1H-benzimidazol-1-yl)phenyl]ethyl propionate

The title compound was prepared according to the procedure described in step 5 of Example 1 from 2-[4-(2-aminoanilino)phenyl]ethanol (step 2) and propionyl chloride.

MS (EI) m/z 322 (M$^+$); $^1$H-NMR (CDCl$_3$) δ 7.79 (1H, d, J=7.7 Hz), 7.43 (2H, d, J=8.6 Hz), 7.34–7.06 (5H, m), 4.38 (2H, t, J=7.0 Hz), 3.07 (2H, t, J=7.0 Hz), 2.80 (2H, q, J=7.5 Hz), 2.36 (2H, q, J=7.6 Hz), 1.35 (3H, t, J=7.5 Hz), 1.15 (3H, t, J=7.6 Hz).

STEP 4. 2-[4-(2-Eethyl-1H-benzimidazol-1-yl)phenyl]ethanol

The title compound was prepared according to the procedure described in step 6 of Example 1 from 2-[4-(2-ethyl-1H-benzimidazol-1-yl)phenyl]ethyl propionate (step 3).

$^1$H-NMR (CDCl$_3$) δ 7.81–7.75 (1H, m), 7.45 (2H, d, J=8.3 Hz), 7.31 (2H, d, J=8.3 Hz), 7.25–7.08 (3H, m), 3.98 (2H, t, J=6.5 Hz), 3.00 (2H, t, J=6.5 Hz), 2.80 (2H, q, J=7.5 Hz), 1.27 )3H, t, J=7.5 Hz).

STEP 5. 2-[4-(2-Ethyl-1H-benzimidazol-1-yl)phenyl]ethyl azide

The title compound was prepared according to the procedure described in step 5 Example 26 from 2-[4-(2-ethyl-1H-benzimidazol-1-yl)phenyl]ethanol (step 4).

MS (EI) m/z 291 (M$^+$); $^1$H-NMR (CDCl$_3$) δ 7.81–7.76 (1H, m), 7.43 (2H, d, J=8.3 Hz), 7.40–7.06 (5H, m), 3.62 (2H, t, J=6.5 Hz), 3.04 (2H, t, J=6.5 Hz), 2.80 (2H, q, J=7.5 Hz), 1.27 (3H, t, J=7.5 Hz).

STEP 6. 2-[4-(2-Ethyl-1H-benzimidazol-1-yl)phenyl]ethylamine

The title compound was prepared according to the procedure described in step 9 of Example 1 from 2-[4-(2-ethyl-1H-benzimidazol-1-yl)phenyl]ethyl azide (step 5).

$^1$H-NMR (CDCl$_3$) δ 7.80–7.74 (1H, m), 7.45–7.06 (7H, m), 3.06 (2H, t, J=6.5 Hz), 2.89 (2H, t, J=6.5 Hz), 2.76 (2H, q, J=7.5 Hz), 1.26 (3H, t, J=7.5 Hz).

STEP 7. 2-Ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-ethyl-1H-benzimidazol-1-yl)phenyl]ethylamine (step 6).

$^1$H-NMR (CDCl$_3$) δ 7.75 (1H, d, J=8.8 Hz), 7.71 (2H, d, J=8.3 Hz), 7.39–7.14 (8H, m), 7.07 (1H, d, J=8.8 Hz), 6.68 (1H, br.s), 3.62–3.54 (2H, m), 2.94 (2H, t, J=6.3 Hz), 2.79 (2H, q, J=7.0 Hz), 2.41 (3H, s), 1.33 (3H, t, J=7.0 Hz).

EXAMPLE 44

2-[4-(2-ETHYL-1H-BENZIMIDAZOL-1-YL)PHENYL]ETHYL(4-METHYLPHENYL)SULFONYLCARBAMATE

The title compound was prepared according to the procedure described in Example 3 from 2-[4-(2-ethyl-1H-benzimidazol-1-yl)phenyl]ethanol (step 4 of Example 43).

$^1$H-NMR (CDCl$_3$) δ 7.93 (2H, d, J=8.3 Hz), 7.85–7.75 (2H, m), 7.40–7.15 (7H, m), 7.08 (1H, d, J=8.8 Hz), 4.77 (1H, br.s) 4.36 (2H, t, J=6.4 Hz), 3.00 (2H, t, J=6.4 Hz), 2.78 (2H, q, J=7.0 Hz), 2.44 (3H, s), 1.32 (3H, t, J=7.0 Hz).

EXAMPLE 45

4-METHYL-2-ETHYL-3-(4-{2-[({[(4-METH-YLPHENYL)SULFONYL]AMINO}CARBONYL)AMINO]ETHYL}PHENYL)-1H-BENZIMIDAZOLE

STEP 1. 2-[4-(3-Methyl-2-nitroanilino)phenyl]ethanol

A mixture of 2-nitro-3-methylaniline (Newman, M. S.; Kannan R. *J. Org. Chem.*, 1976, 41, 3356., 1.9 g, 12.4 mmol), 4-bromophenylethyl alcohol (2.5 g, 12.4 mmol), $K_2CO_3$ (1.7 g, 12.4 mmol and CuI (230 mg, 1.24 mmol) was placed in a sealed tube and heated at 200° C. for 2 h. After cooling, the mixture was poured into water (100 mL) and extracted with ethyl acetate (300 mL). The organic layer was washed with 2N aqueous NaOH (100 mL) and brine (100 mL), then dried ($Na_2SO_4$), and concentrated. Purification by flash column chromatography on silica gel eluting with hexane/ethyl acetate (1:1) to afford 700 mg (21%) of the title compound as an orange oil:

$^1$H-NMR (CDCl$_3$) δ 7.77 (1H, br.s), 7.09–7.45 (6H, m), 6.69 (1H, d, J=6.3 Hz), 3.83 (2H, t, J=6.6 Hz), 2.82 (2H, t, J=6.6 Hz), 2.59 (3H, s).

STEP 2. 2-[4-(2-Amino-3-methylanilino)phenyl]ethanol

The title compound was prepared according to the procedure described in step 2 of Example 26 from 2-[4-(3-methyl-2-nitroanilino)phenyl]ethanol (step 1).

$^1$H-NMR (CDCl$_3$) δ 7.02 (2H, d, J=8.2 Hz), 6.95 (1H, d, J=7.7 Hz), 6.91 (1H, d, J=7.0 Hz), 6.65 (1H, dd, J=7.0 Hz, 7.7 Hz), 6.62 (2H, d, J=8.2 Hz), 5.15 (1H, br.s), 3.75 (2H, t, J=6.6 Hz), 2.73 (2H, t, J=6.6 Hz), 2.19 (3H, s).

STEP 3. 2-[4-(2-Ethyl-4-methyl-1H-benzimidazol-1-yl)phenyl]ethyl propionate

The title compound was prepared according to the procedure described in step 5 of Example 1 from 2-[4-(2-amino-3-methylanilino)phenyl]ethanol (step 2) and propionyl chloride.

TLC Rf=0.6 (hexane: ethyl acetate=1:1).

STEP 4. 2-[4-(2-Ethyl-4-methyl-1H-benzimidazol-1-yl)phenyl]ethanol

The title compound was prepared according to the procedure described in step 6 of Example 1 from 2-[4-(2-ethyl-4-methyl-1H-benzimidazol-1-yl)phenyl]ethyl propionate (step 3).

$^1$H-NMR (CDCl$_3$) δ 7.41–7.43 (2H, m), 7.29 (2H, d, J=6.4 Hz), 7.07 (2H, d, J=6.4 Hz), 6.91–6.94 (1H, m), 3.97 (2H, t, J=6.6 Hz), 2.99 (2H, t, J=6.6 Hz), 2.84 (2H, q, J=7.5 Hz), 2.71 (3H, s), 1.27 (3H, t, J=7.5 Hz).

STEP 5. 1-[4-(2-Chloroethyl)phenyl]-2-ethyl-4-methyl-1H-benzimidazole

The title compound was prepared according to the procedure described in step 7 of Example 1 from 2-[4-(2-ethyl-4-methyl-1H-benzimidazol-1-yl)phenyl]ethanol (step 4).

$^1$H-NMR (CDCl$_3$) δ 7.43 (2H, d, J=8.4 Hz), 7.30 (2H, d, J=8.4 Hz), 7.07–7.09 (2H, m), 6.90–6.95 (1H, m), 3.81 (2H, t, J=7.2 Hz), 3.19 (2H, t, J=7.2 Hz), 2.84 (2H, q, J=7.5 Hz), 2.72 (3H, s), 1.27 (3H, t, J=7.5 Hz).

STEP 6. 2-[4-(2-Ethyl-4-methyl-1H-benzimidazol-1-yl)phenyl]ethyl azide

The title compound was prepared according to the procedure described in step 8 of Example 1 from 1-[4-(2-chloroethyl)phenyl]-2-ethyl-4-methyl-1H-benzimidazole (step 5).

$^1$H-NMR (CDCl$_3$) δ 7.43 (2H, d, J=8.0 Hz), 7.31 (2H, d, J=8.0 Hz), 7.05–7.09 (2H, m), 6.90–6.94 (1H, m), 3.61 (2H, t, J=7.0 Hz), 3.01 (2H, t, J=7.0 Hz), 2.84 (2H, q, J=7.5 Hz), 2.72 (3H, s) 1.27 (3H, t, J=7.5 Hz).

STEP 7. 2-[4-(2-Ethyl-4-methyl-1H-benzimidazol-1-yl)phenyl]ethylamine

The title compound was prepared according to the procedure described in step 9 of Example 1 from 2-[4-(2-ethyl-4-methyl-1H-benzimidazol-1-yl)phenyl]ethyl azide (step 6).

$^1$H-NMR (CDCl$_3$) δ 7.40 (2H, d, J=8.3 Hz), 7.28 (2H, d, 8.3 Hz), 7.04–7.11 (2H, m) 6.86–6.95 (1H, m), 3.07 (2H, t, J=6.6 Hz), 2.87 (2H, t, J=6.6 Hz), 2.84 (2H, q, J=7.5 Hz), 2.71 (3H, s), 1.27 (3H, t, J=7.5 Hz).

STEP 8. 2-Ethyl-4-methyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-ethyl-4-methyl-1H-benzimidazol-1-yl)phenyl]ethylamine (step 7).

MS (ESI) m/z 477 (M+H)$^+$; $^1$H-NMR (DMSO-d$_6$) δ 7.65 (2H, d, J=7.7 Hz), 7.33–7.41 (4H, m), 7.15 (2H, d, J=7.7 Hz), 7.01–7.07 (2H, m), 6.86 (1H, d, J=6.8 Hz), 3.19 (2H, br.s), 2.68–2.74 (4H, m), 2.56 (3H, s), 2.28 (3H, s), 1.21 (3H, t, J=7.1 Hz); IR (KBr) ν$_{max}$ 3390, 1602, 1519, 1429, 1230, 1130, 1085 cm$^{-1}$.

EXAMPLE 46

4-METHYL-2-ETHYL-3-(4-[2-[({[(4-METH-YLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 2-ethyl-4-methyl-1-(4-{2-[({[(4-methylphenyl)sulfonyl]amino}carbonyl)amino]ethyl}phenyl)-1H-benzimidazole (Example 45).

$^1$H-NMR (DMSO-d$_6$) δ 7.65 (2H, d, J=7.7 Hz), 7.33–7.41 (4H, m), 7.15 (2H, d, J=7.7 Hz), 7.01–7.07 (2H, m), 6.86 (1H, d, J=6.8 Hz), 3.19 (2H, br.s), 2.68–2.74 (4H, m), 2.56 (3H, s), 2.28 (3H, s), 1.21 (3H, t, J=7.1 Hz); IR (KBr) ν$_{max}$ 3390, 1602, 1519, 1429, 1230, 1130, 1085 cm$^{-1}$.

EXAMPLE 47

2-ETHYL-5-METHYL-1-(4-{2-[({[(4-METH-YLPHENYL)SULFONYL]AMINO}CARBONYL)AMINO]ETHYL}PHENYL)-1H-BENZIMIDAZOLE

STEP 1. 2-[(4-Methyl-2-nitroanilino)phenyl]ethanol

The title compound was prepared according to the procedure described in step 1 Example 45 from 4-methyl-2-nitroaniline and 4-iodophenylethyl alcohol.

$^1$H-NMR (CDCl$_3$) δ 9.35 (1H, br.s), 8.00 (1H, s), 7.33–7.09 (6H, m), 3.91–3.89 (2H, m), 2.89 (2H, t, J=6.4 Hz), 2.30 (3H, s).

STEP 2. 2-[(2-Amino-4-methylanilino)phenyl]ethanol

The title compound was prepared according to the procedure described in step 2 of Example 28 from 2-[(4-methyl-2-nitroanilino)phenyl]ethanol (step 1).

$^1$H-NMR (CDCl$_3$) δ 7.05 (2H, d, J=8.3 Hz), 6.98 (1H, d, J=7.7 Hz), 6.67–6.64 (3H, m), 6.58–6.55 (1H, m), 5.06 (1H, br.s), 3.80–3.78 (4H, m), 2.77 (2H, t, J=6.4 Hz), 2.28 (3H, s).

STEP 3. 2-[4-(2-Ethyl-5-methyl-1H-benzimidazol-1-yl) phenyl]ethyl propionate

The title compound was prepared according to the procedure described in step 5 of Example 1 from 2-[(2-amino-4-methylanilino)phenyl]ethanol (step 2) and propionyl chloride.

TLC Rf=0.33 (hexane/ethyl acetate=2:1).

STEP 4. 2-[4-(2-Ethyl-5-methyl-1H-benzimidazol-1-yl) phenyl]ethanol

The title compound was prepared according to the procedure described in step 6 of Example 1 from 2-[4-(2-ethyl-5-methyl-1H-benzimidazol-1-yl)phenyl]ethyl propionate (step 3).

$^1$H-NMR (CDCl$_3$) δ 7.55 (1H, s), 7.43 (2H, d, J=8.3 Hz), 7.28 (2H, d, J=8.3 Hz), 6.99–6.95 (2H, m), 3.99 (2H, t, J=6.6 Hz), 3.00 (2H, t, J=6.6 Hz), 2.77 (2H, q, J=7.7 Hz), 2.47 (3H, s), 1.32 (3H, t, J=7.7 Hz)

STEP 5. 2-[4-(2-Ethyl-5-methyl-1H-benzimidazol-1-yl) phenyl]ethyl azide

The title compound was prepared according to the procedure described in step 5 of Example 26 from 2-[4-(2-ethyl-5-methyl-1H-benzimidazol-1-yl)phenyl]ethanol (step 4).

TLC Rf=0.74 (Hexane/ethyl acetate=1:1).

STEP 6. 2-[4-(2-Ethyl-5-methyl-1H-benzimidazol-1-yl) phenyl]ethylamine

The title compound was prepared according to the procedure described in step 9 of Example 1 from 2-[4-(2-ethyl-5-methyl-1H-benzimidazol-1-yl)phenyl]ethyl azide (step 5).

$^1$H-NMR (CDCl$_3$) δ 7.55 (1H, s), 7.43 (2H, d, J=8.2 Hz), 7.29 (2H, d, J=8.2 Hz), 7.01–6.95 (2H, m), 4.85 (2H, br.s), 3.30–3.25 (2H, m), 3.16–3.11 (2H, m), 2.76 (2H, q, J=7.6 Hz), 2.45 (3H, s), 1.31 (3H, t, J=7.6 Hz).

STEP 7. 2-Ethyl-5-methyl-1-(4-{2-[({[(4-methylphenyl) sulfonyl]amino}carbonyl)amino]ethyl}phenyl)-1H-benzimidazole The title compound was prepared according to the procedure described in step 10 of Example 1 from 2-[4-(2-ethyl-5-methyl-1H-benzimidazol-1-yl)phenyl]ethylamine (step 6).

$^1$H-NMR (DMSO-d$_6$) δ 7.76 (2H, d, J=8.4 Hz), 7.42–7.36 (6H, m), 7.00–6.91 (2H, m), 6.53–6.49 (1H, m), 3.29–3.24 (2H, m), 2.79–2.65 (4H, m), 2.40 (3H, s), 2.33 (3H, s), 1.20 (3H, t, J=7.4 Hz).

EXAMPLE 48

2-ETHYL-5-METHYL-1-(4-{2-[({[(4-METHYLPHENYL)SULFONYL]AMINO}CARBONYL) AMINO]ETHYL}PHENYL)-1H-BENZIMIDAZOLE, SODIUM SALT

The title compound was prepared according to the procedure described in Example 2 from 2-ethyl-5-methyl-1-(4-{2-[({[(4-methylphenyl)sulfonyl]amino}carbonyl)amino] ethyl}phenyl)-1H-benzimidazole (Example 47).

$^1$H-NMR (DMSO-d$_6$) δ 7.60 (2H, d, J=7.7 Hz), 7.42–7.33 (5H, m), 7.13 (2H, d, J=7.7 Hz), 6.96 (2H, m), 3.16 (2H, m), 2.71–2.66 (4H, m), 2.39 (3H, s), 2.27 (3H, s), 1.20 (3H, t, J=7.5 Hz); IR (KBr) ν$_{max}$ 1599, 1514, 1285, 1232, 1130, 1086 cm$^{-1}$.

EXAMPLE 49

2-BUTYL-5-METHYL-1-(4-{2-[({[(4-METHYLPHENYL)SULFONYL]AMINO]CARBONYL) AMINO]BUTYL}PHENYL)-1H-BENZIMIDAZOLE

STEP 1. 2-[4-(2-Butyl-5-methyl-1H-benzimidazol-1-yl) phenyl]ethyl pentanoate

The title compound was prepared according to the procedure described in step 5 of Example 1 from 2-[(2-amino-4-methylanilino)phenyl]ethanol (step 2 of Example 47) and pentanoyl chloride.

$^1$H-NMR (CDCl$_3$) δ 7.56–7.55 (1H, m), 7.43–7.40 (2H, m), 7.29–7.26 (2H, m), 7.02–6.94 (2H, m), 4.38 (2H, t, J=6.9 Hz), 3.06 (2H, t, J=6.9 Hz), 2.75 (2H, t, J=7.4 Hz), 2.47 (3H, s) 2.33 (2H, t, J=7.4 Hz), 1.80–1.55 (4H, m), 1.41–1.23 (4H, m), 0.94–0.83 (6H, m).

STEP 2. 2-[4-(2-Butyl-6-methyl-1H-benzimidazol-1-yl) phenyl]ethanol

The title compound was prepared according to the procedure described in step 6 of Example 1 from 2-[4-(2-butyl-6-methyl-1H-benzimidazol-1-yl)phenyl]ethyl pentanoate (step 1).

$^1$H-NMR (CDCl$_3$) δ 7.55 (1H, s), 7.44 (2H, d, J=8.2 Hz), 7.27 (2H, d, J=8.2 Hz), 7.02–6.95 (2H, m), 3.99 (2H, t, J=6.6 Hz), 3.01 (2H, t, J=6.6 Hz), 2.75 (2H, t, J=7.3 Hz), 2.47 (3H, s), 1.79–1.68 (2H, m), 1.36–1.23 (2H, m), 0.85 (3H, t, J=7.3 Hz).

STEP 3. 2-[4-(2-Butyl-6-methyl-1H-benzimidazol-1-yl) phenyl]ethyl azide

The title compound was prepared according to the procedure described in step 5 of Example 26 from 2-[4-(2-butyl-6-methyl-1H-benzimidazol-1-yl)phenyl]ethanol (step 2).

$^1$H-NMR (CDCl$_3$) δ 7.56 (1H, s), 7.42 (2H, d, J=8.4 Hz), 7.29 (2H, d, J=8.4 Hz), 7.03–6.95 (2H, m), 3.61 (2H, t, J=6.9 Hz), 3.01 (2H, t, J=6.9 Hz), 2.75 (2H, t, J=7.3 Hz), 2.47 (3H, s), 1.80–1.68 (2H, m), 1.37–1.26 (2H, m), 0.85 (3H, t, J=7.3 Hz).

STEP 3. 2-[4-(2-Butyl-6-methyl-1H-benzimidazol-1-yl) phenyl]ethylamine

The title compound was prepared according to the procedure described in step 9 of Example 1 from 2-[4-(2-butyl-6-methyl-1H-benzimidazol-1-yl)phenyl]ethyl azide (step 2).

$^1$H-NMR (CDCl$_3$) δ 7.55 (1H, s), 7.40 (2H, d, J=8.3 Hz), 7.26 (2H, d, J=8.3 Hz), 7.01–6.94 (2H, m), 3.15 (2H, t, J=7.3 Hz), 2.98 (2H, t, J=7.3 Hz), 2.74 (2H, t, J=7.7 Hz), 2.46 (3H, s), 1.77–1.67 (2H, m), 1.35–1.28 (2H, m), 0.84 (3H, t, J=7.7 Hz).

STEP 4. 2-Butyl-5-methyl-1-(4-{2-[({[(4-methylphenyl) sulfonyl]amino}carbonyl)amino]ethyl}phenyl)-1H-benzimidazole The title compound was prepared according to the procedure described in step 10 of Example 1 from 2-[4-(2-butyl-6-methyl-1H-benzimidazol-1-yl)phenyl]ethylamine (step 3).

$^1$-NMR (CDCl$_3$) δ 7.76 (2H, d, J=8.2 Hz), 7.54 (1H, m), 7.31–7.21 (6H, m), 7.03–6.95 (2H, m), 6.67–6.63 (1H, m), 3.61–3.54 (2H, m), 2.91 (2H, t, J=7.1 Hz), 2.73 (2H, t, J=7.3 Hz), 2.47 (3H, s), 2.40 (3H, s), 1.76–1.65 (2H, m), 1.36–1.28 (2H, m), 0.83 (3H, t, J=7.3 Hz).

EXAMPLE 50

2-BUTYL-5-METHYL-1-(4-{2-[({[(4-METHYLPHENYL)SULFONYL]AMINO}CARBONYL)AMINO]BUTYL}PHENYL)-1H-BENZIMIDAZOLE, SODIUM SALT

The title compound was prepared according to the procedure described in Example 2 from 2-butyl-5-methyl-1-(4-{2-[({[(4-methylphenyl)sulfonyl]amino}carbonyl)amino]ethyl}phenyl)-1H-benzimidazole (Example 49).

mp 130–140° C.; $^1$H-NMR (DMSO-$d_6$) δ 7.59 (2H, d, J=7.8 Hz), 7.40–7.31 (5H, m), 7.11 (2H, d, J=7.8 Hz), 6.98–6.92 (2H, m), 3.15 (2H, m), 2.71–2.66 (4H, m), 2.39 (3H, s), 2.26 (3H, s), 1.67–1.57 (2H, m), 1.31–1.21 (2H, m), 0.79 (3H, t, J=7.5 Hz); IR (KBr) $v_{max}$ 1599, 1514, 1400, 1130, 1086 cm$^{-1}$.

EXAMPLE 51

6-METHYL-2-ETHYL-3-(4-{2-[({[(4-METHYLPHENYL)SULFONYL]AMINO}CARBONYL)AMINO]ETHYL}PHENYL)-1H-BENZIMIDAZOLE

STEP 1. 2-[4-(5-Methyl-2-nitroanilino)phenyl]ethanol

The title compound was prepared according to the procedure described in step 3 of Example 1 from 2-fuluoro-4-methylnitrobenzene and 4-aminophenylethyl alcohol.

$^1$H-NMR (CDCl$_3$) δ 9.51 (1H, br.s), 8.10 (1H, d, J=8.8 Hz), 7.20–7.31 (4H, m), 6.98 (1H, s), 6.58 (1H, d, J=8.4 Hz), 3.91 (2H, t, J=6.4 Hz), 2.89 (t, J=6.4 Hz), 2.27 (3H, s).

STEP 2. 2-[4-(2-Amino-5-methylanilino)phenyl]ethanol

The title compound was prepared according to the procedure described in step 2 of Example 26 from 2-[4-(5-methyl-2-nitroanilino)phenyl]ethanol (step 1).

$^1$H-NMR (CDCl$_3$) δ 7.07 (2H, d, J=8.3 Hz), 6.93 (1H, s), 6.81 (1H, d, J=8.1 Hz), 6.70–6.72 (3H, m), 3.81 (2H, t, J=6.4 Hz), 3.61 (2H, br.s), 2.78 (2H, t, J=6.4 Hz), 2.22 (3H, s).

STEP 3. 2-[4-(2-Ethyl-6-methyl-1H-benzimidazol-1-yl)phenyl]ethyl propionate

The title compound was prepared according to the procedure described in step 5 of Example 1 from 2-[4-(2-Amino-5-methylanilino)phenyl]ethanol (step 2) and propionyl chloride.

$^1$H-NMR (CDCl$_3$) δ 7.64 (1H, d, J=8.3 Hz), 7.42 (2H, d, J=8.0 Hz), 7.28 (2H, d, J=8.0 Hz), 7.08 (1H, d, J=8.3 Hz), 6.87 (1H, s), 4.38 (2H, t, J=6.9 Hz), 3.06 (2H, t, J=6.9 Hz), 2.76 (2H, q, J=7.5 Hz), 2.41 (3H, s), 2.36 (2H, q, J=7.7 Hz), 1.35 (3H, t, J=7.5 Hz), 1.15 (3H, t, J=7.7 Hz).

STEP 4. 2-[4-(2-Ethyl-6-methyl-1H-benzimidazol-1-yl)phenyl]ethanol

The title compound was prepared according to the procedure described in 6 of Example 1 from 2-[4-(2-ethyl-6-methyl-1H-benzimidazol-1-yl)phenyl]ethyl propionate (step 3).

$^1$H-NMR (CDCl$_3$) δ 7.64 (1H, d, J=8.1 Hz), 7.45 (2H, d, J=8.1 Hz), 7.19–7.30 (2H, m), 7.08 (1H, d, J=8.1 Hz), 6.88 (1H, s), 3.99 (2H, t, J=6.6 Hz), 3.00 (2H, t, J=6.6 Hz), 2.77 (2H, q, J=7.6 Hz), 2.40 (3H, s), 1.33 (3H, t, J=7.6 Hz).

STEP 5. 1-[4-(2-Chloroethyl)phenyl]-2-ethyl-6-methyl-1H-benzimidazole

The title compound was prepared according to the procedure described in step 7 of Example 1 from 2-[4-(2-ethyl-6-methyl-1H-benzimidazol-1-yl)phenyl]ethanol (step 4).

$^1$H-NMR (CDCl$_3$) δ 7.65 (1H, d, J=8.2 Hz), 7.43 (2H, d, J=8.2 Hz), 7.31 (2H, d, J=8.2 Hz), 7.07 (1H, d, J=8.2 Hz), 6.88 (1H, s), 3.82 (2H, t, J=7.0 Hz), 3.19 (2H, t, 7.0 Hz), 2.77 (2H, q, J=7.6 Hz), 2.41 (3H, s), 1.33 (3H, t, J=7.6 Hz).

STEP 6. 2-[4-(2-Ethyl-6-methyl-1H-benzimidazol-1-yl)phenyl]ethyl azide

The title compound was prepared according to the procedure described in step 8 of Example 1 from 1-[4-(2-chloroethyl)phenyl]-2-ethyl-6-methyl-1H-benzimidazole (step 5).

$^1$H-NMR (CDCl$_3$) δ 7.64 (1H, d, J=8.2 Hz), 7.43 (2H, d, J=8.2 Hz), 7.31 (2H, d, J=8.2 Hz), 7.08 (1H, d, J=8.2 Hz), 6.87 (1H, s), 3.62 (2H, t, J=7.0 Hz), 3.01 (2H, t, J=7.0 Hz), 2.77 (2H, q, J=7.6 Hz), 2.37 (3H, s), 1.33 (3H, t, J=7.6 Hz).

STEP 7. 2-[4-(2-Ethyl-6-methyl-1H-benzimidazol-1-yl)phenyl]ethylamine

The title compound was prepared according to the procedure described in step 9 of Example 1 from 2-[4-(2-ethyl-6-methyl-1H-benzimidazol-1-yl)phenyl]ethyl azide (step 6).

$^1$H-NMR (CDCl$_3$) δ 7.64 (1H, d, J=8.3 Hz), 7.40 (2H, d, J=8.2 Hz), 7.28 (2H, d, J=8.2 Hz), 7.07 (1H, d, J=8.3 Hz), 6.88 (1H, s), 3.07 (2H, br.s), 2.87 (2H, t, J=6.8 Hz), 2.76 (2H, q, J=7.6 Hz), 2.40 (3H, s), 1.33 (3H, t, J=7.6 Hz).

STEP 8. 6-Methyl-2-ethyl-3-(4-{2-[({[4-methylphenyl)sulfonyl]amino}carbonyl)amino]ethyl}phenyl)-1H-benzimidazole The title compound was prepared according to the procedure described in step 10 of Example 1 from 2-[4-(2-ethyl-6-methyl-1H-benzimidazol-1-yl)phenyl]ethylamine (step 7).

$^1$H-NMR (CDCl$_3$) δ 7.73 (2H, d, J=8.3 Hz), 7.66 (1H, d, J=8.0 Hz), 7.27–7.38 (6H, m), 7.09 (1H, d, J=8.0 Hz), 6.88 (1H, s), 3.59–3.63 (2H, m), 2.95 (2H, t, J=6.6 Hz), 2.77 (2H, q, J=7.5 Hz), 2.41 (3H, s), 2.39 (3H, s), 1.33 (3H, t, J=7.5 Hz).

EXAMPLE 52

6-METHYL-2-ETHYL-3-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 6-methyl-2-ethyl-3-(4-{2-[({[(4-methylphenyl)sulfonyl]amino}carbonyl)amino]ethyl}phenyl)-1H-benzimidazole (Example 51).

mp 151–165° C.; $^1$H-NMR (DMSO-$d_6$) δ 7.64 (2H, d, J=8.0 Hz), 7.51 (1H, d, J=8.2 Hz), 7.33–7.42 (4H, m), 7.15 (2H, d, J=8.0 Hz), 7.02 (1H, dd, J=1.4 Hz, 8.2 Hz), 6.87 (1H, s), 3.18 (2H, br.s), 2.65–2.78 (4H, m), 2.34 (3H, s), 2.78 (3H, s), 1.21 (3H, t, J=7.6 Hz).

EXAMPLE 53

7-METHYL-2-ETHYL-3-(4-{2-[({[(4-METH-YLPHENYL)SULFONYL]AMINO}CARBONYL)AMINO]ETHYL}PHENYL)-1H-BENZIMIDAZOLE

STEP 1. 2-[4-(2-Methyl-6-nitroanilino)phenyl]ethanol

The title compound was prepared according to the procedure described in step 1 Example 45 from 6-methyl-2-nitroaniline and 4-bromophenylethyl alcohol.

$^1$H-NMR (CDCl$_3$) δ 8.28 (1H, br.s), 7.96 (1H, d, J=8.4 Hz), 7.39–7.44 (1H, m), 7.02–7.12 (3H, m), 6.72 (2H, d, J=8.4 Hz), 3.82 (2H, t, J=6.5 Hz), 2.81 (2H, t, J=6.5 Hz), 2.08 (3H, s).

STEP 2. 2-[4-(2-Amino-6-methylanilino)phenyl]ethanol

The title compound was prepared according to the procedure described in step 2 of Example 26 from 2-[4-(2-methyl-6-nitroanilino)phenyl]ethanol (step 1).

$^1$H-NMR (CDCl$_3$) δ 6.97–7.03 (3H, m), 6.66 (21H, d, J=7.6 Hz), 6.52 (2H, d, J=7.6 Hz), 4.97 (1H, br.s), 3.86 (2H, br.s), 3.79 (2H, t, J=6.4 Hz), 2.76 (2H, t, J=6.4 Hz), 2.16 (3H, s).

STEP 3. 2-[4-(2-Ethyl-7-methyl-1H-benzimidazol-1-yl)phenyl]ethyl propionate

The title compound was prepared according to the procedure described in step 5 of Example 1 from 2-[4-(2-amino-6-methylanilino)phenyl]ethanol (step 2) and propionyl chloride.

TLC Rf=0.6 (hexane:ethyl acetate=1:1).

STEP 4. 2-[4-(2-Ethyl-7-methyl-1H-benzimidazol-1-yl)phenyl]ethanol

The title compound was prepared according to the procedure described in step 6 of Example 1 from 2-[4-(2-ethyl-7-methyl-1H-benzimidazol-1-yl)phenyl]ethyl propionate (step 3).

$^1$H-NMR (CDCl$_3$) δ 7.63 (1H, d, J=8.0 Hz), 7.38–7.41 (2H, m), 7.26–7.31 (2H, m), 7.14 (1H, dd, J=7.4 Hz, 8.0 Hz), 6.91 (1H, d, J=7.4 Hz), 3.98 (2H, t, J=6.6 Hz), 3.01 (2H, t, J=6.6 Hz), 2.63 (2H, q, J=7.5 Hz), 1.89 (3H, s), 1.31 (3H, t, J=7.5 Hz).

STEP 5. 1-[4-(2-Chloroethyl)phenyl]-2-ethyl-7-methyl-1H-benzimidazole

The title compound was prepared according to the procedure described in step 7 of Example 1 from 2-[4-(2-ethyl-7-methyl-1H-benzimidazol-1-yl)phenyl]ethanol (step 4).

$^1$H-NMR (CDCl$_3$) δ 7.64 (1H, d, J=8.1 Hz), 7.26–7.39 (4H, m), 7.14 (1H, dd, J=7.4 Hz, 8.1 Hz), 6.91 (1H, d, J=7.4 Hz), 3.81 (2H, t, J=7.2 Hz), 3.19 (2H, d, J=7.2 Hz), 2.63 (2H, q, J=7.6 Hz), 1.88 (3H, s), 1.32 (3H, t, J=7.6 Hz).

STEP 6. 2-[4-(2-Ethyl-7-methyl-1H-benzimidazol-1-yl)phenyl]ethyl azide

The title compound was prepared according to the procedure described in step 8 of Example 1 from 1-[4-(2-chloroethyl)phenyl]-2-ethyl-7-methyl-1H-benzimidazole (step 5).

$^1$H-NMR (CDCl$_3$) δ 7.64 (1H, d, J=7.4 Hz), 7.39 (2H, d, J=8.0 Hz), 7.31 (2H, d, J=8.0 Hz), 7.14 (1H, dd, J=7.4 Hz, 8.1 Hz), 6.91 (1H, d, J=8.1 Hz), 3.61 (2H, t, J=6.8 Hz), 3.02 (2H, t, J=6.8 Hz), 2.63 (2H, q, J=7.6 Hz), 1.89 (3H, s), 1.31 (3H, t, J=7.5 Hz).

STEP 7. 2-[4-(2-Ethyl-7-methyl-1H-benzimidazol-1-yl)phenyl]ethylamine

The title compound was prepared according to the procedure described in step 9 of Example 1 from 2-[4-(2-ethyl-7-methyl-1H-benzimidazol-1-yl)phenyl]ethyl azide (step 6).

$^1$H-NMR (CDCl$_3$) δ 7.64 (1H, d, J=7.9 Hz), 7.36 (2H, d, J=8.2 Hz), 7.28 (2H, d, J=8.2 Hz), 7.14 (1H, dd, J=7.5 Hz, 7.9 Hz), 6.91 (1H, d, J=7.5 Hz), 3.06 (2H, t, J=6.8 Hz), 2.87 (2H, t, J=6.8 Hz), 2.63 (2H, q, J=7.5 Hz), 1.89 (3H, s), 1.32 (3H, t, J=7.5 Hz).

STEP 8. 2-Ethyl-7-methyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-ethyl-7-methyl-1H-benzimidazol-1-yl)phenyl]ethylamine (step 7).

MS (ESI) m/z 477 (M+H)$^+$, $^1$H-NMR (CDCl$_3$) δ 7.75 (2H, d, J=8.3 Hz), 7.62 (1H, d, J=7.9 Hz), 7.28–7.33 (5H, m), 7.14 (2H, d, J=7.6 Hz), 6.91 (1H, d, J=7.9 Hz), 6.72 (1H, br.s), 3.58 (2H, d, J=6.8 Hz), 2.93 (2H, t, J=6.8 Hz), 2.62 (2H, q, J=7.6 Hz), 2.41 (3H, s), 1.86 (3H, s), 1.29 (3H, t, J=7.6 Hz).

EXAMPLE 54

7-METHYL-2-ETHYL-3-(4-{2-[({[(4-METH-YLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 2-ethyl-7-methyl-1-(4-{2-[({[(4-methylphenyl)sulfonyl]amino}carbonyl)amino]ethyl}phenyl)-1H-benzimidazole (Example 53).

$^1$H-NMR (DMSO-d$_6$) δ 7.63 (2H, d, J=7.4 Hz), 7.47 (1H, d, J=8.1 Hz), 7.36 (4H, s), 7.15 (2H, d, J=7.7 Hz), 7.06 (1H, dd, J=7.2 Hz, 8.1 Hz), 6.87 (1H, d, J=7.2 Hz), 5.99 (1H, br.s), 3.16 (2H, br.s), 2.76 (2H, br.s), 2.52 (2H, q, J=7.6 Hz), 2.28 (3H, s), 1.82 (3H, s), 1.19 (3H, t, J=7.6 Hz);

IR (KBr) ν$_{max}$ 3400, 1610, 1525, 1290, 1132, 1095, 820, 751 cm$^{-1}$.

EXAMPLE 55

4-CHLORO-2-ETHYL-3-(4-{2-[({[(4-METH-YLPHENYL)SULFONYL]AMINO}CARBONYL)AMINO]ETHYL}PHENYL)-1H-BENZIMIDAZOLE

STEP 1. 2-[4-(3-Chloro-2-nitroanilino)phenyl]ethanol

A mixture of 2,6-dichloronitrobenzene (Norman, M. H.; Chen, N.; et al. *PCT Int. Appl.*, WO 9940091 (1999)., Spada, A. P.; Fink, C. A.; Myers, M. R. *PCT Int. Appl.*, WO 9205177 (1992)., 6.3 g, 32.8 mmol), 4-aminophenylethyl alcohol (4.9 g, 36 mmol) and sodium acetate (3.2 g, 39.3 mmol) was placed in a sealed tube and heated at 160° C. for 3 h. After cooling, the mixture was poured into water (100 mL) and extracted with ethyl acetate (300 mL). The organic layer was washed with 2N aqueous NaOH (100 mL) and brine (100 mL), then dried (Na$_2$SO$_4$), and concentrated. Purification by flash column chromatography on silica gel eluting with hexane/ethyl acetate (1:1) to afford 4.57 g (72%) of the title compound as a red oil: $^1$H-NMR (CDCl$_3$) δ 7.09–7.28 (6H, m), 6.91 (1H, dd, J=2.0, 7.1 Hz), 3.87 (2H, t, J=6.2 Hz), 2.86 (2H, t J=6.6 Hz).

STEP 2. 2-[4-(2-Amino-3-chloroanilino)phenyl]ethanol

The title compound was prepared according to the procedure described in step 2 of Example 28 from 2-[4-(3-chloro-2-nitroanilino)phenyl]ethanol (step 1).

$^1$H-NMR (CDCl$_3$) δ 7.06–7.10 (3H, m), 7.00 (1H, dd, J=1.0 Hz, 7.9 Hz), 6.62–6.73 (3H, m), 5.16 (1H, br.s), 4.14 (2H, br.s), 3.81 (2H, t, J=6.1 Hz), 2.77 (2H, t, J=6.1 Hz).

STEP 3. 2-[4-(4-Chloro-2-ethyl-1H-benzimidazol-1-yl)phenyl]ethyl propionate

The title compound was prepared according to the procedure described in step 5 of Example 1 from 2-[4-(2-amino-3-chloroanilino)phenyl]ethanol (step 2) and propionyl chloride.

TLC Rf=0.5 (hexane:ethyl acetate=1:1).

STEP 4. 2-[4-(4-Chloro-2-ethyl-1H-benzimidazol-1-yl)phenyl]ethanol

The title compound was prepared according to the procedure described in step 6 of Example 1 from 2-[4-(4-Chloro-2-ethyl-1H-benzimidazol-1-yl)phenyl]ethyl propionate (step 3).

$^1$H-NMR (CDCl$_3$) δ 7.45 (2H, d, J=8.6 Hz), 7.26–7.31 (3H, m), 7.09 (1H, d, J=7.9 Hz), 6.96 (1H, dd, J=0.9 Hz, 7.9 Hz), 3.99 (2H, t, J=6.6 Hz), 3.00 (2H, t, J=6.6 Hz), 2.84 (2H, q, J=7.5 Hz), 1.30 (3H, t, J=7.5 Hz).

STEP 5. 4-Chloro-1-[4-(2-chloroethyl)phenyl]-2-ethyl-1H-benzimidazole

The title compound was prepared according to the procedure described in step 7 of Example 1 from 2-[4-(4-chloro-2-ethyl-1H-benzimidazol-1-yl)phenyl]ethanol (step 4).

$^1$H-NMR (CDCl$_3$) δ 7.45 (2H, d, J=8.6 Hz), 7.30 (2H, d, J=8.6 Hz), 7.27 (1H, s), 7.10 (1H, d, J=8.1 Hz), 6.98 (1H, d, J=8.1 Hz), 3.81 (2H, t, J=7.1 Hz), 3.19 (2H, t, J=7.1 Hz), 2.84 (2H, q, J=7.6 Hz), 1.31 (3H, t, J=7.6 Hz).

STEP 6. 2-[4-(4-Chloro-2-ethyl-1H-benzimidazol-1-yl)phenyl]ethyl azide

The title compound was prepared according to the procedure described in step 8 of Example 1 from 4-chloro-1-[4-(2-chloroethyl)phenyl]-2-ethyl-1H-benzimidazole (step 5).

$^1$H-NMR (CDCl$_3$) δ 7.45 (2H, d, J=8.2 Hz), 7.29–7.33 (3H, m), 7.10 (1H, dd, J=8.1 Hz, 7.7 Hz), 6.96 (1H, d, J=7.7 Hz), 3.62 (2H, t, J=7.1 Hz), 3.02 (2H, t, J=7.1 Hz), 2.84 (2H, q, J=7.6 Hz), 1.30 (3H, t, J=7.6 Hz).

STEP 7. 2-[4-(4-Chloro-2-ethyl-1H-benzimidazol-1-yl)phenyl]ethylamine

The title compound was prepared according to the procedure described in step 7 of Example 37 from 2-[4-(4-chloro-2-ethyl-1H-benzimidazol-1-yl)phenyl]ethyl azide (step 6).

$^1$H-NMR (CDCl$_3$) δ 7.42 (2H, d, J=8.1 Hz), 7.29–7.33 (3H, m), 7.09 (1H, dd, J=7.7 Hz, 7.9 Hz), 7.99 (1H, d, J=7.9 Hz), 3.07 (2H, t, J=6.8 Hz), 2.87 (2H, t, J=6.8 Hz), 2.85 (2H, q, J=7.6 Hz), 1.30 (3H, t, J=7.6 Hz).

STEP 8. 4-Chloro-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(4-chloro-2-ethyl-1H-benzimidazol-1-yl)phenyl]ethylamine (step 7).

MS (ESI) m/z 498 (M+H)$^+$; $^1$H-NMR (CDCl$_3$) δ 7.73 (2H, d, J=8.5 Hz), 7.28–7.38 (7H, m), 7.09 (1H, d, J=7.9 Hz), 6.97 (1H, d, J=7.9 Hz), 6.69 (1H, br.s), 3.58 (2H, t, J=6.9 Hz), 2.94 (2H, t, J=6.9 Hz), 2.83 (2H, q, J=7.5 Hz), 2.40 (3H, s), 1.31 (3H, t, J=7.5 Hz).

EXAMPLE 56

4-CHLORO-2-ETHYL-3-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 4-chloro-2-ethyl-1-(4-{2-[({[(4-methylphenyl)sulfonyl]amino}carbonyl)amino]ethyl}phenyl)-1H-benzimidazole (Example 54).

$^1$H-NMR (DMSO-d$_6$) δ 7.62 (2H, d, J=8.0 Hz), 7.41 (4H, s), 7.29 (1H, d, J=6.6 Hz), 7.12–7.18 (3H, m), 7.02–7.04 (1H, m), 3.18 (2H, br.s), 2.70–2.79 (4H, m), 2.27 (3H, s), 1.23 (3H, t, J=7.4 Hz); IR (KBr) ν$_{max}$ 3385, 1602, 1519, 1433, 1174, 1130, 1085, 813 cm$^{-1}$.

EXAMPLE 57

5-CHLORO-2-ETHYL-1-(4-{2-[({[(4-METHYLPHENYL)SULFONYL]AMINO}CARBONYL)AMINO]ETHYL}PHENYL)-1H-BENZIMIDAZOLE

STEP 1. 2-[4-(4-Chloro-2-nitroanilino)phenyl]ethanol

The title compound was prepared according to the procedure described in step 3 of Example 1 from 2,5-dichloronitrobenzene and 4-aminophenylethyl alcohol.

$^1$H-NMR (CDCl$_3$) δ 9.42 (1H, s), 8.20 (1H, d, J=2.0 Hz), 7.35–7.10 (6H, m), 3.96–3.85 (2H, m), 2.91 (2H, t, J=7.0 Hz).

STEP 2. 2-[4-(2-Amino-4-chloroanilino)phenyl]ethanol

The title compound was prepared according to the procedure described in step 3 of Example 6 from 2-[4-(4-chloro-2-nitroanilino)phenyl]ethanol (step 1).

$^1$H-NMR (CDCl$_3$) δ 7.30–7.05 (4H, m), 6.83–6.62 (3H, m), 5.15 (1H, br.s), 3.86–3.77 (2H, m), 3.75 (2H, br.s), 2.77 (2H, t, J=7.0 Hz).

STEP 3. 2-[4-(5-Chloro-2-ethyl-1H-benzimidazol-1-yl)phenyl]ethyl propionate

The title compound was prepared according to the procedure described in step 5 of Example 1 from 2-[4-(2-amino-4-chloroanilino)phenyl]ethanol (step 2) and propionyl chloride.

$^1$H-NMR (CDCl$_3$) δ 7.75 (1H, d, J=2.0 Hz), 7.43 (2H, d, J=8.0 Hz), 7.28 (2H, d, J=8.0 Hz), 7.15 (1H, dd, J=2.0, 8.6 Hz), 6.99 (1H, d, J=8.6 Hz), 4.38 (2H, t, J=7.0 Hz), 3.07 (2H, t, J=7.0 Hz), 2.78 (2H, q, J=7.5 Hz), 2.36 (2H, q, J=7.5 Hz), 1.24 (3H, t, J=7.5 Hz), 1.15 (3H, t, J=7.5 Hz).

STEP 4. 2-[4-(5-Chloro-2-ethyl-1H-benzimidazol-1-yl)phenyl]ethanol

The title compound was prepared according to the procedure described in step 6 of Example 1 from 2-[4-(5-chloro-2-ethyl-1H-benzimidazol-1-yl)phenyl]ethyl propionate (step 3).

$^1$H-NMR (CDCl$_3$) δ 7.75 (1H, d, J=2.0 Hz), 7.46 (2H, d, J=8.4 Hz), 7.29 (2H, d, J=8.4 Hz), 7.15 (1H, dd, J=2.0, 8.6 Hz), 7.00 (1H, d, J=8.6 Hz), 3.99 (2H, t, J=6.5 Hz), 3.00 (2H, t, J=6.5 Hz), 2.78 (2H, q, J=7.5 Hz), 1.26 (3H, t, J=7.5 Hz).

STEP 5. 2-[4-(5-Chloro-2-ethyl-1H-benzimidazol-1-yl)phenyl]ethyl azide

The title compound was prepared according to the procedure described in step 5 Example 26 from 2-[4-(5-chloro-2-ethyl-1H-benzimidazol-1-yl)phenyl]ethanol (step 4).

MS (EI) m/z 325 (M$^+$); $^1$H-NMR (CDCl$_3$) δ 7.75 (1H, d, J=2.0 Hz), 7.45 (2H, d, J=8.3 Hz), 7.29 (2H, d, J=8.3 Hz), 7.15 (1H, dd, J=2.0, 8.6 Hz), 6.99 (1H, d, J=8.6 Hz), 3.62 (2H, t, J=7.0 Hz), 3.02 (2H, t, J=7.0 Hz), 2.78 (2H, q, J=7.5 Hz), 1.26 (3H, t, J=7.5 Hz).

STEP 6. 2-[4-(5-Chloro-2-ethyl-1H-benzimidazol-1-yl)phenyl]ethylamine

The title compound was prepared according to the procedure described in step 7 of Example 37 from 2-[4-(5-chloro-2-ethyl-1H-benzimidazol-1-yl)phenyl]ethyl azide (step 5).

$^1$H-NMR (CDCl$_3$) δ 7.75 (1H, d, J=2.0 Hz), 7.41 (2H, d, J=8.3 Hz), 7.27 (2H, d, J=8.3 Hz), 7.14 (1H, dd, J=2.0, 8.6 Hz), 6.99 (1H, d, J=8.6 Hz), 3.08 (2H, t, J=7.0 Hz), 2.86 (2H, t, J=7.0 Hz), 2.77 (2H, q, J=7.5 Hz), 1.34 (3H, t, J=7.5 Hz).

STEP 7. 5-Chloro-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(5-chloro-2-ethyl-1H-benzimidazol-1-yl)phenyl]ethylamine (step 6).

$^1$H-NMR (CDCl$_3$) δ 7.76 (1H, d, J=1.8 Hz), 7.72 (2H, d, J=8.4 Hz), 7.39 (2H, d, J=8.3 Hz), 7.30 (2H, d, J=8.4 Hz), 7.28 (2H, d, J=8.3 Hz), 7.17 (1H, dd, J=8.6, 1.8 Hz), 7.00 (1H, d, J=8.6 Hz), 6.73 (1H, br.s), 3.59–3.53 (2H, m), 2.94 (2H, t, J=7.0 Hz), 2.81 (2H, q, J=7.5 Hz), 1.34 (3H, t, J=7.5 Hz).

EXAMPLE 58

2-[4-(5-CHLORO-2-ETHYL-1H-BENZIMIDAZOL-1-YL)PHENYL]ETHYL(4-METHYLPHENYL)SULFONYLCARBAMATE

The title compound was prepared according to the procedure described in Example 3 from 2-[4-(5-chloro-2-ethyl-1H-benzimidazol-1-yl)phenyl]ethanol (step 4 of Example 57).

$^1$H-NMR (CDCl$_3$) δ 7.92 (2H, d, J=8.4 Hz), 7.74 (1H, d, J=2.0 Hz), 7.34 (2H, d, J=8.4 Hz), 7.33 (2H, d, J=8.4 Hz), 7.23 (2H, d, J=8.4 Hz), 7.16 (1H, dd, J=8.5, 2.0 Hz), 6.99 (1H, d, J=8.5 Hz), 4.74 (1H, br.s), 4.37 (2H, t, J=6.8 Hz), 3.01 (2H, t, J=6.8 Hz), 2.75 (2H, q, J=7.6 Hz), 1.33 (3H, t, J=7.6 Hz).

EXAMPLE 59

6-CHLORO-2-ETHYL-1-(4-{2-[({[(4-METHYLPHENYL)SULFONYL]AMINO}CARBONYL)AMINO]ETHYL}PHENYL)-1H-BENZIMIDAZOLE

STEP 1. 2-[(5-Chloro-2-nitroanilino)phenyl]ethanol

The title compound was prepared according to the procedure described in step 3 of Example 1 from 2,4-dichloronitrobenzene and 4-aminophenylethyl alcohol.

$^1$H-NMR (CDCl$_3$) δ 9.52 (1H, br.s), 8.16 (1H, d, J=9.2H), 7.33 (2H, d, J=8.2 Hz), 7.25 (2H, d, J=8.2 Hz), 7.13 (1H, d, J=2.2 Hz), 6.71 (1H, dd, J=9.2, 2.2 Hz), 3.92 (q, 2H, J=6.4 Hz), 2.92 (t, 2H, J=6.4 Hz).

STEP 2. 2-[(2-Amino-5-chloroanilino)phenyl]ethanol

The title compound was prepared according to the procedure described in step 2 of Example 28 from 2-[(5-chloro-2-nitroanilino)phenyl]ethanol (step 1).

$^1$H-NMR (CDCl$_3$) δ 7.12–7.09 (3H, m), 6.92 (1H, dd, J=8.4, 2.4 Hz), 6.78–6.70 (3H, m), 5.16 (1H, br.s), 3.83 (2H, t, J=6.6 Hz), 2.81 (2H, t, J=6.6 Hz).

STEP 3. 2-[4-(6-Chloro-2-ethyl-1H-benzimidazol-1-yl)phenyl]ethyl propionate

The title compound was prepared according to the procedure described in step 5 of Example 1 from 2-[(2-amino-5-chloroanilino)phenyl]ethanol (step 2) and propionyl chloride.

$^1$H-NMR (CDCl$_3$) δ 7.67 (1H, d, J=8.6 Hz), 7.44 (2H, d, J=8.4 Hz), 7.28 (2H, d, J=8.4 Hz), 7.22 (1H, dd, J=8.4, 2.0 Hz), 7.07 (1H, d, J=2.0 Hz), 4.38 (2H, t, J=7.0 Hz), 3.07 (2H, t, J=7.0 Hz), 2.77 (2H, q, J=7.5 Hz), 2.36 (2H, q, J=7.5 Hz), 1.35 (3H, t, J=7.5 Hz), 1.15 (3H, t, J=7.5 Hz).

STEP 4. 2-[4-(6-Chloro-2-ethyl-1H-benzimidazol-1-yl)phenyl]ethanol

The title compound was prepared according to the procedure described in step 6 of Example 1 from 2-[4-(6-chloro-2-ethyl-1H-benzimidazol-1-yl)phenyl]ethyl propionate (step 3).

$^1$H-NMR (CDCl$_3$) δ 7.67 (1H, d, J=8.6 Hz), 7.46 (2H, d, J=8.6 Hz), 7.30–7.26 (3H, m), 7.22 (1H, dd, J=8.6, 2.2 Hz), 7.08 (1H, d, J=2.0 Hz), 3.99 (2H, q, J=6.4 Hz), 3.01 (2H, t, J=6.4 Hz), 2.78 (2H, q, J=7.6 Hz), 1.72 (1H, t, J=5.6 Hz), 1.35 (3H, t, J=7.6 Hz).

STEP 5. 2-[4-(6-Chloro-2-ethyl-1H-benzimidazol-1-yl)phenyl]ethyl azide

The title compound was prepared according to the procedure described in step 5 of Example 26 from 2-[4-(6-chloro-2-ethyl-1H-benzimidazol-1-yl)phenyl]ethanol (step 4).

MS (EI) m/z 325 (M$^+$).

STEP 6. 2-[4-(6-Chloro-2-ethyl-1H-benzimidazol-1-yl)phenyl]ethylamine

The title compound was prepared according to the procedure described in step 9 of Example 1 from 2-[4-(6-chloro-2-ethyl-1H-benzimidazol-1-yl)phenyl]ethyl azide (step 5).

$^1$H-NMR (CDCl$_3$) δ 7.67 (1H, d, J=8.6 Hz), 7.41 (2H, d, J=8.4 Hz), 7.31–7.19 (3H, m), 7.13 (1H, d, J=2.0 Hz), 4.66 (2H, br.s), 3.23–3.17 (2H, m), 3.08–3.04 (2H, m), 2.75 (2H, q, J=7.5 Hz), 1.33 (3H, t, J=7.5 Hz).

STEP 7. 6-Chloro-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(6-chloro-2-ethyl-1H-benzimidazol-1-yl)phenyl]ethylamine (step 6).

$^1$H-NMR (CDCl$_3$) δ 7.74 (2H, d, J=8.4 Hz), 7.67 (1H, d, J=8.4 Hz), 7.37 (2H, d, J=8.4 Hz), 7.30–7.20 (6H, m), 7.05 (1H, d, J=2.0 Hz), 6.73 (1H, m), 3.62–3.55 (2H, m) 2.93 (2H, t, J=7.2 Hz), 2.77 (2H, t, J=7.5 Hz), 1.32 (3H, t, J=7.5 Hz).

EXAMPLE 60

6-CHLORO-2-ETHYL-1-(4-{2-[({[(4-METH-YLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 6-chloro-2-ethyl-1-(4-{2-[({[(4-methylphenyl)sulfonyl]amino}carbonyl)amino]ethyl}phenyl)-1H-benzimidazole (Example 59).

$^1$H-NMR (DMSO-d$_6$) δ 7.64 (1H, d, J=8.6 Hz), 7.59 (2H, d, J=8.1 Hz), 7.38 (4H, m), 7.22 (1H, dd, J=8.6, 2.0 Hz), 7.11 (2H, d, J=8.1 Hz), 7.05 (1H, d, J=2.0 Hz), 3.15 (2H, m), 2.74–2.66 (4H, m), 2.25 (3H, s), 1.21 (3H, t, J=7.4 Hz); IR (KBr) ν$_{max}$ 1601, 1516, 1398, 1178, 1130, 1084 cm$^{-1}$.

EXAMPLE 61

4-(6-CHLORO-2-ETHYL-1H-BENZIMIDAZOL-1-YL)PHENETHYL-(4-METHYLPHENYL)SULFONYLCARBAMATE

The title compound was prepared according to the procedure described in Example 3 from 2-[4-(6-chloro-2-ethyl-1H-benzimidazol-1-yl)phenyl]ethanol (step 4 of Example 59).

mp 183–187° C.; $^1$H-NMR (DMSO-d$_6$) δ 7.75 (2H, d, J=8.1 Hz), 7.66 (1H, d, J=8.6 Hz), 7.43 (4H, s), 7.40 (2H, d, J=8.1 Hz), 7.24 (1H, dd, J=8.6, 2.0 Hz), 7.03 (1H, d, J=2.0 Hz), 4.27 (2H, t, J=6.6 Hz), 2.95 (2H, t, J=6.6 Hz), 2.70 (2H, q, J=7.5 Hz), 2.34 (3H, s), 1.22 (3H, t, J=7.5 Hz); IR (KBr) ν$_{max}$ 1744, 1516, 1352, 1225, 1165 cm$^{-1}$.

EXAMPLE 62

2-BUTYL-6-CHLORO-1-(4-{2-[({4-METH-YLPHENYL)SULFONYL]AMINO}CARBONYL)AMINO]BUTYL}PHENYL)-1H-BENZIMIDAZOLE

STEP 1. 2-[4-(2-Butyl-6-chloro-1H-benzimidazol-1-yl)phenyl]ethyl pentanoate

The title compound was prepared according to the procedure described in step 5 of Example 1 from 2-[(2-amino-5-chloroanilino)phenyl]ethanol (step 2 of Example 59) and pentanoyl chloride.

$^1$H-NMR (CDCl$_3$) δ 7.66 (1H, d, J=8.4 Hz), 7.44 (2H, d, J=8.1 Hz), 7.28 (2H, d, J=8.1 Hz), 7.22 (1H, dd, J=8.4, 2.0 Hz), 7.06 (1H, d, J=2.0 Hz), 4.38 (2H, t, J=6.8 Hz), 3.07 (2H, t, J=6.8 Hz), 2.74 (2H, t, J=7.7 Hz), 2.33 (2H, t, J=7.5 Hz), 1.81–1.70 (2H, m), 1.66–1.56 (2H, t, J=6.8 Hz), (4H, m), 0.94–0.84 (6H, m).

STEP 2. 2-[4-(2-Butyl-6-chloro-1H-benzimidazol-1-yl)phenyl]ethanol

The title compound was prepared according to the procedure described in step 6 of Example 1 from 2-[4-(2-butyl-6-chloro-1H-benzimidazol-1-yl)phenyl]ethyl pentanoate (step 1).

$^1$H-NMR (CDCl$_3$) δ 7.66 (1H, d, J=8.6 Hz), 7.46 (2H, d, J=8.1 Hz), 7.29–7.26 (2H, m), 7.22 (1H, dd, J=8.6, 2.0 Hz), 7.07 (11H, d, J=2.0 Hz), 4.00 (2H, q, J=6.4 Hz), 3.01 (2H, t, J=6.4 Hz), 2.75 (2H, t, J=7.5 Hz), 2.24–2.19 (1H, m), 1.81–1.71 (2H, m), 1.37–1.26 (2H, m), 0.87 (3H, t, J=7.3 Hz)

STEP 3. 2-[4-(2-Butyl-6-chloro-1H-benzimidazol-1-yl)phenyl]ethyl azide

The title compound was prepared according to the procedure described in step 4 of Example from 2-[4-(2-butyl-6-chloro-1H-benzimidazol-1-yl)phenyl]ethanol (step 2).

$^1$H-NMR (CDCl$_3$) δ 7.66 (1H, d, J=8.6 Hz), 7.45 (2H, d, J=8.3 Hz), 7.29 (2H, d, J=8.3 Hz), 7.22 (1H, dd, J=8.6, 2.0 Hz), 7.07 (1H, d, J=2.0 Hz), 3.62 (2H, t, J=7.0 Hz), 3.02 (2H, t, J=7.0 Hz), 2.74 (2H, t, J=7.5 Hz), 1.80–1.70 (2H, m), 1.40–1.26 (2H, m), 0.86 (2H, t, J=7.3 Hz)

STEP 3. 2-[4-(2-Butyl-6-chloro-1H-benzimidazol-1-yl)phenyl]ethylamine

The title compound was prepared according to the procedure described in step 9 of Example 1 from 2-[4-(2-butyl-6-chloro-1H-benzimidazol-1-yl)phenyl]ethyl azide (step 2).

$^1$H-NMR (CDCl$_3$) δ 7.66 (1H, d, J=8.6 Hz), 7.43 (2H, d, J=8.2 Hz), 7.27 (2H, d, J=8.2 Hz), 7.21 (1H, dd, J=8.6, 2.0 Hz), 7.08 (1H, d, J=2.0 Hz), 3.11 (2H, t, J=7.1 Hz), 2.91 (2H, t, J=7.1 Hz), 2.74 (2H, t, J=7.4 Hz), 1.81–1.70 (2H, m), 1.41–1.27 (2H, m), 0.86 (3H, t, J=7.4 Hz)

STEP 4. 2-Butyl-6-chloro-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-butyl-6-chloro-1H-benzimidazol-1-yl)phenyl]ethylamine (step 3).

$^1$H-NMR (CDCl$_3$) δ 7.75 (2H, d, J=8.4 Hz), 7.66 (1H, d, J=8.2 Hz), 7.38 (2H, d, J=8.4 Hz), 7.30–7.20 (6H, m), 7.05 (1H, d, J=2.0 Hz), 6.77–6.72 (1H, m), 3.61–3.55 (2H, m), 2.96–2.92 (2H, m), 2.74 (2H, t, J=7.5 Hz), 2.39 (3H, s), 1.78–1.67 (2H, m), 1.35–1.26 (2H, m), 0.83 (3H, t, J=7.3 Hz).

EXAMPLE 63

2-BUTYL-6-CHLORO-1-(4-{2-[({[(4-METH-YLPHENYL)SULFONYL]AMINO}CARBONYL)AMINO]BUTYL}PHENYL)-1H-BENZIMIDAZOLE, SODIUM SALT

The title compound was prepared according to the procedure described in Example 2 from 2-butyl-6-chloro-1-(4-{2-[({[(4-methylphenyl)sulfonyl]amino}carbonyl)amino]ethyl}phenyl)-1H-benzimidazole (Example 62).

mp 137–145° C.; $^1$H-NMR (DMSO-d$_6$) δ 7.65–7.63 (1H, m), 7.59 (2H, d, J=7.8 Hz), 7.38 (4H, s), 7.23–7.20 (1H, m), 7.12 (2H, d, J=7.8 Hz), 7.04 (1H, s), 3.15 (2H, m), 2.72–2.67 (4H, m), 2.26 (3H, s), 1.66–1.61 (2H, m), 1.29–1.22 (2H, m), 0.79 (3H, t, J=7.5 Hz); IR (KBr) ν$_{max}$ 1603, 1520, 1458, 1396, 1130, 1086 cm$^{-1}$.

EXAMPLE 64

7-CHLORO-2-ETHYL-3-(4-{2-[({[(4-METH-YLPHENYL)SULFONYL]AMINO}CARBONYL)AMINO]ETHYL}PHENYL)-1H-BENZIMIDAZOLE

STEP 1. 2-[4-(2-Chloro-6-nitroanilino)phenyl]ethanol

The title compound was prepared according to the procedure described in step 3 of Example 1 from 2,3-dichloronitrobenzene and 4-aminophenylethyl alcohol.

$^1$H-NMR (CDCl$_3$) δ 8.11 (1H, br.s), 8.00 (1H, dd, J=1.5 Hz, 8.5 Hz), 7.61 (1H, dd, J=1.5 Hz, 7.9 Hz), 7.12 (2H, d,

J=8.4 Hz), 7.03 (1H, dd, J=7.9 Hz, 8.5 Hz), 6.80 (2H, d, J=8.4 Hz), 3.82 (2H, t, J=6.6 Hz), 2.81 (2H, d, J=6.6 Hz).

STEP 2. 2-[4-(2-Amino-6-chloroanilino)phenyl]ethanol

The title compound was prepared according to the procedure described in step 2 of Example 28 from 2-[4-(2-chloro-6-nitroanilino)phenyl]ethanol (step 1).

$^1$H-NMR (CDCl$_3$) δ 7.04 (2H, d, J=7.8 Hz), 6.97 (1H, dd, J=7.9 Hz, 8.0 Hz), 6.82 (1H, dd, J=1.5 Hz, 7.9 Hz), 6.66 (1H, dd, J=1.5 Hz, 8.0 Hz), 6.59 (2H, d, J=7.8 Hz), 5.36 (1H, br.s), 3.94 (2H, br.s), 3.78 (2H, t, J=6.6 Hz), 2.75 (2H, d, J=6.6 Hz).

STEP 3. 2-[4-(7-Chloro-2-ethyl-1H-benzimidazol-1-yl)phenyl]ethyl propionate

The title compound was prepared according to the procedure described in step 5 of Example 1 from 2-[4-(2-amino-6-chloroanilino)phenyl]ethanol (step 2) and propionyl chloride.

TLC Rf=0.6 (hexane: ethyl acetate=1:1).

STEP 4. 2-[4-(7-Chloro-2-ethyl-1H-benzimidazol-1-yl)phenyl]ethanol

The title compound was prepared according to the procedure described in step 6 of Example 1 from 2-[4-(2-amino-6-chloroanilino)phenyl]ethyl propionate (step 3).

$^1$H-NMR (CDCl$_3$) δ 7.68 (1H, dd, J=1.9 Hz, 7.0 Hz), 7.39 (2H, d, J=8.2 Hz), 7.28 (2H, d, J=8.2 Hz), 7.11–7.20 (2H, m), 3.97 (2H, t, J=6.6 Hz), 3.01 (2H, t, J=6.6 Hz), 2.65 (2H, q, J=7.6 Hz), 1.32 (3H, t, J=7.6 Hz).

STEP 5. 7-Chloro-1-[4-(2-chloroethyl)phenyl]-2-ethyl-1H-benzimidazole

The title compound was prepared according to the procedure described in step 7 of Example 1 from 2-[4-(7-chloro-2-ethyl-1H-benzimidazol-1-yl)phenyl]ethanol (step 4).

$^1$H-NMR (CDCl$_3$) δ 7.69 (1H, dd, J=2.2 Hz, 7.1 Hz), 7.37 (2H, d, J=8.2 Hz), 7.31 (2H, d, J=8.2 Hz), 7.11–7.17 (2H, m), 3.81 (2H, t, J=7.3 Hz), 3.19 (2H, t, J=7.3 Hz), 2.65 (2.65 (2H, q, J=7.5 Hz), 1.33 (3H, t, J=7.5 Hz).

STEP 6. 2-[4-(7-Chloro-2-ethyl-1H-benzimidazol-1-yl)phenyl]ethyl azide

The title compound was prepared according to the procedure described in step 8 of Example 1 from 7-chloro-1-[4-(2-chloroethyl)phenyl]-2-ethyl-1H-benzimidazole (step 5).

$^1$H-NMR (CDCl$_3$) δ 7.69 (1H, dd, J=1.8 Hz, 7.4 Hz), 7.38 (2H, d, J=8.2 Hz), 7.34 (2H, d, J=8.2 Hz), 7.11–7.28 (2H, m), 3.60 (2H, t, J=7.0 Hz), 3.02 (2H, t, J=7.0 Hz), 2.64 (2H, q, J=7.6 Hz), 1.32 (3H, t, J=7.6 Hz).

STEP 7. 2-[4-(7-Chloro-2-ethyl-1H-benzimidazol-1-yl)phenyl]ethylamine

The title compound was prepared according to the procedure described in step 7 of Example 37 from 2-[4-(7-chloro-2-ethyl-1H-benzimidazol-1-yl)phenyl]ethyl azide (step 6).

$^1$H-NMR (CDCl$_3$) δ 7.69 (1H, d, J=7.9 Hz), 7.35 (2H, d, J=8.3 Hz), 7.28 (2H, d, J=8.3 Hz), 7.11–7.19 (2H, m), 3.06 (2H, t, J=6.8 Hz), 2.88 (2H, t, J=6.8 Hz), 2.65 (2H, q, J=7.6 Hz), 1.33 (3H, t, J=7.5 Hz).

STEP 8. 7-Chloro-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(7-chloro-2-ethyl-1H-benzimidazol-1-yl)phenyl]ethylamine (step 7).

MS (ESI) m/z 498 (M+H)$^+$; $^1$H-NMR (CDCl$_3$) δ 7.74 (2H, d, J=8.4 Hz), 7.69 (1H, dd, J=1.9 Hz, 7.4 Hz), 7.29–7.32 (6H, m), 7.11–7.20 (2H, m), 6.72 (1H, br.s), 3.59 (2H, t, J=6.9 Hz), 2.93 (2H, t, J=6.9 Hz), 2.64 (2H, q, J=7.6 Hz), 2.42 (3H, s), 1.31 (3H, t, J=7.6 Hz).

EXAMPLE 65

7-CHLORO-2-ETHYL-3-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 7-chloro-2-ethyl-1-(4-{2-[({[(4-methylphenyl)sulfonyl]amino}carbonyl)amino]ethyl}phenyl)-1H-benzimidazole (Example 64).

$^1$H-NMR (DMSO-d$_6$) δ 7.62–7.64 (3H, m), 7.31–7.39 (4H, m), 7.14–7.20 (4H, m), 6.00 (1H, br.s), 3.17 (2H, br.s), 2.75 (2H, br.s), 2.55 (2H, q, J=7.8 Hz), 2.29 (3H, s), 1.21 (3H, t, J=7.8 Hz); IR (KBr) ν$_{max}$ 3380, 2891, 1605, 1520, 1425, 1285, 1126, 1075, 798 cm$^{-1}$.

EXAMPLE 66

5-FLUORO-2-ETHYL-3-(4-{2-[({[(4-METHYLPHENYL)SULFONYL]AMINO}CARBONYL)AMINO]ETHYL}PHENYL)-1H-BENZIMIDAZOLE

STEP 1. 2-[4-(4-Fluoro-2-nitroanilino)phenyl]ethanol

The title compound was prepared according to the procedure described in step 3 of Example 1 from 2,5-difluoronitrobenzene and 4-aminophenylethyl alcohol.

$^1$H-NMR (CDCl$_3$) δ 9.32 (1H, s), 7.88–7.93 (1H, m), 7.11–7.30 (5H, m), 3.90 (2H, t. J=6.2 Hz), 2.90 (2H, t, J=6.2 Hz).

STEP 2. 2-[4-(2-Amino-4-fluoroanilino)phenyl]ethanol

The title compound was prepared according to the procedure described in step 2 of Example 26 from 2-[4-(4-fluoro-2-nitroanilino)phenyl]ethanol (step 1).

$^1$H-NMR (CDCl$_3$) δ 6.98–7.06 (3H, m), 6.60 (2H, d, J=8.2 Hz), 6.49 (1H, dd, J=2.8 Hz), 12.8 Hz), 6.41 (1H, dd, J=2.8 Hz, 8.4 Hz), 4.99 (1H, br.s), 3.94 (2H, br.s), 3.79 (2H, br.s), 2.76 (2H, t, J=6.4 Hz).

STEP 3. 2-[4-(2-Ethyl-5-fluoro-1H-benzimidazol-1-yl)phenyl]ethyl propionate

The title compound was prepared according to the procedure described in step 5 of Example 1 from 2-[4-(2-amino-4-fluoroanilino)phenyl]ethanol (step 2) and propionyl chloride.

MS (EI) m/z 340 (M$^+$).

STEP 4. 2-[4-(2-Ethyl-5-fluoro-1H-benzimidazol-1-yl)phenyl]ethanol

The title compound was prepared according to the procedure described in step 6 of Example 1 from 2-[4-(2-amino-4-fluoroanilino)phenyl]ethyl propionate (step 3).

$^1$H-NMR (CDCl$_3$) δ 7.40–7.47 (3H, m), 7.28 (2H, d, J=8.0 Hz), 6.88–7.02 (2H, m), 3.98 (2H, t, J=6.3 Hz), 3.01 (2H, t, J=6.3 Hz), 2.78 (2H, q, J=7.5 Hz), 1.34 (3H, t, J=7.5 Hz).

STEP 5. 1-[4-(2-Chloroethyl)phenyl]-2-ethyl-5-fluoro-1H-benzimidazole

The title compound was prepared according to the procedure described in step 7 of Example 1 from 2-[4-(2-ethyl-5-fluoro-1H-benzimidazol-1-yl)phenyl]ethanol (step 4).

$^1$H-NMR (CDCl$_3$) δ 7.42–7.46 (3H, m), 7.31 (2H, d, J=8.1 Hz), 6.89–7.02 (2H, m), 3.81 (2H, t, J=7.1 Hz), 3.19 (2H, t, J=7.1 Hz), 2.78 (2H, q, J=7.6 Hz), 1.35 (3H, t, J=7.6 Hz).

STEP 6. 2-[4-(2-Ethyl-5-fluoro-1H-benzimidazol-1-yl)phenyl]ethyl azide

The title compound was prepared according to the procedure described in step 8 of Example 1 from 1-[4-(2-chloroethyl)phenyl]-2-ethyl-5-fluoro-1H-benzimidazole (step 5).

$^1$H-NMR (CDCl$_3$) δ 7.43–7.45 (3H, m), 7.31 (2H, d, J=8.2 Hz), 6.89–7.02 (2H, m), 3.62 (2H, t, J=7.0 Hz), 3.01 (2H, t, J=7.0 Hz), 2.77 (2H, q, J=7.5 Hz), 1.34 (3H, t, J=7.5 Hz).

STEP 7. 2-[4-(2-Ethyl-5-fluoro-1H-benzimidazol-1-yl)phenyl]ethylamine

The title compound was prepared according to the procedure described in step 9 of Example 1 from 2-[4-(2-ethyl-5-fluoro-1H-benzimidazol-1-yl)phenyl]ethyl azide (step 6).

$^1$H-NMR (CDCl$_3$) δ 7.40–7.46 (3H, m), 7.27–7.29 (2H, m), 6.87–6.99 (2H, m), 3.06 (2H, t, J=7.1 Hz), 2.87 (2H, t, J=7.1 Hz), 2.78 (2H, q, J=7.5 Hz), 1.35 (3H, t, J=7.5 Hz).

STEP 8. 5-Fluoro-2-ethyl-3-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-ethyl-5-fluoro-1H-benzimidazol-1-yl)phenyl]ethylamine (step 7).

MS (ESI) m/z 481 (M+H)$^+$; $^1$H-NMR (CDCl$_3$) δ 7.73 (2H, d, J=8.2 Hz), 7.35–7.45 (3H, m), 7.24–7.29 (4H, m), 6.87–7.00 (2H, m), 6.73 (1H, br.s), 3.57 (2H, t, J=7.0 Hz), 2.93 (2H, t, J=7.0 Hz), 2.77 (2H, q, J=7.6 Hz), 2.39 (3H, s), 1.31 (3H, t, J=7.6 Hz).

EXAMPLE 67

5-FLUORO-2-ETHYL-3-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 5-fluoro-2-ethyl-3-(4-{2-[({[(4-methylphenyl)sulfonyl]amino}carbonyl)amino]ethyl}phenyl)-1H-benzimidazole (Example 66).

mp 135–146° C.; MS (ESI) m/z 481 (M+H)$^+$: $^1$H-NMR (DMSO-d$_6$) δ 7.62 (2H, d, J=8.1 Hz), 7.39–7.48 (5H, m), 6.97–7.15 (4H, m), 5.92 (1H, br.s), 2.67–2.76 (4H, m), 2.51 (2H, br.s), 2.27 (3H, s), 1.23 (3H, t, J=7.6 Hz).

EXAMPLE 68

2-BUTYL-6-FLUORO-1-{2-[({[(4-METHYLPHENYL)SULFONYL]AMINO}CARBONYL)AMINO]ETHYL}-1H-BENZIMIDAZOLE

STEP 1. 2-[4-(5-Fluoro-2-nitroanilino)phenyl]ethanol

The title compound was prepared according to the procedure described in step 3 of Example 1 from 2,4-difluoronitrobenzene and 4-aminophenylethyl alcohol.

$^1$H-NMR (CDCl$_3$) δ 9.61 (1H, br.s), 8.26 (1H, dd, J=6.1, 9.5 Hz), 7.32 (2H, d, J=8.2 Hz), 7.22 (2H, d, J=8.3 Hz), 6.78 (1H, dd, J=2.6, 11.3 Hz), 6.47 (1H, ddd, J=2.2, 7.2, 9.7 Hz), 3.92 (2H, dt, J=6.2, 6.2 Hz), 2.91 (2H, t, J=6.4 Hz), 1.52 (1H, t, J=5.7 Hz).

STEP 2. 2-[4-(2-Amino-5-fluoroanilino)phenyl]ethanol

The title compound was prepared according to the procedure described in step 2 of Example 28 from 2-[4-(5-fluoro-2-nitroanilino)phenyl]ethanol (step 1).

$^1$H-NMR (CDCl$_3$) δ 7.12 (2H, d, J=8.4 Hz), 6.87 (1H, dd, J=2.7, 10.1 Hz), 6.83 (2H, d, J=8.4 Hz), 6.72 (1H, dd, J=5.7, 8.6 Hz), 6.63 (1H, ddd, J=2.7, 8.4, 8.4 Hz), 5.30 (1H, s), 3.83 (2H, t, J=6.4 Hz), 2.80 (2H, t, J=6.4 Hz).

STEP 3. 2-[4-(2-butyl-6-fluoro-1H-benzimidazol-1-yl)phenyl]ethyl pentanoate

The title compound was prepared according to the procedure described in step 5 of Example 1 from 2-[4-(2-amino-5-fluoroanilino)phenyl]ethanol (step 2) and pentanoyl chloride.

$^1$H-NMR (CDCl$_3$) δ 7.67 (1H, dd, J=4.8, 8.8 Hz), 7.44 (2H, d, J=8.3 Hz), 7.28 (2H, d, J=8.1 Hz), 7.04–6.95 (1H, m), 6.76 (1H, dd, J=2.6, 8.8 Hz), 4.38 (2H, t, J=6.8 Hz), 3.07 (2H, J=6.8 Hz), 2.74 (2H, t, J=7.5 Hz), 2.33 (2H, t, J=7.7 Hz), 1.81–1.55 (4H, m), 1.42–1.25 (4H, 6.91 (3H, t, J=7.3 Hz), 0.87 (3H, t, J=7.3 Hz).

STEP 4. 2-[4-(2-Butyl-6-fluoro-1H-benzimidazol-1-yl)phenyl]ethanol

The title compound was prepared according to the procedure described in step 6 of Example 1 from 2-[4-(2-butyl-6-fluoro-1H-benzimidazol-1-yl)phenyl]ethyl pentanoate (step 3).

$^1$H-NMR (CDCl$_3$) δ 7.67 (1H, dd, J=4.8, 8.8 Hz), 7.46 (2H, d, J=8.2 Hz), 7.28 (2H, d, J=8.3 Hz), 6.99 (1H, ddd, J=2.4, 9.0, 9.5 Hz), 4.10–3.85 (2H, m), 3.01 (2H, t, J=6.4 Hz), 2.74 (2H, t, J=7.7 Hz), 1.84–1.69 (2H, m), 1.41–1.27 (2H, m), 0.87 (3H, t, J=7.3 Hz).

STEP 5. 2-[4-(2-Butyl-6-fluoro-1H-benzimidazol-1-yl)phenyl]ethyl azide

The title compound was prepared according to the procedure described in step 5 Example 26 from 2-[4-(2-butyl-6-fluoro-1H-benzimidazol-1-yl)phenyl]ethanol (step 4).

MS (EI) m/z 337 (M$^+$); $^1$H-NMR (CDCl$_3$) δ 7.68 (1H, dd, J=4.8, 8.8 Hz), 7.45 (2H, d, J=8.1 Hz), 7.30 (2H, d, J=8.1 Hz), 7.04–6.94 (1H, m), 6.77 (1H, dd, J=2.4, 8.6 Hz), 3.62 (2H, t, J=7.0 Hz), 3.02 (2H, t, J=6.8 Hz), 2.74 (2H, t, J=7.7 Hz), 1.86–1.69 (2H, m), 1.41–1.2 (2H, m), 0.86 (3H, t, J=7.3 Hz).

STEP 6. 2-[4-(2-Butyl-6-fluoro-1H-benzimidazol-1-yl)phenyl]ethylamine

The title compound was prepared according to the procedure described in step 7 of Example 37 from 2-[4-(2-butyl-6-fluoro-1H-benzimidazol-1-yl)phenyl]ethyl azide (step 5).

$^1$H-NMR (CDCl$_3$) δ 7.67 (1H, dd, J=4.8, 8.8 Hz), 7.42 (2H, d, J=8.1 Hz), 7.27 (2H, d, J=8.2 ), 7.05–6.95 (1H, m), 6.78 (1H, dd, J=2.6, 8.6 Hz), 3.08 (2H, t, J=7.1 Hz), 2.88 (2H, J=6.8 Hz), 2.75 (2H, t, J=7.5 Hz), 1.82–1.69 (2H, m), 1.41–1.24 (2H, m), 0.87 (3H, t, J=7.3 Hz).

STEP 7. 2-Butyl-6-fluoro-3-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-butyl-6-fluoro-1H-benzimidazol-1-yl)phenyl]ethylamine (step 6).

$^1$H-NMR (CDCl$_3$) δ 7.73 (2H, d, J=8.4 Hz), 7.68 (1H, dd, J=4.6, 8.8 Hz), 7.38 (2H, d, J=8.4 Hz), 7.32–7.24 (4H, m), 7.00 (1H, ddd, J=2.4, 8.8, 11.2 Hz), 6.75 (1H, dd, J=2.4, 8.6 Hz), 3.64–3.54 (2H, m), 2.94 (2H, t, J=7.0 Hz), 2.74 (2H, d, J=7.5 Hz), 1.80–1.65 (2H, m), 1.40–1.20 (2H, m), 0.84 (3H, t, J=7.3 Hz).

EXAMPLE 69

2-BUTYL-6-FLUORO-1-{2-[({[(4-METHYLPHENYL)SULFONYL]AMINO}CARBONYL)AMINO]ETHYL}-1H-BENZIMIDAZOLE, SODIUM SALT

The title compound was prepared according to the procedure described in Example 2 from 2-butyl-6-fluoro-3-(4-{2-[({[(4-methylphenyl)sulfonyl]amino}carbonyl)amino]ethyl}phenyl)benzimidazole (Example 69).

$^1$H-NMR (DMSO-d$_6$) δ 7.70–7.57 (3H, m), 7.39 (4H, br), 7.14 (2H, d, J=8.0 Hz), 7.11–7.02 (1H, m), 8.85 (1H, dd, J=2.4, 9.2 Hz), 3.48–3.34 (2H, m), 3.17 (2H, br), 2.80–2.65 (4H, 2.28 (3H, s), 1.72–1.55 (2H, m), 1.35–1.20 (2H, m), 0.80 (3H, t, J=7.1 Hz); IR (KBr) ν$_{max}$ 3387, 2872, 1601, 1516, 1479, 1400, 1130, 1086 cm$^{-1}$.

EXAMPLE 70

2-ETHYL-6-FLUORO-1-(4-{2-[({[(4-METHYLPHENYL)SULFONYL]AMINO}CARBONYL)AMINO]ETHYL}PHENYL)-1H-BENZIMIDAZOLE

STEP 1. 2-[4-(6-Fluoro-2-ethyl-1H-benzimidazol-1-yl)phenyl]ethyl propionate

The title compound was prepared according to the procedure described in step 5 of Example 1 from 2-[4-(2-amino-5-fluoroanilino)phenyl]ethanol (step 2 of Example 68) and propionyl chloride.

MS (EI) m/z 340 (M$^+$); $^1$H-NMR (CDCl$_3$) δ 7.67 (1H, dd, J=4.8, 8.8 Hz), 7.43 (2H, d, J=8.4 Hz), 7.28 (2H, d, J=8.4 Hz), 6.99 (1H, ddd, J=2.5, 8.8, 9.5 Hz), 6.77 (1H, dd, J=2.5, 8.8 Hz), 4.38 (2H, t, J=6.6 Hz), 3.07 (2H, t, J=6.6 Hz), 2.79 (2H, q, J=7.4 Hz), 2.35 (2H, q, J=7.4 Hz), 1.35 (3H, t, J=7.4 Hz), 1.14 (3H, t, J=7.4 Hz).

STEP 2. 2-[4-(6-Fluoro-2-ethyl-1H-benzimidazol-1-yl)phenyl]ethanol

The title compound was prepared according to the procedure described in step 6 of Example 1 from 2-[4-(6-fluoro-2-ethyl-1H-benzimidazol-1-yl)phenyl]ethyl propionate (step 1).

$^1$H-NMR (CDCl$_3$) δ 7.67 (1H, dd, J=4.8, 8.8 Hz), 7.45 (2H, d, J=8.4 Hz), 7.29 (2H, d, J=8.4 Hz), 6.99 (1H, ddd, J=2.5, 8.8, 9.5 Hz), 6.78 (1H, dd, J=2.5, 8.8 Hz), 3.99 (2H, t, J=6.6 Hz), 3.00 (2H, t, J=6.6 Hz), 2.77 (2H, q, J=7.5 Hz), 1.35 (3H, t, J=7.5 Hz).

STEP 3. 6-Fluoro-1-[4-(2-chloroethyl)phenyl]-2-ethyl-1H-benzimidazole

The title compound was prepared according to the procedure described in step 7 Example 1 from 2-[4-(6-fluoro-2-ethyl-1H-benzimidazol-1-yl)phenyl]ethanol (step 2).

MS (EI) m/z 302 (M$^+$).

STEP 4. 2-[4-(6-Fluoro-2-ethyl-1H-benzimidazol-1-yl)phenyl]ethyl azide

The title compound was prepared according to the procedure described in step 8 Example 1 from 6-fluoro-1-[4-(2-chloroethyl)phenyl]-2-ethyl-1H-benzimidazole (step 3).

MS (EI) m/z 309 (M$^+$); $^1$H-NMR (CDCl$_3$) δ 7.68 (1H, dd, J=4.8, 8.8 Hz), 7.44 (2H, d, J=8.3 Hz), 7.31 (2H, d, J=8.3 Hz), 6.99 (1H, ddd, J=2.5, 8.8, 9.6 Hz), 6.77 (1H, dd, J=2.5, 8.8 Hz), 3.62 (2H, t, J=6.9 Hz), 3.02 (2H, t, J=6.9 Hz), 2.77 (2H, q, J=7.4 Hz), 1.34 (3H, t, J=7.4 Hz).

STEP 5. 2-[4-(6-Fluoro-2-ethyl-1H-benzimidazol-1-yl)phenyl]ethylamine

The title compound was prepared according to the procedure described in step 7 of Example 37 from 2-[4-(6-fluoro-2-ethyl-1H-benzimidazol-1-yl)phenyl]ethyl azide (step 4).

$^1$H-NMR (CDCl$_3$) δ 7.68 (1H, dd, J=4.8, 8.8 Hz), 7.43 (2H, d, J=8.2 Hz), 7.28 (2H, d, J=8.2 Hz), 6.98 (1H, ddd, J=2.4, 8.8, 8.8 Hz), 6.82 (1H, dd, J=2.4, 8.8 Hz), 3.37 (2H, br.s), 3.18 (2H, t, J=7.1 Hz), 3.01 (2H, t, J=7.1 Hz), 2.76 (2H, q, J=7.5 Hz), 1.33 (3H, t, J=7.5 Hz).

STEP 6. 2-Ethyl-6-fluoro-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(6-fluoro-2-ethyl-1H-benzimidazol-1-yl)phenyl]ethylamine (step 5).

$^1$H-NMR (CDCl$_3$) δ 7.73 (2H, d, J=8.4 Hz), 7.68 (1H, dd, J=8.7, 4.9 Hz), 7.37 (2H, d, J=8.4 Hz), 7.32–7.23 (4H, m), 7.00 (1H, ddd, J=9.5, 8.7, 2.5 Hz), 6.79–6.69 (2H, m), 3.63–3.53 (2H, m), 2.94 (2H, t, J=7.5 Hz), 2.76 (2H, q, J=7.5 Hz), 2.40 (3H, s), 1.32 (3H, t, J=7.5 Hz).

EXAMPLE 71

5-METHOXY-2-ETHYL-3-(4-[2-[({[(4-METHYLPHENYL)SULFONYL]AMINO}CARBONYL)AMINO]ETHYL]PHENYL)-1H-BENZIMIDAZOLE

STEP 1. 2-[4-(4-Methoxy-2-nitroanilino)phenyl]ethanol

The title compound was prepared according to the procedure described in step 3 of Example 1 from 2-chloro-5-methoxynitrobenzene and 4-aminophenylethyl alcohol.

$^1$H-NMR (CDCl$_3$) δ 9.33 (1H, br.s), 7.63 (1H, d, J=3.0 Hz), 7.17–7.27 (5H, m), 7.04–7.08 (1H, m), 3.88 (2H, br.s), 3.82 (3H, s), 2.88 (2H, t, J=6.6 Hz).

STEP 2. 2-[4-(2-Amino-4-methoxyanilino)phenyl]ethanol

The title compound was prepared according to the procedure described in step 2 of Example 26 from 2-[4-(4-methoxy-2-nitroanilino)phenyl]ethanol (step 1).

$^1$H-NMR (CDCl$_3$) δ 7.03 (2H, d, J=8.6 Hz), 6.98 (1H, d, J=8.4 Hz), 6.59 (2H, d, J=8.6 Hz), 6.28–6.36 (2H, m), 3.77–3.85 (5H, m), 2.76 (2H, t, J=6.6 Hz).

STEP 3. 2-[4-(2-Ethyl-5-methoxy-1H-benzimidazol-1-yl)phenyl]ethyl propionate

The title compound was prepared according to the procedure described in step 5 of Example 1 from 2-[4-(2-amino-4-methoxyanilino)phenyl]ethanol (step 2).

¹H-NMR (CDCl₃) δ 7.40 (2H, d, J=8.0 Hz), 7.12–7.29 (3H, m), 6.97 (1H, d, J=8.8 Hz), 6.82 (1H, dd, J=2.4 Hz, 8.8 Hz), 4.37 (2H, t, J=6.7 Hz), 3.86 (3H, s), 3.05 (2H, t, J=6.7 (2.77 (2H, q, J=7.5 Hz), 2.36 (2H, q, J=7.5 Hz), 1.36 (3H, t, J=7.5 Hz), 1.14 (3H, t, J=7.5 Hz).

STEP 4. 2-[4-(2-Ethyl-5-methoxy-1H-benzimidazol-1-yl)phenyl]ethanol

The title compound was prepared according to the procedure described in step 6 of Example 1 from 2-[4-(2-ethyl-5-methoxy-1H-benzimidazol-1-yl)phenyl]ethyl propionate (step 3).

¹H-NMR (CDCl₃) δ 7.43 (2H, d, J=8.2 Hz), 7.27–7.30 (3H, m), 6.98 (1H, d, J=8.8 Hz), 6.82 (1H, dd, J=2.3 Hz, 8.8 Hz), 3.98 (2H, t, J=6.5 Hz), 3.86 (3H, s), 2.99 (2H, t, J=6.5 Hz), 2.77 (2H, q, J=7.6 Hz), 1.33 (3H, t, J=7.6 Hz).

STEP 5. 1-[4-(2-Chloroethyl)phenyl]-2-ethyl-5-methoxy-1H-benzimidazole

The title compound was prepared according to the procedure described in step 7 of Example 1 from 2-[4-(2-ethyl-5-methoxy-1H-benzimidazol-1-yl)phenyl]ethanol (step 4).

¹H-NMR (CDCl₃) δ 7.42 (2H, d, J=8.2 Hz), 7.26–7.33 (3H, m), 6.99 (1H, d, J=8.8 Hz), 6.82 (1H, dd, J=2.5 Hz, 8.8 Hz), 3.86 (3H, s), 3.81 (2H, t, J=7.2 Hz), 3.18 (2H, t, J=7.2 Hz), 2.78 (2H, q, J=7.6 Hz), 1.34 (3H, t, J=7.6 Hz).

STEP 6. 1-[4-(2-Azidoethyl)phenyl]-2-ethyl-1H-benzimidazol-5-yl methyl ether

The title compound was prepared according to the procedure described in step 8 of Example 1 from 1-[4-(2-chloroethyl)phenyl]-2-ethyl-5-methoxy-1H-benzimidazole (step 5).

¹H-NMR (CDCl₃) δ 7.42 (2H, d, J=8.4 Hz), 7.27–7.32 (3H, m), 6.98 (1H, d, J=8.8 Hz), 6.82 (1H, dd, J=2.3 Hz, 8.8 Hz), 3.87 (3H, s), 3.61 (2H, t, J=6.9 Hz), 3.01 (2H, t, J=6.9 Hz), 2.76 (2H, q, J=7.7 Hz), 1.34 (3H, t, J=7.7 Hz).

STEP 7. 2-[4-(2-Ethyl-5-methoxy-1H-benzimidazol-1-yl)phenyl]ethylamine

The title compound was prepared according to the procedure described in step 9 of Example 1 from 1-[4-(2-azidoethyl)phenyl]-2-ethyl-1H-benzimidazol-5-yl methyl ether (step 6).

¹H-NMR (CDCl₃) δ 7.39 (2H, d, J=8.2 Hz), 7.26–7.30 (3H, m), 6.99 (1H, d, J=8.7 Hz), 6.82 (1H, dd, J=2.3 Hz, 8.7 Hz), 3.86 (3H, s), 3.07 (2H, t, J=6.9 Hz), 2.84 (2H, t, J=6.9 Hz), 2.77 (2H, q, J=7.6 Hz), 1.34 (3H, t, J=7.6 Hz).

STEP 8. 5-Methoxy-2-ethyl-3-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-ethyl-5-methoxy-1H-benzimidazol-1-yl)phenyl]ethylamine (step 7).

¹H-NMR (CDCl₃) δ 7.74 (2H, d, J=8.2 Hz), 7.23–7.34 (7H, m), 6.97 (1H, d, J=8.7 Hz), 6.82 (1H, dd, J=1.8 Hz, 8.7 Hz), 6.67 (1H, br.s), 3.86 (3H, s), 3.57 (2H, t, J=6.4 Hz), 2.92 (2H, t, 6.4 Hz), 2.75 (2H, q, J=7.6 Hz), 2.40 (3H, s), 1.31 (3H, t, J=7.6 Hz).

EXAMPLE 72

5-METHOXY-2-ETHYL-3-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 5-methoxy-2-ethyl-3-(4-{2-[({[(4-methylphenyl)sulfonyl]amino}carbonyl)amino]ethyl}phenyl)-1H-benzimidazole (Example 72).

mp 163–175° C.; ¹H-NMR (DMSO-d₆) δ 7.60 (2H, d, J=7.5 Hz), 7.34–7.41 (4H, m), 7.12–7.18 (3H, m), 6.97 (1H, d, J=8.7 Hz), 6.78 (1H, d, J=8.7 Hz), 3.78 (3H, s), 2.66–2.76 (4H, m), 2.50 (2H, br.s), 2.78 (3H, s), 1.22 (3H, t, J=7.6 Hz); IR (KBr) ν_max 3363, 2833, 1596, 1404, 1128, 1085, 1026, 950 cm⁻¹.

EXAMPLE 73

2-[4-(2-ETHYL-5-METHOXY-1H-BENZIMIDAZOLE-1-YL)PHENYL]ETHYL(4-METHYLPHENYL)SULFONYLCARBAMATE

The title compound was prepared according to the procedure described in Example 3 from 2-[4-(2-ethyl-5-methoxy-1H-benzimidazol-1-yl)phenyl]ethanol (step 4 of Example 71)

mp 95–98° C.; MS (ESI) m/z 494 (M+H)⁺; ¹H-NMR (CDCl₃) δ 7.93 (2H, d, J=8.2 Hz), 7.23–7.30 (3H, m), 7.16 (2H, d, J=8.2 Hz), 7.06 (2H, d, J=8.3 Hz), 6.92 (1H, d, J=8.8 Hz), 6.81 (1H, dd, J=2.2 Hz, 8.6 Hz), 4.33 (2H, t, J=6.3 Hz), 3.84 (3H, s), 2.93 (2H, t, J=6.3 Hz), 2.68 (2H, q, J=7.5 Hz), 2.37 (3H, s), 1.22 (3H, t, J=7.5 Hz); IR (KBr) ν_max 1743, 1596, 1517, 1487, 1444, 1278, 1159, 1074, 813 cm⁻¹.

EXAMPLE 74

2-ETHYL-6-METHOXY-1-(4-{2-[({[(4-METHYLPHENYL)SULFONYL]AMINO}CARBONYL)AMINO]ETHYL}PHENYL)-1H-BENZIMIDAZOLE

STEP 1. 2-[(5-Methoxy-2-nitroanilino)phenyl]ethanol

The title compound was prepared according to the procedure described in step 3 of Example 1 from 2-chloro-4-methoxynitrobenzene and 4-aminophenylethyl alcohol.

¹H-NMR (CDCl₃) δ 9.74 (1H, br.s), 8.18 (1H, d, J=9.5 Hz), 7.30 (2H, d, J=8.4 Hz), 7.24 (2H, d, J=8.4 Hz), 6.55 (1H, d, J=2.8 Hz), 6.34 (1H, dd, J=9.5, 2.8 Hz), 3.90 (2H, m), 3.74 (3H, s), 2.90 (3H, t, J=6.6 Hz).

STEP 2. 2-[(2-Amino-5-methoxyanilino)phenyl]ethanol

The title compound was prepared according to the procedure described in step 2 of Example 28 from 2-[(5-methoxy-2-nitroanilino)phenyl]ethanol (step 1).

¹H-NMR (CDCl₃) δ 7.09 (2H, d, J=8.4 Hz), 6.80 (2H, d, J=8.4 Hz), 6.76–6.73 (2H, 6.54 (1H, dd, J=8.6, 2.8 Hz), 3.81 (2H, t, J=6.6 Hz), 3.71 (3H, s), 2.79 (2H, t, J=6.6 Hz).

STEP 3. 2-[4-(2-Ethyl-6-methoxy-1H-benzimidazol-1-yl)phenyl]ethyl propionate

The title compound was prepared according to the procedure described in step 5 of Example 1 from 2-[(2-amino-5-methoxyanilino)phenyl]ethanol (step 2) and propionyl chloride.

MS (EI) m/z 352 (M⁺).

STEP 4. 2-[4-(2-Ethyl-6-methoxy-1H-benzimidazol-1-yl)phenyl]ethanol

The title compound was prepared according to the procedure described in step 6 of Example 1 from 2-[4-(2-ethyl-6-methoxy-1H-benzimidazol-1-yl)phenyl]ethyl propionate (step 3).

¹H-NMR (CDCl₃) δ 7.63 (1H, d, J=8.8 Hz), 7.45 (2H, d, J=8.3 Hz), 7.29 (2H, d, J=8.3 Hz), 6.89 (1H, dd, J=8.8, 2.6

Hz), 6.56 (1H, d, J=2.6 Hz), 4.00 (2H, t, J=6.6 Hz), 3.75 (3H, s), 3.01 (2H, t, J=6.6 Hz), 2.74 (2H, q, J=7.5 Hz), 1.32 (3H, t, J=7.5 Hz).

STEP 5. 2-[4-(2-Ethyl-6-methoxy-1H-benzimidazol-1-yl)phenyl]ethyl azide

The title compound was prepared according to the procedure described in step 4 of Example 26 from 2-(4-(2-ethyl-6-methoxy-1H-benzimidazol-1-yl)phenyl)ethanol (step 4).

TLC Rf=0.50 (hexane/ethyl acetate=1:1).

STEP 6. 2-[4-(2-Ethyl-6-methoxy-1H-benzimidazol-1-yl)phenyl]ethylamine

The title compound was prepared according to the procedure described in step 9 of Example 1 from 2-[4-(2-ethyl-6-methoxy-1H-benzimidazol-1-yl)phenyl]ethyl azide (step 5).

$^1$H-NMR (CDCl$_3$) δ 7.65 (1H, d, J=8.8 Hz), 7.41 (2H, d, J=8.3 Hz), 7.29 (2H, d, J=8.3 Hz), 6.89 (1H, dd, J=8.8, 2.4 Hz), 6.56 (1H, d, J=2.4 Hz), 3.76 (3H, s), 3.09 (2H, t, J=7.0 Hz), 2.89 (2H, t, J=7.0 Hz), 2.75 (2H, q, J=7.5 Hz), 1.32 (3H, t, J=7.5 Hz).

STEP 7. 2-Ethyl-6-methoxy-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-ethyl-6-methoxy-1H-benzimidazol-1-yl)phenyl]ethylamine (step 6).

$^1$H-NMR (CDCl$_3$) δ 7.75 (2H, d, J=8.2 Hz), 7.62 (1H, d, J=8.7 Hz), 7.35–7.23 (6H, m), 6.89 (1H, dd, J=8.7, 2.5 Hz), 6.66 (1H, m), 6.55 (1H, d, J=2.5 Hz), 3.72 (3H, s), 3.59–3.57 (2H, m), 2.93 (2H, t, J=7.0 Hz), 2.73 (2H, q, J=7.6 Hz), 1.29 (3H, t, J=7.6 Hz).

EXAMPLE 75

2-ETHYL-6-METHOXY-1-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 2-ethyl-6-methoxy-1-(4-{2-[({[(4-methylphenyl)sulfonyl]amino}carbonyl)amino]ethyl}phenyl)-1H-benzimidazole (Example 74).

$^1$H-NMR (DMSO-d$_6$) δ 7.59 (2H, d, J=8.3 Hz), 7.50 (1H, d, J=8.8 Hz), 7.41–7.35 (4H, m), 7.12 (2H, d, J=8.3 Hz), 6.80 (1H, dd, J=8.8, 2.4 Hz), 6.53 (1H, d, J=2.4 Hz), 3.67 (3H, s), 3.15 (2H, m), 2.73–2.62 (4H, m), 1.19 (3H, t, J=7.7 Hz); IR (KBr) σ$_{max}$ 1595, 1516, 1485, 1454, 1400, 1157, 1128, 1086 cm$^{-1}$.

EXAMPLE 76

5-TRIFLUOROMETHYL-2-ETHYL-3-(4-{2-[({[(4-METHYLPHENYL)SULFONYL]AMINO}CARBONYL)AMINO]ETHYL}PHENYL)-1H-BENZIMIDAZOLE

STEP 1. 2-[2-Nitro-4-(trifluoromethyl)anilinolphenyl]ethanol

The title compound was prepared according to the procedure described in step 3 of Example 1 from 2-chloro-5-trifluoromethylnitrobenzene and 4-aminophenylethyl alcohol.

$^1$H-NMR (CDCl$_3$) δ 9.68 (1H, br.s), 8.50 (1H, s), 7.51 (1H, dd, J=2.2 Hz, 9.2 Hz), 7.33 (2H, d, J=8.2 Hz), 7.19–7.26 (3H, m), 3.92 (2H, t, J=6.3 Hz), 2.92 (2H, t, J=6.3 Hz).

STEP 2. 2-[2-Amino-4-(trifluoromethyl)anilinolphenyl]ethanol

The title compound was prepared according to the procedure described in step 2 of Example 26 from 2-[2-nitro-4-(trifluoromethyl)anilino]phenyl}ethanol (step 1).

$^1$H-NMR (CDCl$_3$) δ 7.10–7.16 (3H, m), 6.97 (2H, d, J=8.2 Hz), 6.82 (2H, d, J=8.2 Hz), 3.82 (2H, t, J=6.6 Hz), 2.79 (2H, t, J=6.6 Hz).

STEP 3. 2-[4-[2-Ethyl-5-(trifluoromethyl)-1H-benzimidazol-1-yl]phenyl]ethyl propionate The title compound was prepared according to the procedure described in step 5 of Example 1 from 2-[2-amino-4-(trifluoromethyl)anilino]phenyl}ethanol (step 2) and propionyl chloride.

$^1$H-NMR (CDCl$_3$) δ 8.05 (1H, s), 7.42–7.47 (2H, m), 7.27–7.31 (2H, m), 7.13 (2H, d, =8.4 Hz), 4.39 (2H, t, J=7.0 Hz), 3.08 (2H, t, J=7.0 Hz), 2.80 (2H, q, J=7.6 Hz), 2.36 (2H, q, J=7.6 Hz), 1.36 (3H, t, J=7.6 Hz), 1.14 (3H, t, J=7.6 Hz).

STEP 4. 2-{4-[2-Ethyl-5-(trifluoromethyl)-1H-benzimidazol-1-yl]phenyl}ethanol

The title compound was prepared according to the procedure described in step 6 of Example 1 from 2-{4-[2-ethyl-5-(trifluoromethyl)-1H-benzimidazol-1-yl]phenyl}ethyl propionate (step 3).

$^1$H-NMR (CDCl$_3$) δ 8.05 (1H, s), 7.49 (1H, d, J=8.4 Hz), 7.44 (2H, d, J=8.6 Hz), 7.30 (2H, d, J=8.6 Hz), 7.16 (1H, d, J=8.4 Hz), 4.01 (2H, t, J=6.4 Hz), 3.03 (2H, t, J=6.4 Hz), 2.80 (2H, q, J=7.6 Hz), 1.36 (3H, t, J=7.6 Hz).

STEP 5. 2-{4-[2-Ethyl-5-(trifluoromethyl)-1H-benzimidazol-1-yl]phenyl}ethyl azide The title compound was prepared according to the procedure described in step 5 of Example 26 from 2-{4-[2-ethyl-5-(trifluoromethyl)-1H-benzimidazol-1-yl]phenyl}ethanol (step 4).

$^1$H-NMR (CDCl$_3$) δ: 8.05 (1H, s), 7.22–7.48 (5H, m), 7.15 (1H, d, J=8.4 Hz), 3.62 (2H, t, J=6.8 Hz), 3.02 (2H, t, J=6.8 Hz), 2.80 (2H, q, J=7.5 Hz), 1.36 (3H, t, J=7.5 Hz).

STEP 6. 2-{4-[2-Ethyl-5-(trifluoromethyl)-1H-benzimidazol-1-yl]phenyl}ethylamine The title compound was prepared according to the procedure described in step 9 of Example 1 from 2-{4-[2-ethyl-5-(trifluoromethyl)-1H-benzimidazol-1 yl]phenyl}ethyl azide (step 5).

$^1$H-NMR (CDCl$_3$) δ 8.05 (1H, s), 7.44 (3H, d, J=8.8 Hz), 7.29 (2H, d, J=8.8 Hz), 7.16 (1H, d, J=8.6 Hz), 3.09 (2H, t, J=6.8 Hz), 2.89 (2H, t, J=6.8 Hz), 2.81 (2H, q, J=7.6 Hz), 1.36 (3H, t, J=7.6 Hz).

STEP 7. 5-Trifluoromethyl-2-ethyl-3-(4-{2-[({[(4-methylphenyl)sulfonyl]amino}carbonyl)amino]ethyl}phenyl)-1H-benzimidazole The title compound was prepared according to the procedure described in step 10 of Example 1 from 2-{4-[2-ethyl-5-(trifluoromethyl)-1H-benzimidazol-1 yl]phenyl}ethylamine (step 6).

MS (ESI) m/z 533 (M+H)$^+$; $^1$H-NMR (CDCl$_3$) δ 8.03 (1H, s), 7.80 (2H, d, J=8.2 Hz), 7.73 (2H), d, J=8.2 Hz), 7.38–7.43 (3H, m), 7.26–7.29 (2H, m), 7.13 (1H, d, J=8.4 Hz), 6.70 (1H, br.s), 3.57 (2H, t, 6.7 Hz), 2.94 (2H, t, J=6.7 Hz), 2.80 (2H, q, J=7.6 Hz), 2.43 (3H, s), 1.34 (3H, t, J=7.6 Hz).

EXAMPLE 77

5-TRIFLUOROMETHYL-2-ETHYL-3-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 5-trifluoromethyl-2-ethyl-3-(4-{2-[({[(4-methylphenyl)sulfonyl]amino}carbonyl)amino]ethyl}phenyl)-1H-benzimidazole (Example 76).
$^1$H-NMR (DMSO-$d_6$) δ 8.02 (1H, s), 7.61–7.66 (4H, m), 7.48–7.51 (1H, m), 7.24–7.28 (3H, m), 7.14 (2H, d, 7.9 Hz), 3.09 (2H, br.s), 2.60–2.83 (4H, m), 2.22 (3H, s), 1.13 (3H, t, J=7.5 Hz).

EXAMPLE 78

5-ACETYL-2-ETHYL-3-(4-{2-[({[(4-METHYLPHENYL)SULFONYL]AMINO}CARBONYL)AMINO]ETHYL}PHENYL)-1H-BENZIMIDAZOLE

STEP 1. 1-{4-[4-(2-Hydroxyethyl)anilino]-3-nitrophenyl}ethanone

A mixture of 2-chloro-5-acetylnitrobenzene (Oelschlaeger, H.; Schreiber, O. *Liebigs Ann. Chem.*, 1961, 641, 81., 2 g, 10 mmol), 4-aminophenylethyl alcohol (1.64 g, 12 mmol) and NaHCO$_3$ (1 g, 12 mmol) in DMF (60 mL) was heated at 150° C. for 3 h. After cooling, the mixture was poured into water (100 mL) and extracted with ethyl acetate (300 mL). The organic layer was washed with 2N aqueous NaOH (100 mL) and brine (100 mL), then dried (Na$_2$SO$_4$), and concentrated. Purification by flash column chromatography on silica gel eluting with hexane/ethyl acetate (1:1) to afford 1.36 g (45%) of the title compound as an orange oil; $^1$H-NMR (CDCl$_3$) δ 9.83 (1H, br.s), 8.20 (1H, d, J=2.1 Hz), 7.94 (1H, dd, J=2.1 Hz, 9.3 Hz), 7.34 (2H, d, J=8.2 Hz), 7.24 (2H, d, J=8.2 Hz), 7.16 (1H, d, J=9.3 Hz), 3.91 (2H, t, J=6.6 Hz), 2.92 (2H, t, J=6.6 Hz), 2.57 (3H, s).

STEP 2. 1-{3-Amino-4-[4-(2-hydroxyethyl)anilino]phenyl}ethanone

The title compound was prepared according to the procedure described in step 4 of Example 1 from 1-{4-[4-(2-hydroxyethyl)anilino]-3-nitrophenyl}ethanone (step 1).
$^1$H-NMR (CDCl$_3$) δ: 7.41 (1H, d, J=2.0 Hz), 7.37 (1H, dd, J=2.0 Hz, 8.2 Hz), 7.11–7.17 (3H, m), 6.94 (2H, d, J=8.2 Hz), 5.72 (1H, br.s), 3.85 (2H, t, J=6.6 Hz), 3.65 (2H, br.s), 2.83 (2H, t, J=6.6 Hz), 2.52 (3H, s).

STEP 3. 2-[4-(5-Acetyl-2-ethyl-1H-benzimidazol-1-yl)phenyl)ethyl propionate

The title compound was prepared according to the procedure described in step 5 of Example 1 from 1-{3-amino-4-[4-(2-hydroxyethyl)anilino]phenyl}ethanone (step 2) and propionyl chloride
TLC Rf=0.4 (hexane/ethyl acetate=1:1).

STEP 4. 1-{2-Ethyl-1-[4-(2-hydroxyethyl)phenyl]-1H-benzimidazol-5-yl}ethyl propionate The title compound was prepared according to the procedure described in step 6 of Example 1 from 2-4-(5-acetyl-2-ethyl-1H-benzimidazol-1-yl)phenyl)ethyl propionate (step 3).
$^1$H-NMR (CDCl$_3$) δ 8.39 (1H, d, J=1.2 Hz), 7.89 (1H, dd, J=1.2 Hz, 8.6 Hz), 7.48 (2H, d, J=7.4 Hz), 7.30 (2H, d, J=7.4 Hz), 7.13 (1H, d, J=8.6 Hz), 4.00 (2H, t, J=6.4 Hz), 3.02 (2H, t, J=6.4 Hz), 2.80 (2H, q, J=7.6 Hz), 2.68 (3H, s), 1.38 (2H, t, J=7.6 Hz).

STEP 5. 1-{1-[4-(2-Chloroethyl)phenyl]-2-ethyl-1H-benzimidazol-5-yl}ethanone

The title compound was prepared according to the procedure described in step 7 of Example 1 from 1-{2-ethyl-1-[4-(2-hydroxyethyl)phenyl]-1H-benzimidazol-5-yl}ethanone (step 4).
$^1$H-NMR (CDCl$_3$) δ 8.40 (1H, d, J=1.2 Hz), 7.90 (1H, dd, J=1.2 Hz, 8.4 Hz), 7.47 (2H, d, J=8.4 Hz), 7.32 (2H, d, J=8.4 Hz), 7.13 (1H, d, J=8.4 Hz), 3.83 (2H, t, J=7.3 Hz), 3.21 (2H, t, J=7.3 Hz), 2.82 (2H, q, J=7.6 Hz), 2.68 (3H, s), 1.38 (3H, t, J=7.6 Hz).

STEP 6. 1-{1-[4-(2-Azidoethyl)phenyl]-2-ethyl-1H-benzimidazol-5-yl}ethanone

The title compound was prepared according to the procedure described in step 8 of Example 1 from 1-{1-[4-(2-chloroethyl)phenyl]-2-ethyl-1H-benzimidazol-5-yl}ethanone (step 5).
$^1$H-NMR (CDCl$_3$) δ 8.40 (1H, d, J=1.5 Hz), 7.90 (1H, dd, J=1.5 Hz, 8.6 Hz), 7.46 (2H, d, J=8.3 Hz), 7.12 (2H, d, J=8.3 Hz), 7.02 (1H, d, J=8.6 Hz), 3.63 (2H, t, J=6.9 Hz), 3.03 (2H, t, J=6.9 Hz), 2.80 (2H, q, J=7.4 Hz), 2.67 (3H, s), 1.37 (3H, t, J=7.4 Hz).

STEP 7. 1-{1-[4-(2-Aminoethyl)phenyl]-2-ethyl-1H-benzimidazol-5-yl}ethanone

The title compound was prepared according to the procedure described in step 7 of Example 37 from 1-{1-[4-(2-azidoethyl)phenyl]-2-ethyl-1H-benzimidazol-5-yl}ethanone (step 6).
$^1$H-NMR (CDCl$_3$) δ 8.40 (1H, d, J=1.7 Hz), 7.90 (1H, dd, J=1.7 Hz, 8.6 Hz), 7.43 (2H, d, J=8.2 Hz), 7.30 (2H, d, J=8.2 Hz), 7.13 (1H, d, J=8.6 Hz), 3.08 (2H, t, J=6.7 Hz), 2.88 (2H, t, J=6.7 Hz), 2.80 (2H, q, J=7.6 Hz), 2.68 (3H, s), 1.38 (3H, t, J=7.6 Hz).

STEP 8. 5-Acetyl-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 1-{1-[4-(2-aminoethyl)phenyl]-2-ethyl-1H-benzimidazol-5-yl}ethanone (step 7).
MS (ESI) m/z 505 (M+H)$^+$; $^1$H-NMR CDCl$_3$) δ 8.40 (1H, d, J=1.1 Hz), 7.88 (1H, dd, J=1.1 Hz, 8.6 Hz), 7.73 (2H, d, J=8.4 Hz), 7.40 (2H, d, J=8.4 Hz), 7.27–7.31 (4H, m), 7.10 (1H, d, J=8.6 Hz), 6.74 (1H, br.s), 3.59 (2H, t, J=6.9 Hz), 2.95 (2H, t, J=6.9 Hz), 2.80 (2H, q, J=7.6 Hz), 2.67 (3H, s), 2.40 (3H, s), 1.36 (3H, t, J=7.6 Hz).

EXAMPLE 79

5-ACETYL-2-ETHYL-3-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 5-acetyl-2-ethyl-1-(4-{2-[({[(4-methylphenyl)sulfonyl]amino}carbonyl)amino]ethyl}phenyl)-1H-benzimidazole (Example 78).
mp 155–160° C.; $^1$H-NMR (DMSO-$d_6$) δ 8.32 (1H, d, J=1.6 Hz), 7.81 (1H, dd, J=1.6 Hz, 8.6 Hz), 7.62 (2H, d, J=8.1 Hz), 7.42 (4H, s), 7.12–7.17 (3H, m), 3.18 (2H, br.s), 2.71–2.79 (4H, m), 2.63 (3H, s), 2.27 (3H, s), 1.25 (3H, t, J=7.4 Hz); IR (KBr) $v_{max}$ 3373, 1676, 1604, 1519, 1294, 1130, 1085, 885, 813 cm$^{-1}$.

EXAMPLE 80

2-ETHYL-5-METHYLSULFONYL-1-(4-{2-[({[(4-METHYLPHENYL)SULFONYL]AMINO}CARBONYL)AMINO]ETHYL}PHENYL)-1H-BENZIMIDAZOLE

STEP 1. 2-{4-[4-(Methylsulfonyl)-2-nitroanilino]phenyl}ethanol

A mixture of 2-chloro-5-methylsulfonylnitrobenzene (Kavalek, J.; et al. Collect. *Czech. Chem. Commun*, 1971, 36, 209., 2 g, 8.5 mmol), 4-aminophenylethyl alcohol (1.4 g, 10.2 mmol) and Na$_2$CO$_3$ (1.4 g, 12.7 mmol) in ethanol was stirred at 100° C. for 16 h. The insoluble matter was removed by filtration and washed with ethanol (100 mL). The filtrate was concentrated and the residue was purified by flash column chromatography on silica gel eluting with hexane/ethyl acetate (1:4) to afford 960 mg (34%) of the title compound as yellow solids: $^1$H-NMR (CDCl$_3$) δ 9.84 (1H, br.s), 8.82 (1H, d, J=2.1 Hz), 7.79 (1H, dd, J=2.1 Hz, 9.1 Hz), 7.36 (2H, d, J=8.4 Hz), 7.22–7.38 (3H, m), 3.94 (2H, br.s), 3.07 (3H, s), 2.93 (2H, t, J=6.6 Hz).

STEP 2. 2-{4-[2-Amino-4-(methylsulfonyl)anilino]phenyl}ethanol

The title compound was prepared according to the procedure described in step 2 of Example 28 from 2-{4-[4-(methylsulfonyl)-2-nitroanilino]phenyl}ethanol (step 1).

$^1$H-NMR (CDCl$_3$) δ 7.31 (1H, s), 7.28 (1H, s), 7.16–7.21 (3H, m), 6.96 (2H, d, J=8.5 Hz), 5.56 (1H, br.s), 3.86 (2H, t, J=6.4 Hz), 3.76 (2H, br.s), 3.03 (3H, s), 2.84 (2H, t, J=6.4 Hz).

STEP 3. 2-{4-[2-Ethyl-5-(methylsulfonyl)-1H-benzimidazol-1-yl]phenyl}ethyl propionate The title compound was prepared according to the procedure described in step 5 of Example 1 from 2-{4-[2-amino-4-(methylsulfonyl)anilino]phenyl)ethanol (step 2) and propionyl chloride.

TLC Rf=0.8 (dichloromethane/methanol=10:1).

STEP 4. 2-{4-[2-Ethyl-5-(methylsulfonyl)-1H-benzimidazol-1-yl]phenyl}ethanol

The title compound was prepared according to the procedure described in step 6 of Example 1 from 2-{4-[2-ethyl-5-(methylsulfonyl)-1H-benzimidazol-1-yl]phenyl}ethyl propionate (step 3).

$^1$H-NMR (CDCl$_3$) δ 8.38 (1H, d, J=1.4 Hz), 7.77 (1H, dd, J=1.4 Hz, 8.6 Hz), 7.50 (2H, d, J=8.4 Hz), 7.24–7.32 (2H, m), 7.22 (1H, d, J=8.6 Hz), 4.01 (t, J=6.6 Hz), 3.08 (3H, s), 3.02 (2H, t, J=6.6 Hz), 2.82 (2H, q, J=7.6 Hz), 1.37 (3H, t, J=7.6 Hz).

STEP 5. 1-[4-(2-Chloroethyl)phenyl]-2-ethyl-5-(methylsulfonyl)-1H-benzimidazole

The title compound was prepared according to the procedure described in step 7 of Example 1 from 2-{4-[2-ethyl-5-(methylsulfonyl)-1H-benzimidazol-1-yl]phenyl}ethanol (step 4).

$^1$H-NMR (CDCl$_3$) δ 8.38 (1H, d, J=1.6 Hz), 7.78 (1H, d, J=1.6 Hz, 8.6 Hz), 7.49 (2H, d, J=8.1 Hz), 7.32 (2H, d, J=8.1 Hz), 7.23 (1H, d, J=8.6 Hz), 3.84 (2H, t, J=6.9 Hz), 3.22 (2H, t, J=6.9 Hz), 3.08 (3H, s), 2.82 (2H, q, J=7.5 Hz), 1.38 (3H, t, J=7.5 Hz).

STEP 6. 1-[4-(2-Azidoethyl)phenyl]-2-ethyl-1H-benzimidazol-5-yl methyl sulfone

The title compound was prepared according to the procedure described in step 8 of Example 1 from 1-[4-(2-chloroethyl)phenyl]-2-ethyl-5-(methylsulfonyl)-1H-benzimidazole (step 5).

$^1$H-NMR (CDCl$_3$) δ 8.38 (1H, d, J=1.5 Hz), 7.78 (1H, dd, J=1.5 Hz, 8.6 Hz), 7.49 (2H, d, J=8.4 Hz), 7.32 (2H, d, J=8.4 Hz), 7.21 (1H, d, J=8.6 Hz), 3.64 (2H, t, J=6.9 Hz), 3.08 (3H, s), 3.03 (2H, t, J=6.9 Hz), 2.83 (2H, q, J=7.6 Hz), 1.37 (3H, t, J=7.6 Hz).

STEP 7. 2-{4-[2-Ethyl-5-(methylsulfonyl)-1H-benzimidazol-1-yl]phenyl}ethylamine

The title compound was prepared according to the procedure described in step 7 of Example 37 from 1-[4-(2-azidoethyl)phenyl]-2-ethyl-1H-benzimidazol-5-yl methyl sulfone (step 6).

$^1$H-NMR (CDCl$_3$) δ 8.38 (1H, d, J=1.7 Hz), 7.77 (1H, dd, J=1.7 Hz, 8.6 Hz), 7.46 (2H, d, J=8.4 Hz), 7.21–7.30 (3H, m), 3.03–3.08 (5H, m), 2.89 (2H, t, J=6.7 Hz), 2.82 (2H, q, J=7.6 Hz), 1.37 (3H, t, J=7.6 Hz).

STEP 8. 2-Ethyl-5-(methylsulfonyl)-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-{4-[2-ethyl-5-(methylsulfonyl)-1H-benzimidazol-1-yl]phenyl}ethylamine (step 7

$^1$H-NMR (CDCl$_3$) δ 8.37 (1H, d, J=1.6 Hz), 7.75 (1H, dd, J=1.6 Hz, 8.6 Hz), 7.74 (2H, d, J=8.4 Hz), 7.43 (2H, d, J=8.2 Hz), 7.27–7.32 (4H, m), 7.18 (1H, d, J=8.6 Hz), 6.70 (1H, br.s) 3.59 (2H, t, J=6.8 Hz), 3.08 (3H, s), 2.96 (2H, t. J=6.8 Hz), 2.82 (2H, q, J=7.6 Hz), 2.41 (3H, s), 1.35 (4H, t, J=7.6 Hz).

EXAMPLE 81

2-ETHYL-5-METHYLSULFONYL-3-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 2-ethyl-5-(methylsulfonyl)-1-(4-{2-[({[(4-methylphenyl)sulfonyl]amino}carbonyl)amino]ethyl}phenyl)-1H-benzimidazole (Example 80).

mp 171–178° C.; $^1$H-NMR (DMSO-d$_6$) δ 8.08 (1H, br.s), 7.51–7.62 (3H, m), 7.32 (4H, s), 7.16 (1H, d, J=8.6 Hz), 7.03 (2H, d, J=7.3 Hz), 3.09–3.25 (7H, m), 2.63–2.66 (2.16 (3H, s), 1.13 (3H, t, J=7.3 Hz); IR (KBr) $v_{max}$ 3386, 1604, 1519, 1396, 1299, 1128, 1085, 962, 887 cm$^1$.

EXAMPLE 82

5-CYANO-2-ETHYL-1-(4-{2-[({[(4-METHYLPHENYL)SULFONYL]AMINO}CARBONYL)AMINO]ETHYL}PHENYL)-1H-BENZIMIDAZOLE

STEP 1. 2-[(4-Cyano-2-nitroanilino)phenyl]ethanol

The title compound was prepared according to the procedure described in step 3 of Example 1 from 4-chloro-3-nitrobenzonitrile and 4-aminophenylethyl alcohol.

$^1$H-NMR (CDCl$_3$) δ 9.80 (1H, br.s), 8.54 (1H, d, J=2.0 Hz), 7.50 (1H, dd, J=9.1, 2.0 Hz), 7.36 (2H, d, J=8.4 Hz), 7.23 (2H, d, J=8.4 Hz), 7.16 (1H, d, J=9.1 Hz), 3.94–3.91 (2H, m), 2.93 (2H, t, J=6.6 Hz), 1.81 (1H, m).

STEP 2. 2-[(2-Amino-4-cyanoanilino)phenyl]ethanol

The title compound was prepared according to the procedure described in step 2 of Example 28 from 2-[(4-cyano-2-nitroanilino)phenyl]ethanol (step 1).

$^1$H-NMR (CDCl$_3$) δ 7.18–7.10 (3H, m), 7.01–6.95 (4H, m), 6.09 (1H, m), 3.97 (2H, br.s), 3.83–3.82 (2H, m), 2.83 (2H, t, J=6.8 Hz), 2.31 (1H, m)

STEP 3. 2-[4-(5-Cyano-2-ethyl-1H-benzimidazol-1-yl)phenyl]ethyl propionate

The title compound was prepared according to the procedure described in step 5 of Example 1 from 2-[(2-amino-4-cyanoanilino)phenyl]ethanol (step 2).

MS (EI) m/z 347 (M$^+$).

STEP 4. 2-[4-(5-Cyano-2-ethyl-1H-benzimidazol-1-yl)phenyl]ethanol

The title compound was prepared according to the procedure described in step 6 of Example 1 from 2-[4-(5-cyano-2-ethyl-1H-benzimidazol-1-yl)phenyl]ethyl propionate (step 3).

$^1$H-NMR (CDCl$_3$) δ 8.09 (1H, s), 7.50–7.43 (3H, m), 7.32–7.28 (2H, m), 7.15 (1H, d, J=8.2 Hz), 4.00 (2H, q, H=6.4 Hz), 3.01 (2H, t, J=6.4 Hz), 2.81 (2H, t, J=7.6 Hz), 1.37 (3H, t, J=7.6 Hz),

STEP 5. 2-[4-(5-Cyano-2-ethyl-1H-benzimidazol-1-yl)phenyl]ethyl azide

The title compound was prepared according to the procedure described in step 5 of Example 26 from 2-[4-(5-cyano-2-ethyl-1H-benzimidazol-1-yl)phenyl]ethanol (step 4).

TLC Rf=0.83 (dichloromethane/methanol=10:1).

STEP 6. 2-[4-(5-Cyano-2-ethyl-1H-benzimidazol-1-yl)phenyl]ethylamine

The title compound was prepared according to the procedure described in step 9 of Example 1 from 2-[4-(5-cyano-2-ethyl-1H-benzimidazol-1-yl)phenyl]ethyl azide (step 5).

$^1$H-NMR (CDCl$_3$) δ 8.09 (1H, s), 7.47–7.42 (3H, m), 7.29–7.26 (2H, m), 7.15 (1H, d, J=8.4 Hz), 3.09 (2H, t, J=6.8 Hz), 2.91 (2H, t, J=6.8 Hz), 2.81 (2H, q, J=7.6 Hz), 1.37 (3H, t, J=7.6 Hz).

STEP 7. 5-Cyano-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(5-cyano-2-ethyl-1H-benzimidazol-1-yl)phenyl]ethylamine (step 6).

$^1$H-NMR (CDCl$_3$) δ 8.05 (1H, d, J=0.9 Hz), 7.75 (2H, d, J=8.4 Hz), 7.43–7.40 (3H, m), 7.30–7.26 (4H, m), 7.12 (1H, d, J=8.4 Hz), 6.74 (1H, m), 3.60–3.58 (2H, m), 2.96 (2H, t, J=7.0 Hz), 2.81 (2H, q, J=7.5 Hz), 2.41 (3H, s), 1.34 (3H, t, J=7.5 Hz).

EXAMPLE 83

5-CYANO-2-ETHYL-1-(4-{2-[({[(4-METH-YLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 5-cyano-2-ethyl-1-(4-{2-[({[(4-methylphenyl)sulfonyl]amino}carbonyl)amino]ethyl}benzimidazole (Example 82).

$^1$H-NMR (DMSO-d$_6$) δ 8.19 (1H, d, J=1.5 Hz), 7.59 (2H, d, J=7.9 Hz), 7.54 (1H, dd, J=8.4, 1.5 Hz), 7.41 (4H, s), 7.23 (1H, d, J=8.4 Hz), 7.11 (2H, d, J=7.9 Hz), 3.14 (2H, m), 2.78–2.70 (4H, m), 2.26 (3H, s), 1.24 (3H, t, J=7.4 Hz).

EXAMPLE 84

2-ETHYL-1-(4-{2-[({[(4-METHYLPHENYL)SULFONYL]AMINO}CARBONYL)AMINO]ETHYL}PHENYL)-1H-BENZIMIDAZOLE-5-CARBOXAMIDE

STEP 1. 2-Ethyl-1-[4-(2-hydroxyethyl)phenyl]-1H-benzimidazole-5-carboxamide

To a mixture of 2-[4-(5-cyano-2-ethyl-1H-benzimidazol-1-yl)phenyl]ethanol (step 4 of Example 82, 200 mg, 0.68 mmol), DMSO (0.06 mL, 0.82 mmol) and methanol (10 mL) was added 30% aqueous solution of hydrogen peroxide (0.12 mL, 1.0 mmol) and 0.2 M aqueous NaOH (0.06 mL). The mixture was stirred at 50° C. for 4 h, then cooled. The mixture was poured into water (50 mL) and extracted with ethyl acetate (100 mL). The organic layer was washed with 2N aqueous NaOH (50 mL) and brine (50 mL), then dried (Na$_2$SO$_4$), and concentrated to afford the title compound as pale yellow solids: $^1$H-NMR (CDCl$_3$) δ 8.23 (1H, d, J=1.1 Hz), 7.96 (1H, br.s), 7.76 (1H, dd, J=1.1 Hz, 8.4 Hz), 7.42–7.51 (4H, m), 7.25 (1H, br.s), 7.09 (1H, d, J=8.4 Hz), 3.70 (2H, t, J=6.6 Hz), 2.85 (2H, t, J=6.9 Hz), 2.76 (2H, q, J=7.4 Hz), 1.24 (3H, t, J=7.4 Hz).

STEP 2. 1-[4-(2-Chloroethyl)phenyl]-2-ethyl-1H-benzimidazole-5-carboxamide

The title compound was prepared according to the procedure described in step 7 of Example 1 from 2-ethyl-1-[4-(2-hydroxyethyl)phenyl]-1H-benzimidazole-5-carboxamide (step 1).

$^1$H-NMR (CDCl$_3$) δ 8.17 (1H, d, J=1.7 Hz), 7.79 (1H, dd, J=1.7 Hz, 8.5 Hz), 7.46 (2H, d, J=8.3 Hz), 7.33 (2H, d, J=8.3 Hz), 7.15 (1H, d, J=8.5 Hz), 3.83 (2H, t, J=7.0 Hz), 3.21 (2H, t, J=7.0 Hz), 2.82 (2H, q, J=7.6 Hz), 1.37 (3H, t, J=7.6 Hz).

STEP 3. 1-[4-(2-Azidoethyl)phenyl]-2-ethyl-1H-benzimidazole-5-carboxamide

The title compound was prepared according to the procedure described in step 8 of Example 1 from 1-[4-(2-chloroethyl)phenyl]-2-ethyl-1H-benzimidazole-5-carboxamide (step 2).

$^1$H-NMR (CDCl$_3$) δ 8.17 (1H, d, J=1.5 Hz), 7.78 (1H, dd, J=1.5 Hz, 8.4 Hz), 7.46 (2H, d, J=8.2 Hz), 7.32 (2H, d, J=8.2 Hz), 7.13 (1H, d, J=8.4 Hz), 3.62 (2H, t, J=6.8 Hz), 3.03 (2H, t, J=6.8 Hz), 2.81 (2H, q, J=7.5 Hz), 1.36 (3H, t, J=7.5 Hz).

STEP 4. 1-[4-(2-Aminoethyl)phenyl]-2-ethyl-1H-benzimidazole-5-carboxamide

The title compound was prepared according to the procedure described in step 9 of Example 1 from 1-[4-(2-azidoethyl)phenyl]-2-ethyl-1H-benzimidazole-5-carboxamide (step 3).

$^1$H-NMR (CDCl$_3$) δ 8.21 (1H, d, J=1.5 Hz), 7.79 (1H, dd, J=1.5 Hz, 8.4 Hz), 7.43 (2H, d, J=8.2 Hz), 7.28–7.31 (2H, m), 7.13 (1H, d, J=8.4 Hz), 3.05 (2H, t, J=6.7 Hz), 2.88 (2H, t, J=6.7 Hz), 2.81 (2H, q, J=7.6 Hz), 1.35 (3H, t, J=7.6 Hz).

STEP 5. 2-Ethyl-1-(4-{2-[({[(4-methylphenyl)sulfonyl]amino}carbonyl)amino]ethyl}phenyl)-1H-benzimidazole-5-carboxamide The title compound was prepared according to the procedure described in step 10 of Example 1 from 1-[4-(2-aminoethyl)phenyl]-2-ethyl-1H-benzimidazole-5-carboxamide (step 4).

MS (ESI) m/z 506 (M+H)$^+$; $^1$H-NMR (CD$_3$OD) δ 8.13 (1H, s), 7.65–7.73 (3H, m), 7.32 (2H, d, J=8.2 Hz), 7.16–7.21 (4H, m), 7.00 (1H, d, J=8.6 Hz), 3.31 (2H, t, J=6.9 Hz), 2.75 (2H, t, J=6.9 Hz), 2.69 (2H, q, J=7.6 Hz), 2.21 (3H, s), 1.48 (3H, t, J=7.6 Hz).

EXAMPLE 85

6-CYANO-2-ETHYL-1-(4-{2-[({[(4-METHYLPHENYL)SULFONYL]AMINO}CARBONYL)AMINO]ETHYL}PHENYL)-1H-BENZIMIDAZOLE

STEP 1. 3-[4-(2-Hydroxyethyl)anilino]-4-nitrobenzonitrile

The title compound was prepared according to the procedure described in step 3 of Example 1 from 3-chloro-4-nitrobenzonitrile (Tsuji, K. Chem. Pharm. Bull. 1992, 40, 2399) and 4-aminophenylethyl alcohol.

MS (EI) m/z 383 (M$^+$).

STEP 2. 3-[4-(2-Chloroethyl)anilino]-4-nitrobenzonitrile

The title compound was prepared according to the procedure described in step 7 Example 1 from 3-[4-(2-hydroxyethyl)anilino]-4-nitrobenzonitrile (step 1).

$^1$H-NMR (CDCl$_3$) δ 9.46 (1H, br.s), 8.29 (1H, d, J=8.8 Hz), 7.42 (1H, d, J=1.7 Hz), 7.35 (2H, d, J=8.3 Hz), 7.22 (2H, d, J=8.3 Hz), 6.97 (1H, dd, J=8.8, 1.7 Hz), 3.77 (2H, t, J=7.2 Hz), 3.13 (2H, t, J=7.

STEP 3. 4-Amino-3-[4-(2-chloroethyl)anilino]benzonitrile

The title compound was prepared according to the procedure described in step 4 of Example 1 from 3-[4-(2-chloroethyl)anilino]-4-nitrobenzonitrile (step 2).

MS (EI) m/z 383 (M$^+$).

STEP 4. 1-[4-(2-Chloroethyl)phenyl]-2-ethyl-1H-benzimidazole-6-carbonitrile

The title compound was prepared according to the procedure described in step 5 Example 1 from 4-amino-3-[4-(2-chloroethyl)anilino]benzonitrile (step 3) and propionyl chloride.

MS (EI) m/z 309 (M$^+$); $^1$H-NMR (CDCl$_3$) δ 7.82 (1H, d, J=8.6 Hz), 7.53 (1H, dd, J=8.6, 2.0 Hz), 7.48 (2H, d, J=8.3 Hz), 7.42 (1H, d, J=2.0 Hz), 7.31 (2H, d, J=8.3 Hz), 3.84 (2H, t, J=7.0 Hz), 3.21 (2H, t, J=7.0 Hz), 2.82 (2H, q, J=7.4 Hz), 1.39 (3H, t, J=7.4 Hz).

STEP 5. 2-[4-(6-Cyano-2-ethyl-1H-benzimidazol-1-yl)phenyl]ethyl azide

The title compound was prepared according to the procedure described in step 8 Example 1 from 1-[4-(2-chloroethyl)phenyl]-2-ethyl-1H-benzimidazole-6-carbonitrile (step 4).

MS (EI) m/z 316 (M$^+$); $^1$H-NMR (CDCl$_3$) δ 7.83 (1H, d, J=8.4 Hz), 7.54 (1H, dd, J=8.4, 2.0 Hz), 7.50 (2H, d, J=8.3 Hz), 7.40 (1H, d, J=2.0 Hz), 7.30 (2H, d, J=8.3 Hz), 3.64 (2H, t, J=6.5 Hz), 3.04 (2H, t, J=6.5 Hz), 2.83 (2H, q, J=7.3 Hz), 1.37 (3H, t, J=7.3 Hz).

STEP 6. 2-[4-(6-Cyano-2-ethyl-1H-benzimidazol-1-yl)phenyl]ethylamine

The title compound was prepared according to the procedure described in step 9 of Example 1 from 2-[4-(6-cyano-2-ethyl-1H-benzimidazol-1-yl)phenyl]ethyl azide (step 5).

$^1$H-NMR (DMSO-d$_6$) δ 8.11 (2H, br.s), 7.87 (1H, d, J=8.4 Hz), 7.64 (1H, dd, J=8.4, 2.0 Hz), 7.60–7.53 (5H, m), 3.20–3.02 (4H, m), 2.79 (2H, q, J=7.4 Hz), 1.28 (3H, t, J=7.4 Hz).

STEP 7. 6-Cyano-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(6-cyano-2-ethyl-1H-benzimidazol-1-yl)phenyl]ethylamine (step 6).

$^1$H-NMR (CDCl$_3$) δ 7.83 (1H, d, J=8.4 Hz), 7.74 (2H, d, J=8.4 Hz), 7.53 (1H, dd, J=8.4, 1.7 Hz), 7.43 (2H, d, J=8.4 Hz), 7.39 (1H, d, J=1.5 Hz), 7.33 (2H, d, J=8.4 Hz), 7.29 (2H, d, J=8.4 Hz), 6.75 (1H, br.s), 3.65–3.54 (2H, m), 2.97 (2H, t, J=7.0 Hz), 2.82 (2H, q, J=7.5 Hz), 2.42 (3H, s), 1.37 (3H, t, J=7.5 Hz).

EXAMPLE 86

2-ETHYL-1-(4-{2-[({[(4-METHYLPHENYL)SULFONYL]AMINO}CARBONYL)AMINO]ETHYL}PHENYL)-1H-BENZIMIDAZOLE-6-CARBOXAMIDE

To a solution of 6-cyano-2-ethyl-1-(4-{2-[({[(4-methylphenyl)sulfonyl]amino}carbonyl)amino]ethyl}phenyl)-1H-benzimidazole (Example 85, 162 mg, 0.33 mmol) in 2-methyl-2-propanol (10 mL) was added powdered KOH (66 mg, 1.0 mmol). The resulting mixture was heated at reflux temperature for 3 h. After removal of solvent, the reaction mixture was partitioned between dichloromethane (50 mL) and phosphate buffer (50 mL). The organic phase was separated and the aqueous phase was extracted with dichloromethane (50 mL). The combined organic phases were washed with brine (50 mL), dried (Na$_2$SO$_4$), and concentrated. The residual solids were recrystallized from ethyl acetate to afford 105 mg (63%) of the title compound as white solids: $^1$H-NMR (CDCl$_3$) δ: 7.79 (2H, d, J=8.4 Hz), 7.75 (1H, d, J=8.8 Hz), 7.71–7.63 (2H, m), 7.35–7.25 (4H, m), 7.16 (2H, d, J=8.4 Hz), 6.75 (2H, br.s), 6.55 (1H, br.s), 3.54 (2H, t, J=6.4 Hz), 2.88 (2H, t, J=6.4 Hz), 2.79 (2H, q, J=7.5 Hz), 2.40 (3H, s), 1.34 (3H, t, J=7.5 Hz).

EXAMPLE 87

5-[(TERT-BUTYLAMINO)SULFONYL]-2-ETHYL-1-(4-{2-[({[(4-METHYLPHENYL)SULFONYL]AMINO}CARBONYL)AMINO]ETHYL}PHENYL)-1H-BENZIMIDAZOLE

STEP 1. N-(tert-Butyl)-4-chloro-3-nitrobenzenesulfonamide

To a stirred solution of tert-butylamine (5.1 g, 70 mmol) in dichloromethane (200 mL) was added dropwise a solution of 4-chloro-3-nitrobenzenesulfonyl chloride (17.9 g, 70 mmol) in dichloromethane (100 mL) at room temperature over a period of 30 min, and then the reaction mixture was stirred for 2 h. The reaction mixture was poured into water (100 mL), the organic phase was separated, and the aqueous phase was extracted with ethyl acetate (100 mL). The combined organic extracts were washed with water (50 mL) and brine (20 mL), dried (Na$_2$SO$_4$), and concentrated to give 21.3 g (quant.) of the title compound as yellow solids: $^1$H-NMR (CDCl$_3$) δ 8.38 (1H, d, J=2.0 Hz), 8.02 (1H, dd, J=2.0, 8.6 Hz), 7.70 (1H, d, J=8.6 Hz), 49.5 (1H, br.s), 1.28 (9H, s).

STEP 2. N-(tert-Butyl)-4-[4-(2-hydroxyethyl)anilino]-3-nitrobenzenesulfonamide

The title compound was prepared according to the procedure described in step 3 of Example 1 from N-(tert-butyl)-4-chloro-3-nitrobenzenesulfonamide (step 1) and 4-aminophenylethyl alcohol.

MS (EI) m/z 393 (M$^+$); $^1$H-NMR (CDCl$_3$) δ 9.76 (1H, br.s), 8.75 (1H, d, J=2.0 Hz), 7.74 (1H, dd, J=2.0, 8.5 Hz), 7.35 (2H, d, J=8.3 Hz), 7.24 (2H, d, J=8.3 Hz), 7.17 (1H, d, J=8.5 Hz), 4.42 (1H, br.s), 3.97–3.88 (2H, m), 2.94 (2H, t, J=7.0 Hz), 1.27 (9H, s).

STEP 3. N-(tert-Butyl)-4-[4-(2-chloroethyl)anilino]-3-nitrobenzenesulfonamide

The title compound was prepared according to the procedure described in step 7 Example 1 from N-(tert-butyl)-4-[4-(2-hydroxyethyl)anilino]-3-nitrobenzenesulfonamide (step 2).

MS (EI) m/z 411 (M$^+$); $^1$H-NMR (CDCl$_3$) δ 9.77 (1H, br.s), 8.77 (1H, d, J=2.0 Hz), 7.77 (1H, dd, J=2.0, 8.4 Hz), 7.34 (2H, d, J=8.3 Hz), 7.25 (2H, d, J=8.3 Hz), 7.18 (1H, d, J=8.4 Hz), 4.46 (1H, br.s), 3.76 (2H, t, J=6.8 Hz), 3.13 (2H, t, J=6.8 Hz), 1.28 (9H, s).

STEP 4. 3-Amino-N-(tert-butyl)-4-[4-(2-chloroethyl)anilino]benzenesulfonamide

The title compound was prepared according to the procedure described in step 4 of Example 1 from N-(tert-butyl)-4-[4-(2-chloroethyl)anilino]-3-nitrobenzenesulfonamide (step 3).

$^1$H-NMR (CDCl$_3$) δ 7.31 (1H, d, J=2.0 Hz), 7.26 (1H, dd, J=2.0, 8.3 Hz), 7.15 (1H, d, J=8.3 Hz), 7.14 (2H, d, J=8.4 Hz), 6.89 (2H, d, J=8.4 Hz), 5.49 (1H, br.s), 4.64 (1H, br.s), 3.77 (2H, br.s), 3.69 (2H, t, J=7.4 Hz), 3.02 (2H, t, J=7.4 Hz), 1.24 (9H, s).

STEP 5. N-(tert-Butyl)-1-[4-(2-chloroethyl)phenyl]-2-ethyl-1H-benzimidazole-5-sulfonamide The title compound was prepared according to the procedure described in step 5 Example 1 from 3-amino-N-(tert-butyl)-4-[4-(2-chloroethyl)anilino]benzenesulfonamide (step 4) and propionyl chloride.

MS (EI) m/z 419 (M$^+$); $^1$H-NMR (CDCl$_3$) δ 8.34 (1H, d, J=2.0 Hz), 7.74 (1H, dd, J=2.0, 8.3 Hz), 7.47 (2H, d, J=8.6 Hz), 7.33 (2H, d, J=8.6 Hz), 7.16 (1H, d, J=8.3 Hz), 4.62 (1H, br.s), 3.83 (2H, t, J=7.0 Hz), 3.21 (2H, t, J=7.0 Hz), 2.82 (2H, q, J=7.4 Hz), 1.39 (3H, t, J=7.4 Hz) 1.24 (9H, s).

STEP 6. 1-[4-(2-Azidoethyl)phenyl]-N-(tert-butyl)-2-ethyl-1H-benzimidazole-5-sulfonamide The title compound was prepared according to the procedure described in step 8 Example 1 from N-(tert-butyl)-1-[4-(2-chloroethyl)phenyl]-2-ethyl-1H-benzimidazole-5-sulfonamide (step 5).

MS (EI) m/z 426 (M$^+$); $^1$H-NMR (CDCl$_3$) δ 8.33 (1H, d, J=2.0 Hz), 7.73 (1H, dd, J=2.0, 8.4 Hz), 7.48 (2H, d, J=8.4 Hz), 7.33 (2H, d, J=8.4 Hz), 7.14 (1H, d, J=8.4 Hz), 4.47 (1H, br.s), 3.62 (2H, t, J=7.0 Hz), 3.03 (2H, t, J=7.0 Hz), 2.82 (2H, q, J=7.2 Hz), 1.38 (3H, t, J=7.2 Hz) 1.24 (9H, s).

STEP 7. 1-[4-(2-Aminoethyl)phenyl]-N-(tert-butyl)-2-ethyl-1H-benzimidazole-5-sulfonamide The title compound was prepared according to the procedure described in step 9 of Example 1 from 1-[4-(2-azidoethyl)phenyl]-N-(tert-butyl)-2-ethyl-1H-benzimidazole-5-sulfonamide (step 6).

$^1$H-NMR (CDCl$_3$) δ 8.34 (1H, d, J=1.9 Hz), 7.74 (1H, dd, J=1.9, 8.3 Hz), 7.44 (2H, d, J=8.4 Hz), 7.28 (2H, d, J=8.4 Hz), 7.15 (1H, d, J=8.3 Hz), 4.88 (1H, br.s), 3.09 (2H, t, J=7.0 Hz), 2.95 (2H, t, J=7.0 Hz), 2.83 (2H, q, J=7.4 Hz), 1.37 (3H, t, J=7.4 Hz) 1.23 (9H, s).

STEP 8. 5-[(tert-Butylamino)sulfonyl]-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 1-[4-(2-aminoethyl)phenyl]-N-(tert-butyl)-2-ethyl-1H-benzimidazole-5-sulfonamide (step 7).

MS (ESI) m/z 598 (M+H)$^+$; $^1$H-NMR (CDCl$_3$) δ 8.32 (1H, d, J=1.3 Hz), 7.77–7.69 (3H, m) 7.41(2H, d, J=8.3 Hz), 7.33–7.25 (4H, m), 7.11 (1H, d, J=8.6 Hz), 6.65 (1H, br.s), 4.59 (1H, s), 3.63–3.53 (2H, m), 2.95 (2H, t, J=7.0 Hz), 2.80 (2H, q, J=7.6 Hz), 2.41 (3H, s), 1.36 (3H, t, J=7.6 Hz) 1.23 (9H, s).

EXAMPLE 88

5-(AMINOSULFONYL)-2-ETHYL-1-(4-{2-[({[(4-METHYLPHENYL)SULFONYL]AMINO}CARBONYL)AMINO]ETHYL}PHENYL)-1H-BENZIMIDAZOLE

A solution of 5-[(tert-butylamino)sulfonyl]-2-ethyl-1-(4-{2-[({[(4-methylphenyl)sulfonyl]amino}carbonyl)amino]ethyl}phenyl)-1H-benzimidazole (Example 87, 330 mg, 0.55 mmol) in trifluoroacetic acid (10 mL) was heated at 80° C. for 2 h. The mixture was concentrated and the residue was purified by flash chromatography on silica gel eluting with dichloromethane/methanol (10:1) to afford 215 mg (73%) of the title compound: MS (ESI) m/z 542 (M+H)$^+$; $^1$H-NMR (CDCl$_3$) δ 8.32 (1H, d, J=1.3 Hz), 7.77–7.69 (3H, m), 7.41(2H, d, J=8.3 Hz), 7.33–7.25 (4H, m), 7.11 (1H, d, J=8.6 Hz), 6.65 (1H, br.s), 4.59 (1H, s), 3.63–3.53 (2H, m), 2.95 (2H, t, J=7.0 Hz), 2.80 (2H, q, J=7.6 Hz), 2.41 (3H, s), 1.36 (3H, t, J=7.6 Hz) 1.23 (9H, s).

EXAMPLE 89

2-ETHYL-1-{2-[({[(4-METHYLPHENYL)SULFONYL]AMINO}CARBONYL)AMINO]ETHYL}-5-[(METHYLSULFONYL)AMINO]-1H-BENZIMIDAZOLE

STEP 1. 2-[4-(2,4-Dinitroanilino)phenyl]ethanol

The title compound was prepared according to the procedure described in step 3 of Example 1 from 2-chloro-1,5-dinitrobenzene and 4-aminophenylethyl alcohol.

$^1$H-NMR (CDCl$_3$) δ 9.95 (1H, s), 9.18 (1H, d, J=2.4 Hz), 8.16 (1H, dd, J=2.7, 9.7 Hz), 7.39 (2H, d, J=8.4 Hz), 7.26 (2H, d, J=8.1 Hz), 7.16 (1H, d, J=9.5 Hz), 3.93 (2H, dt, J=5.7, 6.2 Hz), 2.94 (2H, t, J=6.8 Hz), 1.50 (1H, t, J=5.7 Hz).

STEP 2. 2-[4-(2-Amino-4-nitroanilino)phenyl]ethanol

The title compound was prepared according to the procedure described in step 2 of Example 40 from 2-[4-(2,4-dinitroanilino)phenyl]ethanol (step 1).

¹H-NMR (CDCl₃) δ 7.73–7.67 (2H, m), 7.22 (2H, d, J=8.3 Hz), 7.11 (1H, d, J=9.3 Hz), 7.04 (2H, d, J=8.3 Hz), 5.80 (1H, s), 3.88 (2H, dt, J=5.7, 6.0 Hz), 3.69 (2H, br.s), 2.87 (2H, t, J=6.4 Hz), 1.48 (1H, br).

STEP 3. 2-[4-(2-Ethyl-5-nitro-1H-benzimidazol-1-yl)phenyl]ethyl propionate

The title compound was prepared according to the procedure described in step 5 of Example 1 from 2-[4-(2-amino-4-nitroanilino)phenyl]ethanol (step 2) and propionyl chloride.

¹H-NMR (CDCl₃) δ 8.68 (1H, d, J=2.2 Hz), 8.13 (1H, dd, J=2.2, 9.0 Hz), 7.48 (2H, d, J=8.3 Hz), 7.31 (2H, d, J=8.3 Hz), 7.13 (1H, d, J=8.97 Hz), 4.39 (2H, t, J=6.8 Hz), 3.09 (2H, t, J=7.0 Hz), 2.81 (2H, q, J=7.5 Hz), 2.36 (2H, q, J=7.5 Hz), 1.38 (3H, t, J=7.5 Hz), 1.15 (3H, q, J=7.5 Hz),

STEP 4. 2-[4-(5-Amino-2-ethyl-1H-benzimidazol-1-yl)phenyl]ethyl propionate

To a stirred solution of 2-[4-(2-ethyl-5-nitro-1H-benzimidazol-1-yl)phenyl]ethyl propionate (step 3, 1.12 g, 3.0 mmol) in ethanol/water (v/v, 2:1, 15 mL) was added ammonium chloride (80 mg, 1.5 mmol) and iron powder (840 mg, 15 mmol) at room temperature. The mixture was heated at reflux temperature for 4 h and filtered through a pad of Celite. The filtrate was concentrated, and the residue was dissolved in dichloromethane (200 mL), then dried (MgSO₄). Removal of solvent gave 0.84 g (83%) of the title compound as a yellow oil: ¹H-NMR (CDCl₃) δ 7.41 (2H, d, J=8.3 Hz), 7.29 (2H, d, J=8.6 Hz), 7.10 (1H, d, J=1.8 Hz), 6.89 (1H, d, J=8.4 Hz), 6.63 (1H, dd, J=2.2, 8.4 Hz), 4.37 (2H, t, J=7.0 Hz), 3.05 82H, t, J=7.1 Hz), 2.79 (2H, q, J=7.5 Hz), 2.35 (2H, q, J=7.5 Hz), 1.33 (3H, t, J=7.50 Hz), 1.14 (3H, t, J=7.7 Hz).

STEP 5. 2-(4-{2-Ethyl-5-[(methylsulfonyl)amino]-1H-benzimidazol-1-yl}phenyl)ethyl propionate To a stirred solution of 2-[4-(5-amino-2-ethyl-1H-benzimidazol-1-yl)phenyl]ethyl propionate (step 4, 1.18 g, 3.50 mmol) in dichloromethane (20 mL) was added methanesulfonyl chloride (0.40 mL, 5.25 mmol) and pyridine (0.42 mL, 5.25 mmol) at room temperature. After stirring for 6 h, the mixture was poured into 10% aqueous citric acid (100 mL) and extracted with ethyl acetate (100 mL). The aqueous layer was made basic with saturated aqueous sodium bicarbonate (100 mL) and extracted with ethyl acetate (100 mL). The combined organic extracts were washed with brine (100 mL) and dried (MgSO₄), and concentrated to afford 1.28 g (88%) of the title compound as brown amorphous: ¹H-NMR (CDCl₃) δ 8.47 (1H, s), 7.66 (1H, d, J=1.7 Hz), 7.50 (2H, d, J=8.4 Hz), 7.42 (1H, dd, J=2.0, 8.8 Hz), 7.41 (2H, d, J=8.4 Hz), 7.09 (1H, d, J=8.8 Hz), 4.39 (2H, t, J=7.0 Hz), 3.09 (2H, t, J=6.8 Hz), 3.00 (2H, q, J=7.7 Hz), 2.36 (2H, q, J=7.7 Hz), 1.42 (3H, t, J=7.7 Hz), 1.15 (3H, t, J=7.5 Hz).

STEP 6. 2-Ethyl-1-[4-(2-hydroxyethyl)phenyl]-1H-benzimidazol-5-yl}methanesulfonamide The title compound was prepared according to the procedure described in step 6 of Example 1 from 2-(4-{2-ethyl-5-[(methylsulfonyl)amino]-1H-benzimidazol-1-yl}phenyl)ethyl propionate (step 5).

¹H-NMR (CDCl₃) δ 7.63 (1H, d, J=1.8 Hz), 7.46 (2H, d, J=8.2 Hz), 7.29 (2H, d, J=8.4 Hz), 7.18 (1H, dd, J=2.1, 8.6 Hz), 7.07 (1H, d, J=8.6 Hz), 6.68 (1H, br), 3.99 (2H, t, J=6.4 Hz), 3.01 (2H, t, J=6.8 Hz), 2.98 (3H, s), 2.79 (2H, q, J=7.4 Hz), 1.35 (3H, t, J=7.6 Hz).

STEP 7. N-{1-[4-(2-chloroethyl)phenyl]-2-ethyl-1H-benzimidazol-5-yl}methanesulfonamide The title compound was prepared according to the procedure described in step 7 of Example 1 from 2-ethyl-1-[4-(2-hydroxyethyl)phenyl]-1H-benzimidazol-5-yl}methanesulfonamide (step 6).

¹H-NMR (CDCl₃) δ 7.74–6.85 (7H, m), 3.83 (2H, t, J=7.1 Hz), 3.21 (2H, t, J=7.1 Hz), 2.98 (3H, s), 2.85 (2H, q, J=7.5 Hz), 1.38 (3H, t, J=7.5 Hz).

STEP 8. N-{1-[4-(2-Azidoethyl)phenyl]-2-ethyl-1H-benzimidazol-5-yl}methanesulfonamide The title compound was prepared according to the procedure described in step 8 of Example 1 from N-{1-[4-(2-chloroethyl)phenyl]-2-ethyl-1H-benzimidazol-5-yl}methanesulfonamide (step 7).

¹H-NMR (CDCl₃) δ 7.64 (1H, br), 7.45 (2H, d, J=8.3 Hz), 7.31 (2H, d, J=8.1 Hz), 7.19 (1H, dd, J=1.8, 8.8 Hz), 7.07 (1H, d, J=8.4 Hz), 6.81 (1H, s), 3.62 (2H, t, J=6.8 Hz), 3.02 (2H, t, J=7.0 Hz), 2.98 (3H, s), 2.79 (2H, q, J=7.5 Hz), 1.35 (3H, t, J=7.5 Hz).

STEP 9. N-{1-[4-(2-Aminoethyl)phenyl]-6-chloro-2-ethyl-1H-benzimidazol-5-yl}methanesulfonamide The title compound was prepared according to the procedure described in step 9 of Example 1 from N-{1-[4-(2-azidoethyl)phenyl]-2-ethyl-1H-benzimidazol-5-yl}methanesulfonamide (step 8).

MS (EI) m/z 358 (M⁺).

STEP 10. N-{1-[4-(2-aminoethyl)phenyl]-2-ethyl-1H-benzimidazol-5-yl}methanesulfonamide The title compound was prepared according to the procedure described in step 10 of Example 1 from N-{1-[4-(2-aminoethyl)phenyl]-6-chloro-2-ethyl-1H-benzimidazol-5-yl}methanesulfonamide (step 9).

MS (ESI) m/z 556 (M+H)⁺; ¹H-NMR (CDCl₃) δ 9.49 (1H, s), 7.76 (2H, d, J=7.1 Hz), 7.51 (1H, br), 7.42–7.34 (6H, m), 7.07 (1H, d, J=8.6 Hz), 7.01 (1H, d, J=8.6 Hz), 6.53 (1H, br), 3.40–3.33 (2H, m), 2.89 (3H, s), 2.81–2.66 (4H, m), 2.33 (3H, s), 1.21 (3H, t, J=7.5 Hz); IR (KBr) ν$_{max}$ 1697, 1684, 1508, 1458, 1148 cm⁻¹.

EXAMPLE 90

2-ETHYL-5-HYDROXY-1-(4-{2-[({[(4-METHYLPHENYL)SULFONYL]AMINO}CARBONYL)AMINO]ETHYL}PHENYL)-1H-BENZIMIDAZOLE

STEP 1. 1-[4-(2-Bromoethyl)phenyl]-2-ethyl-1H-benzimidazol-5-ol

A mixture of 1-[4-(2-chloroethyl)phenyl]-2-ethyl-5-methoxy-1H-benzimidazole (step 5 of Example 71, 600 mg, 1.9 mmol) in 48% hydrobromic acid (60 mL) was stirred at 100° C. for 6 h. After cooling, the mixture was neutralized with 2N aqueous NaOH and extracted with ethyl acetate (100 mL). The organic layer was washed with brine (50 mL), dried (Na₂SO₄), and concentrated to afford 890 mg (quant.) of the title compound as pale yellow solids: ¹H-NMR (CDCl₃) δ 7.64 (4H, s), 7.16 (2H, m), 6.97–7.01 (1H, m), 3.86 (2H, t, J=7.1 Hz), 3.30 (2H, t, J=7.1 Hz), 2.92 (2H, q, J=7.8 Hz), 1.29 (3H, t, J=7.8 Hz).

STEP 2. 1-[4-(2-Bromoethyl)phenyl]-2-ethyl-1H-benzimidazol-5-yl tert-butyl(dimethyl)silyl ether A mixture of 1-[4-(2-bromoethyl)phenyl]-2-ethyl-1H-benzimidazol-5-ol (step 1, 200 mg, 0.58 mmol), tert-butyldimethylsilyl chloride (100 mg, 0.7 mmol) and imidazole (47 mg, 1.45 mmol) in DMF (5 mL) was stirred at room temperature for 3 h. The reaction mixture was poured into water (50 mL), and extracted with ethyl acetate (100 mL). The organic layer was washed with brine (50 mL), then dried (Na$_2$SO$_4$). After removal of solvent, the crude product was purified by flash column chromatography on silica gel eluting with hexane/ethyl acetate (1:1) to afford 119 mg (45%) of the title compound as white solids: $^1$H-NMR (CDCl$_3$) δ 7.20 (2H, d, J=8.4 Hz), 7.10 (2H, d, J=8.4 Hz), 7.01 (1H, d, J=2.3 Hz), 6.72 (1H, d, J=8.6 Hz), 6.52 (1H, dd, J=2.3 Hz, 8.6 Hz), 3.45 (2H, t, J=7.4 Hz), 3.07 (2H, t, J=7.4 Hz), 2.56 (2H, q, J=7.5 Hz), 1.14 (3H, t, J=7.5 Hz), 0.79 (9H, s), 0.05 (6H, s).

STEP 3. 1-[4-(2-Azidoethyl)phenyl]-2-ethyl-1H-benzimidazol-5-yl tert-butyl(dimethyl)silyl ether The title compound was prepared according to the procedure described in step 8 of Example 1 from 1-[4-(2-bromoethyl)phenyl]-2-ethyl-1H-benzimidazol-5-yl tert-butyl(dimethyl)silyl ether (step 2).

$^1$H-NMR (CDCl$_3$) δ 7.20 (2H, d, J=8.3 Hz), 7.02–7.12 (3H, m), 6.70 (1H, d, J=8.6 Hz), 6.50–6.54 (1H, m), 3.39 (2H, t, J=6.9 Hz), 2.79 (2H, t, J=6.9 Hz), 2.55 (2H, q, J=7.6 Hz), 1.13 (3H, t, J=7.6 Hz), 0.79 (9H, s), 0.00 (6H, s).

STEP 4. 2-[4-(5-{[tert-Butyl(dimethyl)silyl]oxy}-2-ethyl-1H-benzimidazol-1-yl)phenyl]ethylamine The title compound was prepared according to the procedure described in step 7 of Example 37 from 1-[4-(2-azidoethyl)phenyl]-2-ethyl-1H-benzimidazol-5-yl tert-butyl(dimethyl)silyl ether (step 3).

$^1$H-NMR (CDCl$_3$) δ 7.18 (2H, d, J=8.2 Hz), 7.02–7.08 (3H, m), 6.72 (1H, d, J=8.6 Hz), 6.52 (1H, dd, J=2.2 Hz, 8.6 Hz), 2.86 (2H, t, J=6.6 Hz), 2.66 (2H, t, J=6.6 Hz), 2.55 (2H, q, J=7.5 Hz), 1.13 (3H, t, J=7.5 Hz), 0.79 (9H, s), 0.00 (6H, s).

STEP 5. 5-{[tert-Butyl(dimethyl)silyl]oxy}-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(5-{[tert-butyl(dimethyl)silyl]oxy}-2-ethyl-1H-benzimidazol-1-yl)phenyl]ethylamine (step 4).

$^1$H-NMR (CDCl$_3$) δ 7.53 (2H, d, J=8.3 Hz), 7.02–7.13 (7H, m), 6.70 (1H, d, J=8.6 Hz), 6.52 (1H, dd, J=2.2 Hz, 8.6 Hz), 6.46 (1H, br.s), 3.37 (2H, t, J=6.4 Hz), 2.71 (2H, t, J=6.4 Hz), 2.53 (2H, q, J=7.6 Hz), 2.18 (3H, s), 1.11 (3H, t, J=7.6 Hz), 0.79 (9H, s), 0.00 (6H, s).

STEP 6. 2-Ethyl-5-hydroxy-1-(4-{2-[({[(4-methylphenyl)sulfonyl]amino}carbonyl)amino]ethyl}phenyl)-1H-benzimidazole A solution of 5-{[tert-butyl(dimethyl)silyl]oxy}-2-ethyl-1-(4-{2-[({[(4-methylphenyl)sulfonyl]amino}carbonyl)amino]ethyl}phenyl)-1H-benzimidazole (step 5, 78 mg, 0.13 mmol) in THF (5 mL) was added tetrabutylammonium fluoride (1.0 M solution in THF, 0.16 mL, 0.16 mmol) at 0° C. The mixture was stirred at 0° C. for 2.5 h, then concentrated. The residue was dissolved in water (30 mL) and extracted with dichloromethane (50 mL). The organic layer was dried (Na$_2$SO$_4$) and concentrated. The residue was purified by flash column chromatography on silica gel eluting with dichloromethane/methanol (gradient elution from 20:1 to 10:1) to afford 57 mg (92%) of the title compound as white amorphous: MS (ESI) m/z 479 (M+H)$^+$;

$^1$H-NMR (DMSO-d$_6$) δ 7.76 (2H, d, J=7.6 Hz), 7.35–7.39 (6H, m), 6.96 (1H, s), 6.85 (1H, d, J=8.6 Hz), 6.65 (1H, d, J=8.6 Hz), 6.51 (1H, br.s), 3.17 (2H, br.s), 2.76 (2H, t, 6.6 Hz), 2.67 (2H, q, J=7.6 Hz), 2.34 (3H, s), 1.20 (3H, t, J=7.6 Hz).

EXAMPLE 91

2-ETHYL-4,5-DIMETHYL-1-(4-{2-[({[(4-METHYLPHENYL)SULFONYL]AMINO}CARBONYL)AMINO]ETHYL}PHENYL)-1H-BENZIMIDAZOLE

STEP 1. 2-[(3,4-Dimethyl-2-nitroanilino)phenyl]ethanol

The title compound was prepared according to the procedure described in step 1 of Example 45 from 3,4-dimethyl-2-nitroaniline and 4-bromophenylethyl ethanol.

$^1$H-NMR (CDCl$_3$) δ 7.16 (2H, d, J=8.4 Hz), 7.09 (1H, s), 7.03 (2H, d, J=8.4 Hz), 6.91 (1H, s), 3.89–3.81 (2H, m), 2.83 (2H, t, J=6.4 Hz), 2.27 (3H, s), 2.25 (3H, s)

STEP 2. 2-[(2-Amino-3,4-dimethylanilino)phenyl]ethanol

The title compound was prepared according to the procedure described in step 2 of Example 28 from 2-[(3,4-dimethyl-2-nitroanilino)phenyl]ethanol (step 1).

$^1$H-NMR (CDCl$_3$) δ 7.02 (2H, d, J=8.6 Hz), 6.86 (1H, d, J=7.9 Hz), 6.62–6.58 (3H, m), 5.09 (1H, br.s), 3.77 (2H, t, J=6.6 Hz), 2.74 (2H, t, J=6.6 Hz), 2.27 (3H, s), 2.11 (3H, s)

STEP 3. 2-[4-(2-Ethyl-4,5-dimethyl-1H-benzimidazol-1-yl)phenyl]ethyl propionate

The title compound was prepared according to the procedure described in step 5 of Example 1 from 2-[(2-amino-3,4-dimethylanilino)phenyl]ethanol (step 2) and propionyl chloride.

MS (EI) m/z 350 (M$^+$).

STEP 4. 2-[4-(2-Ethyl-4,5-dimethyl-1H-benzimidazol-1-yl)phenyl]ethanol

The title compound was prepared according to the procedure described in step 6 of Example 1 from 2-[4-(2-ethyl-4,5-dimethyl-1H-benzimidazol-1-yl)phenyl]ethyl propionate (step 3).

$^1$H-NMR (CDCl$_3$) δ 7.42 (2H, d, J=8.4 Hz), 7.27 (2H, d, J=8.4 Hz), 6.99 (1H, d, J=8.3 Hz), 6.82 (1H, d, J=8.3 Hz), 3.98 (2H, t, J=6.6 Hz), 2.99 (2H, t, J=6.6 Hz), 2.82 (2H, q, J=7.5 Hz), 2.63 (3H, s), 2.39 (3H, s), 1.26 (3H, t, J=7.5 Hz).

STEP 5. 2-[4-(2-Ethyl-4,5-dimethyl-1H-benzimidazol-1-yl)phenyl]ethyl azide

The title compound was prepared according to the procedure described in step 5 of Example 26 from 2-[4-(2-ethyl-4,5-dimethyl-1H-benzimidazol-1-yl)phenyl]ethanol (step 4).

$^1$H-NMR (CDCl$_3$) δ 7.42 (2H, d, J=8.6 Hz), 7.30 (2H, d, J=8.6 Hz), 7.00 (1H, d, J=8.2 Hz), 6.82 (1H, d, J=8.2 Hz), 3.61 (2H, t, J=7.1 Hz), 3.01 (2H, t, J=7.1 Hz), 2.83 (2H, q, J=7.6 Hz), 2.63 (3H, s), 2.39 (3H, s), 1.26 (3H, t, J=7.6 Hz).

STEP 6. 2-[4-(2-Ethyl-4,5-dimethyl-1H-benzimidazol-1-yl)phenyl]ethylamine

The title compound was prepared according to the procedure described in step 9 of Example 1 from 2-[4-(2-ethyl-4,5-dimethyl-1H-benzimidazol-1-yl)phenyl]ethyl azide (step 5).

$^1$H-NMR (CDCl$_3$) δ 7.39 (2H, d, J=8.4 Hz), 7.28 (2H, d, J=8.4 Hz), 6.99 (1H, d, J=8.2 Hz), 6.83 (1H, d, J=8.2 Hz), 3.09 (2H, t, J=6.6 Hz), 2.92–2.79 (4H, m), 2.63 (3H, s), 2.39 (3H, s), 1.27 (3H, t, J=7.6 Hz)

STEP 7. 2-Ethyl-4,5-dimethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-ethyl-4,5-dimethyl-1H-benzimidazol-1-yl)phenyl]ethylamine (step 6).

¹H-NMR (CDCl₃) δ 7.76 (2H, d, J=8.2 Hz), 7.30–7.19 (6H, m), 7.00 (1H, d, J=8.2 Hz), 6.81 (1H, d, J=8.2 Hz), 6.65 (1H, m), 3.56–3.54 (2H, m), 2.89 (2H, t, J=6.9 Hz), 2.80 (2H, q, J=7.6 Hz), 2.59 (3H, s), 2.38 (6H, s), 1.22 (3H, t, J=7.6 Hz).

EXAMPLE 92

2-ETHYL-4,5-DIMETHYL-1-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 2-ethyl-4,5-dimethyl-1-(4-{2-[({[(4-methylphenyl)sulfonyl]amino}carbonyl)amino]ethyl}phenyl)-1H-benzimidazole (Example 91).

¹H-NMR (DMSO-d₆) δ 7.59 (2H, d, J=8.4 Hz), 7.39–7.30 (4H, m), 7.12 (2H, d, J=8.4 Hz), 6.94 (1H, d, J=8.3 Hz), 6.77 (1H, d, J=8.3 Hz), 3.13 (2H, m), 2.74–2.67 (4H, m), 2.48 (3H, s), 2.30 (3H, s), 2.27 (3H, s), 1.19 (3H, t, J=7.5 Hz); IR (KBr) ν_{max} 1599, 1516, 1425, 1227, 1128, 1086 cm⁻¹.

EXAMPLE 93

4,6-DIMETHYL-2-ETHYL-3-(4-{2-({[(4-METHYLPHENYL)SULFONYL]AMINO}CARBONYL)AMINO]ETHYL}PHENYL)-1H-BENZIMIDAZOLE

STEP 1. 2-[4-(3,5-Dimethyl-2-nitroanilino)phenyl]ethanol

The title compound was prepared according to the procedure described in step 3 of Example 1 from 4,6-dimethyl-2-fluoronitrobenzene and 4-aminophenylethyl alcohol.

¹H-NMR (CDCl₃) δ 8.08 (1H, br.s), 7.22 (2H, d, J=8.4 Hz), 7.13 (2H, d, J=8.4 Hz), 6.91 (1H, s), 6.51 (1H, s), 3.89 (2H, t, J=6.4 Hz), 2.87 (2H, t, J=6.4 Hz), 2.47 (3H, s), 2.22 (3H, s).

STEP 2. 2-[4-(2-Amino-3,5-dimethylanilino)phenyl]ethanol

The title compound was prepared according to the procedure described in step 4 of Example 1 from 2-[4-(3,5-dimethyl-2-nitroanilino)phenyl]ethanol (step 1).

¹H-NMR (CDCl₃) δ 6.97–7.04 (2H, m), 6.78 (1H, s), 6.74 (1H, s), 6.59–6.67 (1H, s), 5.15 (1H, br.s), 3.76 (2H, t, J=6.6 Hz), 2.74 (2H, t, J=6.6 Hz), 2.18 (3H, s), 2.17 (3H, s).

STEP 3. 2-[4-(2-Ethyl-4,6-dimethyl-1H-benzimidazol-1-yl)phenyl]ethyl propionate

The title compound was prepared according to the procedure described in step 5 of Example 1 from 2-[4-(2-amino-3,5-dimethylanilino)phenyl]ethanol (step 2) and propionyl chloride.

TLC Rf=0.7 (hexane/ethyl acetate=1:1).

STEP 4. 2-[4-(2-Ethyl-4,6-dimethyl-1H-benzimidazol-1-yl)phenyl]ethanol

The title compound was prepared according to the procedure described in step 6 of Example 1 from 2-[4-(2-amino-3,5-dimethylanilino)phenyl]ethyl propionate (step 3).

¹H-NMR (CDCl₃) δ 7.42 (2H, d, J=8.1 Hz), 7.27 (2H, d, J=8.1 Hz), 6.90 (1H, s), 6.71 (1H, s), 3.98 (2H, t, J=6.4 Hz), 2.99 (2H, t, J=6.4 Hz), 2.81 (2H, q, J=7.3 Hz), 2.65 (3H, s), 2.36 (3H, s), 1.24 (3H, t, J=7.3 Hz).

STEP 5. 1-[4-(2-Chloroethyl)phenyl]-2-ethyl-4,6-dimethyl-1H-benzimidazole

The title compound was prepared according to the procedure described in step 7 of Example 1 from 2-[4-(2-ethyl-4,6-dimethyl-1H-benzimidazol-1-yl)phenyl]ethanol (step 4).

¹H-NMR (CDCl₃) δ 7.42 (2H, d, J=8.0 Hz), 7.30 (2H, d, J=8.0 Hz), 6.90 (1H, s), 6.71 (1H, s), 3.81 (2H, t, J=7.2 Hz), 3.19 (2H, t, J=7.2 Hz), 2.81 (2H, q, J=7.7 Hz), 2.67 (3H, s), 2.37 (3H, s), 1.25 (3H, t, J=7.7 Hz).

STEP 6. 2-[4-(2-Ethyl-4,6-dimethyl-1H-benzimidazol-1-yl)phenyl]ethyl azide

The title compound was prepared according to the procedure described in step 8 of Example 1 from 1-[4-(2-chloroethyl)phenyl]-2-ethyl-4,6-dimethyl-1H-benzimidazole (step 5).

¹H-NMR (CDCl₃) δ 7.42 (2H, d, J=8.3 Hz), 7.30 (2H, d, J=8.3 Hz), 6.90 (1H, s), 6.69 (1H, s), 3.62 (2H, t, J=7.0 Hz), 3.01 (2H, d, J=7.0 Hz), 2.81 (2H, q, J=7.5 Hz), 2.66 (3H, s), 2.36 (3H, s), 1.25 (3H, t, J=7.5 Hz).

STEP 7. 2-[4-(2-Ethyl-4,6-dimethyl-1H-benzimidazol-1-yl)phenyl]ethylamine

The title compound was prepared according to the procedure described in step 9 of Example 1 from 2-[4-(2-ethyl-4,6-dimethyl-1H-benzimidazol-1-yl)phenyl]ethyl azide (step 6).

¹H-NMR (CDCl₃) δ 7.40 (2H, d, J=8.2 Hz), 7.27 (2H, d, J=8.2 Hz), 6.89 (1H, s), 6.71 (1H, s), 3.07 (2H, t, J=6.9 Hz), 2.77–2.89 (4H, m), 2.67 (3H, s), 2.36 (3H, s), 1.25 (3H, t, J=7.6 Hz).

STEP 8. 2-Ethyl-4,6-dimethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-ethyl-4,6-dimethyl-1H-benzimidazol-1-yl)phenyl]ethylamine (step 7).

mp 108–112° C.; MS (ESI) m/z 491 (M+H)⁺; ¹H-NMR (CDCl₃) δ 7.75 (2H, d, J=8.2 Hz), 7.18–7.29 (6H, m), 6.89 (1H, s), 6.67 (1H, s), 6.62 (1H, br.s), 3.51 (2H, br.s), 2.86 (2H, br.s), 2.76 (2H, q, J=7.4 Hz), 2.63 (3H, s), 2.37 (3H, s), 2.33 (3H, s), 1.20 (3H, t, J=7.4 Hz).

EXAMPLE 94

5,6-DIMETHYL-1-(4-{2-[({[(4-METHYLPHENYL)SULFONYL]AMINO}CARBONYL)AMINO]ETHYL}PHENYL)-1H-BENZIMIDAZOLE

STEP 1. 2-[(4,5-Dimethyl-2-nitroanilino)phenyl]ethanol

The title compound was prepared according to the procedure described in step 1 of Example 45 from 4,5-dimethyl-2-nitroaniline and 4-bromophenylethyl alcohol.

¹H-NMR (CDCl₃) δ 9.39 (1H, br.s), 7.96 (1H, s), 7.27 (2H, d, J=8.4 Hz), 7.21 (2H, d, J=8.4 Hz), 7.01 (1H, s), 3.91 (2H, q, H=6.4 Hz), 2.90 (2H, t, J=6.4 Hz), 2.20 (3H, s), 2.19 (3H, s).

STEP 2. 2-[(2-Amino-4,5-dimethylanilino)phenyl]ethanol

The title compound was prepared according to the procedure described in step 2 of Example 28 from 2-[(4,5-dimethyl-2-nitroanilino)phenyl]ethanol (step 1).

$^1$H-NMR (CDCl$_3$) δ 7.04 (2H, d, J=8.4 Hz), 6.86 (1H, s), 6.64 (2H, d, J=8.4 Hz), 6.61 (1H, s), 3.79 (2H, t, J=6.6 Hz), 2.76 (2H, t, J=6.6 Hz), 2.19 (3H, s), 2.12 (3H, s)

STEP 3. 2-[4-(2-Ethyl-5,6-dimethyl-1H-benzimidazol-1-yl)phenyl]ethyl propionate

The title compound was prepared according to the procedure described in step 5 of Example 1 from 2-[(2-amino-4,5-dimethylanilino)phenyl]ethanol (step 2) and propionyl chloride.

MS (EI) m/z 350 (M$^+$).

STEP 4. 2-[4-(2-Ethyl-5,6-dimethyl-1H-benzimidazol-1-yl)phenyl]ethanol

The title compound was prepared according to the procedure described in step 6 of Example 1 from 2-[4-(2-ethyl-5,6-dimethyl-1H-benzimidazol-1-yl)phenyl]ethyl propionate (step 3).

$^1$H-NMR (CDCl$_3$) δ 7.52 (1H, s), 7.44 (2H, d, J=8.3 Hz), 7.28 (2H, d, J=8.3 Hz), 6.87 (1H, s), 4.00 (2H, t, J=6.6 Hz), 3.01 (2H, t, J=6.6 Hz), 2.76 (2H, q, J=7.5 Hz), 2.36 (3H, s), 2.29 (3H, s), 1.31 (3H, t, J=7.5 Hz).

STEP 5. 2-[4-(2-Ethyl-5,6-dimethyl-1H-benzimidazol-1-yl)phenyl]ethyl azide

The title compound was prepared according to the procedure described in step 5 of Example 26 from 2-[4-(2-ethyl-5,6-dimethyl-1H-benzimidazol-1-yl)phenyl]ethanol (step 4).

TLC Rf=0.70 (hexane/ethyl acetate=1:1).

STEP 6. 2-[4-(2-Ethyl-5,6-dimethyl-1H-benzimidazol-1-yl)phenyl]ethylamine

The title compound was prepared according to the procedure described in step 9 of Example 1 from 2-[4-(2-ethyl-5,6-dimethyl-1H-benzimidazol-1-yl)phenyl]ethyl azide (step 5).

$^1$H-NMR (CDCl$_3$) δ 7.53 (1H, s), 7.40 (2H, d, J=8.1 Hz), 7.28 (2H, d, J=8.1 Hz), 6.87 (1H, s), 3.17 (2H, t, J=7.3 Hz), 3.00 (2H, t, J=7.3 Hz), 2.76 (2H, q, J=7.5 Hz), 2.36 (3H, s), 2.29 (3H, s), 1.31 (3H, t, J=7.5 Hz).

STEP 7. 2-Ethyl-5,6-dimethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(2-ethyl-5,6-dimethyl-1H-benzimidazol-1-yl)phenyl]ethylamine (step 6).

$^1$H-NMR (CDCl$_3$) δ 7.79 (2H, d, J=8.1 Hz); 7.48 (1H, s), 7.29–7.15 (6H, m), 6.86 (1H, s), 6.60 (1H, br.s), 3.57–3.55 (2H, m), 2.91–2.89 (2H, m), 2.70 (2H, q, J=7.5 Hz), 2.39 (3H, s), 2.35 (3H, s), 2.27 (3H, s), 1.25 (3H, t, J=7.5 Hz).

EXAMPLE 95

5,6-DIMETHYL-1-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 2-ethyl-5,6-dimethyl-1-(4-{2-[({[(4-methylphenyl)sulfonyl]amino}carbonyl)amino]ethyl}phenyl)-1H-benzimidazole (Example 94).

$^1$H-NMR (DMSO-d$_6$) δ 7.60 (2H, d, J=8.1 Hz), 7.39–7.32 (5H, m), 7.13 (2H, d, J=8.1 Hz), 6.86 (1H, s), 3.16 (2H, m), 2.73–2.64 (4H, m), 2.29 (3H, s), 2.27 (3H, s), 2.23 (3H, s), 1.20 (3H, t, J=7.4 Hz); IR (KBr) ν$_{max}$ 1599, 1516, 1468, 1404, 1283, 1236, 1130, 1086 cm$^{-1}$.

EXAMPLE 96

5,6-DICHLORO-2-ETHYL-1-(4-{2-[({[(4-METHYLPHENYL)SULFONYL]AMINO}CARBONYL)AMINO]ETHYL}PHENYL)-1H-BENZIMIDAZOLE

STEP 1. 2-[4-(4,5-Dichloro-2-nitroanilino)phenyl]ethanol

The title compound was prepared according to the procedure described in step 3 of Example 1 from 2,4,5-trichloronitrobenzene and 4-aminophenylethyl alcohol.

MS (EI) m/z 327 (M$^+$).

STEP 2. 2-[4-(2-Amino-4,5-dichloroanilino)phenyl]ethanol

The title compound was prepared according to the procedure described in step 2 of Example 28 from 2-[4-(4,5-dichloro-2-nitroanilino)phenyl]ethanol (step 1).

$^1$H-NMR (CDCl$_3$) δ 7.16 (1H, s), 7.11 (2H, d, J=8.0 Hz), 6.87 (1H, s), 6.74 (2H, d, J=8.0 Hz), 5.10 (1H, br.s), 3.90–3.60 (2H, m), 2.79 (2H, t, J=7.0 Hz).

STEP 3. 2-[4-(5,6-Dichloro-2-ethyl-1H-benzimidazol-1-yl)phenyl]ethyl propionate

The title compound was prepared according to the procedure described in step 5 of Example 1 from 2-[4-(2-amino-4,5-dichloroanilino)phenyl]ethanol (step 2) and propionyl chloride.

MS (EI) m/z 390 (M$^+$); $^1$H-NMR (CDCl$_3$) δ 7.84 (1H, s), 7.45 (2H, d, J=8.1 Hz), 7.27 (2H, d, J=8.1 Hz), 7.16 (1H, s), 4.37 (2H, t, J=6.8 Hz), 3.09 (2H, t, J=6.8 Hz), 2.77 (2H, q, J=7.5 Hz), 2.36 (2H, q, J=7.5 Hz), 1.35 (3H, t, J=7.5 Hz), 1.16 (3H, t, J=7.5 Hz).

STEP 4. 2-[4-(5,6-Dichloro-2-ethyl-1H-benzimidazol-1-yl)phenyl]ethanol

The title compound was prepared according to the procedure described in step 6 of Example 1 from 2-[4-(5,6-dichloro-2-ethyl-1H-benzimidazol-1-yl)phenyl]ethyl propionate (step 3).

$^1$H-NMR (CDCl$_3$) δ 7.84 (1H, s), 7.47 (2H, d, J=8.0 Hz), 7.28 (2H, d, J=8.0 Hz), 7.18 (1H, s), 4.10–3.94 (2H, m), 3.01 (2H, t, J=6.4 Hz), 2.77 (2H, q, J=7.5 Hz), 1.34 (3H, t, J=7.5 Hz).

STEP 5. 2-[4-(5,6-Dichloro-2-ethyl-1H-benzimidazol-1-yl)phenyl]ethyl azide

The title compound was prepared according to the procedure described in step 5 Example 26 from 2-[4-(5,6-dichloro-2-ethyl-1H-benzimidazol-1-yl)phenyl]ethanol (step 4).

MS (EI) m/z 359 (M$^+$); $^1$H-NMR (CDCl$_3$) δ 7.85 (1H, s), 7.46 (2H, d, J=8.1 Hz), 7.28 (2H, d, J=8.1 Hz), 7.17 (1H, s), 3.62 (2H, t, J=7.0 Hz), 3.02 (2H, t, J=7.0 Hz), 2.76 (2H, q, J=7.5 Hz), 1.34 (3H, t, J=7.5 Hz).

STEP 6. 2-[4-(5,6-Dichloro-2-ethyl-1H-benzimidazol-1-yl)phenyl]ethylamine

The title compound was prepared according to the procedure described in step 7 of Example 37 from 2-[4-(5,6-dichloro-2-ethyl-1H-benzimidazol-1-yl)phenyl]ethyl azide (step 5).

$^1$H-NMR (CDCl$_3$) δ 7.84 (1H, s), 7.43 (2H, d, J=8.4 Hz), 7.27 (2H, d, J=8.4 Hz), 7.22 (1H, s), 3.14 (2H, t, J=7.2 Hz), 2.97 (2H, t, J=7.2 Hz), 2.76 (2H, q, J=7.6 Hz), 2.10 (2H, br.s), 1.34 (3H, t, J=7.6 Hz).

STEP 7. 5,6-Dichloro-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(5,6-dichloro-2-ethyl-1H-benzimidazol-1-yl)phenyl]ethylamine (step 6).

$^1$H-NMR (CDCl$_3$) δ 8.01 (1H, s), 7.70 (2H, d, J=8.3 Hz), 7.46 (2H, d, J=8.3 Hz), 7.36–7.29, (3H, m) 7.24 (2H, d, J=8.3 Hz), 6.81 (1H, br.s), 3.57–3.46 (2H, m), 3.06–2.88 (4H, m), 2.38 (3H, s), 1.43 (3H, t, J=6.9 Hz).

EXAMPLE 97

2-[4-(5,6-DICHLORO-2-ETHYL-1H-BENZIMIDAZOL-1-YL)PHENYL]ETHYL(4-METHYLPHENYL)SULFONYLCARBAMATE

The title compound was prepared according to the procedure described in Example 3 from 2-[4-(5,6-dichloro-2-ethyl-1H-benzimidazol-1-yl)phenyl]ethanol (step 4 of Example 96).

$^1$H-NMR (CDCl$_3$) δ 7.92 (2H, d, J=8.4 Hz), 7.85 (1H, s), 7.37 (2H, d, J=8.4 Hz), 7.35 (2H, d, J=8.4 Hz), 7.24 (2H, d, J=8.4 Hz), 7.16 (1H, s), 4.72 (1H, br.s), 4.38 (2H, t, J=6.8 Hz), 3.03 (2H, t, J=6.8 Hz), 2.75 (2H, q, J=7.5 Hz), 2.44 (3H, s), 1.34 (3H, t, J=7.5 Hz).

EXAMPLE 98

5,6-DICHLORO-2-ETHYL-1-(4-{2-[HYDROXY({[(4-METHYLPHENYL)SULFONYL]AMINO}CARBONYL)AMINO]ETHYL}PHENYL)-1H-BENZIMIDAZOLE

STEP 1. 1-[4-(2-{(tert-Butoxycarbonyl)[(tert-butoxycarbonyl)oxy]amino}ethyl)phenyl]-5,6-dichloro-2-ethyl-1H-benzimidazole To a stirred mixture of 2-[4-(5,6-dichloro-2-ethyl-1H-benzimidazol-1-yl)phenyl]ethanol (Example 96, 100 mg, 0.3 mmol), N,O-Bis-tert-butoxycarbonylhydroxylamine (Baillie, L. C.; Batsanov, A.; Bearder, J. R.; Whiting, D. A. J. Chem. Soc. Perkin Trans. 1, 1998, 20, 3471, 140 mg, 0.6 mmol) and triphenylphosphine (158 mg, 0.6 mmol) in THF (10 mL) was added diethyl azodicarboxylate (DEAD) (0.1 mL, 0.6 mmol). The mixture was stirred under nitrogen atmosphere at room temperature for 2.5 h. The solvent was removed and the residue was purified by flash column chromatography on silica gel eluting with hexane/ethyl acetate (1:1) to afford 174 mg (quant.) of the title compound as yellow amorphous: $^1$H-NMR (CDCl$_3$) δ 7.84 (1H, s), 7.46 (2H, d, J=8.4 Hz), 7.25 (2H, d, J=8.4 Hz), 7.16 (1H, s), 3.92 (2H, t, J=6.7 Hz), 3.05 (2H, t, J=6.7 Hz), 2.76 (2H, q, J=7.6 Hz), 1.56 (9H, s), 1.46 (9H, s), 1.33 (3H, t, J=7.6 Hz).

STEP 2. N-{2-[4-(5,6-Dichloro-2-ethyl-1H-benzimidazol-1-yl)phenyl]ethyl}hydroxylamine A mixture of 1-[4-(2-{(tert-butoxycarbonyl)[(tert-butoxycarbonyl)oxy]amino}ethyl)phenyl]-5,6-dichloro-2-ethyl-1H-benzimidazole (step 1, 174 mg, 0.3 mmol) and 2N hydrochloric acid (3 mL) in ethyl acetate (20 mL) was stirred at room temperature for 1 day. The reaction mixture was poured into water (100 mL), neutralized with saturated aqueous sodium bicarbonate, and extracted with ethyl acetate (100 mL). The organic layer was washed with brine (50 mL), dried (Na$_2$SO$_4$), and concentrated to afford 162 mg (quant.) of the title compound as a yellow oil: $^1$H-NMR (CDCl$_3$) δ 10.35 (2H, br.s), 7.89 (1H, s), 7.46–7.50 (2H, m), 7.29 (2H, d, J=6.8 Hz), 7.17 (1H, s), 3.37 (2H, t, J=6.9 Hz), 3.12 (2H, t, J=6.9 Hz), 2.80 (2H, q, J=6.9 Hz), 1.34 (3H, m).

STEP 3. 5,6-Dichloro-2-ethyl-1-(4-{2-[hydroxy({[(4-methylphenyl)sulfonyl]amino}carbonyl)amino]ethyl}phenyl)-1H-benzimidazole The reaction was carried out according to the procedure described in step 10 of Example 1 from N-{2-[4-(5,6-dichloro-2-ethyl-1H-benzimidazol-1-yl)phenyl]ethyl}hydroxylamine (step 2).

MS (ESI) m/z 547 (M+H)$^+$; $^1$H-NMR (CDCl$_3$) δ 7.92 (2H, d, J=8.4 Hz), 7.79 (2H, d, J=7.2 Hz), 7.34–7.45 (2H, m), 7.13–7.18 (4H, m), 3.85 (1H, br.s), 3.05 (2H, br.s), 2.66–2.80 (4H, m), 2.38 (3H, s), 1.32 (3H, t, J=7.4 Hz); IR (KBr) ν$_{max}$ 1654, 1517, 1452, 1164, 1095, 869 cm$^{-1}$.

EXAMPLE 99

5,6-DICHLORO-2-ETHYL-1-(4-{CIS-3-[({[(4-METHYLPHENYL)SULFONYL]AMINO}CARBONYL)AMINO]CYCLOBUTYL}PHENYL)-1H-BENZIMIDAZOLE

STEP 1. trans-3-Phenylcyclobutyl benzoate

To a stirred solution of cis-3-phenylcyclobutanol (Eckehard, V. D.; et al. Chem. Ber., 1993, 126, 2759., 4.6 g, 30.2 mmol), triphenylphosphine (3.3 g, 59.1 mmol) and benzoic acid (7.6 mg, 62.3 mmol) was added diethyl azodicarboxylate (DEAD) (10.9 g, 62.3 mmol) at room temperature. The resulting mixture was stirred at room temperature for 40 min, then the mixture was concentrated. The residue was dissolved in diethyl ether (100 mL) and washed with saturated aqueous sodium bicarbonate (50 mL), water (50 mL), and brine (50 mL). The organic layer was dried (Na$_2$SO$_4$), and concentrated. Purification by flash column chromatography on silica gel eluting with hexane/ethyl acetate (10:1) to afford 6.52 g (86%) of the title compound as a pale yellow oil: $^1$H-NMR (CDCl$_3$) δ 7.71–7.20 (10H, m), 5.49–5.41 (1H, m), 3.82–3.72 (1H, m), 2.78–2.64 (4H, m).

STEP 2. trans-3-Phenylcyclobutanol

To a solution of trans-3-phenylcyclobutyl benzoate (step 1, 6.5 g, 26.0 mmol) in methanol (100 mL) was added 4N aqueous LiOH (20 mL, 80 mmol) and the resulting mixture was stirred at room temperature for 10 min. The mixture was concentrated. The residue was dissolved in water (100 mL) and extracted with ethyl acetate (100 mL). The organic layer was washed with brine (100 mL), dried (Na$_2$SO$_4$), and concentrated. Purification by flash column chromatography on silica gel eluting with hexane/ethyl acetate (5:1) to afford 3.65 g (93%) of the title compound as a colorless oil: $^1$H-NMR (CDCl$_3$) δ 7.34–7.16 (5H, m), 4.60–4.51 (1H, m), 3.69–3.59 (1H, m), 2.55–2.37 (4H, m).

STEP 3. trans-3-(4-Nitrophenyl)cyclobutanol

To a mixture of nitric acid (fuming, 2.3 mL) and acetic anhydride (25 mL) was added dropwise a mixture of trans-3-phenylcyclobutyl benzoate (step 2, 3.7 g, 24.6 mmol) and sulfuric acid in acetic anhydride (25 mL) at −23° C. The resulting mixture was stirred in an ice-bath for 1.5 h.

The mixture was poured into ice water (200 mL) and extracted with dichloromethane (2×100 mL). The organic layer was washed with water and brine (100 mL), then dried (Na$_2$SO$_4$), and concentrated. The oily residue was dissolved in methanol (100 mL), and 4N aqueous LiOH (50 mL) was added. The resulting mixture was stirred at room temperature for 10 min, then concentrated. The residue was dissolved in water (100 mL) and extracted with ethyl acetate (100 mL). The organic layer was washed with brine, dried (Na$_2$SO$_4$), and concentrated. Purification by flash column chromatography on silica gel eluting with hexane/ethyl acetate (2:1) to afford 2.7 g (56%) of the title compound as a pale yellow oil: MS (EI) m/z 193 (M$^+$); $^1$H-NMR (CDCl$_3$) δ 8.18 (2H, d, J=8.6 Hz), 7.38 (2H, d, J=8.6 Hz), 4.62–4.52 (1H, m), 3.81–3.71 (1H, m), 2.45–2.45 (4H, m).

STEP 4. trans-3-(4-Aminophenyl)cyclobutanol

To a stirred solution of trans-3-(4-nitrophenyl)cyclobutanol (step 3, 1.0 g, 4.9 mmol) in methanol (20 mL) was added 10% Pd—C (50 mg). The mixture was stirred at room temperature under hydrogen atmosphere for 2.5 h. The palladium catalyst was removed by filtration and washed with methanol (100 mL) and ethyl acetate (100 mL). The filtrate was concentrated under reduced pressure to afford 0.9 g (quant.) of the title compound as pale yellow solids: MS (EI) m/z 163 (M$^+$); $^1$H-NMR (CDCl$_3$) δ 7.03 (2H, d, J=8.3 Hz), 6.66 (2H, d, J=8.3 Hz), 4.56–4.47 (1H, m), 3.58–3.48 (3H, m), 2.48–2.31 (2H, m), 1.73 (1H, d, J=5.1 Hz).

STEP 5. trans-3-[4-(4,5-Dichloro-2-nitroanilino)phenyl]cyclobutanol

The title compound was prepared according to the procedure described in step 3 of Example 1 from 2,4,5-trichloronitrobenzene and trans-3-(4-aminophenyl)cyclobutanol (step 4).

$^1$H-NMR (CDCl$_3$) δ 9.40 (1H, br.s), 8.27 (1H, s), 7.33 (2H, d, J=8.1 Hz), 7.22 (2H, d, J=8.1 Hz), 7.19 (1H, s), 4.63–4.55 (1H, m), 3.73–3.63 (1H, m), 2.57–2.43 (4H, m).
MS (EI) m/z: 352 (M$^+$).

STEP 6. trans-3-[4-(2-Amino-4,5-dichloroanilino)phenyl]cyclobutanol

The title compound was prepared according to the procedure described in step 3 of Example 6 from trans-3-[4-(4,5-dichloro-2-nitroanilino)phenyl]cyclobutanol (step 5).

$^1$H-NMR (CDCl$_3$) δ 7.16 (1H, s), 7.12 (2H, d, J=8.6 Hz), 6.86 (1H, s), 6.75 (2H, d, J=8.6 Hz), 5.08 (1H, br.s), 4.58–4.49 (1H, m), 3.77 (2H, br.s), 3.62–3.52 (1H, m), 2.50–2.34 (4H, m).

STEP 7. trans-3-[4-(5,6-Dichloro-2-ethyl-1H-benzimidazol-1-yl)phenyl]cyclobutyl propionate The title compound was prepared according to the procedure described in step 5 of Example 1 from trans-3-[4-(2-amino-4,5-dichloroanilino)phenyl]cyclobutanol (step 6) and propionyl chloride.

TLC Rf=0.56 (ethyl acetate/hexane=1:1).

STEP 8. trans-3-[4-(5,6-Dichloro-2-ethyl-1H-benzimidazol-1-yl)phenyl]cyclobutanol The title compound was prepared according to the procedure described in step 6 of Example 1 from trans-3-[4-(2-amino-4,5-dichloroanilino)phenyl]cyclobutyl propionate (step 7).

MS (EI) m/z: 360 (M$^+$); $^1$H-NMR (CDCl$_3$) δ 7.85 (1H, br.s), 7.45 (2H, d, J=8.1 Hz), 7.27 (2H, d J=8.1 Hz), 7.18 (1H, br.s), 4.65–4.55 (1H, m), 3.83–3.73 (1H, m), 2.77 (2H, q, J=7.5 Hz), 263–2.48 (4H, m), 1.34 (3H, t, J=7.5 Hz).

STEP 9. cis-3-[4-(5,6-Dichloro-2-ethyl-1H-benzimidazol-1-yl)phenyl]cyclobutyl azide To a stirred solution of trans-3-[4-(5,6-dichloro-2-ethyl-1H-benzimidazol-1-yl)phenyl]cyclobutanol (step 8, 572 mg, 1.6 mmol), triphenylphosphine (623 mg, 2.4 mmol) and diphenylphosphoryl azide (DPPA) (655 mg, 2.4 mmol) in THF (8 mL) was added diethyl azodicarboxylate (415 mg, 2.4 mmol) at room temperature. The resulting mixture was stirred at room temperature for 3 h, then the mixture was diluted with ethyl acetate (100 mL) and washed with water (100 mL) and brine (100 mL). The organic layer was dried (Na$_2$SO$_4$), and concentrated. Purification by flash column chromatography on silica gel eluting with hexane/ethyl acetate (2:1) to afford 506 mg (83%) of the title compound as colorless solids: MS (EI) m/z: 385 (M$^+$); $^1$H-NMR (CDCl$_3$) δ 7.84 (1H, br.s), 7.42 (2H, d, J=8.3 Hz), 7.28 (2H, d, J=8.3 Hz), 7.17 (1H, br.s), 3.98–3.88 (1H, m), 3.37–3.25 (1H, m), 2.89–2.75 (2H, m), 2.77 (2H, q, J=7.6 Hz), 2.34–2.23 (2H, m), 1.34 (3H, t, J=7.6 Hz).

STEP 10. cis-3-[4-(5,6-Dichloro-2-ethyl-1H-benzimidazol-1-yl)phenyl]cyclobutylamine The title compound was prepared according to the procedure described in step 7 of Example 37 from cis-3-[4-(5,6-dichloro-2-ethyl-1H-benzimidazol-1-yl)phenyl]cyclobutyl azide (step 9).

MS (EI) m/z 359 (M$^+$); $^1$H-NMR (CDCl$_3$) δ 7.84 (1H, br.s), 7.41 (2H, d, J=8.4 Hz), 7.24 (2H, d, J=8.4 Hz), 7.17 (1H, br.s), 3.55–3.43 (1H, m), 3.24–3.12 (1H, m), 2.87–2.73 (4H, m), 1.91–1.80 (2H, m), 1.34 (3H, t, J=7.5 Hz).

STEP 11. 5,6-Dichloro-2-ethyl-1-(4-{cis-3-[({[(4-methylphenyl)sulfonyl]amino}carbonyl)amino]cyclobutyl}phenyl)-1H-benzimidazole The title compound was prepared according to the procedure described in step 10 of Example 1 from cis-3-[4-(5,6-dichloro-2-ethyl-1H-benzimidazol-1-yl)phenyl]cyclobutylamine (step 10).

MS (ESI) m/z 557 (M+H)$^+$; $^1$H-NMR (CDCl$_3$) δ 7.85 (1H, br.s), 7.79 (2H, d, J=8.4 Hz), 7.42 (2H, d, J=8.1 Hz), 7.36 (2H, d, J=8.1 Hz), 7.28 (2H, d, J=8.4 Hz), 7.17 (1H, br.s), 4.35–4.26 (1H, m), 3.35–3.25 (1H, m), 2.93–2.83 (2H, m), 2.78 (2H, q, J=7.6 Hz), 2.46 (3H, s), 2.19–2.07 (2H, m), 1.34 (3H, t, J=7.6 Hz).

EXAMPLE 100

5,6-DICHLORO-1-(4-{1,1-DIMETHYL-2-[({[(4-METHYLPHENYL)SULFONYL]AMINO}CARBONYL)AMINO]ETHYL}PHENYL)-2-ETHYL-1H-BENZIMIDAZOLE

STEP 1. 2-[4-(4,5-Dichloro-2-nitroanilino)phenyl]-2-methylpropanenitrile

The title compound was prepared according to the procedure described in step 3 of Example 1 from 2,4,5-trichloronitroaniline and 2-(4-aminophenyl)-2-methylpropanenitrile (Axton, C. A.; et al. *J. Chem. Soc. Perkin Trans.* 1, 1992, 17, 2203).

$^1$H-NMR (CDCl$_3$) δ 9.38 (1H, br), 8.31 (1H, s), 7.54 (2H, d, J=8.58 Hz), 7.30–7.22 (3H, m), 1.75 (6H, s).

STEP 2. 2-[4-(2-Amino-4,5-dichloroanilino)phenyl]-2-methylpropanenitrile

The title compound was prepared according to the procedure described in step 2 of Example 28 from 2-[4-(4,5-dichloro-2-nitroanilino)phenyl]-2-methylpropanenitrile (step 1).

¹H-NMR (CDCl₃) δ 7.41 (1H, s), 7.30 (2H, d, J=8.4 Hz), 7.09 (1H, s), 6.90 (1H, s), 6.80 (2H, d, J=8.4 Hz), 5.22 (2H, s), 1.62 (6H, s).

STEP 3. 2-[4-(5,6-Dichloro-2-ethyl-1H-benzimidazol-1-yl)phenyl]-2-methylpropanenitrile The title compound was prepared according to the procedure described in step 5 of Example 1 from 2-[4-(2-amino-4,5-dichloroanilino)phenyl]-2-methylpropanenitrile (step 2) and propionyl chloride.

¹H-NMR (CDCl₃) δ 7.91 (1H, s), 7.78 (2H, d, J=8.4 Hz), 7.45 (2H, d, J=8.4 Hz), 7.24 (1H, s), 2.83 (2H, q, J=7.5 Hz), 1.89 (6H, s), 1.42 (3H, t, J=7.3 Hz).

STEP 4. 5,6-Dichloro-1-(4-{1,1-dimethyl-2-[({[(4-methylphenyl)sulfonyl]amino}carbonyl)amino]ethyl}phenyl)-2-ethyl-1H-benzimidazole A mixture of 2-[4-(5,6-dichloro-2-ethyl-1H-benzimidazol-1-yl)phenyl]-2-methylpropanenitrile (step 3, 102 mg, 0.28 mmol), PtO₂ (one portion), chloroform (0.5 mL) in ethanol (15 mL) was stirred under hydrogen atmosphere (4.5 Kg/cm²) at room temperature. After 8 h, the mixture was filtered through a pad of Celite, and the filtrate was concentrated. The residue was suspended in dichloromethane (10 mL). To the suspension was added p-toluenesulfonyl isocyanate (0.3 mL, 1.96 mmol), and triethylamine (0.3 mL, 2.1 mmol) at room temperature. After 0.5 h, the mixture was concentrated. The residue was dissolved in dichloromethane (100 mL) and washed with 10% aqueous citric acid (50 mL), water (50 mL), and brine (50 mL). The organic layer was dried (MgSO₄) and concentrated. The residue was purified by preparative TLC (ethyl acetate/hexane=2:1) to give 62 mg (37%) of the title compound as white solids: ¹H-NMR (CDCl₃) δ 7.83 (1H, s), 7.67 (2H, d, J=9.3 Hz), 7.55 (2H, d, J=9.3 Hz), 7.38–7.22 (4H, m), 7.18 (1H, s), 3.45 (1H, br), 2.76 (2H, q, J=8.4 Hz), 2.34 (3H, s), 1.37 (6H, s), 1.31 (3H, t, J=8.2 Hz).

EXAMPLE 101

STEP 1. Ethyl [4-(4,5-dichloro-2-nitroanilino)phenyl]acetate

The title compound was prepared according to the procedure described in step 3 of Example 1 from ethyl 2,4,5-trichloronitrobenzene and 4-aminophenylacetate.

¹H-NMR (CDCl₃) δ 9.41 (1H, s), 8.32 (1H, s), 7.37 (2H, d, J=8.4 Hz), 7.28 (1H, s), 7.22 (2H, d, J=8.3 Hz), 4.19 (2H, q, J=7.1 Hz), 3.66 (2H, s), 1.29 (3H, t, J=7.1 Hz).

STEP 2. Ethyl [4-(2-Amino-4,5-dichloroanilino)phenyl]acetate

The title compound was prepared according to the procedure described in step 2 of Example 28 from ethyl [4-(4,5-dichloro-2-nitroanilino)phenyl]acetate (step 1).

¹H-NMR (CDCl₃) δ 7.16 (1H, s), 7.15 (2H, d, J=7.5 Hz), 6.86 (1H, s), 6.72 (2H, d, J=7.1 Hz), 5.12 (1H, br.s), 4.15 (2H, q, J=7.0 Hz), 3.79 (2H, br), 3.54 (2H, s), 1.26 (3H, t, J=7.1 Hz).

STEP 3. Ethyl [4-(5,6-Dichloro-2-ethyl-1H-benzimidazol-1-yl)phenyl]acetate

The title compound was prepared according to the procedure described in step 5 of Example 1 from ethyl [4-(2-amino-4,5-dichloroanilino)phenyl]acetate (step 2) and propionyl chloride.

¹H-NMR (CDCl₃) δ 7.84 (1H, s), 7.52 (2H, d, J=8.2 Hz), 7.30 (2H, d, J=8.4 Hz), 7.19 (1H, s), 4.22 (2H, q, J=7.1 Hz), 3.75 (2H, s), 2.77 (2H, q, J=7.5 Hz), 1.34 (3H, t, J=7.5 Hz), 1.32 (3H, t, J=7.1 Hz).

STEP 4. [4-(5,6-Dichloro-2-ethyl-1H-benzimidazol-1-yl)phenyl]acetic acid

To a stirred solution of ethyl [4-(5,6-dichloro-2-ethyl-1H-benzimidazol-1-yl)phenyl]acetate (step 3, 1.30 g, 3.4 mmol) in methanol was added 2N aqueous NaOH (3.4 mL) at room temperature. After 1 h, the mixture was concentrated and the residue was diluted in water (200 mL) and the mixture was washed with diethyl ether (100 mL). The aqueous layer was acidified with 2N hydrochloric acid and extracted with ethyl acetate/THF (v/v, 1:1, 300 mL). The organic extract was washed with water (200 mL), brine (200 mL), and dried (MgSO₄). Removal of solvent gave 1.02 g (86%) of the title compound as a white powder: ¹H-NMR (CDCl₃) δ 7.94 (1H, s), 7.56–7.45 (4H, m), 7.26 (1H, s), 3.72 (2H, s), 2.72 (2H, q, J=7.3 Hz), 1.22 (3H, t, J=7.5 Hz).

STEP 5. 2-[4-(5,6-Dichloro-2-ethyl-1H-benzimidazol-1-yl)phenyl]acetamide

A mixture of [4-(5,6-dichloro-2-ethyl-1H-benzimidazol-1-yl)phenyl]acetic acid (step 4, 0.81 g, 2.3 mmol) and thionyl chloride (10 mL) was stirred for 0.5 h, and concentrated. To the residue was added ammonium hydroxide (28% NH₃ in water, 50 mL) and the mixture was extracted with ethyl acetate/THF (v/v, 1:1, 200 mL). The extract was washed with brine (2×100 mL), dried (MgSO₄), and concentrated. The residue was purified by flash column chromatography on silica gel eluting with dichloromethane/methanol (20:1) to give 349 mg (44%) of the title compound as yellow solids: ¹H-NMR (CDCl₃) δ 7.93 (1H, s), 7.58 (1H, br), 7.51 (2H, d, J=8.4 Hz), 7.47 (2H, d, J=8.4 Hz), 7.27 (1H, s), 7.00 (1H, br), 3.51 (2H, s), 2.71 (2H, q, J=7.5 Hz), 1.21 (3H, t, J=7.5 Hz).

STEP 6. 2-[4-(5,6-Dichloro-2-ethyl-1H-benzimidazol-1-yl)phenyl]-N-({[(4-methylphenyl)sulfonyl]amino}carbonyl)acetamide A mixture of 2-[4-(5,6-dichloro-2-ethyl-1H-benzimidazol-1-yl)phenyl]acetamide (step 5, 105 mg, 0.30 mmol), p-toluenesulfonyl isocyanate (0.07 mL, 0.45 mmol), toluene (10 mL) and THF (5 mL) was heated at reflux temperature. After 6 h, an additional 0.1 mL of p-toluenesulfonyl isocyanate was added and the mixture was heated for 3 h. The mixture was cooled and left at room temperature for 2 days. The mixture was concentrated and the residue was purified by preparative TLC (ethyl acetate) to afford 150 mg (92%) of the title compound as colorless amorphous solids: ¹H-NMR (CDCl₃) δ 9.78 (1H, s), 7.95 (2H, d, J=8.3 Hz), 7.84 (1H, s), 7.54 (2H, d, J=8.4 Hz), 7.34 (2H, d, J=8.0 Hz), 7.32 (2H, d, J=8.4 Hz), 7.18 (1H, s), 3.78 (2H, s), 2.77 (2H, q, J=7.5 Hz), 2.41 (3H, s), 1.35 (3H, t, J=7.5 Hz).

EXAMPLE 102

5,6-DICHLORO-1-(4-{2-[({[(4-METHYLPHENYL)SULFONYL]AMINO}CARBONYL)AMINO]ETHYL}PHENYL)-1H-BENZIMIDAZOLE

STEP 1. 2-[4-(5,6-Dichloro-1H-benzimidazol-1-yl)phenyl]ethyl formate

A mixture of 2-[(4,5-dichloro-2-anilino)phenyl]ethanol (450 mg, 1.42 mmol) and formic acid (7 mL) was stirred at reflux for 4 h. After cooling, the mixture was made basic with 2N aqueous NaOH and extracted with ethyl acetate (50 mL). The extracts was dried (MgSO₄) to afford 480 mg (quant.) of the title compound as a brown oil: ¹H-NMR (CDCl₃) δ 8.10 (1H, s), 8.08 (1H, s), 7.95 (1H, s), 7.61 (1H, s), 7.49–7.41 (4H, m), 4.47 (2H, t, J=6.8 Hz), 3.10 (2H, t, J=6.8 Hz).

STEP 2. 2-[4-(5,6-Dichloro-1H-benzimidazol-1-yl)phenyl]ethanol

The title compound was prepared according to the procedure described in step 6 of Example 1 from 2-[4-(5,6-dichloro-1H-benzimidazol-1-yl)phenyl]ethyl formate (step 1).

¹H-NMR (CDCl₃) δ 8.08 (1H, s), 7.96 (1H, s), 7.61 (1H, s), 7.49–7.40 (4H, m), 3.97 (2H, q, J=6.4 Hz), 2.99 (2H, t, J=6.4 Hz).

STEP 3. 2-[4-(5,6-Dichloro-1H-benzimidazol-1-yl)phenyl]ethyl azide

The title compound was prepared according to the procedure described in step 5 of Example 26 from 2-[4-(5,6-dichloro-1H-benzimidazol-1-yl)phenyl]ethanol (step 2).

MS (EI) m/z 332 (M⁺).

STEP 4. 2-[4-(5,6-Dichloro-1H-benzimidazol-1-yl)phenyl]ethylamine

The title compound was prepared according to the procedure described in step 9 of Example 1 from 2-[4-(5,6-dichloro-1H-benzimidazol-1-yl)phenyl]ethyl azide (step 3).

¹H-NMR (CDCl₃) δ 8.09 (1H, s), 7.96 (1H, s), 7.62 (1H, s), 7.45–7.38 (4H, m), 3.06 (2H, m), 2.87 (2H, t, J=6.6 Hz).

STEP 5. 5,6-Dichloro-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(5,6-dichloro-1H-benzimidazol-1-yl)phenyl]ethylamine (step 3).

¹H-NMR (CDCl₃) δ 8.11 (1H, s), 7.96 (1H, s), 7.72 (2H, d, J=8.4 Hz), 7.58 (1H, s), 7.38 (4H, s), 7.28 (2H, d, J=8.4 Hz), 6.72 (1H, m), 3.56 (2H, q, J=6.9 Hz), 2.92 (2H, t, J=6.9 Hz), 2.38 (3H, s).

EXAMPLE 103

5,6-DICHLORO-1-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 5,6-dichloro-1-(4-{2-[({[(4-methylphenyl)sulfonyl]amino}carbonyl)amino]ethyl}phenyl)-1H-benzimidazole (Example 102).

¹H-NMR (DMSO-d₆) δ 8.55 (1H, s), 7.97 (1H, s), 7.71 (1H, s), 7.50–7.44 (4H, m), 7.29 (2H, d, J=8.4 Hz), 7.01 (2H; d, J=8.4 Hz), 3.02 (2H, m), 2.61 (2H, m), 2.16 (3H, s); IR (KBr) ν_max 1601, 1516, 1487, 1450, 1128, 1084 cm⁻.

EXAMPLE 104

6-CHLORO-5-TRIFLUOROMETHYL-1-(4-{2-[({[(4-METHYLPHENYL)SULFONYL]AMINO}CARBONYL)AMINO]ETHYL}PHENYL)-1H-BENZIMIDAZOLE

STEP 1. 2-[(5-CHLORO-4-TRIFLUOROMETHYL-2-NITROANILINO)PHENYL]ETHANOL

The title compound was prepared according to the procedure described in step 3 of Example 1 from 2,4-dichloro-5-trifluoromethylnitrobenzene and 4-aminophenylethyl alcohol.

¹H-NMR (CDCl₃) δ 9.69 (1H, br.s), 8.58 (1H, s), 7.37 (2H, d, J=8.4 Hz), 7.23 (2H, d, J=8.4 Hz), 7.19 (1H, s), 3.93 (2H, t, J=6.4 Hz), 2.94 (2H, t, J=6.4 Hz).

STEP 2. 2-[(2-Amino-5-chloro-4-trifluoromethylanilino)phenyl]ethanol

The title compound was prepared according to the procedure described in step 2 of Example 28 from 2-[(5-chloro-4-trifluoromethyl-2-nitroanilino)phenyl]ethanol (step 1).

¹H-NMR (CDCl₃) δ 7.17–7.15 (3H, m), 7.05 (1H, s), 6.92–6.88 (2H, m), 5.48 (1H, br.s), 3.85 (2H, t, J=6.6 Hz), 2.83 (2H, t, J=6.6 Hz).

STEP 3. 2-[4-(6-Chloro-2-ethyl-5-trifluoromethyl-1H-benzimidazol-1-yl)phenyl]ethyl propionate The title compound was prepared according to the procedure described in step 5 of Example 1 from 2-[(2-amino-5-chloro-4-trifluoromethylanilino)phenyl]ethanol (step 2) and propionyl chloride.

MS (EI) 424 (M⁺).

STEP 4. 2-[4-(6-Chloro-2-ethyl-5-trifluoromethyl-1H-benzimidazol-1-yl)phenyl]ethanol The title compound was prepared according to the procedure described in step 6 of Example 1 from 2-[4-(6-chloro-2-ethyl-5-trifluoromethyl-1H-benzimidazol-1-yl)phenyl]ethyl propionate (step 3).

¹H-NMR (CDCl₃) δ 8.11 (1H, s), 7.50 (2H, d, J=8.3 Hz), 7.29 (2H, d, J=8.3 Hz), 7.21 (1H, s), 4.03–3.98 (2H, m), 3.02 (2H, t, J=6.4 Hz), 2.79 (2H, q, J=7.5 Hz), 1.36 (3H, t, J=7.5 Hz).

STEP 5 2-[4-(6-Chloro-2-ethyl-5-trifluoromethyl-1H-benzimidazol-1-yl)phenyl]ethyl azide The title compound was prepared according to the procedure described in step 5 of Example 26 from 2-[4-(6-Chloro-2-ethyl-5-trifluoromethyl-1H-benzimidazol-1-yl)phenyl]ethanol (step 4).

¹H-NMR (CDCl₃) δ 8.11 (1H, s), 7.49 (2H, d, J=8.4 Hz), 7.30 (2H, d, J=8.4 Hz), 7.20 (1H, s), 3.63 (2H, t, J=6.9 Hz), 3.03 (2H, t, J=6.9 Hz), 2.79 (2H, q, J=7.4 Hz), 1.36 (3H, t, J=7.4 Hz)

STEP 6. 2-[4-(6-Chloro-2-ethyl-5-trifluoromethyl-1H-benzimidazol-1-yl)phenyl]ethylamine The title compound was prepared according to the procedure described in step 9 of Example 1 from 2-[4-(6-chloro-2-ethyl-5-trifluoromethyl-1H-benzimidazol-1-yl)phenyl]ethyl azide (step 5).

¹H-NMR (CDCl₃) δ 8.11 (1H, s), 7.45 (2H, d, J=8.3 Hz), 7.29–7.26 (2H, m), 7.23 (1H, s), 3.11 (2H, t, J=7.0 Hz), 2.92 (2H, t, J=7.0 Hz), 2.79 (2H, q, J=7.5 Hz), 1.36 (3H, t, J=7.5 Hz).

STEP 7 2-Ethyl-6-chloro-5-trifluoromethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 2-[4-(6-chloro-2-ethyl-5-trifluoromethyl-1H-benzimidazol-1-yl)phenyl]ethylamine (step 6).

¹H-NMR (CDCl₃) δ 8.09 (1H, s), 7.74 (2H, d, J=8.4 Hz), 7.42 (2H, d, J=8.2 Hz), 7.30–7.26 (4H, m), 7.18 (1H, s), 6.76 (1H, m), 3.59 (2H, q, J=7.0 Hz), 2.96 (2H, t, J=7.0 Hz), 2.79 (2H, q, J=7.6 Hz), 1.34 (3H, t, J=7.6 Hz).

EXAMPLE 105

6-CHLORO-5-TRIFLUOROMETHYL-1-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 2-ethyl-6-chloro-5-trifluoromethyl-1-(4-{2-[({[(4-methylphenyl)sulfonyl]amino}carbonyl)amino]ethyl}phenyl)-1H-benzimidazole (Example 104).

$^1$H-NMR (DMSO-d$_6$) δ 8.15 (1H, s), 7.59 (2H, d, J=8.4 Hz), 7.46–7.39 (4H, m), 7.33 (1H, s), 7.12 (2H, d, J=8.41 Hz), 3.15 (2H, m), 2.78–2.71 (4H, m), 1.24 (3H, t, J=7.5 Hz); IR (KBr) ν$_{max}$ 1601, 1518, 1431, 1398, 1348, 1306, 1128, 1084 cm$^{-1}$.

EXAMPLE 106

4-(6-CHLORO-2-ETHYL-5-TRIFLUOROMETHYL-1H-BENZIMIDAZOL-1-YL)PHENETHYL-(4-METHYLPHENYL)SULFONYLCARBAMATE

The title compound was prepared according to the procedure described in Example 3 from 2-[4-(6-chloro-2-ethyl-5-trifluoromethyl-1H-benzimidazol-1-yl)phenyl]ethanol (step 4 of Example 104).

mp 170–173° C.; $^1$H-NMR (CDCl$_3$) δ 8.12 (1H, s), 7.94–7.91 (2H, m), 7.41–7.24 (6H, m), 7.19 (1H, s), 4.39 (2H, t, J=6.8 Hz), 3.04 (2H, t, J=6.8 Hz), 2.78 (2H, q, J=7.6 Hz), 2.44 (3H, s), 1.35 (3H, t, J=7.6 Hz); IR (KBr) ν$_{max}$ 1746, 1518, 1342, 1232, 1159, 1132, 1086 cm$^{-1}$.

EXAMPLE 107

4-(6-CHLORO-2-ETHYL-5-TRIFLUOROMETHYL-1H-BENZIMIDAZOL-1-YL)PHENETHYL-(4-METHYLPHENYL)SULFONYLCARBAMATE, SODIUM SALT

The title compound was prepared according to the procedure described in Example 2 from 4-(6-chloro-2-ethyl-5-trifluoromethyl-1H-benzimidazol-1-yl)phenethyl-(4-methylphenyl)sulfonylcarbamate (Example 106).

$^1$H-NMR (DMSO-d$_6$) δ 8.15 (1H, s), 7.59 (2H, d, J=8.1 Hz), 7.47 (4H, s), 7.34 (1H, s), 7.15 (2H, d, J=8.1 Hz), 3.96 (2H, t, J=6.6 Hz), 2.86 (2H, t, J=6.6 Hz), 2.75 (2H, q, J=7.4 Hz), 2.28 (3H, s), 1.24 (3H, t, J=7.4 Hz).

EXAMPLE 108

5-CHLORO-6-METHYL-1-(4-{2-[({1[(4-METHYLPHENYL)SULFONYL]AMINO}CARBONYL)AMINO]ETHYL}PHENYL)-1H-BENZIMIDAZOLE

STEP 1. 2-[(4-Chloro-5-methyl-2-nitroanilino)phenyl]ethanol

The title compound was prepared according to the procedure described in step 3 of Example 1 from 2,5-dichloro-4-methylnitrobenzene and 4-aminophenylethyl alcohol.

$^1$H-NMR (CDCl$_3$) δ 9.40 (1H, s), 8.20 (1H, s), 7.31 (2H, d, J=8.4 Hz), 7.21 (2H, d, J=8.4 Hz), 7.05 (1H, s), 3.93–3.91 (2H, m), 2.91 (2H, t, J=6.4 Hz), 2.29 (3H, s)

STEP 2. 2-[(2-Amino-4-chloro-5-methylanilino)phenyl]ethanol

The title compound was prepared according to the procedure described in step 2 of Example 28 from 2-[(4-chloro-5-methyl-2-nitroanilino)phenyl]ethanol (step 1).

$^1$H-NMR (CDCl$_3$) δ 7.06 (2H, d, J=8.6 Hz), 6.93 (1H, s), 6.79 (1H, s), 6.67 (2H, d, J=8.6 Hz), 3.80 (2H, d, J=6.4 Hz), 2.77 (2H, t, J=6.4 Hz), 2.21 (3H, s).

STEP 3. 2-[4-(5-Chloro-2-ethyl-6-methyl-1H-benzimidazol-1-yl)phenyl]ethyl propionate The title compound was prepared according to the procedure described in step 5 of Example 1 from 2-[(2-amino-4-chloro-5-methylanilino)phenyl]ethanol (step 2) and propionyl chloride.

MS (EI) m/z 370 (M$^+$).

STEP 4. 2-[4-(5-Chloro-2-ethyl-6-methyl-1H-benzimidazol-1-yl)phenyl]ethanol

The title compound was prepared according to the procedure described in step 6 of Example 1 from 2-[4-(5-chloro-2-ethyl-6-methyl-1H-benzimidazol-1-yl)phenyl]ethyl propionate (step 3).

$^1$H-NMR (CDCl$_3$) δ 7.74 (1H, s), 7.47 (2H, d, J=8.3 Hz), 7.27 (2H, d, J=8.3 Hz), 6.93 (1H, s), 4.00 (2H, t, J=6.6 Hz), 3.02 (2H, t, J=6.6 Hz), 2.76 (2H, q, J=7.5 Hz), 2.39 (3H, s), 1.32 (3H, t, J=7.5 Hz).

STEP 5. 2-[4-(5-Chloro-2-ethyl-6-methyl-1H-benzimidazol-1-yl)phenyl]ethyl azide

The title compound was prepared according to the procedure described in step 5 of Example 26 from 2-[4-(5-chloro-2-ethyl-6-methyl-1H-benzimidazol-1-yl)phenyl]ethanol (step 4).

$^1$H-NMR (CDCl$_3$) δ 7.75 (1H, s), 7.45 (2H, d, J=8.4 Hz), 7.30 (2H, d, J=8.4 Hz), 7.27 (1H, s), 3.62 (2H, t, J=7.0 Hz), 3.02 (2H, t, J=7.0 Hz), 2.76 (2H, q, J=7.5 Hz), 2.40 (3H, s), 1.33 (3H, t, J=7.5 Hz).

STEP 6. 2-[4-(5-Chloro-2-ethyl-6-methyl-1H-benzimidazol-1-yl)phenyl]ethylamine

The title compound was prepared according to the procedure described in step 9 of Example 1 from 2-[4-(5-chloro-2-ethyl-6-methyl-1H-benzimidazol-1-yl)phenyl]ethyl azide (step 5).

$^1$H-NMR (CDCl$_3$) δ 7.75 (1H, s), 7.42 (2H, d, J=8.3 Hz), 7.27 (2H, d, J=8.3 Hz), 6.93 (1H, s), 3.10 (2H, t, J=7.0 Hz), 2.90 (2H, t, J=7.0 Hz), 2.76 (2H, q, J=7.5 Hz), 2.40 (3H, s), 1.33 (3H, t, J=7.5 Hz).

STEP 7. 2-Ethyl-5-chloro-6-methyl-1-(4-{2-[([[(4-methylphenyl)sulfonyl]amino]carbonyl)amino}ethyl]phenyl)-1H-benzimidazole The title compound was prepared according to the procedure described in step 10 of Example 1 from 2-[4-(5-chloro-2-ethyl-6-methyl-1H-benzimidazol-1-yl)phenyl]ethylamine (step 6).

$^1$H-NMR (CDCl$_3$) δ 7.75–7.72 (3H, m), 7.38–7.23 (6H, m), 6.91 (1H, s), 6.73–6.69 (1H, m), 3.62–3.55 (2H, m), 2.94 (2H, t, J=6.8 Hz), 2.75 (2H, q, J=7.6 Hz), 2.40 (3H, s), 2.37 (3H, s), 1.30 (3H, t, J=7.6 Hz).

EXAMPLE 109

5-CHLORO-6-METHYL-1-(4-{2-[({[(4-METHYLPHENYL)SULFONYL]AMINO}CARBONYL)AMINO]ETHYL}PHENYL)-1H-BENZIMIDAZOLE, SODIUM SALT

The title compound was prepared according to the procedure described in Example 2 from 2-ethyl-5-chloro-6-methyl-1-(4-{2-[([[(4-methylphenyl)sulfonyl]amino]carbonyl)amino]ethyl}phenyl)-1H-benzimidazole (Example 108).

$^1$H-NMR (DMSO-d$_6$) δ 7.68 (1H, s), 7.60 (2H, d, J=8.1 Hz), 7.41–7.35 (4H, m), 7.13 (2H, d, J=8.1 Hz), 7.05 (1H, s), 3.17–3.15 (2H, m), 2.75–2.65 (4H, m), 2.34 (3H, s), 2.27 (3H, s), 1.20 (3H, t, J=7.5 Hz); IR (KBr) μ$_{max}$ 1599, 1516, 1456, 1402, 1128, 1084, 1001 cm$^{-1}$.

EXAMPLE 110

6-CHLORO-2-ETHYL-1-(4-{2-[({[(4-METHYLPHENYL)SULFONYL]AMINO}CARBONYL)AMINO]ETHYL}PHENYL)-5-[(METHYLSULFONYL)AMINO]-1H-BENZIMIDAZOLE

STEP 1. 2-[4-(5-Chloro-2,4-dinitroanilino)phenyl]ethanol

The title compound was prepared according to the procedure described in step 3 of Example 1 from 2,4-dichloro-1,5-dinitrobenzene and 4-aminophenylethyl alcohol.

$^1$H-NMR (CDCl$_3$) δ 9.81 (1H, br.s), 9.07 (1H, s), 7.40 (2H, d, J=8.3 Hz), 7.25 (2H, d, J=8.3 Hz), 7.17 (1H, s), 3.95 (2H, t, J=6.6 Hz), 2.95 (2H, t, J=6.6 Hz).

STEP 2. 2-[4-(2-Amino-5-chloro-4-nitroanilino)phenyl]ethanol

The title compound was prepared according to the procedure described in step 2 of Example 40 from 2-[4-(5-chloro-2,4-dinitroanilino)phenyl]ethanol (step 1).

$^1$H-NMR (CDCl$_3$) δ 7.54 (1H, s), 7.24 (2H, d, J=8.6 Hz), 7.11 (1H, s), 7.03 (2H, d, J=8.6 Hz), 5.76 (1H, br.s), 3.89 (2H, t, J=6.4 Hz), 3.65 (2H, br.s), 2.87 (2H, t, J=6.4 Hz), 1.28 (1H, s).

STEP 3. 2-[4-(6-Chloro-2-ethyl-5-nitro-1H-benzimidazol-1-yl)phenyl]ethyl propionate The title compound was prepared according to the procedure described in step 5 of Example 1 from 2-[4-(2-amino-5-chloro-4-nitroanilino)phenyl]ethanol (step 2) and propionyl chloride.

TLC Rf=0.8 (hexane/ethyl acetate=1:2).

STEP 4. 2-[4-(6-Chloro-2-ethyl-5-nitro-1H-benzimidazol-1-yl)phenyl]ethanol

The title compound was prepared according to the procedure described in step 6 of Example 1 from 2-[4-(2-amino-5-chloro-4-nitroanilino)phenyl]ethyl propionate (step 3).

$^1$H-NMR (CDCl$_3$) δ 8.34 (1H, s), 7.50 (2H, d, J=8.0 Hz), 7.28 (2H, d, J=8.0 Hz), 7.19 (1H, s), 4.00 (2H, t, J=6.3 Hz), 3.02 (2H, t, J=6.3 Hz), 2.79 (2H, q, J=7.6 Hz), 1.62 (1H, s), 1.36 (3H, t, J=7.6 Hz).

STEP 5. 6-Chloro-1-[4-(2-chloroethyl)phenyl]-2-ethyl-5-nitro-1H-benzimidazole

The title compound was prepared according to the procedure described in step 7 of Example 1 from 2-[4-(6-chloro-2-ethyl-5-nitro-1H-benzimidazol-1-yl)phenyl]ethanol (step 4).

$^1$H-NMR (CDCl$_3$) δ 8.34 (1H, s), 7.50 (2H, d, J=8.4 Hz), 7.31 (2H, d, J=8.4 Hz), 7.19 (1H, s), 3.84 (2H, t, J=7.0 Hz), 3.22 (2H, t, J=7.0 Hz), 2.80 (2H, q, J=7.6 Hz), 1.37 (3H, t, J=7.6 Hz).

STEP 6. 6-Chloro-1-[4-(2-chloroethyl)phenyl]-2-ethyl-1H-benzimidazol-5-ylamine

The title compound was prepared according to the procedure described in step 4 of Example 89 from 6-chloro-1-[4-(2-chloroethyl)phenyl]-2-ethyl-5-nitro-1H-benzimidazole (step 5).

$^1$H-NMR (CDCl$_3$) δ 7.43 (2H, d, J=8.6 Hz), 7.29 (2H, d, J=8.6 Hz), 7.16 (1H, s), 7.02 (1H, s), 3.96 (2H, br.s), 3.81 (2H, t, J=7.1 Hz), 3.19 (2H, t, J=7.1 Hz), 2.74 (2H, q, J=7.5 Hz), 1.33 (3H, t, J=7.5 Hz).

STEP 7. N-{6-Chloro-1-[4-(2-chloroethyl)phenyl]-2-ethyl-1H-benzimidazol-5-yl}methanesulfonamide The title compound was prepared according to the procedure described in step 5 of Example 40 from 6-chloro-1-[4-(2-chloroethyl)phenyl]-2-ethyl-1H-benzimidazol-5-ylamine (step 6).

$^1$H-NMR (CDCl$_3$) δ 7.70 (1H, s), 7.55 (2H, d, J=7.9 Hz), 7.50 (2H, d, J=7.9 Hz), 7.13 (1H, s), 3.95 (2H, t, J=7.0 Hz), 3.16 (2H, t, J=7.0 Hz), 2.97 (3H, s), 2.71 (2H, q, J=7.6 Hz), 1.21 (3H, t, J=7.6 Hz).

STEP 8. N-{1-[4-(2-Azidoethyl)phenyl]-6-chloro-2-ethyl-1H-benzimidazol-5-yl}methanesulfonamide The title compound was prepared according to the procedure described in step 8 of Example 1 from N-{6-chloro-1-[4-(2-chloroethyl)phenyl]-2-ethyl-1H-benzimidazol-5-yl}methanesulfonamide (step 7).

$^1$H-NMR (CDCl$_3$) δ 7.47 (2H, d, J=8.4 Hz), 7.29 (2H, d, J=8.4 Hz), 7.16 (1H, s), 6.78 (1H, s), 3.63 (2H, t, J=6.9 Hz), 2.98–3.05 (5H, m), 2.77 (2H, q, J=7.4 Hz), 1.35 (3H, t, J=7.4 Hz).

STEP 9. N-{1-[4-(2-Aminoethyl)phenyl]-6-chloro-2-ethyl-1H-benzimidazol-5-yl}methanesulfonamide The title compound was prepared according to the procedure described in step 7 of Example 37 from N-{1-[4-(2-azidoethyl)phenyl]-6-chloro-2-ethyl-1H-benzimidazol-5-yl}methanesulfonamide (step 8).

$^1$H-NMR (CDCl$_3$) δ 8.03 (1H, s), 7.43 (2H, d, J=8.4 Hz), 7.26 (2H, d, J=8.4 Hz), 7.17 (1H, s), 3.33 (2H, br.s), 3.08 (2H, t, J=7.0 Hz), 2.96 (3H, s), 2.88 (2H, t, J=7.0 Hz), 2.77 (2H, q, J=7.6 Hz), 1.35 (3H, t, J=7.6 Hz).

STEP 10. 6-Chloro-2-ethyl-1-(4-{2-[({[(4-methylphenyl)sulfonyl]amino}carbonyl)amino]ethyl}phenyl)-5-[(methylsulfonyl)amino]-1H-benzimidazole The title compound was prepared according to the procedure described in step 10 of Example 1 from N-{1-[4-(2-aminoethyl)phenyl]-6-chloro-2-ethyl-1H-benzimidazol-5-yl}methanesulfonamide (step 9).

mp 101–123° C.; MS (ESI) m/z 590 (M+H)$^+$; $^1$H-NMR (CDCl$_3$) δ 8.04 (1H, s), 7.73 (2H, d, J=8.2 Hz), 7.42 (2H, d, J=8.2 Hz), 7.25–7.33 (4H, m), 7.16 (1H, s), 6.68 (1H, br.s), 3.58 (2H, t, J=7.2 Hz), 2.93–2.98 (5H, m), 2.77 (2H, q, J=7.5 Hz), 2.45 (3H, s), 1.35 (3H, t, J=7.5 Hz); IR (KBr) v$_{max}$ 1654, 1517, 1467, 1336, 1151, 1089, 972 cm$^{-1}$.

EXAMPLE 111

6-CHLORO-2-ETHYL-1-(4-{2-[({[(4-METH-YLPHENYL)SULFONYL]AMINO}CARBONYL)AMINO]ETHYL}PHENYL)-1H-BENZIMIDA-ZOLE-5-CARBOXAMIDE

STEP 1. 2-Chloro-4-[4-(2-hydroxyethyl)anilino]-5-nitrobenzonitrile

The title compound was prepared according to the procedure described in step 3 of Example 1 from 2,4-dichloro-5-nitrobenzonitrile (Grivsky, E. M.; Hitchings, G. H. *Ind. Chim. Belge.*, 1974, 39. 490.) and 4-aminophenylethyl alcohol.

$^1$H-NMR (CDCl$_3$) δ 9.81 (1H, br.s), 8.56 (1H, s), 7.39 (2H, d, J=8.3 Hz), 7.23 (2H, d, J=8.3 Hz), 7.15 (1H, s), 3.93 (2H, t, J=6.2 Hz), 2.94 (2H, t, J=6.2 Hz), 1.62 (1H, br.s).

STEP 2. 5-Amino-2-chloro-4-[4-(2-hydroxyethyl)anilino]benzonitrile

The title compound was prepared according to the procedure described in step 2 of Example 28 from 2-chloro-4-[4-(2-hydroxyethyl)anilino]-5-nitrobenzonitrile (step 1).

$^1$H-NMR (CDCl$_3$) δ 7.23 (4H, d, J=8.3 Hz), 6.99–7.33 (2H, m), 3.88 (2H, t, J=6.1 Hz), 3.356 (1H, br.s), 2.87 (2H, t, J=6.1 Hz).

STEP 3. 2-[4-(6-Chloro-5-cyano-2-ethyl-1H-benzimidazol-1-yl)phenyl]ethyl propionate The title compound was prepared according to the procedure described in step 5 of Example 1 from 5-amino-2-chloro-4-[4-(2-hydroxyethyl)anilino]benzonitrile (step 2) and propionyl chloride.

TLC Rf=0.5 (hexane/ethyl acetate=1:2).

STEP 4. 6-Chloro-2-ethyl-1-[4-(2-hydroxyethyl)phenyl]-1H-benzimidazole-5-carbonitrile The title compound was prepared according to the procedure described in step 6 of Example 1 from 2-[4-(6-chloro-5-cyano-2-ethyl-1H-benzimidazol-1-yl)phenyl]ethyl propionate (step 3).

$^1$H-NMR (CDCl$_3$) δ 8.04 (1H, s), 7.52 (2H, d, J=8.4 Hz), 7.29 (2H, d, J=8.4 Hz), 7.19 (1H, s), 4.02 (2H, t, J=6.5 Hz), 3.03 (2H, t, J=6.5 Hz), 2.80 (2H, q, J=7.6 Hz), 1.36 (3H, t, J=7.6 Hz).

STEP 5. 6-Chloro-2-ethyl-1-[4-(2-hydroxyethyl)phenyl]-1H-benzimidazole-5-carboxamide To a mixture of 6-chloro-2-ethyl-1-[4-(2-hydroxyethyl)phenyl]-1H-benzimidazole-5-carbonitrile (step 4, 2.4 g, 7.4 mmol), DMSO (0.7 mL, 8.8 mmol) and methanol (100 mL) was added 30% aqueous hydrogen peroxide (1.3 mL, 11 mmol) and 0.2 M aqueous NaOH (0.7 mL, 0.14 mmol). The mixture was stirred at 50° C. for 2 h. The solvent was removed and the resulting precipitates were collected by filtration. The precipitates were washed with water and dried under reduced pressure to give 1.9 g (76%) of the title compound as pale pink solids: $^1$H-NMR (DMSO-d$_6$) δ 7.69 (1H, br.s), 7.61 (1H, s), 7.33–7.40 (4H, m), 6.95 (1H, s), 4.64 (1H, br.s), 3.59 (2H, t, J=6.4 Hz), 2.74 (2H, t, J=6.4 Hz), 2.62 (2H, q, J=7.4 Hz), 1.11 (3H, t, J=7.4 Hz).

STEP 6. 6-Chloro-1-[4-(2-chloroethyl)phenyl]-2-ethyl-1H-benzimidazole-5-carboxamide The title compound was prepared according to the procedure described in step 7 of Example 1 from 6-chloro-2-ethyl-1-[4-(2-hydroxyethyl)phenyl]-1H-benzimidazole-5-carboxamide (step 5).

$^1$H-NMR (DMSO-d$_6$) δ 7.71 (1H, br.s), 7.62 (1H, s), 7.36–7.47 (5H, m), 6.95 (1H, s), 3.85 (2H, t, J=7.1 Hz), 3.06 (2H, t, J=7.1 Hz), 2.63 (2H, q, J=7.6 Hz), 1.11 (3H, t, J=7.6 Hz).

STEP 7. 1-[4-(2-Azidoethyl)phenyl]-6-chloro-2-ethyl-1H-benzimidazole-5-carboxamide The title compound was prepared according to the procedure described in step 8 of Example 1 from 6-chloro-1-[4-(2-chloroethyl)phenyl]-2-ethyl-1H-benzimidazole-5-carboxamide (step 6).

$^1$H-NMR (DMSO-d$_6$) δ 7.80 (1H, br.s), 7.71 (1H, s), 7.46–7.57 (5H, m), 7.04 (1H, s), 3.65 (2H, t, J=6.9 Hz), 2.98 (2H, t, J=6.9 Hz), 2.72 (2H, q, J=7.5 Hz), 1.21 (3H, t, J=7.5 Hz).

STEP 8. 1-[4-(2-Aminoethyl)phenyl]-6-chloro-2-ethyl-1H-benzimidazole-5-carboxamide The title compound was prepared according to the procedure described in step 7 of Example 37 from 1-[4-(2-azidoethyl)phenyl]-6-chloro-2-ethyl-1H-benzimidazole-5-carboxamide (step 7).

$^1$H-NMR (CDCl$_3$) δ 7.80 (1H, s), 7.71 (1H, s), 7.39–7.50 (5H, m), 7.08 (1H, s), 2.49–2.89 (6H, m), 1.21 (3H, t, J=7.4 Hz).

STEP 9. 6-Chloro-2-ethyl-1-(4-{2-[({[(4-methylphenyl)sulfonyl]amino}carbonyl)amino]ethyl}phenyl)-1H-benzimidazole-5-carboxamide The title compound was prepared according to the procedure described in step 10 of Example 1 from 1-[4-(2-aminoethyl)phenyl]-6-chloro-2-ethyl-1H-benzimidazole-5-carboxamide (step 8).

mp 152–163° C.; MS (ESI) m/z 540 (M+H)$^+$; $^1$H-NMR (DMSO-d$_6$) δ 7.81 (1H, br.s), 7.72–7.75 (3H, m), 7.51 (1H, br.s), 7.33–7.44 (6H, m), 7.06 (1H, s), 3.26 (2H, br.s), 2.68–2.80 (4H, m), 2.34 (3H, s), 1.23 (3H, t, J=7.5 Hz); IR (KBr) ν$_{max}$ 3395, 1664, 1519, 1396, 1161, 1089, 991 cm$^{-1}$.

EXAMPLE 112

6-CHLORO-2-ETHYL-1-(4-{2-[({[(4-METH-YLPHENYL)SULFONYL]AMINO}CARBONYL)AMINO]ETHYL}PHENYL)-1H-BENZIMIDA-ZOLE-5-CARBOXLIC ACID

A mixture of 6-chloro-2-ethyl-1-(4-{2-[({[(4-methylphenyl)sulfonyl]amino}carbonyl)amino]ethyl}phenyl)-1H-benzimidazole-5-carboxamide (Example 111, 140 mg, 0.26 mmol) and KOH (63 mg, 0.8 mmol) in methanol (10 mL) was stirred at 100° C. for 1 day. The mixture was poured into water, acidified with 2N hydrochloric acid, and extracted with ethyl acetate (50 mL). The organic layer was washed with brine (30 mL), dried (Na$_2$SO$_4$), and concentrated. The residue was purified by flash column chromatography on silica gel eluting with dichloromethane/methanol (10:1) to afford 36 mg (25%) of the title compound as white solids: mp 145–150° C.; MS (ESI) m/z 541 (M+H)$^+$; $^1$H-NMR (DMSO-d$_6$) δ 8.10 (1H, s), 7.76 (2H, d, J=7.9 Hz), 7.36–7.47 (6H, m), 7.10 (1H, s), 3.28 (2H, m), 2.69–2.81 (4H, m), 2.34 (3H, s), 1.24 (3H, t, J=7.5 Hz); IR (KBr) ν$_{max}$: 3450, 1701, 1517, 1340, 1163, 1091, 900 cm$^{-1}$.

EXAMPLE 113

N-[6-CHLORO-2-ETHYL-1-(4-{2-[({[(4-METHYLPHENYL)SULFONYL]AMINO}CARBONYL)AMINO]ETHYL}PHENYL)-1H-BENZIMIDAZOL-5-YL]ACETAMIDE

STEP 1. N-{6-Chloro-1-[4-(2-chloroethyl)phenyl]-2-ethyl-1H-benzimidazol-5-yl}acetamide To a solution of 6-chloro-1-[4-(2-chloroethyl)phenyl]-2-ethyl-1H-benzimidazol-5-ylamine (step 6 of Example 110, 100 mg, 0.3 mmol) in pyridine (7 mL) was added dropwise acetyl chloride (0.03 mL, 0.33 mmol) under nitrogen atmosphere at 0° C., and the reaction mixture was stirred at room temperature for 1.5 h. The mixture was poured into water (20 mL) and extracted with ethyl acetate (50 mL). The organic layer was washed with 2N aqueous NaOH (30 mL), brine (30 mL), then dried ($Na_2SO_4$). After removal of solvent, the crude product was purified by flash column chromatography on silica gel eluting with hexane/ethyl acetate (1:3) to afford 110 mg (98%) of the title compound as white solids: $^1$H-NMR ($CDCl_3$) δ: 8.66 (1H, s), 7.56 (1H, br.s), 7.45 (2H, d, J=8.2 Hz), 7.29 (2H, d, J=8.2 Hz), 7.12 (1H, s), 3.82 (2H, t, J=7.1 Hz), 3.19 (2H, t, J=7.1 Hz), 2.77 (2H, q, J=7.6 Hz), 2.26 (3H, s), 1.34 (3H, t, J=7.6 Hz).

STEP 2. N-{1-[4-(2-Azidoethyl)phenyl]-6-chloro-2-ethyl-1H-benzimidazol-5-yl}acetamide The title compound was prepared according to the procedure described in step 8 of Example 1 from N-{6-chloro-1-[4-(2-chloroethyl)phenyl]-2-ethyl-1H-benzimidazol-5-yl}acetamide $^1$H-NMR (DMSO-$d_6$) δ 8.66 (1H, s), 7.55 (1H, br.s), 7.45 (2H, d, J=8.1 Hz), 7.30 (2H, d, J=8.1 Hz), 7.11 (1H, s), 3.62 (2H, t, J=7.1 Hz), 3.02 (2H, t, J=7.1 Hz), 2.76 (2H, q, J=7.6 Hz), 2.26 (3H, s), 1.34 (3H, t, J=7.6 Hz).

STEP 3. N-{1-[4-(2-Aminoethyl)phenyl]-6-chloro-2-ethyl-1H-benzimidazol-5-yl}acetamide The title compound was prepared according to the procedure described in step 7 of Example 37 from N-{1-[4-(2-azidoethyl)phenyl]-6-chloro-2-ethyl-1H-benzimidazol-5-yl}acetamide (step $^1$H-NMR ($CDCl_3$) δ 8.66 (1H, s), 7.55 (1H, br.s), 7.42 (2H, d, J=6.6 Hz), 7.27–7.29 (2H, m), 7.12 (1H, s), 3.08 (2H, t, J=6.9 Hz), 2.88 (2H, t, J=6.9 Hz), 2.75 (2H, q, J=7.4 Hz), 2.26 (3H, s), 1.34 (3H, t, J=7.4 Hz).

STEP 4. N-[6-Chloro-2-ethyl-1-(4-{2-[({[(4-methylphenyl)sulfonyl]amino}carbonyl)amino]ethyl}phenyl)-1H-benzimidazol-5-yl]acetamide The title compound was prepared according to the procedure described in step 10 of Example 1 from N-{1-[4-(2-aminoethyl)phenyl]-6-chloro-2-ethyl-1H-benzimidazol-5-yl}acetamide (step 3).

mp 125–133° C.; MS (ESI) m/z 554 (M+H)$^+$; $^1$H-NMR ($CDCl_3$) δ 8.64 (1H, s), 7.74 (2H, d, J=8.4 Hz), 7.55 (1H, br.s), 7.25–7.39 (1H, s), 7.08 (1H, s), 3.53–3.61 (2H, m), 2.94 (2H, t, J=7.1 Hz), 2.75 (2H, q, J=7.4 Hz), 2.41 (3H, s), 2.27 (3H, s), 1.32 (3H, t, J=7.4 Hz); IR (KBr) $ν_{max}$ 3390, 1676, 1517, 1240, 1161, 1089, 1018, 972 cm$^{-1}$.

EXAMPLE 114

6-ETHYL-5-(4-{2-[({[(4-METHYLPHENYL)SULFONYL]AMINO}CARBONYL)AMINO]ETHYL}PHENYL)-5H-[1,3]DIOXOLO[4,5-f]BENZIMIDAZOLE

STEP 1. 2-{4-[(6-Nitro-1,3-benzodioxol-5-yl)amino]phenyl}ethanol

The title compound was prepared according to the procedure described in step 1 of Example 45 from 5-amino-6-nitro-1,3-benzodioxol and 4-bromophenylethyl alcohol.

$^1$H-NMR ($CDCl_3$) δ: 10.07 (1H, br.s), 7.62 (1H, s), 7.29 (2H, d, J=8.5 Hz), 7.20 (2H, d, J=8.5 Hz), 6.58 (1H, s), 5.98 (2H, s), 3.90 (2H, t, J=6.6 Hz), 2.90 (2H, t, J=6.6 Hz).

STEP 2. 2-{4-[(6-Amino-1,3-benzodioxol-5-yl)amino]phenyl}ethanol

The title compound was prepared according to the procedure described in step 2 of Example 28 from 2-{4-[(6-nitro-1,3-benzodioxol-5-yl)amino]phenyl}ethanol (step 1).

$^1$H-NMR ($CDCl_3$) δ 7.26 (1H, s), 7.04 (2H, d, J=8.2 Hz), 6.60 (2H, d, J=8.2 Hz), 6.39 (1H, s), 5.87 (2H, s), 4.96 (1H, br.s), 3.80 (2H, t, J=6.4 Hz), 3.64 (2H, br.s), 2.76 (2H, t, J=6.4 Hz).

STEP 3. 2-[4-(6-Ethyl-5H-[1,3]dioxolo[4,5-f]benzimidazol-5-yl)phenyl]ethyl propionate The title compound was prepared according to the procedure described in step 5 of Example 1 from 2-{4-[(6-amino-1,3-benzodioxol-5-yl)amino]phenyl}ethanol (step 2) and propionyl alcohol.

TLC Rf=0.5 (hexane/ehtyl acetate=1:2).

STEP 4. 2-[4-(6-Ethyl-5H-[1,3]dioxolo[4,5-f]benzimidazol-5-yl)phenyl]ethanol

The title compound was prepared according to the procedure described in step 6 of Example 1 from 2-{4-[(6-amino-1,3-benzodioxol-5-yl)amino]phenyl}ethyl propionate (step 3).

$^1$H-NMR ($CDCl_3$) δ 7.43 (2H, d, J=8.4 Hz), 7.28 (2H, d, J=8.4 Hz), 7.19 (1H, s), 6.53 (1H, s), 5.94 (2H, s), 3.98 (2H, t, J=6.4 Hz), 2.99 (2H, t, J=6.4 Hz), 2.73 (2H, q, J=7.4 Hz), 1.31 (3H, t, J=7.4 Hz).

STEP 5. 5-[4-(2-Chloroethyl)phenyl]-6-ethyl-5H-[1,3]dioxolo[4,5-f]benzimidazole

The title compound was prepared according to the procedure described in step 7 of Example 1 from 2-[4-(6-ethyl-5H-[1,3]dioxolo[4,5-f]benzimidazol-5-yl)phenyl]ethanol (step 4).

$^1$H-NMR ($CDCl_3$) δ 7.42 (2H, d, J=8.1 Hz), 7.28 (2H, d, J=8.1 Hz), 7.19 (1H, s), 6.54 (1H, s), 5.94 (2H, s), 3.81 (2H, t, J=7.1 Hz), 3,19 (2H, t, J=7.1 Hz), 2.72 (2H, q, J=7.6 Hz), 1.31 (3H, t, J=7.6 Hz).

STEP 6. 2-[4-(6-Ethyl-5H-[1,3]dioxolo[4,5-f]benzimidazol-5-yl)phenyl]ethyl azide The title compound was prepared according to the procedure described in step 8 of Example 1 from 5-[4-(2-chloroethyl)phenyl]-6-ethyl-5H-[1,3]dioxolo[4,5-f]benzimidazole (step 5).

$^1$H-NMR ($CDCl_3$) δ 7.42 (2H, d, J=8.3 Hz), 7.29 (2H, d, J=8.3 Hz), 7.19 (1H, s), 6.53 (1H, s), 5.93 (2H, s), 3.60 (2H, t, J=7.1 Hz), 3.00 (2H, t, J=7.1 Hz), 2.73 (2H, q, J=7.6 Hz), 1.31 (3H, t, J=7.6 Hz).

STEP 7. 2-[4-(6-Ethyl-5H-[1,3]dioxolo[4,5-f]benzimidazol-5-yl)phenyl]ethylamine

The title compound was prepared according to the procedure described in step 9 of Example 1 from 2-[4-(6-ethyl-5H-[1,3]dioxolo[4,5-f]benzimidazol-5-yl)phenyl]ethyl azide (step 6).

$^1$H-NMR (CDCl$_3$) δ 7.40 (2H, d, J=8.2 Hz), 7.22–7.28 (2H, m), 7.19 (1H, s), 6.54 (1H, s), 5.93 (2H, s), 3.05 (2H, t, J=6.8 Hz), 2.86 (2H, t, J=6.8 Hz), 2.73 (2H, q, J=7.6 Hz), 1.31 (3H, t, J=7.6 Hz).

STEP 8. 6-Ethyl-5-(4-{2-[({[(4-methylphenyl)sulfonyl]amino}carbonyl)amino]ethyl}phenyl)-5H-[1,3]dioxolo[4,5-f]benzimidazole The title compound was prepared according to the procedure described in step 10 of Example 1 from 2-[4-(6-ethyl-5H-[1,3]dioxolo[4,5-f]benzimidazol-5-yl)phenyl]ethylamine (step 7).

MS (ESI) m/z 507 (M+H)$^+$; $^1$H-NMR (DMSO-d$_6$) δ 7.75 (2H, d, J=8.1 Hz), 7.35–7.37 (6H, m), 7.16 (1H, s), 6.55 (1H, s), 5.97 (2H, s), 2.76 (2H, t, J=6.9 Hz), 2.65 (2H, q, J=7.6 Hz), 2.50 (2H, br.s), 2.34 (3H, s), 1.18 (3H, t, J=7.6 Hz).

EXAMPLE 115

6-ETHYL-5-(4-{2-[({[(4-METHYLPHENYL)SULFONYL]AMINO}CARBONYL)AMINO]ETHYL}PHENYL)-5H-[1,3]DIOXOLO[4,5-f]BENZIMIDAZOLE, SODIUM SALT

The title compound was prepared according to the procedure described in Example 2 from 6-ethyl-5-(4-{2-[({[(4-methylphenyl)sulfonyl]amino}carbonyl)amino]ethyl}phenyl)-5H-[1,3]dioxolo[4,5-f]benzimidazole (Example 114).

mp 140–155° C.; IR (KBr) ν$_{max}$ 3384, 2873, 1600, 1519, 1460, 1155, 1128, 1085, 1037, 945, 813 cm$^{-1}$.

EXAMPLE 116

2-ETHYL-1-(4-{2-[({[(4-METHYLPHENYL)SULFONYL]AMINO}CARBONYL)AMINO]ETHYL}PHENYL)-6,7-DIHYDRO-1H-[1,4]DIOXINO[2,3-f]BENZIMIDAZOLE

STEP 1. 7-Nitro-2,3-dihydro-1,4-benzodioxin-6-amine

To a mixture of 6,7-dinitro-2,3-dihydrobenzo[1,4]dioxin (Takakis, I. M.; Hadjimihalakis, P. M. J. Heterocyclic. Chem., 1991, 28, 625., 13 g, 57.8 mmol) and acetic acid (150 mL) was added iron powder (9.6 g, 172.5 mmol) at room temperature, then the mixture was refluxed for 30 min. After cooling, the mixture was filtered through a pad of Celite and the filtrate was concentrated. The residue was purified by flash column chromatography on silica gel eluting with hexane/ethyl acetate (gradient elution from 1:1 to 1:2) to afford 3.22 g (28%) of the title compound as orange solid: $^1$H-NMR (CDCl$_3$) δ 7.67 (1H, s), 6.23 (1H, s), 5,85 (2H, br.s), 4.19–4.33 (4H, m).

STEP 2. 2-{4-[(7-Nitro-2,3-dihydro-1,4-benzodioxin-6-yl)amino]phenyl}ethanol

The title compound was prepared according to the procedure described in step 1 of Example 45 from 7-nitro-2,3-dihydro-1,4-benzodioxin-6-amine (step 1) and 4-bromophenylethyl alcohol.

$^1$H-NMR (CDCl$_3$) δ 7.77 (1H, s), 7.26 (2H, d, J=8.4 Hz), 7.19 (2H, d, J=8.4 Hz), 6.64 (1H, s), 4.20–4.31 (4H, m), 3.89 (2H, t, J=6.4 Hz), 2.88 (2H, t, J=6.4 Hz).

STEP 3. 2-{4-[(7-Amino-2,3-dihydro-1,4-benzodioxin-6-yl)amino]phenyl}ethanol

The title compound was prepared according to the procedure described in step 2 of Example 28 from 2-{4-[(7-nitro-2,3-dihydro-1,4-benzodioxin-6-yl)amino]phenyl}ethanol (step 2).

$^1$H-NMR (CDCl$_3$) δ 7.02–7.05 (2H, m), 6.62–6.65 (3H, m), 6.33 (1H, s), 5.00 (1H, br.s), 4.15–4.24 (4H, m), 3.79 (2H, t, J=6.6 Hz), 3.53 (2H, br.s), 2.76 (2H, t, J=6.6 Hz).

STEP 4. 2-[4-(2-Ethyl-6,7-dihydro-1H-[1,4]dioxino[2,3-f]benzimidazol-1-yl)phenyl]ethyl propionate The title compound was prepared according to the procedure described in step 5 of Example 1 from 2-{4-[(7-amino-2,3-dihydro-1,4-benzodioxin-6-yl)amino]phenyl}ethanol (step 3) and propionyl chloride.

TLC Rf=0.5 (hexane:ethyl acetate=1:2).

STEP 5. 2-[4-(2-Ethyl-6,7-dihydro-1H-[1,4]dioxino[2,3-f]benzimidazol-1-yl)phenyl]ethanol The title compound was prepared according to the procedure described in step 6 of Example 1 from 2-{4-[(7-amino-2,3-dihydro-1,4-benzodioxin-6-yl)amino]phenyl}ethyl propionate (step 4).

$^1$H-NMR (CDCl$_3$) δ 7.42 (2H, d, J=8.1 Hz), 7.25–7.28 (3H, m), 6.58 (1H, s), 4.21–4.27 (4H, m), 3.97 (2H, t, J=6.6 Hz), 2.98 (2H, t, J=6.6 Hz), 2.74 (2H, q, J=7.3 Hz), 1.31 (3H, t, J=7.3 Hz).

STEP 6. 1-[4-(2-Chloroethyl)phenyl]-2-ethyl-6,7-dihydro-1H-[1,4]dioxino[2,3-f]benzimidazole The title compound was prepared according to the procedure described in step 7 of Example 1 from 2-[4-(2-ethyl-6,7-dihydro-1H-[1,4]dioxino[2,3-f]benzimidazol-1-yl)phenyl]ethanol (step 5).

$^1$H-NMR (CDCl$_3$) δ 7.40 (2H, d, J=8.1 Hz), 7.26–7.39 (3H, m), 6.58 (1H, s), 4.25 (4H, s), 3.80 (2H, t, J=7.3 Hz), 3.20 (2H, t, J=7.3 Hz), 2.74 (2H, q, J=7.6 Hz), 1.31 (3H, t, J=7.6 Hz).

STEP 7. 2-[4-(2-Ethyl-6,7-dihydro-1H-[1,4]dioxino[2,3-f]benzimidazol-1-yl)phenyl]ethyl azide The title compound was prepared according to the procedure described in step 8 of Example 1 from 1-[4-(2-chloroethyl)phenyl]-2-ethyl-6,7-dihydro-1H-[1,4]dioxino[2,3-f]benzimidazole (step 6).

$^1$H-NMR (CDCl$_3$) δ 7.40 (2H, d, J=8.3 Hz), 7.24–7.29 (3H, m), 6.57 (1H, s), 4.21–4.26 (4H, m), 3.59 (2H, t, J=7.0 Hz), 2.99 (2H, t, J=7.0 Hz), 2.73 (2H, q, J=7.5 Hz), 1.30 (3H, t, J=7.5 Hz).

STEP 8. 2-[4-(2-Ethyl-6,7-dihydro-1H-[1,4]dioxino[2,3-f]benzimidazol-1-yl)phenyl]ethylamine The title compound was prepared according to the procedure described in step 9 of Example 1 from 2-[4-(2-ethyl-6,7-dihydro-1H-[1,4]dioxino[2,3-f]benzimidazol-1-yl)phenyl]ethyl azide (step 6).

$^1$H-NMR (CDCl$_3$) δ 77.40 (2H, d, J=8.3 Hz), 7.24–7.27 (3H, m), 6.62 (1H, s), 4.21 (4H, s), 3.24–3.26 (2H, m), 3.11 (2H, t, J=6.9 Hz), 2.72 (2H, q, J=7.4 Hz), 1.30 (3H, t, J=7.4 Hz).

STEP 9. 2-Ethyl-1-(4-{2-[({[(4-methylphenyl)sulfonyl]amino}carbonyl)amino]ethyl}phenyl)-6,7-dihydro-1H-[1,4]dioxino[2,3-f]benzimidazole The title compound was prepared according to the procedure described in step 10 of Example 1 from 2-[4-(2-ethyl-6,7-dihydro-1H-[1,4]dioxino[2,3-f]benzimidazol-1-yl)phenyl]ethylamine (step 8).

MS (ESI) m/z 521 (M+H)$^+$; $^1$H-NMR (CDCl$_3$) δ 7.76 (2H, d, J=8.4 Hz), 7.18–7.31 (7H, m), 6.64 (1H, br.s), 6.56 (1H, br.s), 4.24 (4H, s), 3.56 (2H, t, J=6.9 Hz), 2.90 (2H, t, J=6.9 Hz), 2.70 (2H, q, J=7.6 Hz), 2.41 (3H, s), 1.27 (3H, t, J=7.6 Hz).

EXAMPLE 317

2-ETHYL-1-(4-{2-[({[(4-METHYLPHENYL)SUL-FONYL]AMINO}CARBONYL)AMINO]ETHYL}PHENYL)-6,7-DIHYDRO-1H-[1,4]DI-OXINO[2,3-f]BENZIMIDAZOLE, SODIUM SALT

The title compound was prepared according to the procedure described in Example 2 from 2-ethyl-1-(4-{2-[({[(4-methylphenyl)sulfonyl]amino}carbonyl)amino]ethyl}phenyl)-6,7-dihydro-1H-[1,4]dioxino[2,3-f]benzimidazole (Example 116).

mp 162–173° C.; $^1$H-NMR (DMSO-d$_6$) δ 7.83 (2H, d, J=8.0 Hz), 7.58 (2H, d, J=8.6 Hz), 7.54 (2H, d, J=8.0 Hz), 7.35 (2H, d, J=8.6 Hz), 7.29 (1H, s), 6.68 (1H, s), 4.42 (4H, s), 3.38 (2H, br.s), 2.94 (2H, t, J=6.9 Hz), 2.86 (2H, q, J=7.6 Hz), 2.49 (3H, s), 1.39 (3H, t, J=7.6 Hz); IR (KBr) ν$_{max}$ 3360, 2875, 1596, 1516, 1468, 1335, 1167, 1130, 1064, 920 cm$^{-1}$.

EXAMPLE 118–EXAMPLE 161

The compounds disclosed hereinafter were prepared according to the following procedure: To a solution of requisite commercially available sulfonamide (0.05 mmol) in DMF (1 mL) was added a suspension of NaH (0.1 mmol) in DMF (0.5 mL) and the mixture was shaken for 5 min. To this mixture was added a solution of phenyl 2-[4-(2-ethyl-5,7-dimethyl-3H-imidazo[4,5-b]pyridin-3-yl)phenyl]ethyl-carbamate (step 1 of Example 18, 7 mg, 0.05 mmol) in DMF (0.5 mL), and the mixture was shaken at room temperature for 30 min. After removal of DMF by nitrogen blow, the residue was dissolved in water (3 mL) and loaded onto a 0.5 g/3 mL BondElute SCX. The solid phase was washed with MeOH (5 mL), and then eluted with 10% HCl/MeOH (3 mL). The eluate was concentrated under reduced pressure to give the title compound.

EXAMPLE 118

3-(4-{2-[({[(3,4-DICHLOROPHENYL)SULFO-NYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 546.6 (M+H)$^+$.

EXAMPLE 119

2-ETHYL-3-{4-[2-({[({3-NITROPHENYL}SULFONYL)AMINO]CARBONYL}AMINO)ETHYL]PHENYL}-5,7-DIMETHYL-3H-IMIDAZO[4,5-b]PYRIDINE, HYDROCHLORIDE

MS (ESI) m/z 523.3 (M+H)$^+$.

EXAMPLE 120

3-(4-{2-[({[(4-CHLOROPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 512.5 (M+H)$^+$.

EXAMPLE 121

2-ETHYL-3-{4-[2-({[({4-NITROPHENYL}SULFONYL)AMINO]CARBONYL}AMINO)ETHYL]PHENYL}-5,7-DIMETHYL-3H-IMIDAZO[4,5-b]PYRIDINE, HYDROCHLORIDE

MS (ESI) m/z 523.3 (M+H)$^+$.

EXAMPLE 122

N-[4-({[({2-[4-(2-Ethyl-5,7-dimethyl-3H-imidazo[4,5-b]pyridin-3-yl)phenyl]ethyl}amino)carbonyl]amino}sulfonyl)phenyl]-2,2-dimethylpropanamide, hydrochloride MS (ESI) m/z 577.5 (M+H)$^+$.

EXAMPLE 123

3-(4-{2-[({[(2-CHLOROPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 512.4 (M+H)$^+$.

EXAMPLE 124

3-(4-{2-[({[(3-CHLOROPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 512.5 (M+H)$^+$.

EXAMPLE 125

3-(4-{2-[({[(5-CHLORO-2-THIENYL)SULFO-NYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 518.6 (M+H)$^+$.

EXAMPLE 126

3-(4-{2-[({[(5-BROMO-2-THIENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 564.2 (M+H)$^+$.

EXAMPLE 127

2-ETHYL-3-{4-[2-({[({2-METHYL-5-NITRO-PHENYL}SULFONYL)AMINO]CARBONYL}AMINO)ETHYL]PHENYL}-5,7-DIMETHYL-3H-IMIDAZO[4,5-b]PYRIDINE, HYDROCHLORIDE

MS (ESI) m/z 537.3 (M+H)$^+$.

EXAMPLE 128

3-(4-{2-[({[(3,4-DIMETHOXYPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 538.4 (M+H)$^+$.

EXAMPLE 129

3-(4-{2-[({[(4-BUTYLPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 534.5 (M+H)$^+$.

EXAMPLE 130

2-ETHYL-3-(4-{2-[({[(4-METHOXYPHENYL)SULFONYL]AMINO}CARBONYL)AMINO]ETHYL}PHENYL)-5,7-DIMETHYL-3H-IMIDAZO[4,5-b]PYRIDINE, HYDROCHLORIDE

MS (ESI) m/z 508.4 (M+H)$^+$.

EXAMPLE 131

2-ETHYL-5,7-DIMETHYL-3-[4-(2-{[({[5-(PHENYLSULFANYL)-2-THIENYL]SULFONYL}AMINO)CARBONYL]AMINO}ETHYL)PHENYL]-3H-IMIDAZO[4,5-b]PYRIDINE, HYDROCHLORIDE

MS (ESI) m/z 592.4 (M+H)$^+$.

EXAMPLE 132

3-(4-{2-[({[(3,5-DICHLOROPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 546.6 (M+H)$^+$.

EXAMPLE 133

3-(4-{2-[({[(2-BROMOPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 558.0 (M+H)$^+$.

EXAMPLE 134

3-(4-{2-[({[(4,5-DICHLORO-2-THIENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 552.6 (M+H)$^+$.

EXAMPLE 135

3-[4-(2-{[({[2-(2,4-DICHLOROPHENOXY)PHENYL]SULFONYL}AMINO)CARBONYL]AMINO}ETHYL)PHENYL]-2-ETHYL-5,7-DIMETHYL-3H-IMIDAZO[4,5-b]PYRIDINE, HYDROCHLORIDE

MS (ESI) m/z 638.8 (M+H)$^+$.

EXAMPLE 136

3-(4-{2-[({[(5-CHLORO-1,3-DIMETHYL-1H-PYRAZOL-4-YL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 530.3 (M+H)$^+$.

EXAMPLE 137

3-(4-{2-[({[(2,4-DIMETHYL-1,3-THIAZOL-5-YL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 523.2 (M+H)$^+$.

EXAMPLE 138

3-(4-{2-[({[(4-CYANOPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 503.2 (M+H)$^+$.

EXAMPLE 139

3-(4-{2-[({[(3,4-DIFLUOROPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 514.3 (M+H)$^+$.

EXAMPLE 140

3-(4-{2-[({[(2,5-DICHLORO-3-THIENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 552.3 (M+H)+.

EXAMPLE 141

N-[5-({[({2-[4-(2-Ethyl-5,7-dimethyl-3H-imidazo[4,5-b]pyridin-3-yl)phenyl]ethyl}amino)carbonyl]amino}sulfonyl)-1,3,4-thiadiazol-2-yl]acetamide, hydrochloride MS (ESI) m/z 543.0 (M+H)+.

EXAMPLE 142

3-{4-[2-({[({4-CHLORO-3-NITROPHENYL}SULFONYL)AMINO]CARBONYL}AMINO)ETHYL]PHENYL}-2-ETHYL-5,7-DIMETHYL-3H-IMIDAZO[4,5-b]PYRIDINE, HYDROCHLORIDE

MS (ESI) m/z 557.2 (M+H)+.

EXAMPLE 143

3-(4-{2-[({[(4-BUTOXYPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 550.4 (M+H)+.

EXAMPLE 144

3-[4-(2-{[({[2,6-DICHLORO-4-(TRIFLUOROMETHYL)PHENYL]SULFONYL}AMINO)CARBONYL]AMINO}ETHYL)PHENYL]-2-ETHYL-5,7-DIMETHYL-3H-IMIDAZO[4,5-b]PYRIDINE, HYDROCHLORIDE

MS (ESI) m/z 614.4 (M+H)+.

EXAMPLE 145

3-[4-(2-{[({[4-(1-ADAMANTYL)PHENYL]SULFONYL}AMINO)CARBONYL]AMINO}ETHYL)PHENYL]-2-ETHYL-5,7-DIMETHYL-3H-IMIDAZO[4,5-b]PYRIDINE, HYDROCHLORIDE

MS (ESI) m/z 612.4 (M+H)+.

EXAMPLE 146

3-(4-{2-[({[(4,5-DIBROMO-2-THIENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 642.0 (M+H)+.

EXAMPLE 147

2-ETHYL-5,7-DIMETHYL-3-[4-(2-{[({[5-(2-THIENYLSULFANYL)-2-THIENYL]SULFONYL}AMINO)CARBONYL]AMINO}ETHYL)PHENYL]-3H-IMIDAZO[4,5-b]PYRIDINE, HYDROCHLORIDE

MS (ESI) m/z 598.2 (M+H)+.

EXAMPLE 148

3-(4-{2-[({[(4-TERT-BUTYLPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 534.4 (M+H)+.

EXAMPLE 149

3-(4-{2-[({[(4-AMINO-3-CHLOROPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 527.3 (M+H)+.

EXAMPLE 150

2-ETHYL-5,7-DIMETHYL-3-(4-{2-[({[(2,4,5-TRICHLOROPHENYL)SULFONYL]AMINO}CARBONYL)AMINO]ETHYL}PHENYL)-3H-IMIDAZO[4,5-b]PYRIDINE, HYDROCHLORIDE

MS (ESI) m/z 580.4 (M+H)+.

EXAMPLE 151

3-(4-{2-[({[(2,5-DIMETHOXYPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 538.3 (M+H)+.

EXAMPLE 152

3-(4-{2-[({[(6-ETHOXY-1,3-BENZOTHIAZOL-2-YL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 579.1 (M+H)+.

EXAMPLE 153

3-(4-{2-[({[(2-AMINO-4-CHLOROPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 527.2 (M+H)$^+$.

EXAMPLE 154

2-ETHYL-5,7-DIMETHYL-3-[4-(2-{[({[5-(2-THIENYLSULFONYL)-2-THIENYL]SULFONYL}AMINO)CARBONYL]AMINO}ETHYL)PHENYL]-3H-IMIDAZO[4,5-b]PYRIDINE, HYDROCHLORIDE

MS (ESI) m/z 630.2 (M+H)$^+$.

EXAMPLE 155

3-[4-(2-{[({[2-CHLORO-5-(TRIFLUOROMETHYL)PHENYL]SULFONYL}AMINO)CARBONYL]AMINO ETHYL)PHENYL]-2-ETHYL-5,7-DIMETHYL-3H-IMIDAZO[4,5-b]PYRIDINE, HYDROCHLORIDE

MS (ESI) m/z 580.2 (M+H)$^+$.

EXAMPLE 156

3-{4-[2-({[(2,3-DIHYDRO-1,4-BENZODIOXIN-6-YLSULFONYL)AMINO]CARBONYL}AMINO)ETHYL]PHENYL}-2-ETHYL-5,7-DIMETHYL-3H-IMIDAZO[4,5-b]PYRIDINE, HYDROCHLORIDE

MS (ESI) m/z 536.2 (M+H)$^+$.

EXAMPLE 157

2-ETHYL-5,7-DIMETHYL-3-[4-(2-{[({[2-(PHENYLSULFANYL)PHENYL]SULFONYL}AMINO)CARBONYL]AMINO}ETHYL)PHENYL]-3H-IMIDAZO[4,5-b]PYRIDINE, HYDROCHLORIDE

MS (ESI) m/z 586.3 (M+H)$^+$.

EXAMPLE 158

3-(4-{2-[({[(4-CHLORO-2,5-DIMETHYLPHENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 540.3 (M+H)$^+$.

EXAMPLE 159

3-(4-{2-[({[(3-BROMO-5-CHLORO-2-THIENYL)SULFONYL]AMINO}CARBONYL)AMINO]ETHYL}PHENYL)-2-ETHYL-5,7-DIMETHYL-3H-IMIDAZO[4,5-b]PYRIDINE, HYDROCHLORIDE

MS (ESI) m/z 598.1 (M+H)$^+$.

EXAMPLE 160

2-ETHYL-5,7-DIMETHYL-3-(4-{2-[({[(4-VINYLPHENYL)SULFONYL]AMINO}CARBONYL)AMINO]ETHYL}PHENYL)-3H-IMIDAZO[4,5-b]PYRIDINE, HYDROCHLORIDE

MS (ESI) m/z 504.4 (M+H)$^+$.

EXAMPLE 161

METHYL 2,4-DICHLORO-5-({[({2-[4-(2-ETHYL-5,7-DIMETHYL-3H-IMIDAZO[4,5-b]PYRIDIN-3-YL)PHENYL]ETHYL}AMINO)CARBONYL]AMINO}SULFONYL)BENZOATE, HYDROCHLORIDE

MS (ESI) m/z 604.5 (M+H)$^+$.

EXAMPLE 162–EXAMPLE 194

The compounds disclosed hereinafter were prepared according to the following procedure: To a mixture of requisite commercially available carbonic acid and dichloromethane was added 1-ethyl-3-(3-dimethylaminopropyl) carbodiimide, hydrochloride (WSC) (0.05 mmol, 0.5 mL), then to the reaction mixture was added a solution of 3-amino-4,6-dimethyl-2-(4-{2-[({[(4-methylphenyl)sulfonyl]amino}carbonyl)amino]ethyl}anilino)pyridine* (0.038 mmol) in dichloromethane (0.5 mL) at room temperature. The reaction mixture was stirred for 3 days at room temperature, then stirred for an additional 1 day at 40° C. After removal of the solvent, the residue was dissolved in MeOH (1 mL) and the solution was filtered through a membrane filter. The filtrate was purified by preparative LC/MS (Shiseido capcell pack UG80 C18 (4.6×50 mm) eluting with MeOH/0.1% HCOOH (v/v, 20/80 to 90/10)) to give the title compound. *3-Amino-4,6-dimethyl-2-(4-{2-[({[(4-methylphenyl)sulfonyl]amino}carbonyl)amino]ethyl}anilino)pyridine was prepared as follows;

STEP 1, 3-{4-[(4,6-Dimethyl-3-nitro-2-pyridinyl)amino]phenyl}propanoic acid

To a solution of 2-chloro-4,6-dimethyl-3-nitropyridine (17.9 g, 96 mmol) and methyl 3-(4-aminophenyl)propanoate (19 g, 96 mmol) in DMSO (100 mL) was added N,N-diisopropylethylamine (26 g, 200 mmol), and the reaction mixture was heated at 140° C. overnight. The reaction mixture was partitioned between water (400 mL) and ethyl acetate/toluene (v/v, 2:1, 300 mL). The organic phase was separated and the aqueous phase was extracted with ethyl acetate/toluene (v/v, 2:1, 200 mL). The combined organic extracts were washed with brine (200 mL), dried (Na$_2$SO$_4$), and concentrated. To a solution of residual oil in methanol (100 mL) was added 2 N aqueous NaOH (150 mL, 300 mmol) and the resulting mixture was stirred at room temperature for 2 h. The volatile component was removed under reduced pressure and the residue was washed with ethyl acetate (200 mL). The aqueous phase was acidified with 2N hydrochloric acid (200 mL, 400 mmol) and extracted with ethyl acetate (3×200 mL). The extracts were washed with brine (200 mL), dried (Na$_2$SO$_4$), and concentrated to give 23.2 g (77%) of the title compound as pale brown solids.

$^1$H-NMR (CDCl$_3$) δ: 9.57 (1H, s), 7.56 (2H, d, J=8.4 Hz), 7.19 (2H, d, J=8.4 Hz), 6.52 (1H, s), 2.95 (2H, t, J=7.5 Hz), 2.66 (2H, t, J=7.5 Hz), 2.55 (3H, s), 2.43 (3H, s).

STEP 2, Phenyl 2-{4-[(4,6-Dimethyl-3-nitro-2-pyridinyl)amino]phenyl}ethylcarbamate To a stirred solution of 3-{4-[(4,6-dimethyl-3-nitro-2-pyridinyl)amino]phenyl}propanoic acid (step 1, 10 g, 31.7 mmol) in dioxane (200 mL) was added diphenylphosphoryl azide (DPPA) (7.54 ml, 35 mmol) and triethylamine (4.87 mL, 35 mmol). The reaction mixture was heated at 120° C. for 2 h. To the reaction mixture was added phenol (6.6 g, 70 mmol) and the reaction mixture was refluxed. After 3 h, to the reaction mixture was added an additional amount of phenol (3.3 g, 35 mmol). The resulting mixture was heated under reflux temperature overnight. The volatile component was removed and the residue was partitioned between aqueous 10% aqueous citric acid (200 mL) and ethyl acetate (300 mL). The organic phase was separated and the aqueous phase was extracted with ethyl acetate (300 mL). The combined organic extracts were washed with water (300 mL) and brine (300 mL), then dried ($Na_2SO_4$), and concentrated. The crude product was purified by flash column chromatography on silica gel eluting with hexane/EtOAc (2:1) to afford 10.3 g (77%) of the title compound as orange solids.

$^1$H-NMR (CDCl$_3$) δ: 9.60 (1H, s), 7.61 (2H, d, J=8.6 Hz), 7.38–7.32 (2H, m), 7.24–7.16 (3H, m), 7.14–7.09 (2H, m), 6.54 (1H, s), 5.06 (1H, br.s), 3.58–3.50 (2H, m), 2.89 (2H, t, J=6.9 Hz), 2.56 (3H, s), 2.44 (3H, s).

STEP 3, 4,6-Dimethyl-2-(4-{2-[({[(4-methylphenyl)sulfonyl]amino}carbonyl)amino]ethyl}anilino)-3-nitropyridine To a stirred solution of phenyl 2-{4-[(4,6-dimethyl-3-nitro-2-pyridinyl)amino]phenyl}ethylcarbamate (step 2, 10.0 g, 24.6 mmol) and p-toluenesulfonamide (6.3 g, 36.8 mmol) in DMF (100 mL) was added sodium hydride (2.0 g, 50 mmol). The reaction mixture was stirred at room temperature for 1 h. The reaction mixture was poured into water (300 mL) and extracted with ethyl acetate/toluene (v/v, 2:1, 2×300 mL). The organic extracts were washed with water (100 mL) and brine (200 mL), then dried ($Na_2SO_4$). Removal of the solvent gave crude product. Recrystallization from ethyl acetate gave 9.6 g (81%) of the title compound as brown solids. The mother liquor was concentrated and the residue was purified by flash column chromatography on silica gel eluting with hexane/ethyl acetate (1:1) to afford 1.9 g (16%) of the title compound as brown solids.

$^1$H-NMR (CDCl$_3$) δ: 9.75 (1H, s), 7.62 (2H, d, J=8.4 Hz), 7.59 (2H, d, J=8.4 Hz), 7.26 (2H, d, J=8.4 Hz), 7.15 (2H, d, J=8.4 Hz), 6.62–6.50 (2H, m), 3.55–3.42 (2H, m), 2.80 (2H, t, J=6.9 Hz), 2.56 (3H, s), 2.43 (3H, s), 2.39 (3H, s).

STEP 4, 3-Amino-4,6-dimethyl-2-(4-{2-[({[(4-methylphenyl)sulfonyl]amino}carbonyl)amino]ethyl}amino)pyridine To a solution of 4,6-dimethyl-2-(4-{2-[({[(4-methylphenyl)sulfonyl]amino}carbonyl)amino]ethyl}amino)-3-nitropyridine (step 3, 11.4 g, 23.6 mmol) in methanol (250 mL) was added 10% Pd—C (2.0 g). The resulting mixture was stirred under the medium pressure of hydrogen (4.0 kgf/cm$^2$) for 4 h. The catalyst was removed by filtration, and the filtrate was concentrated. The residue was recrystallized from ethyl acetate to afford 9.0 g (85%) of the title compound as off white solids.

$^1$H-NMR (CDCl$_3$) δ: 7.69 (2H, d, J=8.0 Hz), 7.26 (2H, d, J=8.0 Hz), 7.00–6.95 (4H, m), 6.61 (1H, s), 6.24 (1H, br.s), 3.44–3.38 (2H, m), 2.70 (2H, t, J=6.7 Hz), 2.39 (3H, s), 2.33 (3H, s), 2.19 (3H, s).

EXAMPLE 162

5,7-DIMETHYL-3-(4-{2-[({[(4-METHYLPHENYL)SULFONYL]AMINO}CARBONYL)AMINO]ETHYL}PHENYL)-2-[3-OXO-3-(2-THIENYL)PROPYL]-3H-IMIDAZO[4,5-b]PYRIDINE, FORMATE

MS (ESI) m/z 602.48 (M+H)$^+$.

EXAMPLE 163

5,7-DIMETHYL-3-(4-{2-[({[(4-METHYLPHENYL)SULFONYL]AMINO{CARBONYL)AMINO]ETHYL}PHENYL)-2-(PHENOXYMETHYL)-3H-IMIDAZO[4,5-b]PYRIDINE, FORMATE

MS (ESI) m/z 570.5 (M+H)$^+$.

EXAMPLE 164

5,7-DIMETHYL-3-(4-{2-[({[(4-METHYLPHENYL)SULFONYL]AMINO}CARBONYL)AMINO]ETHYL}PHENYL)-2-[2-(3-PYRIDINYL)ETHYL]-3H-IMIDAZO[4,5-b]PYRIDINE, FORMATE

MS (ESI) m/z 569.49 (M+H)$^+$.

EXAMPLE 165

5,7-DIMETHYL-3-(4-{2-[({[(4-METHYLPHENYL)SULFONYL]AMINO}CARBONYL)AMINO]ETHYL}PHENYL)-2-(3-OXO-3-PHENYLPROPYL)-3H-IMIDAZO[4,5-b]PYRIDINE, FORMATE

MS (ESI) m/z 596.28 (M+H)$^+$.

EXAMPLE 166

5,7-DIMETHYL-3-(4-{2-[({[(4-METHYLPHENYL)SULFONYL]AMINO}CARBONYL)AMINO]ETHYL}PHENYL)-2-(3-PHENYLPROPYL)-3H-IMIDAZO[4,5-b]PYRIDINE, FORMATE

MS (ESI) m/z 582.52 (M+H)$^+$.

EXAMPLE 167

2-(ETHOXYMETHYL)-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE

MS (ESI) m/z 522.46 (M+H)$^+$.

EXAMPLE 168

5,7-DIMETHYL-3-(4-{2-[({[(4-METHYLPHENYL)SULFONYL]AMINO}CARBONYL)AMINO]ETHYL}PHENYL)-2-[(PHENYLSULFANYL)METHYL]-3H-IMIDAZO[4,5-b]PYRIDINE, FORMATE

MS (ESI) m/z 586.49 (M+H)$^+$.

EXAMPLE 169

5,7-DIMETHYL-3-(4-{2-[({[(4-METHYLPHENYL)SULFONYL]AMINO}CARBONYL)AMINO]ETHYL}PHENYL)-2-PENTYL-3H-IMIDAZO[4,5-b]PYRIDINE, FORMATE

MS (ESI) m/z 534.51 (M+H)$^+$.

EXAMPLE 170

5,7-DIMETHYL-3-(4-{2-[({[(4-METHYLPHENYL)SULFONYL]AMINO}CARBONYL)AMINO]ETHYL}PHENYL)-2-(2-PHENYLETHYL)-3H-IMIDAZO[4,5-b]PYRIDINE, FORMATE

MS (ESI) m/z 568.51 (M+H)$^+$.

EXAMPLE 171

2-(3-BUTYNYL)-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE

MS (ESI) m/z 516.45 (M+H)$^+$.

EXAMPLE 172

5,7-DIMETHYL-3-(4-{2-[({[(4-METHYLPHENYL)SULFONYL]AMINO}CARBONYL)AMINO]ETHYL}PHENYL)-2-(3-THIENYLMETHYL)-3H-IMIDAZO[4,5-b]PYRIDINE, FORMATE

MS (ESI) m/z 560.44 (M+H)$^+$.

EXAMPLE 173

5,7-DIMETHYL-3-(4-{2-[({[(4-METHYLPHENYL)SULFONYL]AMINO}CARBONYL)AMINO]ETHYL}PHENYL)-2-(4-PENTYNYL)-3H-IMIDAZO[4,5-b]PYRIDINE, FORMATE

MS (ESI) m/z 530.46 (M+H)$^+$.

EXAMPLE 174

5,7-DIMETHYL-3-(4-{2-[({[(4-METHYLPHENYL)SULFONYL]AMINO}CARBONYL)AMINO]ETHYL}PHENYL)-2-(2-THIENYLMETHYL)-3H-IMIDAZO[4,5-b]PYRIDINE, FORMATE

MS (ESI) m/z 560.44 (M+H)$^+$.

EXAMPLE 175

5,7-DIMETHYL-3-(4-{2-[({[(4-METHYLPHENYL)SULFONYL]AMINO}CARBONYL)AMINO]ETHYL}PHENYL)-2-(3-PYRIDINYLMETHYL)-3H-IMIDAZO[4,5-b]PYRIDINE, FORMATE

MS (ESI) m/z 555.48 (M+H)$^+$.

EXAMPLE 176

5,7-DIMETHYL-3-(4-{2-[({[(4-METHYLPHENYL)SULFONYL]AMINO}CARBONYL)AMINO]ETHYL}PHENYL)-2-[(2E)-2-PENTENYL]-3H-IMIDAZO[4,5-b]PYRIDINE, FORMATE

MS (ESI) m/z 532.48 (M+H)$^+$.

EXAMPLE 177

2-BENZYL-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE

MS (ESI) m/z 554.48 (M+H)$^+$.

EXAMPLE 178

2-(CYANOMETHYL)-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE

MS (ESI) m/z 503.41 (M+H)$^+$.

EXAMPLE 179

2-(METHOXYMETHYL)-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE

MS (ESI) m/z 508.44 (M+H)$^+$.

EXAMPLE 180

2-HEPTYL-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE

MS (ESI) m/z 562.33 (M+H)$^+$.

EXAMPLE 181

5,7-DIMETHYL-3-(4-{2-[({[(4-METHYLPHENYL)SULFONYL]AMINO}CARBONYL)AMINO]ETHYL}PHENYL)-2-OCTYL-3H-IMIDAZO[4,5-b]PYRIDINE, FORMATE

MS (ESI) m/z 576.37 (M+H)$^+$.

EXAMPLE 182

5,7-DIMETHYL-2-(4-METHYLPENTYL)-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE

MS (ESI) m/z 548.53 (M+H)$^+$.

EXAMPLE 183

2-[(BENZYLOXY)METHYL]-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE

MS (ESI) m/z 584.52 (M+H)$^+$.

EXAMPLE 184

5,7-DIMETHYL-3-(4-{2-[({[(4-METHYLPHENYL)SULFONYL]AMINO}CARBONYL)AMINO]ETHYL}PHENYL)-2-(2-PHENOXYETHYL)-3H-IMIDAZO[4,5-b]PYRIDINE, FORMATE

MS (ESI) m/z 584.33 (M+H)$^+$.

EXAMPLE 185

5,7-DIMETHYL-3-(4-{2-[({[(4-METHYLPHENYL)SULFONYL]AMINO}CARBONYL)AMINO]ETHYL}PHENYL)-2-[3-(2-THIENYL)PROPYL]-3H-IMIDAZO[4,5-b]PYRIDINE, FORMATE

MS (ESI) m/z 588.5 (M+H)$^+$.

EXAMPLE 186

5,7-DIMETHYL-3-(4-{2-[({[(4-METHYLPHENYL)SULFONYL]AMINO}CARBONYL)AMINO]ETHYL}PHENYL)-2-(2-NAPHTHYLMETHYL)-3H-IMIDAZO[4,5-b]PYRIDINE, FORMATE

MS (ESI) m/z 604.37 (M+H)$^+$.

EXAMPLE 187

5,7-DIMETHYL-3-(4-{2-[({[(4-METHYLPHENYL)SULFONYL]AMINO}CARBONYL)AMINO]ETHYL}PHENYL)-2-(4-PHENYLBUTYL)-3H-IMIDAZO[4,5-b]PYRIDINE, FORMATE

MS (ESI) m/z 596.42 (M+H)$^+$.

EXAMPLE 188

5,7-DIMETHYL-3-(4-{2-[({[(4-METHYLPHENYL)SULFONYL]AMINO}CARBONYL)AMINO]ETHYL}PHENYL)-2-(5-PHENYLPENTYL)-3H-IMIDAZO[4,5-b]PYRIDINE, FORMATE

MS (ESI) m/z 610.45 (M+H)$^+$.

EXAMPLE 189

2-(2-ETHOXYETHYL)-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE

MS (ESI) m/z 536.38 (M+H)$^+$.

EXAMPLE 190

2-(2,3-DIHYDRO-1H-INDEN-2-YLMETHYL)-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE

MS (ESI) m/z 594.45 (M+H)$^+$.

EXAMPLE 191

2-(CYCLOPROPYLMETHYL)-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE

MS (ESI) m/z 518.45 (M+H)$^+$.

EXAMPLE 192

5,7-DIMETHYL-3-(4-{2-[({[(4-METHYLPHENYL)SULFONYL]AMINO}CARBONYL)AMINO]ETHYL}PHENYL)-2-[2-(METHYLSULFANYL)ETHYL]-3H-IMIDAZO[4,5-b]PYRIDINE, FORMATE

MS (ESI) m/z 538.44 (M+H)$^+$.

EXAMPLE 193

2-HEXYL-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE, FORMATE

MS (ESI) m/z 548.44 (M+H)$^+$.

EXAMPLE 194

5,7-DIMETHYL-3-(4-{2-[({[(4-METHYLPHENYL)SULFONYL]AMINO}CARBONYL)AMINO]ETHYL}PHENYL)-2-(4-PENTENYL)-3H-IMIDAZO[4,5-b]PYRIDINE, FORMATE

MS (ESI) m/z 532.42 (M+H)$^+$.

EXAMPLE 195

6-CHLORO-5-CYANO-2-ETHYL-1-(4-{2-[({[(4-METHYLPHENYLSULFONYL]AMINO}CARBONYL)AMINO]ETHYL}PHENYL)-1H-BENZIMIDAZOLE

STEP 1. 6-Chloro-1-[4-(2-chloroethyl)phenyl]-2-ethyl-1H-benzimidazole-5-carbonitrile The reaction was carried out according to the procedure described in step 7 of Example 1 from 6-chloro-2-ethyl-1-[4-(2-hydroxyethyl)phenyl]-1H-benzimidazole-5-carbonitrile (Example 111, step 4).

$^1$H-NMR (CDCl$_3$) δ 8.07 (1H, s), 7.50 (2H, d, J=8.4 Hz), 7.30 (2H, d, J=8.4 Hz), 7.19 (1H, s), 3.83 (2H, t, J=7.1 Hz), 3.22 (2H, t, J=7.1 Hz), 2.79 (2H, q, J=7.5 Hz), 1.37 (3H, t, J=7.5 Hz).

STEP 2. 1-[4-(2-Azidoethyl)phenyl]-6-chloro-2-ethyl-1H-benzimidazole-5-carbonitrile The reaction was carried out according to the procedure described in step 8 of Example 1 from 6-chloro-1-[4-(2-chloroethyl)phenyl]-2-ethyl-1H-benzimidazole-5-carbonitrile (step 1).

$^1$H-NMR (CDCl$_3$) δ 8.07 (1H, s), 7.49 (2H, d, J=8.4 Hz), 7.29 (2H, d, J=8.4 Hz), 7.18 (1H, s), 3.64 (2H, t, J=7.0 Hz), 3.04 (2H, t, J=7.0 Hz), 2.79 (2H, q, J=7.6 Hz), 1.36 (3H, t, J=7.6 Hz).

STEP 3. 1-[4-(2-Aminoethyl)phenyl]-6-chloro-2-ethyl-1H-benzimidazole-5-carbonitrile The reaction was carried out according to the procedure described in step 7 of Example 37 from 1-[4-(2-azidoethyl)phenyl]-6-chloro-2-ethyl-1H-benzimidazole-5-carbonitrile (step 2).

$^1$H-NMR (CDCl$_3$) δ 8.06 (1H, s), 7.46 (2H, d, J=8.1 Hz), 7.26 (2H, d, J=8.1 Hz), 7.19 (1H, s), 3.09 (2H, t, J=7.1 Hz), 2.89 (2H, t, J=7.1 Hz), 2.79 (2H, q, J=7.6 Hz), 1.36 (3H, t, J=7.6 Hz).

STEP 4. 6-Chloro-5-cyano-2-ethyl-1-(4-{2-[({[(4-methylphenyl)sulfonyl]amino}carbonyl)amino]ethyl}phenyl)-1H-benzimidazole The reaction was carried out according to the procedure described in step 10 of Example 1 from 1-[4-(2-aminoethyl)phenyl]-6-chloro-2-ethyl-1H-benzimidazole-5-carbonitrile (step 3).

mp 219–224° C.; IR (KBr) v: 3388, 2229, 1708, 1618, 1514, 1466, 1344, 1161, 1089 cm$^{-1}$.

MS (ESI) m/z 522 (M+H)$^+$, 520 M–H)$^-$; $^1$H-NMR (DMSO-d$_6$) δ 8.38 (1H, s), 7.77 (2H, d, J=8.2 Hz), 7.31–7.49 (6H, m), 7.32 (1H, s), 6.53 (1H, br.s), 3.26–3.28 (2H, m), 2.69–2.81 (4H, m), 2.35 (3H, s), 1.25 (3H, t, J=7.6 Hz).

THE SYNTHETIC PROCEDUIRE OF EXAMPLE 196–EXAMPLE 197

The compounds disclosed hereinafter were prepared according to the following procedure: To a mixture of requisite commercially available carbonic acid and dichloromethane (DCM) was added 1-ethyl-3-(3-dimethylaminopropyl)carbodiimide, hydrochloride (WSC) (0.05 mmol, 0.5 mL) followed by a solution of 3-amino-4,6-dimethyl-2-(4-{2-[({[(4-methylphenyl)sulfonyl]amino}carbonyl)amino]ethyl}amino)pyridine (0.038 mmol) in DCM (0.5 mL) at room temperature. The reaction mixture was stirred for 3 days at room temperature, then stirred for an additional day at 40° C. After removal of the solvent, the residue was dissolved in MeOH (1 mL) and the solution was filtered through a membrane filter. The filtrate was purified by preparative LC/MS (Shiseido capcell pack UG80 C18 (20× 50 mm) eluting with MeOH/0.1% HCOOH (v/v, 20/80 to 90/10) to give the title compound.

EXAMPLE 196

N-{[(2-{4-[5,7-DIMETHYL-2-(4-METHYLPENTYL)-3H-IMIDAZO[4,5-b]PYRIDIN-3-YL]PHENYL}ETHYL)AMINO]CARBONYL}-4-METHYLBENZENESULFONAMIDE, FORMATE

MS (ESI) m/z 548.53 (M+H)$^+$.

EXAMPLE 197

N-{[(2-{4-[5,7-DIMETHYL-2-(3-OXO-3-PHENYLPROPYL)-3H-IMIDAZO[4,5-b]PYRIDIN-3-YL]PHENYL}ETHYL)AMINO]CARBONYL}-4-METHYLBENZENESULFONAMIDE, FORMATE

MS (ESI) m/z 596.28 (M+H)$^+$.

THE SYNTHETIC PROCEDUIRE OF EXAMPLE 198–EXAMPLE 216

The compounds disclosed hereinafter were prepared according to the following procedure: The carboxylic acid (0.06 mmol) was dissolved with N,N-diisopropylethylamine (DIEA) (0.106 mmol) and dichloromethane (DCM) (0.3 mL). To this mixture was added 1-hydroxybenzotriazole hydrate (HOBT) (0.06 mmol) in N,N-dimehtylformamide (DMF) (0.02 mL). To the reaction were added 3-amino-4,6-dimethyl-2-(4-{2-[({[(4-methylphenyl)sulfonyl]amino}carbonyl)amino]ethyl}amino)pyridine (0.044 mmol) in DCM (0.3 mL) and DMF (0.08 mL), then O-benzotriazol-1-yl-N,N,N',N'-tetramethyluronium hexafluorophosphate (HBTU) (0.13 mmol) in DMF (0.25 mL). The reaction solution was stirred for 6 hr at room temperature, then heated at 40° C. over night. After removal of the solvent, the residue was dissolved in MeOH (0.8 mL). The solution was loaded onto a Varian BondElute® SCX cartridge (500 mg/3 mL) which was preconditioned with 2 mL of MeOH. The solid-phase matrix was washed with 5 mL of MeOH and then eluted with 2N ammonia/MeOH (3 mL). After the removal of solvent, the product was used for the next step reaction.

The intermediate product of 1$^{st}$ step was dissolved with EtOH (2 mL), then to the reaction solution was added excess 2N aq.NaOH (1 mL). The reaction mixture was stirred at 40° C. to 70° C. over night. After the reaction finished, the solvent was removed. To the residue was added 2N aq.HCl (1 mL, adjusted with pH 7.0). The aqueous layer was extracted with DCM (1 mL×3). The organic layer was concentrated to afford the residue. The crude product was purified by preparative LC/MS (Shiseido capcellpack UG 80 C18 (20×50 mm) eluting with MeOH/0.1% HCOOH (v/v, 20/80 to 90/10) to give the title compound as a formate.

EXAMPLE 198

N-{5-[5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDIN-2-YL]PENTYL}ACETAMIDE, FORMATE

MS (ESI) m/z 591.33 (M+H)$^+$.

EXAMPLE 199

N-{[(2-{4-[5,7-DIMETHYL-2-(5-OXO-5-PHENYLPENTYL)-3H-IMIDAZO[4,5-b]PYRIDIN-3-YL]PHENYL}ETHYL)AMINO]CARBONYL}-4-METHYLBENZENESULFONAMIDE, FORMATE

MS (ESI) m/z 624.37 (M+H)$^+$.

EXAMPLE 200

N-{[(2-{4-[2-(2-CYCLOPENTEN-1-YLMETHYL)-5,7-DIMETHYL-3H-IMIDAZO[4,5-b]PYRIDIN-3-YL]PHENYL}ETHYL)AMINO]CARBONYL}-4-METHYLBENZENESULFONAMIDE, FORMATE

MS (ESI) m/z 544.40 (M+H)$^+$.

EXAMPLE 201

N-{[(2-{4-[2-(1-CYCLOPENTEN-1-YLMETHYL)-5,7-DIMETHYL-3H-IMIDAZO[4,5-b]PYRIDIN-3-YL]PHENYL}ETHYL)AMINO]CARBONYL}-4-METHYLBENZENESULFONAMIDE, FORMATE

MS (ESI) m/z 544.40 (M+H)$^+$.

EXAMPLE 202

(2Z)-3-[5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDIN-2-YL]-N-PROPYL-2-PROPENAMIDE, FORMATE

MS (ESI) m/z 575.44 (M+H)$^+$.

EXAMPLE 203

N-{[(2-{4-[5,7-DIMETHYL-2-(1-METHYL-3-OXO-3-PHENYLPROPYL)-3H-IMIDAZO[4,5-b]PYRIDIN-3-YL]PHENYL}ETHYL)AMINO]CARBONYL}-4-METHYLBENZENESULFONAMIDE, FORMATE

MS (ESI) m/z 610.49 (M+H)$^+$.

EXAMPLE 204

N-{[(2-{4-[5,7-DIMETHYL-2-(3,3,3-TRIFLUORO-2-METHYLPROPYL)-3H-IMIDAZO[4,5-b]PYRIDIN-3-YL]PHENYL}ETHYL)AMINO]CARBONYL}-4-METHYLBENZENESULFONAMIDE, FORMATE

MS (ESI) m/z 574.43 (M+H)$^+$.

EXAMPLE 205

N-({[2-(4-{2-[2-(DIETHYLAMINO)ETHYL]-5,7-DIMETHYL-3H-IMIDAZO[4,5-b]PYRIDIN-3-YL}PHENYL)ETHYL]AMINO}CARBONYL)-4-METHYLBENZENESULFONAMIDE, FORMATE

MS (ESI) m/z 563.49 (M+H)$^+$.

EXAMPLE 206

N-({[2-(4-{2-[2-(4-FLUOROPHENYL)ETHYL]-5,7-DIMETHYL-3H-IMIDAZO[4,5-b]PYRIDIN-3-YL}PHENYL)ETHYL]AMINO}CARBONYL)-4-METHYLBENZENESULFONAMIDE, FORMATE

MS (ESI) m/z 586.46 (M+H)$^+$.

EXAMPLE 207

3-[5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDIN-2-YL]-N,N-DIETHYLPROPANAMIDE, FORMATE

MS (ESI) m/z 591.50 (M+H)$^+$.

EXAMPLE 208

N-[({2-[4-(5,7-DIMETHYL-2-TETRAHYDRO-3-FURANYL-3H-IMIDAZO[4,5-b]PYRIDIN-3-YL)PHENYL]ETHYL}AMINO)CARBONYL]-4-METHYLBENZENESULFONAMIDE, FORMATE

MS (ESI) m/z 534.41 (M+H)$^+$.

EXAMPLE 209

N-{[(2-{4-[5,7-DIMETHYL-2-(1-METHYLBUTYL)-3H-IMIDAZO[4,5-b]PYRIDIN-3-YL]PHENYL}ETHYL)AMINO]CARBONYL}-4-METHYLBENZENESULFONAMIDE, FORMATE

MS (ESI) m/z 534.45 (M+H)$^+$.

EXAMPLE 210

N-{[(2-{4-[2-(CYCLOPENTYLMETHYL)-5,7-DIMETHYL-3H-IMIDAZO[4,5-b]PYRIDIN-3-YL]PHENYL}ETHYL)AMINO]CARBONYL}-4-METHYLBENZENESULFONAMIDE, FORMATE

MS (ESI) m/z 546.46 (M+H)$^+$.

EXAMPLE 211

N-{[(2-{4-[5,7-DIMETHYL-2-(2-METHYLCYCLOPROPYL)-3H-IMIDAZO[4,5-b]PYRIDIN-3-YL]PHENYL}ETHYL)AMINO]CARBONYL}-4-METHYLBENZENESULFONAMIDE, FORMATE

MS (ESI) m/z 518.41 (M+H)$^+$.

EXAMPLE 212

N-[({2-[4-(5,7-DIMETHYL-2-{3-[4-(METHYLOXY)PHENYL]-3-OXOPROPYL}-IMIDAZO[4,5-b]PYRIDIN-3-YL)PHENYL]ETHYL}AMINO)CARBONYL]-4-METHYLBENZENESULFONAMIDE, FORMATE

MS (ESI) m/z 626.45 (M+H)$^+$.

EXAMPLE 213

N-({[2-(4-{2-[3-(3,4-DIMETHYLPHENYL)PROPYL]-5,7-DIMETHYL-3H-IMIDAZO[4,5-b]PYRIDIN-3-YL}PHENYL)ETHYL]AMINO}CARBONYL)-4-METHYLBENZENESULFONAMIDE, FORMATE

MS (ESI) m/z 610.28 (M+H)$^+$.

EXAMPLE 214

N-({[2-(4-{2-[(Z)-2-(4-FLUOROPHENYL)ETHE-NYL]-5,7-DIMETHYL-3H-IMIDAZO[4,5-b]PYRI-DIN-3-YL}PHENYL)ETHYL]AMINO}CARBONYL)-4-METHYLBENZENESULFONAMIDE, FORMATE

MS (ESI) m/z 584.41 (M+H)$^+$.

EXAMPLE 215

N-[({2-[4-(5,7-DIMETHYL-2-{(Z)-2-[2-(METHY-LOXY)PHENYL]ETHENYL}-3H-IMIDAZO[4,5-b]PYRIDIN-3-YL)PHENYL]ETHYL}AMINO)CARBONYL]-4-METHYLBEN-ZENESULFONAMIDE, FORMATE

MS (ESI) m/z 596.29 (M+H)$^+$.

EXAMPLE 216

N-{[(2-{4-[2-(5-HEXYNYL)-5,7-DIMETHYL-3H-IMIDAZO[4,5-b]PYRIDIN-3-YL]PHENYL}ETHYL)AMINO]CARBONYL}-4-METHYLBENZENESULFONAMIDE, FORMATE

MS (ESI) m/z 544.33 (M+H)$^+$.

THE SYNTHETIC PROCEDUIRE OF EXAMPLE 217–EXAMPLE 220

The compounds disclosed hereinafter were prepared according to the following procedure: To a solution of 3-amino-4,6-dimethyl-2-(4-{2-[({[(4-methylphenyl)sulfonyl]amino}carbonyl)amino]ethyl}amino)pyridine (0.044 mmol) in dichloromethane (DCM) (0.2 mL) and DMF (0.05 mL) was added pyridine (0.103 mmol) in DCM (0.2 mL), and excess of acid chloride (0.066 mmol-0.088 mmol) at room temperature. The reaction mixture was stirred at ambient temperature until the starting compound was disappeared (4–6 hr). After the reaction was stopped, to the reaction mixture was added MeOH (0.2 mL), then stirred for 1 hr. The solvent was removed by vacuum centrifuge.

The residue, which was dissolved with MeOH (0.8 mL), was loaded onto a Varian BondElute® SCX cartridge (500 mg/3 mL) which was preconditioned with 2 mL of MeOH. The solid-phase matrix was washed with 5 mL of MeOH and then eluted with 2N ammonia/MeOH (3 mL). The eluate was concentrated in vacuo to provide the intermediate product.

The intermediate product of 1$^{st}$ step was dissolved with EtOH (2 mL), then to the reaction solution was added excess 2N aq.NaOH (1 mL). The reaction mixture was stirred at 70° C. over night. After the removal of solvent, to the residue was added 2N aq.HCl to neutralize. The aqueous layer was extracted with DCM (1 mL×5 times). The organic layer was dried with sodium sulfate, then concentrated. The crude product was purified by preparative LC/MS (Shiseido cap-cellpack UG 80 C18 (20×50 mm) eluting with MeOH/0.1% HCOOH (v/v, 20/80 to 90/10) to give the title compound as a formate.

EXAMPLE 217

4-METHYL-N-[({2-[4-(2,5,7-TRIMETHYL-3H-IMIDAZO[4,5-b]PYRIDIN-3-YL)PHENYL]ETHYL}AMINO)CARBONYL]BENZENESULFONAMIDE, FORMATE

MS (ESI) m/z 478.31 (M+H)$^+$.

EXAMPLE 218

N-{[(2-{4-[2-(2,2-DIMETHYLPROPYL)-5,7-DIMETHYL-3H-IMIDAZO[4,5-b]PYRIDIN-3-YL]PHENYL}ETHYL)AMINO]CARBONYL}-4-METHYLBENZENESULFONAMIDE, FORMATE

MS (ESI) m/z 534.40 (M+H)$^+$.

EXAMPLE 219

N-[({2-[4-(2-CYCLOBUTYL-5,7-DIMETHYL-3H-IMIDAZO[4,5-b]PYRIDIN-3-YL)PHENYL]ETHYL}AMINO)CARBONYL]-4-METHYLBEN-ZENESULFONAMIDE, FORMATE

MS (ESI) m/z 518.38 (M+H)$^+$.

EXAMPLE 220

N-[({2-[4-(2-CYCLOPENTYL-5,7-DIMETHYL-3H-IMIDAZO[4,5-b]PYRIDIN-3-YL)PHENYL]ETHYL}AMINO)CARBONYL]-4-METHYLBEN-ZENESULFONAMIDE, FORMATE

MS (ESI) m/z 532.44 (M+H)$^+$.

EXAMPLE 221

4-(6-CHLORO-2-ETHYL-5-TRIFLUOROM-ETHYL-1H-BENZIMIDAZOL-1-YL)PHEN-ETHYL(4-METHYLPHENYL)SULFONYLCAR-BAMATE P-TOLUENESULFONATE

A mixture of 4-(6-chloro-2-ethyl-5-trifluoromethyl-1H-benzimidazol-1-yl)phenethyl(4-methylphenyl)sulfonylcarbamate (Example 106, 150 mg, 0.265 mmol), p-toluenesulfonic acid (50.5 mg, 0.265 mmol) in acetone (3% H$_2$O, 0.3 ml) was stirred at room temperature for 16 h. The precipitated crystalline solids were filtered, washed with acetone (0.05 ml×5), and dried in vacuo at 40° C. for 2 h to afford 158 mg (81%) of the title compound as white solids.
m.p.: 234.8° C.
$^1$H-NMR (CDCl$_3$) δ 8.66 (1H, br.s), 8.35 (1H, s), 7.85 (2H, d, J=8.1 Hz), 7.81 (2H, d, J=8.4 Hz), 7.53 (2H, d, J=8.4 Hz), 7.39–7.35 (3H, m), 7.29 (2H, d, J=7.9 Hz), 7.19 (2H, d, J=7.9 Hz), 4.35 (2H, t, J=6.2 Hz), 3.13 (2H, q, J=7.6 Hz), 3.04 (2H, t, J=6.3 Hz), 2.42 (3H, s), 2.36 (3H, s), 1.43 (3H, t, J=7.4 Hz).

EXAMPLE 222

4-(6-CHLORO-2-ETHYL-5-TRIFLUOROM-ETHYL-1H-BENZIMIDAZOL-1-YL)PHEN-ETHYL(4-METHYLPHENYL)SULFONYLCAR-BAMATE BENZENESULFONATE

The title compound was prepared according to the procedure described in Example 221 from 4-(6-chloro-2-ethyl-5-trifluoromethyl-1H-benzimidazol-1-yl)phenethyl(4-methylphenyl)sulfonylcarbamate (Example 106).
m.p.: 194.9° C.

¹H-NMR (CDCl₃) δ: 8.83 (1H, br.s), 8.39 (1H, s), 7.99–7.95 (2H, m), 7.81 (2H, d, J=8.4 Hz), 7.54 (2H, d, J=8.4 Hz), 7.41–7.36 (6H, m), 7.29 (2H, d, J=8.4 Hz), 4.34 (2H, t, J=6.1 Hz), 3.14 (2H, q, J=7.6 Hz), 3.03 (2H, t, J=6.1 Hz), 2.41 (3H, s), 1.42 (3H, t, J=7.4 Hz).

EXAMPLE 223

4-(6-CHLORO-2-ETHYL-5-TRIFLUOROM-ETHYL-1H-BENZIMIDAZOL-1-YL)PHEN-ETHYL(4-METHYLPHENYL)SULFONYLCAR-BAMATE METHANESULFONATE

The title compound was prepared according to the procedure described in Example 221 from 4-(6-chloro-2-ethyl-5-trifluoromethyl-1H-benzimidazol-1-yl)phenethyl(4-methylphenyl)sulfonylcarbamate (Example 106).

m.p.: 172.2° C.

¹H-NMR (CDCl₃) δ: 9.03 (1H, br.s), 8.52 (1H, s), 7.81 (2H, d, J=8.2 Hz), 7.56 (2H, d, J=8.2 Hz), 7.40 (2H, d, J=8.1 Hz), 7.39 (1H, s), 7.29 (2H, d, J=8.1 Hz), 4.35 (2H, t, J=6.3 Hz), 3.16 (2H, q, J=7.6 Hz), 3.06 (2H, t, J=6.3 Hz), 2.94 (3H, s), 2.41 (3H, s), 1.45 (3H, t, J=7.6 Hz).

EXAMPLE 224

5-ACETYL-2-ETHYL-3-(4-{2-[({[(4-METH-YLPHENYL)SULFONYL]AMINO}CARBONYL)AMINO]ETHYL}PHENYL)BENZIMIDAZOLE P-TOLUENESULFONATE

A mixture of 5-acetyl-2-ethyl-3-(4-{2-[({[(4-methylphenyl)sulfonyl]amino}carbonyl)amino]ethyl}phenyl)benzimidazole (Example 78, 43 mg, 0.085 mmol), p-toluenesulfonic acid (16.2 mg, 0.085 mmol) in ethanol (0.1 ml) was stirred at room temperature for 16 h. The precipitated crystalline solids were filtered, washed with ethanol (0.05 ml×5), and dried in vacuo at 40° C. for 2 h to afford 54 mg (91%) of the title compound as white solids.

m.p.: 166.7° C.

¹H-NMR (CDCl₃) δ: 9.85 (1H, br.s), 8.50 (1H, s), 8.02 (1H, d, J=8.9 Hz), 7.86 (2H, d, J=8.1 Hz), 7.68 (2H, dd, J=1.8, 8.2 Hz), 7.47 (2H, d, J=8.4 Hz), 7.36–7.31 (3H, m), 7.22 (2H, d, J=8.4 Hz), 7.17 (2H, d, J=8.4 Hz), 7.00 (1H, br.s), 3.47–3.39 (2H, m) 3.14 (2H, q, J=8.4 Hz), J=6.3 Hz), 2.58 (3H, s), 2.35 (3H, s), 2.34 (3H, s), 1.45 (3H, t, J=7.6 Hz).

EXAMPLE 225

5-ACETYL-2-ETHYL-3-(4-{2-[({[(4-METH-YLPHENYL)SULFONYL]AMINO}CARBONYL)AMINO]ETHYL}PHENYL)BENZIMIDAZOLE BENZENESULFONATE

The title compound was prepared according to the procedure described in Example 224 from 5-acetyl-2-ethyl-3-(4-{2-[({[(4-methylphenyl)sulfonyl]amino}carbonyl)amino]ethyl}phenyl)benzimidazole (Example 78).

m.p.: 117.7° C.

¹H-NMR (CDCl₃) δ: 9.62 (1H, br.s), 8.52 (1H, s), 8.05–7.96 (3H, m), 7.67 (2H, d, J=8.2 Hz), 7.49–7.43 (5H, m), 7.37–7.32 (3H, m), 7.19 (2H, d, J=8.2 Hz), 6.92–6.88 (1H, m), 3.48–3.42 (2H, m) 3.17 (2H, q, J=7.6 Hz), 2.89 (2H, t, J=6.1 Hz), 2.61 (3H, s), 2.35 (3H, s), 1.49 (3H, t, J=7.6 Hz).

EXAMPLE 226

4-CHLORO-2-ETHYL-6-METHYL-1-(4-{2-[({[(4-METHYLPHENYL)SULFONYL]AMINO}CARBONYL)AMINO]ETHYL}PHENYL)-1H-IMIDAZO[4,5-c]PYRIDINE

STEP 1. tert-butyl 2-{4-[(2-chloro-6-methyl-3-nitro-4-pyridinyl)amino]phenyl}ethylcarbamate A mixture of 2,4-dichloro-6-methyl-3-nitro-pyridine (Chorvat, Robert J. et al., J. Med. Chem., 1999, 42, 833., 7.5 g, 36.2 mmol), [2-(4-amino-phenyl)-ethyl]-carbamic acid tert-butyl ester (Stark, Peter A. et al., J. Med. Chem., 1992, 35, 4264., 1.14 g, 4.83 mmol) in N,N-diisopropylethylamine (50 ml) was heated at reflux temperature for 16 h. After cooling, the mixture was concentrated. The residue was diluted with dichloromethane (200 ml) and washed with saturated aqueous NaHCO₃ solution (50 ml×2). The organic layer was dried (MgSO₄), and concentrated. Purification by flash column chromatography eluting with hexane/ethyl acetate (1:1) to afford 310 mg (16%) of the title compound as orange solids.

¹H-NMR (CDCl₃) δ: 8.19 (1H, s), 7.28 (2H, d, J=8.4 Hz), 7.16 (2H, d, J=8.3 Hz), 6.69 (1H, s), 4.62 (1H, br s), 3.43–3.37 (2H, m), 2.84 (2H, t, J=7.0 Hz), 2.37 (3H, s), 1.44 (9H, s).

STEP 2. tert-butyl 2-{4-[(3-amino-2-chloro-6-methyl-4-pyridinyl)amino]phenyl}ethylcarbamate The title compound was prepared according to the procedure described in step 1 of Example 6 from tert-butyl 2-{4-[(2-chloro-6-methyl-3-nitro-4-pyridinyl)amino]phenyl}ethylcarbamate (step 1).

¹H-NMR (CDCl₃) δ: 7.18 (2H, d, J=8.3 Hz), 7.03 (2H, d, J=8.2 Hz), 6.76 (1H, s), 6.02 (1H, br. s), 4.61 (1H, br. s), 3.40–3.37 (4H, m), 2.78 (2H, t, J=7.0 Hz), 2.33 (3H, s), 1.44 (9H, s).

STEP 3. tert-butyl 2-[4-(4-chloro-2-ethyl-6-methyl-1H-imidazo[4,5-c]pyridin-1-yl)phenyl]ethylcarbamate A mixture of tert-butyl 2-{4-[(3-amino-2-chloro-6-methyl-4-pyridinyl)amino]phenyl}ethylcarbamate (step 2, 238 mg, 0.63 mmol), propionyl chloride (70 mg, 0.76 mmol) in toluene (4.6 ml) and dichloromethane (0.6 ml) was heated at reflux temperature for 1 h. After cooling, the mixture was diluted with ethyl acetate (100 ml) and washed with 1N aqueous NaOH solution (30 ml×2) and brine (30 ml). The organic layer was dried (MgSO₄), and concentrated. The residue and p-toluenesulfonic acid monohydrate (5 mg, 0.026 mmol) in toluene (5.0 ml) was heated at reflux temperature for 16 h. After cooling, the mixture was diluted with dichloromethane (100 ml) and washed with saturated aqueous NaHCO₃ solution (30 ml) and brine (30 ml). The organic layer was dried (MgSO₄), and concentrated. Purification by PTLC eluting with hexane/ethyl acetate (1:1) to afford 90 mg (34%) of the title compound as a brown oil.

¹H-NMR (CDCl₃) δ: 7.44 (2H, d, J=8.2 Hz), 7.27 (2H, d, J=8.2 Hz), 6.81 (1H, s), 4.75 (1H, br s), 3.52–3.44 (2H, m), 2.94 (2H, t, J=7.1 Hz), 2.82 (2H, q, J=7.6 Hz), 2.55 (3H, s), 1.46 (9H, s), 1.32 (3H, t, J=7.6 Hz).

STEP 4. 2-[4-(4-chloro-2-ethyl-6-methyl-1H-imidazo[4,5-c]pyridin-1-yl)phenyl]ethanamine To a stirred solution of tert-butyl 2-[4-(4-chloro-2-ethyl-6-methyl-1H-imidazo[4,5-c]pyridin-1-yl)phenyl]ethylcarbamate (step 3, 90 mg, 0.22 mmol) in dichloromethane (8.5 ml) was added trifluoroacetic acid (1.0 ml, 13.0 mmol) at 0°

C., and the mixture was stirred at 0° C. for 30 min, then at room temperature for 5 h. The mixture was concentrated, and diluted with dichloromethane (50 ml), washed with saturated aqueous NaHCO$_3$ solution (10 ml) and brine (10 ml). The organic layer was dried (MgSO$_4$), and concentrated. Purification by PTLC eluting with ethyl acetate to afford 50 mg (73%) of the title compound as a brown oil.

$^1$H-NMR (CDCl$_3$) δ: 7.45 (2H, d, J=8.2 Hz), 7.27 (2H, d, J=8.2 Hz), 6.81 (1H, s), 3.09 (2H, t, J=6.9 Hz), 2.89 (2H, t, J=6.8 Hz), 2.83 (2H, q, J=7.4 Hz), 2.55 (3H, s), 1.31 (3H, t, J=7.4 Hz).

STEP 5. 4-chloro-2-ethyl-6-methyl-1-(4-{2-[({[(4-methylphenyl)sulfonyl]amino}carbonyl)amino]ethyl}phenyl)-1H-imidazo[4,5-c]pyridine The title compound was prepared according to the procedure described in step 10 of Example 1 from 2-[4-(4-chloro-2-ethyl-6-methyl-1H-imidazo[4,5-c]pyridin-1-yl)phenyl]ethanamine (step 4).

m.p.: 163° C.

MS (ESI) m/z: 512 [(MH)$^+$], 510 [(M−H)$^-$].

$^1$H-NMR (CDCl$_3$) δ: 7.73 (2H, d, J=8.2 Hz), 7.38–7.21 (6H, m), 6.78 (1H, s), 3.53–3.51 (2H, m), 2.91–2.89 (2H, m), 2.79 (2H, q, J=7.2 Hz), 2.52 (3H, s), 2.37 (3H, s), 1.29 (3H, t, J=7.2 Hz).

EXAMPLE 227

2-[4-(2-ETHYL-4,6-DIMETHYL-1H-IMIDAZO[4,5-c]PYRIDIN-1-YL)PHENYL]ETHYL(4-METHYLPHENYL)SULFONYLCARBAMATE

The title compound was prepared according to the procedure described in Example 3 from 2-[4-(2-ethyl-4,6-dimethyl-1H-imidazo[4,5-c]pyridin-1-yl)phenyl]ethanol (step 4 of Example 42).

m.p.: 158° C.

MS (ESI) m/z: 493 [(MH)$^+$], 491 [(M−H)$^-$].

$^1$H-NMR (DMSO-d$_6$) δ: 7.72 (2H, d, J=8.2 Hz), 7.47 (2H, d, J=8.6 Hz), 7.43 (2H, d, J=8.6 Hz), 7.34 (2H, d, J=8.0 Hz), 6.96 (1H, s), 4.18 (2H, t, J=6.6 Hz), 2.94 (2H, t, J=6.4 Hz), 2.76 (3H, s), 2.74 (2H, q, J=7.3 Hz), 2.50 (3H, s), 2.35 (3H, s), 1.23 (3H, t, J=7.3 Hz).

EXAMPLE 228

2-[4-(8-ETHYL-2,6-DIMETHYL-9H-PURIN-9-YL)PHENYL]ETHYL(4-METHYLPHENYL)SULFONYLCARBAMATE

STEP 1. 2-{4-[(6-chloro-2-methyl-5-nitro-4-pyrimidinyl)amino]phenyl}ethanol

To a stirred solution of 4,6-dichloro-2-methyl-5-nitropyrimidine (Albert et al., J. Chem. Soc., 1954, 3832, 7.5 g, 36.1 mmol) in THF (150 ml) was added 4-aminophenylethyl alcohol (2.47 g, 18.0 mmol), triethylamine (3.65 g, 36.1 mmol), and the mixture was stirred at room temperature for 1 h. The reaction was quenched with water (10 ml), and the mixture was extracted with ethyl acetate (100 ml×3). The organic layer was washed with brine (50 ml), dried (MgSO$_4$), and concentrated. Purification by flash column chromatography eluting with hexane/ethyl acetate (gradient elution from 1:1 to 1:2) to afford 4.0 g (72%) of the title compound as a yellow solid.

$^1$H-NMR (CDCl$_3$) δ: 9.34 (1H, s), 7.50 (2H, d, J=8.4 Hz), 7.28 (2H, d, J=8.8 Hz), 3.89 (2H, t, J=6.6 Hz), 2.90 (2H, t, J=6.4 Hz), 2.57 (3H, s).

STEP 2. diethyl 2-(6-{[4-(2-hydroxyethyl)phenyl]amino}-2-methyl-5-nitro-4-pyrimidinyl)propanedioate To a stirred solution of 2-{4-[(6-chloro-2-methyl-5-nitro-4-pyrimidinyl)amino]phenyl}ethanol (step 1, 2.0 g, 6.48 mmol) in acetone (61 ml) was added diethyl malonate (1.53 g, 9.54 mmol) at 0° C., then aqueous NaOH solution (11N, 2 ml, 22 mmol) was added dropwise over 20 min. After addition, the mixture was stirred at room temperature for 1 h. The reaction was quenched with water (120 ml), and the pH value was adjusted to 8.0 by addition of acetic acid. The whole was extracted with ethyl acetate (100 ml×3). The organic-layer was washed with brine (50 ml), dried (MgSO$_4$), and concentrated. Removal of excess diethyl malonate by azetropical distillation with toluene afforded 3.26 g (72%) of the title compound as a brown oil.

MS (EI) m/z: 432 (M$^+$).

$^1$H-NMR (CDCl$_3$) δ: 10.15 (1H, s), 7.55 (2H, d, J=8.4 Hz), 7.27 (2H, d, J=8.4 Hz), 5.36 (1H, s), 4.31 (4H, q, J=7.1 Hz), 3.90 (2H, t, J=6.6 Hz), 2.90 (2H, t, J=6.4 Hz), 2.56 (3H, s), 1.32 (6H, t, J=7.1 Hz).

STEP 3. 2-{4-[(2,6-dimethyl-5-nitro-4-pyrimidinyl)amino]phenyl}ethanol

A mixture of diethyl 2-(6-{[4-(2-hydroxyethyl)phenyl]amino}-2-methyl-5-nitro-4-pyrimidinyl)propanedioate (step 2, 2.0 g, 6.48 mmol) in 2N aqueous HCl (15 ml) was heated at reflux temperature for 5 h. After cooling, the reaction was quenched with saturated NaHCO$_3$ aqueous solution (100 ml), and the whole was extracted with ethyl acetate (100 ml×3). The organic layer was washed with brine (50 ml), dried (MgSO$_4$), and concentrated. Purification by flash column chromatography eluting with hexane/ethyl acetate (gradient elution from 1:1 to 0:100) to afford 1.33 g (71%) of the title compound as a yellow solid.

MS (EI) m/z: 288 (M$^+$).

$^1$H-NMR (CDCl$_3$) δ: 9.81 (1H, s), 7.56 (2H, d, J=8.4 Hz), 7.27 (2H, d, J=8.4 Hz), 3.92–3.86 (2H, m), 2.89 (2H, t, J=6.4 Hz), 2.76 (3H, s), 2.56 (3H, s).

STEP 4. 2-{4-[(5-amino-2,6-dimethyl-4-pyrimidinyl)amino]phenyl}ethanol

The title compound was prepared according to the procedure described in step 1 of Example 6 from 2-{4-[(2,6-dimethyl-5-nitro-4-pyrimidinyl)amino]phenyl}ethanol (step 3).

MS (EI) m/z: 258 (M$^+$).

$^1$H-NMR (DMSO-d$_6$) δ: 8.14 (1H, s), 7.63 (2H, d, J=8.6 Hz), 7.12 (2H, d, J=8.4 Hz), 4.67 (2H, br.s), 3.58 (2H, t, J=7.3 Hz), 2.67 (2H, t, J=7.2 Hz), 2.28 (3H, s), 2.20 (3H, s).

STEP 5. 2-[4-(8-ethyl-2,6-dimethyl-9H-purin-9-yl)phenyl]ethyl propanoate

The title compound was prepared according to the procedure described in step 5 of Example 1 from 2-{4-[(5-amino-2,6-dimethyl-4-pyrimidinyl)amino]phenyl}ethanol (step 4).

$^1$H-NMR (CDCl$_3$) δ: 7.44 (2H, d, J=8.2 Hz), 7.31 (2H, d, J=8.2 Hz), 4.37 (2H, t, J=6.9 Hz), 3.06 (2H, t, J=6.8 Hz), 2.84 (3H, s), 2.82 (2H, q, J=7.4 Hz), 2.70 (3H, s), 2.35 (2H, q, J=7.6 Hz), 1.31 (3H, t, J=7.6 Hz), 1.15 (3H, t, J=7.6 Hz).

STEP 6. 2-[4-(8-ethyl-2,6-dimethyl-9H-purin-9-yl)phenyl]ethanol

The title compound was prepared according to the procedure described in step 6 of Example 1 from 2-[4-(8-ethyl-2,6-dimethyl-9H-purin-9-yl)phenyl]ethyl propanoate (step 5).

¹H-NMR (CDCl₃) δ: 7.46 (2H, d, J=8.4 Hz), 7.31 (2H, d, J=8.3 Hz), 3.99–3.92 (2H, m), 2.99 (2H, t, J=6.4 Hz), 2.85 (3H, s), 2.83 (2H, q, J=7.5 Hz), 2.70 (3H, s), 1.32 (3H, t, J=7.3 Hz).

STEP 7. 2-[4-(8-ethyl-2,6-dimethyl-9H-purin-9-yl)phenyl]ethyl(4-methylphenyl)sulfonylcarbamate The title compound was prepared according to the procedure described in Example 3 from 2-[4-(8-ethyl-2,6-dimethyl-9H-purin-9-yl)phenyl]ethanol (step 6).

m.p.: 162° C.

MS (ESI) m/z: 494 [(MH)⁺], 492 [(M−H)⁻].

¹H-NMR (CDCl₃) δ: 7.94 (2H, d, J=8.4 Hz), 7.34 (2H, d, J=8.1 Hz), 7.24 (2H, d, J=8.6 Hz), 7.18 (2H, d J=8.4 Hz), 4.36 (2H, t, J=6.4 Hz), 2.97 (2H, t, J=6.2 Hz), 2.86 (3H, s), 2.79 (2H, q, J=7.6 Hz), 2.64 (3H, s), 2.44 (3H, s), 1.28 (3H, t, J=7.6 Hz).

EXAMPLE 229

2-[4-(4,6-DIMETHYL-2-PHENYL-1H-IMIDAZO[4,5-c]PYRIDIN-1-YL)PHENYL]ETHYL (4-METHYLPHENYL)SULFONYLCARBAMATE

STEP 1. 2-[4-(4,6-dimethyl-2-phenyl-1H-imidazo[4,5-c]pyridin-1-yl)phenyl]ethyl benzoate A mixture of 2-{4-[(3-Amino-2,6-dimethyl-4-pyridinyl)amino]phenyl}ethanol (step 2 of Example 42, 500 mg, 1.94 mmol), benzoic acid (4.45 g 36.4 mmol), benzoic anhydride (4.8 g, 21.2 mmol) was heated at 120° C. for 4 h. After cooling, the mixture was diluted with dichloromethane (100 ml). The solution was washed with saturated NaHCO₃ aqueous solution (50 ml), brine (50 ml), dried (MgSO₄), and concentrated. Purification by flash column chromatography eluting with ethyl acetate to afford 813 mg (94%) of the title compound as a white solid.

MS (EI) m/z: 447(M⁺).

¹H-NMR (CDCl₃) δ: 8.02–7.21 (14H, m), 6.87 (1H, s), 4.61 (2H, t, J=7.0 Hz), 3.18 (2H, t, J=6.8 Hz), 2.96 (3H, s), 2.61 (3H, s).

STEP 2. 2-[4-(4,6-dimethyl-2-phenyl-1H-imidazo[4,5-c]pyridin-1-yl)phenyl]ethanol The title compound was prepared according to the procedure described in step 6 of Example 1 from 2-[4-(4,6-dimethyl-2-phenyl-1H-imidazo[4,5-c]pyridin-1-yl)phenyl]ethyl benzoate (step 1).

¹H-NMR (CDCl₃) δ: 7.57–7.18 (9H, m), 6.87 (1H, s), 3.95 (2H, t, J=6.6 Hz), 2.96 (2H, t, J=6.6 Hz), 2.94 (3H, s), 2.59 (3H, s).

STEP 3. 2-[4-(4,6-dimethyl-2-phenyl-1H-imidazo[4,5-c]pyridin-1-yl)phenyl]ethyl(4-methylphenyl)sulfonylcarbamate The title compound was prepared according to the procedure described in Example 3 from 2-[4-(4,6-dimethyl-2-phenyl-1H-imidazo[4,5-c]pyridin-1-yl)phenyl]ethanol (step 2).

m.p.: 194° C.

MS (ESI) m/z: 541 [(MH)⁺], 539 [(M−H)⁻].

¹H-NMR (CDCl₃) δ: 7.89 (2H, d, J=8.2 Hz), 7.46–6.95 (11H, m), 6.77 (1H, s), 4.35 (2H, t, J=6.0 Hz), 3.03 (3H, s), 2.96 (2H, t, J=6.0 Hz), 2.56 (3H, s), 2.42 (3H, s).

EXAMPLE 230

2-[4-(2-BUTYL-4,6-DIMETHYL-1H-IMIDAZO[4,5-c]PYRIDIN-1-YL)PHENYL]ETHYL(4-METHYLPHENYL)SULFONYLCARBAMATE

STEP 1. 2-[4-(2-butyl-4,6-dimethyl-1H-imidazo[4,5-c]pyridin-1-yl)phenyl]ethyl pentanoate The title compound was prepared according to the procedure described in step 1 of Example 229 from 2-{4-[(3-Amino-2,6-dimethyl-4-pyridinyl)amino]phenyl}ethanol (step 2 of Example 42).

¹H-NMR (CDCl₃) δ: 7.44 (2H, d, J=8.1 Hz), 7.26 (2H, d, J=8.2 Hz), 6.71 (1H, s), 4.38 (2H, t, J=6.9 Hz), 3.07 (2H, t, J=6.9 Hz), 2.88 (3H, s), 2.78 (2H, t, J=7.6 Hz), 2.56 (3H, s), 2.33 (2H, t, J=7.4 Hz), 1.74–1.55 (4H, m), 1.41–1.24 (4H, m), 0.91 (3H, t, J=7.2 Hz), 0.84 (3H, t, J=7.2 Hz).

STEP 2. 2-[4-(2-butyl-4,6-dimethyl-1H-imidazo[4,5-c]pyridin-1-yl)phenyl]ethanol

The title compound was prepared according to the procedure described in step 6 of Example 1 from 2-[4-(2-butyl-4,6-dimethyl-1H-imidazo[4,5-c]pyridin-1-yl)phenyl]ethyl pentanoate (step 1).

¹H-NMR (CDCl₃) δ: 7.46 (2H, d, J=8.2 Hz), 7.25 (2H, d, J=8.2 Hz), 6.72 (1H, s), 4.00 (2H, t, J=6.6 Hz), 3.02 (2H, t, J=6.4 Hz), 2.88 (3H, s), 2.78 (2H, t, J=7.6 Hz), 2.54 (3H, s), 1.76–1.64 (2H, m), 1.39–1.25 (2H, m), 0.85 (3H, t, J=7.4 Hz).

STEP 3. 2-[4-(2-butyl-4,6-dimethyl-1H-imidazo[4,5-c]pyridin-1-yl)phenyl]ethyl(4-methylphenyl)sulfonylcarbamate The title compound was prepared according to the procedure described in Example 3 from 2-[4-(2-butyl-4,6-dimethyl-1H-imidazo[4,5-c]pyridin-1-yl)phenyl]ethanol (step 2).

m.p.: 162° C.

MS (ESI) m/z: 521 [(MH)⁺], 519 [(M−H)⁻].

¹H-NMR (CD₃OD) δ: 7.97 (2H, d, J=8.3 Hz), 7.31 (2H, d, J=7.9 Hz), 7.18 (2H, d, J=8.4 Hz), 6.84 (2H, d, J=8.4 Hz), 6.60 (1H, s), 4.34 (2H, t, J=5.5 Hz), 3.03 (3H, s), 2.96 (2H, t, J=5.5 Hz), 2.71 (2H, t, J=7.5 Hz), 2.52 (3H, s), 2.43 (3H, s), 1.72–1.62 (2H, m), 1.36–1.24 (2H, m), 0.84 (3H, t, J=7.3 Hz).

EXAMPLE 231

2-[4-(2-BUTYL-4,6-DIMETHYL-1H-IMIDAZO[4,5-c]PYRIDIN-1-YL)PHENYL]ETHYL(4-METHYLPHENYL)SULFONYLCARBAMATE P-TOLUENESULFONATE

To a solution of 2-[4-(2-butyl-4,6-dimethyl-1H-imidazo[4,5-c]pyridin-1-yl)phenyl]ethyl(4-methylphenyl)sulfonylcarbamate (Example 230) in methanol was added TsOH (1.0 eq.). The resulting mixture was stirred at room temperature for 5 min and concentrated. The residual solids were collected and dried under reduced pressure at 50° C. to afford the title compound as white solids:

¹H-NMR (CDCl₃) δ: 7.89–7.86 (4H, m), 7.49 (2H, d, J=8.3 Hz), 7.30 (2H, d, J=8.1 Hz), 7.24 (2H, d, J=8.3 Hz), 7.18 (2H, d, J=7.9 Hz), 7.03 (1H, s), 4.34 (2H, t, J=6.2 Hz), 3H, s), 3.02 (2H, t, J=6.2 Hz), 2.80 (3H, s), 2.77 (2H, t, J=8.1 Hz), 2.42 (3H, s), 2.34 (3H, s), 1.78–1.68 (2H, m), 1.39–1.27 (2H, m), 0.86 (3H, t, J=7.3 Hz).

EXAMPLE 232

2-[4-(4,6-DIMETHYL-2-(1-METHYLETHYL)-1H-IMIDAZO[4,5-c]PYRIDIN-1-YL)PHENYL]ETHYL(4-METHYLPHENYL)SULFONYLCARBAMATE

STEP 1. 2-{4-[4,6-dimethyl-2-(1-methylethyl)-1H-imidazo[4,5-c]pyridin-1-yl]phenyl}ethyl 2-methylpropanoate The title compound was prepared according to the procedure described in step 1 of Example 229 from 2-{4-[(3-Amino-2,6-dimethyl-4-pyridinyl)amino]phenyl}ethanol (step 2 of Example 42).

$^1$H-NMR (CDCl$_3$) δ: 7.44 (2H, d, J=8.4 Hz), 7.26 (2H, d, J=8.4 Hz), 6.66 (1H, s), 4.38 (2H, t, J=7.0 Hz), 3.08 (2H, t, J=6.8 Hz), 3.12–3.02 (1H, m), 2.89 (3H, s), 2.55 (3H, s), 2.61–2.48 (1H, m), 1.33 (6H, d, J=7.0 Hz), 1.15 (6H, d, J=7.0 Hz).

STEP 2. 2-{4-[4,6-dimethyl-2-(1-methylethyl)-1H-imidazo[4,5-c]pyridin-1-yl]phenyl}ethanol The title compound was prepared according to the procedure described in step 6 of Example 1 from 2-{4-[4,6-dimethyl-2-(1-methylethyl)-1H-imidazo[4,5-c]pyridin-1-yl]phenyl}ethyl 2-methylpropanoate (step 1).

$^1$H-NMR (CDCl$_3$) δ: 7.46 (2H, d, J=8.2 Hz), 7.25 (2H, d, J=8.3 Hz), 6.68 (1H, s), 4.00 (2H, t, J=6.6 Hz), 3.13–3.04 (1H, m), 3.02 (2H, t, J=6.6 Hz), 2.88 (3H, s), 2.53 (3H, s), 1.33 (6H, d, J=7.0 Hz).

STEP 3. 2-{4-[4,6-dimethyl-2-(1-methylethyl)-1H-imidazo[4,5-c]pyridin-1-yl]phenyl}ethyl(4-methylphenyl)sulfonylcarbamate The title compound was prepared according to the procedure described in Example 3 from 2-{4-[4,6-dimethyl-2-(1-methylethyl)-1H-imidazo[4,5-c]pyridin-1-yl]phenyl}ethanol (step 2).

m.p.: 213° C.

MS (ESI) m/z: 507 [(MH)$^+$], 505 [(M−H)$^−$].

$^1$H-NMR (CD$_3$OD) δ: 7.80 (2H, d, J=8.4 Hz), 7.51 (2H, d, J=8.6 Hz), 7.34 (2H, d, J=8.6 Hz), 7.29 (2H, d, J=8.1 Hz), 7.01 (1H, s), 4.26 (2H, t, J=6.6 Hz), 3.15–3.09 (1H, m), 3.00 (2H, t, J=6.4 Hz), 2.90 (3H, s), 2.58 (3H, s), 2.36 (3H, s), 1.33 (6H, d, J=6.8 Hz).

EXAMPLE 233

2-{4-[2-(1,1-DIMETHYLETHYL)-4,6-DIMETHYL-1H-IMIDAZO[4,5-c]PYRIDIN-1-YL]PHENYL}ETHYL(4-METHYLPHENYL)SULFONYLCARBAMATE

STEP 1. 2-{4-[2-(1,1-dimethylethyl)-4,6-dimethyl-1H-imidazo[4,5-c]pyridin-1-yl]phenyl}ethyl 2,2-dimethylpropanoate The title compound was prepared according to the procedure described in step 1 of Example 229 from 2-{4-[(3-Amino-2,6-dimethyl-4-pyridinyl)amino]phenyl}ethanol (step 2 of Example 42).

$^1$H-NMR (CDCl$_3$) δ: 7.41 (2H, d, J=8.4 Hz), 7.26 (2H, d, J=8.4 Hz), 6.35 (1H, s), 4.38 (2H, t, J=6.6 Hz), 3.08 (2H, t, J=6.6 Hz), 2.87 (3H, s), 2.50 (3H, s), 1.34 (9H, s), 1.17 (9H, s).

STEP 2. 2-{4-[2-(1,1-dimethylethyl)-4,6-dimethyl-1H-imidazo[4,5-c]pyridin-1-yl]phenyl}ethanol The title compound was prepared according to the procedure described in step 6 of Example 1 from 2-{4-[2-(1,1-dimethylethyl)-4,6-dimethyl-1H-imidazo[4,5-c]pyridin-1-yl]phenyl}ethyl 2,2-dimethylpropanoate (step 1).

$^1$H-NMR (CDCl$_3$) δ: 7.42 (2H, d, J=8.1 Hz), 7.27 (2H, d, J=8.6 Hz), 6.38 (1H, s), 4.00 (2H, t, J=6.4 Hz), 3.01 (2H, t, J=6.6 Hz), 2.87 (3H, s), 2.50 (3H, s), 1.34 (9H, s).

STEP 3. 2-{4-[2-(1,1-dimethylethyl)-4,6-dimethyl-1H-imidazo[4,5-c]pyridin-1-yl]phenyl}ethyl(4-methylphenyl)sulfonylcarbamate The title compound was prepared according to the procedure described in Example 3 from 2-{4-[2-(1,1-dimethylethyl)-4,6-dimethyl-1H-imidazo[4,5-c]pyridin-1-yl]phenyl}ethanol (step 2).

m.p.: 226° C.

MS (ESI) m/z: 521 [(MH)$^+$], 519 [(M−H)$^−$].

$^1$H-NMR (DMSO-d$_6$) δ: 7.71 (2H, d, J=8.3 Hz), 7.46 (2H, d, J=8.6 Hz), 7.41 (2H, d, J=8.6 Hz), 7.35 (2H, d, J=8.1 Hz), 6.55 (1H, s), 4.20 (2H, t, J=7.0 Hz), 2.95 (2H, t, J=7.0 Hz), 2.74 (3H, s), 2.44 (3H, s), 2.36 (3H, s), 1.27 (9H, s).

EXAMPLE 234

2-[4-(2-CYCLOHEXYL-4,6-DIMETHYL-1H-IMIDAZO[4,5-c]PYRIDIN-1-YL)PHENYL]ETHYL(4-METHYLPHENYL)SULFONYLCARBAMATE

STEP 1. 2-[4-(2-cyclohexyl-4,6-dimethyl-1H-imidazo[4,5-c]pyridin-1-yl)phenyl]ethyl cyclohexanecarboxylate The title compound was prepared according to the procedure described in step 1 of Example 229 from 2-{4-[(3-Amino-2,6-dimethyl-4-pyridinyl)amino]phenyl}ethanol (step 2 of Example 42).

$^1$H-NMR (CDCl$_3$) δ: 7.44 (2H, d, J=8.4 Hz), 7.24 (2H, d, J=8.4 Hz), 6.65 (1H, s), 4.39 (2H, t, J=6.8 Hz), 3.08 (2H, t, J=6.8 Hz), 2.88 (3H, s), 2.54 (3H, s), 2.71–1.21 (22H, m).

STEP 2. 2-[4-(2-cyclohexyl-4,6-dimethyl-1H-imidazo[4,5-c]pyridin-1-yl)phenyl]ethanol The title compound was prepared according to the procedure described in step 6 of Example 1 from 2-[4-(2-cyclohexyl-4,6-dimethyl-1H-imidazo[4,5-c]pyridin-1-yl)phenyl]ethyl cyclohexanecarboxylate (step 1).

$^1$H-NMR (CDCl$_3$) δ: 7.46 (2H, d, J=8.2 Hz), 7.25 (2H, d, J=8.2 Hz), 6.68 (1H, s), 4.01 (2H, t, J=6.4 Hz), 3.02 (2H, t, J=6.4 Hz), 2.88 (3H, s), 2.72–2.70 (1H, m), 2.54 (3H, s), 2.30–1.15 (10H, m).

STEP 3. 2-[4-(2-cyclohexyl-4,6-dimethyl-1H-imidazo[4,5-c]pyridin-1-yl)phenyl]ethyl(4-methylphenyl)sulfonylcarbamate The title compound was prepared according to the procedure described in Example 3 from 2-[4-(2-cyclohexyl-4,6-dimethyl-1H-imidazo[4,5-c]pyridin-1-yl)phenyl]ethanol (step 2).

m.p.: 168° C.

MS (ESI) m/z: 547 [(MH)$^+$], 545 [(M−H)$^−$].

$^1$H-NMR (CD$_3$OD) δ: 7.97 (2H, d, J=8.4 Hz), 7.29 (2H, d, J=8.1 Hz), 7.19 (2H, d, J=8.3 Hz), 6.77 (2H, d, J=8.2 Hz), 6.53 (1H, s), 4.33 (2H, t, J=5.3 Hz), 3.09 (3H, s), 2.97 (2H, t, J=5.5 Hz), 2.65–2.55 (1H, m), 2.50 (3H, s), 2.42 (3H, s), 1.77–1.18 (10H, m).

EXAMPLE 235

2-{4-[4,6-DIMETHYL-2-(3-PHENYLPROPYL)-1H-IMIDAZO[4,5-c]PYRIDIN-1-YL] PHENYL}ETHYL(4-METHYLPHENYL)SULFONYLCARBAMATE

STEP 1. 2-{4-[4,6-dimethyl-2-(3-phenylpropyl)-1H-imidazo[4,5-c]pyridin-1-yl]phenyl}ethyl 4-phenylbutanoate The title compound was prepared according to the procedure described in step 1 of Example 229 from 2-{4-[(3-Amino-2,6-dimethyl-4-pyridinyl)amino]phenyl}ethanol (step 2 of Example 42).

$^1$H-NMR (CDCl$_3$) δ: 7.39 (2H, d, J=8.2 Hz), 7.30–7.15 (10H, m), 7.06 (2H, d, J=6.4 Hz), 6.70 (1H, s), 4.37 (2H, t, J=7.1 Hz), 3.06 (2H, t, J=6.9 Hz), 2.88 (3H, s), 2.80 (2H, t, J=7.6 Hz), 2.68–2.60 (4H, m), 2.54 (3H, s), 2.36 (2H, t, J=7.4 Hz), 2.09–1.91 (4H, m).

STEP 2. 2-{4-[4,6-dimethyl-2-(3-phenylpropyl)-1H-imidazo[4,5-c]pyridin-1-yl]phenyl}ethanol The title compound was prepared according to the procedure described in step 6 of Example 1 from 2-{4-[4,6-dimethyl-2-(3-phenylpropyl)-1H-imidazo[4,5-c]pyridin-1-yl]phenyl}ethyl 4-phenylbutanoate (step 1).

$^1$H-NMR (CDCl$_3$) δ: 7.41 (2H, d, J=8.2 Hz), 7.25–7.15 (5H, m), 7.07 (2H, d, J=6.8 Hz), 6.72 (1H, s), 3.99 (2H, t, J=6.6 Hz), 3.00 (2H, t, J=6.3 Hz), 2.88 (3H, s), 2.81 (2H, t, J=7.6 Hz), 2.64 (2H, d, J=7.6 Hz), 2.55 (3H, s), 2.11–2.00 (2H, m).

STEP 3. 2-{4-[4,6-dimethyl-2-(3-phenylpropyl)-1H-imidazo[4,5-c]pyridin-1-yl]phenyl}ethyl(4-methylphenyl)sulfonylcarbamate The title compound was prepared according to the procedure described in Example 3 from 2-{4-[4,6-dimethyl-2-(3-phenylpropyl)-1H-imidazo[4,5-c]pyridin-1-yl] phenyl}ethanol (step 2).

m.p.: 175° C.

MS (ESI) m/z: 583 [(MH)$^+$], 581 [(M–H)$^-$].

$^1$H-NMR (CDCl$_3$) δ: 7.95 (2H, d, J=8.3 Hz), 7.30–7.14 (7H, m), 7.03 (2H, d, J=8.1 Hz), 6.81 (2H, d, J=8.0 Hz), 6.64 (1H, s), 4.33 (2H, t, J=5.7 Hz), 3.00 (3H, s), 2.95 (2H, t, J=5.7 Hz), 2.72 (2H, t, J=7.5 Hz), 2.62 (2H, t, J=7.4 Hz), 2.51 (3H, s), 2.41 (3H, s), 2.07–1.97 (2H, m).

EXAMPLE 236

4-METHYL-N-{[(2-{4-[5-(METHYLOXY)-2-(1H-PYRAZOL-3-YL)-1H-BENZIMIDAZOL-1-YL] PHENYL}ETHYL)AMINO] CARBONYL}BENZENESULFONAMIDE P-TOLUENESULFONATE

STEP 1. 2-{4-[5-(methyloxy)-2-(1H-pyrazol-3-yl)-1H-benzimidazol-1-yl]phenyl}ethanol A mixture of 2-(4-{[2-amino-4-(methyloxy)phenyl] amino}phenyl)ethanol (step 2 of Example 71, 1.95 g, 7.56 mmol), pyrazol-3-carbaldehyde (726 mg, 7.56 mmol) in ethanol (45 ml) was heated at reflux temperature for 2 h. After cooling, the mixture was concentrated. A mixture of the residue, lead tetraacetate (4.61 g, 8.32 mmol) in benzene (50 ml) was stirred at room temperature for 16 h. The mixture was quenched with saturated NaHCO$_3$ aqueous solution (150 ml). The whole was extracted with ethyl acetate (150 ml×4). The organic layer was washed with water (100 ml×5), brine (50 ml), dried (MgSO$_4$), and concentrated. Purification by flash column chromatography eluting with dichloromethane/methanol (gradient elution from 20:1 to 10:1) to afford 408 mg (16%) of the title compound as an amber solid.

MS (EI) m/z: 334 (M$^+$).

$^1$H-NMR (DMSO-d$_6$) δ: 7.6 (1H, br.s), 7.43 (2H, d, J=7.7 Hz), 7.29–7.23 (3H, m), 7.04 )1H, d, J=8.8 Hz), 6.90 (1H, d, J=8.8 Hz), 6.34 (1H, br.s), 3.85–3.81 (5H, m), 2.92 (2H, t, J=6.6 Hz).

STEP 2. 1-[4-(2-chloroethyl)phenyl]-5-(methyloxy)-2-(1H-pyrazol-3-yl)-1H-benzimidazole The title compound was prepared according to the procedure described in step 7 Example 1 from 2-{4-[5-(methyloxy)-2-(1H-pyrazol-3-yl)-1H-benzimidazol-1-yl] phenyl}ethanol (step 1).

MS (EI) m/z: 352 (M$^+$).

$^1$H-NMR (CDCl$_3$) δ: 8.96 (0.5H, s), 8.11 (0.5H, d, J=2.9 Hz), 7.50 (0.5H, d, J=2.0 Hz), 7.46–7.34 (5H, m), 7.05 (1H, dd, J=16.5, 8.8 Hz), 6.93 (1H, ddd, J=1.4, 9.0, 2.4 Hz), 6.71 (0.5H, dd, J=2.9, 1.1 Hz), 5.81 (1H, s), 3.85 (3H, s), 3.82 (2H, t, J=7.0 Hz), 3.22 (2H, t, J=7.0 Hz).

STEP 3. 1-[4-(2-azidoethyl)phenyl]-5-(methyloxy)-2-(1H-pyrazol-3-yl)-1H-benzimidazole The title compound was prepared according to the procedure described in step 8 Example 1 from 1-[4-(2-chloroethyl)phenyl]-5-(methyloxy)-2-(1H-pyrazol-3-yl)-1H-benzimidazole (step 2).

MS (EI) m/z: 359 (M$^+$).

$^1$H-NMR (CDCl$_3$) δ: 14.05 (1H, br.s), 7.53–7.50 (2H, m), 7.45 (2H, d, J=8.4 Hz), 7.37 (2H, d, J=8.4 Hz), 7.01 (1H, d, J=8.7 Hz), 6.89 (1H, dd, J=8.7, 2.4 Hz), 5.81 (1H, s), 3.85 (3H, s), 3.61 (2H, t, J=6.9 Hz), 3.03 (2H, t, J=6.9 Hz).

STEP 4. 2-{4-[5-(methyloxy)-2-(1H-pyrazol-3-yl)-1H-benzimidazol-1-yl]phenyl}ethylamine The title compound was prepared according to the procedure described in step 9 Example 1 from 1-[4-(2-azidoethyl)phenyl]-5-(methyloxy)-2-(1H-pyrazol-3-yl)-1H-benzimidazole (step 3).

MS (EI) m/z: 333 (M$^+$).

$^1$H-NMR (CDCl$_3$) δ: 7.47 (1H, d, J=2.0 Hz), 7.43–7.29 (5H, m), 7.00 (1H, d, J=8.8 Hz), 6.88 (1H, dd, J=9.0, 2.4 Hz), 5.81 (1H, s), 3.80 (3H, s), 3.09 (2H, t, J=7.1 Hz), 2.90 (2H, t, J=6.8 Hz).

STEP 5. 4-methyl-N-{[(2-{4-[5-(methyloxy)-2-(1H-pyrazol-3-yl)-1H-benzimidazol-1-yl]phenyl}ethyl)amino] carbonyl}benzenesulfonamide The title compound was prepared according to the procedure described in step 10 of Example 1 from 2-{4-[5-(methyloxy)-2-(1H-pyrazol-3-yl)-1H-benzimidazol-1-yl] phenyl}ethylamine (step 4).

MS (ESI) m/z: 531 [(MH)$^+$], 529 [(M–H)$^-$].

$^1$H-NMR (CDCl$_3$) δ: 7.77 (2H, d, J=8.3 Hz), 7.44 (1H, s), 7.24 (2H, d, J=7.5 Hz), 7.14–7.07 (5H, m), 6.98 (1H, d, J=9.0 Hz), 6.88 (1H, d, J=9.0 Hz), 6.10 (1H, s), 3.83 (3H, s), 3.57–3.55 (2H, m), 2.88–2.84 (2H, m), 2.35 (3H, s).

STEP 6. 4-methyl-N-{[(2-{4-[5-(methyloxy)-2-(1H-pyrazol-3-yl)-1H-benzimidazol-1-yl]phenyl}ethyl)amino] carbonyl}benzenesulfonamide p-toluenesulfonamide mono-p-toluenesulfonate The title compound was prepared according to the procedure described in Example 231 from 4-methyl-N-{[(2-{4-[5-(methyloxy)-2-(1H-pyrazol-3-yl)-1H-benzimidazol-1-yl] phenyl}ethyl)amino]carbonyl}benzenesulfonamide (step 5).

¹H-NMR (CDCl₃) δ: 12.65 (1H, s), 9.99 (1H, s), 7.87 (2H, d, J=8.1 Hz), 7.78 (2H, d, J=8.3 Hz), 7.50 (2H, d, J=9.0 Hz), 7.39 (2H, d, J=8.4 Hz), 7.20 (2H, d, J=7.9 Hz), 7.18 (2H, d, J=8.1 Hz), 7.08–6.93 (5H, m), 6.44 (1H, s), 3.76 (3H, s), 3.42–3.40 (2H, m), 2.92–288 (2H, m), 2.86 (6H, s).

EXAMPLE 237

2-{4-[5-METHYLOXY-2-(1H-PYRAZOL-3-YL)-1H-BENZIMIDAZOL-1-YL]PHENYL}ETHYL(4-METHYLPHENYL)SULFONYLCARBAMATE P-TOLUENESULFONATE

STEP 1. 2-{4-[5-(methyloxy)-2-(1H-pyrazol-3-yl)-1H-benzimidazol-1-yl]phenyl}ethyl(4-methylphenyl)sulfonylcarbamate The title compound was prepared according to the procedure described in Example 3 from 2-{4-[5-(methyloxy)-2-(1H-pyrazol-3-yl)-1H-benzimidazol-1-yl]phenyl}ethanol (step 1 of Example 236).

MS (ESI) m/z: 532 [(MH)⁺], 530 [(M−H)⁻].

¹H-NMR (DMSO-d₆) δ: 7.75 (2H, d, J=8.1 Hz), 7.58 (2H, d, J=8.1 Hz), 7.38 (2H, d, J=7.8 Hz), 7.33–7.21 (3H, m), 7.22 (2H, d, J=8.1 Hz), 6.96 (1H, d, J=8.1 Hz), 6.88 (1H, d, J=8.1 Hz), 4.26–4.24 (2H, m), 3.82 (3H, s), 2.95–2.93 (2H, m), 2.34 (3H, s).

STEP 2. 2-{4-[5-(methyloxy)-2-(1H-pyrazol-3-yl)-1H-benzimidazol-1-yl]phenyl}ethyl(4-methylphenyl)sulfonylcarbamate mono-p-toluenesulfonate The title compound was prepared according to the procedure described in Example 231 from 2-{4-[5-(methyloxy)-2-(1H-pyrazol-3-yl)-1H-benzimidazol-1-yl]phenyl}ethyl(4-methylphenyl)sulfonylcarbamate (step 1).

¹H-NMR (CDCl₃) δ: 7.88 (2H, d, J=8.2 Hz), 7.80–7.65 (6H, m), 7.44 (2H, d, J=8.1 Hz), 7.38–7.26 (3H, m), 7.17 (2H, d, J=8.1 Hz), 7.10 (2H, d, J=7.6 Hz), 4.37–4.33 (2H, m), 3.03–2.99 (2H, m), 2.39 (3H, s), 2.35 (3H, s), 2.31 (3H, s).

EXAMPLE 238

2-{4-[6-CHLORO-2-(1,5-DIMETHYL-1H-PYRAZOL-3-YL)-5-(TRIFLUOROMETHYL)-1H-BENZIMIDAZOL-1-YL]PHENYL}ETHYL(4-METYLPHENYL)SULFONYLCARBAMATE

STEP 1. 2-(4-{[5-chloro-2-nitro-4-(trifluoromethyl)phenyl]amino}phenyl)ethyl(4-methylphenyl)sulfonylcarbamate To a stirred solution of 2-(4-{[5-chloro-2-nitro-4-(trifluoromethyl)phenyl]amino}phenyl)ethanol (step 2 of Example 104, 1.0 g, 2.77 mmol) in dichloromethane (45 ml) was added p-toluenesulfonyl isocyanate (574 mg, 2.91 mmol), and the mixture was stirred at room temperature for 2 h. The mixture was quenched with water (100 ml). The organic layer was separated. The aqueous layer was extracted with dichloromethane (100 ml×3). The combined organic layer was washed with brine (50 ml), dried (MgSO₄), and concentrated. Purification by flash column chromatography eluting with hexane/ethyl acetate (gradient elution from 2:1 to 1:1) to afford 1.51 g (98%) of the title compound as an orange solid.

¹H-NMR (CDCl₃) δ: 9.68 (1H, s), 8.58 (1H, s), 7.91 (2H, d, J=8.4 Hz), 7.34 (2H, d, J=7.9 Hz), 7.27 (2H, d, J=7.9 Hz), 7.20 (2H, d, J=8.4 Hz), 7.17 (1H, s), 4.33 (2H, t, J=7.0 Hz), 2.96 (2H, t, J=6.8 Hz), 2.45 (3H, s).

STEP 2. 2-(4-{[2-amino-5-chloro-4-(trifluoromethyl)phenyl]amino}phenyl)ethyl(4-methylphenyl)sulfonylcarbamate To a stirred solution of 2-(4-{[5-chloro-2-nitro-4-(trifluoromethyl)phenyl]amino}phenyl)ethyl(4-methylphenyl)sulfonylcarbamate (step 1, 1.51 g, 2.71 mmol) in methanol (250 ml) was added 5% platinum-sulfided on carbon (600 mg). The mixture was stirred at room temperature for 5 h under hydrogen atmosphere (4 atm). The palladium catalyst was removed by filtration and washed with dichloromethane (100 ml). The filtrate was concentrated under reduced pressure to afford 1.46 g (99%) of the title compound as a brown oil.

¹H-NMR (CDCl₃) δ: 7.90 (2H, d, J=8.4 Hz), 7.33 (2H, d, J=8.2 Hz), 7.16 (1H, s), 7.07 (2H, d, J=8.2 Hz), 7.06 (1H, s), 6.86 (2H, d, J=8.2 Hz), 5.40 (2H, s), 4.26 (2H, t, J=6.9 Hz), 2.85 (2H, t, J=7.2 Hz), 2.44 (3H, s).

STEP 3. 2-(4-{[5-chloro-2-{[(1.5-dimethyl-1H-pyrazol-3-yl)carbonyl]amino}-4-(trifluoromethyl)phenyl]amino}phenyl)ethyl(4-methylphenyl)sulfonylcarbamate To a stirred solution of 2-(4-{[2-amino-5-chloro-4-(trifluoromethyl)phenyl]amino}phenyl)ethyl(4-methylphenyl)sulfonylcarbamate (step 2, 200 mg, 0.379 mmol) in dichloromethane (1.7 ml) was added a solution of 1,5-dimethyl-1H-pyrazole-3-carboxylic acid (63.8 mg, 0.455 mmol) and N,N-diisoprppylethylamine (118 mg, 0.909 mmol) in dichloromethane (1.7 ml), then to the mixture was added a solution of HOBt (61.5 mg, 0.455 mmol) and HBTU (431 mg, 1.14 mmol) in DMF (2.5 ml), and the mixture was stirred at room temperature for 20 h. The mixture was quenched with water (100 ml). The whole was extracted with ethyl acetate (100 ml×3). The combined organic layer was washed with water (100 ml×3), brine (50 ml), dried (MgSO₄), and concentrated. Purification by PTLC eluting with hexane/ethyl acetate (1:1) to afford 145 mg (59%) of the title compound as a red solid.

¹H-NMR (CDCl₃) δ: 8.70 (1H, s), 7.87 (2H, d, J=8.1 Hz), 7.79 (1H, s), 7.28 (2H, d, J=8.1 Hz), 7.04 (2H, d, J=8.3 Hz), 6.95 (2H, d, J=8.3 Hz), 6.72 (1H, s), 6.60 (1H, s), 4.22 (2H, t, J=6.8 Hz), 3.78 (3H, s), 2.84–2.80 (2H, m), 2.40 (3H, s), 2.30 (3H, s).

STEP 4. 2-{4-[6-chloro-2-(1,5-dimethyl-1H-pyrazol-3-yl)-5-(trifluoromethyl)-1H-benzimidazol-1-yl]phenyl{ethyl(4-methylphenyl)sulfonylcarbamate A mixture of 2-(4-{[5-chloro-2-{[(1,5-dimethyl-1H-pyrazol-3-yl)carbonyl]amino}-4-(trifluoromethyl)phenyl]amino}phenyl)ethyl(4-methylphenyl)sulfonylcarbamate (step 3, 145 mg, 0.223 mmol) in 2N NaOH (1 ml) and ethanol (2 ml) was stirred at 50° C. for 85 h. After cooling, the pH value was adjusted to 4.0 by addition of 2N HCl. The mixture was diluted with water (80 ml), and extracted with dichloromethane (80 ml×3). The combined organic layer was washed with brine (50 ml), dried (MgSO₄), and concentrated. Purification by PTLC eluting with hexane/ethyl acetate (1:3) to afford 30 mg (21%) of the title compound as a red solid.

MS (ESI) m/z: 632 [(MH)⁺], 630 [(M−H)⁻].

¹H-NMR (CDCl₃) δ: 8.15 (1H, s), 7.90 (2H, d, J=8.4 Hz), 7.34–7.24 (6H, m), 7.19 (1H, s), 5.81 (1H, s), 4.40 (2H, t, J=6.8 Hz), 3.76 (3H, s), 3.04 (2H, t, J=6.4 Hz), 2.41 (3H, s), 2.20 (3H, s).

163

EXAMPLE 239

N-[({2-[4-(2-BUTYL-4,6-DIMETHYL-1H-IMI-DAZO[4,5-c]PYRIDIN-1-YL)PHENYL]ETHYL}AMINO)CARBONYL]-4-METHYLBEN-ZENESULFONAMIDE

STEP 1. 2-butyl-1-[4-(2-chloroethyl)phenyl]-4,6-dimethyl-1H-imidazo[4,5-c]pyridine The title compound was prepared according to the procedure described in step 7 of Example 1 from 2-[4-(2-butyl-4,6-dimethyl-1H-imidazo[4,5-c]pyridin-1-yl)phenyl]ethanol (step 2 of Example 230).

MS (EI) m/z: 341 (M$^+$).

$^1$H-NMR (CDCl$_3$) δ: 7.45 (2H, d, J=8.2 Hz), 7.28 (2H, d, J=8.2 Hz), 6.73 (1H, s), 3.82 (2H, t, J=7.1 Hz), 3.22 (2H, t, J=7.1 Hz), 2.89 (3H, s), 2.79 (2H, t, J=8.2 Hz), 2.58 (3H, s), 1.76–1.64 (2H, m), 1.39–1.25 (2H, m), 0.84 (3H, t, J=7.2 Hz).

STEP 2. 1-[4-(2-azidoethyl)phenyl]-2-butyl-4,6-dimethyl-1H-imidazo[4,5-c]pyridine The title compound was prepared according to the procedure described in step 8 of Example 1 from 2-butyl-1-[4-(2-chloroethyl)phenyl]-4,6-dimethyl-1H-imidazo[4,5-c]pyridine (step 1).

MS (EI) m/z: 348 (M$^+$).

$^1$H-NMR (CDCl$_3$) δ: 7.46 (2H, d, J=8.2 Hz), 7.29 (2H, d, J=8.6 Hz), 6.72 (1H, s), 3.62 (2H, t, J=6.8 Hz), 3.03 (2H, t, J=6.8 Hz), 2.88 (3H, s), 2.78 (2H, t, J=7.6 Hz), 2.55 (3H, s), 1.74–1.63 (2H, m), 1.38–1.24 (2H, m), 0.84 (3H, t, J=7.3 Hz).

STEP 3. 2-[4-(2-butyl-4,6-dimethyl-1H-imidazo[4,5-c]pyridin-1-yl)phenyl]ethylamine The title compound was prepared according to the procedure described in step 9 of Example 1 from 1-[4-(2-azidoethyl)phenyl]-2-butyl-4,6-dimethyl-1H-imidazo[4,5-c]pyridine (step 2).

MS (EI) m/z: 322 (M$^+$).

$^1$H-NMR (CDCl$_3$) δ: 7.43 (2H, d, J=8.3 Hz), 7.26 (2H, d, J=8.1 Hz), 6.72 (1H, s), 3.10–3.04 (2H, m), 2.90–2.86 (5H, m), 2.78 (2H, t, J=7.7 Hz), 2.55 (3H, s), 1.74–1.64 (2H, m), 1.35–1.25 (2H, m), 0.84 (3H, t, J=7.3 Hz).

STEP 4. N-[({2-[4-(2-butyl-4,6-dimethyl-1H-imidazo[4,5-c]pyridin-1-yl)phenyl]ethyl}amino)carbonyl]-4-methylbenzenesulfonamide The title compound was prepared according to the procedure described in step 10 of Example 1 from 2-[4-(2-butyl-4,6-dimethyl-1H-imidazo[4,5-c]pyridin-1-yl)phenyl]ethylamine (step 3).

MS (ESI) m/z: 520 [(MH)$^+$], 518 [(M–H)$^-$].

$^1$H-NMR (CDCl$_3$) δ: 7.77 (2H, d, J=8.1 Hz), 7.37 (2H, d, J=7.9 Hz), 7.27 (2H, d, J=7.8 Hz), 7.19 (2H, d, J=7.5 Hz), 6.76 (1H, s), 3.57–3.51 (2H, m), 2.92 (2H, t, J=6.6 Hz), 2.88 (3H, s), 2.76 (2H, t, J=7.5 Hz), 2.52 (3H, s), 2.38 (3H, s), 1.73–1.62 (2H, m), 1.36–1.23 (2H, m), 0.82 (3H, t, J=7.3 Hz).

STEP 5. N-[({2-[4-(2-butyl-4,6-dimethyl-1H-imidazo[4,5-c]pyridin-1-yl)phenyl]ethyl}amino)carbonyl]-4-methylbenzenesulfonamide mono-p-toluenesulfonate The title compound was prepared according to the procedure described in Example 231 from N-[({2-[4-(2-butyl-4,6-dimethyl-1H-imidazo[4,5-c]pyridin-1-yl)phenyl]ethyl}amino)carbonyl]-4-methylbenzenesulfonamide (step 4).

$^1$H-NMR (CDCl$_3$) δ: 9.85 (1H, br.s), 7.78 (4H, d, J=8.1 Hz), 7.45 (2H, d, J=7.9 Hz), 7.27–7.13 (6H, m), 7.01 (1H, s), 3.45–3.43 (2H, m), 3.03 (3H, s), 2.89–2.87 (2H, m), 2.79–2.73 (5H, m), 2.36 (3H, s), 2.34 (3H, s), 1.74–1.65 (2H, m), 1.35–1.23 (2H, m), 0.84 (3H, t, J=7.2 Hz).

EXAMPLE 240

2-[4-(2-ETHYL-5,7-DIMETHYL-3H-IMIDAZO[4,5-b]PYRIDIN-3-YL)PHENYL]-1-METHYL-ETHYL(4-METHYLPHENYL)SULFONYLCAR-BAMATE MONO-HYDROCHLORIDE

To a solution of 2-[4-(2-ethyl-5,7-dimethyl-3h-imidazo[4,5-b]pyridin-3-yl)phenyl]-1-methylethyl(4-methylphenyl)sulfonylcarbamate (example 7, 694 mg, 1.37 mmol) in methanol (4 ml) was added 10% hcl in methanol (2 ml) at room temperature. This mixture was concentrated, and treated with diethylether to afford 624 mg (90%) of the title compound as a slight yellow solid.

$^1$H-NMR (DMSO-d$_6$) δ: 11.92 (1H, br.s), 7.76 (2H, d, J=7.9 Hz), 7.49–7.39 (6H, m), 7.26 (1H, br.s), 4.98–4.88 (1H, m), 2.94–2.83 (4H, m), 2.63 (3H, s), 2.46 (3H, s), 2.34 (3H, s), 1.23 (3H, t, J=7.5 Hz), 1.12 (3H, d, J=6.1 Hz).

MS (ESI) m/z: 507 [(MH)$^+$], 505 [(M–H)$^-$].

EXAMPLE 241

N-{[(2-{4-[5,7-DIMETHYL-2-(3-PHENYLPRO-PYL)-3H-IMIDAZO[4,5-b]PYRIDIN-3-YL]PHENYL}ETHYL)AMINO]CARBONYL}-4-ME-THYLBENZENESULFONAMIDE

A mixture of n-{[(2-{4-[(3-amino-4,6-dimethyl-2-pyridinyl)amino]phenyl}ethyl)amino]carbonyl}-4-methylbenzenesulfonamide (step 4 of example 162, 86 mg, 0.19 mmol), 4-phenylbutyric acid (37 mg, 0.23 mmol) and 1-ethyl-3-(3-dimethylaminopropyl)carbodiimide hydrochloride (40 mg, 0.21 mmol) was stirred at room temperature for 5 days. The mixture was concentrated to give an orange syrup. This material was dissolved in toluene (8 ml), added p-toluenesulfonic acid mono-hydrate (3 mg, 0.02 mol), then stirred under reflux temperature for 5 h. The mixture was diluted with dichloromethane and washed with diluted hydrochloric acid. The organic layer was concentrated. Purification by tlc developing with hexane/ethyl acetate (1:3) gave 32 mg (29%) of the title compound as a colorless solid.

$^1$H-NMR (CDCl$_3$) □: 7.85 (2H, d, J=8.4 Hz), 7.31–7.01 (11H, m), 6.91 (1H, s), 3.52–3.45 (2H, m), 2.83 (2H, t, J=6.4 Hz), 2.71–2.65 (2H, m), 2.64 (3H, s), 2.58–2.53 (2H, m), 2.41 (3H, s), 2.39 (3H, s), 2.00–1.90 (2H, m).

MS (ESI) m/z: 582 [(MH)$^+$], 580 [(M–H)$^-$].

EXAMPLE 242

N-{[(2-{4-[5,7-DIMETHYL-2-(3-OXO-3-PHE-NYLPROPYL)-3H-IMIDAZO[4,5-B]PYRIDIN-3-YL]PHENYL}ETHYL)AMINO]CARBONYL}-4-METHYLBENZENESULFONAMIDE

The title compound was prepared according to the procedure described in Example 241 from N-{[(2-{4-[(3-amino-4,6-dimethyl-2-pyridinyl)amino]phenyl}ethyl)amino]carbonyl}-4-methylbenzenesulfonamide (step 4 of Example 162) and 3-benzoylpropionic acid.

$^1$H-NMR (CDCl$_3$) δ: 8.04–7.14 (11H, m), 6.90 (1H, s), 6.20–6.15 (1H, m), 3.50–3.38 (4H, m), 3.03–2.81 (4H, m), 2.56 (3H, s), 2.44 (3H, s), 2.41 (3H, s).

MS (ESI) m/z: 596 [(MH)$^+$], 594 [(M–H)$^-$].

EXAMPLE 243

2-{4-[6-CHLORO-2-ETHYL-5-(TRIFLUOROMETHYL)-1H-BENZIMIDAZOL-1-YL]PHENYL}ETHYL 3-PYRIDINYLSULFONYLCARBAMATE

STEP 1. 2-{4-[6-chloro-2-ethyl-5-(trifluoromethyl)-1H-benzimidazol-1-yl]phenyl}ethyl phenyl carbonate To a stirred solution of 2-[4-(6-Chloro-2-ethyl-5-trifluoromethyl-1H-benzimidazol-1-yl)phenyl]ethanol (step 4 of Example 104, 3.90 g, 10.6 mmol) in dichloromethane (20 mL) and pyridine (2 ml) was added dropwise phenyl chloroformate (1.6 mL, 12.7 mmol), and the mixture was stirred at room temperature for 16 h. The reaction mixture was diluted with dichloromethane (50 mL), washed with water (50 ml). The organic layer was dried over $Na_2SO_4$, and concentrated under reduced pressure. Purification by flash column chromatography eluting with hexane/ethyl acetate (3:1) afforded 4.2 g (82%) of the title compound as a colorless syrup.

$^1$H NMR (CDCl$_3$) δ 8.12 (1H, s), 7.53–7.15 (10H, m), 4.56 (2H, t, J=6.8 Hz), 3.20 (2H, t, J=6.8 Hz), 2.79 (2H, q, J=7.6 Hz), 1.36 (3H, t, J=7.6 Hz).

MS (EI) m/z: 488 (M$^+$).

STEP 2. 2-{4-[6-chloro-2-ethyl-5-(trifluoromethyl)-1H-benzimidazol-1-yl]phenyl}ethyl-3-pyridinylsulfonylcarbamate To a stirred solution of 3-pyridinesulfonamide (Rafik, Karaman; et al., *J. Am. Chem. Soc.*, 1992, 114, 4889, 120 mg, 0.76 mmol) in DMF (3 mL) was added NaH (60% oil dispersion, 27 mg, 0.68 mmol) at room temperature. After 10 min., phenyl 2-[4-(2-ethyl-5,7-dimethyl-3H-imidazo[4,5-b]pyridin-3-yl)phenyl]ethylcarbamate (step 1, 313 mg, 0.64 mmol) was added, and the mixture was stirred for 9 h at 80° C. The mixture was diluted with ethyl acetate (50 mL), and washed with water and brine. The organic layer was dried (Na2SO4) and concentrated. Purification by TLC developing with dichloromethane/methanol (6:1) and TLC developing with dichloromethane/methanol (10:1) gave 67 mg (19%) of the title compound as colorless solid.

$^1$H-NMR (CDCl$_3$) δ 9.18 (1H, s), 8.73–8.72 (1H, m), 8.32–8.29 (1H, m), 8.09 (1H, s), 7.40–7.15 (6H, m), 4.33–4.29 (2H, m), 2.99–2.94 (2H, m), 2.78–2.71 (2H, m), 1.35–1.32 (3H, m).

MS (ESI) m/z: 553 (MH$^+$), 551 ([M–H]$^-$)

EXAMPLE 244

2-{4-[6-CHLORO-2-ETHYL-5-(TRIFLUOROMETHYL)-1H-BENZIMIDAZOL-1-YL]PHENYL}ETHYL 2-PYRIDINYLSULFONYLCARBAMATE

The title compound was prepared according to the procedure described in step 2 of Example 243 from 2-pyridinesulfonamide (Naito, T.; et al., *Chem. Pharm. Bull.*, 1955, 3, 38) and 2-[4-(2-ethyl-5,7-dimethyl-3H-imidazo[4,5-b]pyridin-3-yl)phenyl]ethylcarbamate (step 1 Example 243).

m.p.: 127.0–130.0° C.

$^1$H-NMR (CDCl$_3$) δ 8.76–8.73 (1H, m), 8.24–8.21 (2H, m), 8.16 (1H, s), 8.03–7.97 (1H, m), 7.62–7.56 (1H, m), 7.37 (2H, d, J=8.2 Hz), 7.23 (2H, d, J=8.2 Hz), 7.17 (1H, s), 4.37 (2H, t, J=6.8 Hz), 3.01 (2H, t, J=6.8 Hz), 2.77 (2H, q, J=7.6 Hz), 1.35 (3H, t, J=7.6 Hz).

MS (ESI) m/z: 553 (MH$^+$), 551 ([M–H]$^-$).

EXAMPLE 245

2-{4-[6-CHLORO-2-ETHYL-5-(TRIFLUOROMETHYL)-1H-BENZIMIDAZOL-1-YL]PHENYL}ETHYL 4-PYRIDINYLSULFONYLCARBAMATE

The title compound was prepared according to the procedure described in step 2 of Example 243 from 4-pyridinesulfonamide (Comrie, A. M.; et al., *J. Chem. Soc.*, 1958, 3514) and 2-[4-(2-ethyl-5,7-dimethyl-3H-imidazo[4,5-b]pyridin-3-yl)phenyl]ethylcarbamate (step 1 of Example 243).

$^1$H-NMR (CDCl$_3$) δ 8.82 (2H, d, J=5.2 Hz), 8.10 (1H, s), 7.87 (2H, d, J=4.9 Hz), 7.44 (2H, d, J=7.9 Hz), 7.27 (2H, d, J=7.9 Hz), 7.20 (1H, s), 4.34 (2H, t, J=7.3 Hz), 3.04 (2H, t, J=7.3 Hz), 2.78 (2H, q, J=7.6 Hz), 1.36 (3H, t, J=7.6 Hz).

MS (ESI) m/z: 553 (MH$^+$), 551 ([M–H]$^-$).

EXAMPLE 246

2-[4-(5-ACETYL-2-ETHYL-1H-BENZIMIDAZOL-1-YL)PHENYL]-1-METHYLETHYL(4-METHYLPHENYL)SULFONYLCARBAMATE

STEP 1. 1-(4-[4-(2-hydroxypropyl)phenyl]amino}-3-nitrophenyl)ethanone

The title compound was prepared according to the procedure described in step 1 of Example 162 from 1-(4-chloro-3-nitrophenyl)ethanone and 1-(4-aminophenyl)-2-propanol (step 1 of Example 6).

$^1$H-NMR (CDCl$_3$) δ: 9.85 (1H, br.s), 8.83–8.82 (1H, m), 7.99–7.95 (1H, m), 7.33 (2H, d, J=8.4 Hz), 7.24 (2H, d, J=8.4 Hz), 7.18 (1H, d, J=9.0 Hz), 4.13–4.04 (1H, m), 2.87–2.72 (2H, m), 2.58 (3H, s), 1.29 (3H, d, J=6.2 Hz).

STEP 2. 1-(3-amino-4-{[4-(2-hydroxypropyl)phenyl]amino}phenyl)ethanone

The title compound was prepared according to the procedure described in step 4 of Example 1 from 1-(4-{[4-(2-hydroxypropyl)phenyl]amino}-3-nitrophenyl)ethanone (step 1).

MS (EI) m/z: 284 (M$^+$).

STEP 3. 2-[4-(5-acetyl-2-ethyl-1H-benzimidazol-1-yl)phenyl]-1-methylethyl propanoate The title compound was prepared according to the procedure described in step 5 of Example 1 from 1-(3-amino-4-{[4-(2-hydroxypropyl)phenyl]amino}phenyl)ethanone (step 2).

$^1$H-NMR (CDCl$_3$) δ: 8.41–8.40 (1H, m), 8.83–8.82 (1H, m), 7.92–7.89 (1H, m), 7.43 (2H, d, J=8.4 Hz), 7.29 (2H, d, J=8.4 Hz), 7.12–7.09 (1H, m), 5.25–5.18 (1H, m), 3.07–2.88 (H, m), 2.80 (2H, q, J=7.3 Hz), 2.68 (3H, s), 2.34–2.26 (2H, m), 1.37 (3H, q, J=7.5 Hz), 1.32 (3H, d, J=62 Hz), 1.10 (3H, t, J=7.5 Hz).

STEP 4. 1-{2-ethyl-1-[4-(2-hydroxypropyl)phenyl]-1H-benzimidazol-5-yl}ethanone

The title compound was prepared according to the procedure described in step 6 of Example 1 from 2-[4-(5-acetyl-2-ethyl-1H-benzimidazol-1-yl)phenyl]-1-methylethyl propanoate (step 3).

¹H-NMR (CDCl₃) δ: 8.39 (1H, s), 7.89–7.86 (1H, m), 7.47 (2H, d, J=8.3 Hz), 7.29 (2H, d, J=8.3 Hz), 7.13–7.10 (1H, m), 4.23–4.13 (1H, m), 2.94–2.86 (2H, m), 2.80 (2H, q, J=7.5 Hz), 2.66 (3H, s), 1.39–1.33 (6H, m).

STEP 5. 2-[4-(5-acetyl-2-ethyl-1H-benzimidazol-1-yl)phenyl]-1-methylethyl(4-methylphenyl)sulfonylcarbamate The title compound was prepared according to the procedure described in Example 3 from 1-{2-ethyl-1-[4-(2-hydroxypropyl)phenyl]-1H-benzimidazol-5-yl}ethanone (step 4).

¹H-NMR (CDCl₃) δ 8.40 (1H, d, J=1.1 Hz), 7.91–7.86 (3H, m), 7.32–7.24 (4H, m), 7.17 (2H, d, J=7.9 Hz), 7.07 (1H, d, J=8.4 Hz), 5.09–5.03 (1H, m), 2.99–2.75 (2H, m), 2.77 (2H, q, J=7.5 Hz), 2.67 (3H, s), 2.37 (3H, s), 1.33 (3H, t, J=7.5 Hz), 1.21 (3H, d, J=6.1 Hz).

MS (ESI) m/z: 520 (MH⁺), 518 ([M–H]⁻).

EXAMPLE 247

2-{4-[6-CHLORO-2-ETHYL-5-(TRIFLUOROMETHYL)-1H-BENZIMIDAZOL-1-YL]PHENYL}-1-METHYLETHYL(4-METHYLPHENYL)SULFONYLCARBAMATE

STEP 1. 1-(4-{[5-chloro-2-nitro-4-(trifluoromethyl)phenyl]amino}phenyl)-2-propanol The title compound was prepared according to the procedure described in step 1 of Example 162 from 2,4-dichloro-5-nitrobenzotrifluoride and 1-(4-aminophenyl)-2-propanol (step 1 of Example 6).

¹H-NMR (CDCl₃) δ: 9.69 (1H, br.s), 8.58 (1H, s), 7.36 (2H, d, J=8.4 Hz), 7.24 (2H, d, J=8.4 Hz), 7.20 (1H, s), 4.13–4.06 (1H, m), 2.88–2.73 (2H, m), 1.48 (1H, d, J=4.2 Hz), 1.30 (3H, d, J=6.2 Hz).

STEP 2. 1-(4-{[2-amino-5-chloro-4-(trifluoromethyl)phenyl]amino}phenyl)-2-propanol The title compound was prepared according to the procedure described in step 2 of Example 28 from 1-(4-{[5-chloro-2-nitro-4-(trifluoromethyl)phenyl]amino}phenyl)-2-propanol (step 1).

¹H-NMR (CDCl₃) δ: 7.17 (1H, s), 7.15 (2H, d, J=8.4 Hz), 7.06 (1H, s), 6.90 (2H, d, J=8.4 Hz), 4.05–3.98 (1H, m), 2.79–2.61 (2H, m), 1.26 (3H, d, J=6.3 Hz).

STEP 3. 2-{4-[6-chloro-2-ethyl-5-(trifluoromethyl)-1H-benzimidazol-1-yl]phenyl}-1-methylethyl propanoate The title compound was prepared according to the procedure described in step 5 of Example 1 from 1-(4-{[2-amino-5-chloro-4-(trifluoromethyl)phenyl]amino}phenyl)-2-propanol (step 2).

MS (EI) m/z: 438 (M⁺).

STEP 4. 1-{4-[6-chloro-2-ethyl-5-(trifluoromethyl)-1H-benzimidazol-1-yl]phenyl}-2-propanol The title compound was prepared according to the procedure described in step 6 of Example 1 from 2-{4-[6-chloro-2-ethyl-5-(trifluoromethyl)-1H-benzimidazol-1-yl]phenyl}-1-methylethyl propanoate (step 3).

¹H-NMR (CDCl₃) δ: 8.12 (1H, s), 7.47 (2H, d, J=8.4 Hz), 7.28 (2H, d, J=8.4 Hz), 7.21 (1H, s), 4.20–4.10 (1H, m), 2.95–2.83 (2H, m), 2.79 (2H, q, J=7.5 Hz), 1.56 (1H, d, J=4.2 Hz), 1.36 (3H, t, J=7.5 Hz), 1.34 (3H, d, J=6.2 Hz).

STEP 5. 2-{4-[6-chloro-2-ethyl-5-(trifluoromethyl)-1H-benzimidazol-1-yl]phenyl}-1-methylethyl(4-methylphenyl)sulfonylcarbamate The title compound was prepared according to the procedure described in Example 3 from 1-{4-[6-chloro-2-ethyl-5-(trifluoromethyl)-1H-benzimidazol-1-yl]phenyl}-2-propanol (step 4).

¹H-NMR (CDCl₃) δ: 8.09 (1H, s), 7.87 (2H, d, J=8.4 Hz), 7.41 (2H, d, J=8.4 Hz), 7.31 (2H, d, J=8.4 Hz), 7.24 (2H, d, J=8.4 Hz), 7.21 (1H, s), 5.06–5.00 (1H, m), 3.04–2.74 (4H, m), 2.40 (3H, s), 1.36 (3H, t, J=7.5 Hz), 1.23 (3H, d, J=6.2 Hz).

MS (ESI) m/z: 580 (MH⁺), 578 ([M–H]⁻).

EXAMPLE 248

(1S)-2-[4-(5-ACETYL-2-ETHYL-1H-BENZIMIDAZOL-1-YL)PHENYL]-1-METHYLETHYL(4-METHYLPHENYL)SULFONYLCARBAMATE

STEP 1. (2S)-1-(4-nitrophenyl)-2-propanol and (1R)-1-methyl-2-(4-nitrophenyl)ethyl propanoate To a mixture of 1-(4-nitrophenyl)-2-propanol (Schadt, F. L. et al., J. Am. Chem. Soc., 1978, 100, 228., 2.5 g, 13.8 mmol) and propanoic anhydride (1.8 g, 13.8 mmol) in benzene (34 ml) was added Lipase PS/Celite (0.5 g, Bianichi, D. et al. J. Org. Chem. 1988, 53, 5531). The resulting mixture was stirred at room temperature for 72 h. The reaction mixture was filtered through a pad of Celite. The filtrate was washed with saturated aqueous sodium hydrogencarbonate and brine. The organic layer was dried (MgSO4), and concentrated. Purification by flash column chromatography eluting with hexane/diethyl ether (4:1 to 1:1) afforded 1.91 g (58%) of (1R)-1-methyl-2-(4-nitrophenyl)ethyl propanoate as a slight yellow oil and 1.14 g (46%) of (2S)-1-(4-nitrophenyl)-2-propanol as a colorless solid (93% e.e.). Recrystallization of 1.14 g of (2S)-1-(4-nitrophenyl)-2-propanol from hexane/diethyl ether afforded 617 mg of a colorless needle (99% e.e.).

(1R)-1-methyl-2-(4-nitrophenyl)ethyl propanoate

¹H-NMR (CDCl₃) δ: 8.16 (2H, d, J=8.8 Hz), 7.37 (2H, d, J=8.8 Hz), 5.22–5.11 (1H, m), 3.04–2.87 (2H, m), 2.30–2.19 (2H, m), 1.26 (3H, d, J=6.1 Hz), 1.07 (3H, t, J=7.5 Hz).

(2S)-1-(4-nitrophenyl)-2-propanol

¹H-NMR (CDCl₃) δ: 8.18 (2H, d, J=8.8 Hz), 7.39 (2H, d, J=8.8 Hz), 4.14–4.04 (1H, m), 2.92–2.79 (2H, m), 1.49 (1H, d, J=4.0 Hz), 1.28 (3H, d, J=6.1 Hz).

[α]²³_D +31.0° (c 1.00, diethyl ether)

STEP 2. (2S)-1-(4-aminophenyl)-2-propanol

The title compound was prepared according to the procedure described in step 4 of Example 1 from (2S)-1-(4-nitrophenyl)-2-propanol (step 1).

¹H-NMR (CDCl₃) δ: 7.00 (2H, d, J=8.4 Hz), 6.65 (2H, d, J=8.4 Hz), 3.99–3.89 (1H, m), 3.60 (2H, br.s) 2.73–2.52 (2H, m), 1.22 (3H, d, J=6.2 Hz).

STEP 3. 1-[4-({4-[(2S)-2-hydroxypropyl]phenyl}amino)-3-nitrophenyl]ethanone

The title compound was prepared according to the procedure described in step 1 of Example 162 from 1-(4-chloro-3-nitrophenyl)ethanone and (2S)-i-(4-aminophenyl)-2-propanol (step 2).

¹H-NMR (CDCl₃) δ: 9.85 (1H, br.s), 8.83–8.82 (1H, m), 7.99–7.95 (1H, m), 7.33 (2H, d, J=8.4 Hz), 7.24 (2H, d, J=8.4 Hz), 7.18 (1H, d, J=9.0 Hz), 4.13–4.04 (1H, m), 2.87–2.72 (2H, m), 2.58 (3H, s), 1.29 (3H, d, J=6.2 Hz).

STEP 4. 1-[3-amino-4-({4-[(2S)-2-hydroxypropyl]phenyl}amino)phenyl]ethanone

The title compound was prepared according to the procedure described in step 4 of Example 1 from 1-[4-({4-[(2S)-2-hydroxypropyl]phenyl}amino)-3-nitrophenyl]ethanone (step 3).

MS (EI) m/z: 284 (M+).

STEP 5. (1S)-2-[4-(5-acetyl-2-ethyl-1H-benzimidazol-1-yl)phenyl]-1-methylethyl propanoate The title compound was prepared according to the procedure described in step 5 of Example 1 from 1-[3-amino-4-({4-[(2S)-2-hydroxypropyl]phenyl}amino)phenyl]ethanone (step 4).

$^1$H-NMR (CDCl$_3$) δ: 8.41–8.40 (1H, m), 8.83–8.82 (1H, m), 7.92–7.89 (1H, m), 7.43 (2H, d, J=8.4 Hz), 7.29 (2H, d, J=8.4 Hz), 7.12–7.09 (1H, m), 5.25–5.18 (1H, m), 3.07–2.88 (2H, m), 2.80 (2H, q, J=7.3 Hz), 2.68 (3H, s), 2.34–2.26 (2H, m), 1.37 (3H, q, J=7.5 Hz), 1.32 (3H, d, J=6.2 Hz), 1.10 (3H, t, J=7.5 Hz).

STEP 6. 1-(2-ethyl-1-{4-[(2S)-2-hydroxypropyl]phenyl}-1H-benzimidazol-5-yl)ethanone The title compound was prepared according to the procedure described in step 6 of Example 1 from (1S)-2-[4-(5-acetyl-2-ethyl-1H-benzimidazol-1-yl)phenyl]-1-methylethyl propanoate (step 5).

$^1$H-NMR (CDCl$_3$) δ: 8.39 (1H, d, J=1.1 Hz), 7.87 (1H, dd, J=8.6, 1.1 Hz), 7.48 (2H, d, J=8.4 Hz), 7.30 (2H, d, J=8.4 Hz), 7.12 (1H, d, J=8.6 Hz), 4.22–4.12 (1H, m), 2.94–2.89 (2H, m), 2.80 (2H, q, J=7.5 Hz), 2.69 (3H, s), 2.42 (1H, br.s), 1.37 (3H, t, J=7.5 Hz), 1.33 (3H, d, J=6.2 Hz).

STEP 7. (1S)-2-[4-(5-acetyl-2-ethyl-1H-benzimidazol-1-yl)phenyl]-1-methylethyl(4-methylphenyl)sulfonylcarbamate The title compound was prepared according to the procedure described in Example 3 from 1-(2-ethyl-1-{4-[(2S)-2-hydroxypropyl]phenyl}-1H-benzimidazol-5-yl)ethanone (step 6).

$^1$H-NMR (CDCl$_3$) δ: 8.40 (1H, d, J=1.1 Hz), 7.91–7.86 (3H, m), 7.32–7.24 (4H, m), 7.17 (2H, d, J=7.9 Hz), 7.07 (1H, d, J=8.4 Hz), 5.09–5.03 (1H, m), 2.99–2.75 (2H, m), 2.77 (2H, q, J=7.5 Hz), 2.67 (3H, s), 2.37 (3H, s), 1.33 (3H, t, J=7.5 Hz), 1.21 (3H, d, J=6.1 Hz).

MS (ESI) m/z: 520 (MH+), 518 ([M−H]−).

$[α]^{24}_D$ −3.09° (c 0.120, methanol)

EXAMPLE 249

(1R)-2-[4-(5-ACETYL-2-ETHYL-1H-BENZIMIDAZOL-1-YL)PHENYL]-1-METHYLETHYL(4-METHYLPHENYL)SULFONYLCARBAMATE

STEP 1. (2R)-1-(4-nitrophenyl)-2-propanol

To a solution of (1R)-1-methyl-2-(4-nitrophenyl)ethyl propanoate (step 1 of Example 248, 1.91 g, 8.05 mmol) in ethanol (20 ml) was added 2N aqueous NaOH (5 ml) at room temperature. The resulting mixture was stirred at room temperature for 2 h. The reaction mixture was poured into water, extracted with diethyl ether (2×50 ml). The organic layer was washed with brine, dried (MgSO4), and concentrated. Purification by flash column chromatography eluting with hexane/diethyl ether (1:1) afforded 1.16 g (80%) of title compound as a colorless solid (79% e.e.). Recrystallization from hexane/diethyl ether afforded 717 mg of a colorless needle (99% e.e.).

$^1$H-NMR (CDCl$_3$) δ: 8.18 (2H, d, J=8.8 Hz), 7.39 (2H, d, J=8.8 Hz), 4.14–4.04 (1H, m), 2.92–2.79 (2H, m), 1.49 (1H, d, J=4.0 Hz), 1.28 (3H, d, J=6.1 Hz).

$[α]^{23}_D$ −32.6° (c 1.00, diethyl ether)

STEP 2. (2R)-1-(4-aminophenyl)-2-propanol

The title compound was prepared according to the procedure described in step 4 of Example 1 from (2R)-1-(4-nitrophenyl)-2-propanol (step 1).

$^1$H-NMR (CDCl$_3$) δ: 7.00 (2H, d, J=8.4 Hz), 6.65 (2H, d, J=8.4 Hz), 3.99–3.89 (1H, m), 3.60 (2H, br.s) 2.73–2.52 (2H, m), 1.22 (3H, d, J=6.2 Hz).

STEP 3. 1-[4-({4-[(2R)-2-hydroxypropyl]phenyl}amino)-3-nitrophenyl]ethanone

The title compound was prepared according to the procedure described in step 1 of Example 162 from 1-(4-chloro-3-nitrophenyl)ethanone and (2R)-1-(4-aminophenyl)-2-propanol (step 2).

$^1$H-NMR (CDCl$_3$) δ: 9.85 (1H, br.s), 8.83–8.82 (1H, m), 7.99–7.95 (1H, m), 7.33 (2H, d, J=8.4 Hz), 7.24 (2H, d, J=8.4 Hz), 7.18 (1H, d, J=9.0 Hz), 4.13–4.04 (1H, m), 2.87–2.72 (2H, m), 2.58 (3H, s), 1.29 (3H, d, J=6.2 Hz).

STEP 4. 1-[3-amino-4-({4-[(2R)-2-hydroxypropyl]phenyl}amino)phenyl]ethanone

The title compound was prepared according to the procedure described in step 4 of Example 1 from 1-[4-({4-[(2R)-2-hydroxypropyl]phenyl}amino)-3-nitrophenyl]ethanone (step 3).

MS (EI) m/z: 284 (M+).

STEP 5. (1R)-2-[4-(5-acetyl-2-ethyl-1H-benzimidazol-1-yl)phenyl]-1-methylethyl propanoate The title compound was prepared according to the procedure described in step 5 of Example 1 from 1-[3-amino-4-({4-[(2R)-2-hydroxypropyl]phenyl}amino)phenyl]ethanone (step 4).

$^1$H-NMR (CDCl$_3$) δ: 8.41–8.40 (1H, m), 8.83–8.82 (1H, m), 7.92–7.89 (1H, m), 7.43 (2H, d, J-8.4 Hz), 7.29 (2H, d, J=8.4 Hz), 7.12–7.09 (1H, m), 5.25–5.18 (1H, m), 3.07–2.88 (2H, m), 2.80 (2H, q, J=7.3 Hz), 2.68 (3H, s), 2.34–2.26 (2H, m), 1.37 (3H, q, J=7.5 Hz), 1.32 (3H, d, J=6.2 Hz), 1.10 (3H, t, J=7.5 Hz).

STEP 6. 1-(2-ethyl-1-{4-[(2R)-2-hydroxypropyl]phenyl}-1H-benzimidazol-5-yl)ethanone The title compound was prepared according to the procedure described in step 6 of Example 1 from (1R)-2-[4-(5-acetyl-2-ethyl-1H-benzimidazol-1-yl)phenyl]-1-methylethyl propanoate (step 5).

$^1$H-NMR (CDCl$_3$) δ: 8.39 (1H, d, J=1.1 Hz), 7.87 (1H, dd, J=8.6, 1.1 Hz), 7.48 (2H, d, J=8.4 Hz), 7.30 (2H, d, J=8.4 Hz), 7.12 (1H, d, J=8.6 Hz), 4.22–4.12 (1H, m), 2.94–2.89 (2H, m), 2.80 (2H, q, J=7.5 Hz), 2.69 (3H, s), 2.42 (1H, br.s), 1.37 (3H, t, J=7.5 Hz), 1.33 (3H, d, J=6.2 Hz).

STEP 7. (1R)-2-[4-(5-acetyl-2-ethyl-1H-benzimidazol-1-yl)phenyl]-1-methylethyl(4-methylphenyl)sulfonylcarbamate The title compound was prepared according to the procedure described in Example 3 from 1-(2-ethyl-1-{4-[(2R)-2-hydroxypropyl]phenyl}-1H-benzimidazol-5-yl)ethanone (step 6).

$^1$H-NMR (CDCl$_3$) δ: 8.40 (1H, d, J=1.1 Hz), 7.91–7.86 (3H, m), 7.32–7.24 (4H, m), 7.17 (2H, d, J=7.9 Hz), 7.07 (1H, d, J=8.4 Hz), 5.09–5.03 (1H, m), 2.99–2.75 (2H, m), 2.77 (2H, q, J=7.5 Hz), 2.67 (3H, s), 2.37 (3H, s), 1.33 (3H, t, J=7.5 Hz), 1.21 (3H, d, J=6.1 Hz).

MS (ESI) m/z: 520 (MH+), 518 ([M−H]−).

$[α]^{24}_D$ +6.05° (c 0.118, methanol).

EXAMPLE 250

(1S)-2-{4-[6-CHLORO-2-ETHYL-5-(TRIFLUO-ROMETHYL)-1H-BENZIMIDAZOL-1-YL]PHE-NYL}-1-METHYLETHYL(4-METHYLPHENYL) SULFONYLCARBAMATE

STEP 1. (2S)-1-(4-{[5-chloro-2-nitro-4-(trifluoromethyl)phenyl]amino}phenyl)-2-propanol The title compound was prepared according to the procedure described in step 1 of Example 162 from 2,4-dichloro-5-nitrobenzotrifluoride and (2S)-1-(4-aminophenyl)-2-propanol (step 2 of Example 248).

$^1$H-NMR (CDCl$_3$) δ: 9.69 (1H, br.s), 8.58 (1H, s), 7.36 (2H, d, J=8.4 Hz), 7.24 (2H, d, J=8.4 Hz), 7.20 (1H, s), 4.13–4.06 (1H, m), 2.88–2.73 (2H, m), 1.48 (1H, d, J=4.2 Hz), 1.30 (3H, d, J=6.2 Hz).

STEP 2. (2S)-1-(4-{[2-amino-5-chloro-4-(trifluoromethyl)phenyl]amino}phenyl)-2-propanol The title compound was prepared according to the procedure described in step 2 of Example 28 from (2S)-1-(4-{[5-chloro-2-nitro-4-(trifluoromethyl)phenyl]amino}phenyl)-2-propanol (step 1).

$^1$H-NMR (CDCl$_3$) δ: 7.17 (1H, s), 7.15 (2H, d, J=8.4 Hz), 7.06 (1H, s), 6.90 (2H, d, J=8.4 Hz), 4.05–3.98 (1H, m), 2.79–2.61 (2H, m), 1.26 (3H, d, J=6.3 Hz).

STEP 3. (1S)-2-{4-[6-chloro-2-ethyl-5-(trifluoromethyl)-1H-benzimidazol-1-yl]phenyl}-1-methylethyl propanoate The title compound was prepared according to the procedure described in step 5 of Example 1 from (2S)-i-(4-{[2-amino-5-chloro-4-(trifluoromethyl)phenyl]amino}phenyl)-2-propanol (step 2).

MS (EI) m/z: 438 (M$^+$).

STEP 4. (2S)-1-{4-[6-chloro-2-ethyl-5-(trifluoromethyl)-1H-benzimidazol-1-yl]phenyl}-2-propanol The title compound was prepared according to the procedure described in step 6 of Example 1 from (1S)-2-{4-[6-chloro-2-ethyl-5-(trifluoromethyl)-1H-benzimidazol-1-yl]phenyl}-1-methylethyl propanoate (step 3).

$^1$H-NMR (CDCl$_3$) δ: 8.12 (1H, s), 7.47 (2H, d, J=8.4 Hz), 7.28 (2H, d, J=8.4 Hz), 7.21 (1H, s), 4.20–4.10 (1H, m), 2.95–2.83 (2H, m), 2.79 (2H, q, J=7.5 Hz), 1.56 (1H, d, J=4.2 Hz), 1.36 (3H, t, J=7.5 Hz), 1.34 (3H, d, J=6.2 Hz).

STEP 5. (1S)-2-{4-[6-chloro-2-ethyl-5-(trifluoromethyl)-1H-benzimidazol-1-yl]phenyl}-1-methylethyl(4-methylphenyl)sulfonylcarbamate The title compound was prepared according to the procedure described in Example 3 from (2S)-1-{4-[6-chloro-2-ethyl-5-(trifluoromethyl)-1H-benzimidazol-1-yl]phenyl}-2-propanol (step 4).

m.p.: 200.3° C.

$^1$H-NMR (CDCl$_3$) δ: 8.09 (1H, s), 7.87 (2H, d, J=8.4 Hz), 7.41 (2H, d, J=8.4 Hz), 7.31 (2H, d, J=8.4 Hz), 7.24 (2H, d, J=8.4 Hz), 7.21 (1H, s), 5.06–5.00 (1H, m), 3.04–2.74 (4H, m), 2.40 (3H, s), 1.36 (3H, t, J=7.5 Hz), 1.23 (3H, d, J=6.2 Hz).

MS (ESI) m/z: 580 (MH$^+$), 578 ([M−H]$^−$).

[α]$^{24}_D$+1.31° (c 0.398, methanol)

ee: 98%.

EXAMPLE 251

(1S)-2-{4-[6-CHLORO-2-ETHYL-5-(TRIFLUO-ROMETHYL)-1H-BENZIMIDAZOL-1-YL]PHE-NYL}-1-METHYLETHYL(4-METHYLPHENYL) SULFONYLCARBAMATE MONO-P-TOLUENESULFONATE

The title compound was prepared according to the procedure described in Example 231 from (1S)-2-{4-[6-chloro-2-ethyl-5-(trifluoromethyl)-1H-benzimidazol-1-yl]phenyl}-1-methylethyl(4-methylphenyl)sulfonylcarbamate (step 5 of Example 250).

$^1$H-NMR (DMSO-d$_6$) δ: 11.91 (1H, br.s), 8.23 (1H, s), 7.75 (2H, d, J=8.3 Hz), 7.50–7.37 (9H, m), 7.11 (2H, d, J=8.1 Hz), 4.97–4.91 (1H, m), 2.92–2.76 (4H, m), 2.30 (3H, s), 2.27 (3H, s), 1.24 (3H, t, J=7.3 Hz), 1.14 (3H, d, J=6.2 Hz).

MS (ESI) m/z: 580 (MH$^+$), 578 ([M−H]$^−$).

EXAMPLE 252

(1R)-2-{4-[6-CHLORO-2-ETHYL-5-(TRIFLUO-ROMETHYL)-1H-BENZIMIDAZOL 1-YL]PHE-NYL}-1-METHYLETHYL(4-METHYLPHENYL) SULFONYLCARBAMATE

STEP 1. (2R)-1-(4-{[5-chloro-2-nitro-4-(trifluoromethyl)phenyl]amino}phenyl)-2-propanol The title compound was prepared according to the procedure described in step 1 of Example 162 from 2,4-dichloro-5-nitrobenzotrifluoride and (2R)-1-(4-aminophenyl)-2-propanol (step 2 of Example 249).

$^1$H-NMR (CDCl$_3$) δ: 9.69 (1H, br.s), 8.58 (1H, s), 7.36 (2H, d, J=8.4 Hz), 7.24 (2H, d, J=8.4 Hz), 7.20 (1H, s), 4.13–4.06 (1H, m), 2.88–2.73 (2H, m), 1.48 (1H, d, J=4.2 Hz), 1.30 (3H, d, J=6.2 Hz).

STEP 2. (2R)-1-(4-{[2-amino-5-chloro-4-(trifluoromethyl)phenyl]amino}phenyl)-2-propanol The title compound was prepared according to the procedure described in step 2 of Example 28 from (2R)-1-(4-{[5-chloro-2-nitro-4-(trifluoromethyl)phenyl]amino}phenyl)-2-propanol (step 1).

$^1$H-NMR (CDCl$_3$) δ: 7.17 (1H, s), 7.15 (2H, d, J=8.4 Hz), 7.06 (1H, s), 6.90 (2H, d, J=8.4 Hz), 4.05–3.98 (1H, m), 2.79–2.61 (2H, m), 1.26 (3H, d, J=6.3 Hz).

STEP 3. (1R)-2-{4-[6-chloro-2-ethyl-5-(trifluoromethyl)-1H-benzimidazol-1-yl]phenyl}-1-methylethyl propanoate The title compound was prepared according to the procedure described in step 5 of Example 1 from (2R)-1-(4-{[2-amino-5-chloro-4-(trifluoromethyl)phenyl]amino}phenyl)-2-propanol (step 2).

MS (EI) m/z: 438 (M$^+$).

STEP 4. (2R)-1-{4-[6-chloro-2-ethyl-5-(trifluoromethyl)-1H-benzimidazol-1-yl]phenyl}-2-propanol The title compound was prepared according to the procedure described in step 6 of Example 1 from (1R)-2-{4-[6-chloro-2-ethyl-5-(trifluoromethyl)-1H-benzimidazol-1-yl]phenyl}-1-methylethyl propanoate (step 3).

$^1$H-NMR (CDCl$_3$) δ 8.12 (1H, s), 7.47 (2H, d, J=8.4 Hz), 7.28 (2H, d, J=8.4 Hz), 7.21 (1H, s), 4.20–4.10 (1H, m), 2.95–2.83 (2H, m), 2.79 (2H, q, J=7.5 Hz), 1.56 (1H, d, J=4.2 Hz), 1.36 (3, t, J=7.5 Hz), 1.34 (3H, d, J=6.2 Hz).

STEP 5. (1R)-2-{4-[6-chloro-2-ethyl-5-(trifluoromethyl)-1H-benzimidazol-1-yl]phenyl}-1-methylethyl(4-methylphenyl)sulfonylcarbamate The title compound was prepared according to the procedure described in Example 3 from (2R)-1-{4-[6-chloro-2-ethyl-5-(trifluoromethyl)-1H-benzimidazol-1-yl]phenyl}-2-propanol (step 4).

m.p.: 199.9° C.

$^1$H-NMR (CDCl$_3$) δ: 10.70 (1H, br.s), 8.10 (1H, s), 7.89 (2H, d, J=8.3 Hz), 7.40 (2H, d, J=8.3 Hz), 7.30 (2H, d, J=8.3 Hz), 7.22 (2H, d, J=8.3 Hz), 7.20 (1H, s), 5.32–5.00 (1H, m), 3.04–2.82 (2H, m), 2.78 (2H, q, J=7.5 Hz), 2.40 (3H, s), 1.36 (3H, t, J=7.5 Hz), 1.23 (3H, d, J=6.2 Hz).

MS (ESI) m/z: 580 (MH$^+$), 578 ([M–H]$^-$).

$[α]^{24}_D$ –2.19° (c 0.402, methanol)

ee: 97%.

EXAMPLE 253

N-{[(2-{4-[6-CHLORO-2-ETHYL-5-(TRIFLUOROMETHYL)-1H-BENZIMIDAZOL-1-YL]PHENYL}-1-METHYLETHYL)AMINO]CARBONYL}-4-METHYLBENZENESULFONAMIDE

STEP 1. 1-[4-(2-azidopropyl)phenyl]-6-chloro-2-ethyl-5-(trifluoromethyl)-1H-benzimidazole To a stirred solution of 1-{4-[6-chloro-2-ethyl-5-(trifluoromethyl)-1H-benzimidazol-1-yl]phenyl}-2-propanol (step 8 of Example 247, 1.96 g, 5.12 mmol), triphenylphosphine (1.75 g, 6.66 mmol) and diphenylphosphoryl azide (1.83 mg, 6.66 mmol) in tetrahydrofuran (15 ml) was added diethyl azodicarboxylate (1. 16 mg, 6.66 mmol) at room temperature. The resulting mixture was stirred at temperature for 3 h, then under reflux temperature. The mixture was diluted with ethyl acetate and washed with water and brine. The organic layer was dried (Na2SO4), and concentrated. Purification by flash column chromatography eluting with hexane/ethyl acetate (2:1) and TLC developing with hexane/ethyl acetate (1:1) afforded 769 mg (37%) of the title compound as a slight yellow syrup.

$^1$H-NMR (CDCl$_3$) δ: 8.12 (1H, s), 7.47 (2H, d, J=8.3 Hz), 7.30 (2H, d, J=8.3 Hz), 7.21 (1H, s), 3.85–3.77 (1H, m), 2.92–2.89 (2H, m), 2.80 (2H, q, J=7.5 Hz), 1.37 (3H, d, J=6.6 Hz), 1.36 (3H, t, J=7.5 Hz).

MS (ESI) m/z: 408 (MH$^+$).

STEP 2. 2-{4-[6-chloro-2-ethyl-5-(trifluoromethyl)-1H-benzimidazol-1-yl]phenyl}-1-methylethylamine The title compound was prepared according to the procedure described in step 7 of Example 37 from 1-[4-(2-azidopropyl)phenyl]-6-chloro-2-ethyl-5-(trifluoromethyl)-1H-benzimidazole (step 1).

$^1$H-NMR (CDCl$_3$) δ: 8.12 (1H, s), 7.44 (2H, d, J=8.3 Hz), 7.28 (2H, d, J=8.3 Hz), 7.21 (1, s), 3.49–3.26 (1H, m), 2.86–2.95 (2H, m), 2.79 (2H, q, J=7.5 Hz), 1.36 (3H, t, J=7.5 Hz), 1.20 (3H, d, J=6.2 Hz).

STEP 3. N-{[(2-{4-[6-chloro-2-ethyl-5-(trifluoromethyl)-1H-benzimidazol-1-yl]phenyl}-1-methylethyl)amino]carbonyl}-4-methylbenzenesulfonamide The title compound was prepared according to the procedure described in step 10 of Example 1 from 2-{4-[6-chloro-2-ethyl-5-(trifluoromethyl)-1H-benzimidazol-1-yl]phenyl}-1-methylethylamine (step 2).

$^1$H-NMR (CDCl$_3$) δ: 8.12 (1H, s), 7.73 (2H, d, J=8.4 Hz), 7.41 (2H, d, J=8.3 Hz), 7.29–7.23 (4H, m), 7.17 (1H, s), 4.20–4.11 (1H, m), 2.99–2.82 (2H, m), 2.78 (2H, q, J=7.3 Hz), 2.38 (3H, s), 1.35 (3H, t, J=7.3 Hz), 1.24 (3H, d, J=6.6 Hz).

MS (ESI) m/z: 579 (MH$^+$), 577 ([M–H]$^-$).

EXAMPLE 254

N-{[((1S)-2-{4-[6-CHLORO-2-ETHYL-5-(TRIFLUOROMETHYL)-1H-BENZIMIDAZOL-1-YL]PHENYL}-1-METHYLETHYL)AMINO]CARBONYL}-4-METHYLBENZENESULFONAMIDE

STEP 1. 1-[4-[(2s)-2-azidopropyl)phenyl]-6-chloro-2-ethyl-5-(trifluoromethyl)-1H-benzimidazole The title compound was prepared according to the procedure described in step 1 of Example 253 from (2R)-1-{4-[6-chloro-2-ethyl-5-(trifluoromethyl)-1H-benzimidazol-1-yl]phenyl}-2-propanol (step 4 of Example 252).

$^1$H-NMR (CDCl$_3$) δ: 8.12 (1H, s), 7.46 (2H, d, J=7.9 Hz), 7.29 (2H, d, J=7.9 Hz), 7.21 (1H, s), 3.84–3.77 (1H, m), 2.92–2.89 (2H, m), 2.79 (2H, q, J=7.6 Hz), 1.39–1.33 (6H, m).

STEP 2. (1S)-2-{4-[6-chloro-2-ethyl-5-(trifluoromethyl)-1H-benzimidazol-1-yl]phenyl}-1-methylethylamine The title compound was prepared according to the procedure described in step 7 of Example 37 from 1-[4-[(2s)-2-azidopropyl)phenyl]-6-chloro-2-ethyl-5-(trifluoromethyl)-1H-benzimidazole (step 1).

$^1$H-NMR (CDCl$_3$) δ 8.12 (1H, s), 7.44 (2H, d, J=8.3 Hz), 7.28 (2H, d, J=8.3 Hz), 7.21 (1H, s), 3.49–3.26 (1H, m), 2.86–2.65 (2H, m), 2.79 (2H, q, J=7.5 Hz), 1.36 (3H, t, J=7.5 Hz), 1.20 (3H, d, J=6.2 Hz).

STEP 3. N-{[((1S)-2-{4-[6-chloro-2-ethyl-5-(trifluoromethyl)-1H-benzimidazol-1-yl]phenyl}-1-methylethyl)amino]carbonyl}-4-methylbenzenesulfonamide The title compound was prepared according to the procedure described in step 10 of Example 1 from (1S)-2-{4-[6-chloro-2-ethyl-5-(trifluoromethyl)-1H-benzimidazol-1-yl]phenyl}-1-methylethylamine (step 2).

m.p.: 141.0–143.0° C.

$^1$H-NMR (CDCl$_3$) δ: 8.12 (1H, s), 7.73 (2H, d, J=8.3 Hz), 7.41 (2H, d, J=8.3 Hz), 7.30 (2H, d, J=8.3 Hz), 7.25 (2H, d, J=8.3 Hz), 7.17 (1H, s), 6.58 (1H, d, J=7.7 Hz), 4.22–4.14 (1H, m), 2.82–2.30 (2H, m), 2.78 (2H, q, J=7.6 Hz), 2.39 (3H, s), 1.35 (3H, t, J=7.5 Hz), 1.24 (3H, d, J=6.6 Hz).

MS (ESI) m/z: 579 (MH$^+$), 691 ([M+CF$_3$COOH–H]$^-$).

$[α]^{24}_D$ –5.08° (c 0.394, methanol)

ee: 99%.

EXAMPLE 255

N-{[((1R)-2-{4-[6-CHLORO-2-ETHYL-5-(TRIFLUOROMETHYL)-1H-BENZIMIDAZOL-1-YL]PHENYL}-1-METHYLETHYL)AMINO]CARBONYL}-4-METHYLBENZENESULFONAMIDE

STEP 1. 1-[4-[(2R)-2-azidopropyl)phenyl]-6-chloro-2-ethyl-5-(trifluoromethyl)-1H-benzimidazole The title compound was prepared according to the procedure described in step 1 of Example 253 from (2S)-1-{4-[6-chloro-2-ethyl-5-(trifluoromethyl)-1H-benzimidazol-1-yl]phenyl}-2-propanol (step 4 of Example 250).

¹H-NMR (CDCl₃) δ: 8.12 (1H, s), 7.46 (2H, d, J=7.9 Hz), 7.29 (2H, d, J=7.9 Hz), 7.21 (1H, s), 3.84–3.77 (1H, m), 2.92–2.89 (2H, m), 2.79 (2H, q, J=7.6 Hz), 1.39–1.33 (6H, m).

STEP 2. (1R)-2-{4-[6-chloro-2-ethyl-5-(trifluoromethyl)-1H-benzimidazol-1-yl]phenyl}-1-methylethylamine The title compound was prepared according to the procedure described in step 7 of Example 37 from 1-[4-[(2R)-2-azidopropyl)phenyl]-6-chloro-2-ethyl-5-(trifluoromethyl)-1H-benzimidazole (step 1).

¹H-NMR (CDCl₃) δ: 8.12 (1H, s), 7.44 (2H, d, J=8.3 Hz), 7.28 (2H, d, J=8.3 Hz), 7.21 (1H, s), 3.49–3.26 (1H, m), 2.86–2.65 (2H, m), 2.79 (2H, q, J=7.5 Hz), 1.36 (3H, t, J=7.5 Hz), 1.20 (3H, d, J=6.2 Hz).

STEP 3. N-{[((1R)-2-{4-[6-chloro-2-ethyl-5-(trifluoromethyl)-1H-benzimidazol-1-yl]phenyl}-1-methylethyl)amino]carbonyl}-4-methylbenzenesulfonamide The title compound was prepared according to the procedure described in step 10 of Example 1 from (1R)-2-{4-[6-chloro-2-ethyl-5-(trifluoromethyl)-1H-benzimidazol-1-yl]phenyl}-1-methylethylamine (step 2).

m.p.: 138.0–141.0° C.

¹H-NMR (CDCl₃) δ: 8.12 (1H, s), 7.73 (2H, d, J=8.3 Hz), 7.41 (2H, d, J=8.3 Hz), 7.30 (2H, d, J=8.3 Hz), 7.25 (2H, d, J=8.3 Hz), 7.17 (1H, s), 6.58 (1H, d, J=7.7 Hz), 4.22–4.14 (1H, m,), 2.82–2.30 (2H, m), 2.78 (2H, q, J=7.6 Hz), 2.39 (3H, s), 1.35 (3H, t, J=7.5 Hz), 1.24 (3H, d, J=6.6 Hz).

MS (ESI) m/z: 579 (MH⁺), 691 ([M+CF₃COOH−H]⁻).

[α]²⁴_D +3.43° (c 0.408, methanol)

ee: 99%.

EXAMPLE 256

2-{4-[6-CHLORO-2-(1H-PYRAZOL-3-YL)-5-(TRIFLUOROMETYL)-1H-BENZIMIDAZOL-1-YL]PHENYL}ETHYL(4-METHYLPHENYL)SULFONYLCARBAMATE

STEP 1. 2-{4-[6-chloro-2-(1H-pyrazol-3-yl)-5-(trifluoromethyl)-1H-benzimidazol-1-yl]phenyl}ethanol A mixture of 2-(4-{[2-amino-5-chloro-4-(trifluoromethyl)phenyl]amino}phenyl)ethanol (step 2 of Example 104, 2.28 g, 5.85 mmol) and 1H-pyrazole-3-carbaldehyde (562 mg, 2.85 mmol) in ethanol (35 ml) was stirred under reflux temperature for 1 h. The mixture was concentrated and dissolved in benzene (40 ml). To this solution was added lead tetraacetate (2.85 g, 6.44 mmol) at rt. After stirring at room temperature for 18 h, to the mixture were added saturated aqueous sodium hydrogencarbonate (50 ml) and ethyl acetate. The organic layer was separated and washed with brine, dried (Na2SO4) and concentrated. Purification by flash column chromatography eluting with dichloromethane/methanol (20:1 to 10:1), then dichloromethane/2-propanol (5:1) afforded 979 mg (41%) of the title compound as a slight brown solid.

¹H-NMR (CDCl₃/CD3OD=4/1) δ: 8.12 (1H, br.s), 7.74 (1H, s), 7.59 (1H, br.s), 7.47 (2H, d, J=7.9 Hz), 7.34–7.30 (3H, m), 6.36 (1H, br.s), 3.87 (2H, br.t, J=6.8 Hz), 2.95 (2H, t, J=6.8 Hz).

MS (ESI) m/z: 407 (MH⁺), 405 ([M−H]⁻).

STEP 2. 2-{4-[6-chloro-2-(1H-pyrazol-3-yl)-5-(trifluorometyl)-1H-benzimidazol-1-yl]phenyl}ethyl(4-methylphenyl)sufonylcarbamate The title compound was prepared according to the procedure described in Example 3 from 2-{4-[6-chloro-2-(1H-pyrazol-3-yl)-5-(trifluoromethyl)-1H-benzimidazol-1-yl]phenyl}ethanol (step 1).

¹H-NMR (CDCl₃) δ: 8.18 (1H, s), 7.91 (2H, d, J=8.3 Hz), 7.54–7.53 (1H, m), 7.34–7.23 (8H, m), 6.31 (1H, br.s), 4.40 (2H, t, J=6.4 Hz), 3.01 (2H, t, J=6.4 Hz), 2.42 (3H, s).

MS (ESI) m/z: 604 (MH⁺), 602 ([M−H]⁻).

EXAMPLE 257

2-{4-[6-CHLORO-2-(1H-PYRAZOL-3-YL)-5-(TRIFLUOROMETYL)-1H-BENZIMIDAZOL-1-YL]PHENYL}ETHYL(4-METHYLPHENYL)SULFONYLCARBAMATE MONO-P-TOLUENESULFONATE

The title compound was prepared according to the procedure described in Example 231 from 2-{4-[6-chloro-2-(1H-pyrazol-3-yl)-5-(trifluoromethyl)-1H-benzimidazol-1-yl]phenyl}ethyl(4-methylphenyl)sulfonylcarbamate (step 2 of Example 256).

¹H-NMR (DMSO-d6) δ: 8.24 (1H, s), 7.77–7.74 (2H, m), 7.48–7.38 (10H, m), 7.26 (1H, s), 7.11 (2H, d, J=7.9 Hz), 6.44 (1H, br.s), 4.30–4.20 (2H, m), 2.98–2.93 (2H, m), 2.33 (3H, s), 2.27 (3H, s).

MS (ESI) m/z: 604 (MH⁺), 602 ([M−H]⁻).

EXAMPLE 258

(1S)-2-[4-(2-Ethyl-5,7-dimethyl-3H-imidazo[4,5-B]pyridin-3-yl)phenyl]-1-methylethyl(4-methylphenyl)sufonylcarbamate mono-hydrochloride STEP 1. (2S)-1-{4-[(4,6-dimethyl-3-nitro-2-pyridinyl)amino]phenyl}-2-propanol The title compound was prepared according to the procedure described in step 1 of Example 162 from 2-chloro-4,6-dimethyl-3-nitropyridine (step 2 of Example 1) and (2S)-1-(4-aminophenyl)-2-propanol (step 2 of Example 248).

¹H-NMR (CDCl₃) δ: 9.58 (1H, br.s), 7.59 (2H, d, J=8.6 Hz), 7.19 (2H, d, J=8.6 Hz), 6.53 (1H, s), 4.05–3.98 (1H, m), 2.82–2.63 (2H, m), 2.55 (3H, s), 2.43 (3H, s), 1.26 (3H, d, J=6.3 Hz).

STEP 2. (2S)-1-{4-[(3-amino-4,6-dimethyl-2-pyridinyl)amino]phenyl}-2-propanol

The title compound was prepared according to the procedure described in step 2 of Example 28 from (2S)-1-{4-[(4,6-dimethyl-3-nitro-2-pyridinyl)amino]phenyl}-2-propanol 1).

¹H-NMR (CDCl₃) δ: 7.13–7.07 (4H, m), 6.60 (1H, s), 6.21 (1H, br.s), 4.02–3.91 (1H, m), 3.26 (2H, br.s), 2.77–2.57 (2H, m), 2.37 (3H, s), 2.20 (3H, s), 1.24 (3H, d, J=6.1 Hz).

STEP 3. (1S)-2-[4-(2-ethyl-5,7-dimethyl-3H-imidazo[4,5-b]pyridin-3-yl)phenyl]-1-methylethyl propanoate The title compound was prepared according to the procedure described in step 5 of Example 1 from (2S)-1-{4-[(3-amino-4,6-dimethyl-2-pyridinyl)amino]phenyl}-2-propanol (step 2).

MS (EI) m/z: 365 (M⁺).

STEP 4. (2S)-1-{4-(2-ethyl-5,7-dimethyl-3H-imidazo[4,5-b]pyridin-3-yl)phenyl]-2-propanol The title compound was prepared according to the procedure described in step 6 of Example 1 from (1S)-2-[4-(2-Ethyl-5,7-dimethyl-3H-imidazo[4,5-b]pyridin-3-yl)phenyl]-1-methylethyl propanoate (step 3).

$^1$H-NMR (CDCl$_3$) δ: 7.42 (2H, d, J=8.4 Hz), 7.35 (2H, d, J=8.4 Hz), 6.91 (1H, s), 4.18–4.05 (1H, m), 2.92–2.75 (4H, m), 2.66 (3H, s), 2.52 (3H, s), 1.34–1.25 (6H, m).

STEP 5. (1S)-2-[4-(2-ethyl-5,7-dimethyl-3H-imidazo[4,5-b]pyridin-3-yl)phenyl]-1-methylethyl(4-methylphenyl)sulfonylcarbamate The title compound was prepared according to the procedure described in Example 3 from (2S)-1-[4-(2-Ethyl-5,7-dimethyl-3H-imidazo[4,5-b]pyridin-3-yl)phenyl]-2-propanol (step 4).

$^1$H-NMR (CDCl$_3$) δ: 7.92 (2H, d, J=8.2 Hz), 7.33 (2H, d, J=8.2 Hz), 7.30–7.26 (4H, m), 5.14–5.02 (1H, m), 2.99–2.77 (4H, m), 2.66 (3H, s), 2.51 (3H, s), 2.42 (3H, s), 1.29–1.23 (6H, m).

MS (ESI) m/z: 507 (MH$^+$), 505 ([M−H]$^−$).

STEP 6. 2-[4-(2-ethyl-5,7-dimethyl-3H-imidazo[4,5-b]pyridin-3-yl)phenyl]-1-methylethyl(4-methylphenyl)sulfonylcarbamate mono-hydrochloride The title compound was prepared according to the procedure described in Example 240 from (1S)-2-[4-(2-ethyl-5,7-dimethyl-3H-imidazo[4,5-b]pyridin-3-yl)phenyl]-1-methylethyl(4-methylphenyl)sulfonylcarbamate (step 5).

$^1$H-NMR (DMSO-d$_6$) δ: 11.92 (1H, br.s), 7.76 (2H, d, J=7.9 Hz), 7.49–7.39 (6H, m), 7.26 (1H, br.s), 4.98–4.88 (1H, m), 2.94–2.83 (4H, m), 2.63 (3H, s), 2.46 (3H, s), 2.34 (3H, s), 1.23 (3H, t, J=7.5 Hz), 1.12 (3H, d, J=6.1 Hz).

MS (ESI) m/z: 507 [(MH)$^+$], 505 [(M−H)$^−$].

$[α]^{24}_D$ −12.49° (c 1.014, methanol)

EXAMPLE 259

2-[4-(6-acetyl-2-ethyl-3H-imidazo[4,5-B]pyridin-3-yl)phenyl]-1-methylethyl(4-methylphenyl)sulfonylcarbamate STEP 1. 1-[6-({4-[2-hydroxypropyl]phenyl}amino)-5-nitro-3-pyridinyl]ethanone The title compound was prepared according to the procedure described in step 1 of Example 162 from 1-(6-chloro-5-nitro-3-pyridinyl)ethanone (Paul, B. et al. *J. Med. Chem.*, 1990, 33, 2231–2239.) and 1-(4-aminophenyl)-2-propanol (step 1 of Example 6).

$^1$H-NMR (CDCl$_3$) δ: 10.37 (1H, br.s), 9.06–9.03 (2H, m), 7.60 (2H, d, J=8.3 Hz), 7.29 (2H, d, J=8.3 Hz), 4.10–4.00 (1H, m), 2.86–2.69 (2H, m), 2.60 (3H, s), 1.53 (1H, d, J=4.0 Hz), 1.28 (3H, d, J=6.2 Hz).

MS (EI) m/z: 315 (M$^+$).

STEP 2. 1-[5-amino-6-({4-[(2-hydroxypropyl]phenyl}amino)-3-pyridinyl]ethanone

To a solution of 1-[6-({4-[2-hydroxypropyl]phenyl}amino)-5-nitro-3-pyridinyl]ethanone (step 1, 1.54 g, 4.88 mmol) in tetrahydrofuran (10 ml) and ethanol (30 ml) was added 10% palladium on carbon (150 mg). The resulting mixture was stirred for 19 h under hydrogen atmosphere. The mixture was filtered through a pad of Celite and the filtrate was concentrated to afford 1.74 g (100%) of the title compound as green syrup.

$^1$H-NMR (CDCl$_3$) δ: 8.46 (1H, d, J=1.8 Hz), 7.56 (1H, d, J=1.8 Hz), 7.50 (2H, d, J=8.3 Hz), 7.20 (2H, d, J=8.3 Hz), 6.85 (1H, br.s), 3.76–3.67 (1H, m), 3.38 (21, br.s), 2.81–2.62 (2H, m), 2.53 (3H, s), 1.26 (3H, d, J=6.1 Hz).

STEP 3. 2-[4-(6-acetyl-2-ethyl-3H-imidazo[4,5-b]pyridin-3-yl)phenyl]-1-methylethyl propanoate The title compound was prepared according to the procedure described in step 5 of Example 1 from 1-[5-amino-6-({4-[(2-hydroxypropyl]phenyl}amino)-3-pyridinyl]ethanone (step 2).

MS (EI) m/z: 379 (M$^+$).

STEP 4. 1-(2-ethyl-3-{4-[2-hydroxypropyl]phenyl}-3H-imidazo[4,5-b]pyridin-6-yl)ethanone The title compound was prepared according to the procedure described in step 6 of Example 1 from 2-[4-(6-acetyl-2-ethyl-3H-imidazo[4,5-b]pyridin-3-yl)phenyl]-1-propanoate (step 3).

$^1$H-NMR (CDCl$_3$) δ: 8.93 (1H, d, J=1.8 Hz), 8.59 (1H, d, J=1.8 Hz), 7.48 (2H, d, J=8.3 Hz), 7.36 (2H, d, J=8.3 Hz), 4.18–4.08 (1H, m), 2.94–2.80 (2H, m), 2.68 (3H, s), 1.39 (3H, t, J=7.5 Hz), 1.33 (3H, d, J=6.2 Hz).

STEP 5. 2-[4-(6-ACETYL-2-ETHYL-3H-IMIDAZO[4,5-b]PYRIDIN-3-YL)PHENYL]-1-METHYLETHYL(4-METHYLPHENYL)SULFONYLCARBAMATE

The title compound was prepared according to the procedure described in Example 3 from 1-(2-ethyl-3-{4-[2-hydroxypropyl]phenyl}-3H-imidazo[4,5-b]pyridin-6-yl)ethanone (step 4).

$^1$H-NMR (CDCl$_3$) δ: 8.93 (1H, d, J=1.8 Hz), 8.60 (1H, d, J=1.8 Hz), 7.92 (2H, d, J=8.4 Hz), 7.38–7.29 (6H, m), 5.12–5.03 (1H, m), 3.03–2.82 (4H, m), 2.69 (3H, s), 2.43 (3H, s), 1.28–1.24 (6H, m).

MS (ESI) m/z: 521 [(MH)$^+$], 519 [(M−H)$^−$].

EXAMPLE 260

(1S)-2-[4-(6-ACETYL-2-ETHYL-3H-IMIDAZO[4,5-B]PYRIDIN-3-YL)PHENYL]-1-METHYLETHYL(4-METHYLPHENYL)SULFONYLCARBAMATE

STEP 1. 1-[6-({4-[(2S)-2-hydroxypropyl]phenyl}amino)-5-nitro-3-pyridinyl]ethanone The title compound was prepared according to the procedure described in step 1 of Example 162 from 1-(6-chloro-5-nitro-3-pyridinyl)ethanone (Paul, B. et al. *J. Med. Chem.*, 1990, 33, 2231–2239.) and (2S)-1-(4-aminophenyl)-2-propanol (step 2 of Example 248).

$^1$H-NMR (CDCl$_3$) δ: 10.37 (1H, br.s), 9.06–9.03 (2H, m), 7.60 (2H, d, J=8.3 Hz), 7.29 (2H, d, J=8.3 Hz), 4.10–4.00 (1H, m), 2.86–2.69 (2H, m), 2.60 (3H, s), 1.53 (1H, d, J=4.0 Hz), 1.28 (3H, d, J=6.2 Hz).

STEP 2. 1-[5-amino-6-({4-[(2S)-2-hydroxypropyl]phenyl}amino)-3-pyridinyl]ethanone The title compound was prepared according to the procedure described in step 2 of Example 259 from 1-[6-({4-[(2S)-2-hydroxypropyl]phenyl}amino)-5-nitro-3-pyridinyl]ethanone (step 1).

$^1$H-NMR (CDCl$_3$) δ: 8.46 (1H, d, J=1.8 Hz), 7.56 (1H, d, J=1.8 Hz), 7.50 (2H, d, J=8.3 Hz), 7.20 (2H, d, J=8.3 Hz), 6.85 (1H, br.s), 3.76–3.67 (1H, m), 3.38 (2H, br.s), 2.81–2.62 (2H, m), 2.53 (3H, s), 1.26 (3H, d, J=6.1 Hz).

STEP 3. (1S)-2-[4-(6-acetyl-2-ethyl-3H-imidazo[4,5-b]pyridin-3-yl)phenyl]-1-methylethyl propanoate The title compound was prepared according to the procedure described in step 5 of Example 1 from 1-[5-amino-6-({4-[(2S)-2-hydroxypropyl]phenyl}amino)-3-pyridinyl]ethanone (step 2).

MS (EI) m/z: 379 (M$^+$).

STEP 4. 1-(2-ethyl-3-{4-[(2S)-2-hydroxypropyl]phenyl}-3H-imidazo[4,5-b]pyridin-6-yl)ethanone The title compound was prepared according to the procedure described in step 6 of Example 1 from (1S)-2-[4-(6-acetyl-2-ethyl-3H-imidazo[4,5-b]pyridin-3-yl)phenyl]-1-methylethyl propanoate (step 3).

$^1$H-NMR (CDCl$_3$) δ: 8.93 (1H, d, J=1.8 Hz), 8.59 (1H, d, J=1.8 Hz), 7.48 (2H, d, J=8.3 Hz), 7.36 (2H, d, J=8.3 Hz), 4.18–4.08 (1H, m), 2.94–2.80 (2H, m), 2.68 (3H, s), 1.39 (3H, t, J=7.5 Hz), 1.33 (3H, d, J=6.2 Hz).

STEP 5. (1S)-2-[4-(6-acetyl-2-ethyl-3H-imidazo[4,5-b]pyridin-3-yl)phenyl]-1-methylethyl(4-methylphenyl)sulfonylcarbamate The title compound was prepared according to the procedure described in Example 3 from 1-(2-ethyl-3-{4-[(2S)-2-hydroxypropyl]phenyl}-3H-imidazo[4,5-b]pyridin-6-yl)ethanone (step 4).

$^1$H-NMR (CDCl$_3$) δ: 8.93 (1H, d, J=1.8 Hz), 8.60 (1H, d, J=1.8 Hz), 7.92 (2H, d, J=8.4 Hz), 7.38–7.29 (6H, m), 5.12–5.03 (1H, m), 3.03–2.82 (4H, m), 2.69 (3H, s), 2.43 (3H, s), 1.28–1.24 (6H, m).

MS (ESI) m/z: 521 [(MH)$^+$], 519 [(M−H)$^−$].

EXAMPLE 261

(1S)-2-[4-(6-ACETYL-2-ETHYL-3H-IMIDAZO[4,5-B]PYRIDIN-3-YL)PHENYL]-1-METHYLETHYL(4-METHYLPHENYL)SULFONYLCARBAMATE MONO-P-TOLUENESULFONATE

The title compound was prepared according to the procedure described in Example 231 from (1S)-2-[4-(6-acetyl-2-ethyl-3H-imidazo[4,5-b]pyridin-3-yl)phenyl]-1-methylethyl(4-methylphenyl)sulfonylcarbamate (step 5 of Example 260).

$^1$H-NMR (DMSO-d6) δ: 11.93 (1H, br.s), 8.90 (1H, d, J=1.8 Hz), 8.63 (1H, d, J=1.8 Hz), 7.76 (2H, d, J=8.4 Hz), 7.38–7.29 (8H, m), 7.11 (2H, d, J=8.4 Hz), 4.96–4.87 (1H, m), 2.90–2.79 (4H, m), 2.32 (3H, s), 2.27 (3H, s), 1.26 (3H, t, J=7.5 Hz), 1.12 (3H, d, J=6.2 Hz).

MS (ESI) m/z: 521 [(MH)$^+$], 519 [(M−H)$^−$].

[α]$^{24}_D$−8.17° (c 1.020, methanol)

EXAMPLE 262

2-{4-[6-CHLORO-2-(2-PYRIDINYL)-5-(TRIFLUOROMETYL)-1H-BENZIMIDAZOL-1-YL]PHENYL}ETHYL(4-METHYLPHENYL)SULFONYLCARBAMATE MONO-P-TOLUENESULFONATE

STEP 1. 2-{4-[6-chloro-2-(2-pyridinyl)-5-(trifluoromethyl)-1h-benzimidazol-1-yl]phenyl}ethanol A mixture of 2-(4-{[2-amino-5-chloro-4-(trifluoromethyl)phenyl]amino}phenyl)ethanol (1.83 g, 5.54 mmol), 2-pyridinecarboxaldehyde (0.53 ml, 5.54 mmol), and EtOH (40 ml) was refluxed for 1 hour. After cooling to room temperature, the solvent was removed. The residue was dissolved with benzene (50 ml) and treated with Pb(OAc)$_4$ (3.38 g, 6.10 mmol) at room temperature for 1 hour. The mixture was diluted with EtOAc and the solution was washed with sat. NaHCO$_3$ aq. and brine. The organic fraction was dried over MgSO$_4$, then filtered. After evaporation in vacuo, the residue was purified by silica-gel column chromatography eluting with hexane/EtOAc=5/2 to afford 1.20 g (52%) of the title compound.

$^1$H-NMR (CDCl$_3$) δ: 8.42–8.39 (1H, m), 8.23 (1H, s), 8.10–8.07 (1H, m), 7.79–7.75 (1H, m), 7.40–7.23 (6H, m), 3.97 (2H, t, J=6.6 Hz), 2.99 (2H, t, J=6.6 Hz)

MS (ESI) m/z: 418 ([M+H]$^+$), 476 ([M+CF$_3$CO$_2$]$^−$)

STEP 2. 2-{4-[6-chloro-2-(2-pyridinyl)-5-(trifluoromethyl)-1h-benzimidazol-1-yl]phenyl}ethyl(4-methylphenyl)sulfonylcarbamate The title compound was prepared according to the procedure described in example 3 from 2-{4-[6-chloro-2-(2-pyridinyl)-5-(trifluoromethyl)-1H-benzimidazol-1-yl]phenyl}ethanol.

$^1$H-NMR (CDCl$_3$) δ: 8.39–8.37 (1H, m), 8.23 (1H, s), 8.10–8.06 (1H, m), 7.92–7.87 (2H, m), 7.81–7.76 (1H, m), 7.33–7.18 (8H, m), 4.35 (2H, t, J=6.8 Hz), 2.98 (2H, t, J=6.8 Hz), 2.41 (3H, s)

MS (ESI) m/z: 615 ([M+H]$^+$), 613 ([M−H]$^−$)

EXAMPLE 263

2-{4-[6-CHLORO-2-(2-PYRIDINYL)-5-(TRIFLUOROMETYL)-1H-BENZIMIDAZOL-1-YL]PHENYL}ETHYL(4-METHYLPHENYL)SULFONYLCARBAMATE MONO-P-TOLUENESULFONATE

The title compound was prepared according to the procedure described in Example 231 from 2-{4-[6-chloro-2-(2-pyridinyl)-5-(trifluoromethyl)-1H-benzimidazol-1-yl]phenyl}ethyl(4-methylphenyl)sulfonylcarbamate.

MS (ESI) m/z: 615 ([M+H]$^+$)

EXAMPLE 264

N-{[(2-{4-[6-CHLORO-2-(2-PYRIDINYL)-5-(TRIFLUOROMETYL)-1H-BENZIMIDAZOL-1-YL]PHENYL}ETHYL)AMINO]CARBONYL}-4-METHYLBENZENESULFONAMIDE MONO-P-TOLUENESULFONATE

STEP 1. 6-chloro-1-[4-(2-chloroethyl)phenyl]-2-(2-pyridinyl)-5-(trifluoromethyl)-1H-benzimidazole The title compound was prepared according to the procedure described in step 7 of Example 1 from 2-{4-[6-chloro-2-(2-pyridinyl)-5-(trifluoromethyl)-1H-benzimidazol-1-yl]phenyl}ethanol (step 1 of Example 262).

$^1$H-NMR (CDCl$_3$) δ: 8.41–8.39 (1H, m), 8.24 (1H, s), 8.11 (1H, d, J=8.8 Hz), 7.82–7.76 (1H, m), 7.38 (2H, d, J=8.4 Hz), 7.35 (1H, s), 7.30–7.25 (3H, m), 3.31 (2H, t, J=7.2 Hz), 3.19 (2H, t, J=7.2 Hz).

STEP 2. 1-[4-(2-azidoethyl)phenyl]-6-chloro-2-(2-pyridinyl)-5-(trifluoromethyl)-1H-benzimidazole The title compound was prepared according to the procedure described in step 8 of Example 1 from 6-chloro-1-[4-(2-chloroethyl)phenyl]-2-(2-pyridinyl)-5-(trifluoromethyl)-1H-benzimidazole (step 1).

$^1$H-NMR (CDCl$_3$) δ: 8.40–8.39 (1H, m), 8.24 (1H, s), 8.10 (1H, d, J=7.9 Hz), 7.81–7.75 (1H, m), 7.39 (2H, d,

J=8.4 Hz), 7.34 (1H, s), 7.29–7.25 (3H, m), 3.61 (2H, t, J=6.8 Hz), 3.01 (2H, t, J=6.8 Hz).

STEP 3. 2-{4-[6-chloro-2-(2-pyridinyl)-5-(trifluoromethyl)-1H-benzimidazol-1-yl]phenyl}ethylamine The title compound was prepared according to the procedure described in step 7 of Example 37 from 1-[4-(2-azidoethyl)phenyl]-6-chloro-2-(2-pyridinyl)-5-(trifluoromethyl)-1H-benzimidazole (step 2).

$^1$H-NMR (CDCl$_3$) δ: 8.37–8.36 (1H, m), 8.19 (1H, s), 8.03–8.00 (1H, m), 7.78–7.71 (1H, m), 7.32–7.18 (6H, m), 3.02 (2H, t, J=6.8 Hz), 2.82 (2H, t, J=6.8 Hz), 2.17 (2H, br.s).

STEP 4. N-{[(2-{4-[6-chloro-2-(2-pyridinyl)-5-(trifluoromethyl)-1H-benzimidazol-1-yl]phenyl}ethyl)amino]carbonyl}-4-methylbenzenesulfonamide The title compound was prepared according to the procedure described in step 10 of Example 1 from 2-{4-[6-chloro-2-(2-pyridinyl)-5-(trifluoromethyl)-1H-benzimidazol-1-yl]phenyl}ethylamine (step 3).

$^1$H-NMR (CDCl$_3$) δ: 8.42–8.39 (1H, m), 8.24 (1H, s), 8.10 (1H, d, J=8.1 Hz), 7.81–7.75 ((1H, m), 7.69 (2H, d, J=8.3 Hz), 7.33–7.24 (8H, m), 6.72–6.69 (1H, m), 3.63–3.56 (2H, m), 2.93 (2H, t, J=6.8 Hz), 2.38 (3H, s).

MS (ESI) m/z: 614 [(MH)$^+$], 612 [(M−H)$^−$].

STEP 5. N-{[(2-{4-[6-chloro-2-(2-pyridinyl)-5-(trifluoromethyl)-1H-benzimidazol-1-yl]phenyl}ethyl)amino]carbonyl}-4-methylbenzenesulfonamide mono-p-toluenesulfonate The title compound was prepared according to the procedure described in Example 231 from N-{[(2-{4-[6-chloro-2-(2-pyridinyl)-5-(trifluoromethyl)-1H-benzimidazol-yl]phenyl}ethyl)amino]carbonyl}-4-methylbenzenesulfonamide (step 4).

$^1$H-NMR (DMSO-d6) δ: 10.63 (1H, br.s), 8.41–8.39 (1H, m), 8.35 (1H, s), 8.08–7.95 (2H, m), 7.75 (2H, d, J=8.3 Hz), 7.49 (2H, d, J=8.3 Hz), 7.44–7.27 (8H, m), 7.10 (2H, d, J=7.7 Hz), 6.61–6.57 (1H, m), 3.30–3.23 (2H, m), 2.74 (2H, t, J=7.0 Hz), 2.31 (3H, s), 2.27 (3H, s).

MS (ESI) m/z: 614 [(MH)$^+$], 612 [(M−H)$^−$].

EXAMPLE 265

N-{[(2-{4-[6-CHLORO-2-(1H-PYRAZOL-3-YL)-5-(TRIFLUOROMETYL)-1H-BENZIMIDAZOL-1-YL]PHENYL}ETHYL)AMINO]CARBONYL}-4-METHYLBENZENESULFONAMIDE MONO-P-TOLUENESULFONATE

STEP 1. 6-chloro-1-[4-(2-chloroethyl)phenyl]-2-(1H-pyrazol-3-yl)-5-(trifluoromethyl)-1H-benzimidazole The title compound was prepared according to the procedure described in step 7 of Example 1 from 2-{4-[6-chloro-2-(1H-pyrazol-3-yl)-5-(trifluoromethyl)-1H-benzimidazol-1-yl]phenyl}ethanol (step 1, Example 255).

$^1$H-NMR (DMSO-d6) δ: 13.29 (1H, s), 8.25 (1H, s), 7.83–7.81 (1H, m), 7.52–7.43 (4H, m), 7.23 (1H, s), 6.67–6.65 (1H, m), 3.95 (2H, t, J=7.0 Hz), 3.16 (2H, t, J=7.0 Hz).

STEP 2. 1-[4-(2-azidoethyl)phenyl-6-chloro-(1H-pyrazol-3-yl)-5-(trifluoromethyl)-1H-benzimidazole The title compound was prepared according to the procedure described in step 8 of Example 1 from 6-chloro-1-[4-(2-chloroethyl)phenyl]-2-(1H-pyrazol-3-yl)-5-(trifluoromethyl)-1H-benzimidazole (step 1).

$^1$H-NMR (DMSO-d6) δ: 13.27 (1H, s), 8.25 (1H, s), 7.82 (1H, s), 7.52–7.43 (4H, m), 7.21 (1H, s), 6.65 (1H, s), 3.67 (2H, t, J=7.0 Hz), 2.99 (2H, t, J=7.0 Hz).

STEP 3. 2-{4-[6-chloro-2-(1H-pyrazol-3-yl)-5-(trifluoromethyl)-1H-benzimidazol-1-yl]phenyl}ethylamine The title compound was prepared according to the procedure described in step 7 of Example 37 from 1-[4-(2-azidoethyl)phenyl-6-chloro-2-(1H-pyrazol-3-yl)-5-(trifluoromethyl)-1H-benzimidazole (step 2).

MS (EI) m/z: 405 (M$^+$).

STEP 4. N-{[(2-{4-[6-chloro-2-(1H-pyrazol-3-yl)-5-(trifluoromethyl)-1H-benzimidazol-1-yl]phenyl}ethyl)amino]carbonyl}-4-methylbenzenesulfonamide The title compound was prepared according to the procedure described in step 10 of Example 1 from 2-{4-[6-chloro-2-(1H-pyrazol-3-yl)-5-(trifluoromethyl)-1H-benzimidazol-1-yl]phenyl}ethylamine (step 3).

$^1$H-NMR (CDCl$_3$) δ: 8.17 (1H, s), 7.69 (2H, d, J=8.4 Hz), 7.57 (1H, d, J=2.2 Hz), 7.30–7.18 (8H, m), 6.82–6.77 (1H, m), 6.60 (1H, d, J=2.2 Hz), 3.64–3.58 (2H, m), 2.91 (2H, t, J=6.4 Hz), 2.39 (3H, s).

STEP 5. N-{[(2-{4-[6-chloro-2-(1H-pyrazol-3-yl)-5-(trifluoromethyl)-1H-benzimidazol-1-yl]phenyl ethyl)amino]carbonyl}-4-methylbenzenesulfonamide mono-p-toluenesulfonate The title compound was prepared according to the procedure described in Example 231 from N-{[(2-{4-[6-chloro-2-(1H-pyrazol-3-yl)-5-(trifluoromethyl)-1H-benzimidazol-1-yl]phenyl ethyl)amino]carbonyl}-4-methylbenzenesulfonamide (step 4).

$^1$H-NMR (DMSO-d6) δ: 10.64 (1H, br.s), 8.24 (1H, s), 8.35 (1H, s), 7.78–7.75 (3H, m), 7.49–7.80 (8H, m), 7.11 (2H, d, J=7.9 Hz), 6.60–6.57 (1H, m), 6.38–6.37 (1H, m), 3.33–3.26 (2H, m), 2.78 (2H, t, J=7.2 Hz), 2.32 (3H, s), 2.28 (3H, s).

MS (ESI) m/z: 603 [(MH)$^+$], 601 [(M−H)$^−$].

EXAMPLE 266

3-(3-CHLORO-4-{2-[({[(4-METHYLPHENYL)SULFONYL]AMINO}CARBONYL)AMINO]ETHYL}PHENYL)-2-ETHYL-5,7-DIMETHYL-3H-IMIDAZO[4,5-b]PYRIDINE

STEP 1. diethyl 2-(2-chloro-4-nitrophenyl)malonate

Diethylmalonate (5.2 ml, 34.2 mmol) was added to the suspension of NaH (1.4 g, 34.2 mmol) in 80 ml of 1,4-dioxane followed by the successive addition of CuBr (4.9 g, 34.2 mmol) and 3-chloro-4-fluoronitrobenzene (5.0 g, 28.5 mmol). The mixture was stirred at room temperature for 0.5 h and under reflux temperature for 12 h. The mixture was poured into water, and the precipitate was filtered off through a pad of celite. The filtrate was extracted with ethyl acetate (2×50 ml). The organic layer was washed with brine, dried (MgSO$_4$), and concentrated to give a green oil. This mixture was purified by SiO2 column chromatography developing with hexane/ethyl acetate (10/1) gave 7.6 g (85%) of the title compound as yellow oil $^1$H-NMR (CDCl$_3$) δ: 8.30 (1H, d, J=2.4 Hz), 8.16 (1H, dd, J=2.2, 8.6 Hz), 7.74 (1H, d, J=8.6 Hz), 5.27 (1H, s), 4.28 (2H, q, J=7.2 Hz), 4.27 (2H, q, J=7.2 Hz), 1.29 (6H, t, J=7.2 Hz).

STEP 2. 2-(2-chloro-4-nitrophenyl)acetic acid

To a solution of diethyl 2-(2-chloro-4-nitrophenyl)malonate (step 1, 7.6 g, 24.2 mmol) in methanol (18 ml) was added 6M-NaOH (12 ml) and stirred for 1 h at 50° C. The reaction was quenched by the addition of saturated citric acid aqueous solution (16 ml) and water. The organic layer was extracted with ethyl acetate (2×50 ml), washed with brine, dried (MgSO$_4$) and concentrated to give 4.52 g (87%) of title compound as light yellow solid.

$^1$H-NMR (CDCl$_3$) δ: 12.6 (1H, br.s), 8.30 (1H, d, J=2.6 Hz), 8.18 (1H, dd, J=2.4, 8.4 Hz), 7.73 (1H, d, J=8.6 Hz), 3.90 (2H, s).

STEP 3. methyl 2-(2-chloro-4-nitrophenyl)acetate

To a solution of 2-(2-chloro-4-nitrophenyl)acetic acid (step 2, 4.5 g, 21 mmol) in dimethyl acetate/methanol (4/1) was added trimethylsillylchloride (0.3 ml) and stirred for 7 h at room temprature.The solvent was removed and the residue was purified by SiO$_2$ column chromatography with developing hexane/ethyl acetate (10/1) to give 3.6 g (74%) of title compound as yellow oil.

$^1$H-NMR (CDCl$_3$) δ: 8.28 (1H, d, J=2.3 Hz), 8.11 (1H, dd, J=2.3, 8.6 Hz), 7.50 (1H, d, J=8.6 Hz), 3.88 (2H, s), 3.74 (3H, s).

STEP 4. methyl 2-(4-amino-2-chlorophenyl)acetate

To a solution of methyl 2-(2-chloro-4-nitrophenyl)acetate (step 3, 3.6 g, 15.6 mmol) in ethanol/water (4/1) were added Fe (4.4 g, 78.0 mmol) and NH$_4$Cl (409 mg, 7.8 mmol). The mixture was stirred for 1 h under reflux temperature. The solvent was removed and the residue was diluted with CH$_2$Cl$_2$. The mixture was washed with brine, dried (MgSO$_4$) and concentrated to give 2.59 g (83%) of title compound as orange oil.

The title compound was prepared according to the procedure described in step 2 of Example 28 from methyl methyl 2-(2-chloro-4-nitrophenyl)acetate (step 3)

$^1$H-NMR (CDCl$_3$) δ: 7.04 (1H, d, J=8.2 Hz), 6.72 (1H, d, J=2.3 Hz), 6.54 (1H, d, J=2.5, 8.2 Hz), 3.70 (3H, s), 3.66 (2H, s).

STEP 5. methyl {2-chloro-4-[(4,6-dimethyl-3-nitro-2-pyridinyl)amino]phenyl}acetate To a mixture of methyl 2-(4-amino-2-chlorophenyl)acetate (step 4, 2.6 g, 13.0 mmol) and 4,6-Dimethyl-3-nitro-2-pyridine (step 2 of Example 1, 2.4 g, 13.0 mmol) in DMSO was added diisopropylethylamine. The resulting mixture was stirred for 9 h at 50° C. To the mixture was poured into water and extracted with ethyl acetate (3×30 ml). The organic layer was washed with brine, dried (MgSO$_4$) and concentrated to give a brown oil. This was purified by SiO$_2$ column chromatography with developing hexane/ethyl acetate (10/1) to give 1.4 g (29%) of title compound as yellow solid.

$^1$H-NMR (CDCl$_3$) δ: 9.55 (1H, br.s), 7.90 (1H, d, J=2.2 Hz), 7.43 (1H, dd, J=2.2, 8.3 Hz), 7.24 (1H, d, J=8.3 Hz), 6.59 (1H, s), 3.76 (2H, s), 3.72 (3H, s), 2.56 (3H, s), 2.46 (3H, s).

MS (EI) m/z: 349 (M$^+$).

STEP 6. methyl 2-chloro-{4-[(3-amino-4,6-dimethyl-2-pyridinyl)amino]phenyl}acetate The title compound was prepared according to the procedure described in step 2 of Example 28 from methyl {2-chloro-4-[(4,6-dimethyl-3-nitro-2-pyridinyl)amino]phenyl}acetate (step 5)

$^1$H-NMR (CDCl$_3$) δ: 7.26 (1H, d, J=2.2 Hz), 7.20 (1H, d, J=8.3 Hz), 7.00 (1H, dd, J=2.2, 8.3 Hz), 6.64 (1H, s), 6.37 (1H, br.s), 3.70 (3H, s), 3.27 (1H, br.s), 2.68 (3H, s), 2.38 (3H, s), 2.20 (3H, s).

STEP 7. methyl 2-[2-chloro-4-(2-ethyl-5,7-dimethyl-3H-imidazo[4,5-b]pyridin-3-yl)phenylethyl acetate The title compound was prepared according to the procedure described in step 5 of Example 1 from methyl 2-chloro-{4-[(3-amino-4,6-dimethyl-2-pyridinyl)amino]phenyl}acetate (step 6)

$^1$H-NMR (CDCl$_3$) δ: 7.50 (1H, d, 8.3 Hz), 7.47 (1H, d, J=2.2 Hz), 7.31 (1H, dd, J=2.2, 8.3 Hz), 6.92 (1H, s), 3.87 (2H, s), 3.77 (3H, s), 2.85 (2H, q, J=7.5 Hz), 2.65 (3H, s), 2.53 (3H, s), 1.31 (3H, t, J=7.5 Hz).

MS (EI) m/z: 357 (M$^+$).

STEP 8. 2-[2-chloro-4-(2-ethyl-5,7-dimethyl-3H-imidazo[4,5-b]pyridin-3-yl)phenylethanol To a solution of methyl 2-[2-chloro-4-(2-ethyl-5,7-dimethyl-3H-imidazo[4,5-b]pyridin-3-yl)phenylethyl acetate (step 7, 1.13 g, 3.15 mmol) was added carefully LAH and stirred for 1 h at room temperature. The reaction was quenched with water and the mixture was diluted with ethyl acetate (50 ml). To this mixture was added saturated potassium sodium tartarate aqueous solution (50 ml) and stirred for 2.5 h. The organic layer was separated and aqueous layer was extracted with ethyl acetate (2×20 ml). The combined organic layer was washed with brine, dried (Mg2SO4) and concentrated to give 1.0 g of title compound as white solid.

$^1$H-NMR (CDCl$_3$) δ: 7.41–7.53 (2H, m), 7.25–7.29 (1H, m), 6.92 (1H, s), 3.96 (2H, m), 3.11(3H, t, J=7.4 Hz), 2.82 (2H, m), 2.65 (3H, s), 2.53 (3H, s), 1.30 (3H, t, J=7.4 Hz).

MS (EI) m/z: 329 (M$^+$).

STEP 9. 3-[3-chloro-4-(2-chloroethyl)phenyl-2-ethyl-5,7-dimethyl-3H-imidazo[4,5-b]pyridine The title compound was prepared according to the procedure described in step 7 of Example 1 from methyl 2-[2-chloro-4-(2-ethyl-5,7-dimethyl-3H-imidazo[4,5-b]pyridin-3-yl)phenylethanol (step 8)

$^1$H-NMR (CDCl$_3$) δ: 7.45–7.52 (2H, m), 7.23–7.31 (1H, m), 6.92 (1H, s), 3.82 (2H, t, J=7.3 Hz), 3.29 (2H, t, J=7.3 Hz), 2.83 (2H, q, J=7.6 Hz), 2.65 (3H, s), 2.53 (3H, s), 1.30 (3H, t, J=7.6 Hz).

STEP 10. 3-[4-(2-azidoethyl)-3-chlorophenyl-2-ethyl-5,7-dimethyl-3H-imidazo[4,5-b]pyridine The title compound was prepared according to the procedure described in step 8 of Example 1 from 3-[3-chloro-4-(2-chloroethyl)phenyl-2-ethyl-5,7-dimethyl-3H-imidazo[4,5-b]pyridine (step 9)

$^1$H-NMR (CDCl$_3$) δ: 7.45–7.48 (2H, m), 7.29 (1H, dd, J=2.1, 7.9 Hz), 6.92 (1H, s), 3.62 (1H, t, J=7.1 Hz), 3.12 (1H, t, J=7.3 Hz), 2.83 (2H, q, J=7.4 Hz), 2.65 (3H, s), 2.53 (3H, s), 1.30 (3H, t, J=7.4 Hz).

STEP 11. 2-{2-chloro-4-(-2-ethyl-5,7-dimethyl-3H-imidazo[4,5-b]pyridin-3-yl)phenyl]ethanamine To a solution of methyl 3-[4-(2-azidoethyl)-3-chlorophenyl-2-ethyl-5,7-dimethyl-3H-imidazo[4,5-b]pyridine (step 10, 430 mg, 1.2 mmol) in ethanol/water (4/1) were added Fe (335 mg, 6.0 mmol) and NH$_4$Cl (409 mg, 7.8 mmol). The mixture was stirred for 1 h under reflux temperature. The solvent was removed and the residue was diluted with CH$_2$Cl$_2$.The mixture was washed with brine, dried (MgSO$_4$) and concentrated to give 390 mg of title compound as orange oil.

¹H-NMR (CDCl₃) δ: 7.44 (2H, d, J=7.4 Hz), 7.25 (1H, m), 6.92 (1H, s), 2.92–3.15 (6H, m), 2.83 (2H, q, J=7.4 Hz), 2.65 (3H, s), 2.53 (3H, s), 1.30 (3H, t, J=7.4 Hz).

STEP 12. 2-[2-chloro-4-(-2-ethyl-5,7-dimethyl-3H-imidazo[4,5-b]pyridin-3-yl)phenyl]ethanamine The title compound was prepared according to the procedure described in step 10 of Example 1 from 2-[2-chloro-4-(-2-ethyl-5,7-dimethyl-3H-imidazo[4,5-b]pyridin-3-yl)phenyl]ethanamine (Step 11)

¹H-NMR (CDCl₃) δ: 7.83 (2H, d, J=8.4 Hz), 7.28–7.36 (4H, m), 7.14 (1H, d, J=7.7 Hz), 6.92 (1H, s), 6.28 (1H, br.s), 3.58 (2H, dt, J=6.3 Hz), 3.02 (2H, t, J=6.4 Hz), 2.74 (2H, q, J=7.6 Hz), 2.66 (3H, s), 2.45 (3H, s), 2.41 (3H, s), 1.25 (3H, t, J=7.6 Hz).

MS (ESI) m/z: 526 (M⁺).

EXAMPLE 267

3-(2-CHLORO-4-{2-[({[(4-METHYLPHENYL)SULFONYL]AMINO}CARBONYL)AMINO]ETHYL}PHENYL)-2-ETHYL-5,7-DIMETHYL-3H-IMIDAZO[4,5-b]PYRIDINE

STEP 1. 2-{3-chloro-4-[(4,6-dimethyl-3-nitro-2-pyridinyl)amino]phenyl}ethanol

The title compound was prepared according to the procedure described in step 3 of Example 1 from 4,6-Dimethyl-3-nitro-2-pyridine (0.66 g, 3.8 mmol, step 2 of Example 1) and 4-amino-2-chloro-phenylethanol (0.72 g, 3.8 mmol, *Eur. J. Med. Chem.*, 1996, 3, 133.).

¹H-NMR (CDCl₃) δ: 9.85 (1H, s), 8.37 (1H, d, J=8.4 Hz), 7.31 (1H, d, J=2.0 Hz), 7.14 (1H, dd, J=2.0, 8.3 Hz), 6.60 (1H, s), 3.87 (2H, dt, J=6.2, 6.4 Hz), 2.84 (2H, t, J=6.4 Hz), 2.56 (3H, s), 2.46 (3H, s), 1.40 (1H, t, J=6.2 Hz).

MS (EI) m/z: 321 (M⁺).

STEP 2. methyl 3-chloro-{4-[(3-amino-4,6-dimethyl-2-pyridinyl)amino]phenyl}ethanol The title compound was prepared according to the procedure described in step 2 of Example 28 from 2-{3-chloro-4-[(4,6-dimethyl-3-nitro-2-pyridinyl)amino]phenyl}ethanol (step 1).

¹H-NMR (CDCl₃) δ: 7.26 (1H, d, J=2.2 Hz), 7.20 (1H, d, J=8.3 Hz), 7.00 (1H, dd, J=2.2, 8.3 Hz), 6.64 (1H, s), 6.37 (1H, br.s), 3.70 (3H, s), 3.27 (1H, br.s), 2.68 (3H, s), 2.38 (3H, s), 2.20 (3H, s).

STEP 3. 2-[2-chloro-4-(2-ethyl-5,7-dimethyl-3H-imidazo[4,5-b]pyridin-3-yl)phenylethyl propionate The title compound was prepared according to the procedure described in step 5 of Example 1 from 3-chloro-{4-[(3-amino-4,6-dimethyl-2-pyridinyl)amino]phenyl}ethyl propionate (step 2).

¹H-NMR (CDCl₃) δ: 7.50 (1H, d, 8.3 Hz), 7.47 (1H, d, J=2.2 Hz), 7.31 (1H, dd, J=2.2, 8.3 Hz), 6.92 (1H, s), 3.87 (2H, s), 3.77 (3H, s), 2.85 (2H, q, J=7.5 Hz), 2.65 (3H, s), 1.31 (3H, t, J=7.5 Hz).

MS (EI) m/z: 357 (M⁺).

STEP 4. 2-[3-chloro-4-(2-ethyl-5,7-dimethyl-3H-imidazo[4,5-b]pyridin-3-yl)phenylethanol The title compound was prepared according to the procedure described in step 6 of Example 1 from methyl 2-[2-chloro-4-(2-ethyl-5,7-dimethyl-3H-imidazo[4,5-b]pyridin-3-yl)phenylethyl propionate (step 3).

¹H-NMR (CDCl₃) δ: 7.51 (1H, s), 7.34 (2H, s), 6.91 (1H, s), 3.96 (2H, dd, J=6.2, 12.0 Hz), 2.96 (2H, t, J=7.4 Hz), 2.70 (2H, m), 2.66 (3H, s), 2.51 (3H, s), 1.67 (1H, br.t, J=6.2 Hz), 1.28 (3H, t, J=7.4 Hz).

MS (ESI) m/z: 329 (M⁺).

STEP 5. 3-{2-chloro-4-(2-chloroethyl)phenyl-2-ethyl-5,7-dimethyl-3H-imidazo[4,5-b]pyridine The title compound was prepared according to the procedure described in step 7 of Example 1 from 2-[3-chloro-4-(2-ethyl-5,7-dimethyl-3H-imidazo[4,5-b]pyridin-3-yl)phenylethanol (step 4).

¹H-NMR (CDCl₃) δ: 7.49 (1H, d, J=1.3 Hz), 7.34–7.49 (2H, m), 6.91 (1H, s), 3.80 (2H, t, J=7.2 Hz), 3.17 (2H, t, J=7.0 Hz), 2.60–2.85 (2H, m), 2.66 (3H, s), 2.51 (3H, s), 1.28 (3H, t, J=7.5 Hz).

MS (EI) m/z: 347 [(M−H)⁻].

STEP 6. 3-[4-(2-azidoethyl)-3-chlorophenyl-2-ethyl-5,7-dimethyl-3H-imidazo[4,5-b]pyridine The title compound was prepared according to the procedure described in step 8 of Example 1 from 3-[2-chloro-4-(2-chloroethyl)phenyl-2-ethyl-5,7-dimethyl-3H-imidazo[4,5-b]pyridine (step 5).

¹H-NMR (CDCl₃) δ: 7.49 (1H, m, J=1.8 Hz), 7.31–7.38 (2H, m), 6.91 (1H, s), 3.62 (2H, t, J=7.0 Hz), 2.98 (2H, t, J=7.3 Hz), 2.60–2.80 (2H, m), 2.66 (3H, s), 2.51 (3H, s), 1.27 (3H, t, J=7.5 Hz).

MS (EI) m/z: 354 (M⁺).

STEP 7. 2-[3-chloro-4-(-2-ethyl-5,7-dimethyl-3H-imidazo[4,5-b]pyridin-3-yl)phenyl]ethanamine To a stirred solution of 3-[4-(2-azidoethyl)-3-chlorophenyl-2-ethyl-5,7-dimethyl-3H-imidazo[4,5-b]pyridine (step 6, 149 mg, 0.4 mmol) in THF (4 ml) was added triphenylphosphine (116 mg, 0.4 mmol) at room temperature. After completion of the addition, the stirring was continued for an additional 2.5 h at the same temperature and 3.5 h under reflux temperature. To the resulting mixture was added H₂O (1.0 ml) at room temperature, and the solvent was removed. The mixture was dissolved in CH₂Cl₂ (100 ml), washed with brine. The Organic layer was dried (MgSO₄), and concentrated to give a yellow oil.

MS (EI) m/z: 328 (M⁺).

STEP 8. 2-[3-chloro-4-(-2-ethyl-5,7-dimethyl-3H-imidazo[4,5-b]pyridin-3-yl)phenyl]ethanamine The title compound was prepared according to the procedure described in step 10 of Example 1 from 2-[3-chloro-4-(-2-ethyl-5,7-dimethyl-3H-imidazo[4,5-b]pyridin-3-yl)phenyl]ethanamine (step 7).

¹H-NMR (CDCl₃) δ: 7.88 (1H, s), 7.85 (1H, s), 7.19–7.34 (5H, m), 6.92 (1H, s), 6.94 (1H, s), 6.13 (1H, br.s), 3.54 (2H, m), 2.78 (2H, t, J=6.4 Hz), 2.67 (3H, s), 2.63 (3H, m), 2.42 (3H, s), 2.40 (3H, s), 1.25 (3H, t, J=7.5 Hz).

MS (EI) m/z: 526 (M⁺).

EXAMPLE 268

2-ETHYL-3-(3-METHOXY-4-{2-[({[(4-METHYLPHENYL)SULFONYL]AMINO}CARBONYL)AMINO]ETHYL}PHENYL)-5,7-DIMETHYL-3H-IMIDAZO[4,5-b]PYRIDINE

STEP 1. diethyl 2-(2-methoxy-4-nitrophenyl)malonate

The title compound was prepared according to the procedure described in step 1 of Example 266 from 4-bromo-3-methoxynitrobenzene.

¹H-NMR (CDCl₃) δ: 7.78 (1H, dd, J=2.2, 8.4 Hz), 7.75 (1H, d, J=2.2 Hz), 7.54 (1H, d, J=8.4 Hz), 5.15 (1H, s), 4.25 (2H, q, J=7.2 Hz), 4.25 (2H, q, J=7.2 Hz), 3.94 (3H, s), 1.28 (6H, t, J=7.2 Hz).

STEP 2. 2-(2-methoxy-4-nitrophenyl)acetic acid

The title compound was prepared according to the procedure described in step 2 of Example 266 from diethyl 2-(2-methoxy-4-nitrophenyl)malonate (step 1).

¹H-NMR (CDCl₃) δ:12.4 (1H, br.s), 7.82 (1H, dd, J=2.2, 8.4 Hz), 7.75 (1H, dd, J=2.2 Hz), 7.50 (1H, d, J=8.4 Hz), 3.90 (3H, s), 3.66 (2H, s).

STEP 3. methyl 2-(2-methoxy-4-nitrophenyl)acetate

To a solution of 2-(2-methoxy-4-nitrophenyl)acetic acid (step 2, 1.2 g, 5.5 mmol) in methanol/dichloromethane (11 ml, 1/1) was added trimethylsillyldiazomethane (2 M, 5.6 ml, 11.8 mmol) and stirred for 10 min at room temperature. The mixture was quenched with saturated citric acid aqueous solution and the extracted with ethyl acetate (3×20 ml). The organic layer was washed with brine, dried (MgSO₄) and concentrated to give 1.2 g of title compound as orange solid.

¹H-NMR (CDCl₃) δ: 7.83 (1H, dd, J=2.2, 8.3 Hz), 7.73 (1H, dd, J=2.2 Hz), 7.34 (1H, d, J=8.1 Hz), 3.93 (3H, s), 3.71 (2H, s), 3.71 (3H, s).

STEP 4. methyl 2-(4-amino-2-methoxyphenyl)acetate

To a solution of methyl 2-(2-methoxy-4-nitrophenyl)acetate (step 3, 1.2 g, 5.5 mmol) in methanol (10 ml) was added 10% Pd/C (130 mg, 0.12 mmol) and stirred under hydrogen atmosphere for 3 h at room temperature. The catalyst was filtered off through a pad of celite and well washed with ethanol and ethyl acetate. The filtrate was concentrated to give 1.1 g of title compound as pink oil.

¹H-NMR (CDCl₃) δ: 6.94 (1H, d, J=7.7 Hz), 6.26 (1H, d, J=2.0 Hz), 6.23 (1H, s), 3.70 (3H, s), 3.76 (3H, s), 3.67 (3H, s), 3.52 (2H, s).

STEP 5. methyl {4-[(4,6-dimethyl-3-nitro-2-pyridinyl)amino]-2-methoxyphenyl}acetate The title compound was prepared according to the procedure described in step 3 of Example 1 from methyl 2-(4-amino-2-methoxyphenyl)acetate (step 4).

¹H-NMR (CDCl₃) δ: 9.60 (1H, s), 7.47 (1H, d, J=1.7 Hz), 7.06–7.15 (2H, m), 6.55 (1H, s), 3.84 (3H, s), 3.69 (3H, s), 3.62 (2H, s), 2.56 (3H, s), 2.44 (3H, s).

MS (EI) m/z: 345 (M⁺).

STEP 6. methyl {4-[(3-amino-4,6-dimethyl-2-pyridinyl)amino]-2-methoxyphenyl}acetate The title compound was prepared according to the procedure described in step 2 of Example 28 from methyl {4-[(4,6-dimethyl-3-nitro-2-pyridinyl)amino]-2-methoxyphenyl}acetate (step 5).

¹H-NMR (CDCl₃) δ: 7.03 (1H, d, J=5.1 Hz), 7.02 (1H, s), 6.60 (1H, s), 6.57 (1H, dd, J=2.2, 8.3 Hz), 3.79 (3H, s), 3.68 (3H, s), 3.56 (2H, s), 3.25–3.35(br.s, 2H), 2.38 (3H, s), 2.20 (3H, s).

MS (EI) m/z: 315 (M⁺).

STEP 7. methyl 2-[4-(2-ethyl-5,7-dimethyl-3H-imidazo[4,5-b]pyridin-3-yl)-2-methoxyphenylethyl acetate The title compound was prepared according to the procedure described in step 5 of Example 1 from methyl {4-[(3-amino-4,6-dimethyl-2-pyridinyl)amino]-2-methoxyphenyl}acetate (step 6).

¹H-NMR (CDCl₃) δ: 7.36 (1H, d, J=7.9 Hz), 6.89–6.99 (3H, m), 3.84 (2H, s), 3.74 (3H, s), 3.71 (2H, s), 2.85 (2H, q, J=7.5 Hz), 2.66 (3H, s), 2.53 (3H, s), 1.30 (3H, t, J=7.5 Hz).

MS (EI) m/z: 353 (M⁺).

STEP 8. 2-[4-(2-ethyl-5,7-dimethyl-3H-imidazo[4,5-b]pyridin-3-yl)-2-methoxyphenylethanol The title compound was prepared according to the procedure described in step 8 of Example 266 from methyl 2-[4-(2-ethyl-5,7-dimethyl-3H-imidazo[4,5-b]pyridin-3-yl)-2-methoxyphenylethyl acetate (step 7).

¹H-NMR (CDCl₃) δ: 7.33 (1H, d, J=7.7 Hz), 6.87–6.95 (3H, m), 3.90 (2H, dt, J=6.0, 6.2 Hz), 3.84 (3H, s), 2.98(2H, t, J=6.4 Hz), 2.84(2H, q, J=7.5 Hz), 2.66 (3H, s), 1.76 (1H, br.t), 1.30 (3H, t, J=7.5 Hz).

MS (EI) m/z: 324 [(M–H)⁻].

STEP 9. 3-[4-(2-chloroethyl)-3-methoxyphenyl-2-ethyl-5,7-dimethyl-3H-imidazo[4,5-b]pyridine The title compound was prepared according to the procedure described in step 7 of Example 1 from 2-[4-(2-ethyl-5,7-dimethyl-3H-imidazo[4,5-b]pyridin-3-yl)-2-methoxyphenylethanol (step 8).

¹H-NMR (CDCl₃) δ: 7.33 (1H, d, J=7.7 Hz), 6.87–6.94 (3H, m), 3.84 (3H, s), 3.77 (3H, t, J=7.6 Hz), 3.16 (2H, t, J=7.3 Hz), 2.84 (2H, q, J=7.6 Hz), 2.66 (3H, s), 2.53 (3H, s), 1.30 (3H, t, J=7.6 Hz).

STEP 10. 3-[4-(2-azidoethyl)-3-methoxyphenyl-2-ethyl-5,7-dimethyl-3H-imidazo[4,5-b]pyridine The title compound was prepared according to the procedure described in step 8 of Example 1 from 3-[4-(2-chloroethyl)-3-methoxyphenyl-2-ethyl-5,7-dimethyl-3H-imidazo[4,5-b]pyridine (step 9).

¹H-NMR (CDCl₃) δ: 7.45–7.48 (2H, m), 7.29 (1H, dd, J=2.1, 7.9 Hz), 6.92 (1H, s), 3.62 ((1H, t, J=7.1 Hz), 3.12 (1H, t, J=7.3 Hz), 2.83 (2H, q, J=7.4 Hz), 2.65 (3H, s), 2.53 (3H, s), 1.30 (3H, t, J=7.4 Hz).

STEP 11. 2-[4-(-2-ethyl-5,7-dimethyl-3H-imidazo[4,5-b]pyridin-3-yl-2-methoxyl)phenyl]ethanamine The title compound was prepared according to the procedure described in step 9 of Example 1 from 3-[4-(2-azidoethyl)-3-methoxyphenyl-2-ethyl-5,7-dimethyl-3H-imidazo[4,5-b]pyridine (step 10).

¹H-NMR (CDCl₃) δ: 7.30 (1H, d, J=7.7 Hz), 6.92 (1H, dd, J=2.0, 7.9 Hz), 6.91 (1H, br.s), 6.86 (1H, d, J=2.0 Hz), 3.83 (3H, s), 2.65 (3H, s), 2.99 (2H, br.t, J=4.5 Hz), 2.85 (2H, q, J=8.3 Hz), 2.84 (2H, q, J=7.7 Hz), 2.66 (3H, s), 2.53 (3H, s), 1.29 (3H, t, J=7.7 Hz).

STEP 12. 2-ethyl-(3-methoxy-4-{2-[({[(4-methylphenyl)sulfonyl]amino}carbonyl)amino]ethyl}phenyl)-5,7-dimethyl-3H-imidazo[4,5-b]pyridine The title compound was prepared according to the procedure described in step 10 of Example 1 from 2-[4-(-2-ethyl-5,7-dimethyl-3H-imidazo[4,5-b]pyridin-3-yl-2-methoxyl)phenyl]ethanamine (step 11).

¹H-NMR (CDCl₃) δ: 7.86 (2H, d, J=8.3 Hz), 7.30 (4H, m), 7.14 (1H, d, J=8.1 Hz), 7.01 (1H, d, J=7.9 Hz), 6.92 (1H, s), 6.79 (1H, d, J=2.0 Hz), 6.63 (1H, dd, J=1.8, 7.7 Hz), 6.04 (1H, br.t, J=5.1 Hz), 3.74 (3H, s), 3.51 (2H, dt, J=6.0 Hz), 2.85 (2H, t, J=6.2 Hz), 2.70 (2H, q, J=7.5 Hz), 2.66 (3H, s), 2.44 (3H, s), 2.41 (3H, s), 1.23 (3H, t, J=7.5 Hz).

MS (ESI) m/z: 522 [(M+H)⁺], 520 [(M–H)⁻].

EXAMPLE 269

2-ETHYL-3-(3-METHYL-4-{2-[([[(4-METHYLPHENYL)SULFONYL]AMINO}CARBONYL)AMINO]ETHYL}PHENYL)-5,7-DIMETHYL-3H-IMIDAZO[4,5-b]PYRIDINE

STEP 1. diethyl 2-(2-methyl-4-nitrophenyl)malonate

The title compound was prepared according to the procedure described in step 1 of Example 268 from 4-bromo-3-methylnitrobenzene.

$^1$H-NMR (CDCl$_3$) δ: 8.10 (1H, s), 8.05–8.10 (1H, m), 7.62 (1H, d, J=9.2 Hz), 4.93 (1H, s), 4.26 (2H, q, J=7.3 Hz), 4.25 (2H, q, J=7.3 Hz), 2.46 (3H, s), 1.28 (6H, t, J=7.3 Hz).

STEP 2. 2-(2-methyl-4-nitrophenyl)acetic acid

The title compound was prepared according to the procedure described in step 2 of Example 266 from diethyl 2-(2-methyl-4-nitrophenyl)malonate (step 1)

$^1$H-NMR (CDCl$_3$) δ: 8.08 (1H, br.s), 8.02 (1H, dd, J=8.6 Hz), 7.49 (1H, d, J=8.4 Hz), 3.77 (2H, s), 2.35 (3H, s).

STEP 3. methyl 2-(2-methyl-4-nitrophenyl)acetate

The title compound was prepared according to the procedure described in step 3 of Example 266 from 2-(2-methyl-4-nitrophenyl)acetic acid (step 2).

$^1$H-NMR (CDCl$_3$) δ: 8.07 (1H, d, J=2.1 Hz), 8.02 (1H, dd, J=2.3, 5.9 Hz), 7.36 (1H, d, J=8.4 Hz), 3.74 (2H, s), 3.71 (3H, s), 2.42 (3H, s).

STEP 4. methyl 2-(4-amino-2-methylphenyl)acetate

The title compound was prepared according to the procedure described in step 4 of Example 268 from methyl 2-(2-methyl-4-nitrophenyl)acetate (step 3)

$^1$H-NMR (CDCl$_3$) δ: 6.97 (1H, d, J=7.9 Hz), 6.48–6.52 (2H, m), 3.67 (3H, s), 3.57 (2H, br.s), 3.53 (3H, s), 2.22 (3H, s).

STEP 5. methyl {4-[(4,6-dimethyl-3-nitro-2-pyridinyl)amino]-2-methylphenyl}acetate The title compound was prepared according to the procedure described in step 3 of Example 1 from methyl 2-(4-amino-2-methylphenyl)acetate (step 4).

$^1$H-NMR (CDCl$_3$) δ: 7.54 (1H, br.d, J=8.3 Hz), 7.38 (1H, br.s), 7.17 (1H, d, J=8.39 Hz), 6.52 (1H, s), 3.69 (3H, s), 3.63 (2H, s), 2.55 (3H, s), 2.43 (3H, s), 2.32 (3H, s).

MS (EI) m/z: 345 (M$^+$).

STEP 6. methyl {4-[(3-amino-4,6-dimethyl-2-pyridinyl)amino]-2-methylphenyl}acetate The title compound was prepared according to the procedure described in step 2 of Example 28 from methyl {4-[(4,6-dimethyl-3-nitro-2-pyridinyl)amino]-2-methylphenyl}acetate (step 5).

$^1$H-NMR (CDCl$_3$) δ: 7.07 (1H, d, J=9.0 Hz), 6.91–6.93 (2H, m), 6.62 (1H, s), 6.36 (1H, br.s), 3.79 (3H, s), 3.67 (3H, s), 3.57 (2H, s), 3.30 (br.s, 2H), 2.37 (3H, s), 2.26 (3H, s), 2.2 (3H, s).

STEP 7. methyl 2-[4-(2-ethyl-5,7-dimethyl-3H-imidazo[4,5-b]pyridin-3-yl)-2-methylphenyl acetate The title compound was prepared according to the procedure described in step 5 of Example 1 from methyl {4-[(3-amino-4,6-dimethyl-2-pyridinyl)amino]-2-methylphenyl}acetate (step 6).

$^1$H-NMR (CDCl$_3$) δ: 7.39 (1H, d, J=7.6 Hz), 7.17–7.25 (2H, m), 6.90 (1H, s), 3.74 (3H, s), 3.72 (2H, s), 2.82 (2H, q, J=7.4 Hz), 2.65 (3H, s), 2.52 (3H, s), 2.40 (3H, s), 1.28 (3H, t, J=7.6 Hz).

MS (EI) m/z: 337 (M$^+$).

STEP 8. 2-[4-(2-ethyl-5,7-dimethyl-3H-imidazo[4,5-b]pyridin-3-yl)-2-methylphenylethanol The title compound was prepared according to the procedure described in step 8 of Example 266 from methyl 2-[4-(2-ethyl-5,7-dimethyl-3H-imidazo[4,5-b]pyridin-3-yl)-2-methylphenylethyl acetate (step 7).

$^1$H-NMR (CDCl$_3$) δ: 7.35 (1H, d, J=7.9 Hz), 7.17 (1H, s), 7.16 (1H, d, J=7.9 Hz), 6.90 (1H, s), 3.84 (2H, dt, J=6.8 Hz), 2.96 (2H, t, J=7.0 Hz), 2.81 (2H, q, J=7.5 Hz), 2.66 (3H, s), 2.52 (3H, s), 2.40 (s, 3H), 1.91 (1H, br.t), 1.28 (3H, t, J=7.5 Hz).

MS (EI) m/z: 324 [(M–H)$^-$].

STEP 9. 3-[4-(2-chloroethyl)-3-methylphenyl-2-ethyl-5,7-dimethyl-3H-imidazo[4,5-b]pyridine The title compound was prepared according to the procedure described in step 7 of Example 1 from 2-[4-(2-ethyl-5,7-dimethyl-3H-imidazo[4,5-b]pyridin-3-yl)-2-methylphenylethanol (step 8).

$^1$H-NMR (CDCl$_3$) δ: 7.35 (1H, d, J=8.4 Hz), 7.17–7.19 (2H, m), 6.90 (1H, s), 3.75 (2H, t, J=7.6 Hz), 3.17 (2H, t, J=7.6 Hz), 2.81 (2H, q, J=7.5 Hz), 2.65 (3H, s), 2.41 (3H, s), 2.36 (3H, s), 1.28 (3H, t, J=7.5 Hz).

STEP 10. 3-[4-(2-azidoethyl)-3-methylphenyl-2-ethyl-5,7-dimethyl-3H-imidazo[4,5-b]pyridine The title compound was prepared according to the procedure described in step 8 of Example 1 from 3-[4-(2-chloroethyl)-3-methylphenyl-2-ethyl-5,7-dimethyl-3H-imidazo[4,5-b]-pyridine (step 9).

$^1$H-NMR (CDCl$_3$) δ: 7.34 (1H, d, J=8.7 Hz), 7.19–7.26 (2H, m), 6.90 (1H, s), 3.62 (1H, t, J=7.1 Hz), 3.56 (2H, t, J=7.6 Hz), 2.99 (2H, t, J=7.6 Hz), 2.81 (2H, q, J=7.6 Hz), 2.65 (3H, s), 2.52 (3H, s), 2.41 (3H, s), 1.27 (3H, t, J=7.6 Hz).

STEP 11. 2-[4-(-2-ethyl-5,7-dimethyl-3H-imidazo[4,5-b]pyridin-3-yl-2-methyl)phenyl]ethanamine The title compound was prepared according to the procedure described in step 9 of Example 1 from 3-[4-(2-azidoethyl)-3-methylphenyl-2-ethyl-5,7-dimethyl-3H-imidazo[4,5-b]pyridine (step 10).

$^1$H-NMR (CDCl$_3$) δ: 7.32 (1H, d, J=7.7 Hz), 7.14–7.16 (2H, m), 6.91 (1H, br.s), 6.90 (1H, s), 3.02 (2H, br.t, J=7.3 Hz), 2.77–2.87 (4H, m), 2.65 (3H, s), 2.53 (3H, s), 2.40 (3H, s), 1.28 (3H, t, J=7.5 Hz).

STEP 12. 2-ethyl-(3-methyl-4-{2-[({[(4-methylphenyl)sulfonyl]amino}carbonyl)amino]ethyl}phenyl)-5,7-dimethyl-3H-imidazo[4,5-b]pyridine The title compound was prepared according to the procedure described in step 10 of Example 1 from 2-[4-(-2-ethyl-5,7-dimethyl-3H-imidazo[4,5-b]pyridin-3-yl-2-methyl)phenyl]ethanamine (step 11).

$^1$H-NMR (CDCl$_3$) δ: 7.86 (1H, d, J=8.0 Hz), 7.31 (1H, d, J=8.0 Hz), 7.03 (1H, d, J=7.9 Hz), 6.91 (1H, s), 6.85 (1H, d, J=8.4 Hz), 6.07–6.11 (1H, m), 3.51 (2H, q, J=6.4 Hz), 2.85 (2H, t, J=6.4 Hz), 261–2.69 (2H, m), 2.69 (3H, s), 2.44 (3H, s), 2.28 (3H, s), 1.23 (3H, t, J=7.5 Hz).

MS (ESI) m/z: 506 [(M+H)$^+$], 504 [(M–H)$^-$].

EXAMPLE 270

6-CHLORO-2-ETHYL-1-(6-{2-[({[(4-METHYLPHENYL)SULFONYL]AMINO}CARBONYL)AMINO]ETHYL}-3-PYRIDINYL)-5-(TRIFLUOROMETYL)-1H-BENZIMIDAZOLE

STEP 1. (4-amino-2-pyridinyl)acetonitrile

The title compound was prepared according to the procedure described in step 2 of Example 28 from (4-nitro-2-pyridinyl)acetonitrile (8.6 g, 52.9 mmol, Katz; R. B.; Voyle, M., Synthesis., 1989, 4, 314.).

$^1$H-NMR (CDCl$_3$) δ: 8.04 (1H, d, J=2.8 Hz), 7.17 (1H, d, J=8.2 Hz), 6.99 (1H, dd, J=2.8, 8.4 Hz), 3.81 (2H, s), 3.76 (2H, br.s).

STEP 2. {5-[5-chloro-2-nitro-4-(trifluoromehyl)anilino]-2-pyridinyl}acetonitrile The title compound was prepared according to the procedure described in step 3 of Example 1 from (5-aminopyridine-2-yl)acetonitrile (step 1).

$^1$H-NMR (CDCl$_3$) δ: 9.66 (1H, s), 8.60 (2H, m), 7.71 (1H, dd, J=2.6, 8.4 Hz), 7.60 (1H, d, J=8.3 Hz), 7.13 (1H, s), 4.03 (2H, s)

MS (EI) m/z: 356 (M$^+$).

STEP 3. {5-[2-amino-5-chloro-4-(trifluoromehyl)anilino]-2-pyridinyl}acetonitrile The title compound was prepared according to the procedure described in step 2 of Example 28 from {5-[5-chloro-2-nitro-4-(trifluoromehyl)anilino]-2-pyridinyl}acetonitrile (step 2).

$^1$H-NMR (CDCl$_3$) δ: 8.25 (1H, d, J=2.1 Hz), 7.12–7.34 (3H, m), 5.47 (1H, br.s), 3.89 (2H, s), 3.78 (2H, br.s).

STEP 4. {5-[6-chloro-2-ethyl-5-(trifluoromethyl)-1H-benzimidazol-1-yl]-2-pyridinyl}acetonitrile The title compound was prepared according to the procedure described in step 5 of Example 1 from {5-[2-amino-5-chloro-4-(trifluoromehyl)anilino]-2-pyridinyl}acetonitrile (step 3).

$^1$H-NMR (CDCl$_3$) δ: 8.66 (1H, s), 8.15 (1H, s), 7.73–7.83 (2H, m), 7.12(1H, s), 4.12(2H, s), 2.79 (2H, q, J=7.6 Hz), 1.40 (3H, t, J=7.6 Hz).

STEP 5. 2-{5-[6-chloro-2-ethyl-5-(trifluoromehyl)-1H-benzimidazol-1-yl-2-pyridinyl}ethanamine To a solution of {5-[6-chloro-2-ethyl-5-(trifluoromehyl)-1H-benzimidazol-1-yl]-2-pyridinyl}acetonitrile (step 4, 1.0 g, 2.8 mmol), in ammonia-ethanol (30 ml) was added Raney-Ni and stirred for 8 h under hydrogen atmosphere (3.0 kgf/cm$^2$). The catalyst was filtered off and the solvent was removed. The residue was diluted with ethyl acetate, washed with brine, dried (MgSO$_4$) and concentrated to give 813 mg of title compound as black solid.

MS (EI) m/z: 368 (M$^+$).

STEP 6. 6-chloro-2-ethyl-1-(6-{2-[({[(4-methylphenyl)sulfonyl]amino}carbonyl)amino]ethyl}-3-pyridinyl)-5-(trifluoromehyl)-1H-benzimidazol The title compound was prepared according to the procedure described in step 10 of Example 1 from 2-{5-[6-chloro-2-ethyl-5-(trifluoromehyl)-1H-benzimidazol-1-yl]-2-pyridinyl}ethanamine (step 5).

$^1$H-NMR (CDCl$_3$) δ: 8.63 (1H, d, J=2.2 Hz), 8.14 (1H, s), 7.77 (2H, d, J=8.3 Hz), 7.66 (1H, dd, J=2.6, 8.3 Hz), 7.45 (1H, d, J=8.3 Hz), 7.30 (2H, d, J=8.4 Hz), 7.21(1H, s), 3.73–3.80 (2H, m), 3.17 (2H, t, J=6.2 Hz), 2.79 (2H, q, J=7.5 Hz), 2.42 (3H, s), 1.38 (3H, t, J=7.5 Hz).

MS (ESI) m/z: 566 [(M+H)$^+$], 564 [(M–H)$^-$].

EXAMPLE 271

6-CHLORO-2-ETHYL-1-(6-{2-[({[(4-METHYLPHENYL)SULFONYL]AMINO}CARBONYL)AMINO]ETHYL}-3-PYRIDINYL)-5-(TRIFLUOROMETYL)-1H-BENZIMIDAZOLE SODIUMSALT

The title compound was prepared according to the procedure described in Example 2 from 6-chloro-2-ethyl-1-(6-{2-[({[(4-methylphenyl)sulfonyl]amino}carbonyl)amino]ethyl}-3-pyridinyl)-5-(trifluoromehyl)-1H-benzimidazol (Example 270).

$^1$H-NMR (DMSO-d$_6$) δ: 8.71 (1H, br.s), 8.20 (1H, br.s) 7.95 (1H, m), 7.43–7.64 (4H, m), 7.12 (2H, br.s), 6.09 (1H, br.s), 3.39 (2H, br.s), 2.92 (2H, br.s), 2.73 (2H, br.s), 2.28 (3H, br.s), 1.27 (3H, br.s).

MS (ESI) m/z: 566 [(M+H)$^+$], 564 [(M–H)$^-$].

EXAMPLE 272

2-{5-[6-CHLORO-2-ETHYL-5-(TRIFLUOROMETYL)-1H-BENZIMIDAZOL-1-YL]-2-PYRIDINYL}ETHYL(4-METHYLPHENYL)SULFONYLCARBAMATE

STEP 1. 1ethyl(5-amino-2-pyridinyl)acetate

To a solution of (5-amino-2-pyridinyl)acetic acid (1.46 g, 9.6 mmol, Daisley; R. W.; Hanbali, J. R., *Synthetic Communications*., 1981, 11(9), 743.) in ethanol was added conc. H$_2$SO$_4$ and stirred for 16.5 h under hydrogen atmosphere at room temperature. The mixture was neutralized with saturated NaHCO$_3$ aqueous solution and the solvent was removed. The mixture was diluted with water and extracted with ethyl acetate (5×20 ml). The organic layer was washed with brine, dried (MgSO$_4$) and concentrated to give 1.2 g of title compound as brown oil.

$^1$H-NMR (CDCl$_3$) δ: 8.04 (1H, d, J=2.8 Hz), 7.07 (1H, d, J=8.2 Hz), 6.96 (1H, dd, J=2.6, 8.2 Hz), 4.71(2H, q, J=7.1 Hz), 3.72 (2H, s), 3.66 (2H, br.s), 1.25 (3H, t, J=7.1 Hz).

STEP 2. ethyl {5-[5-chloro-2-nitro-4-(trifluoromehyl)anilino]-2-pyridinyl}acetate The title compound was prepared according to the procedure described in step 3 of Example 1 from ethyl(5-amino-2-pyridinyl)acetate (step 1).

$^1$H-NMR (CDCl$_3$) δ: 9.66 (1H, s), 8.60 (2H, m), 7.71 (1H, dd, J=2.6, 8.4 Hz), 7.60 (1H, d, J=8.3 Hz), 7.13 (1H, s), 4.03 (2H, s)

MS (EI) m/z: 356 (M$^+$).

STEP 3. ethyl {5-[2-amino-5-chloro-4-(trifluoromehyl)anilino]-2-pyridinyl}acetate The title compound was prepared according to the procedure described in step 2 of Example 28 from ethyl {5-[5-chloro-2-nitro-4-(trifluoromehyl)anilino]-2-pyridinyl}acetate (step 2).

$^1$H-NMR (CDCl$_3$) δ: 7.25 (1H, d, J=1.5 Hz), 7.21 (1H, m), 7.16 (1H, s), 7.09 (1H, s), 7.47 (1H, d, J=8.2 Hz), 5.47 (1H, s), 4.20 (2H, q, J=7.2 Hz), 3.80 (2H, s), 3.77 (2H, br.s), 1.28 (3H, t, J=7.2 Hz).

STEP 4. ethyl {5-[6-chloro-2-ethyl-5-(trifluoromehyl)-1H-benzimidazol-1-yl]-2-pyridinyl}acetate The title compound was prepared according to the procedure described in step 5 of Example 1 from ethyl {5-[2-amino-5-chloro-4-(trifluoromehyl)anilino]-2-pyridinyl}acetate (step 3).

$^1$H-NMR (CDCl$_3$) δ: 8.61 (1H, d, J=2.0 Hz), 8.14 (1H, s), 7.71 (1H, dd, J=2.0, 8.2 Hz), 7.62 (1H, d, J=8.2 Hz), 7.21 (1H, s), 4.27 (1H, q, J=7.3 Hz), 4.01 (2H, s), 2.79 (2H, q, J=7.6 Hz), 1.38 (3H, t, J=7.4 Hz), 1.33 (3H, t, J=7.1 Hz).

STEP 5. 2-{5-[6-chloro-2-ethyl-5-(trifluoromehyl)-1H-benzimidazol-1-yl]-2-pyridinyl}ethanol The title compound was prepared according to the procedure described in step 8 of Example 266 from ethyl {5-[6-chloro-2-ethyl-5-(trifluoromehyl)-1H-benzimidazol-1-yl]-2-pyridinyl}acetate (step 4).

$^1$H-NMR (CDCl$_3$) δ: 8.57 (1H, d, J=2.50 Hz), 8.13 (1H, s), 7.67 (1H, dd, J=2.6, 8.2 Hz), 7.49 (1H, d, J=8.2 Hz), 7.20 (1H, s), 4.15 (1H, q, J=5.6 Hz), 3.20 (2H, t, J=5.4 Hz), 2.79 (2H, q, J=7.4 Hz), 1.39 (3H, t, J=7.6 Hz).

STEP 6. 2-{5-[6-chloro-2-ethyl-5-(trifluoromehyl)-1H-benzimidazol-1-yl]-2-pyridinyl}ethyl](4-methylphenyl)sulfonylcarbamate The title compound was prepared according to the procedure described in Example 3 from 2-{5-[6-chloro-2-ethyl-5-(trifluoromehyl)-1H-benzimidazol-1-yl]-2-pyridinyl}ethanol (step 5).

$^1$H-NMR (CDCl$_3$) δ: 8.59 (1H, d, J=2.3 Hz), 8.13 (1H, s), 7.88 (2H, d, J=8.4 Hz), 7.65 (1H, dd, J=2.5, 8.2 Hz), 7.44 (1H, d, J=8.1 Hz), 7.32 (2H, d, J=8.1 Hz), 7.20(1H, s), 4.57 (2H, t, J=6.4 Hz), 3.25 (2H, t, J=6.6 Hz), 2.79 (2H, q, J=7.4 Hz), 2.42 (3H, s), 1.38 (3H, t, J=7.4 Hz).

MS (ESI) m/z: 567 [(M+H)$^+$].

EXAMPLE 273

2-{5-[6-CHLORO-2-ETHYL-5-(TRIFLUOROMETYL)-1H-BENZIMIDAZOL-1-YL]-2-PYRIDINYL}ETHYL(4-METHYLPHENYL)SULFONYLCARBAMATE HYDROCHLORIDE

The title compound was prepared according to the procedure described in Example 240 from 2-{5-[6-chloro-2-ethyl-5-(trifluoromehyl)-1H-benzimidazol-1-yl]-2-pyridinyl}ethyl](4-methylphenyl)sulfonylcarbamate (Example 273).

$^1$H-NMR (DMSO-d$_6$) 8:11.9 (1H, br.s), 8.72 (1H, br.s), 8.18 (1H, s), 8.03–8.07 (1H, m), 7.74 (1H, d, J=7.6 Hz), 7.58 (1H, d, J=8.2 Hz), 7.43 (2H, d, J=5.1 Hz), 7.39 (1H, s), 4.45 (2H, t, J=6.2 Hz), 3.17 (2H, t, J=6.2 Hz), 2.76 (2H, q, J=7.6 Hz), 2.35 (3H, s), 1.27 (3H, t, J=7.3 Hz).

MS (ESI) m/z: 567 [(M+H)$^+$], 565 [(M–H)$^-$].

EXAMPLE 274

2-ETHYL-3-(4-{2-[({[4-PYRIDINYLSULFONYL]AMINO}CARBONYL)AMINO]ETHYL}PHENYL)-5,7-DIMETHYL-3H-IMIDAZO[4,5-b]PYRIDINE

The title compound was prepared according to the procedure described in step 2 of Example 18 from phenyl 2-[4-(2-ethyl-5,7-dimethyl-3H-imidazo[4,5-b]pyridin-3-yl)phenyl]ethylcarbamate (step 1 of Example 18) and pyridinyl-4-sulfonamide (Chem, Ji-Wang; Leu, Yu-Ling; et al., J. Med. Chem., 1997, 40, 2276.; Graham, Samuel L.; Shepard, Kenneth L.; et al., J. Med. Chem., 1989, 32, 2548).

m.p.: 227.9–228.7° C.

$^1$H-NMR (CDCl$_3$) δ: 8.63 (2H, d, J=5.9 Hz), 7.65 (2H, d, J=5.9 Hz), 7.36 (4H, s), 6.96 (1H, s), 3.20 (2H, br.s), 2.75(br.s, 2H), 2.70 (2H, q, J=7.6 Hz), 2.53 (2H, s), 2.40 (3H, s), 1.20 (3H, t, J=7.6 Hz).

MS (ESI) m/z: 479 [(M+H)$^+$], 477 [(M–H)$^-$].

EXAMPLE 275

2-ETHYL-3-(4-{2-[({[2-PYRIDINYLSULFONYL]AMINO}CARBONYL)AMINO]ETHYL}PHENYL)-5,7-DIETHYL-3H-IMIDAZO[4,5-b]PYRIDINE

The title compound was prepared according to the procedure described in step 2 of Example 18 from phenyl 2-[4-(2-ethyl-5,7-dimethyl-3H-imidazo[4,5-b]pyridin-3-yl)phenyl]ethylcarbamate (step 1 of Example 18) and pyridinyl-2-sulfonamide (Chem, Ji-Wang; Leu, Yu-Ling; et al., J. Med. Chem., 1997, 40, 2276.; Graham, Samuel L.; Shepard, Kenneth L.; et al., J. Med. Chem., 1989, 32, 2548).

$^1$H-NMR (CDCl$_3$) δ: 8.51 (1H, br.s), 8.08 (1H, br.s), 7.94 (1H, br.s), 7.29 (2H, s), 7.19 (1H, br.s), 6.91 (1H, s), 2.81 (2H, br.s), 2.73 (2H, q, J=7.6 Hz), 2.66 (3H, s), 2.78 (3H, s), 2.49 (m, 2H), 1.26 (3H, t, J=7.3 Hz).

MS (ESI) m/z: 479 [(M+H)$^+$], 477 [(M–H)$^-$].

EXAMPLE 276

2-ETHYL-3-(4-{2-[({[3-PYRIDINYLSULFONYL]AMINO}CARBONYL)AMINO]ETHYL}PHENYL)-5,7-DIMETHYL-3H-IMIDAZO[4,5-b]PYRIDINE

The title compound was prepared according to the procedure described in step 2 of Example 18 from phenyl 2-[4-(2-ethyl-5,7-dimethyl-3H-imidazo[4,5-b]pyridin-3-yl)phenyl]ethylcarbamate (step 1 of Example 18) and pyridinyl-3-sulfonamide (Chem, Ji-Wang; Leu, Yu-Ling; et al., J. Med. Chem., 1997, 40, 2276.; Graham, Samuel L.; Shepard, Kenneth L.; et al., J. Med. Chem., 1989, 32, 2548).

$^1$H-NMR (CDCl$_3$) δ: 9.15 (1H, d, J=1.9 Hz), 8.83 (1H, dd, J=1.9, 5.1 Hz), 8.34 (1H, dd, J=6.5 Hz), 7.50 (1H, dd, J=4.9, 8.1 Hz), 7.12–7.23 (4H, m), 6.93 (1H, s), 5.92 (1H, br.s), 3.51 (2H, q, J=5.9 Hz), 2.86 (2H, m), 2.69 (3H, m), 2.66 (3H, s), 2.43(3H, s), 1.27 (3H, t, J=7.6 Hz).

MS (ESI) m/z: 479 [(M+H)$^+$]

EXAMPLE 277

2-{4-[6-CHLORO-2-ETHYL-5-(TRIFLUOROMETYL)-1H-BENZIMIDAZOL-1-YL]-2-PHENYL}ETHYL-(2-CHLOROPHENYL)SULFONYLCARBAMATE

The title compound was prepared according to the procedure described in step 2 of Example 243 from 2-{4-[6-chloro-2-ethyl-5-(trifluoromethyl)-1H-benzimidazol-1-yl]phenyl}ethyl phenyl carbonate and 2-chlorophenylsulfonamide.

$^1$H-NMR (CDCl$_3$) δ: 8.18 (1H, s), 8.07 (1H, d, J=7.8 Hz), 7.69 (1H, d, J=3.8 Hz), 7.59 (1H, dd, J=4.3, 8.1 Hz), 7.51 (2H, d, J=8.4 Hz), 7.44 (2H, d, J=8.4 Hz), 7.31 (1H, s), 4.29

(2H, t, J=6.2 Hz), 2.94 (2H, t, J=6.5 Hz), 2.76 (2H, q, J=7.6 Hz), 1.26 (3H, t, J=7.3 Hz)

m.p. 202.4–202.8° C.

MS (ESI) m/z: 586 [(M+H)⁺], 584 [(M−H)⁻]

EXAMPLE 278

2-[4-(2-ETHYL-5,7-DIMETHYL-3H-IMIDAZO[4,5-b]PYRIDIN-3-YL)PHENYL]-1,1-DIMETHYLETHYL(4-METHYLPHENYL)SULFONYLCARBAMATE

STEP 1. 2-methyl-1-(4-nitrophenyl)-2-propanol

To a solution of 1,1-dimethyl-2-(4-nitrophenyl)ethyl acetate (52 mmol) in MeOH (50 ml) was added 4N—LiOH (40 ml) and the mixture was stirred at 50° C. for 2 h. After the solvent was removed, this mixture was diluted with water and extracted with EtOAc (4×50 ml). The organic layer was washed with brine, dried (MgSO₄) and concentrated. This crude was purified by SiO₂ column chromatography developing with hexane/ethyl acetate (5/1) to give the title compound as yellow oil (3.3 g, 33%).

¹H-NMR (CDCl₃) δ: 8.17 (2H, d, J=8.9 Hz), 7.40 (2H, d, J=8.6 Hz), 2.88 (2H, s), 1.63 (1H, br.s), 1.25 (6H, s)

STEP 2. 1-(4-aminophenyl)-2-methyl-2-propanol

The title compound was prepared according to the procedure described in step 2 of Example 28 from 2-methyl-1-(4-nitrophenyl)-2-propanol (step 1).

¹H-NMR (CDCl₃) δ: 7.00 (2H, d, J=8.4 Hz), 6.65 (2H, d, J=8.4 Hz), 3.61 (2H, br.s), 2.65 (2H, s), 1.39 (1H, br.s), 1.20 (6H, s)

STEP 3. 1-[4-[(4-,6-dimethyl-3-nitro-2-pyridinyl)amino]phenyl}-2-methyl-2-propanol The title compound was prepared according to the procedure described in step 5 of Example 266 from 1-(4-aminophenyl)-2-methyl-2-propanol (step 2)

¹H-NMR (CDCl₃) δ: 9.60 (1H, s), 7.59 (2H, d, J=8.7 Hz), 7.19 (2H, d, J=8.4 Hz), 6.52 (1H, s), 2.75 (2H, s), 2.54 (3H, s), 2.43 (3H, s), 1.24 (6H, s)

STEP 4. 1-[4-[(3-amino-4,6-dimethyl-2-pyridinyl)amino]phenyl}-2-methyl-2-propanol The title compound was prepared according to the procedure described in step 2 of Example 28 from 1-{4-[(4,6-dimethyl-3-nitro-2-pyridinyl)amino]phenyl}-2-methyl-2-propanol (step 3)

¹H-NMR (CDCl₃) δ: 7.10 (4H, s), 6.61 (1H, s), 6.33 (2H, s), 3.28 (1H, br.s), 2.70 (2H, s), 2.37 (3H, s), 2.20 (3H, s), 1.22 (6H, s)

STEP 5. 2-[4-(2-ethyl-5,7-dimethyl-3H-imidazo[4,5-b]pyridin-3-yl)phenyl]-2-methyl-2-propanol The title compound was prepared according to the procedure described in step 5 of Example 1 from 1-{4-[(3-amino-4,6-dimethyl-2-pyridinyl)amino]phenyl}-2-methyl-2-propanol (step 4).

¹H-NMR (CDCl₃) δ: 7.42 (2H, d, J=8.1 Hz), 7.33 (2H, d, J=8.47 Hz), 6.91 (1H, s), 2.87 (2H, s), 2.84 (2H, q, J=7.6 Hz), 2.66 (3H, s), 2.52 (3H, s), 1.31 (6H, s), 1.28 (2H, d, J=7.6 Hz)

STEP 6. 2-[4-(2-ethyl-5,7-dimethyl-3H-imidazo[4,5-b]pyridin-3-yl)phenyl]-1,1-dimethylethyl]methylphenyl)sulfonylcarbamate The title compound was prepared according to the procedure described in Example 3 from 2-[4-(2-ethyl-5,7-dimethyl-3H-imidazo[4,5-b]pyridin-3-yl)phenyl]-2-methyl-2-propanol (step 5).

¹H-NMR (CDCl₃) δ: 7.94 (2H, t, J=8.6 Hz), 7.33 (2H, d, J=8.6 Hz), 7.16 (4H, m), 6.93 (1H, s), 3.10 (2H, s), 2.81 (2H, q, J=7.6 Hz), 2.67 (3H, s), 2.54 (3H, s), 2.40 (3H, s), 1.48 (6H, s), 1.28 (3H, t, J=7.6 Hz)

m.p. 173.5–174.0° C.

MS (ESI) m/z: 521 [(M+H)⁺], 519 [(M−H)⁻]

EXAMPLE 279

6-CHLORO-2-ETHYL-1-(6-{2-[({[(4-METHYLPHENYL)SULFONYL]AMINO}CARBONYL)AMINO]ETHYL}-3-PYRIDINYL)-5-(TRIFLUOROMETYL)-1H-BENZIMIDAZOLE

STEP 1. (6-{[5-chloro-2-nitro-4-(trifluoromehyl)phenyl]amino}-3-pyridinyl)methanol The title compound was prepared according to the procedure described in step 5 of Example 266 from 1-(6-amino-3-pyridinyl)methanol.

¹H-NMR (CDCl₃) δ: 10.51 (1H, br.s), 9.26 (1H, s), 8.60 (1H, s), 8.42 (1H, s), 7.79 (1H, d, J=8.1 Hz), 7.01 (1H, d, J=8.1 Hz), 4.75 (2H, s).

STEP 2. (6-{[2-amino-5-chloro-4-(trifluoromehyl)phenyl]amino}-3-pyridinyl}methanol The title compound was prepared according to the procedure described in step 2 of Example 28 from {5-[5-chloro-2-nitro-4-(trifluoromehyl)anilino]-3-pyridinyl}methanol (step 1).

MS (EI) m/z: 317 (M⁺).

STEP 3. {6-[6-chloro-2-ethyl-5-(trifluoromehyl)-1H-benzimidazol-1-yl]-3-pyridinyl}methyl propionate The title compound was prepared according to the procedure described in step 5 of Example 1 from (6-{[2-amino-5-chloro-4-(trifluoromehyl)phenyl]amino}-3-pyridinyl}methanol.(Step 2).

MS (EI) m/z: 411 (M⁺).

STEP 4 {6-[6-chloro-2-ethyl-5-(trifluoromehyl)-1H-benzimidazol-1-yl]-3-pyridinyl}methanol;

The title compound was prepared according to the procedure described in step 6 of Example 1 from {5-[5-chloro-2-nitro-4-(trifluoromehyl)anilino]-3-pyridinyl}methyl propionate (step 3).

¹H-NMR (CDCl₃) δ: 8.67 (1H, s), 8.19 (1H, s), 8.09 (1H, d, J=8.6 Hz), 7.79 (1H, d, J=8.4 Hz), 7.65 (1H, s), 5.54 (1H, t, J=5.6 Hz), 4.69 (2H, d, J=5.6 Hz), 2.95 (2H, q, J=7.3 Hz), 1.27 (3H, t, J=7.2 Hz).

STEP 5 6-chloro-1-[5-(chloromethyl)-2-pyridinyl]-2-ethyl-5-(trifluoromehyl)-1H-benzimidazole The title compound was prepared according to the procedure described in step 7 of Example 1 from {5-[5-chloro-2-nitro-4-(trifluoromehyl)anilino]-3-pyridinyl}methanol (step 4).

¹H-NMR (CDCl₃) δ: 8.72 (1H, d, J=2.2 Hz), 8.12 (1H, s), 8.07 (1H, dd, J=2.2, 8.1 Hz), 7.45–7.48 (2H, m), 4.72 (2H, s), 3.01 (2H, q, J=7.6 Hz), 1.39 (3H, t, J=7.6 Hz).

STEP 6 {6-[6-chloro-2-ethyl-5-(trifluoromethyl)-1H-benzimidazol-yl]-3-pyridinyl}acetonitrile To a solution of 6-chloro-1-[5-(chloromethyl)-2-pyridinyl]-2-ethyl-5-(trifluoromehyl)-1H-benzimidazole (from step 5, 550 mg, 1.5 mmol) in DMF (5 ml) and water (1 ml) was added KCN (470 g, 7.2 mmol) at room temperature, and then the reaction mixture was stirred for 2 h. The mixture was diluted with water and extracted with ethyl acetate/toluene (4/1) solution (3×30 ml). The organic layer was washed with water, dried (MgSO$_4$) and concentrated. This was purified by SiO$_2$ column chromatography developing with hexane/ethyl acetate (1/) gave 198 mg (37%) of title compound as orange oil.

$^1$H-NMR (CDCl$_3$) δ: 8.70 (1H, d, J=2.6 Hz), 8.13 (1H, s), 8.06 (1H, dd, J=2.6, 8.0 Hz), 7.52 (1H, d, J=8.20 Hz), 7.47 (1H, s), 3.94 (2H, s), 3.01 (2H, q, J=7.5 Hz), 1.40 (3H, t, J=7.5 Hz)

STEP 7 2-{6-[6-chloro-2-ethyl-5-(trifluoromethyl)-1H-benzimidazol-yl]-3-pyridinyl}ethanamine The title compound was prepared according to the procedure described in step 5 of Example 270 from {6-[6-chloro-2-ethyl-5-(trifluoromethyl)-1H-benzimidazol-yl]-3-pyridinyl}acetonitrile (step 6).

MS (EI) m/z: 368 (M$^+$).

STEP 8 6-chloro-2-ethyl-1-(6-{2-[({[(4-methylphenyl)sulfonyl]amino}carbonyl)amino]ethyl}2-pyridinyl)-5-(trifluoromehyl)-1H-benzimidazol The title compound was prepared according to the procedure described in step 10 of Example 1 from 2-{5-[6-chloro-2-ethyl-5-(trifluoromehyl)-1H-benzimidazol-1-yl]-3-pyridinyl}ethanamine (step 7).

$^1$H-NMR (CDCl$_3$) δ: 8.50 (1H, s), 8.12 (1H, s), 7.817 (1H, d, J=6.0 Hz), 7.72 (2H, d, J=8.4 Hz), 7.42 (1H, s), 7.24–7.37 (3H, m), 7.21(1H, s), 6.77 1, br.s), 3.60 (2H, dt, J=6.2 Hz), 2.94–3.01 (4H, m), 2.37 (3H, s), 1.37 (3H, t, J=7.5 Hz).

MS (ESI) m/z: 566 [(M+H)$^+$], 564 [(M−H)$^−$].

EXAMPLE 280

2-{4-[5-CHLORO-2-ETHYL-5-(TRIFLUOROMETYL)-1H-BENZIMIDAZOL-1-YL]PHENYL}-1,1-DIMETHYLETHYL(4-METHYLPHENYL)SULFONYLCARBAMATE

STEP 1. 1-(4-{[5-chloro-2-nitro-4-(trifluoromethyl)phenyl]amino}phenyl)-2-methyl-2-propanol The title compound was prepared according to the procedure described in step 5 of Example 266 from 1-(4-aminophenyl)-2-methyl-2-propanol $^1$H-NMR (CDCl$_3$) δ: 9.70 (1H, br.s), 8.58 (1H, s), 7.36 (2H, d, J=8.4 Hz), 7.21–7.25 (3H, m), 2.83 (2H, s), 1.28 (6H, s)

MS (EI) m/z: 388 (M$^+$)

STEP 2. 1-(4-{[2-amino-5-chloro-4-(trifluoromethyl)phenyl]amino}phenyl)-2-methyl-2-propanol The title compound was prepared according to the procedure described in step 2 of Example 28 from 1-(4-{[5-chloro-2-nitro-4-(trifluoromethyl)phenyl]amino}phenyl)-2-methyl-2-propanol (step 1)

$^1$H-NMR (CDCl$_3$) δ: 7.10 (4H, s), 6.61 (1H, s), 6.33 (2H, s), 3.28 (1H, br.s), 2.70 (2H, s), 2.37 (2H, s), 2.20 (3H, s), 1.22 (6H, s)

MS (EI) 388 (M$^+$)

STEP 3. 1-{4-[6-chloro-2-ethyl-5-(trifluoromethyl)-1H-benzimidazol-1-yl]phenyl}-2-methyl-2-propanol The title compound was prepared according to the procedure described in step 5 of Example 1 from 1-(4-{[2-amino-5-chloro-4-(trifluoromethyl)phenyl]amino}phenyl)-2-methyl-2-propanol (step 2).

$^1$H-NMR (CDCl$_3$) δ: 8.12 (1H, s), 7.48 (2H, d, J=8.4 Hz), 7.28 (2H, d, J=8.4 Hz), 7.22 (1H, s), 2.90 (2H, s), 2.80 (2H, q, J=7.3 Hz), 1.36 (3H, t, J=7.3 Hz) 1.32 (6H, s)

MS (EI) m/z: 396 (M$^+$)

STEP 4. 2-{4-[5-chloro-2-ethyl-5-(trifluoromethyl)-1H-benzimidazol-1-yl]phenyl}-1,1-dimethylethyl(4-methylphenyl)sulfonylcarbamate The title compound was prepared according to the procedure described in Example 3 from 2-[4-(2-ethyl-5,7-dimethyl-3H-imidazo[4,5-b]pyridin-3-yl)phenyl]-2-methyl-2-propanol (step 3).

$^1$H-NMR (CDCl$_3$) δ: 8.12 (1H, s), 7.94 (2H, d, J=8.7 Hz), 7.36 (2H, d, J=8.1 Hz), 7.15–7.27 (5H, m), 3.16 (2H, s), 2.78 (2H, q, J=7.6 Hz), 2.43 (3H, s), 1.47 (6H, s), 1.37 (3H, t, J=7.6 Hz)

m.p. 174.6–175.3° C.

MS (ESI) m/z: 594 [(M+H)$^+$], 592 [(M−H)$^−$]

EXAMPLE 281

2-{4-[6-CHLORO-2-ETHYL-5-(TRIFLUOROMETYL)-1H-BENZIMIDAZOL-1-YL]PHENYL}ETHYL(2,4-DIMETHYL-1,3-THIAZOL-5-YL)SULFONYLCARBAMATE

The title compound was prepared according to the procedure described in step 2 of Example 243 from 2-{4-[6-chloro-2-ethyl-5-(trifluoromethyl)-1H-benzimidazol-1-yl]phenyl}ethyl phenyl carbonate and 2,4-dimethyl-1,3-thiazol-5-ylsulfonamide.

$^1$H-NMR (CDCl$_3$) δ: 8.12 (1H, s), 7.41 (2H, d, J=7.9 Hz), 7.27 (2H, d, J=7.9 Hz), 7.20 (1H, s), 4.45 (2H, t, J=6.9 Hz), 3.08 (2H, t, J=6.6 Hz), 2.79 (2H, q, J=7.7 Hz), 2.71 (3H, s), 2.68 (3H, s), 1.36 (3H, t, J=7.7 Hz)

m.p. 168.3–169.0° C.

MS (ESI) m/z: 587 [(M+H)$^+$], 585 [(M−H)$^−$]

EXAMPLE 282

2-{4-[6-CHLORO-2-ETHYL-5-(TRIFLUOROMETYL)-1H-BENZIMIDAZOL-1-YL]PHENYL}ETHYL(5-CHLORO-1,3-DIMETHYL-1H-PYRAZOL-4-YL)SULFONYLCARBAMATE

The title compound was prepared according to the procedure described in step 2 of Example 243 from 2-{4-[6-chloro-2-ethyl-5-(trifluoromethyl)-1H-benzimidazol-1-yl]phenyl}ethyl phenyl carbonate and 5-chloro-1,3-dimethyl-1H-pyrazol-4-yl sulfonamide.

$^1$H-NMR (CDCl$_3$) δ: 8.12 (1H, s), 7.41 (2H, d, J=7.9 Hz), 7.27 (2H, d, J=7.9 Hz), 7.20 (1H, s), 4.45 (2H, t, J=6.9 Hz), 3.08 (2H, t, J=6.6 Hz), 2.79 (2H, q, J=7.7 Hz), 2.71 (3H, s), 2.68 (3H, s), 1.36 (3H, t, J=7.7 Hz)

m.p. 192.0–192.7° C.

MS (ESI) m/z: 604 [(M+H)$^+$], 602 [(M−H)$^−$]

EXAMPLE 283

2-{4-[5-CHLORO-2-ETHYL-5-(TRIFLUO-ROMETYL)-1H-BENZIMIDAZOL-1-YL]PHENYL}PROPYL(4-METHYLPHENYL)SULFONYLCARBAMATE

STEP 1. 2-(4-aminophenyl)1-propanol

To a stirred solution of 2-(4-amino-phenyl)-propionic acid ethyl ester (5.0 g, 25.9 mmol, Takahashi, I. et al., *Heterocycles* 1996, 43, 2343–2346.) in tetrahydrofurane (200 ml) was slowly added lithiumaluminium hydride (1.96 g, 51.8 mmol), and the mixture was stirred at room temperature for 14 h. The reaction mixture was quenched with 25% ammonia solution (50 ml) under ice-bath cooling. The resulting precipitate was filtered off, and the filtrate concentrated under reduced pressure to afford 3.88 g (99%) of the title compound as slight brown syrup.

$^1$H-NMR (CDCl$_3$) δ: 7.03 (2H, d, J=8.5 Hz), 6.66 (2H, d, J=8.5 Hz), 3.70–3.57 (4H, m), 2.90–2.78 (1H, m), 1.34–1.30 (1H, m), 1.22 (3H, d, J=7.1 Hz).

MS (EI) m/z: 151 (M$^+$).

STEP 2. 2-(4-{[5-chloro-2-nitro-4-(trifluoromethyl)phenyl]amino}phenyl)-1-propanol The title compound was prepared according to the procedure described in step 5 of Example 266 from 2-(4-aminophenyl)1-propanol (step 1)

$^1$H-NMR (CDCl$_3$) δ: 9.69 (1H, br.s), 8.58 (1H, s), 7.38 (2H, d, J=8.3 Hz), 7.21–7.26 (3H, m), 3.77 (2H, m), 3.03 (1H, m), 1.41 (1H, t, J=5.7 Hz), 1.33 (3H, d, J=7.1 Hz)

STEP 3. 2-(4-{[2-amino-5-chloro-4-(trifluoromethyl)phenyl]amino}phenyl)-1-propanol The title compound was prepared according to the procedure described in step 2 of Example 28 from 2-(4-{[5-chloro-2-nitro-4-(trifluoromethyl)phenyl]amino}phenyl)-1-propanol (step 2)

$^1$H-NMR (CDCl$_3$) δ: 7.21–7.26 (3H, m), 7.07 (1H, s), 6.93 (2H, d, J=8.4 Hz), 5.41 (1H, br.s), 3.68–3.69 (2H, br.s), 2.93 (1H, m), 1.38 (1H, br.s), 1.28 (3H, d, J=7.1 Hz)

STEP 4. 2-{4-[6-chloro-2-ethyl-5-(trifluoromethyl)-1H-benzimidazol-1-yl]phenyl}-1-propanol The title compound was prepared according to the procedure described in step 5 of Example 1 from 2-(4-{[2-amino-5-chloro-4-(trifluoromethyl)phenyl]amino}phenyl)1-propanol (step 3).

$^1$H-NMR (CDCl$_3$) δ: 8.12 (1H, s), 7.49 (2H, d, J=2.3 Hz), 7.30 (2H, d, J=8.4 Hz), 7.22 (1H, s), 3.83 (2H, m), 3.11 (1H, m), 2.80 (2H, q, J=7.6 Hz) 1.57 (1H, m), 1.33–1.40 (6H, m).

STEP 5. 2-{4-[5-chloro-2-ethyl-5-(trifluoromethyl)-1H-benzimidazol-1-yl]phenyl}-1,1-dimethylethyl(4-methylphenyl)sulfonylcarbamate The title compound was prepared according to the procedure described in Example 3 from 2-[4-(2-ethyl-5,7-dimethyl-3H-imidazo[4,5-b]pyridin-3-yl)phenyl]-1-propanol (step 4).

$^1$H-NMR (CDCl$_3$) δ: 8.11 (1H, s), 7.904 (2H, d, J=8.4 Hz), 7.40 (2H, d, J=8.4 Hz), 7.34 (2H, d, J=8.4 Hz), 7.27 (1H, s), 7.24 (1H, s), 7.20 (1H, s), 4.19–4.30 (2H, m), 3.20 (1H, m), 2.78 (2H, q, J=7.5 Hz), 2.43 (3H, s), 1.53 (3H, t, J=7.56 Hz), 1.34 (3H, t, J=6.9 Hz)

m.p. 179.9–180.5° C.

MS (ESI) m/z: 581 [(M+H)$^+$], 579 [(M−H)$^−$]

EXAMPLE 284

2-[4-(5-ACETYL-2-ETHYL-1H-BENZIMIDAZOL-1-YL)PHENYL]-1,1-DIMETHYLETHYL (4-METHYLPHENYL)SULFONYLCARBAMATE

STEP 1. 1-(4-{[4-hydroxy-2-methylpropyl)phenyl]amino}-3-nitrophenyl)ethanone

The title compound was prepared according to the procedure described in step 5 of Example 266 from 1-(4-aminophenyl)-2-methyl-2-propanol $^1$H-NMR (CDCl$_3$) δ: 9.85 (1H, br.s), 8.83 (1H, s), 7.97 (1H, d, J=9.0 Hz), 7.10–7.40 (4H, m), 2.82 (2H, s), 2.58 (3H, s), 1.28 (6H, s)

STEP 2. 1-(3-amino-4-{[4-(2-hydroxy-2-methylpropyl)phenyl]amino}phenyl)ethanone

The title compound was prepared according to the procedure described in step 2 of Example 28 from 1-(4-{[4-hydroxy-2-methylpropyl)phenyl]amino}-3-nitrophenyl)ethanone (step 1)

$^1$H-NMR (CDCl$_3$) δ: 7.38–7.46 (2H, m), 7.16 (2H, dd, J=8.4 Hz), 6.96 (2H, d, J=8.4 Hz), 5.62 (2H, br.s), 3.60 (1H, br.s), 2.73 (2H, s), 2.54 (3H, s), 1.39 (1H, br.s), 1.24 (6H, s)

STEP 3. 1-{2-ethyl-1-[4-(2-hydroxy-2-methylpropyl)phenyl]-1H-benzimidazol-5-yl}ethanone The title compound was prepared according to the procedure described in step 5 of Example 1 from 1-(3-amino-4-{[4-(2-hydroxy-2-methylpropyl)phenyl]amino}phenyl)ethanone (step 2).

$^1$H-NMR (CDCl$_3$) δ: 8.40 (1H, s), 7.90 (1H, d, J=8.6 Hz), 7.46 (2H, d, J=8.1 Hz), 7.30 (2H, d, J=8.1 Hz), 7.14 (1H, d, J=8.6 Hz), 2.96 (2H, s), 2.82 (2H, q, J=7.6 Hz), 2.68 (3H, s), 1.63 (1H, br.s), 1.38 (3H, t, J=7.6 Hz), 1.32 (6H, s)

STEP 4. 2-[4-(5-acetyl-2-ethyl-1H-benzimidazol-1-yl)phenyl]-1,1-dimethylethyl(4-methylphenyl)sulfonylcarbamate The title compound was prepared according to the procedure described in Example 3 from 1-{2-ethyl-1-[4-(2-hydroxy-2-methylpropyl)phenyl]-1H-benzimidazol-5-yl}ethanone (step 3).

$^1$H-NMR (CDCl$_3$) δ: 8.41 (1H, s), 7.88–7.95 (3H, m), 7.09–7.35 (7H, m), 3.14 (2H, s), 2.80 (2H, q, J=7.6 Hz), 2.68 (3H, s), 2.40 (3H, s), 1.45 (6H, s), 1.38 (3H, t, J=7.6 Hz)

m.p. 103.4–104.2° C.

MS (ESI) m/z: 534 [(M+H)$^+$], 532 [(M−H)$^−$]

EXAMPLE 285

2-{4-[6-CHLORO-2-ETHYL-5-(TRIFLUOROMETHTYL)-1H-BENZIMIDAZOL-1-YL]PHENYL}ETHYL(5-METHYL-2-PYRIDINYL)SULFONYLCARBAMATE MONOHYDROCHLORIDE

The title compound was prepared according to the procedure described in step 2 of Example 243 from 2-{4-[6-chloro-2-ethyl-5-(trifluoromethyl)-1H-benzimidazol-1-yl]phenyl}ethyl phenyl carbonate.

$^1$H-NMR (CDCl$_3$) δ: 8.57 (1H, s), 8.15 (1H, s), 8.12 (1H, d, J=8.0 Hz), 7.77 (1H, d, J=7.9 Hz), 7.37 (1H, d, J=7.9 Hz), 7.17–7.25 (4H, m,), 4.36 (2H, t, J=6.6 Hz), 3.00 (2H, t, J=6.6 Hz), 2.77 (2H, q, J=7.5 Hz), 2.46 (3H, s), 1.36 (3H, t, J=7.3 Hz)

m.p. 205.8° C.

MS (ESI) m/z: 567 [(M+H)$^+$], 565 [(M−H)$^−$]

EXAMPLE 286

2-{4-[6-CHLORO-2-ETHYL-5-(TRIFLUO-ROMETYL)-1H-BENZIMIDAZOL-1-YL]PHENYL}ETHYL(5-METHYL-2-PYRIDINYL) SULFONYLCARBAMATE MONO-HYDROCHLORIDE MONO-HYDROCHLORIDE

The title compound was prepared according to the procedure described Example 240 from 2-{4-[6-chloro-2-ethyl-5-(trifluoromethyl)-1H-benzimidazol-1-yl]phenyl}ethyl(5-methyl-2-pyridinyl)sulfonylcarbamate (Example 285).

$^1$H-NMR (CDCl$_3$) δ: 8.53 (1H, s), 8.49 (1H, s), 8.08 (1H, d, J=7.6 Hz), 7.78 (1H, d, J=6.8 Hz), 7.53 (2H, br.s), 7.41 (3H, br.s), 4.38 (2H, t, J=5.9 Hz), 3.21 (2H, br.s), 3.07 (2H, t, J=5.9 Hz), 2.47 (3H, s), 1.51 (3H, br.s)

m.p. 200.2° C.

MS (ESI) m/z: 567 [(M+H)$^+$], 565 [(M–H)$^−$]

EXAMPLE 287

2-{5-[6-CHLORO-2-ETHYL-5-(TRIFLUO-ROMETYL)-1H-BENZIMIDAZOL-1-YL]-3-PYRIDINYL}ETHYL(4-METHYLPHENYL)SUL-FONYLCARBAMATE

STEP 1. benzyl ethyl 2-(6-nitro-3-pyridinyl)malonate

To a mixture of 5-bromo-2-nitropyridine (8.66 g, 42.7 mmol) and benzyl ethyl malonate (9.50 g, 42.7 mmol) in tetrahydrofuran (160 ml) and dimethylformamide (40 ml) was added K$_2$CO$_3$ (5.90 g, 42.7 mmol) and stirred under reflux temperature for 20 h. The mixture was diluted with water (1l) and extracted with ethyl acetate (3×200 ml). The organic layer was washed with brine, dried (MgSO$_4$) and concentrated to give 5.26 g of title compound as orange oil.

$^1$H-NMR (CDCl$_3$) δ: 8.61 (1H, d, J=2.2 Hz), 8.26 (1H, d, J=8.4 Hz), 8.19 (1H, dd, J=2.1, 8.6 Hz), 7.29–7.38 (5H, m), 5.22 (2H, d, J=3.6 Hz), 4.84 (1H, s), 4.22 (2H, m), 1.23 (3H, t, J=7.1 Hz).

STEP 2. ethyl (6-nitro-3-pyridinyl)acetate

To a solution of benzyl ethyl 2-(6-nitro-3-pyridinyl)malonate (5.26 g, 15.3 mmol,) in ethanol was added palladium on carbon (530 mg) and stirred for 6 h under hydrogen atmosphere at room temperature. The catalyst was filtered off through a pad of celite and the filtrate was concentrated to give a title compound as yellow brown oil.

$^1$H-NMR (CDCl$_3$) δ: 7.95 (1H, d, J=1.8 Hz), 7.40 (1H, dd, J=2.4, 8.4 Hz), 6.48 (1H, d, J=8.4 Hz), 4.42 (2H, br.s), 4.14 (2H, q, J=7.1 Hz), 3.46 (2H, s), 1.26 (3H, t, J=7.1 Hz).

STEP 3. 2-(6-amino-3-pyridinyl)ethanol

To a solution of ethyl(6-nitro-3-pyridinyl)acetate (468 mg, 2.60 mmol) in tetrahydrofuran was added LiAlH$_4$ and stirred for 2 h at room temperature. The reaction was quenched with saturated 25% NH$_3$ aqueous solution and the precipitate was removed. The filtrate was concentrated to give a title compound as yellow oil.

$^1$H-NMR (CDCl$_3$) δ: 7.73 (1H, d, J=2.8 Hz), 7.23 (1H, dd, J=8.6 Hz), 6.37 (1H, d, J=2.6, 8.1 Hz), 5.63 (2H, br.s), 3.49 (2H, t, J=7.3 Hz), 2.51 (2H, t, J=7.3 Hz).

MS (EI) m/z: 138 (M$^+$).

STEP 4. (6-{[5-chloro-2-nitro-4-(trifluoromehyl)phenyl]amino}-3-pyridinyl)ethanol The title compound was prepared according to the procedure described in step 3 of Example 1 from 2-(6-amino-3-pyridinyl)ethanol (step 3).

$^1$H-NMR (CDCl$_3$) δ: 8.49 (1H, s), 8.32 (1H, d, J=2.2 Hz), 7.64 (1H, dd, J=2.4, 8.4 Hz), 7.36 (1Hs), 6.97 (1H, d, J=8.4 Hz), 3.91 (2H, t, J=6.5 Hz), 2.89 (2H, t, J=6.5 Hz)

MS (EI) m/z: 361 (M$^+$).

STEP 5. (6-{[2-amino-5-chloro-4-(trifluoromethyl)phenyl]amino}-3-pyridinyl)ethanol The title compound was prepared according to the procedure described in step 2 of Example 28 from (6-{[5-chloro-2-nitro-4-(trifluoromehyl)phenyl]amino}-3-pyridinyl)ethanol (step 4).

MS (EI) m/z: 331 (M$^+$).

STEP 6. 2-{6-[6-chloro-2-ethyl-5-(trifluoromehyl)-1H-benzimidazol-1-yl]-3-pyridinyl}ethylpropionate To (6-{[2-amino-5-chloro-4-(trifluoromehyl)phenyl]amino}-3-pyridinyl)ethanol (787 mg, 2.37 mmol, from step 5) was added propionic acid and propionic anhydride and stirred at 120° C. for 15 h. The mixture was quenched with NaOH and extracted with dichloromethane (3×30 ml). The organic layer was washed with brine, dried (MgSO$_4$) and concentrated to give 5.26 g of title compound as orange oil.

$^1$H-NMR (CDCl$_3$) δ: 8.58 (1H, d, J=1.9 Hz), 8.12 (1H, s), 7.83 (1H, dd, J=2.2, 8.1 Hz), 7.45 (1H, s), 7.39 (1H, d, J=8.1 Hz), 4.40 (2H, t, J=6.8 Hz), 4.12 (2H, q, J=7.3 Hz), 3.10 (2H, t, J=6.5 Hz), 2.99 (2H, q, J=7.6 Hz), 2.29–2.44 (2H, m), 1.38 (3H, t, J=7.4 Hz), 1.15 (3H, t, J=7.6 Hz).

STEP 5. 2-{6-[6-chloro-2-ethyl-5-(trifluoromehyl)-1H-benzimidazol-1-yl]-3-pyridinyl}ethanol The title compound was prepared according to the procedure described in step 8 of Example 266 from 2-{6-[6-chloro-2-ethyl-5-(trifluoromehyl)-1H-benzimidazol-1-yl]-2-pyridinyl}ethylpropionate (step 4).

$^1$H-NMR (CDCl$_3$) δ: 8.60 (1H, d, J=2.3 Hz), 8.11 (1H, s), 7.91 (1H, dd, J=2.5, 8.0 Hz), 7.45 (1H, s), 7.38 (1H, d, J=8.1 Hz), 4.01 (1H, t, J=6.2 Hz), 3.72–3.77 (2H, m), 2.94–3.04 (2H, m), 1.38 (3H, t, J=7.4 Hz).

STEP 6. 2-{6-[6-chloro-2-ethyl-5-(trifluoromehyl)-1H-benzimidazol-1-yl]-3-pyridinyl}ethyl-(4-methylphenyl)sulfonylcarbamate The title compound was prepared according to the procedure described in Example 3 from 2-{6-[6-chloro-2-ethyl-5-(trifluoromehyl)-1H-benzimidazol-1-yl]-2-pyridinyl}ethanol (step 5).

$^1$H-NMR (CDCl$_3$) δ: 8.33 (1H, d, J=1.9 Hz), 8.08 (1H, s), 7.91 (2H, d, J=8.4 Hz), 7.70 (1H, dd, J=2.4, 8.1 Hz), 7.29–7.42 (4H, m), 7.20(1H, s), 4.39 (2H, t, J=6.2 Hz), 3.00 (2H, t, J=6.2 Hz), 2.93 (2H, t, J=7.6 Hz), 2.43 (3H, s), 1.32 (3H, t, J=7.4 Hz).

MS (ESI) m/z: 567 [(M+H)$^+$], 565 [(M–H)$^−$].

EXAMPLE 288

2-{5-[6-CHLORO-2-ETHYL-5-(TRIFLUO-ROMETYL)-1H-BENZIMIDAZOL-1-YL]-3-PYRIDINYL}ETHYL(4-METHYLPHENYL)SUL-FONYLCARBAMATE MONO-HYDROCHLORIDE

STEP 1.

The title compound was prepared according to the procedure described in Example 240 from 2-{5-[6-chloro-2- ethyl-5-(trifluoromehyl)-1H-benzimidazol-1-yl]-3-pyridinyl}ethyl1-(4-methylphenyl)sulfonylcarbamate (Example 287).

¹H-NMR (CDCl₃) δ: 8.40 (1H, br.s), 8.49 (1H, br.s), 8.12 (1H, br.s), 7.82 (2H, br.s), 7.65 (1H, br.s), 7.25–7.28 (2H, m), 4.40 (2H, br.s), 3.35 (1H, s), 3.12 (2H, br.s), 2.41 (3H, s), 2.43 (3H, s), 1.53 (3H, br.s).

MS (ESI) m/z: 567 [(M+H)⁺], 565 [(M−H)⁻].

EXAMPLE 289

2-{4-[6-CHLORO-2-ETHYL-5-(TRIFLUOROMETYL)-1H-BENZIMIDAZOL-1-YL]PHENYL}ETHYL-5-ISOQUINOLINYLSULFONYLCARBAMATE

The title compound was prepared according to the procedure described in step 2 of Example 243 from 2-{4-[6-chloro-2-ethyl-5-(trifluoromethyl)-1H-benzimidazol-1-yl]phenyl}ethyl phenyl carbonate and 5-isoquinolinylsulfonamide.

¹H-NMR (CDCl₃) δ: 9.39 (1H, s), 8.70 (2H, t, J=6.3 Hz), 8.43 (1H, d, J=6.2 Hz), 8.29 (1H, d, J=8.1 Hz), 8.12 (1H, s,), 7.78 (1H, t, J=7.6 Hz), 7.16–7.33 (5H, m), 4.32 (2H, t, J=6.9 Hz), 2.97 (2H, t, J=6.8 Hz), 2.77 (2H, q, J=7.4 Hz), 1.346 (3H, t, J=7.4 Hz)

MS (ESI) m/z: 603 [(M+H)⁺], 601 [(M−H)⁻]

EXAMPLE 290

2-{4-[6-CHLORO-2-ETHYL-5-(TRIFLUOROMETYL)-1H-BENZIMIDAZOL-1-YL]PHENYL]ETHYL-5-QUINOLINYLSULFONYLCARBAMATE

The title compound was prepared according to the procedure described in step 2 of Example 243 from 4-(6-chloro-2-ethyl-5-trifluoromethyl-1-benzimidazol-1-yl)phenethyl-(4-methylphenyl)sulfonylcarbamate and 5-quinolinylsufonamide ¹H-NMR (CDCl₃) δ: 8.43 (1H, d, J=8.6 Hz), 8.20–8.25 (2H, m), 8.13 (1H, s), 8.12 (1H, s,), 7.81–7.91 (2H, m), 7.68–7.72 (1H, m), 7.30–7.34 (2H, m), 7.12–7.16 (3H, m), 4.37 (2H, t, J=6.6 Hz), 2.98 (2H, t, J=6.3 Hz), 2.74 (2H, q, J=7.4 Hz), 1.35 (3H, t, J=7.4 Hz).

MS (ESI) m/z: 567 [(M+H)⁺], 565 [(M−H)⁻]

EXAMPLE 291

2-{4-[6-CHLORO-2-ETHYL-5-(TRIFLUOROMETYL)-1H-BENZIMIDAZOL-1-YL]PHENYL}ETHYL-[5-(DIMETHYLAMINO)-1-NAPHTHNYL]SULFONYLCARBAMATE

The title compound was prepared according to the procedure described in step 2 of Example 243 from 2-{4-[6-chloro-2-ethyl-5-(trifluoromethyl)-1H-benzimidazol-1-yl]phenyl}ethyl phenyl carbonate and 5-(dimethylamino)-1-naphthnylsulfonamide.

¹H-NMR (CDCl₃) δ: 8.61 (1H, d, J=8.4 Hz), 8.46 (1H, dd, J=1.2, 7.5 Hz), 8.12 (1H, s), 87.58 (2H, t, J=8.3 Hz), 7.12–7.24 (6H, m), 4.30 (2H, t, J=6.8 Hz), 2.93 (2H, t, J=6.8 Hz), 2.75 (2H, q, J=7.5 Hz), 1.35 (3H, t, J=7.5 Hz)

m.p. 203.4° C.

MS (ESI) m/z: 645 [(M+H)⁺], 643 [(M−H)⁻]

EXAMPLE 292

2-{4-[6-CHLORO-2-ETHYL-5-(TRIFLUOROMETYL)-1H-BENZIMIDAZOL-1-YL]PHENYL}ETHYL-(1-METHYL-1H-IMIDAZOL-4-YL)SULFONYLCARBAMATE

The title compound was prepared according to the procedure described in step 2 of Example 243 from 2-{4-[6-chloro-2-ethyl-5-(trifluoromethyl)-1H-benzimidazol-1-yl]phenyl}ethyl phenyl carbonate and 1-methyl-1H-imidazol-4-ylsulfonamide.

¹H-NMR (CDCl₃) δ: 8.13 (1H, s), 7.72 (1H, d, J=1.5 Hz), 7.55 (1H, d, J=1.3 Hz), 7.41 (2H, d, J=8.2 Hz), 7.26 (2H, d, J=8.2 Hz), 7.20 (1H, s), 4.38 (2H, t, J=6.6 Hz), 3.78 (3H, s,), 3.04 (2H, d, J=6.8 Hz), 2.79 (2H, q, J=7.6 Hz), 1.36 (3H, t, J=7.6 Hz)

m.p. 204.3° C.

MS (ESI) m/z: 556 [(M+H)⁺], 554 [(M−H)⁻]

EXAMPLE 293

2-{4-[6-CHLORO-2-ETHYL-5-(TRIFLUOROMETYL)-1H-BENZIMIDAZOL-1-YL]PHENYL}ETHYL-(1-METHYL-1H-IMIDAZOL-4-YL)SULFONYLCARBAMATE MONO HYDROCHLORIDE

The title compound was prepared according to the procedure described in Example 240 from 2-{4-[6-chloro-2-ethyl-5-(trifluoromethyl)-1H-benzimidazol-1-yl]phenyl}ethyl-(1-methyl-1H-imidazol-4-yl)sulfonylcarbamate (Example 292).

MS (ESI) m/z: 556 [(M+H)⁺], 554 [(M−H)⁻]

EXAMPLE 294

2-{4-[6-CHLORO-2-ETHYL-5-(TRIFLUOROMETYL)-1H-BENZIMIDAZOL1-YL]PHENYL}ETHYL-(1,2-DIMETHYL-1H-IMIDAZOL-4-YL)SULFONYLCARBAMATE

The title compound was prepared according to the procedure described in step 2 of Example 243 from 2-{4-[6-chloro-2-ethyl-5-(trifluoromethyl)-1H-benzimidazol-1-yl]phenyl}ethyl phenyl carbonate and 1,2-dimethyl-1H-imidazol-4-ylsulfonamide.

¹H-NMR (CDCl₃) δ: 8.12 (1H, s), 7.63 (1H, s), 7.41 (2H, d, J=8.2 Hz), 7.25 (2H, d, J=8.2 Hz), 7.19 (1H, s), 4.37 (2H, t, J=6.8 Hz), 3.64 (3H, s), 3.04 (2H, d, J=6.6 Hz), 2.79 (2H, q, J=7.6 Hz), 2.42 (3H, s), 1.36 (3H, t, J=7.6 Hz)

m.p. 221.2° C.

MS (ESI) m/z: 570 [(M+H)⁺], 568 [(M−H)⁻]

EXAMPLE 295

2-{4-[6-CHLORO-2-ETHYL-5-(TRIFLUOROMETYL)-1H-BENZIMIDAZOL 1-YL]PHENYL}ETHYL-(1,2-DIMETHYL-1H-IMIDAZOL-4-YL)SULFONYLCARBAMATE DI-HYDROCHLORIDE

The title compound was prepared according to the procedure described in Example 240 from 2-{4-[6-chloro-2-ethyl-5-(trifluoromethyl)-1H-benzimidazol-1-yl]phenyl}ethyl-(1,2-dimethyl-1H-imidazol-4-yl)sulfonylcarbamate (Example 294).

MS (ESI) m/z: 570 [(M+H)⁺], 568 [(M−H)⁻]

EXAMPLE 296

2-{4-[5,7-DIMETHYL-2-(1H-PYRAZOL-3-YL)-3H-IMIDAZO[4,5-b]PYRIDINE-3-YL-]PHENYL}ETHYL(4-METHYLPHENYL)SULFONYLCARBAMATE

STEP 1. 2-{4-[5,7-dimethyl-2-(1H-pyrazol-3-yl)-3H-imidazo[4,5-b]pyridin-3-yl]phenyl}ethanol The title compound was prepared according to the procedure described in step 1 of Example 236 from 4-[(3-amino-4,6-dimethyl-2-pyridinyl)amino]phenylethanol.

$^1$H-NMR (DMSO-d$_6$) δ: 13.15 (1H, br.s), 7.77 (3H, s), 7.35 (2H, d, J=7.7 Hz), 7.25 (2H, d, J=7.7 Hz), 7.02 (1H, s), 6.53 (1H, s), 4.75 (2H, t, J=4.8 Hz), 3.71 (2H, q, J=6.8 Hz), 2.81 (1H, t, J=6.6 Hz), 258 (3H, s), 2.42 (3H, s)

STEP 2. 2-{4-[5,7-dimethyl-2-(1H-pyrazol-3-yl)3H-imidazo[4,5-b]pyridine-3-yl-]phenyl}ethyl(4-methylphenyl)sufonylcarbamate The title compound was prepared according to the procedure described in Example 3 from 2-{4-[5,7-dimethyl-2-(1H-pyrazol-3-yl)-3H-imidazo[4,5-b]pyridin-3-yl]phenyl}ethanol (step 1).

$^1$H-NMR (DMSO-d$_6$) δ: 13.14 (1H, br.s), 7.69–7.78 (3H, m), 7.21–7.43 (6H, m), 7.02 (1H, s), 6.52 (1H, s), 4.18 (2H, t, J=6.4 Hz), 2.89 (2H, t, J=6.4 Hz), 2.58 (2H, s), 2.41(3H, s), 2.32 (3H, s)

MS (ESI) m/z: 531 (MH$^+$), 529 ([M−H]$^−$)

EXAMPLE 297

2-{4-[5,7-DIMETHYL-2-(1H-PYRAZOL-3-YL)3H-IMIDAZO[4,5-b]PYRIDINE-3-YL-]PHENYL}ETHYL(4-METHYLPHENYL)SULFONYLCARBAMATE SODIUM SALT

STEP 1. 2-{4-[5,7-dimethyl-2-(1H-pyrazol-3-yl)-3H-imidazo[4,5-b]pyridin-3-yl]phenyl}ethanol The title compound was prepared according to the procedure described in Example 2 from 2-{4-[5,7-dimethyl-2-(1H-pyrazol-3-yl)3H-imidazo[4,5-b]pyridine-3-yl-]phenyl}ethyl(4-methylphenyl)sufonylcarbamate (Example 296).

$^1$H-NMR (CDCl$_3$) δ: 9.85 (1H, s), 8.37 (1H, d, J=8.4 Hz), 7.31 (1H, d, J=2.0 Hz), 7.14 (1H, dd, J=2.0, 8.3 Hz), 6.60 (1H, s), 3.87 (2H, dt, J=6.2, 6.4 Hz), 2.84 (2H, t, J=6.4 Hz), 2.56 (3H, s), 2.46 (3H, s), 1.40 (1H, t, J=6.2 Hz).

MS (ESI) m/z: 531 (MH$^+$), 529 ([M−H]$^−$)

EXAMPLE 298

N-{[(2-{4-[5,7-DIMETHYL-2-(1H-PYRAZOL-3-YL)-3H-IMIDAZO[4,5-b]PYRIDINE-3-YL]PHENYL}ETHYL)AMINO]CARBONYL}-4-METHYLBENZENESULFONAMIDE

STEP 1. 3-[4-(2-chloroethyl)phenyl]-5,7-dimethyl-2-(1H-pyrazol-3-yl)-3H-imidazo[4,5-b]pyridine The title compound was prepared according to the procedure described in step 2 of Example 28 from 2-{4-[5,7-dimethyl-2-(1H-pyrazol-3-yl)-3H-imidazo[4,5-b]pyridin-3-yl]phenyl}ethanol (Example 297, step 1).

$^1$H-NMR (CDCl$_3$) δ: 13.15 (1H, s), 7.77 (2H, br.s), 7.43 (2H, br.s), 7.20 (2H, br.s), 7.04 (1H, s), 6.54 (1H, br.s), 3.96 (2H, t, J=6.8 Hz), 3.15 (2H, tm J=6.8 Hz), 2.60 (3H, s), 2.30 (3H, s).

STEP 2. 3-[4-(2-azidoethyl)phenyl]-5,7-dimethyl-2-(1H-pyrazol-3-yl)-3H-imidazo[4,5-b]pyridine The title compound was prepared according to the procedure described in step 5 of Example 1 from 3-[4-(2-chloroethyl)phenyl]-5,7-dimethyl-2-(1H-pyrazol-3-yl)-3H-imidazo[4,5-b]pyridine (step 1).

$^1$H-NMR (DMSO-d$_6$) δ: 13.15 (1H, br.s), 9.85 (1H, br.s), 7.76 (1H, br.s), 7.41 (2H, d, J=8.1 Hz), 7.31 (2H, d, J=8.1 Hz), 7.04 (1H, s), 6.53 (1H, s), 3.69 (2H, t, J=6.6 Hz), 2.95 (2H, t, J=6.8 Hz), 2.58 (3H, s), 2.42 (3H, s),

MS (EI) m/z: 358 (M$^+$).

STEP 3. 2-{4-[5,7-dimethyl-2-(1H-pyrazol-3-yl)-3H-imidazo[4,5-b]pyridin-3-yl]phenyl}ethanamine The title compound was prepared according to the procedure described in step 6 of Example 1 from 3-[4-(2-azidoethyl)phenyl]-5,7-dimethyl-2-(1H-pyrazol-3-yl)-3H-imidazo[4,5-b]pyridine (step 2).

$^1$H-NMR (DMSO-d$_6$) δ: 9.83 (1H, br.s), 7.68 (2H, br.s), 7.23–7.43 (5H, m), 7.04 (1H, s), 5.75 (1H, s), 2.68–2.90 (4H, m), 2.59 (3H, s), 2.42 (3H, s),

MS (EI) m/z: 332 (M$^+$).

STEP 4. N-{[(2-{4-[5,7-dimethyl-2-(1H-pyrazol-3-yl)-3H-imidazo[4,5-b]pyridine-3-yl]phenyl}ethyl)amino]carbonyl}-4-methylbenzenesulfonamide The title compound was prepared according to the procedure described in step 7 of Example 1 from 2-{4-[5,7-dimethyl-2-(1H-pyrazol-3-yl)-3H-imidazo[4,5-b]pyridin-3-yl]phenyl}ethanamine (step 3)

$^1$H-NMR (CD3OD) δ: 7.80 (2H, d, J=8.2 Hz), 7.58 (1H, br.s), 7.20–7.35 (6H, m), 7.08 (1H, s), 6.20 (1H, br.s), 3.42 (2H, t, J=6.8 Hz), 2.84 (2H, t, J=6.9 Hz), 2.68 (2H, s), 2.50 (3H, s), 2.34 (3H, s)

MS (ESI) m/z: 530 (MH$^+$), 528 ([M−H]$^−$)

EXAMPLE 299

2-[4-(5-CYANO-2-ETHYL-6-METHYL-1H-BENZIMIDAZOL-1-YL)PHENYL]ETHYL(4-METHYLPHENYL)SULFONYLCARBAMATE

STEP 1. 4-chloro-2-methyl-5-nitrobenzonitrile

To a solution of 4-chloro-2-methyl-5-nitrobenzonitrile (10 g, 66 mmol) in conc. H$_2$SO$_4$ was added KNO$_3$ (7.0 g, 69.3 mmol) at 0° C. in small portions, and then the reaction mixture was stirred overnight at ambient temperature. It was then poured into ice and extracted with AcOEt. The combined extracts was washed by sat. NaHCO$_3$ aq., dried over MgSO$_4$ and concentrated. The resulting precipitates were collected by filtration, washed with ether, and dried under reduced pressure to give 5.5 g (42%) of the title compound.

$^1$H-NMR (CDCl$_3$) δ: 8.19 (1H, s), 7.57 (1H, s), 2.64 (3H, s).

STEP 2. 4-{[4-(2-hydroxylethyl)phenyl]amino}-2-methyl-5-nitrobenzonitrile

The title compound was prepared according to the procedure described in step 3 of Example 1 from 3-bromo-6-chloro-2,4-dimethyl-5-nitropyridine (step 2).

$^1$H-NMR (CDCl$_3$) δ: 9.76 (1H, br.s), 8.51 (1H, s), 7.36 (1H, d, J=8.4 Hz), 7.22 (1H, d, J=8.3 Hz), 6.96 (1H, s), 3.94 (2H, dd, J=11.7, 6.2 Hz), 2.94 (2H, t, J=6.4 Hz), 2.42 (3H, s)

STEP 3. 5-amino-4-{[4-(2-hydroxylethyl)phenyl]amino}-2-methylbenzonitrile

The title compound was prepared according to the procedure described in step 4 of Example 1 from 2-{4-[(5-bromo-4,6-dimethyl-3-nitro-2-pyridinyl)amino]phenyl}ethanol (step 3).

$^1$H-NMR (CDCl$_3$) δ: 7.19 (1h, d, J=8.4 Hz), 6.94–7.00 (4H, m), 5.59 (1H, br.s), 3.84–3.90 (2H, m), 3.50 (2H, br.s), 2.85 (2H, t, J=6.4 Hz), 2.37 (3H, s).

STEP 5. 2-[4-(5-cyano-2-ethyl-6-methyl-1H-benzimidazo-1-yl)phenyl]ethyl propanoate The title compound was prepared according to the procedure described in step 5 of Example 1 from 2-{4-[(3-amino-5-bromo-4,6-dimethyl-2-pyridinyl)amino]phenyl}ethanol (step 4).

MS (EI) m/z: 361 (M$^+$)

STEP 6. 2-ethyl-1-[4-(2-hydroxylethyl)phenyl]-6-methyl-1H-benzimidazole-5-carbonitrile The title compound was prepared according to the procedure described in step 6 of Example 1 from 2-[4-(6-bromo-2-isopropyl-5,7-dimethyl-3H-imidazo[4,5-b]pyridin-3-yl)phenyl]ethyl 2-methylpropanoate (step 5).

$^1$H-NMR (CDCl$_3$) δ: 8.00 (1H, s), 7.50 (2H, d, J=8.4 Hz), 7.29 (2H, d, J=8.4 Hz), 6.98(1H, s), 4.01 (2H, t, J=6.4 Hz), 3.03 (2H, t, J=6.6 Hz), 2.79 (2H, q, J=7.5 Hz), 2.56 (3H, s), 1.35 (3H, t, J=7.5 Hz)

STEP 7. 2-[4-(5-cyano-2-ethyl-6-methyl-1H-benzimidazol-1-yl)phenyl]ethyl(4-methylphenyl)sulfonylcarbamate The title compound was prepared according to the procedure described in Example 3 from 2-ethyl-1-[4-(2-hydroxylethyl)phenyl]-6-methyl-1H-benzimidazole-5-carbonitrile (step 6).

$^1$H-NMR (CDCl$_3$) δ: 8.03 (1H, s), 7.92 (2H, d, J=8.4 Hz), 7.39 (2H, d, J=8.4 Hz), 7.35 (2H, d, J=8.1 Hz), 7.26 (2H, d, J=8.1 Hz), 6.96(1H, s), 4.39 (2H, t, J=6.8 Hz), 3.04 (2H, t, J=6.6 Hz), 2.77 (2H, q, J=7.7 Hz), 2.57 (3H, s), 2.44 (3H, s), 1.35 (3H, t, J=7.5 Hz)

EXAMPLE 300

N-[({2-[4-(5-CYANO-2-ETHYL-6-METHYL-1H-BENZIMIDAZOL-1-YL)PHENYL]ETHYL}AMINO)CARBONYL](4-METHYLBENZENESULFOAMIDE

STEP 1.1-[4-(2-chloroethyl)phenyl]-2-ethyl-6-methyl-1H-benzimidazole-5-carbonitrile The title compound was prepared according to the procedure described in step 7 of Example 1 from 2-[4-(6-bromo-2-isopropyl-5,7-dimethyl-3H-imidazo[4,5-b]pyridin-3-yl)phenyl]ethanol (step 6).

$^1$H-NMR (CDCl$_3$) δ: 8.02 (1H, s), 7.48 (2H, d, J=8.4 Hz), 7.30 (2H, d, J=8.4 Hz), 6.96–6.98 (1H, m), 3.83 (2H, t, J=7.1 Hz), 3.21 (2H, t, J=7.0 Hz), 2.78 (2H, q, J=7.5 Hz), 2.58 (3H, s), 1.35 (3H, t, J=7.5 Hz).

STEP 2. 1-[4-(2-azidoethyl)phenyl]-2-ethyl-6-methyl-1H-benzimidazole-5-carbonitrile The title compound was prepared according to the procedure described in step 8 of Example 1 from 6-bromo-3-[4-(2-chloroethyl)phenyl]-2-isopropyl-5,7-dimethyl-3H-imidazo[4,5-b]pyridine (step 7).

MS (EI) m/z: 412 (M$^+$)

$^1$H-NMR (CDCl$_3$) δ: 8.02 (1H, s), 7.48 (2H, d, J=8.0 Hz), 7.30 (2H, d, J=8.2 Hz), 6.95 (1H, s), 3.63 (2H, t, J=6.8 Hz), 3.03 (2H, t, J=7.0 Hz), 2.78 (2H, q, J=7.5 Hz), 2.57 (3H, s), 1.35 (3H, t, J=7.3 Hz).

STEP 3. 1-[4-(2-aminoethyl)phenyl]-2-ethyl-6-methyl-1H-benzimidazole-5-carbonitrile The title compound was prepared according to the procedure described in step 9 of Example 1 from 2-[4-(6-bromo-2-isopropyl-5,7-dimethyl-3H-imidazo[4,5-b]pyridin-3-yl)phenyl]ethyl azide (step 8).

$^1$H-NMR (CDCl$_3$) δ: 7.49 (2H, d, J=8.3 Hz), 7.28 (2H, d, J=8.3 Hz), 6.93 (1H, s), 6.60 (2H, br.s), 3.32–3.00 (5H, m), 2.65 (3H, s), 2.48 (3H, s), 1.31 (6H, d, J=6.8 Hz).

STEP 4. N-[({2-[4-(5-cyano-2-ethyl-6-methyl-1H-benzimidazol-1-yl)phenyl]ethyl}amino)carbonyl](4-methylbenzenesulfoamide The title compound was prepared according to the procedure described in step 10 of Example 1 from [4-(2-isopropyl-5,7-dimethyl-3H-imidazo[4,5-b]pyridin-3-yl)phenyl]ethylamine (step 9).

$^1$H-NMR (CDCl$_3$) δ: 8.00 (1H, s), 7.72 (2H, d, J=8.4 Hz), 7.42 (2H, d, J=8.4 Hz), 7.28–7.32 (4H, m), 6.95(1H, m), 3.56–3.63 (2H, m), 2.96 (2H, t, J=7.1 Hz), 2.78 (2H, q, J=7.7 Hz), 2.54 (3H, s), 2.41 (3H, s), 1.34 (3H, t, J=7.5 Hz)

EXAMPLE 301

2-AMINO-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE DI-HYDROCHLORIDE

STEP 1. 2-AMINO-5,7-DIMETHYL-3-(4-{2-[({[(4-METHYLPHENYLSULFONYL]AMINO}CARBONYL)AMINO]ETHYL}PHENYL)-3H-IMIDAZO[4,5-b]PYRIDINE

To a stirred solution of N-{[(2-{4-[(3-amino-4,6-dimethyl-2-pyridinyl)amino]phenyl}ethyl)amino]carbonyl}-4-methylbenzenesulfonamide (300 mg, 0.66 mmol) in THF (6 ml) was added a solution of BrCN (175 mg, 1.65 mmol) in water (2 ml). The resultant mixture was stirred at room temperature for 16 hours. The mixture was diluted with CH$_2$Cl$_2$ and washed with brine. The organic layer was dried over MgSO$_4$ and filtered. After concentration in vacuo, the residue was purified by preparative TLC (CH$_2$Cl$_2$/MeOH=10/1) to afford 224 mg (71%) of the title compound.

$^1$H-NMR (DMSO-d$_6$) δ: 10.82 (1H, s), 8.54 (2H, s), 7.79 (2H, d, J=8.3 Hz), 7.51–7.40 (6H, m), 7.06 (1H, s), 6.91 (1H, t, J=5.5 Hz), 3.29–3.24 (2H, m), 2.80–2.76 (2H, m), 2.48 (3H, s), 2.38 (3H, s), 2.36 (3H, s)

MS (ESI) m/z: 479 ([M+H]$^+$), 477 ([M−H]$^-$)

STEP 2. 2-AMINO-5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDINE DI-HYDROCLORIDE

The title compound was prepared according to the procedure described in Example 240 from 2-amino-5,7-dimethyl-3-(4-{2-[({[(4-methylphenyl)sulfonyl]amino}carbonyl)amino]ethyl}phenyl)-3H-imidazo[4,5-b]pyridine.

MS (ESI) m/z: 479 ([M+H]$^+$), 477 ([M−H]$^-$)

EXAMPLE 302

5,7-DIMETHYL-3-(4-{2-[({[(4-METHYLPHENYL)SULFONYL]AMINO}CARBONYL)AMINO]ETHYL}PHENYL)-2-(METHYLSULFANYL)-3H-IMIDAZO[4,5-b]PYRIDINE

A mixture of N-{[(2-{4-[(3-amino-4,6-dimethyl-2-pyridinyl)amino]phenyl}ethyl)amino]carbonyl}-4-methylbenzenesulfonamide (110 mg, 0.24 mmol), di-2-pyridylthiocarbonate (68 mg, 0.29 mmol), and THF (5 ml) was stirred at room temperature for 3 days. The mixture was diluted with $CH_2Cl_2$ and washed with 0.1M HCl and brine. The organic fraction was dried over $MgSO_4$, and filtered. The solvent was removed to give N-[({2-[4-[(5,7-dimethyl-2-sulfanyl-3H-imidazo[4,5-b]pyridin-3-yl)phenyl]ethyl}amino)carbonyl]-4-methylbenzenesulfonamide [MS (ESI) m/z: 496 ([M+H]$^+$), 494 ([M−H]$^−$)]. This was dissolved with THF (2 ml), then 1M NaOMe in MeOH (0.49 ml) and MeI (45 μl, 0.73 mmol) was added to the mixture at room temperature. After 1 hour, the mixture was evaporated in vacuo and the residue was purified by preparative TLC ($CH_2Cl_2$/MeOH=10/1) to afford 31 mg (25%) of the title compounds.

$^1$H-NMR (CDCl$_3$) δ: 7.86 (2H, d, J=8.4 Hz), 7.31 (2H, d, J=8.1 Hz), 7.22–7.16 (4H, m), 6.88 (1H, s), 6.02 (1H, t, J=5.6 Hz), 3.51–3.45 (2H, m), 2.83 (2 h, t, J=6.2 Hz), 2.67 (3H, s), 2.62 (3H, s), 2.42 (3H, s), 2.417 (3H, s)

MS (ESI) m/z: 510 ([M+H]$^+$), 508 ([M−H]$^−$)

EXAMPLE 303

5,7-DIMETHYL-2-(METHYLAMINO)-3-(4-{2-[({[(4-METHYLPHENYL)SULFONYL]AMINO}CARBONYL)AMINO]ETHYL}PHENYL)-3H-IMIDAZO[4,5-b]PYRIDINE

A mixture of N-{[(2-{4-[(3-amino-4,6-dimethyl-2-pyridinyl)amino]phenyl}ethyl)amino]carbonyl}-4-methylbenzenesulfonamide (300 mg, 0.66 mmol), methylisothiocyanate (56 μl, 0.86 mmol), and THF (6 ml) was stirred at room temperature for 3 days. The solvent was removed to give N-{[(2-{4-[(4,6-dimethyl-{[(methylamino)carbonothioyl]amino}-2-pyridinyl)amino]phenyl}ethyl)amino]carbonyl}-4-methylbenzenesulfonamide [MS (ESI) m/z: 527 ([M+H]$^+$), 525 ([M−H]$^−$)]. This was dissolved with MeCN (4 ml) and treated with MeI (54 μl) at 0° C. for 20 hours. After concentration under reduced pressure, the residue was purified by preparative TLC (EtOAc/EtOH=20/1) to afford 170 mg (52%) of the title compounds.

$^1$H-NMR (CD$_3$OD) δ: 7.72 (2H, d, J=8.3 Hz), 7.24 (4H, d, J=7.9 Hz), 7.15 (2H, d, J=8.4 Hz), 6.70 (1H, s), 3.28 (2H, t, J=7.0 Hz), 2.90 (3H, s), 2.72 (2H, t, J=7.0 Hz), 2.41 (3H, s), 2.26 (3H, s), 2.24 (3H, s)

MS (ESI) m/z: 493 ([M+H]$^+$), 491 ([M−H]$^−$)

EXAMPLE 304

5,7-DIMETHYL-2-(METHYLAMINO)-3-(4-{2-[({[(4-METHYLPHENYL)SULFONYL]AMINO}CARBONYL)AMINO]ETHYL}PHENYL)-3H-IMIDAZO[4,5-b]PYRIDINE MONO-HYDROCHLORIDE

The title compound was prepared according to the procedure described in Example 240 from 5,7-dimethyl-2-(methylamino)-3-(4-{2-[({[(4-methylphenyl)sulfonyl]amino}carbonyl)amino]ethyl}phenyl)-3H-imidazo[4,5-b]pyridine hydrochloride.

MS (ESI) m/z: 493 ([M+H]$^+$), 491 ([M−H]$^−$)

EXAMPLE 305

N-[5,7-DIMETHYL-3-(4-{2-[({[(4-METHYLPHENYL)SULFONYL]AMINO}CARBONYL)AMINO]ETHYL}PHENYL)-3H-IMIDAZO[4,5-b]PYRIDIN-2-YL]ACETAMIDE 2-amino-5,7-dimethyl-3-(4-{2-[({[(4-methylphenyl)sulfonyl]amino}carbonyl)amino]ethyl}phenyl)-3H-imidazo[4,5-b]pyridine (73 mg) was treated with pyridine (1 ml) and $Ac_2O$ (0.2 ml) at room temperature for 3 hours. After evaporation in vacuo, the residue was purified by preparative TLC (hexane/acetone=1/1) to afford 4 mg (5%) of the title compounds.

$^1$H-NMR (CDCl$_3$) δ: 7.79 (2H, d, J=8.4 Hz), 7.34–7.22 (7H, m), 7.04 (1H, s), 6.30 (1H, br.s), 3.51–3.48 (2H, m), 2.87–2.83 (2H, m), 2.66 (3H, s), 2.53 (3H, s), 2.42 (3H, s), 2.26 (3H, s),

MS (ESI) m/z: 521 ([M+H]$^+$), 519 ([M−H]$^−$)

EXAMPLE 306

5,7-DIMETHYL-2-(DIMETHYLAMINO)-3-(4-{2-[({[(4-METHYLPHENYL)SULFONYL]AMINO}CARBONYL)AMINO]ETHYL}PHENYL)-3H-IMIDAZO[4,5-b]PYRIDINE

To a stirred solution of 2-amino-5,7-dimethyl-3-(4-{2-[({[(4-methylphenyl)sulfonyl]amino}carbonyl)amino]ethyl}phenyl)-3H-imidazo[4,5-b]pyridine (70 mg) in THF (1 ml) was added NaH (21 mg, 0.88 mmol) at room temperature. After 10 min, MeI (27 μl) was added to the mixture and stirred at room temperature for 2 days. The mixture was poured into ice-water and extracted with $CH_2Cl_2$, and the organic fraction was dried over $MgSO_4$, then filtered. After removal of solvent by evaporation, the residue was purified by preparative TLC ($CH_2Cl_2$/MeOH=10/1) to afford 27 mg (36%) of the title compounds.

$^1$H-NMR (CDCl$_3$) δ: 7.86 (2H, d, J=8.4 Hz), 7.32–7.24 (4H, m), 7.16 (2H, d, J=8.4 Hz), 6.77 (1H, s), 6.04 (1H, t, J=5.7 Hz), 3.50–3.44 (2H, m), 2.78 (2H, t, J=6.3 Hz), 2.71 (6H, s), 2.55 (3H, s), 2.41 (3H, s), 2.34 (3H, s)

MS (ESI) m/z: 507 ([M+H]$^+$), 505 ([M−H]$^−$)

EXAMPLE 307

2-[4-(2-AMINO-5,7-DIMETHYL-3H-IMIDAZO[4,5-b]PYRIDIN-3-YL)PHENYL]ETHYL(4-METHYLPHENYL)SULFONYLCARBAMATE

STEP 1. 2-{4-[(4,6-dimethyl-3-nitro-2-pyridinyl)amino]phenyl}ethyl(4-methylphenyl)sulfonylcarbamate The title compound was prepared according to the procedure described in Example 3 from 2-{4-[(4,6-dimethyl-3-nitro-2-pyridinyl)amino]phenyl}ethanol.

$^1$H-NMR (CDCl$_3$) δ: 9.55 (1H, s), 7.89 (2H, d, J=8.3 Hz), 7.54 (2H, d, J=8.6 Hz), 7.32 (2H, d, J=8.6 Hz), 7.11 (2H, d, J=8.4 Hz), 6.54 (1H, s), 4.28 (2H, t, J=7.0 Hz), 2.88 (2H, t, J=7.0 Hz), 2.55 (3H, s), 2.43 (6H, s)

MS (ESI) m/z: 485 ([M+H]$^+$), 483 ([M−H]$^−$)

STEP 2. 2-{4-[(3-amino-4,6-dimethyl-2-pyridinyl)amino]phenyl}ethyl(4-methylphenyl)sulfonylcarbamate The title compound was prepared according to the procedure described in step 4 of Example 1 from 2-{4-[(4,6-dimethyl-3-nitro-2-pyridinyl)amino]phenyl}ethyl(4-methylphenyl)sulfonylcarbamate.

$^1$H-NMR (CDCl$_3$) δ: 7.82 (2H, d, J=8.3 Hz), 7.25 (2H, d, J=8.3 Hz), 6.93 (2H, d, J=8.4 Hz), 6.84 (2H, d, J=8.4 Hz), 6.66 (1H, s), 4.22 (2H, t, J=6.6 Hz), 2.77 (2H, t, J=6.6 Hz), 2.39 (3H, s), 2.37 (3H, s), 2.22 (3H, s)

MS (ESI) m/z: 455 ([M+H]$^+$), 453 ([M−H]$^−$)

STEP 3. 2-[4-(2-amino-5,7-dimethyl-3H-imidazo[4,5-b]pyridin-3-yl)phenyl]ethyl(4-methylphenyl)sulfonylcarbamate The title compound was prepared according to the procedure described in Example 127 from 2-{4-[(3-amino-4,6-dimethyl-2-pyridinyl)amino]phenyl}ethyl(4-methylphenyl)sulfonylcarbamate.

$^1$H-NMR (DMSO-d$_6$) δ: 7.76 (2H, d, J=8.3 Hz), 7.42–7.35 (6H, m), 6.78 (1H, s), 6.61 (1H, br.s), 4.22 (2H, t, J=6.6 Hz), 2.92 (2H, d, J=6.6 Hz), 2.373 (3H, s), 2.365 (3H, s), 2.32 (3H, s)

MS (ESI) m/z: 480 ([M+H]$^+$), 478 ([M−H]$^−$)

EXAMPLE 308

2-{4-[5,7-DIMETHYL-2-(METHYLAMINO)-3H-IMIDAZO[4,5-b]PYRIDIN-3-YL]PHENYL}ETHYL(4-METHYLPHENYL)SULFONYLCARBAMATE

The title compound was prepared according to the procedure described in Example 129 from 2-{4-[(3-amino-4,6-dimethyl-2-pyridinyl)amino]phenyl}ethyl(4-methylphenyl)sulfonylcarbamate.

$^1$H-NMR (DMDO-d$_6$) δ: 7.78 (2H, d, J=8.1 Hz), 7.43–7.33 (7H, m), 6.77 (1H, s), 6.43 (1H, br.s), 4.25 (2H, t, J=6.6 Hz), 2.93 (2H, t, J=6.6 Hz), 2.88 (3H, s), 2.41 (3H, s), 2.37 (3H, s), 2.31 (3H, s)

MS (ESI) m/z: 494 ([M+H]$^+$), 492 ([M−H]$^−$)

EXAMPLE 309

2-{4-[5,7-DIMETHYL-2-(METHYLSULFANYL)-3H-IMIDAZO[4,5-b]PYRIDIN-3-YL]PHENYL}ETHYL(4-METHYLPHENYL)SULFONYLCARBAMATE

The title compound was prepared according to the procedure described in Example 128 from 2-{4-[(3-amino-4,6-dimethyl-2-pyridinyl)amino]phenyl}ethyl(4-methylphenyl)sulfonylcarbamate.

$^1$H-NMR (CDCl$_3$) δ: 7.92 (2H, d, J=8.4 Hz), 7.36–7.22 (6H, m), 6.88 (1H, s), 4.32 (2H, t, J=6.6 Hz), 2.93 (2H, t, J=6.6 Hz), 2.72 (3H, s), 2.62 (3H, s), 2.48 (3H, s), 2.41 (3H, s)

MS (ESI) m/z: 511 ([M+H]$^+$), 509 ([M−H]$^−$)

EXAMPLE 310

2-{4-[5,7-DIMETHYL-2-(METHYLSULFONYL)-3H-IMIDAZO[4,5-b]PYRIDIN-3-YL]PHENYL}ETHYL(4-METHYLPHENYL)SULFONYLCARBAMATE

To a stirred solution of 2-{4-[5,7-dimethyl-2-(methylsulfanyl)-3H-imidazo[4,5-b]pyridin-3-yl]phenyl}ethyl(4-methylphenyl)sulfonylcarbamate (100 mg, 0.20 mmol) in AcOH (1 ml) was added a solution of KMnO$_4$ (62 mg, 0.39 mmol) in water (2 ml) at room temperature. After 1 hour, the mixture was poured into ice-sat. NaHCO$_3$ aq. and extracted with CH$_2$Cl$_2$. The organic layer was dried over MgSO$_4$, and the filtered. After concentration in vacuo, the residue was purified by preparative TLC (CH$_2$Cl$_2$/MeOH=10/1) to afford 70 mg (66%) of the title compounds.

$^1$H-NMR (CDCl$_3$) δ: 7.91 (2H, d, J=8.4 Hz), 7.47 (2H, d, J=8.2 Hz), 7.34–7.26 (4H, m), 7.08 (1H, s), 4.35 (2H, t, J=6.7 Hz), 3.45 (3H, s), 2.96 (2H, t, J=6.7 Hz), 2.68 (3H, s), 2.55 (3H, s), 2.42 (3H, s)

MS (ESI) m/z: 543 ([M+H]$^+$), 541 ([M−H]$^−$)

EXAMPLE 311

5-ACETYL-2-(METHYLAMINO)-1-(4-{2-[({[(4-METHYLPHENYL)SULFONYL]AMINO}CARBONYL)AMINO]ETHYL}PHENYL)-1H-BENZIMIDAZOLE

The title compound was prepared according to the procedure described in Example 129 from N-{[(2-{4-[(4-acetyl-2-aminophenyl)amino]phenyl}ethyl)amino]carbonyl}-4-methylbenzenesulfonamide.

$^1$H-NMR (CDCl$_3$) δ: 8.06 (1H, s), 7.75–7.66 (3H, m), 7.38–7.26 (6H, m), 6.89 (1H, d, J=8.3 Hz), 6.60 (1H, br.s), 3.55 (2H, dd, J=12.5 and 6.6 Hz), 3.08 (3H, s), 2.91 (2H, t, J=6.6 Hz), 2.61 (3H, s), 2.38 (3H, s)

MS (ESI) m/z: 506 ([M+H]$^+$), 504 ([M−H]$^−$)

EXAMPLE 312

2-{4-[6-CHLORO-2-(3-PYRIDINYL)-5-(TRIFLUOROMETHYL)-1H-BENZIMIDAZOL-1-YL]PHENYL}ETHYL(4-METHYLPHENYL)SULFONYLCARBAMATE

STEP 1. 2-{4-[6-chloro-2-(3-pyridinyl)-5-(trifluoromethyl)-1H-benzimidazol-1-yl]phenyl}ethanol The title compound was prepared according to the procedure described in Example 138 from 2-(4-{[2-amino-5-chloro-4-(trifluoromethyl)phenyl]amino}phenyl)ethanol.

$^1$H-NMR (CDCl$_3$) δ: 8.70 (1H, dd, J=2.2 and 0.7 Hz), 8.62 (1H, dd, J=4.5 and 1.7 Hz), 8.23 (1H, s), 8.01–7.97 (1H, m), 7.45 (2H, dd, J=6.5 and 2.2 Hz), 7.37–7.24 (7H, m), 3.97 (2H, t, J=6.6 Hz), 2.99 (2H, t, J=6.6 Hz)

MS (ESI) m/z: 418 ([M+H]$^+$), 476 ([M+CF$_3$CO$_2$]$^−$)

STEP 2. 2-{4-[6-chloro-2-(3-pyridinyl)-5-(trifluoromethyl)-1H-benzimidazol-1-yl]phenyl}ethyl(4-methylphenyl)sulfonylcarbamate The title compound was prepared according to the procedure described in Example 3 from 2-{4-[6-chloro-2-(3-pyridinyl)-5-(trifluoromethyl)-1H-benzimidazol-1-yl]phenyl}ethanol.

$^1$H-NMR (CDCl$_3$) δ: 8.73 (1H, dd, J=4.9 and 1.8 Hz), 8.40–8.36 (1H, m), 8.23 (1H, s), 7.91 (1H, dd, J=2.2 and 0.7 Hz), 7.84–7.80 (2H, m), 7.49–7.43 (2H, m), 7.31–7.17 (6H, m), 4.44 (2H, t, J=6.2 Hz), 3.02 (2H, t, J=6.2 Hz), 2.41 (3H, s)

MS (ESI) m/z: 615 ([M+H]$^+$), 613 ([M−H]$^−$)

EXAMPLE 313

2-{4-[6-CHLORO-2-(4-PYRIDINYL)-5-(TRIFLUOROMETHYL)-1H-BENZIMIDAZOL-1-YL]PHENYL}ETHYL(4-METHYLPHENYL)SULFONYLCARBAMATE

STEP 1. 2-{4-[6-chloro-2-(4-pyridinyl)-5-(trifluoromethyl)-1H-benzimidazol-1-yl]phenyl}ethanol The title compound was prepared according to the procedure described in Example 138 from 2-(4-{[2-amino-5-chloro-4-(trifluoromethyl)phenyl]amino}phenyl)ethanol.

$^1$H-NMR (CDCl$_3$) δ: 8.60 (2H, dd, J=4.6 and 1.7 Hz), 8.25 (1H, s), 7.49–7.44 (4H, m), 7.37 (1H, s), 7.27–7.23 (2H, m), 4.00 (2H, t, J=6.4 Hz), 3.02 (2H, t, J=6.4 Hz)

MS (ESI) m/z: 418 ([M+H]$^+$), 476 ([M+CF$_3$CO$_2$]$^-$)

STEP 2. 2-{4-[6-chloro-2-(4-pyridinyl)-5-(trifluoromethyl)-1H-benzimidazol-1-yl]phenyl}ethyl(4-methylphenyl)sulfonylcarbamate The title compound was prepared according to the procedure described in Example 3 from 2-{4-[6-chloro-2-(4-pyridinyl)-5-(trifluoromethyl)-1H-benzimidazol-1-yl]phenyl}ethanol.

$^1$H-NMR (CDCl$_3$) δ: 8.60 (2H, dd, J=4.8 and 1.5 Hz), 8.27 (1H, s), 7.89 (2H, d, J=8.3 Hz), 7.44–7.18 (9H, m), 4.39 (2H, t, J=6.4 Hz), 3.03 (2H, t, J=6.4 Hz), 2.40 (3H, s)

MS (ESI) m/z: 615 ([M+H]$^+$), 613 ([M–H]$^-$)

EXAMPLE 314

2-{4-[6-CHLORO-2-(2-METHYLPHENYL)-5-(TRIFLUOROMETHYL)-1H-BENZIMIDAZOL-1-YL]PHENYL}ETHYL(4-METHYLPHENYL)SULFONYLCARBAMATE

STEP 1. 2-{4-[6-chloro-2-(2-methylphenyl)-5-(trifluoromethyl)-1H-benzimidazol-1-yl]phenyl}ethanol The title compound was prepared according to the procedure described in Example 138 from 2-(4-{[2-amino-5-chloro-4-(trifluoromethyl)phenyl]amino}phenyl)ethanol.

$^1$H-NMR (CDCl$_3$) δ: 8.22 (1H, s), 7.47 (1H, s), 7.33–7.10 (8H, m), 3.89 (2H, t, J=6.4 Hz), 2.89 (2H, t, J=6.4 Hz), 2.20 (3H, s)

MS (ESI) m/z: 431 ([M+H]$^+$)

STEP 2. 2-{4-[6-chloro-2-(2-methylphenyl)-5-(trifluoromethyl)-1H-benzimidazol-1-yl]phenyl}ethyl(4-methylphenyl)sufonylcarbamate The title compound was prepared according to the procedure described in Example 3 from 2-{4-[6-chloro-2-(2-methylphenyl)-5-(trifluoromethyl)-1H-benzimidazol-1-yl]phenyl}ethanol.

$^1$H-NMR (CDCl$_3$) δ: 8.24 (1H, s), 7.78 (2H, d, J=8.2 Hz), 7.46 (1H, s), 7.35–7.09 (8H, m), 7.00 (2H, d, J=8.4 Hz), 4.27 (2H, t, J=6.8 Hz), 2.88 (2H, t, J=6.8 Hz), 2.41 (3H, s), 2.11 (3H, s)

MS (ESI) m/z: 628 ([M+H]$^+$), 489 ([M+CH$_3$CO$_2$]$^-$)

EXAMPLE 315

2-{4-[6-CHLORO-2-(1,3-THIAZOL-2-YL)-5-(TRIFLUOROMETHYL)-1H-BENZIMIDAZOL-1-YL]PHENYL}ETHYL(4-METHYLPHENYL)SULFONYLCARBAMATE

STEP 1. 2-{4-[6-chloro-2-(1,3-thiazol-2-yl)-5-(trifluoromethyl)-1H-benzimidazol-1-yl]phenyl}ethanol The title compound was prepared according to the procedure described in Example 138 from 2-(4-{[2-amino-5-chloro-4-(trifluoromethyl)phenyl]amino}phenyl)ethanol.

$^1$H-NMR (CDCl$_3$) δ: 8.23 (1H, s), 7.75 (1H, d, J=3.1 Hz), 7.47–7.45 (3H, m), 7.36–7.27 (3H, m), 3.99 (2H, t, J=6.4 Hz), 3.03 (2H, t, J=6.4 Hz)

MS (ESI) m/z: 424 ([M+H]$^+$), 482 ([M+CH$_3$CO$_2$]$^-$)

STEP 2. 2-{4-[6-chloro-2-(1,3-thiazol-2-yl)-5-(trifluoromethyl)-1H-benzimidazol-1-yl]phenyl}ethyl(4-methylphenyl)sulfonylcarbamate The title compound was prepared according to the procedure described in Example 3 from 2-{4-[6-chloro-2-(1,3-thiazol-2-yl)-5-(trifluoromethyl)-1H-benzimidazol-1-yl]phenyl}ethanol.

$^1$H-NMR (CDCl$_3$) δ: 8.23 (1H, s), 7.91 (2H, d, J=8.4 Hz), 7.74 (1H, d, J=3.1 Hz), 7.46 (1H, d, J=3.1 Hz), 7.38–7.26 (7H, m), 4.40 (2H, t, J=6.8 Hz), 3.04 (2H, t, J=6.8 Hz), 2.42 (3H, s)

MS (ESI) m/z: 621 ([M+H]$^+$), 619 ([M–H]$^-$)

EXAMPLE 316

2-{4-[6-CHLORO-2-(1H-IMIDAZOL-4-YL)-5-(TRIFLUOROMETHYL)-1H-BENZIMIDAZOL-1-YL]PHENYL}ETHYL(4-METHYLPHENYL)SULFONYLCARBAMATE

STEP 1. 2-{4-[6-chloro-2-(1H-imidazol-4-yl)-5-(trifluoromethyl)-1H-benzimidazol-1-yl]phenyl}ethanol The title compound was prepared according to the procedure described in Example 138 from 2-(4-{[2-amino-5-chloro-4-(trifluoromethyl)phenyl]amino}phenyl)ethanol.

$^1$H-NMR (CDCl$_3$/CD$_3$OD=4/1) δ: 8.09 (1H, s), 7.65 (1H, s), 7.50 (2H, d, J=8.7 Hz), 7.33 (2H, d, J=8.2 Hz), 7.25 (1H, s), 6.91 (1H, s), 3.93 (2H, t, J=6.4 Hz), 3.00 (2H, t, J=6.4 Hz)

MS (ESI) m/z: 407 ([M+H]$^+$), 405 ([M–H]$^-$)

STEP 2. 2-{4-[6-chloro-2-(1H-imidazol-4-yl)-5-(trifluoromethyl)-1H-benzimidazol-1-yl]phenyl}ethyl(4-methylphenyl)sulfonylcarbamate The title compound was prepared according to the procedure described in Example 3 from 2-{4-[6-chloro-2-(1H-imidazol-4-yl)-5-(trifluoromethyl)-1H-benzimidazol-1-yl]phenyl}ethanol.

MS (ESI) m/z: 604 ([M+H]$^+$), 602 ([M–H]$^-$)

EXAMPLE 317

2-[4-(5,6-DIMETHYL-1H-BENZIMIDAZOL-1-YL)PHENYL]ETHYL(4-METHYLPHENYL)SULFONYLCARBAMATE

STEP 1. 4-(2-hydroxyethyl)phenylboronic acid

To a stirred solution of 4-bromophenethylalcohol (5.00 g, 24.9 mmol) in THF (80 ml) was added a solution of 1.5M n-BuLi in hexane (39.8 ml, 59.7 mmol) at −78° C. over 30 min. After 1 hour, a solution of B(O$^i$Pr)$_3$ (8.61 ml, 37.3 mmol) in THF (20 ml) was added slowly to the mixture at −78° C. The resultant mixture was warmed to room temperature, and treated with 2M HCl (100 ml) for 1 hour. This was extracted with CH$_2$Cl$_2$ and dried over MgSO$_4$, then filtered. After evaporation in vacuo, the residue was purified by silica-gel column chromatography eluting with CH$_2$Cl$_2$/MeOH=20/1 to afford 2.61 g (63%) of the title compound.

$^1$H-NMR (CD$_3$OD) δ: 7.64–7.48 (2H, m), 7.19–7.13 (2H, m), 3.70 (2H, t, J=7.2 Hz), 2.77 (2H, t, J=7.2 Hz)

MS (ESI) m/z: 165 ([M−H]$^-$)

STEP 2. 4-{2-[({[(4-methylphenyl)sulfonyl]amino}carbonyl)oxy]ethyl}phenylboronic acid 4-(2-hydroxyethyl)phenylboronic acid (1.00 g, 6.02 mmol) was treated with pTsNCO (1.01 ml, 6.63 mmol) and pyridine (90 ml) at room temperature for 2 hours. The mixture was poured into ice-2M HCl and extracted with EtOAc. The organic layer was dried over MgSO$_4$, and filtered. After removal of solvent, the residue was purified by silica-gel column chromatography eluting with CH$_2$Cl$_2$/MeOH=20/1 to afford 2.20 g (quant.) of the title compound.

$^1$H-NMR (DMSO-d$_3$) δ: 11.95 (1H, br.s), 7.97 (1H, s), 7.75–7.67 (2H, m), 7.40 (2H, d, J=8.6 Hz), 7.13 (2H, d, J=7.7 Hz), 4.18 (2H, t, J=6.6 Hz), 2.81 (2H, t, J=6.6 Hz), 2.40 (3H, s)

MS (ESI) m/z: 381 ([M+NH4]$^+$), 362 ([M−H]$^-$)

STEP 3. 2-[4-(5,6-dimethyl-1H-benzimidazol-1-yl)phenyl]ethyl(4-methylphenyl)sulfonylcarbamate A mixture of 4-{2-[({[(4-methylphenyl)sulfonyl]amino}carbonyl)oxy]ethyl}phenylboronic acid (100 mg, 0.28 mmol), 5,6-dimethylbenzimidazole (40 mg, 0.28 mmol), Cu(OAc)$_2$ (60 mg, 0.33 mmol), triethylamine (115 μl, 0.83 mmol), MS4A (100 mg), and CH$_2$Cl$_2$ (4 ml) was stirred at room temperature for 1 week. After filtration through a bed of celite, the filtrate was diluted with CH$_2$Cl$_2$, and washed with water. The organic fraction was dried over MgSO$_4$ and filtered. After concentration under reduced pressure, the residue was purified by preparative TLC (CH$_2$Cl$_2$/MeOH=10/1) to afford 28 mg (22%) of the title compound.

$^1$H-NMR (CDCl$_3$) δ: 7.82 (2H, d, J=8.4 Hz), 7.72 (1H, s), 7.57 (1H, s), 7.33 (2H, d, J=8.1 Hz), 7.12 (2H, d, J=8.4 Hz), 7.07 (1H, s), 7.01 (2H, d, J=8.4 Hz), 4.39 (2H, t, J=6.1 Hz), 2.94 (2H, t, J=6.1 Hz), 2.42 (3H, s), 2.39 (3H, s), 2.26 (3H, s)

MS (ESI) m/z: 464 ([M+H]$^+$), 462 ([M−H]$^-$)

EXAMPLE 318

6-CHLORO-5-CYANO-2-ETHYL-1-(4-{2-[({[(4-METHYLPHENYLSULFONYL]AMINO}CARBONYL)AMINO]ETHYL}PHENYL)-1H-BENZIMIDAZOLE

STEP 1. 6-chloro-1-[4-(2-chloroethyl)phenyl]-2-ethyl-1H-benzimidazole-5-carbonitrile The title compound was prepared according to the procedure described in step 7 of Example 1 from 6-chloro-2-ethyl-1-[4-(2-hydroxyethyl)phenyl]-1H-benzimidazole-5-carbonitrile (Example 111, step 4).

$^1$H-NMR (CDCl$_3$) δ 8.07 (1H, s), 7.50 (2H, d, J=8.4 Hz), 7.30 (2H, d, J=8.4 Hz), 7.19 (1H, s), 3.83 (2H, t, J=7.1 Hz), 3.22 (2H, t, J=7.1 Hz), 2.79 (2H, q, J=7.5 Hz), 1.37 (3H, t, J=7.5 Hz).

STEP 2. 1-[4-(2-azidoethyl)phenyl]-6-chloro-2-ethyl-1H-benzimidazole-5-carbonitrile The title compound was prepared according to the procedure described in step 8 of Example 1 from 6-chloro-1-[4-(2-chloroethyl)phenyl]-2-ethyl-1H-benzimidazole-5-carbonitrile (step 1).

$^1$H-NMR (CDCl$_3$) δ 8.07 (1H, s), 7.49 (2H, d, J=8.4 Hz), 7.29 (2H, d, J=8.4 Hz), 7.18 (1H, s), 3.64 (2H, t, J=7.0 Hz), 3.04 (2H, t, J=7.0 Hz), 2.79 (2H, q, J=7.6 Hz), 1.36 (3H, t, J=7.6 Hz).

STEP 3. 1-[4-(2-aminoethyl)phenyl]-6-chloro-2-ethyl-1H-benzimidazole-5-carbonitrile The title compound was prepared according to the procedure described in step 7 of Example 37 from 1-[4-(2-azidoethyl)phenyl]-6-chloro-2-ethyl-1H-benzimidazole-5-carbonitrile (step 2).

$^1$H-NMR (CDCl$_3$) δ 8.06 (1H, s), 7.46 (2H, d, J=8.1 Hz), 7.26 (2H, d, J=8.1 Hz), 7.19 (1H, s), 3.09 (2H, t, J=7.1 Hz), 2.89 (2H, t, J=7.1 Hz), 2.79 (2H, q, J=7.6 Hz), 1.36 (3H, t, J=7.6 Hz).

STEP 4. 6-chloro-5-cyano-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 1-[4-(2-aminoethyl)phenyl]-6-chloro-2-ethyl-1H-benzimidazole-5-carbonitrile (step 3).

mp 219–224° C.; IR (KBr) v: 3388, 2229, 1708, 1618, 1514, 1466, 1344, 1161, 1089 cm$^{-1}$.

MS (ESI) m/z 522 (M+H)$^+$, 520 (M−H)$^-$; $^1$H-NMR (DMSO-d$_6$) δ 8.38 (1H, s), 7.77 (2H, d, J=8.2 Hz), 7.31–7.49 (6H, m), 7.32 (1H, s), 6.53 (1H, br.s), 3.26–3.28 (2H, m), 2.69–2.81 (4H, m), 2.35 (3H, s), 1.25 (3H, t, J=7.6 Hz).

EXAMPLE 319

6-CHLORO-5-(DIMETHYLAMINO)-2-ETHYL-1-(4-{2-[({[(4-METHYLPHENYL)SULFONYL]AMINO}CARBONYL)AMINO]ETHYL}PHENYL)-1H-BENZIMIDAZOLE

STEP 1. N-{6-chloro-1-[4-(2-chloroethyl)phenyl]-2-ethyl-1H-benzimidazol-5-yl}-N,N-dimethylamine A mixture of 6-Chloro-1-[4-(2-chloroethyl)phenyl]-2-ethyl-1H-benzimidazol-5-ylamine (Example 110, step 6, 100 mg, 0.3 mmol) and NaBH$_4$(153 mg, 4 mmol) in THF (5 ml) was added to the mixture of 38% folmaldehyde (0.5 ml, 5.6 mmol) and 3M aqueous H$_2$SO$_4$ (0.4 ml, 0.12 mmol) at 0° C. The mixture was stirred at room temperature for 5 h. The reaction mixture was poured into water, and extracted with ethyl acetate (100 ml). The organic layer was washed with brine (50 ml), then dried (Na$_2$SO$_4$). After removal of solvent, the crude product was purified by flash column chromatography eluting with hexane/ethyl acetate (1:2) to afford 48 mg (46%) of the title compound as white solids.

MS (EI) m/z: 361 (M$^+$).

$^1$H-NMR (CDCl$_3$) δ: 7.54 (1H, s), 7.44 (2H, d, J=8.3 Hz), 7.29 (2H, d, J=8.3 Hz), 7.13 (1H, s), 3.82 (2H, t, J=7.0 Hz), 3.19 (2H, t, J=7.0 Hz), 2.82 (6H, s), 2.75 (2H, q, J=7.6 Hz), 1.35 (3H, t, J=7.6 Hz).

STEP 2. N-{1-[4-(2-azidoethyl)phenyl]-6-chloro-2-ethyl-1H-benzimidazol-5-yl}-N,N-dimethylamine The title compound was prepared according to the procedure described in step 8 of Example 1 from N-{6-chloro-1-[4-(2-chloroethyl)phenyl]-2-ethyl-1H-benzimidazol-5-yl}dimethylamine (step 1).

¹H-NMR (CDCl₃) δ: 7.54 (1H, s), 7.43 (2H, d, J=8.2 Hz), 7.29 (2H, d, J=8.2 Hz), 7.12 (1H, s), 3.62 (2H, t, J=7.0 Hz), 3.01 (2H, t, J=7.0 Hz), 2.82 (6H, s), 2.75 (2H, q, J=7.6 Hz), 1.34 (2H, t, J=7.6 Hz).

STEP 3. N-{1-[4-(2-aminoethyl)phenyl]-6-chloro-2-ethyl-1H-benzimidazol-5-yl}-N,N-dimethylamine The title compound was prepared according to the procedure described in step 7 of Example 37 from N-{1-[4-(2-azidoethyl)phenyl]-6-chloro-2-ethyl-1H-benzimidazol-5-yl}-N,N-dimethylamine (step 2).

¹H-NMR (CDCl₃) δ: 7.54 (1H, s), 7.41 (2H, d, J=8.1 Hz), 7.27 (2H, d, J=8.1 Hz), 7.13 (1H, s), 3.08 (2H, t, J=6.9 Hz), 2.87 (2H, t, J=6.9 Hz), 2.82 (6H, s), 2.75 (2H, q, J=7.6 Hz), 1.35 (3H, t, J=7.6 Hz).

STEP 4. 6-chloro-5-(dimethylamino)-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from N-{1-[4-(2-aminoethyl)phenyl]-6-chloro-2-ethyl-1H-benzimidazol-5-yl}-N,N-dimethylamine (step 3).

m.p.: 108–114° C.

MS (ESI) m/z: 540 (MH⁺), 538 ([M−H]⁻).

¹H-NMR (CDCl₃) δ: 7.73 (2H, d,=8.0 Hz), 7.54 (1H, s), 7.25–7.39 (6H, m), 7.11 (1H, s), 6.73 (1H, br.s), 3.58 (2H, q, J=6.9 Hz), 2.94 (2H, t, J=6.9 Hz), 2.71–2.82 (8H, m), 2.40 (3H, s), 1.33 (3H, t, J=7.6 Hz).

EXAMPLE 320

6-CHLORO-2-ETHYL-5-(METHYLAMINO)-1-(4-{2-[({[(4-METHYLPHENYL)SULFONYL]AMINO}CARBONYL)AMINO]ETHYL}PHENYL)-1H-BENZIMIDAZOLE

STEP 1. 6-chloro-1-[4-(2-chloroethyl)phenyl]-2-ethyl-1H-benzimidazol-5-ylformamide A solution of acetic anhydride (0.14 ml) in THF (5 ml) was added formic acid (0.06 ml, 1.65 mmol) at 0° C. under nitrogen and the mixture was stirred at 60° C. for 2 h. Then the mixture was recooled to 0° C. and was added 6-Chloro-1-[4-(2-chloroethyl)phenyl]-2-ethyl-1H-benzimidazol-5-ylamine(Example 110, step 6, 100 mg, 0.3 mmol) in THF (2 ml). The mixture was stirred at room temperature for 2 h. The volatile component was removed under reduced pressure, and the residue was dissolved with ethyl acetate (100 ml). The organic layer was washed with 2N aqueous NaOH (50 ml), brine (50 ml), then dried (Na2SO4). After removal of solvent, the crude product was purified by flash column chromatography eluting with hexane/ethyl acetate (1:10) to afford 68 mg (67%) of the title compound as pale yellow solids.

MS (EI) m/z: 361 (M⁺).

¹H-NMR (CDCl₃) δ: 8.53–8.76 (1H, br.s), 7.66 (1H, s), 7.44–7.48 (2H, m), 7.26–7.31 (2H, m), 7.18 (1H, s), 3.83 (2H, t, J=6.9 Hz), 3.20 (2H, t, J=6.9 Hz), 2.78 (2H, q, J=7.4 Hz), 1.32–1.39 (3H, m).

STEP 2. N-{6-chloro-1-[4-(2-chloroethyl)phenyl]-2-ethyl-1H-benzimidazol-5-yl}-N-methylamine A solution of (6-chloro-1-[4-(2-chloroethyl)phenyl]-2-ethyl-1H-benzimidazol-5-ylformamide, step 1, 112 mg, 0.3 mmol) in THF (15 ml) was added Me₂S BH₃ (0.07 ml, 0.77 mmol) under nitrogen at room temperature. The mixture was refluxed for 1 h. Then the mixture was cooled to room temperature and was added methanol (3 ml) and 2N aqueous HCl (12 ml). The mixture was stirred at 70° C. for 30 min. The volatile component was removed under reduced pressure, and the residue was dissolved with ethyl acetate (100 ml). The organic layer was washed with saturated aqueous NaHCO₃ (50 ml), brine (50 ml), then dried (Na2SO4). After removal of solvent, the crude product was purified by flash column chromatography eluting with hexane/ethyl acetate (1:4) to afford 93 mg (87%) of the title compound as white solids.

MS (EI) m/z: 347 (M⁺).

¹H-NMR (CDCl₃) δ: 7.42 (2H, d, J=8.2 Hz), 7.29 (2H, d, J=8.2 Hz), 7.04 (1H, s), 7.03 (1H, s), 3.81 (2H, t, J=6.9 Hz), 3.18 (2H, t, J=6.9 Hz), 2.95 (3H, s), 2.75 (2H, q, J=7.6 Hz), 1.34 (3H, t, J=7.6 Hz).

STEP 3. N-{1-[4-(2-azidoethyl)phenyl]-6-chloro-2-ethyl-1H-benzimidazol-5-yl}-N-methylamine The title compound was prepared according to the procedure described in step 8 of Example 1 from N-{6-chloro-1-[4-(2-chloroethyl)phenyl]-2-ethyl-1H-benzimidazol-5-yl}-N-methylamine (step 2).

¹H-NMR (CDCl₃) δ: 7.42 (2H, d, J=8.3 Hz), 7.29 (2H, d, J=8.3 Hz), 7.04–7.03 (2H, m), 4.19 (1H, br.s), 3.61 (2H, t, J=7.0 Hz), 3.00 (2H, t, J=7.0 Hz), 2.95 (3H, s), 2.75 (2H, q, J=7.6 Hz), 1.33 (3H, t, J=7.6 Hz).

STEP 4. N-{1-[4-(2-aminoethyl)phenyl]-6-chloro-2-ethyl-1H-benzimidazol-5-yl}-N-methylamine The title compound was prepared according to the procedure described in step 7 of Example 37 from N-{1-[4-(2-azidoethyl)phenyl]-6-chloro-2-ethyl-1H-benzimidazol-5-yl}-N-methylamine (step 3).

¹H-NMR (CDCl₃) δ: 7.39 (2H, d, J=8.4 Hz), 7.25 (2H, d, J=8.4 Hz), 7.06 (1H, s), 7.03 (1H, s), 3.64 (2H, br.s), 3.15 (2H, t, J=7.2 Hz), 2.94–2.99 (5H, m), 2.73 (2H, q, J=7.5 Hz), 1.32 (3H, t, J=7.5 Hz).

STEP 5. 6-chloro-2-ethyl-5-(methylamino)-1-(4-{2-[({[(4-methylphenyl)sulfonyl]amino}carbonyl)amino]ethyl}phenyl)-1H-benzimidazole The title compound was prepared according to the procedure described in step 10 of Example 1 from N-{1-[4-(2-aminoethyl)phenyl]-6-chloro-2-ethyl-1H-benzimidazol-5-yl}-N-methylamine (step 4).

m.p.: 95–100° C.

MS (ESI) m/z: 526 (MH⁺), 524 ([M−H]⁻).

¹H-NMR (CDCl₃) δ: 7.73 (2H, d, J=8.4 Hz), 7.23–7.36 (7H, m), 7.03 (1H, s), 3.57 (2H, t, J=6.6 Hz), 2.89–2.94 (5H, m), 2.73 (2H, q, J=7.4 Hz), 1.32 (3H, t, J=7.4 Hz).

EXAMPLE 321

4-CYANO-2-ETHYL-1-(4-{2-[({[(4-METHYLPHENYL)SULFONYL]AMINO}CARBONYL)AMINO]ETHYL}PHENYL)-1H-BENZIMIDAZOLE

STEP 1. 3-chloro-2-nitrobenzamide

A mixture of 3-chloro-2-nitro-benzoic acid (1 g, 4.9 mmol) and thionyl chloride (9 ml) was stirred at 80° C. for 1 h. The thionyl chloride was removed under reduced pressure, and the residue was dissolved with dichloromethane (15 ml). The mixture was cooled to 0° C. and was added 30% aqueous NH3 (2 ml) dropwise. The mixture was stirred at 0° C. for 25 min. The reaction mixture was poured into water and extracted with ethyl acetate (300 ml). The organic layer was washed with saturated aqueous Na₂CO₃ (100 ml), and brine (100 ml). This organic phase was dried (Na$_2$SO$_4$) and concentrated under reduced pressure to give 1.2 g (quant.) of the title compound as pale orange solids.

$^1$H-NMR (CDCl$_3$) δ: 7.68–7.92 (3H, m).

STEP 2. 3-chloro-2-nitrobenzonitrile

A solution of 3-chloro-2-nitrobenzamide (step 1, 1.2 g, 4.9 mmol) in DMF (8 ml) was added thionyl chloride (2 ml, 24.8 mmol) in DMF (3 ml) dropwise at room temperature. The mixture was stirred at 120° C. for 2.5 h. The mixture was poured into ice-water and extracted with ethyl acetate (200 ml). The organic layer was washed with saturated aqueous NaHCO$_3$ (100 ml), brine (100 ml), then dried (MgSO4), and concentrated. The residue was purified by flash chromatography eluting with hexane/ethyl acetate (3:1/1:2) to give 1 g (quant.) of the title compound as pale yellow solids.

$^1$H-NMR (CDCl$_3$) δ: 7.61–7.68 (1H, m), 7.74–7.78 (2H, m).

STEP 3. 2-[4-(3-cyano-2-nitroanilino)phenyl]ethanol

The title compound was prepared according to the procedure described in step 3 of Example 1 from 3-chloro-2-nitrobenzonitrile (step 2) and 4-aminophenylethyl alcohol.

MS (EI) m/z: 283 (M$^+$).

$^1$H-NMR (CDCl$_3$) δ: 9.37 (1H, br.s), 7.15–7.41 (7H, m), 3.91 (2H, t, J=6.4 Hz), 2.91 (2H, t, J=6.4 Hz).

STEP 4. 2-amino-3-[4-(2-hydroxyethyl)anilino]benzonitrile

The title compound was prepared according to the procedure described in step 2 of Example 40 from 2-[4-(3-Cyano-2-nitroanilino)phenyl]ethanol (step 3).

MS (EI) m/z: 253 (M$^+$).

$^1$H-NMR (CDCl$_3$) δ: 7.22–7.28 (2H, m), 7.10 (2H, d, J=8.4 Hz), 6.69–6.75 (3H, m), 5.13 (1H, br.s), 4.54 (2H, br.s), 3.84 (2H, t, J=6.4 Hz), 2.80 (2H, t, J=6.4 Hz).

STEP 5. 2-[4-(4-cyano-2-ethyl-1H-benzimidazol-1-yl)phenyl]ethyl propionate

The title compound was prepared according to the procedure described in step 5 of Example 1 from 2-amino-3-[4-(2-hydroxyethyl)anilino]benzonitrile (step 4).

TLC, Rf=0.6, hexane:ethyl acetate (1:1).

STEP 6. 2-ethyl-1-[4-(2-hydroxyethyl)phenyl]-1H-benzimidazole-4-carbonitrile

The title compound was prepared according to the procedure described in step 6 of Example 1 from 2-[4-(4-cyano-2-ethyl-1H-benzimidazol-1-yl)phenyl]ethyl propionate (step 5).

MS (EI) m/z: 291 (M$^+$).

$^1$H-NMR (CDCl$_3$) δ: 7.58 (1H, d, J=6.3 Hz), 7.49 (2H, d, J=8.3 Hz), 7.19–7.32 (4H, m), 4.01 (2H, t, J=6.4 Hz), 3.02 (2H, t, J=6.4 Hz), 2.86 (2H, q, J=7.6 Hz), 1.34 (3H, t, J=7.6 Hz).

STEP 7. 1-[4-(2-chloroethyl)phenyl]-2-ethyl-1H-benzimidazole-4-carbonitrile

The title compound was prepared according to the procedure described in step 7 of Example 1 from 2-ethyl-1-[4-(2-hydroxyethyl)phenyl]-1H-benzimidazole-4-carbonitrile (step 6).

$^1$H-NMR (DMSO-d$_6$) δ: 7.72 (1H, dd, J=1.2 Hz, 7.4 Hz), 7.51–7.60 (4H, m), 7.30–7.42 (2H, m), 3.97 (2H, t, J=7.0 Hz), 3.18 (2H, t, J=7.0 Hz), 2.79 (2H, q, J=7.6 Hz), 1.26 (3H, t, J=7.6 Hz).

STEP 8. 1-[4-(2-azidoethyl)phenyl]-2-ethyl-1H-benzimidazole-4-carbonitrile

The title compound was prepared according to the procedure described in step 8 of Example 1 from 1-[4-(2-chloroethyl)phenyl]-2-ethyl-1H-benzimidazole-4-carbonitrile (step 7).

$^1$H-NMR (CDCl$_3$) δ: 7.59 (1H, dd, J=1.2 Hz, 7.3 Hz), 7.48 (2H, d, J=8.0 Hz), 7.19–7.32 (4H, m), 3.63 (2H, t, J=6.6 Hz), 3.03 (2H, t, J=6.6 Hz), 2.84 (2H, q, J=7.6 Hz), 1.31 (3H, t, J=7.6 Hz).

STEP 9. 1-[4-(2-aminoethyl)phenyl]-2-ethyl-1H-benzimidazole-4-carbonitrile

The title compound was prepared according to the procedure described in step 7 of Example 37 from 1-[4-(2-azidoethyl)phenyl]-2-ethyl-1H-benzimidazole-4-carbonitrile (step 8).

$^1$H-NMR (CDCl$_3$) δ: 7.58 (1H, dd, J=1.3 Hz, 7.4 Hz), 7.44 (2H, d, J=8.2 Hz), 7.19–7.32 (4H, m), 3.08 (2H, t, J=6.7 Hz), 2.81–2.93 (4H, m), 1.33 (3H, t, J=7.5 Hz).

STEP 10. 4-cyano-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 1-[4-(2-aminoethyl)phenyl]-2-ethyl-1H-benzimidazole-4-carbonitrile (step 9).

m.p.: 95–103° C.

IR (KBr) ν: 2225, 1676, 1516, 1433, 1340, 1161, 1091, 794, 663 cm$^{-1}$.

MS (ESI) m/z: 488 (MH$^+$), 486 ([M–H]$^-$).

$^1$H-NMR (CDCl$_3$) δ: 7.72 (2H, d, J=8.1 Hz), 7.59 (1H, d, J=7.0 Hz), 7.42 (2H, d, J=8.1 Hz), 7.18–7.32 (6H, m), 6.72 (1H, br.s), 3.57 (2H, t, J=7.1 Hz), 2.96 (2H, t, J=7.1 Hz), 2.85 (2H, q, J=7.6 Hz), 2.41 (3H, s), 1.33 (3H, t, J=7.6 Hz).

EXAMPLE 322

2-ETHYL-1-(4-{2-[({[(4-METHYLPHENYL)SULFONYL]AMINO}CARBONYL)AMINO]ETHYL}PHENYL)-1H-BENZIMIDAZOLE-4-CARBOXAMIDE

STEP 1. 2-ethyl-1-(4-{2-[({[(4-methylphenyl)sulfonyl]amino}carbonyl)amino]ethyl}phenyl)-1H-benzimidazole-4-carboxamide To a stirred suspension of 2-{4-[(3-amino-4,6-dimethyl-2-pyridinyl)amino]phenyl}ethanol (step 4, 820 mg, 3.3 mmol) in toluene (30 ml) was added dropwise propionyl chloride (630 mg, 6.8 mmol) at 0° C., and the reaction mixture was refluxed for 1.5 h. After cooling, the mixture was poured into water (50 ml) and extracted with ethyl acetate (100 ml). The organic layer was washed with 2N aqueous NaOH (50 ml) and brine (50 ml), then dried (Na2SO4). The solvent was removed under reduced pressure and the residue was dissolved with THF(20 ml) and methanol (20 ml). The mixture was added 4N aqueous LiOH (10 ml) and stirred at room temperature for 14 h. The mixture was evaporated. The residue was dissolved with ethyl acetate (100 ml) and washed with water (50 ml). The organic layer was washed with brine (50 ml), and dried (Na2SO4). After removal of solvent, the crude product was purified by flash column chromatography eluting with hexane/ethyl acetate (1:2/1:5/0:1) to afford 260 mg (26%) of the title compound as white solids.

MS (EI) m/z: 309 (M$^+$).

$^1$H-NMR (CDCl$_3$) δ: 9.81 (1H, br.s), 8.13 (1H, dd, J=2.0 Hz, 7.0 Hz), 7.47 (2H, d, J=8.0 Hz), 7.25–7.31 (4H, m), 5.99

(1H, br.s), 4.00 (2H, t, J=6.4 Hz), 3.01 (2H, t, J=6.4 Hz), 2.82 (2H, q, J=7.6 Hz), 1.37 (3H, t, J=7.6 Hz).

STEP 2. 1-[4-(2-chloroethyl)phenyl]-2-ethyl-1H-benzimidazole-4-carboxamide

The title compound was prepared according to the procedure described in step 7 of Example 1 from 2-[4-(6-chloro-2-ethyl-5-nitro-1H-benzimidazol-1-yl)phenyl]ethanol (step 1).

$^1$H-NMR (DMSO-d$_6$) δ: 9.29 (1H, br.s), 7.81–7.91 (1H, m), 7.79 (1H, br.s), 7.49–7.60 (4H, m), 7.24–7.33 (2H, m), 3.97 (2H, t, J=6.8 Hz), 3.18 (2H, t, J=6.8 Hz), 2.80 (2H, q, J=7.5 Hz), 1.27 (3H, t, J=7.5 Hz).

STEP 3. 1-[4-(2-azidoethyl)phenyl]-2-ethyl-1H-benzimidazole-4-carboxamide

The title compound was prepared according to the procedure described in step 8 of Example 1 from 6-chloro-1-[4-(2-chloroethyl)phenyl]-2-ethyl-1H-benzimidazole-5-carboxamide (step 2).

$^1$H-NMR (DMSO-d$_6$) δ:9.29 (1H, br.s), 7.89 (1H, d, J=7.3 Hz), 7.79 (1H, br.s), 7.51–7.59 (4H, m), 7.22–7.33 (2H, m), 3.68 (2H, t, J=6.6 Hz), 3.01 (2H, t, J=6.6 Hz), 2.77 (2H, q, J=7.5 Hz), 1.27 (3H, t, J=7.5 Hz).

STEP 4. 1-[4-(2-aminoethyl)phenyl]-2-ethyl-1H-benzimidazole-4-carboxamide

The title compound was prepared according to the procedure described in step 7 of Example 37 from 1-[4-(2-azidoethyl)phenyl]-6-chloro-2-ethyl-1H-benzimidazole-5-carboxamide (step 3).

$^1$H-NMR (DMSO-d$_6$) δ: 9.30 (1H, br.s), 7.89 (1H, d, J=6.5 Hz), 7.81 (1H, br.s), 7.48–7.49 (4H, m), 7.26–7.30 (2H, m), 2.77–2.89 (6H, m), 1.28 (3H, t, J=6.4 Hz).

STEP 5. 2-ethyl-1-(4-{2-[({[(4-methylphenyl)sulfonyl]amino}carbonyl)amino]ethyl}phenyl)-1H-benzimidazole-4-carboxamide The title compound was prepared according to the procedure described in step 10 of Example 1 from 1-[4-(2-aminoethyl)phenyl]-6-chloro-2-ethyl-1H-benzimidazole-5-carboxamide (step 4).

m.p.: 208–214° C.

IR (KBr) ν: 3336, 1664, 1589, 1508, 1406, 1342, 1168, 976 cm$^1$.

MS (ESI) m/z: 506 (MH$^+$), 504 ([M–H]$^-$).

$^1$H-NMR (DMSO-d$_6$) δ: 9.29 (1H, br.s), 7.89 (1H, dd, J=1.3 Hz, 7.2 Hz), 7.75–7.79 (3H, m), 7.22–7.49 (8H, m), 6.54 (1H, br.s), 2.75–2.83 (4H, m), 2.35 (3H, s), 1.27 (3H, t, J=7.4 Hz).

EXAMPLE 323

6-CHLORO-2-ETHYL-1-(4-{2-[({[(4-METHYLPHENYL)SULFONYL]AMINO}CARBONYL)AMINO]ETHYL}PHENYL)-5-(METHYLSULFONYL)-1H-BENZIMIDAZOLE

STEP 1. 1,5-dichloro-2-(methylsulfinyl)-4-nitrobenzene

A mixture of (2,4-dichloro-phenyl)-methyl sulfone (Ono Mitsunori, Nakamura Yoshisada, Sato Shingo, Itoh Isamu, *Chem. Lett*, 1988, 395–398.; 3.33 g, 16 mmol) and sulfuric acid (conc, 14 ml) was added a mixture of sulfuric acid (4 ml) and nitric acid (fuming, 2 ml) dropwise under ice-water bath. The mixture was stirred at 55° C. for 1 h. The mixture was poured onto ice-water and neutralized with 6N aqueous NaOH and then extracted with dichloromethane. The organic layer was washed with brine and dried (Na2SO4). The solvent was removed under reduced pressure and the residue was purified by flash chromatography eluting with hexane/ethyl acetate (2:1/1:1) to give 3 g (74%) of the title compound as white solids.

$^1$H-NMR (CDCl$_3$) δ: 8.45 (1H, s), 7.65 (1H, s), 2.89 (3H, s).

STEP 2. 1,5-dichloro-2-(methylsulfonyl)-4-nitrobenzene

A solution of 1,5-dichloro-2-(methylsulfinyl)-4-nitrobenzene (1.0 g, 3.9 mmol) in dichloromethane (50 ml) was added 3-Chloroperoxybenzoic acid (1.7 g, 9.8 mmol). The mixture was stirred under nitrogen at room temperature for 3 h. The mixture was added saturated aqueous NaHCO$_3$ (20 ml) and extracted with dichloromethane (50 ml). The organic layer was washed with brine (50 ml), dried (Na$_2$SO$_4$) and concentrated. The residue was purified by flash chromatography eluting with hexane/ethyl acetate (2:1) to give 1 g (100%) of the title compound as white solids.

MS (EI) m/z: 269 (M$^+$).

$^1$H-NMR (CDCl$_3$) δ: 8.68 (1H, s), 7.81 (1H, s), 3.30 (3H, s).

STEP 3. 2-{4-[5-chloro-4-(methylsulfonyl)-2-nitroanilino]phenyl}ethanol

The title compound was prepared according to the procedure described in step 3 of Example 1 from 1,5-dichloro-2-(methylsulfonyl)-4-nitrobenzene and 4-aminophenylethyl alcohol (step 2).

MS (EI) m/z: 370 (M$^+$).

$^1$H-NMR (CDCl$_3$) δ: 9.81 (1H, br.s), 8.99 (1H, s), 7.39 (2H, d, J=8.4 Hz), 7.24 (2H, d, J=8.4 Hz), 7.18 (1H, s), 3.94 (2H, t, J=6.2 Hz), 3.25 (3H, s), 2.95 (2H, t, J=6.2 Hz).

STEP 4. 2-{4-[2-amino-5-chloro-4-(methylsulfonyl)anilino]phenyl}ethanol

The title compound was prepared according to the procedure described in step 2 of Example 40 from 2-{4-[5-chloro-4-(methylsulfonyl)-2-nitroanilino]phenyl}ethanol (step 3).

MS (EI) m/z: 340(M$^+$).

$^1$H-NMR (CDCl$_3$) δ: 7.50 (1H, s), 7.22 (2H, d, J=8.4 Hz), 7.15 (1H, s), 7.00 (2H, d, J=8.4 Hz), 5.71 (1H, br.s), 3.88 (2H, t, J=6.4 Hz), 3.67 (2H, br.s), 3.22 (3H, s), 2.86 (2H, t, J=6.4 Hz).

STEP 5. 2-{4-[6-chloro-2-ethyl-5-(methylsulfonyl)-1H-benzimidazol-1-yl]phenyl}ethyl propionate The title compound was prepared according to the procedure described in step 5 of Example 1 from 2-{4-[2-amino-5-chloro-4-(methylsulfonyl)anilino]phenyl}ethanol (step 4).

TLC, Rf=0.7, hexane:ethyl acetate (1:2).

STEP 6. 2-{4-[6-chloro-2-ethyl-5-(methylsulfonyl)-1H-benzimidazol-1-yl]phenyl}ethanol The title compound was prepared according to the procedure described in step 6 of Example 1 from 2-{4-[6-chloro-2-ethyl-5-(methylsulfonyl)-1H-benzimidazol-1-yl]phenyl}ethyl propionate (step 5).

MS (EI) m/z: 378 (M$^+$).

$^1$H-NMR (CDCl$_3$) δ: 8.60 (1H, s), 7.52 (2H, d, J=8.3 Hz), 7.28 (2H, d, J=8.3 Hz), 7.10 (1H, s), 3.97–4.04 (2H, m), 3.29 (3H, s), 3.03 (2H, t, J=6.5 Hz), 2.80 (2H, q, J=7.6 Hz), 1.36 (3H, t, J=7.6 Hz).

STEP 7. 6-chloro-1-[4-(2-chloroethyl)phenyl]-2-ethyl-1H-benzimidazol-5-yl methyl sulfone The title compound was prepared according to the procedure described in step 7 of Example 1 from 2-{4-[6-chloro-2-ethyl-5-(methylsulfonyl)-1H-benzimidazol-1-yl]phenyl}ethanol (step 6).

$^1$H-NMR (CDCl$_3$) δ: 8.62 (1H, s), 7.50 (2H, d, J=8.4 Hz), 7.31 (2H, d, J=8.4 Hz), 7.24 (1H, s), 3.83 (2H, t, J=7.1 Hz), 3.29 (3H, s), 3.22 (2H, t, J=7.1 Hz), 2.80 (2H, q, J=7.6 Hz), 1.37 (3H, t, J=7.6 Hz).

STEP 8. 1-[4-(2-azidoethyl)phenyl]-6-chloro-2-ethyl-1H-benzimidazol-5-yl methyl sulfone The title compound was prepared according to the procedure described in step 8 of Example 1 from 6-chloro-1-[4-(2-chloroethyl)phenyl]-2-ethyl-1H-benzimidazol-5-yl methyl sulfone (step 7).

$^1$H-NMR (CDCl$_3$) δ: 8.62 (1H, s), 7.50 (2H, d, J=8.4 Hz), 7.25 (2H, d, J=8.4 Hz), 7.23 (1H, s), 3.64 (2H, t, J=6.9 Hz), 3.29 (3H, s), 3.04 (2H, t, J=6.9 Hz), 2.80 (2H, q, J=7.6 Hz), 1.36 (3H, t, J=7.6 Hz).

STEP 9. 2-{4-[6-chloro-2-ethyl-5-(methylsulfonyl)-1H-benzimidazol-1-yl]phenyl}ethamine The title compound was prepared according to the procedure described in step 7 of Example 37 from 1-[4-(2-azidoethyl)phenyl]-6-chloro-2-ethyl-1H-benzimidazol-5-yl methyl sulfone (step 8).

$^1$H-NMR (CDCl$_3$) δ: 8.61 (1H, s), 7.47 (2H, d, J=8.4 Hz), 7.28 (2H, d, J=8.4 Hz), 7.24 (1H, s), 3.29 (3H, s), 3.10 (2H, t, J=7.1 Hz), 2.90 (2H, t, J=7.1 Hz), 2.80 (2H, q, J=7.5 Hz), 1.37 (3H, t, J=7.5 Hz).

STEP 10. 6-chloro-2-ethyl-1-(4-{2-[({[(4-methylphenyl)sulfonyl]amino}carbonyl)amino]ethyl}phenyl)-5-(methylsulfonyl)-1H-benzimidazole The title compound was prepared according to the procedure described in step 10 of Example 1 from 2-{4-[6-chloro-2-ethyl-5-(methylsulfonyl)-1H-benzimidazol-1-yl]phenyl}ethanamine (step 9).

m.p.: 105–118° C.

IR (KBr) v: 2879, 1676, 1518, 1458, 1309, 1142, 1089, 993 cm$^{-1}$.

MS (ESI) m/z: 575 (MH$^+$), 573 ([M–H]$^-$).

$^1$H-NMR (CDCl$_3$) δ: 8.59 (1H, s), 7.75 (2H, d, J=8.4 Hz), 7.43 (2H, d, J=8.4 Hz), 7.29–7.33 (4H, m), 7.21 (1H, s), 6.69 (1H, br.s), 3.55–3.62 (2H, m), 3.29 (3H, s), 2.96 (2H, t, J=6.9 Hz), 2.80 (3H, q, J=7.5 Hz), 2.41 (3H, s), 1.34 (3H, t, J=7.5 Hz).

EXAMPLE 324

6-CHLORO-2-ETHYL-1-(4-{2-[({[(4-METHYLPHENYL)SULFONYL]AMINO}CARBONYL)AMINO]ETHYL}PHENYL)-5-(METHYLSULFONYL)-1H-BENZIMIDAZOLE SODIUM SALT

The title compound was prepared according to the procedure described in Example 2 from 6-chloro-2-ethyl-1-(4-{2-[({[(4-methylphenyl)sulfonyl]amino}carbonyl)amino]ethyl}phenyl)-5-(methylsulfonyl)-1H-benzimidazole (Example 323)

m.p.: 175–183° C.

IR (KBr) v: 3375, 1604, 1516, 1458, 1139, 1083, 993 cm$^{-1}$.

EXAMPLE 325

2-{4-[6-CHLORO-2-ETHYL-5-(METHYLSULFONYL)-1H-BENZIMIDAZOL-1-YL]PHENYL}ETHYL(4-METHYLPHENYL)SULFONYLCARBAMATE

STEP 1. 2-{4-[6-chloro-2-ethyl-5-(methylsulfonyl)-1H-benzimidazol-1-yl]phenyl}ethyl(4-methylphenyl)sulfonylcarbamate The title compound was prepared according to the procedure described in Example 3 from 2-{4-[6-chloro-2-ethyl-5-(methylsulfonyl)-1H-benzimidazol-1-yl]phenyl}ethanol (Example 323, step 6).

m.p.: 105–110° C.

IR (KBr) v: 1751, 1517, 1458, 1309, 1163, 1141, 1089 cm$^{-1}$.

MS (ESI) m/z: 576 (MH$^+$), 574 ([M–H]$^-$).

$^1$H-NMR (CDCl$_3$) δ: 8.60 (1H, s), 7.91–7.94 (2H, m), 7.21–7.43 (7H, m), 4.40 (2H, br.s), 3.31 (3H, s), 3.05 (2H, br.s), 2.78–2.81 (2H, m), 2.44 (3H, s), 1.33 (3H, t, J=7.6 Hz).

EXAMPLE 326

5-(AMINOSULFONYL)-6-CHLORO-2-ETHYL-1-(4-{2-[({[(4-METHYLPHENYL)SULFONYL]AMINO}CARBONYL)AMINO]ETHYL}PHENYL)-1H-BENZIMIDAZOLE

STEP 1. 2,4-dichloro-5-nitrobenzenesulfonyl chloride 2,4-Dichloronitrobenzene (10 g, 52 mmol) was added ClSO3H (8 ml, 120 mmol) dropwise under ice-water bath. The mixture was stirred at 130° C. for 26 h. The mixture was cooled to rt and poured onto ice-water. The resulting precipitates were collected by filtration and dried under reduced pressure to give 9 g (60%) of the title compound as brown solids.

MS (EI) m/z: 290 (M$^+$).

$^1$H-NMR (CDCl$_3$) δ: 8.70 (1H, s), 7.90 (1H, s).

STEP 2. N-(tert-butyl)-2,4-dichloro-5-nitrobenzenesulfonamide

The title compound was prepared according to the procedure described in step 1 of Example 87 from 2,4-dichloro-5-nitrobenzenesulfonyl chloride and tert-butylamine (step 1).

$^1$H-NMR (CDCl$_3$) δ: 8.65 (1H, s), 7.74 (1H, s), 5.01 (1H, br.s), 1.27 (9H, s).

STEP 3. N-(tert-butyl)-2-chloro-4-[4-(2-hydroxyethyl)anilino]-5-nitrobenzenesulfonamide The title compound was prepared according to the procedure described in step 1 of Example 162 from N-(tert-butyl)-2,4-dichloro-5-nitrobenzenesulfonamide and 4-aminophenylethyl alcohol (step 2).

$^1$H-NMR (CDCl$_3$) δ: 9.72 (1H, br.s), 8.95 (1H, s), 7.37 (2H, d, J=8.3 Hz), 7.24 (2H, d, J=8.3 Hz), 7.17 (1H, s), 4.79 (1H, br.s), 3.90–3.96 (2H, m), 2.94 (2H, t, J=6.4 Hz), 1.26 (9H, s).

STEP 4. 5-amino-N-(tert-butyl)-2-chloro-4-[4-(2-hydroxyethyl)anilino]benzenesulfonamide The title compound was prepared according to the procedure described in step 2 of Example 40 from N-(tert-butyl)-2-chloro-4-[4-(2-hydroxyethyl)anilino]-5-nitrobenzenesulfonamide (step 3).

MS (EI) m/z: 397(M$^+$)

¹H-NMR (CDCl₃) δ: 7.51 (1H, s), 7.20 (2H, d, J=8.4 Hz), 7.14 (1H, s), 6.95 (2H, d, J=8.4 Hz), 5.22 (1H, br.s), 4.89 (1H, br.s), 3.87 (2H, t, J=6.4 Hz), 2.85 (2H, t, J=6.4 Hz), 1.23 (9H, s).

STEP 5. 2-[4-(6-chloro-2-ethyl-5-nitro-1H-benzimidazol-1-yl)phenyl]ethyl propionate The title compound was prepared according to the procedure described in step 5 of Example 1 from 5-amino-N-(tert-butyl)-2-chloro-4-[4-(2-hydroxyethyl)anilino]benzenesulfonamide (step 4).

TLC, Rf=0.8, hexane:ethyl acetate (1:2).

STEP 6. N-(tert-butyl)-6-chloro-2-ethyl-1-[4-(2-hydroxyethyl)phenyl]-1H-benzimidazole-5-sulfonamide The title compound was prepared according to the procedure described in step 6 of Example 1 from 2-[4-(6-Chloro-2-ethyl-5-nitro-1H-benzimidazol-1-yl)phenyl]ethyl propionate (step 5).

¹H-NMR (CDCl₃) δ: 8.57 (1H, s), 7.49 (2H, d, J=8.4 Hz), 7.29 (2H, d, J=8.4 Hz), 7.20 (1H, s), 4.98 (1H, br.s), 4.00 (2H, br.s), 3.02 (2H, t, J=6.4 Hz), 2.79 (2H, q, J=7.5 Hz), 1.37 (3H, t, J=7.5 Hz), 1.21 (9H, s).

STEP 7. N-(tert-butyl)-6-chloro-1-[4-(2-chloroethyl)phenyl]-2-ethyl-1H-benzimidazole-5-sulfonamide The title compound was prepared according to the procedure described in step 7 of Example 1 from N-(tert-butyl)-6-chloro-2-ethyl-1-[4-(2-hydroxyethyl)phenyl]-1H-benzimidazole-5-sulfonamide (step 6).

¹H-NMR (CDCl₃) δ: 8.58 (1H, s), 7.49 (2H, d, J=8.4 Hz), 7.32 (2H, d, J=8.4 Hz), 7.19 (1H, s), 4.96 (1H, br.s), 3.83 (2H, t, J=7.0 Hz), 3.21 (2H, t, J=7.0 Hz), 2.80 (2H, q, J=7.6 Hz), 1.37 (3H, t, J=7.6 Hz), 1.22 (9H, s).

STEP 8. 1-[4-(2-azidoethyl)phenyl]-N-(tert-butyl)-6-chloro-2-ethyl-1H-benzimidazole-5-sulfonamide The title compound was prepared according to the procedure described in step 8 of Example 1 from N-(tert-butyl)-6-chloro-1-[4-(2-chloroethyl)phenyl]-2-ethyl-1H-benzimidazole-5-sulfonamide (step 7).

¹H-NMR (CDCl₃) δ: 8.57 (1H, s), 7.48 (2H, d, J=8.2 Hz), 7.32 (2H, d, J=8.2 Hz), 7.19 (1H, s), 4.96 (1H, br.s), 3.63 (2H, t, J=6.9 Hz), 3.03 (2H, t, J=6.9 Hz), 2.79 (2H, q, J=7.4 Hz), 1.37 (3H, t, J=7.4 Hz), 1.21 (9H, s).

STEP 9. 1-[4-(2-aminoethyl)phenyl]-N-(tert-butyl)-6-chloro-2-ethyl-1H-benzimidazole-5-sulfonamide The title compound was prepared according to the procedure described in step 7 of Example 37 from 1-[4-(2-azidoethyl)phenyl]-N-(tert-butyl)-6-chloro-2-ethyl-1H-benzimidazole-5-sulfonamide (step 8).

¹H-NMR (CDCl₃) δ: 8.57 (1H, s), 7.44 (2H, d, J=8.5 Hz), 7.29 (2H, d, J=8.5 Hz), 7.20 (1H, s), 5.03 (1H, br.s), 3.09 (2H, t, J=6.9 Hz), 2.89 (2H, t, J=6.9 Hz), 2.79 (2H, q, J=7.6 Hz), 1.37 (3H, t, J=7.6 Hz), 1.22 (9H, s).

STEP 10. 5-[(tert-butylamino)sulfonyl]-6-chloro-2-ethyl-1-(4-{2-[({[(4-methylphenyl)sulfonyl]amino}carbonyl)amino]ethyl}phenyl)-1H-benzimidazole The title compound was prepared according to the procedure described in step 10 of Example 1 from 1-[4-(2-aminoethyl)phenyl]-N-(tert-butyl)-6-chloro-2-ethyl-1H-benzimidazole-5-sulfonamide (step 9).

¹H-NMR (CDCl₃) δ: 8.54 (1H, s), 7.78 (2H, d, J=8.3 Hz), 7.41 (2H, d, J=8.3 Hz), 7.31 (2H, d, J=8.2 Hz), 7.23 (2H, d, J=8.2 Hz), 7.16 (1H, s), 6.61 (1H, br.s), 5.21 (1H, br.s), 3.54–3.60 (2H, m), 2.95 (2H, t, J=6.9 Hz), 2.78 (2H, q, J=7.5 Hz), 2.41 (3H, s), 1.35 (3H, t, J=7.5 Hz), 1.21 (9H, s).

STEP 11. 5-(aminosulfonyl)-6-chloro-2-ethyl-1-(4-{2-[({[(4-methylphenyl)sulfonyl]amino}carbonyl)amino]ethyl}phenyl)-1H-benzimidazole The title compound was prepared according to the procedure described in step 1 of Example 88 from 5-[(tert-butylamino)sulfonyl]-6-chloro-2-ethyl-1-(4-{2-[({[(4-methylphenyl)sulfonyl]amino}carbonyl)amino]ethyl}phenyl)-1H-benzimidazole (step 9).

m.p.: 163–170° C.

IR (KBr) ν: 1676, 1517, 1400, 1340, 1159, 1089, 995 cm⁻¹.

MS (ESI) m/z: 576 (MH⁺), 574 ([M–H]⁻).

¹H-NMR (DMSO-d₆) δ: 8.25 (1H, s), 7.77 (2H, d, J=8.3 Hz), 7.55 (2H, br.s), 7.37–7.48 (6H, m), 7.20 (1H, s), 6.54 (1H, br.s), 3.27 (2H, br.s), 2.71–2.81 (4H, m), 2.34 (3H, s), 1.23 (3H, t, J=7.6 Hz).

EXAMPLE 327

2-{4-[5-(AMINOSULFONYL)-6-CHLORO-2-ETHYL-1H-BENZIMIDAZOL-1-YL]PHENYL}ETHYL(4-METHYLPHENYL)SULFONYLCARBAMATE

STEP 1. 2-(4-{5-[(tert-butylamino)sulfonyl]-6-chloro-2-ethyl-1H-benzimidazol-1-yl}phenyl)ethyl(4-methylphenyl)sulfonylcarbamate The title compound was prepared according to the procedure described in Example 3 from N-(tert-butyl)-6-chloro-2-ethyl-1-[4-(2-hydroxyethyl)phenyl]-1H-benzimidazole-5-sulfonamide (Example 326, step 6).

¹H-NMR (CDCl₃) δ: 8.58 (1H, s), 7.93 (2H, d, J=8.2 Hz), 7.33–7.39 (4H, m), 7.20 (2H, d, J=~8.2 Hz), 7.16 (1H, s), 5.07 (1H, br.s), 4.38 (2H, t, J=6.2 Hz), 3.03 (2H, t, J=6.2 Hz), 2.78 (2H, q, J=7.5 Hz), 2.44 (3H, s), 1.35 (3H, t, J=7.5 Hz), 1.21 (9H, s).

STEP 2. 2-{4-[5-(aminosulfonyl)-6-chloro-2-ethyl-1H-benzimidazol-1-yl]phenyl}ethyl(4-methylphenyl)sulfonylcarbamate The title compound was prepared according to the procedure described in step 1 of Example 88 from 2-(4-{5-[(tert-butylamino)sulfonyl]-6-chloro-2-ethyl-1H-benzimidazol-1-yl}phenyl)ethyl(4-methylphenyl)sulfonylcarbamate (step 1).

m.p.: 110–115° C.

IR (KBr) ν: 1676, 1517, 1400, 1340, 1159, 1089, 995 cm⁻¹.

MS (ESI) m/z: 576 (MH⁺), 574 ([M–H]⁻).

¹H-NMR (DMSO-d₆) δ: 8.25 (1H, s), 7.76 (2H, d, J=8.4 Hz), 7.55 (2H, br.s), 7.47 (4H, s), 7.41 (2H, d, J=8.4 Hz), 7.20 (1H, s), 4.29 (2H, t, L=6.6 Hz), 2.96 (2H, t, J=6.6 Hz), 2.75 (2H, q, J=7.5 Hz), 2.35 (3H, s), 1.24 (3H, t, J=7.5 Hz).

EXAMPLE 328

2-[4-(6-CHLORO-5-CYANO-2-ETHYL-1H-BENZIMIDAZOL-1-YL)PHENYL]ETHYL(4-METHYLPHENYL)SULFONYLCARBAMATE

STEP 1. 2-[4-(6-chloro-5-cyano-2-ethyl-1H-benzimidazol-1-yl)phenyl]ethyl(4-methylphenyl)sulfonylcarbamate The title compound was prepared according to the procedure described in Example 3 from 6-chloro-2-ethyl-1-[4-(2-hydroxyethyl)phenyl]-1H-benzimidazole-5-carbonitrile (Example 111, step 4).

m.p.: 85–98° C.

IR (KBr) v: 1747, 1618, 1517, 1465, 1348, 1290, 1163, 1089 cm$^{-1}$

MS (ESI) m/z: 523 (MH+), 521 ([M−H]−)

$^1$H-NMR (CDCl$_3$) δ: 8.07 (1H, s), 7.92 (2H, d, J=8.4 Hz), 7.40 (2H, d, J=8.4 Hz), 7.35 (2H, d, J=8.1 Hz), 7.25 (2H, d, J=8.1 Hz), 7.17 (1H, s), 4.39 (2H, t, J=6.8 Hz), 3.04 (2H, t, J=6.8 Hz), 2.78 (2H, q, J=7.6 Hz), 2.44 (3H, s), 1.35 (3H, t, J=7.6 Hz).

EXAMPLE 329

N-[({2-[4-(5-CYANO-2-ETHYL-4,6-DIMETHYL-1H-BENZIMIDAZOL-1-YL)PHENYL]ETHYL}AMINO)CARBONYL]-4-METHYLBENZENESULFONAMIDE

STEP 1. 4-cyano-3,5-dimethyl-2-nitrophenyl trifluoromethanesulfonate

To a solution of 4-hydroxy-2,6-dimethyl-3-nitro-benzonitrile (v.Auwers; Saurwein; Fortsch. Ch. Phys.; 18; Heft 2, S. 23; 2.6 g, 13.4 mmol) in dichloromethane (150 ml) was added triflic anhydride (3.4 ml, 20 mmol) and pyridine (1.5 ml, 20 mmol) at 0° C. The mixture was stirred at room temperature for 1.5 h. The reaction mixture was poured into water, and extracted with ethyl acetate (100 ml). The organic layer was washed with brine (50 ml), then dried (Na$_2$SO$_4$). After removal of solvent, the crude product was purified by flash column chromatography eluting with hexane/ethyl acetate (2:1) to afford 3 g (69%) of the title compound as pale yellow solids.

MS (EI) m/z: 324 (M+)

$^1$H-NMR (CDCl$_3$) δ: 7.34 (1H, s), 2.68 (3H, s), 2.61 (3H, s).

STEP 2. 2-{4-[(4-cyano-3,5-dimethyl-2-nitrophenyl)amino]phenyl}ethyl acetate

The title compound was prepared according to the procedure described in step 3 of Example 1 from 4-cyano-3,5-dimethyl-2-nitrophenyl trifluoromethanesulfonate (step 1).

$^1$H-NMR (CDCl$_3$) δ: 8.08 (1H, br.s), 7.27 (2H, d, J=8.4 Hz), 7.15 (2H, d, J=8.4 Hz), 4.30 (2H, t, J=7.0 Hz), 2.96 (2H, t, J=7.0 Hz), 2.65 (3H, s), 2.41 (3H, s), 2.05 (3H, s).

STEP 3. 2-{4-[(4-cyano-3,5-dimethyl-2-nitrophenyl)amino]phenyl)ethyl acetate

The title compound was prepared according to the procedure described in step 3 of Example 6 from 2-{4-[(4-cyano-3,5-dimethyl-2-nitrophenyl)amino]phenyl}ethyl acetate (step 2).

$^1$H-NMR (CDCl$_3$) δ: 7.14 (2H, d, J=8.4 Hz), 6.85–6.89 (3H, m), 5.50 (1H, br.s), 4.26 (2H, t, J=7.1 Hz), 3.54 (2H, br.s), 2.89 (2H, t, J=7.1 Hz), 2.41 (3H, s), 2.37 (3H, s), 2.05 (3H, s).

STEP 4. 2-[4-(5-cyano-2-ethyl-4,6-dimethyl-1H-benzimidazol-1-yl)phenyl}ethyl acetate The title compound was prepared according to the procedure described in step 5 of Example 1 from 2-{4-[(4-cyano-3,5-dimethyl-2-nitrophenyl)amino]phenyl}ethyl acetate (step 3).

$^1$H-NMR (CDCl$_3$) δ: 7.45–7.47 (2H, m), 7.26–7.29 (2H, m), 6.79 (1H, br.s), 4.37 (2H, t, J=7.0 Hz), 3.08 (2H, t, J=7.0 Hz), 2.83–2.89 (5H, m), 2.56 (3H, s), 2.09 (3H, s), 1.28 (3, br.s).

STEP 5. 2-ethyl-1-[4-(2-hydroxyethyl)phenyl]-4,6-dimethyl-1H-benzimidazole-5-carbonitrile The title compound was prepared according to the procedure described in step 6 of Example 1 from 2-[4-(5-cyano-2-ethyl-4,6-dimethyl-1H-benzimidazol-1-yl)phenyl]ethyl acetate (step 4).

MS (EI) m/z: 319 (M+)

$^1$H-NMR (CDCl$_3$) δ: 7.40–7.51 (4H, m), 6.93 (1H s), 3.68–3.75 (2H, m), 2.85 (2H, t, J=6.7 Hz), 2.68–2.76 (5H, m), 2.50 (3H, s), 1.22 (3H, t, J=7.4 Hz).

STEP 6. 1-[4-(2-chloroethyl)phenyl]-2-ethyl-4,6-dimethyl-1H-benzimidazole-5-carbonitrile The title compound was prepared according to the procedure described in step 7 Example 1 from 2-ethyl-1-[4-(2-hydroxyethyl)phenyl]-4,6-dimethyl-1H-benzimidazole-5-carbonitrile (step 5).

$^1$H-NMR (CDCl$_3$) δ: 7.45 (2H, d, J=8.3 Hz), 7.28 (2H, d, J=8.3 Hz), 6.79 (1H, s), 3.83 (2H, t, J=7.1 Hz), 3.21 (2H, t, J=7.1 Hz), 2.88 (3H, s), 2.81 (2H, q, J=7.6 Hz), 2.55 (3H, s), 1.29 (3H, t, J=7.6 Hz).

STEP 7. 1-[4-(2-azidoethyl)phenyl]-2-ethyl-4,6-dimethyl-1H-benzimidazole-5-carbonitrile The title compound was prepared according to the procedure described in step 8 Example 1 from 1-[4-(2-chloroethyl)phenyl]-2-ethyl-4,6-dimethyl-1H-benzimidazole-5-carbonitrile (step 6).

MS (EI) m/z: 412 (M+)

$^1$H-NMR (CDCl$_3$) δ: 7.47 (2H, d, J=8.1 Hz), 7.28 (2H, d, J=8.1 Hz), 6.78 (1H, s), 3.63 (2H, t, J=6.8 Hz), 3.03 (2H, t, J=6.8 Hz), 2.87 (3H, s), 2.80 (2H, q, J=7.6 Hz), 2.55 (3H, s), 1.29 (3H, t, J=7.6 Hz).

STEP 8. 1-[4-(2-aminoethyl)phenyl]-2-ethyl-4,6-dimethyl-1H-benzimidazole-5-carbonitrile The title compound was prepared according to the procedure described in step 7 of Example 37 from 1-[4-(2-azidoethyl)phenyl]-2-ethyl-4,6-dimethyl-1H-benzimidazole-5-carbonitrile (step 7).

$^1$H-NMR (CDCl$_3$) δ: 7.43 (2H, d, J=8.6 Hz), 7.25 (2H, d, J=8.6 Hz), 6.79 (1H, s), 3.08 (2H, t, J=7.0 Hz), 2.63–2.91 (7H, m), 2.55 (3H, s), 1.29 (3H, t, J=7.6 Hz).

STEP 9. N-[({2-[4-(5-cyano-2-ethyl-4,6-dimethyl-1H-benzimidazol-1-yl)phenyl]ethyl}amino)carbonyl]-4-methylbenzenesulfonamide The title compound was prepared according to the procedure described in step 10 of Example 1 from 1-[4-(2-aminoethyl)phenyl]-2-ethyl-4,6-dimethyl-1H-benzimidazole-5-carbonitrile (step 8).

m.p.: 140–145° C.

IR (KBr) v: 3340, 2214, 1664, 1517, 1338, 1166, 1091 cm$^{-1}$

MS (ESI) m/z: 516 (MH+), 514 ([M−H]−)

$^1$H-NMR (CDCl$_3$) δ: 7.71 (2H, d, J=8.4 Hz), 7.41 (2H, d, J=8.4 Hz), 7.25–7.31 (4H, m), 6.77 (1H, s), 6.73 (1H, br.s), 3.55–3.62 (2H, m), 2.95 (2H, t, J=7.0 Hz), 2.87 (3H, s), 2.80 (2H, q, J=7.6 Hz), 2.52 (3H, s), 2.41 (3H, s), 1.28 (3H, t, J=7.6 Hz).

EXAMPLE 330

2-{4-[5-(AMINOCARBONYL)-6-CHLORO-2-ETHYL-1H-BENZIMIDAZOL-1-YL]PHENYL}ETHYL(4-METHYLPHENYL)SULFONYLCARBAMATE

STEP 1. 2-{4-[5-(aminocarbonyl)-6-chloro-2-ethyl-1H-benzimidazol-1-yl]phenyl}ethyl(4-methylphenyl)sulfonylcarbamate The title compound was prepared according to the procedure described in Example 3 from 6-chloro-2-ethyl-1-[4-(2-hydroxyethyl)phenyl]-1H-benzimidazole-5-carboxamide (Example 111, step 5)

m.p.: 170–175° C.

IR (KBr) v: 3463, 3342, 1747, 1685, 1593, 1161, 1080, 881 cm$^{-1}$

MS (ESI) m/z: 541 (MH$^+$), 539 ([M−H]$^-$)

$^1$H-NMR (CDCl$_3$) δ: 8.13 (1H, s), 7.96 (2H, d, J=8.4 Hz), 7.40 (2H, d, J=8.4 Hz), 7.36 (2H, d, J=8.1 Hz), 7.01 (2H, d, J=8.1 Hz), 6.94 (1H, s), 6.55 (1H, br.s), 4.38 (2H, t, J=6.1 Hz), 3.01 (2H, t, J=6.1 Hz), 2.70 (2H, q, J=7.5 Hz), 2.45 (3H, s), 1.29 (3H, t, J=7.5 Hz).

EXAMPLE 331

2-[4-(5-CYANO-2-ETHYL-4,6-DIMETHYL-1H-BENZIMIDAZOL-1-YL)PHENYL]ETHYL(4-METHYLPHENYL)SULFONYLCARBAMATE

STEP 1. 2-[4-(5-cyano-2-ethyl-4,6-dimethyl-1H-benzimidazol-1-yl)phenyl]ethyl(4-methylphenyl)sulfonylcarbamate The title compound was prepared according to the procedure described in Example 3 from 2-ethyl-1-[4-(2-hydroxyethyl)phenyl]-4,6-dimethyl-1H-benzimidazole-5-carbonitrile (Example 329, step 5)

m.p.: 208–213° C.

IR (KBr) v: 1747, 1517, 1230, 1161, 1089 cm$^{-1}$

MS (ESI) m/z: 517 (MH$^+$), 515 ([M−H]$^-$)

$^1$H-NMR (DMSO-d$_6$) δ: 7.76 (2H, d, J=8.4 Hz), 7.40–7.48 (6H, m), 6.91 (1H, s), 4.27 (2H, t, J=6.7 Hz), 2.96 (2H, t, J=6.7 Hz), 2.67–2.73 (5H, m), 2.48 (3H, s), 2.36 (3H, s), 1.21 (3H, t, J=7.6 Hz).

EXAMPLE 332

2-[4-(5-ACETYL-2-ETHYL-1H-BENZIMIDAZOL-1-YL)PHENYL]ETHYL(4-METHYLPHENYL)SULFONYLCARBAMATE

STEP 1. 2-[4-(5-acetyl-2-ethyl-1H-benzimidazol-1-yl)phenyl]ethyl(4-methylphenyl)sulfonylcarbamate The title compound was prepared according to the procedure described in Example 3 from 1-{2-ethyl-1-[4-(2-hydroxyethyl)phenyl]-1H-benzimidazol-5-yl}ethanone (Example 78, step 4)

m.p.: 188–190° C.

IR (KBr) v: 1743. 1683, 1606, 1515, 1348, 1163, 1076 cm$^{-1}$

MS (ESI) m/z: 506 (MH$^+$), 504 ([M−H]$^-$)

$^1$H-NMR (DMSO-d$_6$) δ: 8.33 (1H, d, J=1.4 Hz), 7.82 (1H, dd, J=1.4 Hz, 8.4 Hz) 7.76 (2H, d, J=8.4 Hz), 7.45 (4H, s), 7.40 (2H, d, J=8.4 Hz), 7.14 (1H, d, J=8.4 Hz), 4.28 (2H, t, J=6.5 Hz), 2.97 (2H, t, J=6.5 Hz), 2.75 (2H, q, J=7.4 Hz), 2.64 (3H, s), 2.35 (3H, s), 3H, s), 1.25 (3H, t, J=7.4 Hz).

EXAMPLE 333

6-CHLORO-2-ETHYL-N-METHYL-1-(4-{2-[({[(4-METHYLPHENYL)SULFONYL]AMINO}CARBONYL)AMINO]ETHYL}PHENYL)-1H-BENZIMIDAZOLE-5-CARBOXAMIDE

STEP 1. 2,4-dichloro-N-methyl-5-nitrobenzamide

To a solution of 2,4-dichloro-5-nitrobenzoic acid (8 g, 33.9 mmol) in toluene (200 ml) was added thionyl chloride (12.4 ml, 169 mmol) at room temperature. The mixture was stirred at 80° C. for 5 h. The solvent was removed and the residue was dissolved with tetrahydrofurane (60 ml). The mixture was added 40% methylamine (1.4 ml, 33.9 mmol) at 0° C. and the mixture was stirred at room temperature for 2.5 h. The volatile component was removed under reduced pressure, and the residue was extracted with ethyl acetate (100 ml). The organic layer was washed with water (100 ml), brine (100 ml), then dried (Na$_2$SO$_4$). After removal of solvent, the crude product was purified by flash column chromatography eluting with hexane/ethyl acetate (2:1/1:1/1:2) to afford 5.3 g (63%) of the title compound as pale yellow solids.

$^1$H-NMR (CDCl$_3$) δ: 8.27 (1H, s), 7.65 (1H, s), 3.15 (3H, s).

STEP 2. 2-chloro-4-{[4-(2-hydroxyethyl)phenyl]amino}-N-methyl-5-nitrobenzamide

The title compound was prepared according to the procedure described in step 3 of Example 1 from 2,4-dichloro-N-methyl-5-nitrobenzamide (step 1).

$^1$H-NMR (CDCl$_3$) δ: 9.62 (1H, s), 8.22 (1H, s), 7.24–7.35 (4H, m), 6.95 (1H, s), 3.60–3.67 (2H, m), 2.73–2.79 (5H, m).

STEP 3. 5-amino-2-chloro-4-{[4-(2-hydroxyethyl)phenyl]amino}-N-methylbenzamide

The title compound was prepared according to the procedure described in step 2 of Example 28 from 2-chloro-4-{[4-(2-hydroxyethyl)phenyl]amino}-N-methyl-5-nitrobenzamide (step 2).

$^1$H-NMR (CDCl$_3$) δ: 7.28 (1H, s), 7.15 (2H, d, J=8.4 Hz), 7.08 (1H, s), 6.89 (2H, d, J=8.4 Hz), 6.53 (1H, br.s), 5.41 (1H, br.s), 3.84–3.86 (2H, m), 3.66 (2H, br.s), 3.00 (3H, d, J=5.0 Hz), 2.83 (2H, t, J=6.6 Hz).

STEP 4. 6-chloro-2-ethyl-1-[4-(2-hydroxyethyl)phenyl]-N-methyl-1H-benzimidazole-5-carboxamide The title compound was prepared according to the procedure described in step 5 of Example 1 from 5-amino-2-chloro-4-{[4-(2-hydroxyethyl)phenyl]amino}-N-methyl-benzamide (step 3).

MS (EI) m/z: 357 (M+)

$^1$H-NMR (CDCl$_3$) δ: 7.98 (1H, s), 7.47 (2H, d, J=8.1 Hz), 7.27 (2H, d, J=8.1 Hz), 7.09 (1H, s), 6.23 (1H, br.s), 3.96–4.02 (2H, m), 3.05 (3H, d, J=4.9 Hz), 3.00 (2H, t, J=6.4 Hz), 2.77 (2H, q, J=7.6 Hz), 1.34 (3H, t, J=7.6 Hz).

STEP 5. 6-chloro-1-[4-(2-chloroethyl)phenyl]-2-ethyl-N-methyl-1H-benzimidazole-5-carboxamide The title compound was prepared according to the procedure described in step 7 Example 1 from 6-chloro-2-ethyl-1-[4-(2-hydroxyethyl)phenyl]-N-methyl-1H-benzimidazole-5-carboxamide (step 4).

$^1$H-NMR (CDCl$_3$) δ: 7.98 (1H, s), 7.47 (2H, d, J=8.3 Hz), 7.31 (2H, d, J=8.3 Hz), 7.10 (1H, s), 6.35 (1H, br.s), 3.83

(2H, t, J=6.9 Hz), 3.21 (2H, t, J=6.9 Hz), 3.05 (3H, d, J=4.9 Hz), 2.82 (2H, q, J=7.6 Hz), 1.36 (3H, t, J=7.6 Hz).

STEP 6. 1-[4-(2-azidoethyl)phenyl]-6-chloro-2-ethyl-N-methyl-1H-benzimidazole-5-carboxamide The title compound was prepared according to the procedure described in step 8 Example 1 from 6-chloro-1-[4-(2-chloroethyl)phenyl]-2-ethyl-N-methyl-1H-benzimidazole-5-carboxamide (step 5).

MS (EI) m/z: 382 (M+)

$^1$H-NMR (CDCl$_3$) δ: 7.94 (1H, s), 7.46 (2H, d, J=8.0 Hz), 7.27 (2H, d, J=8.0 Hz), 7.06 (1H, s), 3.63 (2H, t, J=7.0 Hz), 2.98–3.06 (5H, m), 2.77 (2H, q, J=7.5 Hz), 1.34 (3H, t, J=7.6 Hz).

STEP 7. 1-[4-(2-aminoethyl)phenyl]-6-chloro-2-ethyl-N-methyl-1H-benzimidazole-5-carboxamide The title compound was prepared according to the procedure described in step 7 of Example 37 from 1-[4-(2-azidoethyl)phenyl]-6-chloro-2-ethyl-N-methyl-1H-benzimidazole-5-carboxamide (step 6).

$^1$H-NMR (CDCl$_3$) δ: 7.91 (1H, s), 7.42 (2H, d, J=8.4 Hz), 7.24 (2H, d, J=8.4 Hz), 7.06 (1H, s), 6.55 (1H, br.s), 3.03–3.10 (5H, m), 2.72–2.83 (2H, m), 1.33 (3H, t, J=7.6 Hz).

STEP 8. 6-chloro-2-ethyl-N-methyl-1-(4-{2-[({[(4-methylphenyl)sulfonyl]amino}carbonyl)amino]ethyl}phenyl)-1H-benzimidazole-5-carboxamide The title compound was prepared according to the procedure described in step 10 of Example 1 from 1-[4-(2-aminoethyl)phenyl]-6-chloro-2-ethyl-N-methyl-1H-benzimidazole-5-carboxamide (step 7).

m.p.: 122–135° C.

IR (KBr) ν: 2877, 1637, 1519, 1400, 1340, 1161, 1091 cm$^{-1}$

MS (ESI) m/z: 554 (MH$^+$), 552 ([M−H]$^−$)

$^1$H-NMR (CDCl$_3$) δ: 7.79–7.84 (3H, m), 7.28–7.33 (4H, m), 7.12 (2H, d, J=8.2 Hz), 6.96 (1H, s), 6.80 (1H, br.s), 6.70 (1H, br.s), 3.48–3.54 (2H, m), 3.08 (3H, d, J=4.8 Hz), 2.89 (2H, t, J=6.9 Hz), 2.72 (2H, q, J=7.5 Hz), 2.41 (3H, s), 1.30 (3H, t, J=7.5 Hz).

EXAMPLE 334

2-(4-{6CHLORO-2-ETHYL-5-[(METHYLAMINO) CARBONYL]-1H-BENZIMIDAZOL-1-YL}PHENYL)ETHYL(4-METHYLPHENYL)SULFONYLCARBAMATE

STEP 1. 2-(4-{6-chloro-2-ethyl-5-[(methylamino)carbonyl]-1H-benzimidazol-1-yl}phenyl)ethyl(4-methylphenyl)sulfonylcarbamate The title compound was prepared according to the procedure described in Example 3 from 6-chloro-2-ethyl-1-[4-(2-hydroxyethyl)phenyl]-N-methyl-1H-benzimidazole-5-carboxamide (Example 333, step 4).

m.p.: 201–204° C.

MS (ESI) m/z: 555 (MH$^+$), 553 ([M−H]$^−$)

$^1$H-NMR (DMSO-d$_6$) δ: 8.27–8.29 (1H, m), 7.76 (2H, d, J=8.1 Hz), 7.69 (1H, s), 7.40–7.48 (6H, m), 7.06 (1H, s), 4.28 (2H, t, J=6.3 Hz), 2.96 (2H, t, J=6.3 Hz), 2.69–2.78 (5H, m), 2.36 (3H, s), 1.23 (3H, t, J=7.5 Hz).

EXAMPLE 335

2-{4-[6CHLORO-5-[(DIMETHYLAMINO)CARBONYL]-2-(1-METHYLETHYL)-1H-BENZIMIDAZOL-1-YL]PHENYL}ETHYL(4-METHYLPHENYL)SULFONYLCARBAMATE

STEP 1. 2,4-dichloro-N,N-dimethyl-5-nitrobenzamide

To a solution of 2,4-dichloro-5-nitrobenzoic acid (4 g, 17 mmol) in toluene (50 ml) was added thionyl chloride (6 ml, 84 mmol) at room temperature. The mixture was stirred at 80° C. for 2 days. The solvent was removed and the residue was dissolved with tetrahydrofurane (30 ml). The mixture was added 50% dimethylamine (760 mg) at 0° C. and the mixture was stirred at room temperature over night. The volatile component was removed under reduced pressure, and the residue was extracted with ethyl acetate (100 ml). The organic layer was washed with water (50 ml), brine (50 ml), then dried (Na$_2$SO$_4$). After removal of solvent, the crude product was purified by flash column chromatography eluting with hexane/ethyl acetate (1:1) to afford 3.6 g (82%) of the title compound as pale yellow solids.

$^1$H-NMR (CDCl$_3$) δ: 7.90 (1H, s), 7.65 (1H, s), 3.15 (3H, s), 2.91 (3H, s).

STEP 2. 2-chloro-4-{[4-(2-hydroxyethyl)phenyl]amino}-N,N-dimethyl-5-nitrobenzamide The title compound was prepared according to the procedure described in step 3 of Example 1 from 2,4-dichloro-N,N-dimethyl-5-nitrobenzamide (step 1).

MS (EI) m/z: 363 (M+)

$^1$H-NMR (CDCl$_3$) δ: 9.52 (1H, br.s), 8.20 (1H, s), 7.34 (2H, d, J=8.2 Hz), 7.22 (2H, d, J=8.2 Hz), 7.16 (1H, s), 3.92 (2H, m), 3.13 (3H, s), 2.89–2.94 (5H, m).

STEP 3. 5-amino-2-chloro-4-{[4-(2-hydroxyethyl)phenyl]amino}-N,N-dimethylbenzamide The title compound was prepared according to the procedure described in step 2 of Example 28 from 2-chloro-4-{[4-(2-hydroxyethyl)phenyl]amino}-N,N-dimethyl-5-nitrobenzamide (step 2).

$^1$H-NMR (CDCl$_3$) δ: 7.05–7.11 (3H, m), 6.79 (2H, d, J=8.5 Hz), 6.63 (1H, s), 5.59 (1H, s), 3.79–3.83 (4H, m), 3.11 (3H, s), 2.92 (3H, s), 2.79 (2H, t, J=6.4 Hz).

STEP 4. 2-{4-[6-chloro-5-[(dimethylamino)carbonyl]-2-(1-methylethyl)-1H-benzimidazol-1-yl]phenyl}ethyl propanoate The title compound was prepared according to the procedure described in step 5 of Example 1 from 5-amino-2-chloro-4-{[4-(2-hydroxyethyl)phenyl]amino}-N,N-dimethylbenzamide (step 3).

STEP 5. 6-chloro-1-[4-(2-hydroxyethyl)phenyl]-N,N-dimethyl-2-(1-methylethyl)-1H-benzimidazole-5-carboxamide The title compound was prepared according to the procedure described in step 6 of Example 1 from 2-{4-[6-chloro-5-[(dimethylamino)carbonyl]-2-(1-methylethyl)-1H-benzimidazol-1-yl]phenyl}ethyl propanoate (step 4).

MS (EI) m/z: 371 (M+)

$^1$H-NMR (CDCl$_3$) δ: 7.66 (1H, s), 7.46 (2H, d, J=8.5 Hz), 7.27 (2H, d, J=8.5 Hz), 7.12 (1H, s), 3.95–4.00 (2H, m), 3.17 (3H, s), 3.00 (2H, d, J=6.6 Hz), 2.87 (3H, s), 2.78 (2H, q, J=7.5 Hz), 1.34 (3H, t, J=7.5 Hz).

233

STEP 6. 2-{4-[6-chloro-5-[(dimethylamino)carbonyl]-2-(1-methylethyl)-1H-benzimidazol-1-yl]phenyl}ethyl(4-methylphenyl)sulfonylcarbamate The title compound was prepared according to the procedure described in Example 3 from 6-chloro-1-[4-(2-hydroxyethyl)phenyl]-N,N-dimethyl-2-(1-methylethyl)-1H-benzimidazole-5-carboxamide (step 5).

m.p.: 173–176° C.

IR (KBr) ν: 1741, 1637, 1519, 1398, 1344, 1159, 1078, 904 cm$^{-1}$

MS (ESI) m/z: 569 (MH$^+$), 567 ([M−H]$^−$)

$^1$H-NMR (CDCl$_3$) δ: 7.93 (2H, d, J=8.4 Hz), 7.70 (1H, s), 7.27–7.34 (4H, m), 7.09–7.12 (3H, m), 4.35 (2H, t, J=6.6 Hz), 3.19 (3H, s), 2.98 (2H, t, J=6.6 Hz), 2.88 (3H, s), 2.74 (2H, q, J=7.5 Hz), 2.42 (3H, s), 1.29 (3H, t, J=7.5 Hz).

EXAMPLE 336

2-(4-{6-CHLORO-2-ETHYL-5-[(METHYLOXY)METHYL]-1H-BENZIMIDAZOL-1-YL}PHENYL)ETHYL(4-METHYLPHENYL)SULFONYLCARBAMATE

STEP 1. 1,5-dichloro-2-[(methyloxy)methyl]-4-nitrobenzene

To a solution of 1,5-dichloro-2-(chloromethyl)-4-nitrobenzene (Hagmann, William K.; Dorn, Conrad P.; Frankshun, Robert A.; O'Grady, Laura A.; Bailey, Philip J.; et al.; JMCMAR; J. Med. Chem.; EN; 29; 8; 1986; 1436–1441, 10.6 g, 44 mmol) in methanol (30 ml) was added sodium methoxide (44 ml, 66 mmol) at room temperature. The mixture was stirred at 80° C. for 21 h. The volatile component was removed under reduced pressure, and the residue was extracted with ethyl acetate (100 ml). The organic layer was washed with water (50 ml), brine (50 ml), then dried (Na$_2$SO$_4$). After removal of solvent, the crude product was purified by flash column chromatography eluting with hexane/ethyl acetate (6:1/4:1) to afford 2.8 g (27%) of the title compound as pale yellow oil.

$^1$H-NMR (CDCl$_3$) δ: 8.01 (1H, s), 7.09 (1H, s), 4.49 (2H, s), 3.96 (3H, s).

STEP 2. 2-[4-({5-chloro-4-[(methyloxy)methyl]-2-nitrophenyl}amino)phenyl]ethanol The title compound was prepared according to the procedure described in step 3 of Example 1 from 1,5-dichloro-2-[(methyloxy)methyl]-4-nitrobenzene (step 1).

$^1$H-NMR (CDCl$_3$) δ: 9.45 (1H, br.s), 8.28 (1H, s), 7.17–7.33 (5H, m), 4.44 (2H, s), 3.91 (1H, br.s), 3.45 (3H, s), 2.91 (2H, t, J=6.6 Hz).

STEP 3. 2-[4-({2-amino-5-chloro-4-[(methyloxy)methyl]phenyl}amino)phenyl]ethanol The title compound was prepared according to the procedure described in step 2 of Example 28 from 2-[4-({5-chloro-4-[(methyloxy)methyl]-2-nitrophenyl}amino)phenyl]ethanol (step 2).

$^1$H-NMR (CDCl$_3$) δ: 7.07–7.01 (3H, m), 6.88 (1H, s), 6.74 (2H, d, J=8.4 Hz), 5.16 (1H, br.s), 4.47 (2H, s), 3.82 (2H, t, J=6.6 Hz), 3.71 (2H, br.s), 3.46 (3H, s), 2.79 (2H, t, J=6.6 Hz).

STEP 4. 2-(4-{6-chloro-2-ethyl-5-[(methyloxy)methyl]-1H-benzimidazol-1-yl}phenyl)ethanol The title compound was prepared according to the procedure described in step 5 of Example 1 from 2-[4-({2-amino-5-chloro-4-[(methyloxy)methyl]phenyl}amino)phenyl]ethanol (step 3).

MS (EI) m/z: 344 (M+)

234

$^1$H-NMR (CDCl$_3$) δ: 7.82 (1H, s), 7.46 (2H, d, J=8.2 Hz), 7.28 (2H, d, J=8.2 Hz), 7.12 (1H, s), 4.65 (1H, s), 3.99 (2H, br.s), 3.45 (3H, s), 3.00 (3H, t, J=7.6 Hz), 2.78 (2H, q, J=7.6 Hz), 1.34

STEP 5. 2-(4-{6-chloro-2-ethyl-5-[(methyloxy)methyl]-1H-benzimidazol-1-yl}phenyl)ethyl(4-methylphenyl)sulfonylcarbamate The title compound was prepared according to the procedure described in Example 3 from 2-(4-{6-chloro-2-ethyl-5-[(methyloxy)methyl]-1H-benzimidazol-1-yl}phenyl)ethanol (step 4).

m.p.: 174.5° C.

IR (KBr) ν: 3377, 2813, 1718, 1519, 1398, 1342, 1159, 1093, 1062 cm$^{-1}$

MS (ESI) m/z: 542 (MH$^+$), 540 ([M−H]$^−$)

$^1$H-NMR (CDCl$_3$) δ: 7.94 (2H, d, J=8.2 Hz), 7.83 (1H, s), 7.08–7.33 (7H, m), 4.64 (s, 2H), 4.37 (2H, t, J=6.4 Hz), 3.46 (3H, s), 2.97 (2H, t, J=6.4 Hz), 2.73 (2H, q, J=7.5 Hz), 2.42 (3H, s), 1.26 (3H, t, J=7.5 Hz).

EXAMPLE 337

2-{4-[6-CHLORO-2-ETHYL-5-(HYDROXYMETHYL)-1H-BENZIMIDAZOL-1-YL]PHENYL}ETHYL(4-METHYLPHENYL)SULFONYLCARBAMATE

STEP 1. 2-{4-[6-chloro-5-(chloromethyl)-2-ethyl-1H-benzimidazol-1-yl]phenyl}ethanol The title compound was prepared according to the procedure described in step 5 of Example 1 from 2-[4-({2-amino-5-chloro-4-[(methyloxy)methyl]phenyl}amino)phenyl]ethanol (Example 336, step 3).

MS (EI) m/z: 348 (M+)

$^1$H-NMR (CDCl$_3$) δ: 7.83 (1H, s), 7.46 (2H, d, J=8.2 Hz), 7.27 (2H, d, J=8.2 Hz), 7.15 (1H, s), 4.84 (2H, s), 3.96–4.02 (2H, m), 3.00 (2H, t, J=6.4 Hz), 2.77 (2H, q, J=7.5 Hz), 1.34 (2H, t, J=7.5 Hz).

STEP 2. 6-chloro-5-(chloromethyl)-1-[4-(2-{[(1,1-dimethylethyl)(dimethyl)silyl]oxy}ethyl)phenyl]-2-ethyl-1H-benzimidazole The title compound was prepared according to the procedure described in step 2 of Example 90 from 2-{4-[6-chloro-5-(chloromethyl)-2-ethyl-1H-benzimidazol-1-yl]phenyl}ethanol (step 1).

MS (EI) m/z: 405 (M+)

$^1$H-NMR (CDCl$_3$) δ: 7.83 (1H, s), 7.43 (2H, d, J=8.4 Hz), 7.23 (2H, d, J=8.4 Hz), 7.11 (1H, s), 4.85 (2H, s), 3.91 (2H, t, J=6.4 Hz), 2.94 (2H, t, J=6.4 Hz), 2.76 (2H, q, J=7.5 Hz), 1.33 (3H, t, J=7.5 Hz), 0.87 (9H, s), 0.00 (6H, s).

STEP 3. {6-chloro-1-[4-(2-{[(1,1-dimethylethyl)(dimethyl)silyl]oxy}ethyl)phenyl]-2-ethyl-1H-benzimidazol-5-yl}methyl propanoate To a solution of 6-chloro-5-(chloromethyl)-1-[4-(2-{[(1,1-dimethylethyl)(dimethyl)silyl]oxy}ethyl)phenyl]-2-ethyl-1H-benzimidazole (step 2, 403 mg, 0.86 mmol) in N,N-dimethylformamide (10 ml) was added propionic acid (0.06 ml, 0.86 mmol) and NaHCO$_3$ (144 mg, 1.72 mmol) at room temperature. The mixture was stirred at 60° C. for 7 h. The mixture was added water (50 ml) and extracted with ethyl acetate(100 ml). The organic layer was washed with brine (50 ml), then dried (Na$_2$SO$_4$). After removal of solvent, the crude product was purified by flash column chromatography eluting with hexane/ethyl acetate (8:1/4:1) to afford 235 mg (53%) of the title compound as pale yellow oil.

¹H-NMR (CDCl₃) δ: 7.81 (1H, s), 7.43 (2H, d, J=8.5 Hz), 7.24 (2H, d, J=8.5 Hz), 7.11 (1H, s), 5.33 (2H, s), 3.91 (2H, t, J=6.6 Hz), 2.93 (2H, t, J=6.6 Hz), 2.77 (2H, q, J=7.5 Hz), 2.42 (2H, q, J=7.5 Hz), 1.33 (3H, t, J=7.5 Hz), 1.18 (3H, t, J=7.5 Hz), 0.87 (9H, s), 0.00 (6H, s).

STEP 4. {6-chloro-2-ethyl-1-[4-(2-hydroxyethyl)phenyl]-1H-benzimidazol-5-yl}methyl propanoate The title compound was prepared according to the procedure described in step 6 of Example 90 from {6-chloro-1-[4-(2-{[(1,1-dimethylethyl)(dimethyl)silyl]oxy}ethyl) phenyl]-2-ethyl-1H-benzimidazol-5-yl}methyl propanoate (step 3).

MS (EI) m/z: 386 (M+)

¹H-NMR (CDCl₃) δ: 7.70 (1H, s), 7.37 (2H, d, J=8.3 Hz), 7.17 (2H, d, J=8.3 Hz), 7.04 (1H, s), 5.21 (2H, s), 3.88 (2H, d, J=6.6 Hz), 2.91 (2H, t, J=6.6 Hz), 2.67 (2H, q, J=7.5 Hz), 2.32 (2H, q, J=7.5 Hz), 1.24 (3H, t, J=7.5 Hz), 1.08 (3H, t, J=7.5 Hz).

STEP 5. [6-chloro-2-ethyl-1-(4-{2-[({[(4-methylphenyl)sulfonyl]amino}carbonyl)oxy]ethyl}phenyl)-1H-benzimidazol-5-yl]methyl propanoate The title compound was prepared according to the procedure described in Example 3 from {6-chloro-2-ethyl-1-[4-(2-hydroxyethyl)phenyl]-1H-benzimidazol-5-yl}methyl propanoate (step 4).

¹H-NMR (CDCl₃) δ: 7.92 (2H, d, J=8.3 Hz), 7.81 (1H, s), 7.32–7.36 (4H, m), 7.21–7.25 (2H, m), 7.10 (1H, s), 5.32 (2H, s), 4.38 (2H, t, J=6.7 Hz), 3.02 (2H, t, J=6.7 Hz), 2.76 (2H, q, J=7.6 Hz), 2.37–2.49 (5H, m), 1.33 (3H, t, J=7.6 Hz), 1.18 (3H, t, J=7.6 Hz).

STEP 6. 2-{4-[6-chloro-2-ethyl-5-(hydroxymethyl)-1H-benzimidazol-1-yl]phenyl}ethyl(4-methylphenyl)sulfonylcarbamate The title compound was prepared according to the procedure described in step 6 of Example 1 from [6-chloro-2-ethyl-1-(4-{2-[({[(4-methylphenyl)sulfonyl]amino}carbonyl)oxy]ethyl}phenyl)-1H-benzimidazol-5-yl] methyl propanoate (step 5).

m.p.: 172.7° C.

IR (KBr) ν: 1745, 1519, 1240, 1160, 1089, 1058 cm⁻¹

MS (ESI) m/z: 528 (MH⁺), 526 ([M−H]⁻)

¹H-NMR (DMSO-d₆) δ: 7.74–7.77 (3H, m), 7.39–7.46 (6H, m), 7.03 (1H, s), 4.63 (2H, s), 4.27 (2H, t, J=6.6 Hz), 2.95 (2H, t, J=6.6 Hz), 2.72 (2H, q, J=7.5 Hz), 2.34 (3H, s), 1.23 (3H, t, J=7.5 Hz).

EXAMPLE 338

N-({[2-(4-{6-CHLORO-2-ETHYL-5-[(METHYLOXY)METHYL]-1H-BENZIMIDAZOL-1-YL}PHENYL)ETHYL]AMINO}CARBONYL)-4-METHYLBENZENSULFONAMIDE

STEP 1. 1-[4-(2-azidoethyl)phenyl]-6-chloro-2-ethyl-5-[(methyloxy)methyl]-1H-benzimidazole The title compound was prepared according to the procedure described in step 5 of Example 26 from 2-(4-{6-chloro-2-ethyl-5-[(methyloxy)methyl]-1H-benzimidazol-1-yl}phenyl)ethanol (Example 336, step 4).

MS (EI) m/z: 369 (M⁺)

¹H-NMR (CDCl₃) δ: 7.82 (1H, s), 7.45 (2H, d, J=8.4 Hz), 7.30 (2H, d, J=8.4 Hz), 7.11 (1H, s), 4.65 (2H, s), 3.62 (2H, t, J=7.0 Hz), 3.45 (3H, s), 3.02 (2H, t, J=J=7.0 Hz), 2.77 (2H, q, J=7.7 Hz), 1.34 (3H, t, J=7.7 Hz).

STEP 2. 2-(4-{6-chloro-2-ethyl-5-[(methyloxy)methyl]-1H-benzimidazol-1-yl}phenyl)ethanamine The title compound was prepared according to the procedure described in step 9 of Example 1 from 1-[4-(2-azidoethyl)phenyl]-6-chloro-2-ethyl-5-[(methyloxy)methyl]-1H-benzimidazole (step 1).

¹H-NMR (CDCl₃) δ: 7.82 (1H, s), 7.42 (2H, d, J=8.4 Hz), 7.24–7.29 (2H, m), 7.12 (1H, s), 4.65 (1H, s), 3.45 (3H, ds), 3.08 (2H, t, J=6.7 Hz), 2.88 (2H, t, J=6.7 Hz), 2.77 (2H, q, J=7.6 Hz), 1.34 (3H, t, J=7.6 Hz).

STEP 3. N-({[2-(4-{6-chloro-2-ethyl-5-[(methyloxy)methyl]-1H-benzimidazol-1-yl}yl)phenyl)ethyl]amino}carbonyl)-4-methylbenzenesulfonamide The title compound was prepared according to the procedure described in step 10 of Example 1 from 2-(4-{6-chloro-2-ethyl-5-[(methyloxy)methyl]-1H-benzimidazol-1-yl}phenyl)ethanamine (step 2).

m.p.: 134.6° C.

IR (KBr) ν: 3377, 2813, 1718, 1519, 1398, 1342, 1159, 1093, 1062 cm⁻¹

MS (ESI) m/z: 541 (MH⁺), 539 ([M−H]⁻)

¹H-NMR (CDCl₃) δ: 7.82 (1H, s), 7.72 (2H, d, J=8.4 Hz), 7.24–7.39 (4H, m), 7.09 (1H, s), 6.72 (1H, br.s), 4.65 (2H, s), 3.57 (2H, m), 3.45 (3H, s), 2.93 (2H, d, J=6.8 Hz), 2.77 (2H, q, J=7.5 Hz), 2.40 (3H, s), 1.32 (3H, t, J=7.5 Hz).

EXAMPLE 339

2-{4-[6-CHLORO-2-[3-(4PYRIDINYL)PROPYL]-5-(TRIFLUOROMETHYL)-1H-BENZIMIDAZOL-1-YL]PHENYL}ETHYL(4-METHYLPHENYL) SULFONYLCARBAMATE

STEP 1. 2-(4-{5-chloro-2-nitro-4-(trifluoromethyl)phenyl]amino}phenyl)ethyl acetate To a mixture of 2-(4-{[5-chloro-2-nitro-4-(trifluoromethyl)phenyl]amino}phenyl)ethanol (Example 104, step 1, 8.1 g, 22.4 mmol) and pyridine (1.8 ml, 22.45 mmol) in dichloromethane (200 ml) was added acetyl chloride (1.6 ml, 22.4 mmol) at 0° C. The mixture was stirred at 0° C. for 45 min. The mixture was added water (50 ml) and extracted with dichloromethane (300 ml). The organic layer was washed with brine (100 ml), then dried (Na₂SO₄). After removal of solvent, the crude product was purified by flash column chromatography eluting with hexane/ethyl acetate (2:1) to afford 8.6 g (95%) of the title compound as yellow solids.

¹H-NMR (CDCl₃) δ: 9.68 (1H, br.s), 8.57 (1H, s), 7.35 (2H, d, J=8.4 Hz), 7.22 (2H, d, J=8.4 Hz), 7.17 (1H, s), 4.33 (2H, t, J=7.0 Hz), 3.00 (2H, t, J=7.0 Hz), 2.06 (3H, s).

STEP 2. 2-(4-{[2-amino-5-chloro-4-(trifluoromethyl)phenyl]amino}phenyl)ethyl acetate The title compound was prepared according to the procedure described in step 2 of Example 28 from 2-(4-{[5-chloro-2-nitro-4-(trifluoromethyl)phenyl]amino}phenyl) ethyl acetate (step 1).

¹H-NMR (CDCl₃) δ: 7.13–7.16 (3H, m), 7.06 (1H, s), 6.89 (2H, d, J=8.4 Hz), 5.43 (1H, br.s), 4.26 (2H, t, J=7.2 Hz), 3.69 (2H, br.s), 2.89 (2H, d, J=7.2 Hz), 2.04 (3H, s).

STEP 3. 2-(4-{5-chloro-2-{[4-(4-pyridinyl)butanoyl]amino}-4-(trifluoromethyl)phenyl]amino}phenyl)ethyl acetate A mixture of 2-(4-{[2-amino-5-chloro-4-(trifluoromethyl)phenyl]amino}phenyl)ethyl acetate (step 2, 250 mg, 0.67 mmol), 4-(4-pyridinyl)butanoic acid (200 mg, 1 mmol), and WSC (191 mg, 1 mmol) in dichloromethane (7 ml) was stirred at room temperature for 1.5 h. The mixture was added water (5 ml) and extracted with dichloromethane(30 ml). The organic layer was washed with brine (5 ml), then dried ($Na_2SO_4$). The solvent was removed under reduced pressure to afford the title compound as pale brown amorphous.

MS (EI) m/z: 519 (M+)

STEP 4. 2-{4-[6-chloro-2-[3-(4-pyridinyl)propyl]-5-(trifluoromethyl)-1H-benzimidazol-1-yl]phenyl}ethanol A mixture of 2-(4-{[5-chloro-2-{[4-(4-pyridinyl)butanoyl]amino}-4-(trifluoromethyl)phenyl]amino}phenyl) ethyl acetate (step 3, 220 mg, 0.42 mmol) and 2N NaOH (15 ml) in ethanol (20 ml) was stirred at 40° C. for 7 h. The solvent was removed and the residue was added water (50 ml). The mixture was extracted with ethyl acetate(100 ml). The organic layer was washed with brine (50 ml), then dried ($Na_2SO_4$). After removal of solvent, the crude product was purified by flash column chromatography eluting with dichloromethane:methanol (20:1) to afford 105 mg (54%) of the title compound as pale brown oil.

$^1$H-NMR (CDCl$_3$) δ: 8.40–8.42 (2H, m), 8.10 (1H, s), 7.43 (2H, d, J=8.3 Hz), 7.16–7.19 (3H, m), 7.02 (2H, d, J=6.0 Hz), 4.00 (2H, t, J=6.2 Hz), 3.00 (2H, t, J=6.2 Hz), 2.75 (2H, t, J=7.3 Hz), 2.68 (2H, t, J=7.3 Hz), 2.11–2.19 (2H, m).

STEP 5. 2-{4-[6-chloro-2-[3-(4-pyridinyl)propyl]-5-(trifluoromethyl)-1H-benzimidazol-1-yl]phenyl}ethyl(4-methylphenyl)sulfonylcarbamate The title compound was prepared according to the procedure described in Example 3 from 2-{4-[6-chloro-2-[3-(4-pyridinyl)propyl]-5-(trifluoromethyl)-1H-benzimidazol-1-yl]phenyl}ethanol (step 4).

m.p.: 80–87° C.

IR (KBr) v: 1743, 1610, 1517, 1431, 1346, 1161 cm$^{-1}$

MS (ESI) m/z: 657 (MH$^+$), 655 ([M–H]$^-$)

$^1$H-NMR (CDCl$_3$) δ: 8.32 (2H, d, J=6.0 Hz), 8.09 (1H, s), 7.99 (2H, d, J=8.2 Hz), 7.34 (2H, d, J=8.2 Hz), 7.22 (2H, d, J=8.2 Hz), 7.15 (1H, s), 6.94–7.02 (4H, m), 4.48 (2H, t, J=5.4 Hz), 3.01 (2H, t, J=5.4 Hz), 2.74 (2H, t, J=6.0 Hz), 2.54 (2H, t, J=7.9 Hz), 2.44 (3H, s), 2.16–2.21 (2H, m).

EXAMPLE 340

2-{4-[6-CHLORO-2-[3-(3-PYRIDINYL)PROPYL]-5-(TRIFLUOROMETHYL)-1H-BENZIMIDAZOL-1-YL]PHENYL}ETHYL(4-METHYLPHENYL)SULFONYLCARBAMATE

Step 1. 2-(4-{[5-Chloro-2-{[4-(3-pyridinyl)butanoyl]amino}-4-(trifluoromethyl)phenyl]amino}phenyl)ethyl acetate The title compound was prepared according to the procedure described in step 3 of Example 339 from 2-(4-{[2-amino-5-chloro-4-(trifluoromethyl)phenyl]amino}phenyl) ethyl acetate (Example 339, step 2).

$^1$H-NMR (CDCl$_3$) δ: 8.43 (2H, br.s), 7.50–7.71 (2H, m), 7.15–7.28 (6H, m), 6.96 (2H, d, J=8.3 Hz), 6.43 (1H, br.s), 4.26 (2H, t, J=7.0 Hz), 2.90 (2H, t, J=7.0 Hz), 2.70 (2H, t, J=7.3 Hz), 2.41 (2H, t, J=7.3 Hz), 2.03–2.08 (5H, m).

STEP 2. 2-{4-[6-chloro-2-[3-(3-pyridinyl)propyl]-5-(trifluoromethyl)-1H-benzimidazol-1-yl]phenyl}ethanol The title compound was prepared according to the procedure described in step 4 of Example 339 from 2-(4-{[5-chloro-2-{[4-(3-pyridinyl)butanoyl]amino}-4-(trifluoromethyl)phenyl]amino}phenyl)ethyl acetate (step 1).

MS (EI) m/z: 459 (M$^+$)

$^1$H-NMR (CDCl$_3$) δ: 8.33 (1H, d, J=4.4 Hz), 8.09 (1H, s), 7.62 (1H, s), 7.43–7.50 (3H, m), 7.16–7.22 (4H, m), 4.02 (2H, t, J=5.6 Hz), 2.99 (2H, t, J=5.6 Hz), 2.74 (2H, t, J=7.5 Hz), 2.64 (2H, t, J=6.6 Hz), 2.04–2.13 (2H, m).

STEP 3. 2-{4-[6-chloro-2-[3-(3-pyridinyl)propyl]-5-(trifluoromethyl)-1H-benzimidazol-1-yl]phenyl}ethyl(4-methylphenyl)sulfonylcarbamate The title compound was prepared according to the procedure described in Example 3 from 2-{4-[6-chloro-2-[3-(3-pyridinyl)propyl]-5-(trifluoromethyl)-1H-benzimidazol-1-yl]phenyl}ethanol (step 2).

m.p.: 90–95° C.

IR (KBr) v: 1743, 1517, 1431, 1346, 1301, 1161, 1130, 1085 cm$^{-1}$

MS (ESI) m/z: 657 (MH$^+$), 655 ([M–H]$^-$)

$^1$H-NMR (CDCl$_3$) δ: 8.59 (1H, dd, J=1.7 Hz, 5.1 Hz), 8.08 (1H, s), 7.95 (2H, d, J=8.3 Hz), 7.86 (1H, d, J=1.7 Hz), 7.54–7.58 (1H, m), 7.27–7.34 (5H, m), 7.20 (1H, s), 7.12 (2H, d, J=8.4 Hz), 4.46 (2H, t, J=5.1 Hz), 3.00 (2H, t, J=5.1 Hz), 2.77–2.82 (2H, m), 2.62 (2H, t, J=7.0 Hz), 2.43 (3H, s), 1.85–1.91 (2H, m).

EXAMPLE 341

2-{4-[6-CHLORO-2-[3-OXO-3-(3-PYRIDINYL)PROPYL]-5-(TRIFLUOROMETHYL)-1H-BENZIMIDAZOL-1-YL]PHENYL}ETHYL(4-METHYLPHENYL)SULFONYLCARBAMATE

STEP 1. 2-(4-{[5-chloro-2-{[4-oxo-4-(3-pyridinyl)butanoyl]amino}-4-(trifluoromethyl)phenyl]amino}phenyl) ethyl acetate The title compound was prepared according to the procedure described in step 3 of Example 339 from 2-(4-{[2-amino-5-chloro-4-(trifluoromethyl)phenyl]amino}phenyl) ethyl acetate (Example 339, step 2).

$^1$H-NMR (CDCl$_3$) δ: 9.19 (1H, d, J=2.2 Hz), 8.80 (1H, dd, J=1.8 Hz, 3.9 Hz), 8.20 (1H, d, J=7.9 Hz), 7.64 (2H, br.s), 7.44 (1H, dd, J=5.8 Hz, 7.9 Hz), 7.28 (1H, s), 7.19 (2H, d, J=8.3 Hz), 7.05 (2H, d, J=8.3 Hz), 6.70 (1H, br.s), 4.27 (2H, t, J=7.1 Hz), 3.49 (2H, t, J=5.5 Hz), 2.92 (2H, t, J=7.1 Hz), 2.78 (2H, t, J=5.8 Hz), 2.05 (3H, s).

Step 2. 3-[6-Chloro-1-[4-(2-hydroxyethyl)phenyl]-5-(trifluoromethyl)-1H-benzimidazol-2-yl]-1-(3-pyridinyl)-1-propanone The title compound was prepared according to the procedure described in step 4 of Example 339 from 2-(4-{[5-chloro-2-{[4-oxo-4-(3-pyridinyl)butanoyl]amino}-4-(trifluoromethyl)phenyl]amino}phenyl)ethyl acetate (step 1).

$^1$H-NMR (CDCl$_3$) δ: 9.05–9.06 (1H, m), 8.77–8.79 (1H, m), 8.24–8.28 (1H, m), 8.06 (1H, s), 7.54 (2H, d, J=8.5 Hz), 7.40–7.46 (3H, m), 3.97–4.04 (2H, m), 3.66 (2H, t, J=7.0 Hz), 3.19 (2H, t, J=7.0 Hz), 3.02 (2H, t, J=6.4 Hz).

STEP 3. 2-{4-[6-chloro-2-[3-oxo-3-(3-pyridinyl)propyl]-5-(trifluoromethyl)-1H-benzimidazol-1-yl]phenyl}ethyl(4-methylphenyl)sulfonylcarbamate The title compound was prepared according to the procedure described in Example 3 from 3-[6-chloro-1-[4-(2- hydroxyethyl)phenyl]-5-(trifluoromethyl)-1H-benzimidazol-2-yl]-1-(3-pyridinyl)-1-propanone (step 2).

m.p.: 89–95° C.

IR (KBr) v: 2972, 1747, 1693, 1517, 1346, 1230, 1161, 1085 cm$^{-1}$

MS (ESI) m/z: 671 (MH$^+$), 669 ([M–H]$^-$)

$^1$H-NMR (CDCl$_3$) δ: 8.91 (1H, s), 8.83–8.85 (1H, m), 8.23–8.27 (1H, m), 8.05 (1H, s), 7.92 (2H, d, J=8.2 Hz), 7.33–7.48 (7H, m), 7.21 (1H, s), 4.43 (2H, t, J=6.3 Hz), 3.47 (2H, t, J=7.1 Hz), 3.25 (2H, t, J=7.1 Hz), 3.04 (2H, t, J=6.3 Hz), 2.43 (3H, s).

EXAMPLE 342

2-{4-[6-CHLORO-2-[3-OXO-3-(2-PYRIDINYL)PROPYL]-5-(TRIFLUOROMETHYL)-1H-BENZIMIDAZOL-1-YL]PHENYL}ETHYL(4-METHYLPHENYL)SULFONYLCARBAMATE

STEP 1. 2-(4-{[5-chloro-2-{[4-oxo-4-(2-pyridinyl)butanoyl]amino}-4-(trifluoromethyl)phenyl]amino}phenyl)ethyl acetate The title compound was prepared according to the procedure described in step 3 of Example 339 from 2-(4-{[2-amino-5-chloro-4-(trifluoromethyl)phenyl]amino}phenyl)ethyl acetate (Example 339, step 2).

MS (EI) m/z: 533 (M$^+$)

STEP 2. 3-[6-chloro-1-[4-(2-hydroxyethyl)phenyl]-5-(trifluoromethyl)-1H-benzimidazol-2-yl]-1-(2-pyridinyl)-1-propanone The title compound was prepared according to the procedure described in step 4 of Example 339 from 2-(4-{[5-chloro-2-{[4-oxo-4-(2-pyridinyl)butanoyl]amino}-4-(trifluoromethyl)phenyl]amino}phenyl)ethyl acetate (step 1).

$^1$H-NMR (CDCl$_3$) δ: 8.67–8.69 (1H, m), 7.84 (1H, s), 7.96–7.99 (1H, m), 7.81–7.84 (1H, m), 7.39–7.51 (5H, m), 7.23 (1H, s), 3.96–4.02 (2H, m), 3.91 (2H, t, J=6.9 Hz), 3.15 (2H, t, J=6.9 Hz), 3.01 (2H, t, J=6.4 Hz).

STEP 3. 2-{4-[6-chloro-2-[3-oxo-3-(2-pyridinyl)propyl]-5-(trifluoromethyl)-1H-benzimidazol-1-yl]phenyl}ethyl(4-methylphenyl)sulfonylcarbamate The title compound was prepared according to the procedure described in of Example 3 from 3-[6-chloro-1-[4-(2-hydroxyethyl)phenyl]-5-(trifluoromethyl)-1H-benzimidazol-2-yl]-1-(2-pyridinyl)-1-propanone (step 2).

m.p.: 233.6° C.

IR (KBr) v: 1743, 1703, 1515, 1481, 1336, 1203, 1120, 1087, 995 cm$^{-1}$

MS (ESI) m/z: 671 (MH$^+$), 669 ([M–H]$^-$)

$^1$H-NMR (DMSO-d$_6$) δ: 8.74–8.76 (1H, m), 8.13 (1H, S), 7.90–8.03 (2H, m), 7.77 (2H, d, J=8.1 Hz), 7.66–7.70 (1H, m), 7.49–7.58 (4H, m), 7.42 (2H, d, J=8.1 Hz), 7.34 (1H, s), 4.30 (2H, t, J=6.4 Hz), 3.83 (2H, t, J=6.4 Hz), 3.09 (2H, t, J=6.4 Hz), 2.98 (2H, t, J=6.4 Hz), 2.50 (3H, s).

EXAMPLE 343

2-{4-[6-CHLORO-2-[3-(2PYRIDINYL)PROPYL]-5-(TRIFLUOROMETHYL)-1H-BENZIMIDAZOL-1-YL]PHENYL}ETHYL(4-METHYLPHENYL)SULFONYLCARBAMATE

STEP 1. 2-(4-{[5-chloro-2-{[4-(2-pyridinyl)butanoyl]amino}-4-(trifluoromethyl)phenyl]amino}phenyl)ethyl acetate The title compound was prepared according to the procedure described in step 3 of Example 339 from 2-(4-{[2-amino-5-chloro-4-(trifluoromethyl)phenyl]amino}phenyl)ethyl acetate (Example 339, step 2).

$^1$H-NMR (CDCl$_3$) δ: 9.26 (1H, br.s), 8.39–8.41 (1H, m), 7.86 (1H, s), 7.69–7.72 (1H, m), 7.49 (1H, s), 7.25–7.28 (1H, m), 7.15–7.21 (3H, m), 7.00 (2H, d, J=8.4 Hz), 4.27 (2H, t, J=7.1 Hz), 2.98 (2H, t, J=6.3 Hz), 2.91 (2H, t, J=7.1 Hz), 2.33 (2H, t, J=5.9 Hz), 2.05 (3H, s).

STEP 2. 2-{4-[6-chloro-2-[3-(2-pyridinyl)propyl]-5-(trifluoromethyl)-1H-benzimidazol-1-yl]phenyl}ethanol The title compound was prepared according to the procedure described in step 4 of Example 339 from 2-(4-{[5-chloro-2-{[4-(2-pyridinyl)butanoyl]amino}-4-(trifluoromethyl)phenyl]amino}phenyl)ethyl acetate (step 1).

$^1$H-NMR (CDCl$_3$) δ: 8.43–8.45 (1H, m), 8.09 (1H, s), 7.53–7.59 (1H, m), 7.45 (2H, d, J=8.2 Hz), 7.22–7.25 (3H, m), 7.05–7.13 (2H, m), 3.98 (2H, t, J=6.3 Hz), 3.00 (2H, t, J=6.3 Hz), 2.84 (4H, t, J=7.5 Hz), 2.18–2.22 (2H, m), 1.81–1.90 (2H, m).

STEP 3. 2-{4-[6-chloro-2-[3-(2-pyridinyl)propyl]-5-(trifluoromethyl)-1H-benzimidazol-1-yl]phenyl}ethyl(4-methylphenyl)sulfonylcarbamate The title compound was prepared according to the procedure described in Example 3 from 2-{4-[6-chloro-2-[3-(2-pyridinyl)propyl]-5-(trifluoromethyl)-1H-benzimidazol-1-yl]phenyl}ethanol (step 2).

m.p.: 193° C.

IR (KBr) v: 1747, 1626, 1517, 1433, 1350, 1159, 1120, 1085 cm$^{-1}$

MS (ESI) m/z: 657 (MH$^+$), 655 ([M–H]$^-$)

$^1$H-NMR (CDCl$_3$) δ: 8.47–8.49 (1H, m), 8.08 (1H, s), 7.90 (2H, d, J=8.4 Hz), 7.60–7.66 (1H, m), 7.36 (2H, d, J=8.4 Hz), 7.11–7.22 (7H, m), 4.44 (2H, t, J=6.0 Hz), 3.01 (2H, t, J=6.0 Hz), 2.82–2.88 (4H, m), 2.45 (3H, s), 1.84–1.94 (2H, m).

EXAMPLE 344

2-{4-[6-CHLORO-2-[3-(2PYRIDINYL)PROPYL]-5-(TRIFLUOROMETHYL)-1H-BENZIMIDAZOL-1-YL]PHENYL}ETHYL(4-METHYLPHENYL)SULFONYLCARBAMATE P-TOLUENESULFONATE

The title compound was prepared according to the procedure described in Example 231 from 2-{4-[6-chloro-2-[3-(2-pyridinyl)propyl]-5-(trifluoromethyl)-1H-benzimidazol-1-yl]phenyl}ethyl(4-methylphenyl)sulfonylcarbamate (Example 343)

m.p.: 108–110° C.

IR (KBr) v: 3062, 1745, 1456, 1232, 1163, 1010 cm$^{-1}$

EXAMPLE 345

N-{[(2-{4-[2-Ethyl-5-(1-hydroxethyl)-1H-benzimidazol-1-yl]phenyl}ethyl)amino]carbonyl}-4-methylbenzenesulfonamide STEP 1. N-{[(2-{4-[2-ethyl-5-(1-hydroxyethyl)-1H-benzimidazol-1-yl]phenyl}ethyl)amino]carbonyl}-4-methylbenzenesulfonamide A mixture N-[({2-[4-(5-acetyl-2-ethyl-1H-benzimidazol-1-yl)phenyl]ethyl}amino)carbonyl]-4-methylbenzenesulfonamide (Example 78, 238 mg, 0.47 mmol) and 2N NaOH (0.1 ml) in ethanol (10 ml) was added a mixture of NaBH$_4$ (178 mg, 0.47 mmol) and 2N NaOH (0.1 ml) in ethanol (4 ml) at room temperature. The mixture was stirred at room temperature for 4 h. The mixture was added water (10 ml) and neutralized with NH$_4$Cl. The mixture was extracted with ethyl acetate(50 ml). The organic layer was washed with brine (10 ml), then dried (Na$_2$SO$_4$). After removal of solvent, the crude product was purified by flash column chromatography eluting with hexane/ethyl acetate (1:4/1:6)/CH$_2$Cl$_2$:methanol(10:1) to afford 198 mg (83%) of the title compound as white solids.

m.p.: 190° C.

IR (KBr) v: 3384, 2979, 1716, 1514, 1404, 1159, 1087 cm$^{-1}$

MS (ESI) m/z: 507 (MH$^+$), 505 ([M–H]$^-$)

$^1$H-NMR (CDCl$_3$) δ: 7.73–7.76 (3H, m), 7.21–7.34 (7H, m), 7.20 (1H, d, J=8.5 Hz), 6.66 (1H, br.s), 5.02 (1H, q, J=6.4 Hz), 3.52–3.59 (2H, m), 2.91 (2H, t, J=7.0 Hz), 2.75 (2H, q, J=7.5 Hz), 2.39 (3H, s), 1.54 (3H, d, J=6.4 Hz), 1.30 (3H, t, J=7.5 Hz).

EXAMPLE 346

N-{[(2-{4-[2-Ethyl-5-(1-hydroxethyl)-1H-benzimidazol-1-yl]phenyl}ethyl)amino]carbonyl}-4-methylbenzenesulfonamide p-toluenesulfonate The title compound was prepared according to the procedure described in Example 231 from N-{[(2-{4-[2-ethyl-5-(1-hydroxyethyl)-1H-benzimidazol-1-yl]phenyl}ethyl)amino]carbonyl}-4-methylbenzenesulfonamide (Example 345)

m.p.: 110–115° C.

IR (KBr) v: 3062, 1708, 1519, 1340, 1163 cm$^{-1}$

EXAMPLE 347

N-({[2-(4-{2-Ethyl-5-[1-(methyloxy)ethyl]-1H-benzimidazol-1-yl}phenyl)ethyl]amino}carbonyl)-4-methylbenzenesulfonamide STEP 1. N-({[2-(4-{2-ethyl-5-[1-(methyloxy)ethyl]-1H-benzimidazol-1-yl}phenyl)ethyl]amino}carbonyl)-4-methylbenzenesulfonamide A solution of N-{[(2-{4-[2-ethyl-5-(1-hydroxyethyl)-1H-benzimidazol-1-yl]phenyl}ethyl)amino]carbonyl}-4-methylbenzenesulfonamide (Example 345, 151 mg, 0.3 mmol) in CH$_2$Cl$_2$ (15 ml) was added thionyl chloride (0.1 ml, 1.5 mmol) at room temperature. The mixture was stirred at room temperature for 2 h. The solvent was removed and the residue was dissolved with methanol (15 ml). The mixture was added triethylamine (0.08 ml, 0.6 mmol) and stirred at room temperature for 5 h. The solvent was removed and the residue was extracted with CH$_2$Cl$_2$ (50 ml). The organic layer was washed with water(10 ml), brine (10 ml), then dried (Na$_2$SO$_4$). After removal of solvent, the crude product was purified by flash column chromatography eluting with hexane/ethyl acetate (1:6)/CH$_2$Cl$_2$:methanol(10:1) to afford 139 mg (89%) of the title compound as white solids.

MS (ESI) m/z: 521 (MH$^+$), 519 ([M–H]$^-$)

$^1$H-NMR (CDCl$_3$) δ: 7.65–7.75 (3H, m), 7.27–7.37 (6H, m), 7.16–7.20 (1H, m), 7.16–7.20 (1H, m), 7.07 (1H, d, J=8.3 Hz), 6.69 (1H, br.s), 4.42 (1H, q, J=6.5 Hz), 3.54–3.62 (2H, m), 3.22 (3H, s), 2.93 (2H, t, J=7.0 Hz), 2.93 (2H, t, J=7.0 Hz), 2.78 (2H, q, J=7.6 Hz), 2.39 (3H, s), 1.49 (3H, d, J=6.5 Hz.), 1.32 (3H, t, J=7.6 Hz).

EXAMPLE 348

N-({[2-(4-{2-Ethyl-5-[1-(methyloxy)ethyl]-1H-benzimidazol-1-yl}phenyl)ethyl]amino}carbonyl)-4-methylbenzenesulfonamide p-toluenesulfonate The title compound was prepared according to the procedure described in Example 231 from N-({[2-(4-{2-ethyl-5-[1-(methyloxy)ethyl]-1H-benzimidazol-1-yl}phenyl)ethyl]amino}carbonyl)-4-methylbenzenesulfonamide (Example 347)

m.p.: 110–115° C.

IR (KBr) v: 3064, 1710, 1519, 1452, 1340, 1163, 1033 cm$^{-1}$

EXAMPLE 349

N-{[(2-{4-[2-Ethyl-5-(1-hydroxy-1-methylethyl)-1H-benzimidazol-1-yl]phenyl}ethyl)amino]carbonyl}-4-methylbenzenesulfonamide p-toluenesulfonate STEP 1. N-{[(2-{4-[2-ethyl-5-(1-hydroxy-1-methylethyl)-1H-benzimidazol-1-yl]phenyl}ethyl)amino]carbonyl}-4-methylbenzenesulfonamide A solution of N-[({2-[4-(5-acetyl-2-ethyl-1H-benzimidazol-1-yl)phenyl]ethyl}amino)carbonyl]-4-methylbenzenesulfonamide (Example 78, 100 mg, 0.19 mmol) in tetrahydrfurane (15 ml) was added MeMgI (1.2 ml, 0.99 mmol) dropwise under nitrogen at 0° C. The mixture was stirred at 0° C. for 1 h and then was stirred at rt for 30 min. The mixture was added water (10 ml) and extracted with CH$_2$Cl$_2$ (50 ml). The organic layer was washed with brine (10 ml), then dried (Na$_2$SO$_4$). After removal of solvent, the crude product was purified by flash column chromatography eluting with CH$_2$Cl$_2$:methanol (30:1/20:1/10:1) to afford 100 mg (97%) of the title compound as white solids.

MS (ESI) m/z: 521 (MH$^+$), 519 ([M–H]$^-$)

$^1$H-NMR (CDCl$_3$) δ: 7.87 (1H, s), 7.76 (2H, d, J=7.9 Hz), 7.17–7.38 (7H, m), 7.00 (1H, d, J=8.5 Hz), 6.69 (1H, br.s), 3.52 (2H, br.s), 2.88 (2H, br.s), 2.73 (2H, br.s), 2.36 (3H, s), 1.62 (6H, s), 1.27 (3H, m).

STEP 2. N-{[(2-{4-[2-ethyl-5-(1-hydroxy-1-methylethyl)-1H-benzimidazol-1-yl]phenyl}ethyl)amino]carbonyl}-4-methylbenzenesulfonamide p-toluenesulfonate The title compound was prepared according to the procedure described in Example 231 from N-{[(2-{4-[2-ethyl-5-(1-hydroxy-1-methylethyl)-1H-benzimidazol-1-yl]phenyl}ethyl)amino]carbonyl}-4-methylbenzenesulfonamide (Step 1).

m.p.: 146–150° C.

IR (KBr) v: 2871, 1685, 1519, 1448, 1340, 1124 cm$^{-1}$

EXAMPLE 350

2-ETHYL-4,6-DIMETHYL-1-(4-{2-[({[(4-METHYLPHENYL)SULFONYL]AMINO}CARBONYL)AMINO]ETHYL}PHENYL)-1H-BENZIMIDAZOLE-5-CARBOXAMIDE

STEP 1. 1-[4-(2-chloroethyl)phenyl]-2-ethyl-4,6-dimethyl-1H-benzimidazole-5-carboxamide A solution of 1-[4-(2-chloroethyl)phenyl]-2-ethyl-4,6-dimethyl-1H-benzimidazole-5-carbonitrile (Example 329, step 6, 997 mg, 2.95 mmol) in c.H$_2$SO$_4$ (50 ml) was stirred at 80° C. for 15 h. The mixture was poured onto ice and was neutralized with NaOH. The mixture was extracted with ethyl acetate (600 ml). The organic layer was washed with brine (300 ml), then dried (Na$_2$SO$_4$). The solvent was removed to afford 871 mg (83%) of the title compound as white solids.

MS (EI) m/z: 355 (M+)

$^1$H-NMR (CDCl$_3$) δ: 7.43 (2H, d, J=8.4 Hz), 7.28 (2H, d, J=8.4 Hz), 6.73 (1H, s), 6.73 (1H, s), 6,56 (1H, br.s), 5.88 (1H, br.s), 3.82 (2H, t, J=7.0 Hz), 3.19 (2H, t, J=7.0 Hz), 2.82 (2H, q, J=7.6 Hz), 2.72 (3H, s), 2.41 (3H, s), 1.26 (3H, t, J=7.6 Hz).

STEP 2. 1-[4-(2-azidoethyl)phenyl]-2-ethyl-4,6-dimethyl-1H-benzimidazole-5-carboxamide The title compound was prepared according to the procedure described in step 8 Example 1 from 1-[4-(2-chloroethyl)phenyl]-2-ethyl-4,6-dimethyl-1H-benzimidazole-5-carboxamide (step 1).

$^1$H-NMR (CDCl$_3$) δ: 7.44 (2H, d, J=8.4 Hz), 7.27–7.30 (2H, m), 6.73 (1H, s), 5.97 (1H, br.s), 5.72 (1H, br.s), 3.62 (2H, t, J=7.1 Hz), 3.02 (2H, t, J=7.1 Hz), 2.80 (2H, q, J=7.5 Hz), 2,73 (3H, s), 2.42 (3H, s), 1.26 (3H, t, J=7.5 Hz).

STEP 3. 1-[4-(2-aminoethyl)phenyl]-2-ethyl-4,6-dimethyl-1H-benzimidazole-5-carboxamide The title compound was prepared according to the procedure described in step 9 of Example 1 from 1-[4-(2-azidoethyl)phenyl]-2-ethyl-4,6-dimethyl-1H-benzimidazole-5-carboxamide (step 2).

$^1$H-NMR (CDCl$_3$) δ: 7.41 (2H, d, J=8.2 Hz), 7.26 (2H, d, J=8.2 Hz), 6.74 (1H, s), 6.00 (1H, br.s), 5.76 (1H, br.s), 3.07 (2H, t, J=7.1 Hz), 2.87 (2H, t, J=7.1 Hz), 2.81 (2H, q, J=7.5 Hz), 2.74 (3H, s), 2.43 (3H, s), 1.26 (3H, t, J=7.5 Hz).

STEP 4. 2-ethyl-4,6-dimethyl-1-(4-{2-[({[(4-methylphenyl)sulfonyl]amino}carbonyl)amino]ethyl}phenyl)-1H-benzimidazole-5-carboxamide The title compound was prepared according to the procedure described in step 10 of Example 1 from 1-[4-(2-aminoethyl)phenyl]-2-ethyl-4,6-dimethyl-1H-benzimidazole-5-carboxamide (step 3).

MS (ESI) m/z: 534 (MH$^+$), 532 ([M–H]$^-$)

$^1$H-NMR (CD$_3$OD) δ: 7.88 (1H, s), 7.80 (2H, d, J=8.3 Hz), 7.25–7.42 (6H, m), 6.74 (1H, br.s), 3.42 (2H, t, J=6.8 Hz), 2.86 (2H, t, J=6.8 Hz), 2.79 (2H, q, J=7.6 Hz), 2.65 (3H, s), 2.37 (3H, s), 2.34 (3H, s), 1.21 (3H, t, J=7.6 Hz).

STEP 5. 2-ethyl-4,6-dimethyl-1-(4-{2-[({[(4-methylphenyl)sulfonyl]amino}carbonyl)amino]ethyl}phenyl)-1H-benzimidazole-5-carboxamide p-toluenesulfonate The title compound was prepared according to the procedure described in Example 231 from 2-ethyl-4,6-dimethyl-1-(4-{2-[({[(4-methylphenyl)sulfonyl]amino}carbonyl)amino]ethyl}phenyl)-1H-benzimidazole-5-carboxamide (step 4).

EXAMPLE 351

N-{[(2-{4-[2-Ethyl-5-(trifluoroacetyl)-1H-benzimidazol-1-yl]phenyl}ethyl)amino]carbonyl}-4-methylbenzenesulfonamide p-toluenesulfonate STEP 1. 2,2,2-trifluoro-1-(4-{[4-(2-hydroxyethyl)phenyl]amino}-3-nitrophenyl)ethanone The title compound was prepared according to the procedure described in step 1 of Example 45 from 1-(4-amino-3-nitrophenyl)-2,2,2-trifluoroethanone.

$^1$H-NMR (CDCl$_3$) δ: 9.47 (1H, br.s), 8.10 (1H, d, J=2.6 Hz), 7.16–7.33 (6H, m), 3.87–3.94 (2H, m), 2.91 (2H, t, J=6.4 Hz), 1.43 (1H, t, J=5.6 Hz).

STEP 2. 1-(3-amino-4-{[4-(2-hydroxyethyl)phenyl]amino}phenyl)-2,2,2-trifluoroethanone The title compound was prepared according to the procedure described in step 4 of Example 1 from 2,2,2-trifluoro-1-(4-{[4-(2-hydroxyethyl)phenyl]amino}-3-nitrophenyl)ethanone (step 1).

$^1$H-NMR (CDCl$_3$) δ: 7.05–7.09 (3H, m), 6.57–6.70 (4H, m), 3.82 (2H, t, J=6.6 Hz), 2.78 (2H, t, J=6.6 Hz).

STEP 3. 2-{4-[2-ethyl-5-(trifluoroacetyl)-1H-benzimidazol-1-yl]phenyl}ethyl propanoate The title compound was prepared according to the procedure described in step 5 of Example 1 from 1-(3-amino-4-{[4-(2-hydroxyethyl)phenyl]amino}phenyl)-2,2,2-trifluoroethanone (step 2).

$^1$H-NMR (CDCl$_3$) δ: 7.65 (1H, s), 7.45 (2H, d, J=8.3 Hz), 7.29 (2H, d, J=8.3 Hz), 7.06 (2H, s), 4.38 (2H, t, J=6.9 Hz), 3.07 (2H, t, J=6.9 Hz), 2.79 (2H, q, J=7.4 Hz), 2.35 (2H, q, J=7.5 Hz), 1.35 (3H, t, J=7.4 Hz), 1.14 (3H, t, J=7.5 Hz).

STEP 4. 1-{2-ethyl-1-[4-(2-hydroxyethyl)phenyl]-1H-benzimidazol-5-yl}-2,2,2-trifluoroethanone The title compound was prepared according to the procedure described in step 6 of Example 1 from 2-{4-[2-ethyl-5-(trifluoroacetyl)-1H-benzimidazol-1-yl]phenyl}ethyl propanoate (step 3).

$^1$H-NMR (CDCl$_3$) δ: 7.65 (1H, s), 7.47 (2H, d, J=8.4 Hz), 7.29 (2H, d, J=8.4 Hz), 7.06 (2H, s), 3.96–4.03 (2H, m), 3.01 (2H, t, J=6.6 Hz), 2.79 (2H, q, J=7.6 Hz), 1.35 (3H, t, J=7.6 Hz).

STEP 5. 1-{1-[4-(2-chloroethyl)phenyl]-2-ethyl-1H-benzimidazol-5-yl}-2,2,2-trifluoethanone The title compound was prepared according to the procedure described in step 7 Example 1 from 1-{2-ethyl-1-[4-(2-hydroxyethyl)phenyl]-1H-benzimidazol-5-yl}-2,2,2-trifluoroethanone (step 4).

$^1$H-NMR (CDCl$_3$) δ: 7.66 (1H, s), 7.45 (2H, d, J=8.4 Hz), 7.31 (2H, d, J=8.4 Hz), 7.07 (2H, s), 3.82 (2H, t, J=7.0 Hz), 3.20 (2H, t, J=7.0 Hz), 2.79 (2H, q, J=7.6 Hz), 1.36 (3H, t, J=7.6 Hz).

STEP 6. 1-{1-[4-(2-azidoethyl)phenyl]-2-ethyl-1H-benzimidazol-5-yl}-2,2,2-trifluoethanone The title compound was prepared according to the procedure described in step 8 Example 1 from 1-{1-[4-(2-chloroethyl)phenyl]-2-ethyl-1H-benzimidazol-5-yl}-2,2,2-trifluoroethanone (step 5).

$^1$H-NMR (CDCl$_3$) δ: 7.65 (1H, s), 7.46 (2H, d, J=8.4 Hz), 7.31 (2H, d, J=8.4 Hz), 7.06 (1H, s), 3.62 (2H, t, J=7.0 Hz), 3.02 (2H, t, J=7.0 Hz), 2.79 (2H, q, J=7.5 Hz), 1.35 (3H, t, J=7.5 Hz).

STEP 7. 1-{1-[4-(2-aminoethyl)phenyl]-2-ethyl-1H-benzimidazol-5-yl}-2,2,2-trifluorethanone The title compound was prepared according to the procedure described in step 9 of Example 1 from 1-{1-[4-(2-azidoethyl)phenyl]-2-ethyl-1H-benzimidazol-5-yl}-2,2,2-trifluoroethanone (step 6).

$^1$H-NMR (CDCl$_3$) δ: 7.65 (1H, s), 7.43 (2H, d, J=8.5 Hz), 7.28 (2H, d, J=8.5 Hz), 7.07 (2H, s), 3.09 (2H, t, J=6.7 Hz), 2.89 (2H, t, J=6.7 Hz), 2.79 (2H, q, J=7.4 Hz), 1.35 (3H, t, J=7.4 Hz).

STEP 8. N-{[(2-{4-[2-ethyl-5-(trifluoroacetyl)-1H-benzimidazol-1-yl]phenyl}ethyl)amino]carbonyl}-4-methylbenzenesulfonamide The title compound was prepared according to the procedure described in step 10 of Example 1 from 1-{1-[4-(2-aminoethyl)phenyl]-2-ethyl-1H-benzimidazol-5-yl}-2,2,2-trifluoroethanone (step 7).

MS (ESI) m/z: 547 (MH$^+$), 545 ([M−H]$^−$)

$^1$H-NMR (CDCl$_3$) δ: 7.72 (2H, d, J=8.4 Hz), 7.64 (1H, s), 7.39 (2H, d, J=8.4 Hz), 7.27–7.29 (4H, m), 7.02–7.04 (2H, m), 6.75 (1H, br.s), 3.55–3.62 (2H, m), 2.94 (2H, t, J=6.9 Hz), 2.79 (2H, q, J=7.5 Hz), 2.39 (3H, s), 1.33 (3H, t, J=7.5 Hz).

STEP 9. N-{[(2-{4-[2-ethyl-5-(trifluoroacetyl)-1H-benzimidazol-1-yl]phenyl}ethyl)amino]carbonyl}-4-methylbenzenesulfonamide p-toluenesulfonate The title compound was prepared according to the procedure described in Example 231 from N-{[(2-{4-[2-ethyl-5-(trifluoroacetyl)-1H-benzimidazol-1-yl]phenyl}ethyl)amino]carbonyl}-4-methylbenzenesulfonamide (step 8)

m.p.: 194.1° C.

IR (KBr) ν: 3589, 1701, 1627, 1521, 1458, 1330, 1091 cm$^{-1}$

EXAMPLE 352

2-{4-[2-ETHYL-5-(TRIFLUOROACETYL)-1H-BENZIMIDAZOL-1-YL]PHENYL}ETHYL (4-METHYLPHENYL)SULFONYLCARBAMATE P-TOLUENESULFONATE

STEP 1. 2-{4-[2-ethyl-5-(trifluoroacetyl)-1H-benzimidazol-1-yl]phenyl}ethyl(4-methylphenyl)sulfonylcarbamate The title compound was prepared according to the procedure described in Example 3 from 1-{2-ethyl-1-[4-(2-hydroxyethyl)phenyl]-1H-benzimidazol-5-yl}-2,2,2-trifluoroethanone (Example 351, step 4).

MS (ESI) m/z: 548 (MH$^+$), 546 ([M−H]$^−$)

$^1$H-NMR (CDCl$_3$) δ: 7.93 (2H, d, J=8.4 Hz), 7.64(1H, s), 7.28–7.35 (4H, m), 7.20 (2H, d, J=8.4 Hz), 7.05–7.07 (2H, m), 4.37 (2H, t, J=6.6 Hz), 3.00 (2H, t, J=6.6 Hz), 2.76 (2H, q, J=7.6 Hz), 2.43 (3H, s), 1.31 (3H, t, J=7.6 Hz).

STEP 2. 2-{4-[2-ethyl-5-(trifluoroacetyl)-1H-benzimidazol-1-yl]phenyl}ethyl(4-methylphenyl)sulfonylcarbamate p-toluenesulfonate The title compound was prepared according to the procedure described in Example 231 from 2-{4-[2-ethyl-5-(trifluoroacetyl)-1H-benzimidazol-1-yl]phenyl}ethyl(4-methylphenyl)sulfonylcarbamate (Step 1)

m.p.: 92–97° C.

IR (KBr) ν: 1745, 1519, 1458, 1350, 1222, 1163, 1122 cm$^{-1}$

EXAMPLE 353

2-{4-[5-ACETYL-2-(1H-PYRAZOL-3-YL)-1H-BENZIMIDAZOL-1-YL]PHENYL}ETHYL (4-METHYLPHENYL)SULFONYLCARBAMATE P-TOLUENESULFONATE

STEP 1. 1-[1-[4-(2-hydroxyethyl)phenyl]-2-(1H-pyrazol-3-yl)-1H-benzimidazol-5-yl]ethanone The title compound was prepared according to the procedure described in step 1 of Example 236 from 1-(3-amino-4-{[4-(2-hydroxyethyl)phenyl]amino}phenyl)ethanone (Example 78, step 2).

MS (EI) m/z: 345 (M+)

$^1$H-NMR (CDCl$_3$) δ: 8.53 (1H, s), 7.94 (1H, d, J=8.4 Hz), 7.48–7.53 (3H, m), 7.37 (2H, d, J=8.2 Hz), 7.27 (1H, s), 7.18 (1H, d, J=8.4 Hz), 6.03 (1H, br.s), 4.02 (2H, t, J=6.6 Hz), 3.05 (2H, t, J=6.6 Hz), 2.69 (3H, s).

STEP 2. 2-{4-[5-acetyl-2-(1H-pyrazol-3-yl)-1H-benzimidazol-1-yl]phenyl}ethyl(4-methylphenyl)sulfonylcarbamate The title compound was prepared according to the procedure described in Example 3 from 1-[1-[4-(2-hydroxyethyl)phenyl]-2-(1H-pyrazol-3-yl)-1H-benzimidazol-5-yl]ethanone (step 1).

MS (ESI) m/z: 544 (MH$^+$), 542 ([M−H]$^−$)

$^1$H-NMR (DMSO-d$_6$) δ: 8.41 (1H, s), 7.77–7.89 (4H, m), 7.38–7.42 (7H, m), 7.12 (1H, d, J=8.5 Hz), 6.65 (1H, br.s), 4.29 (2H, t, J=6.6 Hz), 2.96 (2H, t, J=6.6 Hz), 2.66 (3H, s), 2.35 (3H, s).

STEP 3. 2-{4-[5-acetyl-2-(1H-pyrazol-3-yl)-1H-benzimidazol-1-yl]phenyl}ethyl(4-methylphenyl)sulfonylcarbamate p-toluenesulfonate The title compound was prepared according to the procedure described in Example 231 from 2-{4-[5-acetyl-2-(1H-pyrazol-3-yl)-1H-benzimidazol-1-yl]phenyl}ethyl(4-methylphenyl)sulfonylcarbamate (step 2)

m.p.: 204° C.

IR (KBr) ν: 3249, 1755, 1676, 1595, 1517, 1440, 1332, 1207, 1161, 1008 cm$^{-1}$

EXAMPLE 354

N-{[(2-{4-[6-CHLORO-2-[1-(METHYLOXY)ETHYL]-5-(TRIFLUOROMETHYL)-1H-BENZIMIDAZOL-1-YL]PHENYL}ETHYL)AMINO]CARBONYL}-4-METHYLBENZENESULFONAMIDE P-TOLUENESULFONATE

STEP 1. 2-(4-{[5-chloro-2-[(2-hydroxypropanoyl)amino]-4-(trifluoromethyl)phenyl]amino}phenyl)ethyl acetate The title compound was prepared according to the procedure described in step 3 of Example 339 from 2-(4-{[2-amino-5-chloro-4-(trifluoromethyl)phenyl]amino}phenyl)ethyl acetate (Example 339, step 2).

MS (EI) m/z: 444 (M$^+$)

STEP 2. 2-{4-[6-chloro-2-(1-hydroxyethyl)-5-(trifluoromethyl)-1H-benzimidazol-1-yl]phenyl}ethyl acetate The title compound was prepared according to the procedure described in step 4 of Example 339 from 2-(4-{[5-chloro-2-[(2-hydroxypropanoyl)amino]-4-(trifluoromethyl)phenyl]amino}phenyl)ethyl acetate (step 1)

$^1$H-NMR (CDCl$_3$) δ: 8.14 (1H, s), 7.48 (2H, d, J=8.4 Hz), 7.34 (2H, d, J=8.4 Hz), 7.24 (1H, s), 4.88–4.98 (1H, m), 4.38 (2H, t, J=7.0 Hz), 3.66 (1H, d, J=8.1 Hz), 3.08 (2H, t, J=7.0 Hz), 2.09 (3H, s), 1.57 (3H, d, J=6.6 Hz).

STEP 3. 1-[6-chloro-1-[4-(2-hydroxyethyl)phenyl]-5-(trifluoromethyl)-1H-benzimidazol-2-yl]ethanol The title compound was prepared according to the procedure described in step 6 of Example 1 from 2-{4-[6-chloro-2-(1-hydroxyethyl)-5-(trifluoromethyl)-1H-benzimidazol-1-yl]phenyl}ethyl acetate (step 2)

MS (ESI) m/z: 384 (M$^+$)

¹H-NMR (CDCl₃) δ: 8.14 (1H, s), 7.49 (2H, d, J=8.6 Hz), 7.34 (2H, d, J=8.6 Hz), 7.25 (1H, s), 4.89–4.96 (1H, m), 3.98 (2H, t, J=6.2 Hz), 3.36 (1H, d, J=5.5 Hz), 3.01 (2H, t, J=6.2 Hz), 1.54 (3H, m).

STEP 4. 1-[6-chloro-1-[4-(2-{[(1,1-dimethylethyl)(diphenyl)silyl]oxy}ethyl)phenyl]-5-(trifluoromethyl)-1H-benzimidazol-2-yl]ethanol A mixture of 1-[6-chloro-1-[4-(2-hydroxyethyl)phenyl]-5-(trifluoromethyl)-1H-benzimidazol-2-yl]ethanol (step 3, 461 mg, 1.19 mmol), tert-Butyldiphenylsilyl chloride (0.35 ml, 1.3 mmol), triethylamine (0.2 ml, 1.4 mmol) and N,N-dimetylaminopyridine (6 mg, 0.05 mmol) in dichloromethane (11 ml) was stirred under nitrogen at room temperature for 4 h. was added water (50 ml) and extracted with dichloromethane (100 ml). The organic layer was washed with water (50 ml), brine (50 ml), then dried (Na₂SO₄). After removal of solvent, the crude product was purified by flash column chromatography eluting with hexane/ethyl acetate (3:1/1:1) to afford 590 mg (80%) of the title compound as white amorphous.

¹H-NMR (CDCl₃) δ: 8.14 (1H, s), 7.59–7.63 (4H, m), 7.34–7.46 (8H, m), 7.22–7.30 (3H, m), 4.87–4.96 (1H, m), 3.94 (2H, t, J=6.4 Hz), 3.29 (1H, d, J=8.1 Hz), 2.97 (2H, t, J=6.4 Hz), 1.52 (3H, d, J=6.6 Hz), 1.03 (9H, s).

STEP 5. 6-chloro-1-[4-(2-{[(1,1-dimethylethyl)(diphenyl)silyl]oxy}ethyl)phenyl]-2-[1-(methyloxy)ethyl]-5-(trifluoromethyl)-1H-benzimidazole A solution of 1-[6-chloro-1-[4-(2-{[(1,1-dimethylethyl)(diphenyl)silyl]oxy}ethyl)phenyl]-5-(trifluoromethyl)-1H-benzimidazol-2-yl]ethanol (step 4, 590 mg, 0.95 mmol) in DMF (10 ml) was added NaH (45 mg, 1.13 mmol). Then the mixture was added MeI (0.08 ml, 1.23 mmol) at room temperature. The mixture was stirred at room temperature for 1 h. The mixture was added water (30 ml) and extracted with ethyl acetate (100 ml). The organic layer was washed with water (50 ml), brine (50 ml), then dried (Na₂SO₄). After removal of solvent, the crude product was purified by flash column chromatography eluting with hexane/ethyl acetate (3:1) to afford 550 mg (91%) of the title compound as colorless oil.

¹H-NMR (CDCl₃) δ: 8.17 (1H, s), 7.20–7.70 (15H, m), 4.54 (1H, q, J=6.6 Hz), 3.95 (2H, t, J=6.6 Hz), 3.22 (3H, s), 2.97 (2H, t, J=6.6 Hz), 1.55 (3H, d, J=6.6 Hz), 1.03 (9H, s).

STEP 6. 2-{4-[6-chloro-2-[1-(methyloxy)ethyl]-5-(trifluoromethyl)-1H-benzimidazol-1-yl]phenyl}ethanol The title compound was prepared according to the procedure described in step 6 of Example 90 from 6-chloro-1-[4-(2-{[(1,1-dimethylethyl)(diphenyl)silyl]oxy}ethyl)phenyl]-2-[1-(methyloxy)ethyl]-5-(trifluoromethyl)-1H-benzimidazole (step 5).

MS (ESI) m/z:398

¹H-NMR (CDCl₃) δ: 8.18 (1H, s), 7.49 (2H, d, J=8.4 Hz), 7.33 (2H, d, J=8.4 Hz), 7.24 (1H, s), 4.58 (1H, q, J=6.6 Hz), 4.00 (2H, br.s), 3.24 (3H, s), 3.02 (2H, t, J=6.5 Hz), 1.55 (3H, m).

STEP 7. 6-chloro-1-[4-(2-chloroethyl)phenyl]-2-[1-(methyloxy)ethyl]-5-(trifluoromethyl)-1H-benzimidazole The title compound was prepared according to the procedure described in step 7 of Example 1 from 2-{4-[6-chloro-2-[1-(methyloxy)ethyl]-5-(trifluoromethyl)-1H-benzimidol-1-yl]phenyl}ethanol (step 6).

MS (ESI) m/z:416 (M⁺)

¹H-NMR (CDCl₃) δ:8.18 (1H, s), 7.48 (2H, d, J=8.5 Hz), 7.35 (2H, d, J=8.5 Hz), 7.23 (1H, s), 5.57 (1H, q, J=6.6 Hz), 3.83 (2H, t, J=7.1 Hz), 3.19–3.24 (5H, m), 1.57 (3H, d, J=6.6 Hz).

STEP 8. 1-[4-(2-azidoethyl)phenyl]-6-chloro-2-[1-(methyloxy)ethyl]-5-(trifluoromethyl)-1H-benzimidazole The title compound was prepared according to the procedure described in step 8 of Example 1 from 6-chloro-1-[4-(2-chloroethyl)phenyl]-2-[1-(methyloxy)ethyl]-5-(trifluoromethyl)-1H-benzimidazole (step 7).

MS (ESI) m/z:423 (M⁺)

¹H-NMR (CDCl₃) δ: 8.18 (1H, s), 7.48 (2H, d, J=8.2 Hz), 7.35 (2H, d, J=8.2 Hz), 7.22 (1H, s), 4.57 (1H, q, =6.6 Hz), 3.63 (2H, t, J=6.9 Hz), 3.23 (3H, s), 3.04 (2H, t, J=6.9 Hz), 1.56 (3H, d, J=6.6 Hz).

STEP 9. 2-{4-[6-chloro-2-[1-(methyloxy)ethyl]-5-(trifluoromethyl)-1H-benzimidazol-1-yl]phenyl}ethanamine The title compound was prepared according to the procedure described in step 7 of Example 37 from 1-[4-(2-azidoethyl)phenyl]-6-chloro-2-[1-(methyloxy)ethyl]-5-(trifluoromethyl)-1H-benzimidazole (step 8).

¹H-NMR (CDCl₃) δ: 8.18 (1H, s), 7.45 (2H, d, J=8.4 Hz), 7.32 (2H, d, J=8.4 Hz), 7.24 (1H, s), 4.57 (1H, q, J=6.6 Hz), 3.23 (3H, s), 3.10 (2H, br.s), 2.90 (2H, t, J=6.6 Hz), 1.57 (3H, d, J=6.6 Hz).

STEP 10. N-{[(2-{4-[6-chloro-2-[1-(methyloxy)ethyl]-5-(trifluoromethyl)-1H-benzimidazol-1-yl]phenyl}ethyl)amino]carbonyl}-4-methylbenzenesulfonamide The title compound was prepared according to the procedure described in step 10 of Example 1 from 2-{4-[6-chloro-2-[1-(methyloxy)ethyl]-5-(trifluoromethyl)-1H-benzimidazol-1-yl]phenyl}ethanamine (step 9).

MS (ESI) m/z: 595 (MH⁺), 593 ([M−H]⁻)

¹H-NMR (CDCl₃) δ: 8.18 (1H, s), 7.73 (2H, d, J=8.4 Hz), 7.42 (2H, d, J=8.6 Hz), 7.27–7.34 (4H, m), 7.21 (1H, s), 6.76 (1H, br.s), 4.57 (1H, q, J=6.6 Hz), 3.56–3.63 (2H, m), 3.23 (3H, s), 2.96 (2H, t, J=7.1 Hz), 2.41 (3H, s), 1.56 (3H, d, J=6.6 Hz).

STEP 11. N-{[(2-{4-[6-chloro-2-[1-(methyloxy)ethyl]-5-(trifluoromethyl)-1H-benzimidazol-1-yl]phenyl}ethyl)amino]carbonyl}-4-methylbenzenesulfonamide p-toluenesulfonate The title compound was prepared according to the procedure described in Example 231 from N-{[(2-{4-[6-chloro-2-[1-(methyloxy)ethyl]-5-(trifluoromethyl)-1H-benzimidazol-1-yl]phenyl}ethyl)amino]carbonyl}-4-methylbenzenesulfonamide (step 10)

IR (KBr) ν: 2873, 1712, 1517, 1454, 1342, 1122, 1033, 1010 cm⁻¹

EXAMPLE 355

2-{4-[2-ETHYL-5-(1-HYDROXYETHYL)-1H-BENZIMIDAZOL-1-YL]PHENYL}ETHYL (4-METHYLPHEHYL)SULFONYLCARBAMATE P-TOLUENESULFONATE

STEP 1. 2-{4-[2-ethyl-5-(1-hydroxyethyl)-1H-benzimidazol-1-yl]phenyl}ethyl(4-methylphenyl)sulfonylcarbamate The title compound was prepared according to the procedure described in Example 345 from 2-[4-(5-acetyl-2-ethyl-1H-benzimidazol-1-yl)phenyl]ethyl(4-methylphenyl)sulfonylcarbamate (Example 332)

MS (ESI) m/z: 508 (MH⁺), 506 ([M−H]⁻)

¹H-NMR (CDCl₃) δ: 7.94 (2H, d, J=8.3 Hz), 7.77 (1H, s), 7.03–7.35 (8H, m), 5.04 (1H, q, J=6.4 Hz), 4.36 (2H, t, J=6.6 Hz), 2.97 (2H, t, J=6.6 Hz), 2.74 (2H, q, J=7.5 Hz), 2.43 (3H, s), 1.56 (3H, d, J=6.4 Hz), 1.28 (3H, t, J=7.5 Hz).

STEP 2. 2-{4-[2-ethyl-5-(1-hydroxyethyl)-1H-benzimidazol-1-yl]phenyl}ethyl(4-methylphenyl)sulfonylcarbamate p-toluenesulfonate The title compound was prepared according to the procedure described in Example 231 from 2-{4-[2-ethyl-5-(1-hydroxyethyl)-1H-benzimidazol-1-yl]phenyl}ethyl(4-methylphenyl)sulfonylcarbamate (step 1)

m.p.: 96–110° C.

IR (KBr) v: 1743, 1519, 1456, 1163, 1033, 1010 cm$^{-1}$

EXAMPLE 356

2-{4-[2-ETHYL-4-METHYL-5-(METHYLOXY)-1H-BENZIMIDAZOL-1-YL]PHENYL}ETHYL(4-METHYLPHENYL)SULFONYLCARBAMATE P-TOLUENESULFONATE

STEP 1. 2-(4-{[3-methyl-4-(methyloxy)-2-nitrophenyl]amino}phenyl)ethanol

The title compound was prepared according to the procedure described in step 3 of Example 1 from 1-chloro-3-methyl-4-(methyloxy)-2-nitrobenzene MS (EI) m/z: 302 (M$^+$)

$^1$H-NMR (CDCl$_3$) δ: 7.11–7.20 (3H, m), 6.89–6.96 (3H, m), 6.53 (1H, br.s), 3.83 (5H, br.s), 2.81 (2H, t, J=6.4 Hz), 2.25 (3H, s).

STEP 2. 2-(4-{[2-amino-3-methyl-4-(methyloxy)phenyl]amino}phenyl)ethanol

The title compound was prepared according to the procedure described in step 4 of Example 1 from 2-(4-{[3-methyl-4-(methyloxy)-2-nitrophenyl]amino}phenyl)ethanol (step 1).

MS (EI) m/z: 272 (M$^+$)

$^1$H-NMR (CDCl$_3$) δ: 7.03 (2H, d, J=8.6 Hz), 6.92 (1H, d, J=8.6 Hz), 6.57 (2H, d, J=8.6 Hz), 6.32 (2H, d, J=8.6 Hz), 5.01 (1H, br.s), 3.77–3.90 (7H, m), 2.76 (2H, t, J=6.4 Hz), 2.09 (3H, s).

STEP 3. 2-{4-[2-ethyl-4-methyl-5-(methyloxy)-1H-benzimidazol-1-yl]phenyl}ethyl propanoate The title compound was prepared according to the procedure described in step 5 of Example 1 from 2-(4-{[2-amino-3-methyl-4-(methyloxy)phenyl]amino}phenyl)ethanol (step 2).

MS (EI) m/z: 366 (M$^+$)

STEP 4. 2-{4-[2-ethyl-4-methyl-5-(methyloxy)-1H-benzimidazol-1-yl]phenyl}ethanol The title compound was prepared according to the procedure described in step 6 of Example 1 from 2-{4-[2-ethyl-4-methyl-5-(methyloxy)-1H-benzimidazol-1-yl]phenyl}ethyl propanoate (step 3).

$^1$H-NMR (CDCl$_3$) δ: 7.42 (2H, d, =8.1 Hz), 7.27 (2H, d, J=8.1 Hz), 6.84 (2H, s), 3.97 (2H, t, J=6.4 Hz), 3.86 (3H, s), 2.99 (2H, t, J=6.4 Hz), 2.81 (2H, q, J=7.7 Hz), 2.58 (3H, s), 1.26 (3H, t, J=7.7 Hz).

STEP 5. 2-{4-[2-ethyl-4-methyl-5-(methyloxy)-1H-benzimidazol-1-yl]phenyl}ethyl(4-methylphenyl)sulfonylcarbamate The title compound was prepared according to the procedure described in Example 3 from 2-{4-[2-ethyl-4-methyl-5-(methyloxy)-1H-benzimidazol-1-yl]phenyl}ethanol (step 4).

MS (ESI) m/z: 508 (MH$^+$), 506 ([M–H]$^-$)

$^1$H-NMR (CDCl$_3$) δ: 7.98 (2H, d, J=8.3 Hz), 7.33 (2H, d, J=8.9 Hz), 6.88–6.91 (6H, m), 4.28 (2H, t, J=6.0 Hz), 3.89 (3H, s), 2.84 (2H, t, J=6.0 Hz), 2.74 (2H, q, J=7.5 Hz), 2.56 (3H, s), 2.43 (3H, s), 1.05 (3H, t, J=7.5 Hz).

STEP 6. 2-{4-[2-ethyl-4-methyl-5-(methyloxy)-1H-benzimidazol-1-yl]phenyl}ethyl(4-methylphenyl)sulfonylcarbamate p-toluenesulfonate The title compound was prepared according to the procedure described in Example 231 from 2-{4-[2-ethyl-4-methyl-5-(methyloxy)-1H-benzimidazol-1-yl]phenyl}ethyl(4-methylphenyl)sulfonylcarbamate (step 5)

m.p.: 94–103° C.

IR (KBr) v: 1747, 1458, 1232, 1163, 1120 cm$^{-1}$

EXAMPLE 357

2-[4-(2-ETHYL-5-PHENYL-1H-BENZIMIDAZOL-1-YL)PHENYL]ETHYL(4-METHYLPHENYL)SULFONYLCARBAMATE

STEP 1. 2-{4-[(4-bromo-2-nitrophenyl)amino]phenyl}ethanol

The title compound was prepared according to the procedure described in step 1 of Example 162 from 2,5-dibromonitrobenzene.

$^1$H-NMR (CDCl$_3$) δ: 9.43 (1H, br.s), 8.34 (1H, d, J=2.4 Hz), 7.43–7.39 (1H, m), 7.30 (2H, d, J=8.3 Hz), 7.20 (2H, d, J=8.3 Hz), 7.08 (1H, d, J=9.2 Hz), 3.94–3.88 (2H, d, J=6.4 Hz), 1.43 (1H, t, J=5.7 Hz).

STEP 2. 2-{4-[(2-amino-4-bromophenyl)amino]phenyl}ethanol

The title compound was prepared according to the procedure described in step 2 of Example 28 from 2-{4-[(4-bromo-2-nitrophenyl)amino]phenyl}ethanol (step 1).

$^1$H-NMR (CDCl$_3$) δ: 7.08 (2H, d, J=8.4 Hz), 6.97–6.93 (2H, m), 6.84 (1H, dd, J=8.3, 2.2 Hz), 6.69 (2H, d, J=8.6 Hz), 5.04 (1H, br.s), 3.80 (2H, br.s), 3.82 (2H, t, J=6.4 Hz), 2.79 (2H, t, J=6.4 Hz).

STEP 3. 2-[4-(5-bromo-2-ethyl-1H-benzimidazol-1-yl)phenyl]ethyl propionate

The title compound was prepared according to the procedure described in step 5 of Example 1 from 2-{4-[(2-amino-4-bromophenyl)amino]phenyl}ethanol (step 2).

MS (EI) m/z 401 (M$^+$)

STEP 4. 2-[4-(5-bromo-2-ethyl-1H-benzimidazol-1-yl)phenyl]ethanol

The title compound was prepared according to the procedure described in step 6 of Example 1 from 2-[4-(5-bromo-2-ethyl-1H-benzimidazol-1-yl)phenyl]ethyl propionate (step 3).

$^1$H-NMR (CDCl$_3$) δ: 7.90 (1H, s), 7.45 (2H, d, J=8.1 Hz), 7.26–7.30 (3H, m), 6.96 (1H, d, J=8.4 Hz), 3.98 (2H, m), 3.00 (2H, t, J=6.4 Hz), 2.78 (2H, q, J=7.6 Hz), 1.34 (3H, t, J=7.6 Hz).

STEP 5. 2-[4-(2-ethyl-5-phenyl-1H-benzimidazol-1-yl)phenyl]ethanol

To a solution of 2-[4-(5-bromo-2-ethyl-1H-benzimidazol-1-yl)phenyl]ethanol (step 4, 116 mg, 0.57 mmol) in 1,2-dimethoxyethane (DME, 6 ml) was added PhB(OH)$_2$ (141 mg, 1.16 mmol), K$_2$CO$_3$ (240 mg, 1.75 mmol) and Pd(PPh$_3$)$_4$ (67 mg, 0.06 mmol). This mixture was stirred at 95° C. for 11 h. The reaction mixture was diluted with water and extracted with CH$_2$Cl$_2$ (4×10 ml). The organic layer was dried (MgSO$_4$) and concentrated to give brown oil. This mixture was purified by SiO$_2$ preparative TLC (hexane/ethyl acetate=1/5) to afford 52 mg (27%) of the title compound.

MS (EI) m/z 342 (M$^+$)

¹H-NMR (CDCl₃) δ: 8.00 (1H, d, J=1.6 Hz), 7.65 (2H, dd, J=1.6, 8.4 Hz), 7.42–7.48 (5H, m), 7.32–7.35 (3H, m), 7.15 (2H, d, J=8.4 Hz), 4.00 (2H, brt), 3.01 (2H, t, J=6.5 Hz), 2.82 (2H, q, J=7.6 Hz), 1.37 (3H, t, J=7.6 Hz).

STEP 6. 2-[4-(2-ethyl-5-phenyl-1H-benzimidazol-1-yl)phenyl]ethyl(4-methylphenyl)sulfonylcarbamate The title compound was prepared according to the procedure described in Example 3 from 2-[4-(2-ethyl-5-phenyl-1H-benzimidazol-1-yl)phenyl]ethanol (step 5).

MS (ESI) m/z 540 [M+H]⁺, 538 [M−H]⁻.

¹H-NMR (CDCl₃) δ: 8.00 (1H, s), 7.94 (2H, d, J=8.2 Hz), 7.65 (2H, d, J=8.6 Hz), 7.43 (3H, m), 7.29–7.36 (7H, m), 7.15 (2H, d, J=8.4 Hz), 4.39 (2H, t, J=6.8 Hz), 3.01 (2H, t, J=6.4 Hz), 2.70 (2H, q, J=7.4 Hz), 2.43 (s, 3H), 1.35 (3H, t, J=7.6 Hz).

EXAMPLE 358

2-{4-[2-ETHYL-5-(5-PYRIMIDINYL)-1H-BENZIMIDAZOL-1-YL]PHENYL}ETHYL(4-METHYLPHENYL)SULFONYLCARBAMATE

STEP 1. 2-{4-[2-ethyl-5-(4,4,5,5-tetramethyl-1,3,2-dioxaborolan-2-yl)-1H-benzimidazol-1-yl]phenyl}ethanol To a solution of 2-[4-(5-bromo-2-ethyl-1H-benzimidazol-1-yl)phenyl]ethanol (Example 357 step 4, 2.5 g, 7.24 mmol) and bis(pinacolato)diboron (1.84 g, 7.24 mmol) in DMSO was added KOAc (2.13 g, 21.7 mmol), 1,1'-Bis(diphenylphosphino)ferrocene (241 mg, 0.43 mmol) and Pd(dppf)Cl₂·CH₂Cl₂ (362 mg, 0.44 mmol). This mixture was stirred at 80° C. for 7 h. The reaction mixture was diluted with water and extracted with ethyl acetate (3×80 ml). The organic layer was washed with brine, dried (MgSO₄) and concentrated to give black oil. This mixture was purified by neutral SiO₂ chromatography eluting with hexane/ethyl acetate (1:4) to afford 1.38 g (35%) of the title compound as pink solids.

MS (EI) m/z 391 [M−H]⁺

¹H-NMR (CDCl₃) δ: 8.25 (1H, s), 7.64 (2H, dd, J=0.8, 8.1 Hz), 7.45 (2H, d, J=8.4 Hz), 7.30 (2H, d, J=8.4 Hz), 7.08 (1H, d, J=8.1 Hz), 3.99 (2H, t, J=6.5 Hz), 3.00 (2H, t, J=6.5 Hz), 2.81 (2H, q, J=7.6 Hz), 1.36 (12H, s), 1.32 (3H, t, J=7.8 Hz).

STEP 2. 2-{4-[2-ethyl-5-(5-pyrimidinyl)-1H-benzimidazol-1-yl]phenyl}ethanol

To a solution of 2-{4-[2-ethyl-5-(4,4,5,5-tetramethyl-1,3,2-dioxaborolan-2-yl)-1H-benzimidazol-1-yl]phenyl}ethanol (step 1, 100 mg, 0.26 mmol) and 5-bromopyrimidine (45 mg, 0.28 mmol) in 1,2-dimethoxyethane (3.5 ml) was added sat. NaHCO₃ aq. (1.2 ml) and Pd(PPh₃)₄ (60 mg, 0.05 mmol). This mixture was stirred at 70° C. for 17 h. The reaction mixture was diluted with water and extracted with CH₂Cl₂ (3×10 ml). The organic layer was dried (MgSO₄) and concentrated to give light brown oil. This mixture was purified by SiO₂ preparative TLC (CH₂Cl₂/methanol=10/1) to afford 45 mg (50%) of the title compound.

MS (EI) m/z 344 (M⁺)

¹H-NMR (CDCl₃) δ: 9.19 (1H, s), 9.00 (2H, s), 7.99 (1H, s), 7.49 (2H, d, J=8.2 Hz), 7.31–7.42 (3H, m), 7.23 (1H, d, J=8.4 Hz), 4.00 (2H, q, J=6.1 Hz), 3.02 (2H, t, J=6.4 Hz), 2.83 (2H, q, J=7.6 Hz), 1.39 (3H, t, J=7.6 Hz).

STEP 3. 2-{4-[2-ethyl-5-(5-pyrimidinyl)-1H-benzimidazol-1-yl]phenyl}ethyl(4-methylphenyl)sulfonylcarbamate The title compound was prepared according to the procedure described in Example 3 from 2-{4-[2-ethyl-5-(5-pyrimidinyl)-1H-benzimidazol-1-yl]phenyl}ethanol (step 2).

MS (ESI) m/z 542 [M+H]⁺, 540 [M−H]⁻.

¹H-NMR (CDCl₃) δ: 9.20 (1H, s), 8.97 (2H, s), 7.30–7.42 (4H, m), 7.24 (2H, d, J=8.2 Hz), 7.14 (2H, d, J=8.2 Hz), 4.41 (2H, t, J=6.4 Hz), 3.03 (2H, t, J=6.1 Hz), 2.89 (2H, q, J=7.4 Hz), 2.43 (3H, s), 1.34 (3H, t, J=7.4 Hz).

EXAMPLE 359

2-{4-[2-ETHYL-5-(4-PYRIDINYL)-1H-BENZIMIDAZOL-1-YL]PHENYL}ETHYL(4-METHYLPHENYL)SULFONYLCARBAMATE

STEP 1. 2-{4-[2-ethyl-5-(4-pyridinyl)-1H-benzimidazol-1-yl]phenyl}ethanol

The title compound was prepared according to the procedure described in step 1 of Example 358 from 4-bromopyridine hydrochloride (step 2).

MS (EI) m/z 343 (M)⁺.

¹H-NMR (CDCl₃) δ: 8.66 (2H, d, J=6.1 Hz), 8.07 (1H, d, J=1.2 Hz), 7.57 (2H, d, J=6.1 Hz), 7.45–7.52 (3H, m), 7.34 (2H, d, J=8.4 Hz), 7.20 (1H, d, J=8.4 Hz), 4.00 (2H, br.s), 3.03 (2H, t, J=6.6 Hz), 2.83 (2H, q, J=7.4 Hz), 1.39 (3H, t, J=7.4 Hz).

STEP 2. 2-{4-[2-ethyl-5-(4-pyridinyl)-1H-benzimidazol-1-yl]phenyl}ethyl(4-methylphenyl)sulfonylcarbamate The title compound was prepared according to the procedure described in Example 3 from 2-{4-[2-ethyl-5-(4-pyridinyl)-1H-benzimidazol-1-yl]phenyl}ethanol (step 1).

MS (ESI) m/z 541 [M+H]⁺, 539 [M−H]⁻.

¹H-NMR (CDCl₃) δ: 8.52 (2H, d, J=5.8 Hz), 8.00 (1H, s), 7.94 (2H, d, J=8.1 Hz), 7.48 (2H, d, J=5.8 Hz), 7.23–7.40 (5H, m), 7.20 (2H, d, J=8.1 Hz), 7.00 (2H, d, J=8.2 Hz), 4.41 (2H, t, J=5.8 Hz), 3.02 (2H, t, J=5.8 Hz), 2.76 (2H, q, J=7.4 Hz), 2.39 (3H, s), 1.32 (3H, t, J=7.4 Hz).

EXAMPLE 360

2-{4-[2-ETHYL-5-(3-PYRIDINYL)-1H-BENZIMIDAZOL-1-YL]PHENYL}ETHYL(4-METHYLPHENYL)SULFONYLCARBAMATE

STEP 1. 2-{4-[2-ethyl-5-(3-pyridinyl)-1H-benzimidazol-1-yl]phenyl}ethanol

The title compound was prepared according to the procedure described in step 1 of Example 358 from 3-bromopyridine.

MS (EI) m/z 343 (M)⁺.

¹H-NMR (CDCl₃) δ: 8.91 (1H, d, J=1.8 Hz), 8.55–8.61 (1H, m), 8.00 (1H, s), 7.90–7.97 (1H, m), 7.48 (2H, d, J=8.2 Hz), 7.42 (1H, d, J=8.7 Hz), 7.35 (2H, d, J=8.2 Hz), 7.21 (1H, d, J=8.4 Hz), 4.00 (2H, m), 3.02 (2H, t, J=6.5 Hz), 2.83 (2H, q, J=7.6 Hz), 1.92 (1H, s), 1.39 (3H, t, J=7.6 Hz).

STEP 2. 2-{4-[2-ethyl-5-(3-pyridinyl)-1H-benzimidazol-1-yl]phenyl}ethyl(4-methylphenyl)sulfonylcarbamate The title compound was prepared according to the procedure described in Example 3 from 2-{4-[2-ethyl-5-(3-pyridinyl)-1H-benzimidazol-1-yl]phenyl}ethanol (step 1).

MS (ESI) m/z 541 [M+H]⁺, 539 [M−H]⁻.

¹H-NMR (CDCl₃) δ: 8.76 (1H, s), 8.63 (1H, m), 7.87–8.01 (4H, m), 7.22–7.50 (6H, m), 7,23–7.40 (5H, m), 7.16 (2H, d, J=8.2 Hz), 7.00 (1H, d, J=8.2 Hz), 4.42 (2H, br.s), 3.01 (2H, br.s), 2.74 (2H, q, J=7.4 Hz), 2.43 (3H, s), 1.31 (3H, t, J=7.4 Hz).

EXAMPLE 361

2-{4-[2-ETHYL-5-(2-PYRIDINYL)-1H-BENZIMI-DAZOL-1-YL]PHENYL}ETHYL(4-METH-YLPHENYL)SULFONYLCARBAMATE

STEP 1. 2-{4-[2-ethyl-5-(2-pyridinyl)-1H-benzimidazol-1-yl]phenyl}ethanol

The title compound was prepared according to the procedure described in step 1 of Example 358 from 2-bromopyridine.

MS (EI) m/z 343 (M)⁺.

¹H-NMR (CDCl₃) δ: 8.70 (1H, dd, J=1.5, 5.3 Hz), 8.32 (1H, d, J=1.5 Hz), 8.00 (1H, dd, J=1.5, 8.4 Hz), 7.76–7.80 (2H, m), 7.48 (2H, d, J=8.2 Hz), 7.35 (2H, d, J=8.2 Hz), 7.16–7.23 (2H, m), 3.93–4.05 (2H, m), 3.01 (2H, t, J=6.6 Hz), 2.83 (2H, q, J=7.6 Hz), 1.91 (1H, s), 1.38 (3H, t, J=7.6 Hz).

STEP 2. 2-{4-[2-ethyl-5-(2-pyridinyl)-1H-benzimidazol-1-yl]phenyl}ethyl(4-methylphenyl)sulfonylcarbamate The title compound was prepared according to the procedure described in Example 3 from 2-{4-[2-ethyl-5-(2-pyridinyl)-1H-benzimidazol-1-yl]phenyl}ethanol (step 1).

MS (ESI) m/z 541 [M+H]⁺, 539 [M−H]⁻.

¹H-NMR (CDCl₃) δ: 8.68 (1H, d, J=4.6 Hz), 8.31 (1H, s), 7.88–7.98 (3H, m), 7.73–7.82 (2H, m), 7.17–7.26 (5H, m), 7.07–7.17 (3H, m), 4.29 (2H, t, J=6.3 Hz), 2.90 (2H, t, J=6.4 Hz), 2.73 (2H, q, J=7.6 Hz), 2.36 (3H, s), 1.28 (3H, t, J=7.6 Hz).

EXAMPLE 362

2-{4-[2-ETHYL-5-(4-PYRIDINYL)-1H-BENZIMI-DAZOL-1-YL]PHENYL}ETHYL(4-METH-YLPHENYL)SULFONYLCARBAMATE

STEP 1. 2-{4-[2-ethyl-5-(1-methyl-1H-pyrazol-4-yl)-1H-benzimidazol-1-yl]phenyl}ethanol The title compound was prepared according to the procedure described in step 1 of Example 358 from 4-bromo-1-methyl-1H-pyrazole (Huettel et al., *Liebigs Ann. Chem.*, 1955, 593, 179).

MS (EI) m/z 343 (M⁺)

¹H-NMR (CDCl₃) δ: 7.86 (1H, s), 7.78 (1H, s), 7.46 (2H, d, J=8.4 Hz), 7.28–7.35 (3H, m), 7.09 (2H, d, J=8.2 Hz), 3.99 (2H, m), 3.01 (2H, t, J=6.4 Hz), 2.81 (2H, q, J=7.6 Hz), 1.36 (3H, t, J=7.6 Hz).

STEP 2. 2-{4-[2-ethyl-5-(1-methyl-1H-pyrazol-4-yl)-1H-benzimidazol-1-yl]phenyl}ethyl(4-methylphenyl)sulfonylcarbamate The title compound was prepared according to the procedure described in Example 3 from 2-{4-[2-ethyl-5-(1-methyl-1H-pyrazol-4-yl)-1H-benzimidazol-1-yl]phenyl}ethanol (step 1).

MS(ESI) m/z 544 [M+H]⁺, 542 [M−H]⁻.

¹H-NMR (CDCl₃) δ: 7.95 (1H, s), 7.92 (1H, s), 7.86 (4H, m), 7.77 (1H, s), 7.62 (1H, s), 7.24–7.40 (7H, m), 7.06 (21H, d, J=7.7 Hz), 4.39 (2H, t, J=6.0 Hz), 3.97 (3H, s), 3.02 (2H, q, J=6.3 Hz), 2.78 (2H, q, J=7.4 Hz), 2.44 (3H. s), 1.35 (3H, t, J=7.4 Hz).

EXAMPLE 363

2-{4-[6-CHLORO-2-[3-OXO-3-(1-PYRROLODO-NYL)PROPYL]-5-(TRIFLUOROMETHYL)-1H-BENZIMIDAZOL-1-YL]PHENYL}ETHYL(4-ME-THYLPHENYL)SULFONYLCARBAMATE

The title compound was prepared according to the procedure described in Example 339 from 2-(4-{[2-amino-5-chloro-4-(trifluoromethyl)phenyl]amino}phenyl)ethyl acetate (Example 339, step 2) and 4-oxo-4-(1-pyrrolidinyl)butanoic acid (McCasland; Proskow, *J. Org. Chem.*, 1957, 22, 122.).

m.p.: 98–105° C.

IR (KBr) v: 2875, 1747, 1624, 1517, 1400, 1346, 1130, 1085 cm⁻¹

MS (ESI) m/z: 663 (MH⁺), 661 ([M−H]⁻)

¹H-NMR (CDCl₃) δ: 8.08 (1H, s), 7.92 (2H, d, J=8.2 Hz), 7.22–7.36 (7H, m), 4.38 (2H, t, J=6.6 Hz), 3.49 (2H, t, J=6.8 Hz), 3.43 (2H, t, J=6.8 Hz), 2.97–3.07 (4H, m), 2.88 (2H, m), 2.44 (3H, s), 1.94–1.98 (2H, m), 1.82–1.86 (2H, in).

EXAMPLE 364

2-{4-[6-CHLORO-2-[3-OXO-3-(1-PIPERIDINYL)PROPYL]-5-(TRIFLUOROMETHYL)-1H-BENZ-IMIDAZOL-1-YL]PHENYL}ETHYL(4-METH-YLPHENYL)SULFONYLCARBAMATE

The title compound was prepared according to the procedure described in Example 339 from 2-(4-{[2-amino-5-chloro-4-(trifluoromethyl)phenyl]amino}phenyl)ethyl acetate (Example 339, step 2) and 4-oxo-4-(1-piperidinyl)butanoic acid (Becker, Frederick F.; Banik, Bimal K., *Bioorg. Med. Chem. Lett.*, 1998, 20, 2877).

m.p.: 210° C.

IR (KBr) v: 1753, 1649, 1515, 1433, 1406, 1366, 1161, 1118, 1091 cm⁻¹

MS (ESI) m/z: 677 (MH⁺), 675 ([M−H]⁻)

¹H-NMR (CDCl₃) δ: 8.14 (1H, s), 7.78 (2H, d, J=8.4 Hz), 7.47–7.56 (4H, m), 7.42 (2H, d, J=8.4 Hz), 7.31 (1H, s), 4.29 (2H, t, J=6.6 Hz), 3.37–3.40 (4H, m), 2.92–2.99 (6H, m), 2.36 (3H, s), 1.50–1.56 (4H, m), 1.35–1.36 (2H, m).

EXAMPLE 365

2-{4-[6-CHLORO-2-[3-(2-OXO-1-PYRROLIDI-NYL)PROPYL]-5-(TRIFLUOROMETHYL)-1H-BENZIMIDAZOL-1-YL]PHENYL}ETHYL(4-METHYLPHENYL)SULFONYLCARBAMATE

The title compound was prepared according to the procedure described in Example 339 from 2-(4-{[2-amino-5-chloro-4-(trifluoromethyl)phenyl]amino}phenyl)ethyl acetate (Example 339, step 2) and 4-(2-oxo-1-pyrrolidinyl)butanoic acid (Miyano, Seiji; Fujii, Shinichiro; Yamashita, Osamu; Toraishi, Naoko; Sumoto, Kunihiro, *J. Heterocycl. Chem.*, 1982, 19, 1465).

m.p.: 85–90° C.

IR (KBr) v: 1745, 1624, 1517, 1433, 1348, 1299, 1161, 1130, 1085 cm⁻¹

MS (ESI) m/z: 663 (MH⁺), 661 ([M−H]⁻)

¹H-NMR (CDCl₃) δ: 8.09 (1H, s), 7.91 (2H, d, J=8.5 Hz), 7.19–7.33 (7H, m), 4.42 (2H, t, J=6.0 Hz), 3.38 (2H, t, J=7.0 Hz), 3.27 (2H, t, J=7.0 Hz), 3.00 (2H, t, J=6.0 Hz), 2.70–2.75 (2H, m), 2.42 (3H, s), 2.37–2.40 (2H, m), 1.93–2.04 (4H, m).

EXAMPLE 366

2-{4-[6-CHLORO-2-[3-(2-OXO-1-PIPERIDINYL)PROPYL]-5-(TRIFLUOROMETHYL)-1H-BENZIMIDAZOL-1-YL]PHENYL}ETHYL(4-METHYLPHENYL)SULFONYLCARBAMATE

The title compound was prepared according to the procedure described in Example 339 from 2-(4-{[2-amino-5-chloro-4-(trifluoromethyl)phenyl]amino}phenyl)ethyl acetate (Example 339, step 2) and 4-(2-oxo-1-piperidinyl)butanoic acid (Miyano, Seiji; Fujii, Shinichiro; Yamashita, Osamu; Toraishi, Naoko; Sumoto, Kunihiro, J. Heterocycl. Chem., 1982, 19, 1465).

m.p.: 98–105° C.

IR (KBr) v: 1745, 1618, 1433, 1348, 1301, 1230, 1161, 1130, 1085 cm⁻¹

MS (ESI) m/z: 677 (MH⁺), 675 ([M−H]⁻)

¹H-NMR (CDCl₃) δ: 8.08 (1H, s), 7.89 (2H, d, J=8.0 Hz), 7.16–7.29 (7H, m), 4.40 (2H, t, J=5.9 Hz), 3.35 (2H, t, J=7.2 Hz), 3.25–3.27 (2H, m), 2.98 (2H, t. J=5.9 Hz), 2.73 (2H, t, J=7.2 Hz), 2.35–2.40 (5H, m), 1.92–1.99 (2H, m), 1.73–1.76 (4H, m).

EXAMPLE 367

N-{[(2-{4-[6-CHLORO-2-(1-HYDROXYETHYL)-5-(TRIFLUOROMETHYL)-1H-BENZIMIDAZOL-1-YL]PHENYL}ETHYL)AMINO]CARBONYL}-4-METHYLBENZENESULFONAMIDE

STEP 1. 1-[6-chloro-1-[4-(2-chloroethyl)phenyl]-5-(trifluoromethyl)-1H-benzimidazol-2-yl]ethanol The title compound was prepared according to the procedure described in Example 339, step 3 & Example 1, step 5 from 4-chloro-N²-[4-(2-chloroethyl)phenyl]-5-(trifluoromethyl)-benzenediamine and lactic acid.

¹H-NMR (CDCl₃) δ: 8.14 (1H, s), 7.49 (2H, d, J=8.2 Hz), 7.37 (2H, d, J=8.2 Hz), 4.90 (1H, m), 3.83 (2H, t, J=6.8 Hz), 3.75 (1H, d, H=S8.1 Hz), 3.22 (2H, t, J=6.8 Hz), 1.57 (3H, d, J=6.9 Hz).

STEP 2. N-{[(2-{4-[6-chloro-2-(1-hydroxyethyl)-5-(trifluoromethyl)-1H-benzimidazol-1-yl]phenyl}ethyl)amino]carbonyl}-4-methylbenzenesulfonamide The title compound was prepared according to the procedure described in Example 1 from 1-[6-chloro-1-[4-(2-chloroethyl)phenyl]-5-(trifluoromethyl)-1H-benzimidazol-2-yl]ethanol (step 1).

m.p.: 220° C.

IR (KBr) v: 3348, 1706, 1533, 1519, 1434, 1344, 1328, 1126 cm⁻¹

MS (ESI) m/z: 581 (MH⁺), 579 ([M−H]⁻)

¹H-NMR (CDCl₃) δ: 8.23 (1H, s), 7.78 (2H, d, J=8.1 Hz), 7.32–7.50 (7H, m), 6.58 (1H, br.s), 5.66 (1H, br.s), 4.78 (1H, br.s), 3.30–3.32 (2H, m), 2.79–2.82 (2H, m), 2.34 (3H, s), 1.51 (3H, d, J=6.8 Hz).

EXAMPLE 368

N-{[(2-{4-[2-ACETYL-6-CHLORO-5-(TRIFLUOROMETHYL)-1H-BENZIMIDAZOL-1-YL]PHENYL}ETHYL)AMINO]CARBONYL}-4-METHYLBENZENESULFONAMIDE

STEP 1. 1-[6-chloro-1-[4-(2-chloroethyl)phenyl]-5-(trifluoromethyl)-1H-benzimidazol-2-yl]ethanone A solution of 1-[6-chloro-1-[4-(2-chloroethyl)phenyl]-5-(trifluoromethyl)-1H-benzimidazol-2-yl]ethanol (Example 367, step 1, 400 mg, 1 mmol) in CH₂Cl₂ was added MnO2 (2.7 g, 32 mmol). The mixture was stirred at room temperature for 24 h. This was directly purified by flash column chromatography eluting with hexane/ethyl acetate (4:1) to afford 350 mg (88%) of the title compound as white solids.

¹H-NMR (CDCl₃) δ: 8.31 (1H, s), 7.44 (2H, d, J=8.1 Hz), 7.23–7.28 (3H, m), 3.82 (2H, t, J=7.3 Hz), 3.21 (2H, t, J=7.3 Hz), 2.80 (3H, s).

STEP 2. N-{[(2-{4-[2-acetyl-6-chloro-5-(trifluoromethyl)-1H-benzimidazol-1-yl]phenyl}ethyl)amino]carbonyl}-4-methylbenzenesulfonamide The title compound was prepared according to the procedure described in Example 1 from 1-[6-chloro-1-[4-(2-chloroethyl)phenyl]-5-(trifluoromethyl)-1H-benzimidazol-2-yl]ethanone (step 1)

m.p.: 225° C.

IR (KBr) v: 3350, 1697, 1519, 1326, 1294, 1134, 1083 cm⁻¹

MS (ESI) m/z: 579 (MH⁺), 577 ([M−H]⁻)

¹H-NMR (CDCl₃) δ: 8.31 (1H, s), 7.74 (2H, d, J=8.4 Hz), 7.21–7.39 (7H, m), 6.70 (1H, br.s), 3.55–3.62 (2H, m), 2.94 (2H, t, J=7.2 Hz), 2.81 (3H, s), 2.40 (3H, s).

EXAMPLE 369

N-{[(2-{4-[6-CHLORO-2-(1-HYDROXY-1-METHYLETHYL)-5-(TRIFLUOROMETHYL)-1H-BENZIMIDAZOL-1-YL]PHENYL}ETHYL)AMINO]CARBONYL}-4-METHYLBENZENESULFONAMIDE

STEP 1. 2-[6-chloro-1-[4-(2-chloroethyl)phenyl]-5-(trifluoromethyl)-1H-benzimidazol-2-yl]-2-propanol The title compound was prepared according to the procedure described in Example 339, step 3 & Example 1, step 5 from 2-hydroxyisobutyric acid and 4-chloro-N²-[4-(2-chloroethyl)phenyl]-5-(trifluoromethyl)-1,2-benzenediamine.

¹H-NMR (CDCl₃) δ: 8.13 (1H, s), 7.46 (2H, d, J=8.2 Hz), 7.34 (2H, d, J=8.2 Hz), 7.00 (1H, s), 3.84 (2H, t, J=7.0 Hz), 3.38 (1H, s), 3.22 (2H, t, J=7.00 Hz), 1.53 (6H, s).

STEP 2. N-{[(2-{4-[6-chloro-2-(1-hydroxy-1-methylethyl)-5-(trifluoromethyl)-1H-benzimidazol-1-yl]phenyl}ethyl)amino]carbonyl}-4-methylbenzenesulfonamide The title compound was prepared according to the procedure described in Example 1 from 2-[6-chloro-1-[4-(2-chloroethyl)phenyl]-5-(trifluoromethyl)-1H-benzimidazol-2-yl]-2-propanol (step 1)

¹H-NMR (CDCl₃) δ: 8.13 (1H, s), 7.73 (2H, d, J=8.2 Hz), 7.30–7.39 (6H, m), 6.99 (1H, s), 6.68 (1H, br.s), 3.55–3.66 (2H, m), 2.95 (2H, t, J=6.6 Hz), 2.42 (3H, s), 1.13 (6H, d, J=6.2 Hz).

EXAMPLE 370

N-{[(2-{4-[6-CHLORO-2-(1-HYDROXY-1-METH-YLETHYL)-5-(TRIFLUOROMETHYL)-1H-BEN-ZIMIDAZOL-1-YL]PHENYL}ETHYL)AMINO]CARBONYL}-4-METHYLBENZENESULFONAMIDE MONO P-TOLUENESULFONATE

The title compound was prepared according to the procedure described in Example 231 from N-{[(2-{4-[6-chloro-2-(1-hydroxy-1-methylethyl)-5-(trifluoromethyl)-1H-benzimidazol-1-yl]phenyl}ethyl)amino]carbonyl}-4-methylbenzenesulfonamide (Example 369).

m.p.: 146–150° C.

IR (KBr) ν: 1685, 1515, 1448, 1340, 1124, 1089, 1010 cm$^{-1}$

EXAMPLE 371

N-{1-[6-CHLORO-1-(4-{2-[({[(4-METHYLPHE-NYL)SULFONYL]AMINO}CARBONYL)AMINO]ETHYL}PHENYL)-5-(TRIFLUOROM-ETHYL)-1H-BENZIMIDAZOL-2-YL]ETHYL}ACETAMIDE

STEP 1. 1,1-dimethylethyl 1-[6-chloro-1-[4-(2-hydroxyethyl)phenyl]-5-(trifluoromethyl)-1H-benzimidazol-2-yl]ethylcarbamate The title compound was prepared according to the procedure described in Example 339, step 3 & Example 1, step 5 from N-(tert-butoxycarbonyl)-alanine and 2-(4-{[2-amino-5-chloro-4-(trifluoromethyl)phenyl]amino} phenyl)ethyl acetate (Example 339, step 2).

MS (EI) m/z: 483 (M$^+$)

$^1$H-NMR (CDCl$_3$) δ: 8.12 (1H, s), 7.50 (2H, d, J=8.6 Hz), 7.35–7.37 (2H, m), 7.24 (1H, s), 5.46 (1H, br.s), 4.92–4.98 (1H, m), 3.95–4.02 (2H, m), 3.00 (2H, t, J=6.5 Hz), 1.43 (3H, s), 1.40 (9H, s).

STEP 2. 1,1-dimethylethyl 1-[6-chloro-1-(4-{2-[({[(4-methylphenyl)sulfonyl]amino}carbonyl)amino]ethyl}phenyl)-5-(trifluoromethyl)-1H-benzimidazol-2-yl]ethylcarbamate The title compound was prepared according to the procedure described in Example 1 from 1,1-dimethylethyl 1-[6-chloro-1-[4-(2-hydroxyethyl)phenyl]-5-(trifluoromethyl)-1H-benzimidazol-2-yl]ethylcarbamate (step 1)

$^1$H-NMR (CDCl$_3$) δ: 8.13 (1H, s), 7.79 (2H, d, J=8.2 Hz), 7.15–7.35 (7H, m), 6.50 (1H, br.s), 5.55 (1H, d, J=8.6 Hz), 4.88–4.93 (1H, m), 3.46–3.52 (2H, m), 2.87–2.96 (2H, m), 2.41 (3H, s), 1.40 (12H, s).

STEP 3. N-{[(2-{4-[2-(1-aminoethyl)-6-chloro-5-(trifluoromethyl)-1H-benzimidazol-1-yl]phenyl}ethyl)amino]carbonyl}-4-methylbenzenesulfonamide A solution of 1,1-dimethylethyl 1-[6-chloro-1-(4-{2-[({[(4-methylphenyl)sulfonyl]amino}carbonyl)amino]ethyl}phenyl)-5-(trifluoromethyl)-1H-benzimidazol-2-yl]ethylcarbamate (step 2, 190 mg, 0.28 mmol) in CH$_2$Cl$_2$ (2 ml) was added trifluoroacetic acid (1 ml) and stirred at room temperature for 2 h. The mixture was added water (10 ml) and extracted with CH$_2$Cl$_2$ (20 ml). The organic layer was washed with brine (10 ml), then dried (Na$_2$SO$_4$). After removal of solvent, the crude product was purified by flash column chromatography eluting with CH$_2$Cl$_2$/MeOH (10:1/5:1) to afford 160 mg (99%) of the title compound as white solids.

MS (ESI) m/z: 580 (MH$^+$), 578 ([M−H]$^-$)

STEP 4. N-1-[6-chloro-1-(4-{2-[({[(4-methylphenyl)sulfonyl]amino}carbonyl)amino]ethyl}phenyl)-5-(trifluoromethyl)-1H-benzimidazol-2-yl]ethyl)acetamide A mixture of N-{[(2-{4-[2-(1-aminoethyl)-6-chloro-5-(trifluoromethyl)-1H-benzimidazol-1-yl]phenyl}ethyl)amino]carbonyl}-4-methylbenzenesulfonamide (step 3, 100 mg, 0.17 mmol) in CH$_2$Cl$_2$ (12 ml) was added acetyl chloride (0.01 ml, 0.18 mmol) and stirred at room temperature for 5 h. The mixture was added water (10 ml) and extracted with CH$_2$Cl$_2$ (20 ml). The organic layer was washed with brine (10 ml), then dried (Na2SO4). After removal of solvent, the crude product was purified by flash column chromatography eluting with CH$_2$Cl$_2$/MeOH (10:1) to afford 59 mg (53%) of the title compound as white solids.

MS (ESI) m/z: 622 (MH$^+$), 620 ([M−H]$^-$)

$^1$H-NMR (CDCl$_3$) δ: 8.14 (1H, s), 7.80 (2H, d, J=8.2 Hz), 7.25–7.40 (7H, m), 7.00 (1H, br.s), 6.03 (1H, br.s), 5.15–5.20 (1H, m), 3.43–3.68 (2H, m), 2.88–2.98 (2H, m), 2.39 (3H, s), 1.96 (3H, s), 1.51 (3H, d, J=6.9 Hz).

EXAMPLE 372

N-{1-[6-CHLORO-1-(4-{2-[({[(4-METHYLPHE-NYL)SULFONYL]AMINO}CARBONYL)AMINO]ETHYL}PHENYL)-5-(TRIFLUOROM-ETHYL)-1H-BENZIMIDAZOL-2-YL]ETHYL}ACETAMIDE MONO P-TOLUENESULFONATE

The title compound was prepared according to the procedure described in Example 231 from N-{1-[6-chloro-1-(4-{2-[({[(4-methylphenyl)sulfonyl]amino}carbonyl)amino]ethyl}phenyl)-5-(trifluoromethyl)-1H-benzimidazol-2-yl]ethyl}acetamide (Example 371).

m.p.: 135–142° C.

IR (KBr) ν: 3267, 1676, 1517, 1456, 1236, 1163, 1122, 1010 cm$^{-1}$

EXAMPLE 373

2-{4-[2-ETHYL-5-(PHENYLCARBONYL)-1H-BENZIMIDAZOL-1-YL]PHENYL}ETHYL (4-METHYLPHENYL)SULFONYLCARBAMATE

STEP 1. (3-amino-4-{[4-(2-hydroxyethyl)phenyl]amino}phenyl)(phenyl)methanone

The title compound was prepared according to the procedure described in Example 78 from (4-chloro-3-nitrophenyl)(phenyl)methanone.

$^1$H-NMR (CDCl$_3$) δ: 7.77 (2H, d, J=6.9 Hz), 7.42–7.55 (3H, m), 7.36 (1H, s), 7.14–7.25 (4H, m), 6.97 (2H, d, J=8.5 Hz), 5.64 (1H, s), 3.83–3.89 (2H, m), 3.64 (2H, br.s), 2.84 (2H, t, J=6.6 Hz), 1.47 (1H, br.s).

STEP 2. {2-ethyl-1-[4-(2-hydroxyethyl)phenyl]-1H-benzimidazol-5-yl}(phenyl)methanone The title compound was prepared according to the procedure described in Example 1 from (3-amino-4-{[4-(2-hydroxyethyl)phenyl]amino}phenyl)(phenyl)methanone (step 1.).

$^1$H-NMR (CDCl$_3$) δ: 8.21 (1H, s), 7.80–7.84 (3H, m), 7.44–7.57 (5H, m), 7.27–7.34(2H, m), 7.18 (1H, d, J=8.4 Hz), 3.98–4.03 (2H, m), 3.02 (2H, t, =6.3 Hz), 2.81 (2H, q, J=7.6 Hz), 1.89 (1H, t, J=5.4 Hz), 1.37 (3H, t, J=7.6 Hz).

STEP 3. 2-{4-[2-ethyl-5-(phenylcarbonyl)-1H-benzimidazol-1-yl]phenyl}ethyl(4-methylphenyl)sulfonylcarbamate The title compound was prepared according to the procedure described in Example 3 from{2-ethyl-1-[4-(2-hydroxyethyl)phenyl]-1H-benzimidazol-5-yl}(phenyl)methanone (step 2).

MS (ESI) m/z: 568 (MH$^+$), 566 ([M–H]$^-$)

$^1$H-NMR (CDCl$_3$) δ: 8.21 (1H, s), 7.92 (2H, d, J=8.4 Hz), 7.79–7.84 (3H, m), 7.44–7.58 (3H, m), 7.23–7.36 (6H, m), 7.15 (1H, d, J=8.6 Hz), 4.37 (2H, t, J=6.6 Hz), 3.01 (2H, t, J=6.6 Hz), 2.79 (2H, q, J=7.6 Hz), 2.42 (3H, s), 1.34 (3H, t, J=7.6 Hz).

EXAMPLE 374

2-{4-[2-ETHYL-5-(PHENYLCARBONYL)-1H-BENZIMIDAZOL-1-YL]PHENYL}ETHYL(4-METHYLPHENYL)SULFONYLCARBAMATE MONO P-TOLUENESULFONATE

The title compound was prepared according to the procedure described in Example 231 from 2-{4-[2-ethyl-5-(phenylcarbonyl)-1H-benzimidazol-1-yl]phenyl}ethyl(4-methylphenyl)sulfonylcarbamate (Example 373).

m.p.: 102–107° C.

IR (KBr) v: 1747, 1654, 1517, 1448, 1033, 1008 cm$^{-1}$

EXAMPLE 375

N-{[(2-{4-[2-Ethyl-5-(phenylcarbonyl)-1H-benzimidazol-1-yl]phenyl}ethyl)amino]carbonyl}-4-methylbenzenesulfonamide STEP 1. N-{[(2-{4-[2-ethyl-5-(phenylcarbonyl)-1H-benzimidazol-1-yl]phenyl}ethyl)amino]carbonyl}-4-methylbenzenesulfonamide The title compound was prepared according to the procedure described in Example 78 from{2-ethyl-1-[4-(2-hydroxyethyl)phenyl]-1H-benzimidazol-5-yl}(phenyl)methanone (Example 373, step 2).

MS (ESI) m/z: 567 (MH$^+$), 565 ([M–H]$^-$)

$^1$H-NMR (CDCl$_3$) δ: 8.20 (1H, s), 7.72–7.83 (5H, m), 7.28–7.60 (9H, m), 7.15 (1H, d, J=8.6 Hz), 6.74 (1H, br.s), 3.59 (2H, m), 2.94 (2H, t, J=7.1 Hz), 2.82 (2H, q, J=7.4 Hz), 2.94 (3H, s), 1.35 (3H, t, J=7.4 Hz).

EXAMPLE 376

N-{[(2-{4-[2-Ethyl-5-(phenylcarbonyl)-1H-benzimidazol-1-yl]phenyl}ethyl)amino]carbonyl}-4-methylbenzenesulfonamide mono p-toluenesulfonate The title compound was prepared according to the procedure described in Example 231 from N-{[(2-{4-[2-ethyl-5-(phenylcarbonyl)-1H-benzimidazol-1-yl]phenyl}ethyl)amino]carbonyl}-4-methylbenzenesulfonamide (Example 375).

m.p.: 198° C.

IR (KBr) v: 1697, 1660, 1596, 1519, 1446, 1319, 1035 cm$^{-1}$

EXAMPLE 377

2-{4-[2-[1-(ACETYLAMINO)-1-METHYLETHYL]-6-CHLORO-5-(TRIFLUOROMETHYL)-1H-BENZIMIDAZOL-1-YL]PHENYL}ETHYL(4-METHYLPHENYL)SULFONYLCARBAMATE

STEP 1. 2-{4-[6-chloro-2-(1-chloro-1-methylethyl)-5-(trifluoromethyl)-1H-benzimidazol-1-yl]phenyl}ethyl acetate To a solution of 2-{4-[6-chloro-2-(1-hydroxy-1-methylethyl)-5-(trifluoromethyl)-1H-benzimidazol-1-yl]phenyl}ethyl acetate (300 mg, 0.68 mmol) in dichloromethane (15 ml) was added thionyl chloride (0.07 ml, 1.02 mmol) and the reaction mixture was refluxed overnight. The reaction mixture was poured into water (10 ml) and the mixture was extracted with dichloromethane (30 ml). The organic layer was washed with brine (10 ml), then dried (Na$_2$SO$_4$). The solvent was removed to give 273 mg (87%) of the title compound as white amorphous.

MS (EI) m/z: 458 (M$^+$).

STEP 2. 2-{4-[2-(1-azido-1-methylethyl)-6-chloro-5-(trifluoromethyl)-1H-benzimidazol-1-yl]phenyl}ethyl acetate A mixture of 2-{4-[6-chloro-2-(1-chloro-1-methylethyl)-5-(trifluoromethyl)-1H-benzimidazol-1-yl]phenyl}ethyl acetate (step 1, 273 mg, 0.68 mmol), sodium azide (88 mg, 1.36 mmol), KI (112 mg, 0.68 mmol) in DMF (8 ml) was stirred under nitrogen at room temperature for 5.5 h. The reaction mixture was poured into water (5 ml) and the aqueous mixture was extracted with ethyl acetate(30 ml). The organic layer was washed with water (5 ml) and brine (10 ml), then dried (Na$_2$SO$_4$). After removal of solvent, the crude product was purified by flash column chromatography eluting with hexane/ethyl acetate (2/1) to afford 133 mg (42%) of the title compound as yellow oil.

MS (EI) m/z: 465 (M$^+$)

$^1$H-NMR (CDCl$_3$) δ: 8.17 (1H, s), 7.46 (2H, d, J=8.4 Hz), 7.35 (2H, d, J=8.4 Hz), 7.02 (1H, s), 4.39 (2H, t, J=7.0 Hz), 3.09 (2H, t, J=7.0 Hz), 2.08 (3H, s), 1.70 (6H, s).

STEP 3. 2-{4-[2-(1-amino-1-methylethyl)-6-chloro-5-(trifluoromethyl)-1H-benzimidazol-1-yl]phenyl}ethyl acetate A mixture of 2-{4-[2-(1-azido-1-methylethyl)-6-chloro-5-(trifluoromethyl)-1H-benzimidazol-1-yl]phenyl}ethyl acetate (step 2, 133 mg, 0.28 mmol) and Lindlar catalyst (13 mg) in methanol (5 ml) was stirred under H$_2$ atmosphere at room temperature for 2.5 h. The catalyst was removed by filtration through a pad of celite and the filtrates were concentrated to give the title compound as yellow oil (121 mg, 98%).

MS (EI) m/z: 439 (M$^+$)

STEP 4. 2-{4-[2-[1-(acetylamino)-1-methylethyl]-6-chloro-5-(trifluoromethyl)-1H-benzimidazol-1-yl]phenyl}ethyl acetate To a solution of 2-{4-[2-(1-amino-1-methylethyl)-6-chloro-5-(trifluoromethyl)-1H-benzimidazol-1-yl]phenyl}ethyl acetate (step 3, 121 mg, 0.27 mmol) in dichloromethane (5 ml) was added acetyl chloride (0.02 ml, 0.3 mmol). The reaction mixture was stirred at room temperature for 7 h. To the reaction mixture was added water (5 ml) and the aqueous mixture was extracted with dichloromethane (30 ml). The organic layer was washed with water (5 ml) and brine (10 ml), then dried (Na$_2$SO$_4$). After removal of solvent, the crude product was purified by flash column chromatography eluting with CH$_2$Cl$_2$/methanol (10/1) to afford 76 mg (57%) of the title compound as white amorphous.

MS (EI) m/z: 481 (M$^+$)

$^1$H-NMR (CDCl$_3$) δ: 8.14 (1H, s), 7.42 (2H, d, J=8.2 Hz), 7.28 (2H, d, J=8.4 Hz), 6.91 (1H, s), 4.38 (2H, t, J=6.6 Hz), 3.07 (2H, t, J=6.6 Hz), 2.06 (3H, s), 1.75 (6H, s), 1.68 (3H, s).

STEP 5. N-{1-[6-chloro-1-[4-(2-hydroxyethyl)phenyl]-5-(trifluoromethyl)-1H-benzimidazol-2-yl]-1-methylethyl}acetamide The title compound was prepared according to the procedure described in step 6 of Example 1 2-(4-[2-[1-(acetylamino)-1-methylethyl]-6-chloro-5-(trifluoromethyl)-1H-benzimidazol-1-yl]phenyl}ethyl acetate (step 4).

$^1$H-NMR (CDCl$_3$) δ: 8.13 (1H, s), 7.44 (2H, d, J=8.4 Hz), 7.27 (2H, d, J=8.4 Hz), 6.92 (1H, s), 5.95 (1H, br.s), 3.98 (2H, t, J=6.4 Hz), 2.99 (2H, t, J=6.4 Hz), 1.68–1.75 (9H, m).

STEP 6. 2-{4-[2-[1-(acetylamino)-1-methylethyl]-6-chloro-5-(trifluoromethyl)-1H-benzimidazol-1-yl]phenyl}ethyl(4-methylphenyl)sulfonylcarbamate The title compound was prepared according to the procedure described in Example 3 from N-{1-[6-chloro-1-[4-(2-hydroxyethyl)phenyl]-5-(trifluoromethyl)-1H-benzimidazol-2-yl]-1-methylethyl}acetamide (step 5).

MS (ESI) m/z: 637 (MH$^+$), 635 ([M–H]$^-$)

$^1$H-NMR (CD$_3$OD) δ: 8.04 (1H, s), 7.83 (2H, d, J=8.4 Hz), 7.45 (2H, d, J=8.4 Hz), 7.34 (2H, d, J=8.5 Hz), 7.26 (2H, d, J=8.5 Hz), 6.93 (1H, s), 4.32 (2H, t, J=6.4 Hz), 3.02 (2H, t, J=6.4 Hz), 2.37 (3H, s), 1.75 (6H, s), 1.53 (3H, s).

EXAMPLE 378

2-{4-[2-[1-(ACETYLAMINO)-1-METHYL-ETHYL]-6-CHLORO-5-(TRIFLUOROMETHYL)-1H-BENZIMIDAZOL-1-YL]PHENYL}ETHYL(4-METHYLPHENYL)SULFONYLCARBAMATE P-TOLUENESULFONATE

The title compound was prepared according to the procedure described in Example 231 from N-{[(2-{4-[6-chloro-2-[1-(methyloxy)ethyl]-5-(trifluoromethyl)-1H-benzimidazol-1-yl]phenyl}ethyl)amino]carbonyl}-4-methylbenzenesulfonamide (Example 377)

IR (KBr) ν: 1751, 1508, 1450, 1340, 1161, 1122 cm$^{-1}$

EXAMPLE 379

6-CHLORO-2-ETHYL-1-(4-{2-[METHYL({[(4-METHYLPHENYL)SULFONYL]AMINO}CARBONYL)AMINO]ETHYL}PHENYL)-1H-BENZIMIDAZOLE-5-CARBOXAMIDE

STEP 1. 2-{4-[5-(aminocarbonyl)-6-chloro-2-ethyl-1H-benzimidazol-1-yl]phenyl}ethyl methanesulfonate A mixture of 6-chloro-2-ethyl-1-[4-(2-hydroxyethyl)phenyl]-1H-benzimidazole-5-carboxamide (Example 111, step 4, 500 mg, 1.45 mmol), triethylamine (293 mg, 2.90 mmol) and methansulfonyl chloride (322 mg, 2.9 mmol) in dichloromethane (20 ml) was stirred at room temperature for 6 h. The reaction mixture was poured into water, and extracted with dichloromethane (50 ml). The organic layer was washed with brine (50 ml), then dried (Na$_2$SO$_4$). After removal of solvent, the crude product was purified by TLC with hexane/ethyl acetate (1:1) to afford 304 mg (50%) of the title compound as white solids.

MS (ESI) m/z: 422 ([M+H]$^+$).

$^1$H-NMR (CDCl$_3$) δ: 7.54 (1H, s), 7.44 (2H, d, J=8.3 Hz), 7.29 (2H, d, J=8.3 Hz), 7.13 (1H, s), 3.82 (2H, t, J=7.0 Hz), 3.19 (2H, t, J=7.0 Hz), 2.82 (6H, s), 2.75 (2H, q, J→7.6 Hz), 1.35 (3H, t, J=7.6 Hz).

STEP 2. 6-chloro-2-ethyl-1-{4-[2-(methylamino)ethyl]phenyl}-1H-benzimidazole-5-carboxamide A mixture of 2-{4-[5-(aminocarbonyl)-6-chloro-2-ethyl-1H-benzimidazol-1-yl]phenyl}ethyl methanesulfonate (step 1, 304 mg, 0.72 mmol), a solution of methyl amine (40% in methanol, 10 ml) and water (5 ml) in a sealed tube was heated overnight at 100° C. The reaction mixture was partitioned between dichloromethane (30 ml) and water (30 ml). The organic phase was separated and the aqueous phase was extracted with dichloromethane (50 ml). The combined organic phases were washed with brine (50 ml) and dried (Na$_2$SO$_4$). After removal of solvent, the crude product was purified by TLC with dichloromethane/methanol (10:1) to afford 154 mg (60%) of the title compound as yellow solids.

$^1$H-NMR (CDCl$_3$) δ: 7.54 (1H, s), 7.43 (2H, d, J=8.2 Hz), 7.29 (2H, d, J=8.2 Hz), 7.12 (1H, s), 3.62 (2H, t, J=7.0 Hz), 3.01 (2H, t, J=7.0 Hz), 2.82 (6H, s), 2.75 (2H, q, J=7.6 Hz), 1.34 (2H, t, J=7.6 Hz).

STEP 3. 6-chloro-2-ethyl-1-(4-{2-[methyl({[(4-methylphenyl)sulfonyl]amino}carbonyl)amino]ethyl}phenyl)-1H-benzimidazole-5-carboxamide The reaction was carried out according to the procedure described in step 10 of Example 1 from 6-chloro-2-ethyl-1-{4-[2-(methylamino)ethyl]phenyl}-1H-benzimidazole-5-carboxamide (step 2).

MS (ESI) m/z: 554 (MH$^+$), 552 ([M–H]$^-$).

$^1$H-NMR (CDCl$_3$) δ: 8.09 (1H, s), 7.97–7.94 (2H, d, J=8.4 Hz), 7.40–7.31 (4H, m), 7.16–7.13 (2H, d, J=8.4 Hz), 7.07 (1H, s), 6.36 (1H, br), 3.52 (2H, br), 2.98 (2H, br), 2.93 (3H, s), 2.78–2.69 (2H, d, J=7.6 Hz), 2.42 (3H, s), 1.34–1.28 (3H, t, J=7.6 Hz).

EXAMPLE 380

6-CHLORO-2-ETHYL-1-(4-{2-[METHYL({[(4-METHYLPHENYL)SULFONYL]AMINO}CARBONYL)AMINO]ETHYL}PHENYL)-1H-BENZIMIDAZOLE-5-CARBOXAMIDE SODIUM SALT

The title compound was prepared according to the procedure described in Example 2 from 6-chloro-2-ethyl-1-(4-{2-[methyl({[(4-methylphenyl)sulfonyl]amino}carbonyl)amino]ethyl}phenyl)-1H-benzimidazole-5-carboxamide (Example 379).

MS (ESI) m/z: 554 (MH$^+$), 552 ([M–H]$^-$).

EP4 Anta Onists: Azole Compounds of Formula II

Preferred embodiments of the azole compounds (II) are as follows:

R$^1$ is lower alkyl substituted with carboxy; carboxy; protected carboxy; carbamoyl; a heterocyclic group; lower alkoxy substituted with carbamoyl; aryl substituted with carboxy, carbamoyl or a heterocyclic group; or amino optionally substituted with lower alkylsulfonyl (more preferably lower alkyl substituted with carboxy; carboxy; carbamoyl; tetrazolyl; lower alkoxy substituted with carbamoyl; aryl substituted with carboxy or carbamoyl), R$^2$ is hydrogen or lower alkyl, Q is

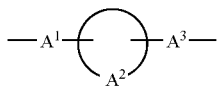

[in which -A$^1$- is a single bond or lower alkylene (more preferably methylene),

is cyclo(C$_5$–C$_9$)alkene, cyclo(C$_3$–C$_9$)alkane or bicyclo (C$_6$–C$_9$)alkene, bicyclo(C$_5$–C$_9$)alkane (more preferably cyclo(C$_5$–C$_7$)alkene, cyclo(C$_5$–C$_7$)alkane, bicyclo[2.2.1] heptene or bicyclo[2.2.1]heptane), and
-A$^3$- is a single bond or lower alkylene (more preferably single bond)], and
X is O.

ASSAYS OF THE PRESENT INVENTION

Several lines of evidence suggest that the interaction of cytokines and prostaglandins are critical in developing atherosclerotic disorders. However, the precise mechanisms by which atherosclerotic plaques are formed and the relationship of plaque formation to prostaglandins and cytokines is not defined. Until now, the relation with cytokine production and PGE$_2$ have been studied using isolated cell(s) or cell lines, i.e., macrophage, monocytes and T-cell in vitro (Zeng, L. I. et al., J. Pharmacol. Exp. Ther., 1998, 286, 1420–1426; Blaine, T. A. et al., 1997, J. Bone Joint Surg., 79-A, 1519–1528). For instance, The IL-6 production by human leukemic T cells of the HSB.2 cultured line is enhanced by PGE2. HSB.2 cells coexpress the EP2, EP3 and EP4 subtypes of PGE2 receptors. In these cells, EP4/EP2/EP3 receptor selective agonist misoprostol, but not the EP3 receptor selective agonist M&B28767, induced increases in IL-6 production (Zeng, et al., 1998). The enhanced induction of IL-6 production by PGE2 was mimicked by dibutyryl-cAMP, and inhibited by protein kinase A inhibitor, suggesting that EP4 and/or EP2 receptors appear to mediate PGE2-induced increases in IL-6 production by HSB.2 T cells through a cAMP dependent-mechanism. To the contrary, EP4 and EP2 agonists inhibited IL-1-induced IL-6 production in rat synovial lymphocytes with arthritis (Kurihara, Y et al., Clin. Exp. Immunol. Vol. 123, 323–330, 2001).

Thus, the modulation of cytokine production by PGE2 in peripheral mononuclear cells appears to be diverse in each condition. In atherosclerotic lesions, macrophages and T cellare detected in the plaque (van der Wal, A. C. et al., Circulation, 1994, 89, 36–44). However, interaction of cytokines and PGs in atherosclerotic plaque lesions is not clear. Therefore there is a need for a more specific therapeutic targeting system to control monocytes and T-cell activation.

We have newly found that the application of only PGE$_2$ to the human whole blood cells enhanced IL-6 production to a great extent. One embodiment of this invention is a more specific therapeutic targeting system to control IL-6 production. In addition, this system is a useful method for the detection of molecular target of atherosclerosis and IL-6 related disorders.

The test agents used for screening assays of the present invention may be selected individually or obtained from a compound library. Such agents include peptides, combinatorial chemistry-derived molecular libraries made of D- and/or L-configuration amino acids, phosphopeptides, anti-EP4 antibodies, EP4 antisense nucleic acids, and small organic and inorganic compounds. Libraries include biological libraries, libraries of natural compounds, peptide libraries (libraries of molecules having the functions of peptides, but with novel, non-peptide backbones which are resistant to enzymatic degradation yet remain bioactive) (see, e.g., Zuckermann, J. Med. Chem. 37: 2678–85, 1994), spatially addressable parallel solid phase or solution phase libraries, synthetic library methods requiring deconvolution, the "one-bead one-compound" library method, and synthetic library methods using affinity chromatography selection.

Examples of methods for the synthesis of molecular libraries can be found in the art, for example, in DeWitt et al., Proc. Natl. Acad. Sci. 90: 6909, 1993; Erd et al., Proc. Natl. Acad. Sci. 91: 11422, 1994; Zuckermann et al., J. Med. Chem. 37: 2678,1994; Cho et al., Science, 261: 1303, 1995; Carrellet al., Angew. Chem. Int. Ed. Engl. 33: 2061, 1994; and Gallop et al., J. Med. Chem. 37: 1233, 1994.

Libraries of compounds may be presented in solution (e.g., Houghten, Biotechniques, 13: 412–421, 1992), or on beads (Lam, Nature 354: 82–84, 1991), on chips (Fodor, Nature 364: 555–556, 1993), bacteria or spores (Ladner, U.S. Pat. No. 5,223,409), plasmids (Cullet al., Proc. Natl. Acad. Sci. USA. 89: 1865–1869, 1992) or on phage (Scott et al., Science 249: 386–390, 1990; Devlin, Science 249: 404–406, 1990; Cwirla et al., Proc. Natl. Acad. Sci. (USA) 87: 6378–6382, 1990; Felici, J. Mol. Biol. 222: 301–310, 1991; Ladner, supra).

What is claimed is:

1. A method of treating atherosclerosis comprising administering to a mammal, in need thereof, an effective amount of an EP4 receptor antagonist; wherein said EP4 receptor antagonist is a compound of Formula I

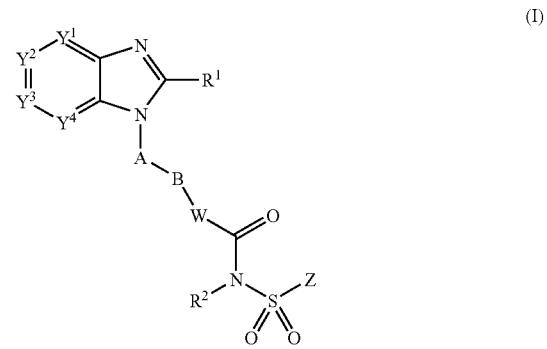

(I)

or a pharmaceutically acceptable salt thereof, wherein
one of Y$^1$, Y$^2$, Y$^3$ and Y$^4$ is N and the others are independently selected from CH or C(L);
R$^1$ is H, C$_{1-8}$ alkyl, C$_{2-8}$ alkenyl, C$_{2-8}$ alkynyl, C$_{3-7}$ cycloalkyl, C$_{1-8}$ alkoxy, halo-substituted C$_{1-8}$ alkoxy, C$_{1-8}$ alkyl-S(O)m-, Q$^1$-, pyrrolidinyl, piperidyl, oxopyrrolidinyl, oxopiperidyl, amino, mono- or di-(C$_{1-8}$ alkyl)amino, C$_{1-4}$alkyl-C(=O)—N(R$^3$)— or C$_{1-4}$alkyl-S (O)m-N(R$^3$)—, wherein said C$_{1-8}$ alkyl, C$_{2-8}$ alkenyl and C$_{2-8}$ alkynyl are optionally substituted with halo, C$_{1-3}$ alkyl, hydroxy, oxo, C$_{1-4}$ alkoxy-, C$_{1-4}$ alkyl-S(O) m-, C$_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$-, $Q^1$-C(=O)—, $Q^1$-O—, $Q^1$-S(O)m-, $Q^1$-C$_{1-4}$alkyl-O—, $Q^1$-C$_{1-4}$alkyl-S(O)m-, $Q^1$-C$_{1-4}$alkyl-C(O)—N(R$^3$)—, $Q^1$-C$_{1-4}$alkyl-N(R$^3$)— or C$_{1-4}$alkyl-C(O)—N(R$^3$—;

$Q^1$ is a 5–12 membered monocyclic or bicyclic aromatic ring optionally containing up to 4 heteroatoms selected from O, N and S, and is optionally substituted with halo, C$_{1-4}$ alkyl, halo-substituted C$_{1-4}$ alkyl, hydroxy, C$_{1-4}$ alkoxy, halo-substituted C$_{1-4}$ alkoxy, C$_{1-4}$ alkylthio, nitro, amino, mono- or di-(C$_{1-4}$alkyl)amino, cyano, HO—C$_{1-4}$ alkyl, C$_{1-4}$ alkoxy-C$_{1-4}$alkyl, C$_{1-4}$ alkylsulfonyl, aminosulfonyl, C$_{1-4}$alkylC(=O)—, HO(O=)C—, C$_{1-4}$alkyl-O(O=)C—, R$^3$N(R$^4$)C(=O)—, C$_{1-4}$ alkylsulfonylamino, C$_{3-7}$ cycloalkyl, R$^3$C(=O)N(R$^4$)— or NH$_2$(HN=)C—;

A is a 5–6 membered monocyclic aromatic ring optionally containing up to 3 heteroatoms selected from O, N and S, wherein said 5–6 membered monocyclic aromatic ring is optionally substituted with up to 3 substituents selected from halo, C$_{1-4}$ alkyl, halo-substituted C$_{1-4}$ alkyl, hydroxy, C$_{1-4}$ alkoxy, halo-substituted C$_{1-4}$ alkoxy, C$_{1-4}$alkylthio, nitro, amino, mono- or di-(C$_{1-4}$alkyl)amino, cyano, HO—C$_{1-4}$ alkyl, C$_{1-4}$ alkoxy-C$_{1-4}$alkyl, C$_{1-4}$ alkylsulfonyl, aminosulfonyl, acetyl, R$^3$N(R$^4$)C(=O)—, HO(O=)C—, C$_{1-4}$alkyl-O(O=)C—, C$_{1-4}$ alkylsulfonylamino, C$_{3-7}$ cycloalkyl, R$^3$C(=O)N(R$^4$)— and NH$_2$(HN=)C—;

B is halo-substituted C$_{1-6}$ alkylene, C$_{3-7}$ cycloalkylene, C$_{2-6}$ alkenylene, C$_{2-6}$ alkynylene, —O—C$_{1-5}$ alkylene, C$_{1-2}$ alkylene-O—C$_{1-2}$ alkylene or C$_{1-6}$ alkylene optionally substituted with an oxo group or C$_{1-3}$ alkyl;

W is NH, N—C$_{1-4}$ alkyl, O, S, N—OR$^5$ or a covalent bond;

R$^2$ is H, C$_{1-4}$ alkyl, OH or C$_{1-4}$ alkoxy;

Z is a 5–12 membered monocyclic or bicyclic aromatic ring optionally containing up to 3 heteroatoms selected from O, N and S, wherein said 5–12 membered monocyclic or bicyclic aromatic ring is optionally substituted with halo, C$_{1-4}$ alkyl, halo-substituted C$_{1-4}$ alkyl, C$_{1-4}$ alkenyl, C$_{1-4}$ alkynyl, hydroxy, C$_{1-4}$ alkoxy, halo-substituted C$_{1-4}$ alkoxy, C$_{1-4}$ alkylthio, nitro, amino, mono- or di-(C$_{1-4}$ alkyl)amino, cyano, HO—C$_{1-4}$ alkyl, C$_{1-4}$ alkoxy-C$_{1-4}$alkyl, C$_{1-4}$ alkylsulfonyl, aminosulfonyl, C$_{1-4}$alkylC(=O)—, R$^3$C(=O)N(R$^4$)—, HO(O=)C—, C$_{1-4}$alkyl-O(O=)C—, C$_{1-4}$ alkylsulfonylamino, C$_{3-7}$ cycloalkyl, NH$_2$(HN=)C—, Q$^2$-S(O)m-, Q$^2$-O—, Q$^2$N(R$^3$)— or Q$^2$-;

L is halo, C$_{1-4}$ alkyl, halo-substituted C$_{1-4}$ alkyl, hydroxy, C$_{1-4}$ alkoxy, halo-substituted C$_{1-4}$ alkoxy, C$_{1-4}$ alkylthio, nitro, amino, mono- or di-(C$_{1-4}$ alkyl)amino, cyano, HO—C$_{1-4}$ alkyl, C$_{1-4}$ alkoxy-C$_{1-4}$alkyl, C$_{1-4}$ alkylsulfonyl, aminosulfonyl, C$_{1-4}$alkylC(=O)—, HO(O=)C—, C$_{1-4}$alkyl-O(O=)C—, C$_{1-4}$ alkylsulfonylamino, C$_{3-7}$ cycloalkyl, R$^3$C(=O)N(R$^4$)—, NH$_2$(HN=)C—, R$^3$N(R$^4$)C(=O)—, R$^3$N(R$^4$)S(O)m-, Q$^2$-, Q$^2$-C(=O)—, Q$^2$-O—, Q$^2$-C$_{1-4}$alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;

R$^3$ and R$^4$ are independently selected from H and C$_{1-4}$ alkyl;

R$^5$ is H, C$_{1-4}$ alkyl, C$_{1-4}$ alkyl-(O=)C— or C$_{1-4}$ alkyl-O—(O=)C—; and Q$^2$ is a 5–12 membered monocyclic or bicyclic aromatic ring, or a 5–12 membered tricyclic ring optionally containing up to 3 heteroatoms selected from O, N and S, wherein said 5–12 membered monocyclic or bicyclic aromatic ring is optionally substituted with halo, C$_{1-4}$ alkyl, halo-substituted C$_{1-4}$ alkyl, C$_{1-4}$ alkenyl, C$_{1-4}$ alkynyl, hydroxy, C$_{1-4}$ alkoxy, halo-substituted Cl$_{1-4}$ alkoxy, C$_{1-4}$ alkylthio, nitro, amino, mono- or di-(C$_{1-4}$ alkyl)amino, cyano, HO—C$_{1-4}$ alkyl, C$_{1-4}$ alkoxy-C$_{1-4}$ alkyl, C$_{1-4}$ alkylsulfonyl, aminosulfonyl, C$_{1-4}$alkyl-(O=)C—, R$^3$(R$^4$)C(=O)N—, HO(O=)C—, C$_{1-4}$ alkyl-O(O=)C—, C$_{1-4}$ alkylsulfonylamino, C$_{3-7}$ cycloalkyl, C$_{1-4}$ alkyl-C(=O)NH— or NH$_2$(HN=)C—.

2. The method according to claim 1, wherein said EP4 receptor antagonist is N-[({2-[4-(2-ethyl-5,7-dimethyl-3H-imidazo[4,5-b]pyridin-3-yl)phenyl]ethyl}amino)carbonyl]-4-methylbenzene sulfonamide or a pharmaceutically acceptable of salt thereof.

3. The method according to claim 1, wherein said EP4 receptor antagonist is 2-ethyl-4,6-dimethyl-1-(4-{2-[({[(4-methylphenyl)sulfonyl]amino}carbonyl)amino]ethyl}phenyl)-1H-imidazo[4,5-c]pyridine or a pharmaceutically acceptable salt thereof.

* * * * *